United States Patent
Kai et al.

(10) Patent No.: US 8,101,644 B2
(45) Date of Patent: Jan. 24, 2012

(54) PYRROLINONE DERIVATIVE AND PHARMACEUTICAL COMPOSITION COMPRISING THE SAME

(75) Inventors: Hiroyuki Kai, Osaka (JP); Shunji Shinohara, Koka (JP); Takayuki Kameyama, Koka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 12/450,548

(22) PCT Filed: Mar. 28, 2008

(86) PCT No.: PCT/JP2008/056107
§ 371 (c)(1), (2), (4) Date: Sep. 30, 2009

(87) PCT Pub. No.: WO2008/120725
PCT Pub. Date: Oct. 9, 2008

(65) Prior Publication Data
US 2010/0210632 A1    Aug. 19, 2010

(30) Foreign Application Priority Data
Mar. 30, 2007 (JP) ................ 2007-091624

(51) Int. Cl.
*A61K 31/4162* (2006.01)
*A61K 31/407* (2006.01)
*C07D 487/02* (2006.01)
*C07D 231/00* (2006.01)

(52) U.S. Cl. ........ 514/405; 514/414; 514/421; 548/453; 548/454; 548/360.5

(58) Field of Classification Search .......................... None
See application file for complete search history.

(56) References Cited

U.S. PATENT DOCUMENTS

| | | | |
|---|---|---|---|
| 5,508,300 A * | 4/1996 | Duplantier | 514/403 |
| 2007/0037974 A1 | 2/2007 | Brotherton-Pleiss et al. | |
| 2007/0049534 A1 | 3/2007 | Dillon et al. | |
| 2007/0049609 A1 | 3/2007 | Broka et al. | |
| 2007/0049610 A1 | 3/2007 | Dillon et al. | |
| 2007/0049758 A1 | 3/2007 | Dillon et al. | |

FOREIGN PATENT DOCUMENTS

| | | |
|---|---|---|
| FR | 2.097.038 | 3/1972 |
| JP | 42-1873 | 1/1967 |
| RU | 2 067 575 | 10/1996 |
| WO | 02/094767 | 11/2002 |
| WO | 03/030897 | 4/2003 |
| WO | 2005/095359 | 10/2005 |
| WO | 2006/044000 | 4/2006 |
| WO | 2007/025900 | 3/2007 |

OTHER PUBLICATIONS

Vippagunta et al., Advanced Drug Delivery Reviews, vol. 48, p. 3-26 (on p. 3), 2001.*

International Search Report dated May 20, 2008 for PCT application corresponding to the present U.S. application.
International Preliminary Report on Patentability dated Oct. 22, 2009 including English translation of PCT Written Opinion of the International Searching Authority for PCT application corresponding to the present U.S. application.
Kennedy, C., "P2X Receptors: Targets for Novel Analgesics?" The Neuroscientist, vol. 11, No. 4, pp. 345-356 (2005).
Cockayne et al., "$P2X_2$ Knockout Mice and $P2X_2/P2X_3$ Double Knockout Mice Reveal a Role for the $P2X_2$ Receptor Subunit in Mediating Multiple Sensory Effects of ATP," J. Physiol., vol. 567, No. 2, pp. 621-639 (2005).
Gein et al., "Synthesis and Antiinflammatory and Analgesic Activity of 1-(2-Aminoethyl)-5-Aryl-4-Acyl-3-Hydroxy-3-Pyrrolin-2-Ones," Pharmaceutical Chemistry Journal, vol. 39, No. 9, pp. 484-487 (2005).
Gein et al., "Synthesis and Pharmacological Activity of 5-Aryl-4-Acetyl-1-Carboxyalkyl-Tetrahydropyrrole-2,3-Diones," Pharmaceutical Chemistry Journal, vol. 31, No. 5, pp. 251-254 (1997).
Shieh et al., "P2X Receptor Ligands and Pain," Expert Opin. Ther. Patents, vol. 16, No. 8, pp. 1113-1127 (2006).
North, R., "$P2X_3$ Receptors and Peripheral Pain Mechanisms," J. Physiol., vol. 554, No. 2, pp. 301-308 (2003). Kennedy et al., "Crossing the Pain Barrier: P2 Receptors as Targets for Novel Analgesics," J. Physiol., vol. 553, No. 3, pp. 683-694 (2003).
Gever et al., "Pharmacology of P2X Channels," Pflugers Arch—Eur. J. Physiol., vol. 452, pp. 513-537 (2006).
Jarvis et al., "A-317491, A Novel Potent and Selective Non-Nucleotide Antagonist of $P2X_3$ and $P2X_{2/3}$ Receptors, Reduces Chronic Inflammatory and Neuropathic Pain in the Rat," PNAS, vol. 99, No. 26, pp. 17179-17184 (2002).
Gein et al., "Synthesis and Pharmacological Activity of 5-Ary1-4-Acetyl-1-Carboxyalkyltetrahydrop3rrrole-2,3-Diones," Khimiko-Farmatsevticheskii Zhurnal, vol. 31, No. 5, pp. 33-36 (1997).
Koz'Minych et al., "1, 3, 4, 6-Tetracarbonyl Compounds. Part 2. Preparation of Biologically Active 2-Hydroxy-2, 3-dihydro-3-Pyrrolones and Aroylpyruvic Acid-Substituted Amides," Khimiko-Farmatsevticheskii Zhurnal, vol. 30, No. 7, pp. 31-35 (1996).
Zankowska-Jasinska et al.,"The New Synthesis of the Pyrrolo [3,4-e] [1,4] Diazepine Derivatives," Prace Chemiczne, vol. 32, pp. 75-82 (1989).

(Continued)

*Primary Examiner* — Yong Chu
(74) *Attorney, Agent, or Firm* — Wenderoth, Lind & Ponack, L.L.P.

(57) ABSTRACT

The present invention provides a compound represented by the formula (I):

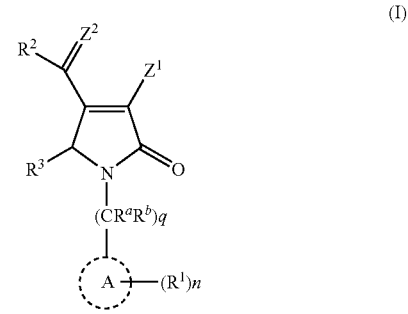

(I)

wherein $R^1$, $R^2$, $R^3$, $Z^1$, $Z^2$, $R^a$, $R^b$, q, A and n are as defined in the description, a pharmaceutically acceptable salt or solvate thereof. The compound is useful as $P2X_3$ and/or $P2X_{2/3}$ receptor antagonist.

3 Claims, No Drawings

OTHER PUBLICATIONS

RN 671764-08-2 Registry, ED Entered STN: Apr. 6, 2004, CN 2,3-Pyrrolidinedione, 4-(hydroxyphenylmethylene)-1-[5-(4-methoxyphenyl)-1, 3, 4-oxadiazol-2-yl]-5-phenyl- (CA Index Name) MF C26 H19 N3 O5, SR Chemical Library, URL: https://stnweb-japan.cas.org/, retrieval date: Apr. 28, 2008.

Gein et al., "Synthesis and Biological Activity of 5-Aryl-4-Acyl-3-Hydroxy-1-Morpholinoalkyl-3-Pyrrrolin-2-Ones," Pharmaceutical Chemistry Journal, vol. 41, No. 5, pp. 256-263 (2007).

Yavari et al., "Triphenylphosphine-Mediated Reaction Between Dimethyl Acetylenedicarboxylate and NH-Acids Derived from Diaminobenzenes," Phosphorus, Sulfur and Silicon, vol. 181, pp. 771-777 (2006).

El-Maati, T., "Anisylidine Pyruvic Acid in Heterocyclic Synthesis," Bollettino Chimico Farmaceutico vol. 138, No. 6, pp. 272-279 (1999).

Andreichikov et al., "Chemistry of Oxalyl Derivatives of Methyl Ketones. XLIV. Synthesis of 4-Aroyl-1, 5-Diphenyltetra-Hydropyrrole-2, 3-Diones and their Reaction with Amines and Hydrazine," Journal of Organic Chemistry USSR (English Translation, 1987 Plenum Publishing Corporation, pp. 1572-1577) Zhurnal Organicheskoi Khimii, vol. 22, No. 8, pp. 1749-1756 (1986).

Gein et al., "Synthese und Biologische Aktivität von 1,5-Diaryl-3-Alkylamino-4-Carboxymethyl-2,5-Dihydropyrrol-2-Onen und 1, 5-Diaryl-4-Carboxymethyltetrahydropyrrol-2,3-Dionen," Pharmazie, vol. 48, No. 2, pp. 107-109 (1993).

Westphal, G., "Über die Bildung von Pyrrolo[3.4-c]-pyrazolen," Journal Für Praktische Chemie (Leipzig), vol. 311, No. 3, pp. 379-382 (1969).

Khimiko-Farmatsevticheskii Zhurnal, vol. 27, No. 5 pp. 42-45 (1993).

Supplementary European Search Report issued Mar. 23, 2011 in corresponding European Application No. 08 73 9225.

* cited by examiner

PYRROLINONE DERIVATIVE AND PHARMACEUTICAL COMPOSITION COMPRISING THE SAME

TECHNICAL FIELD

The invention relates to P2X receptor, specifically to a compound useful for the treatment of diseases or conditions associated with a $P2X_3$ receptor, specifically to a $P2X_3$ and/or $P2X_2/_3$ receptor, and a pharmaceutical composition comprising such compound.

BACKGROUND ART

ATP (adenosine triphosphate) is known to serve as a source of energy in cells and a substrate of phosphorylation, as well as an extracellular messenger. It is known that ATP is released from a cell by various stimulation such as cellular injury, inflammation, nociceptive stimulus, reduced blood oxygen level, and also known to be released together with another messenger from a primary sensory nerve terminal. ATP thus released mediates various extracellular signal transductions through an ATP receptor (Non-Patent Document 6, Non-Patent Document 7).

ATP receptor is categorized into ionotropic P2X family and G protein-coupled P2Y family. For P2X family, seven subtypes have been reported, and a member of this family forms a homo-trimeric structure or a hetero-trimeric structure together with another member of this subtype and functions as a non-specific cation channel (Non-Patent Document 8).

ATP is known to cause pain, and studies with $P2X_3$ knockout and knockdown methodologies have shown that $P2X_3$ receptor mediates transmission of chronic pain. $P2X_3$ receptors are expressed in a specific manner on peripheral sensory nerve to form a homo-complex or hetero-complex with $P2X_2$ ($P2X_2/_3$) (Non-Patent Document 1).

Later, the compound A-317491 was reported as a specific antagonist to $P2X_3$ and $P2X_2/_3$ receptors. A-317491 is tri-substituted-N-[(1S)-1,2,3,4-tetrahydro-1-naphthalenyl]benzamide derivative represented by the formula:

[Chemical Formula 1]

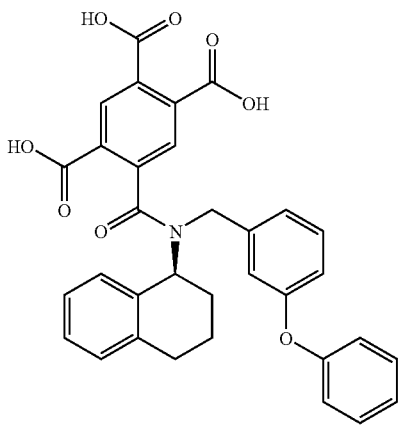

(Patent Document 1). It was reported to exhibit an antagonist activity to $P2X_3$ and $P2X_2/_3$ receptors and analgesic action in neuropathic pain model and inflammatory pain model (Non-Patent Document 9). This indicates that pain sensation is transmitted via $P2X_3$ or $P2X_2/_3$ receptor and that a $P2X_3$ or $P2X_2/_3$ receptor antagonist is useful as an analgesic. Also, compounds that exhibit $P2X_3$ or $P2X_2/_3$ receptor antagonizing effect are described in Patent Documents 2-7.

Additionally, it was recently reported that vesical reflex was strongly reduced in $P2X_3$ knockout mouse (Non-Patent Document 2), suggesting that a $P2X_3$ antagonist is useful in the treatment of diseases caused by overactive bladder.

Non-Patent Documents 3 and 4 disclose that the compounds having similar structures to the compounds of the invention show an analgetic activity. However, the structures of these compounds differ from the compounds of the invention.

[Patent Document1] WO02/094767

[Patent Document2] WO2005/095359

[Patent Document3] US20070037974

[Patent Document4] US20070049758

[Patent Document5]US20070049610

[Patent Document6] US20070049609

[Patent Document7] US20070049534

[Non-Patent Document 1] Neuroscientist 11 (2005) pp. 345-356

[Non-Patent Document 2] J. Physiol. 567.2 (2005) pp. 621-639

[Non-Patent Document 3] Pharmaceutical Chemistry Journal Vol. 39, No. 9, (2005), pp 484-487

[Non-Patent Document 4] Pharmaceutical Chemistry Journal Vol. 31, No. 5, (1997), pp 251-254

[Non-Patent Document 5] Expert Opin. Ther. Patens (2006) 16(8) 113-1127.

[Non-Patent Document 6] J. Physiology (2003), 554(2), 301-308

[Non-Patent Document 7] J. Physiology (2003), 553(3), 683-694

[Non-Patent Document 8] Pflungers Arch Eur J physiol (2006), 452, 513-537

[Non-Patent Document 9] PNAS (2002), 99(26), 17179-17184

DISCLOSURE OF INVENTION

Problems to be Resolved by the Invention

The present invention provides a novel $P2X_3$ and/or $P2X_2/_3$ receptor antagonist.

Means of Solving the Problems

During studies to solve the problems described above, the inventors have discovered novel compounds that bind specifically to $P2X_3$ and/or $P2X_2/3$ receptor and exhibit an antagonizing effect, and thus, achieved the inventions described below.

[1] A P2X₃ and/or P2X₂/₃ receptor antagonist comprising a compound of the formula (I):

[Chemical Formula 2]

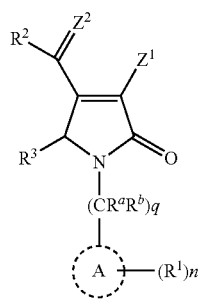

(I)

wherein $Z^1$ is hydroxy optionally protected, hydroxyamino optionally protected or amino optionally substituted;

$Z^2$ is =O or =N-E wherein E is hydrogen, hydroxy, lower alkyl optionally substituted, lower alkoxy optionally substituted, or amino optionally substituted, or

[Chemical Formula 3]

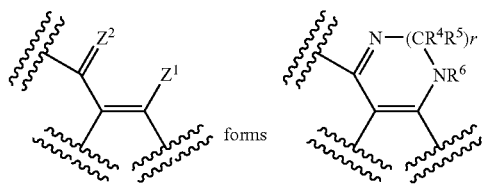

in which $R^4$ and $R^5$ are independently hydrogen or lower alkyl, $R^6$ is hydrogen, lower alkyl optionally substituted or acyl, r is an integer 0 to 2;

A is cycloalkyl, cycloalkenyl, aryl or heterocyclyl;

$R^a$ and $R^b$ are independently hydrogen or lower alkyl;

q is an integer 0 to 4;

each $R^1$ is independently halogen, hydroxy, lower alkyl optionally substituted, lower alkenyl optionally substituted, lower alkynyl optionally substituted, lower alkoxy optionally substituted, lower alkylthio optionally substituted, acyl optionally substituted, carboxy, lower alkoxycarbonyl optionally substituted, carbamoyl optionally substituted, lower alkylcarbamoyl optionally substituted, amino optionally substituted, sulfamoyl optionally substituted, cyano, nitro, cycloalkyl optionally substituted, cycloalkenyl optionally substituted, aryl optionally substituted or heterocyclyl optionally substituted;

n is an integer 0 to 3, provided that A-(R¹)n may be hydrogen when

[Chemical Formula 4]

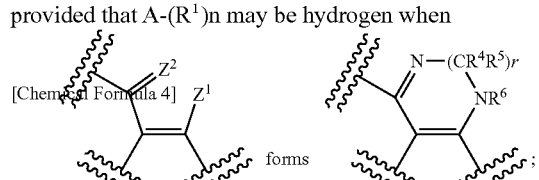

$R^2$ is alkyl optionally substituted, lower alkoxy optionally substituted, lower alkylcarbamoyl optionally substituted, cycloalkyl optionally substituted, cycloalkenyl optionally substituted, aryl optionally substituted or heterocyclyl optionally substituted;

$R^3$ is hydrogen, alkyl optionally substituted, cycloalkyl optionally substituted, cycloalkenyl optionally substituted, aryl optionally substituted or heterocyclyl optionally substituted, or a pharmaceutically acceptable salt or solvate thereof.

[2] A P2X₃ and/or P2X₂/₃ receptor antagonist according to [1] wherein $Z^1$ is hydroxy and $Z^2$ is =O.

[3] A P2X₃ and/or P2X₂/₃ receptor antagonist according to [1] wherein r is 0.

[4] A P2X₃ and/or P2X₂/₃ receptor antagonist according to any one of [1] to [3] wherein A is phenyl, pyridyl or thiazolyl.

[5] A P2X₃ and/or P2X₂/₃ receptor antagonist according to any one of [1] to [4] wherein $R^1$ is lower alkoxycarbonyl optionally substituted or heterocyclyl optionally substituted.

[6] A P2X₃ and/or P2X₂/₃ receptor antagonist according to any one of [1] to [5] wherein $R^2$ is lower alkyl optionally substituted, phenyl optionally substituted or pyridyl optionally substituted.

[7] A P2X₃ and/or P2X₂/₃ receptor antagonist according to any one of [1] to [6] wherein $R^3$ is alkyl having from 3 to 10 carbon atoms, cycloalkyl or phenyl optionally substituted.

[8] A P2X₃ and/or P2X₂/₃ receptor antagonist according to any one of [1] to [7] wherein q is 0.

[9] A P2X₃ and/or P2X₂/₃ receptor antagonist according to any one of [1] to [7] wherein q is 1.

[10] A compound of the formula (I'):

[Chemical Formula 5]

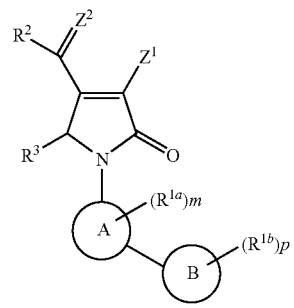

(I')

wherein $Z^1$ is hydroxy optionally protected, hydroxyamino optionally protected or amino optionally substituted; $Z^2$ is =O or =N-E wherein E is hydrogen, hydroxy, lower alkyl optionally substituted, lower alkoxy optionally substituted, or amino optionally substituted, or

[Chemical Formula 6]

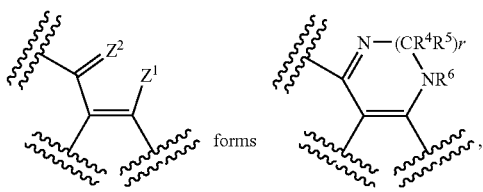

in which $R^4$ and $R^5$ are independently hydrogen or lower alkyl, $R^6$ is hydrogen, lower alkyl optionally substituted or acyl, r is an integer 0 to 2;

A and B are independently cycloalkyl, cycloalkenyl, aryl or heterocyclyl;

$R^{1a}$ and $R^{1b}$ are independently halogen, hydroxy, lower alkyl optionally substituted, lower alkenyl optionally substituted, lower alkynyl optionally substituted, lower alkoxy optionally substituted, lower alkylthio optionally substituted, acyl optionally substituted, carboxy, lower alkoxycarbonyl optionally substituted, carbamoyl optionally substituted, lower alkylcarbamoyl optionally substituted, amino optionally substituted, sulfamoyl optionally substituted, cyano or nitro;

m and p are independently an integer 0 to 2;

$R^2$ is alkyl optionally substituted, lower alkoxy optionally substituted, lower alkylcarbamoyl optionally substituted, cycloalkyl optionally substituted, cycloalkenyl optionally substituted, aryl optionally substituted or heterocyclyl optionally substituted;

$R^3$ is hydrogen, lower alkyl optionally substituted, cycloalkyl optionally substituted, cycloalkenyl optionally substituted, aryl optionally substituted or heterocyclyl optionally substituted;

provided that a compound wherein A is pyrazolone and B is phenyl is excluded, or a pharmaceutically acceptable salt or solvate thereof.

[11] A compound according to [10] or a pharmaceutically acceptable salt or solvate thereof wherein $Z^1$ is hydroxy optionally protected; $Z^2$ is =O; $R^2$ is alkyl optionally substituted, lower alkoxy optionally substituted, cycloalkyl optionally substituted, cycloalkenyl optionally substituted, aryl optionally substituted or heterocyclyl optionally substituted.

[12] A compound according to [10] or a pharmaceutically acceptable salt or solvate thereof wherein r is 0, $R^2$ is alkyl optionally substituted, lower alkoxy optionally substituted, cycloalkyl optionally substituted, cycloalkenyl optionally substituted, aryl optionally substituted or heterocyclyl optionally substituted.

[13] A compound according to any one of [9] to [12] or a pharmaceutically acceptable salt or solvate thereof wherein A is phenyl, pyridyl or thiazolyl.

[14] A compound of the formula (I″):

[Chemical Formula 7]

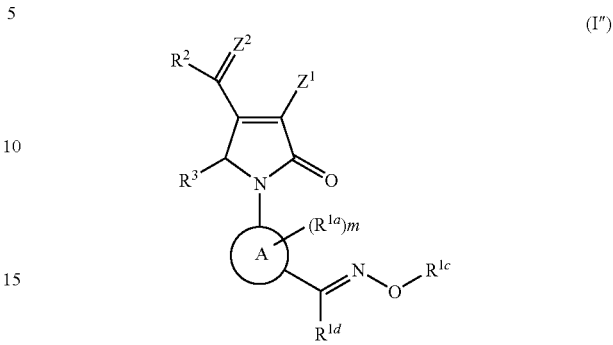

wherein $Z^1$ is hydroxy optionally protected, hydroxyamino optionally protected or amino optionally substituted; $Z^2$ is =O or =N-E wherein E is hydrogen, hydroxy, lower alkyl optionally substituted, lower alkoxy optionally substituted, or amino optionally substituted, or

[Chemical Formula 8]

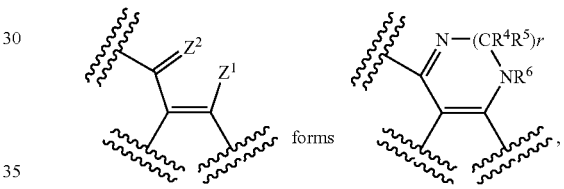

in which $R^4$ and $R^5$ are independently hydrogen or lower alkyl, $R^6$ is hydrogen, lower alkyl optionally substituted or acyl, r is an integer 0 to 2;

A is cycloalkyl, cycloalkenyl, aryl or heterocyclyl;

each $R^{1a}$ is independently halogen, hydroxy, lower alkyl optionally substituted, lower alkoxy optionally substituted, lower alkylthio optionally substituted, acyl optionally substituted, carboxy, lower alkoxycarbonyl optionally substituted, carbamoyl optionally substituted, lower alkylcarbamoyl optionally substituted, amino optionally substituted, sulfamoyl optionally substituted, cyano or nitro;

m is an integer 0 to 2;

$R^{1c}$ and $R^{1d}$ are independently hydrogen or lower alkyl optionally substituted;

$R^2$ is alkyl optionally substituted, lower alkoxy optionally substituted, lower alkylcarbamoyl optionally substituted, cycloalkyl optionally substituted, cycloalkenyl optionally substituted, aryl optionally substituted or heterocyclyl optionally substituted;

$R^3$ is hydrogen, lower alkyl optionally substituted, cycloalkyl optionally substituted, cycloalkenyl optionally substituted, aryl optionally substituted, or heterocyclyl optionally substituted, or a pharmaceutically acceptable salt or solvate thereof.

[15] A compound according to [14] or a pharmaceutically acceptable salt or solvate thereof wherein $Z^1$ is hydroxy optionally protected; $Z^2$ is =O; $R^2$ is alkyl optionally substituted, lower alkoxy optionally substituted, cycloalkyl optionally substituted, cycloalkenyl optionally substituted, aryl optionally substituted or heterocyclyl optionally substituted.

[16] A compound according to [14] or a pharmaceutically acceptable salt or solvate thereof wherein r is 0; $R^2$ is alkyl optionally substituted, lower alkoxy optionally substituted, cycloalkyl optionally substituted, cycloalkenyl optionally substituted, aryl optionally substituted or heterocyclyl optionally substituted.

[17] A compound according to any one of [14] to [16] or a pharmaceutically acceptable salt or solvate thereof wherein A is phenyl, pyridyl or thiazolyl.

[18] A pharmaceutical composition comprising a compound according to any one of [10] to [17] or a pharmaceutically acceptable salt or solvate thereof.

[19] A $P2X_3$ and/or $P2X_2/_3$ receptor antagonist comprising a compound according to any one of [10] to [17] or a pharmaceutically acceptable salt or solvate thereof.

[20] Use of a compound according to any one of [10] to [17] or a pharmaceutically acceptable salt or solvate thereof for the treatment and/or prevention of diseases associated with a $P2X_3$ and/or $P2X_2/_3$ receptor.

[21] A method for the treatment and/or prevention of diseases associated with a $P2X_3$ and/or $P2X_2/_3$ receptor comprising administering a compound according to any one of [10] to [17] or a pharmaceutically acceptable salt or solvate thereof.

In another embodiment, the inventions as described below are provided.

[1'] A $P2X_3$ or $P2X_2/_3$ receptor antagonist comprising a compound of the formula (I):

[Chemical Formula 9]

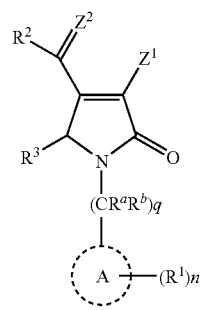

(I)

wherein
$Z^1$ is hydroxy optionally protected, hydroxyamino optionally protected or amino optionally substituted;
$Z^2$ is O or NOH, or

[Chemical Formula 10]

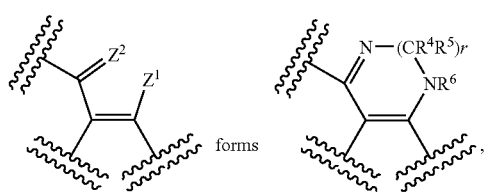

in which $R^4$ and $R^5$ are independently hydrogen or lower alkyl, $R^6$ is hydrogen, lower alkyl or acyl, r is an integer 0 to 2;
A is cycloalkyl, cycloalkenyl, aryl or heterocyclyl;
$R^a$ and $R^b$ are independently hydrogen or lower alkyl;

q is 0 or 1;
each $R^1$ is independently halogen, hydroxy, lower alkyl optionally substituted, lower alkoxy optionally substituted, lower alkylthio optionally substituted, acyl optionally substituted, carboxy, lower alkoxycarbonyl optionally substituted, carbamoyl optionally substituted, lower alkylcarbamoyl optionally substituted, amino optionally substituted, sulfamoyl optionally substituted, cyano, nitro, cycloalkyl optionally substituted, cycloalkenyl optionally substituted, aryl optionally substituted or heterocyclyl optionally substituted;
n is an integer 0 to 3;
provided that A-$(R^1)$n may be hydrogen when

[Chemical Formula 11]

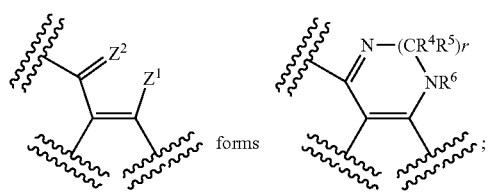

$R^2$ is lower alkyl optionally substituted, cycloalkyl optionally substituted, cycloalkenyl optionally substituted, aryl optionally substituted or heterocyclyl optionally substituted;
$R^3$ is hydrogen, alkyl optionally substituted, cycloalkyl optionally substituted, cycloalkenyl optionally substituted, aryl optionally substituted or heterocyclyl optionally substituted,
or a pharmaceutically acceptable salt or solvate thereof.

[2'] A $P2X_3$ or $P2X_2/_3$ receptor antagonist according to [1'] wherein $Z^1$ is hydroxy and $Z^2$ is O.

[3'] A $P2X_3$ or $P2X_2/_3$ receptor antagonist according to [1'] or [2'] wherein A is phenyl.

[4'] A $P2X_3$ or $P2X_2/_3$ receptor antagonist according to according to any one of [1'] to [3'] wherein $R^1$ is lower alkoxycarbonyl optionally substituted or heterocyclyl optionally substituted.

[5'] A $P2X_3$ or $P2X_2/_3$ receptor antagonist according to any one of [1'] to [4'] wherein $R^2$ is phenyl optionally substituted or pyridyl optionally substituted.

[6'] A $P2X_3$ or $P2X_2/_3$ receptor antagonist according to any one of [1'] to [5'] wherein $R^3$ is alkyl having from 3 to 10 carbon atoms, cycloalkyl or phenyl optionally substituted.

[7'] A $P2X_3$ or $P2X_2/_3$ receptor antagonist according to any one of [1'] to [6'] wherein q is 0.

[8'] A compound of the formula (I'):

[Chemical Formula 12]

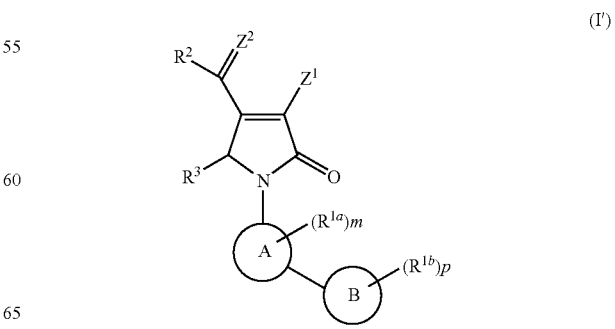

(I')

wherein
Z¹ is hydroxy optionally protected, hydroxyamino optionally protected or amino optionally substituted; Z² is O or NOH, or

[Chemical Formula 13]

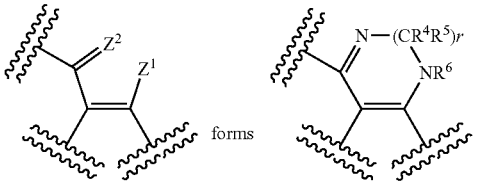

forms in which $R^4$ and $R^5$ are independently hydrogen or lower alkyl, $R^6$ is hydrogen, lower alkyl or acyl, r is an integer 0 to 2;
A and B are independently cycloalkyl, cycloalkenyl, aryl or heterocyclyl;
$R^{1a}$ and $R^{1b}$ are independently halogen, hydroxy, lower alkyl optionally substituted, lower alkoxy optionally substituted, lower alkylthio optionally substituted, acyl optionally substituted, carboxy, lower alkoxycarbonyl optionally substituted, carbamoyl optionally substituted, lower alkylcarbamoyl optionally substituted, amino optionally substituted, sulfamoyl optionally substituted, cyano or nitro;
m and p are independently an integer 0 to 2;
$R^2$ is lower alkyl optionally substituted, cycloalkyl optionally substituted, cycloalkenyl optionally substituted, aryl optionally substituted or heterocyclyl optionally substituted;
$R^3$ is lower alkyl optionally substituted, cycloalkyl optionally substituted, cycloalkenyl optionally substituted, aryl optionally substituted or heterocyclyl optionally substituted;
provided that a compound wherein A is pyrazolone and B is phenyl is excluded,
or a pharmaceutically acceptable salt or solvate thereof.
[9'] A compound according to [8'] or a pharmaceutically acceptable salt or solvate thereof wherein Z¹ is hydroxy optionally protected; Z² is O; $R^2$ is cycloalkyl optionally substituted, cycloalkenyl optionally substituted, aryl optionally substituted or heterocyclyl optionally substituted.
[10'] A compound of the formula (I"):

[Chemical Formula 14]

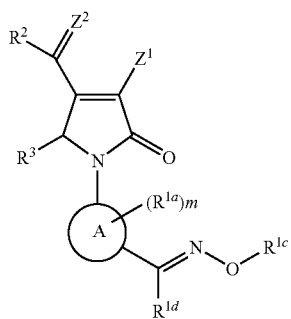

(I")

wherein
Z¹ is hydroxy optionally protected, hydroxyamino optionally protected or amino optionally substituted;
Z² is O or NOH, or

[Chemical Formula 15]

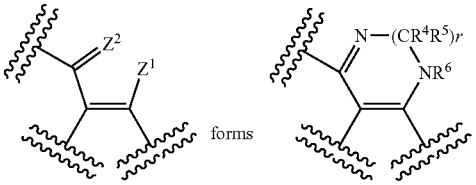

forms in which $R^4$ and $R^5$ are independently hydrogen or lower alkyl, $R^6$ is hydrogen, lower alkyl or acyl, r is an integer 0 to 2;
A is cycloalkyl, cycloalkenyl, aryl or heterocyclyl;
each $R^{1a}$ is independently halogen, hydroxy, lower alkyl optionally substituted, lower alkoxy optionally substituted, lower alkylthio optionally substituted, acyl optionally substituted, carboxy, lower alkoxycarbonyl optionally substituted, carbamoyl optionally substituted, lower alkylcarbamoyl optionally substituted, amino optionally substituted, sulfamoyl optionally substituted, cyano or nitro;
m is an integer 0 to 2;
$R^{1c}$ and $R^{1d}$ are independently is hydrogen or lower alkyl optionally substituted;
$R^2$ is lower alkyl optionally substituted, cycloalkyl optionally substituted, cycloalkenyl optionally substituted, aryl optionally substituted or heterocyclyl optionally substituted;
$R^3$ is lower alkyl optionally substituted, cycloalkyl optionally substituted, cycloalkenyl optionally substituted, aryl optionally substituted, or heterocyclyl optionally substituted,
or a pharmaceutically acceptable salt or solvate thereof.
[11'] A pharmaceutical composition comprising a compound according to any one of [8'] to [10'] or a pharmaceutically acceptable salt or solvate thereof.
[12'] A $P2X_3$ or $P2X_{2/3}$ receptor antagonist comprising a compound according to any one of [8'] to [10'] or a pharmaceutically acceptable salt or solvate thereof.
[13'] A $P2X_3$ or $P2X_{2/3}$ receptor antagonist according to any one of [1'] to [7'] which is an analgesic.
[14'] An analgesic comprising a compound according to any one of [8'] to [10'] or a pharmaceutically acceptable salt or solvate thereof.
[15'] A method of relieving pain comprising administering a compound according to any one of [1'] to [10'] or a pharmaceutically acceptable salt or solvate thereof.
[16'] Use of a compound according to any one of [1'] to [10'] or a pharmaceutically acceptable salt or solvate thereof for the manufacture of an analgesic.

BEST MODE FOR CARRYING OUT THE INVENTION

The compound of the invention has characteristic structures, which are as follows:
1) it has pyrrolin-2-one ring as a basic skeleton; and
2-1) it has an enol-type hydroxyl group at 3-position of said pyrroline ring; or 2-2) it has substituents on 3-position and 4-position of said pyrroline ring together to form a nitrogen-containing heterocycle of the formula:

[Chemical Formula 16]

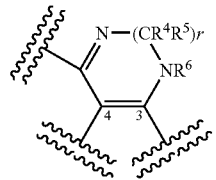

wherein $R^4$, $R^5$, $R^6$ and r are as defined above; and
3) it has a substituent of the formula:

[Chemical Formula 17]

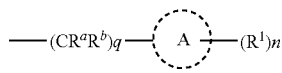

wherein A, $R^1$, $R^a$, $R^b$, n and q are as defined above, on the nitrogen at 1-position of said pyrroline ring, provided that said nitrogen at 1-position may have no substituent in case of (2-2);
3-1) it has a substituent of the formula:

[Chemical Formula 18]

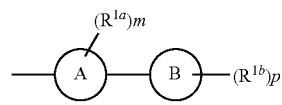

wherein A, B, $R^{1a}$, $R^{1b}$, m and p are as defined above, on the nitrogen at 1-position of said pyrroline ring;
3-2) it has a substituent of the formula:

[Chemical Formula 19]

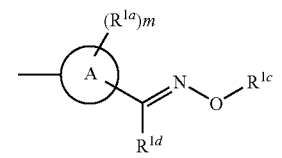

wherein A, $R^{1a}$, $R^{1c}$, $R^{1d}$ and m are as defined above, on the nitrogen at 1-position of said pyrroline ring.
When n, m and/or p are an integer two or more in the above formulae (I), (I') and (I"), $R^1$s, $R^{1a}$s and/or $R^{1b}$s may be each the same or different from each other.

As used throughout the specification, the following terms have the following meaning unless specifically indicated.

The term "alkyl" means a straight or branched chain monovalent hydrocarbon group containing from 1 to 10, preferably from 1 to 8, more preferably from 1 to 6 carbons, such as methyl, ethyl, n-propyl, isopropyl, n-butyl, isobutyl, sec-butyl, tert-butyl, n-pentyl, isopentyl, neo-pentyl, n-hexyl, isohexyl, n-heptyl, isoheptyl, n-octyl, isooctyl, n-nonyl and n-decyl.

The term "lower alkyl" means a straight or branched chain monovalent hydrocarbon group containing from 1 to 6, preferably from 1 to 3 carbons, such as, methyl, ethyl, n-propyl, isopropyl, n-butyl, isobutyl, sec-butyl, tert-butyl, n-pentyl, isopentyl, neo-pentyl, n-hexyl, isohexyl.

The term "acyl" denotes a group of the formula R—CO—, wherein R is, for example, "lower alkyl" as defined above or "lower alkenyl", "aryl", "heterocyclyl", "cycloalkyl" or "cycloalkenyl" as defined bellow.

The term "cycloalkyl" means a monocyclic or polycyclic saturated cyclic carbon chain containing from 3 to 10 carbons. Monocyclic cycloalkyl includes, for example, cyclopropyl, cyclobutyl, cyclopentyl, cyclohexyl, cycloheptyl, cyclooctyl, cyclononyl, cyclodecyl. Polycyclic cycloalkyl includes norbornanyl, etc.

The term "cycloalkenyl" means non-aromatic monocyclic or polycyclic ring system of 3 to 10 carbons containing at least one carbon-carbon double bond. Monocyclic cycloalkenyl includes cyclopentenyl, cyclohexenyl, etc., and polycyclic cycloalkenyl includes norbornyl, etc.

The term "aryl" means aromatic hydrocarbon which is monocyclic or a fused ring, such as phenyl, 1-naphthyl, 2-naphthyl, anthryl, phenanthryl and indenyl, etc.

The term "heterocyclyl" means aromatic or non-aromatic monocyclic or fused-cyclic group, which is derived from a five- to seven-membered ring having at least one nitrogen atom, oxygen atom, and/or sulphur atom in the ring, a fused ring consisting of two or more said five- to seven-membered rings, or a fused ring consisting of said five- to seven-membered ring fused to one or more "aryl", "cycloalkyl" or "cycloalkenyl" as defined above. For example, non-aromatic heterocyclic groups such as pyrrolinyl, pyrrolidino, pyrrolidinyl, imidazolynyl, imidazolidinyl, pyrazolinyl, pyrazolidinyl, piperidino, piperidyl, piperidino, piperazinyl, morpholinyl, morpholino, thiomorpholinyl, thiomorpholino, tetrahydropyranyl, dihydropyridyl, dihydropyridazinyl, dihydropyrazinyl, dioxanyl, oxathiolanyl, thianyl, tetrahydrofuryl, tetrahydropyranyl, tetrahydrothiazolinyl, tetrahydroisothiazolinyl, etc.;

monocyclic aromatic heterocyclic groups such as pyrrolyl, pyrazinyl, pyrazolyl, tetrazolyl, furyl, thienyl, pyridyl, imidazolyl, triazolyl, tetrazolyl, triazinyl, pyridazinyl, pyrimidinyl, pyrazinyl, isoxazolyl, thiazolyl, isothiazolyl, thiadiazolyl, oxazolyl and oxadiazolyl, etc; and heterocyclic groups fused to another ring such as indolyl, isoindolyl, indazolyl, indolizinyl, indolinyl, isoindolinyl, quinolyl, isoquinolyl, cinnolinyl, phthalazinyl, quinazolinyl, naphthyridinyl, quinoxalinyl, purinyl, pteridinyl, benzopyranyl, benzimidazolyl, benzisoxazolyl, benzoxazolyl, benzoxadiazolyl, benzisothiazolyl, benzothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, benzimidazolynyl, benzodioxanyl, tetrahydroquinoline, tetrahydrobenzothienyl, etc.

The term "halogen" means fluorine, chlorine, bromine and iodine.

The term "lower alkoxy" means a group of the formula RO— wherein R is as defined above for lower alkyl, such as methoxy, ethoxy, propoxy, isopropoxy, butoxy, isobutoxy, sec-butoxy, tert-butoxy, pentoxy, isopentoxy, neopentoxy, hexoxy, etc.

The term "lower alkylthio" means a group of the formula RS— wherein R is as defined above for lower alkyl, such as methylthio, ethylthio, propylthio, isopropylthio, butylthio, isobutylthio, sec-butylthio, tert-butylthio, pentylthio, isopentylthio, neopentylthio, hexylthio, etc.

The term "lower alkoxycarbonyl" means a group of the formula ROCO— wherein R is as defined above for lower alkyl, such as methyloxycarbonyl, ethyloxycarbonyl, n-propyloxycarbonyl, isopropyloxycarbonyl, n-butyloxycarbonyl, tert-butyloxycarbonyl, n-pentyloxycarbonyl, etc.

The term "lower alkylcarbamoyl" includes mono- or di-lower alkylcarbamoyl wherein alkyl moiety contains from 1 to 6 carbons, such as methylcarbamoyl, ethylcarbamoyl, n-propylcarbamoyl, isopropylcarbamoyl, n-butylcarbamoyl, dimethylcarbamoyl, diethylcarbamoyl, dipropylcarbamoyl, etc.

Substituents for "lower alkyl optionally substituted", "lower alkenyl optionally substituted", "lower alkynyl optionally substituted", "lower alkoxy optionally substituted", "lower alkylthio optionally substituted", "lower alkoxycarbonyl optionally substituted", and "lower alkylcarbamoyl optionally substituted" include but are not limited to one or more same or different substituent selected from the group consisting of:

hydroxy, carboxy, halogen (F, Cl, Br, I), halo(lower)alkoxy (e.g., $CF_3O$), cycloalkyl (e.g., cyclopropyl), cycloalkenyl (e.g., cyclopropenyl), lower alkoxy (e.g., methoxy, ethoxy, propoxy, butoxy, etc.), lower alkenyloxy (e.g., vinyloxy, allyloxy, etc.), lower alkoxycarbonyl (e.g., methoxycarbonyl, ethoxycarbonyl, tert-butoxycarbonyl, etc.), nitro, nitroso, amino, lower alkylamino (e.g., methylamino, ethylamino, dimethylamino, etc.), acylamino (e.g., acetylamino, benzoylamino, etc.), aralkylamino (e.g., benzylamino, tritylamino), hydroxyamino, imino, hydroxyimino, lower alkylimino (e.g., methylimino, ethylimino, dimethylimino, etc.), lower alkoxyimino (e.g., methoxyimino, ethoxyimino, etc.), acylimino (e.g., acetylimino, benzoylimino, etc.), azido, aryl (e.g., phenyl, etc.), aralkyl (e.g., benzyl, etc.), aralkyloxy (e.g., benzyloxy), cyano, isocyano, isocyanato, thiocyanato, isothiocyanato, mercapto, lower alkylthio (e.g., methylthio, etc.), lower alkylsulfonyl (e.g., methanesulfonyl, ethanesulfonyl), carbamoyl, lower alkylcarbamoyl (e.g., methylcarbamoyl, ethylcarbamoyl, dimethylcarbamoyl, etc.), sulfamoyl, lower alkylsulfamoyl, acyl (e.g., formyl, acetyl, etc.), formyloxy, thioformyl, thiocarboxy, dithiocarboxy, thiocarbamoyl, sulfino, sulfo, hydrazino, azido, ureido, amidino, guanidino, phthalimido, tri-lower alkylsilyl (e.g., trimethylsilyl, etc.), oxo, and the substituents as described below in the following Examples.

Substituents for "acyl optionally substituted" are as defined above for "lower alkyl optionally substituted". If R in acyl(R—CO—) is "aryl", "heterocyclyl", "cycloalkyl" or "cycloalkenyl", then the substituent may be lower alkyl (e.g., methyl, ethyl, isopropyl, tert-butyl, etc.), halo(lower)alkyl (e.g., $CF_3$, $CH_2CF_3$, $CH_2CCl_3$, etc.), lower alkenyl, lower alkynyl (e.g., ethynyl), etc.

Substituents for "carbamoyl optionally substituted" and "sulfamoyl optionally substituted" are one or more same or different group selected from, but are not limited to, the group consisting of:

hydroxy, carboxy, halogen (F, Cl, Br, I), lower alkenyl (e.g., vinyl), lower alkynyl (e.g., ethynyl), cycloalkyl (e.g., cyclopropyl), cycloalkenyl (e.g., cyclopropenyl), lower alkoxycarbonyl (e.g., methoxycarbonyl, ethoxycarbonyl, tert-butoxycarbonyl, etc.), amino, lower alkylamino (e.g., methylamino, ethylamino, dimethylamino, etc.), acylamino (e.g., acetylamino, benzoylamino, etc.), aralkylamino (e.g., benzylamino, tritylamino), hydroxyamino, aryl (e.g., phenyl, etc.), cyano, isocyano, isocyanato, thiocyanato, isothiocyanato, acyl (e.g., formyl, acetyl, etc.) and the substituents as described in the following Examples.

Substituents for "amino optionally substituted" are one or more same or different group selected from, but are not limited to, the group consisting of:

hydroxy, halogen (F, Cl, Br, I), halo(lower)alkyl (e.g., $CF_3$, $CH_2CF_3$, $CH_2CCl_3$, etc.), hydroxy(lower)alkyl (e.g., hydroxyethyl, —$C(CH_3)_2CH_2OH$, etc.), halo(lower)alkoxy (e.g., $CF_3O$), lower alkyl (e.g., methyl, ethyl, isopropyl, tert-butyl, etc.), lower alkenyl (e.g., vinyl), lower alkynyl (e.g., ethynyl), cycloalkyl (e.g., cyclopropyl), cycloalkenyl (e.g., cyclopropenyl), lower alkoxy (e.g., methoxy, ethoxy, propoxy, butoxy, etc.), lower alkyloxycarbonyl (tert-butyloxycarbonyl, etc.), lower alkenyloxy (e.g., vinyloxy, allyloxy, etc.), amino, lower alkylamino (e.g., methylamino, ethylamino, dimethylamino, etc.), acylamino (e.g., acetylamino, benzoylamino, etc.), aralkylamino (e.g., benzylamino, tritylamino), hydroxyamino, imino, hydroxyimino, lower alkylimino (e.g., methylimino, ethylimino, dimethylimino, etc.), lower alkoxyimino (e.g., methoxyimino, ethoxyimino, etc.), acylimino (e.g., acetylimino, benzoylimino, etc.), aryl (e.g., phenyl, etc.), aralkyl (e.g., benzyl, etc.), cyano, acyl (e.g., formyl, acetyl, etc.), and the substituents as described in the following Examples.

Substituents for "cycloalkyl optionally substituted", "cycloalkenyl optionally substituted", "aryl optionally substituted", "heterocyclyl optionally substituted", "phenyl optionally substituted", and "pyridyl optionally substituted" are one or more same or different group selected from, but are not limited to, the group consisting of:

hydroxy, carboxy, halogen (F, Cl, Br, I), halo(lower)alkyl (e.g., $CF_3$, $CH_2CF_3$, $CH_2CCl_3$, etc.), halo(lower)alkoxy (e.g., $CF_3O$), lower alkyl (e.g., methyl, ethyl, isopropyl, tert-butyl, etc.), lower alkenyl (e.g., vinyl), lower alkynyl (e.g., ethynyl), cycloalkyl (e.g., cyclopropyl), cycloalkenyl (e.g., cyclopropenyl), lower alkoxy (e.g., methoxy, ethoxy, propoxy, butoxy, etc.), lower alkenyloxy (e.g., vinyloxy, allyloxy, etc.), lower alkoxycarbonyl (e.g., methoxycarbonyl, ethoxycarbonyl, tert-butoxycarbonyl, etc.), nitro, nitroso, amino, lower alkylamino (e.g., methylamino, ethylamino, dimethylamino, etc.), acylamino (e.g., acetylamino, benzoylamino, etc.), aralkylamino (e.g., benzylamino, tritylamino), hydroxyamino, imino, hydroxyimino, lower alkylimino (e.g., methylimino, ethylimino, dimethylimino, etc.), lower alkoxyimino (e.g., methoxyimino, ethoxyimino, etc.), acylimino (e.g., acetylimino, benzoylimino, etc.), azido, aryl (e.g., phenyl, etc.), aralkyl (e.g., benzyl, etc.), aralkyloxy (e.g., benzyloxy, etc.), cyano, isocyano, isocyanato, thiocyanato, isothiocyanato, mercapto, lower alkylthio (e.g., methylthio, etc.), lower alkylsulfonyl (e.g., methanesulfonyl, ethanesulfonyl), carbamoyl optionally substituted (e.g., carbamoyl, N-methyl-N-methoxycarbamoyl, etc.), lower alkylcarbamoyl optionally substituted (e.g., methylcarbamoyl, ethylcarbamoyl, dimethylcarbamoyl, hydroxy ethylcarbamoyl, trifluoromethylcarbamoyl, trifluoro ethylcarbamoyl, etc.), sulfamoyl, lower alkylsulfamoyl, acyl (e.g., formyl, acetyl, etc.), formyloxy, thioformyl, thiocarboxy, dithiocarboxy, thiocarbamoyl, sulfino, sulfo, hydrazino, azido, ureido, amidino, guanidino, phthalimido, oxo, and the substituents as described below in the following Examples.

The halogen moiety in said "halo(lower)alkyl" and "halo(lower)alkoxy" is as defined above for "halogen".

The alkyl or lower alkyl moiety in said "halo(lower)alkyl", "lower alkylamino", "lower alkylimino", "lower alkylsulfonyl", "lower alkylsulfamoyl", "lower alkylcarbamoyl", "aralkyl" and "aralkylamino" is as defined above for "lower alkyl".

The lower alkoxy moiety of said "halo(lower)alkoxy" and "lower alkoxyimino" is as defined above for "lower alkoxy".

The term "lower alkenyl" includes a straight or branched chain alkenyl containing from 2 to 6 carbons, preferably containing from 2 to 3 carbons, having one or more double bond at any position, and includes vinyl, propenyl, isopropenyl, butenyl, isobutenyl, prenyl, butadienyl, pentenyl, isopentenyl, pentadienyl, hexenyl, isohexenyl and hexadienyl, etc.

The lower alkenyl moiety of "lower alkenyloxy" is as defined above for "lower alkenyl".

The term "lower alkynyl" means a straight or branched chain alkynyl containing from 2 to 6 carbons, preferably containing from 2 to 3 carbons, and includes ethynyl, propynyl, butynyl, pentynyl and hexynyl, etc. They have one or more triple bond at any position, and optionally, have a double bond.

The aryl moiety of "aralkylamino" and "aralkyl" is as defined above for "aryl".

The acyl moiety of "acyl", "acylamino" and "acylimino" is as defined above for "acyl".

The protecting groups for "hydroxy optionally protected" and "hydroxyamino optionally protected" are well known in the art and include for example, a group that forms ether and substituted ether, such as methyl, methoxymethyl, t-butoxymethyl, 1-ethoxyethyl and benzyl, etc.; a group that forms silyl ether, such as trimethylsilyl, triethylsilyl, tert-butyldimethylsilyl and methyldiisopropylsilyl; a group that forms ester, such as formate, acetate and trichloroacetate, etc.; a group that forms carbonate, such as methyl carbonate, 2,2,2-trichloroethyl carbonate, and p-nitrophenyl carbonate, etc.; a group that forms sulfonyl, such as methanesulfonyl, p-toluenesulfonyl, etc.

Preferred embodiments of the compound (I), (I') or (I") of the invention include:
a compound wherein $Z^1$ is hydroxy or hydroxyamino;
a compound wherein $Z^1$ is hydroxy;
a compound wherein $Z^2$ is O or NOH;
a compound wherein $Z^2$ is O;
a compound wherein

[Chemical Formula 20]

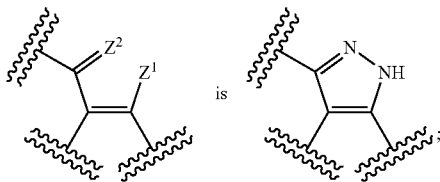

a compound wherein A is aryl or heterocyclyl;
a compound wherein A is phenyl;
a compound wherein $R^2$ is aryl optionally substituted or aromatic heterocyclyl optionally substituted (e.g., thienyl, pyridyl, imidazolyl, pyrimidinyl, isoxazolyl, thiazolyl, isothiazolyl, thiadiazolyl, oxazolyl, pyrazolyl and oxadiazolyl, etc.);
a compound wherein $R^2$ is phenyl optionally substituted;
a compound wherein $R^3$ is alkyl optionally substituted, cycloalkyl optionally substituted, aryl optionally substituted or heterocyclyl optionally substituted;
a compound wherein $R^3$ is alkyl, cycloalkyl, phenyl optionally substituted or aromatic heterocyclyl optionally substituted (e.g., thienyl, pyridyl, imidazolyl, pyrimidinyl, isoxazolyl, thiazolyl, isothiazolyl, thiadiazolyl, oxazolyl, pyrazolyl oxadiazolyl, quinolyl, etc.);
a compound wherein $R^3$ is alkyl, cycloalkyl, phenyl optionally substituted.

Preferred embodiments of the compound (I) of the invention include:
a compound wherein q is 0;
a compound wherein n is 1 or 2; $R^1$ is halogen, lower alkyl optionally substituted, carboxy, lower alkoxycarbonyl optionally substituted, aryl optionally substituted or heterocyclyl optionally substituted;
a compound wherein n is 1 or 2; $R^1$ is lower alkoxycarbonyl optionally substituted, aryl optionally substituted or heterocyclyl optionally substituted;
a compound wherein n is 1 or 2; $R^1$ is lower alkoxycarbonyl optionally substituted, phenyl optionally substituted, non-aromatic heterocyclyl optionally substituted (e.g., dioxolanyl, imidazolynyl, imidazolidinyl, pyrazolinyl, isooxazolinyl, oxazolinyl, thiazolinyl, isothiazolinyl, etc.), aromatic heterocyclyl optionally substituted (e.g., thienyl, pyridyl, imidazolyl, pyrimidinyl, isoxazolyl, thiazolyl, isothiazolyl, thiadiazolyl, oxazolyl, pyrazolyl, oxadiazolyl, etc.).

Preferred embodiments of the compound (I') of the invention include:
a compound wherein B is non-aromatic heterocyclyl optionally substituted (e.g., dioxolanyl, imidazolynyl, imidazolidinyl, pyrazolinyl, isooxazolinyl, oxazolinyl, thiazolinyl, isothiazolinyl, etc.), aromatic heterocyclyl optionally substituted (e.g., thienyl, pyridyl, imidazolyl, pyrimidinyl, isoxazolyl, thiazolyl, isothiazolyl, thiadiazolyl, oxazolyl, pyrazolyl, oxadiazolyl, etc.);
a compound wherein m and p are independently 0 or 1, and $R^{1a}$ and $R^{1b}$ are independently halogen, hydroxy, lower alkyl or lower alkoxy.

Preferred embodiments of the compound (I") of the invention include:
a compound wherein m is 0 or 1, $R^{1a}$ is halogen, hydroxy, lower alkyl or lower alkoxy;
a compound wherein $R^{1c}$ is hydrogen, lower alkyl optionally substituted;
a compound wherein $R^{1d}$ is hydrogen, lower alkyl optionally substituted;
a compound wherein $R^{1c}$ and $R^{1d}$ are independently hydrogen or lower alkyl optionally substituted.

General procedures for the synthesis of the compound of the invention are described below. Starting materials and reaction reagents used in such synthesis are commercially available or can be prepared according to methods well known in the art using compounds commercially available.

The compound (I) of the invention, i.e., the compound of the general formula (I) (compounds represented by other formulae also can be referred to as such manner), may be prepared via the routes as described below.

[Route 1]

[Chemical Formula 21]

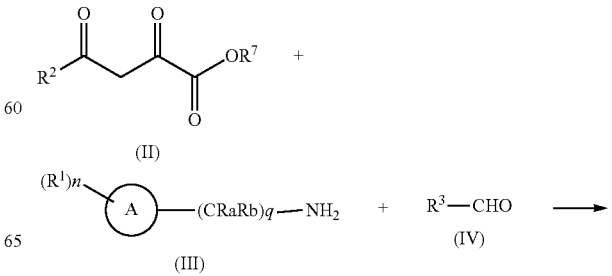

-continued

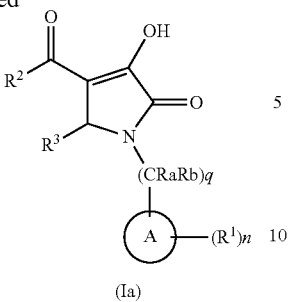
(Ia)

wherein, $R^7$ is lower alkyl; all other variables are as defined above.

As shown, the compound of the invention of the general formula (Ia) may be prepared by the reaction of compound (II), compound (III) and compound (IV) without solvent or in an appropriate solvent, in the presence or absence of acid.

In this reaction, compound (III) and compound (IV) may be used in an amount of one equivalent or more, preferably 1 to 3 equivalent, in respect of compound (II).

Acid that may be used includes acetic acid, para-toluenesulfonic acid, hydrochloric acid, etc.

Solvent that may be used includes aromatic hydrocarbons (e.g., toluene, benzene, xylene, etc.), saturated hydrocarbons (e.g., cyclohexane, hexanes, etc.), ethers (e.g., tetrahydrofuran, diethyl ether, dioxane, etc.) and mixture thereof.

The temperature for such reaction may be −10° C. to 150° C., preferably 20° C. to 100° C. Reaction time depends on the compound, such reaction may be conducted for 10 minutes to 80 hours.

Optionally, desired compound (Ia) thus obtained may be purified according to conventional methods (e.g., column chromatography, recrystallization, etc.).

[Route 2]

[Chemical Formula 22]

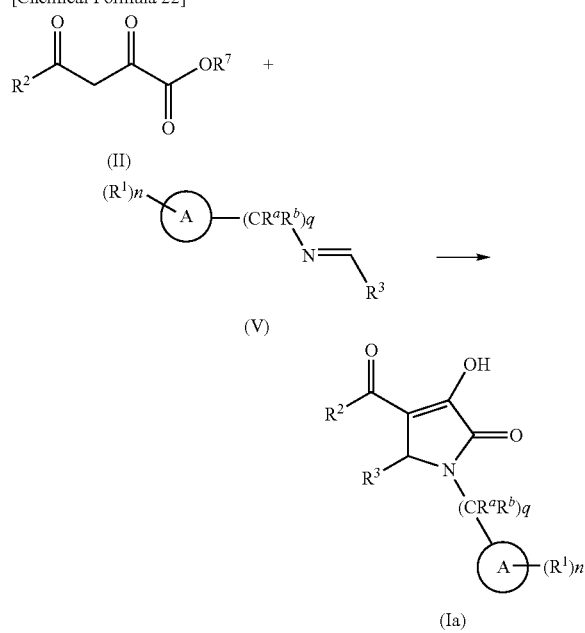

wherein all variables are as defined above.

As shown, the compound of the invention represented by the general formula (Ia) may be prepared by the reaction of compound (II) and compound (V) without solvent or in an appropriate solvent, in the presence or absence of acid.

In this reaction, compound (V) can be used in an amount of one equivalent or more, preferably 1 to 3 equivalent, in respect of compound (II).

Acid that may be used includes acetic acid, para-toluenesulfonic acid, hydrochloric acid, etc.

Solvent that may be used includes aromatic hydrocarbons (e.g., toluene, benzene, xylene, etc.), saturated hydrocarbons (e.g., cyclohexane, hexanes, etc.), ethers (e.g., tetrahydrofuran, diethyl ether, dioxane, etc.) and mixture thereof.

The temperature for such reaction may be −10° C. to 150° C., preferably 20° C. to 100° C. Although reaction time depends on the compound, such reaction may be conducted for 10 minutes to 80 hours.

Optionally, desired compound (Ia) thus obtained may be purified according to conventional methods (e.g., column chromatography, recrystallization, etc.).

[Route 3]

[Chemical Formula 23]

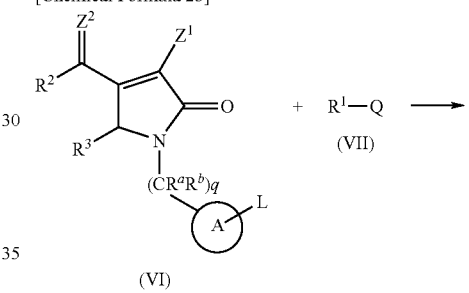

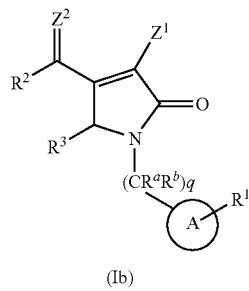

(Ib)

wherein, one of L and Q is dihydroxyborane, di(lower)alkylborane or di(lower)alkoxyborane and the other is halogen or —OSO$_2$(C$_s$F$_{2s+1}$) wherein s is an integer 1 to 4, and all other variants are as defined above.

As shown, the compound of the invention represented by the general formula (Ib) may be prepared by Suzuki coupling of compound (VI) with compound (VII) in an appropriate solvent, in the presence of a palladium catalyst and a base.

In this reaction, compound (VII) can be used in an amount of one equivalent or more, preferably 1 to 3 equivalent, in respect of compound (VI).

Base that may be used includes metal hydroxide (e.g., sodium hydroxide, potassium hydroxide, etc.), metal hydride (e.g., sodium hydride, lithium hydride, etc.), metal carbonate (e.g., sodium carbonate, potassium carbonate, cesium carbonate, etc.), etc. Such base can be used in an amount of one equivalent or more, preferably 1 to 5 equivalent, in respect of compound (VI).

Palladium catalyst that can be used includes tris(dibenzylideneacetone)-dipalladium(0), palladium acetate (II), dichlorobis(triphenylphosphine)-palladium (II) or tetrakis(triphenylphosphine)palladium(II), etc., and may be used in an amount of 0.001 equivalent or more, preferably 0.01 to 1 equivalent, in respect of compound (VI).

Solvent that may be used includes aromatic hydrocarbons (e.g., toluene, benzene, xylene, etc.), saturated hydrocarbons (e.g., cyclohexane, hexanes, etc.), ethers (e.g., tetrahydrofuran, diethyl ether, dioxane, dimethoxyethane, etc.), N,N-dimethylformamide, water and mixture thereof, etc.

The temperature for such reaction may be $-10°$ C. to $180°$ C., preferably $20°$ C. to $120°$ C., optionally under microwave radiation. Although reaction time depends on the compound, such reaction may be conducted for 10 minute to 80 hours.

Optionally, desired compound (Ib) thus obtained may be purified according to conventional methods (e.g., column chromatography, recrystallization, etc.).

[Route 4]

[Chemical Formula 24]

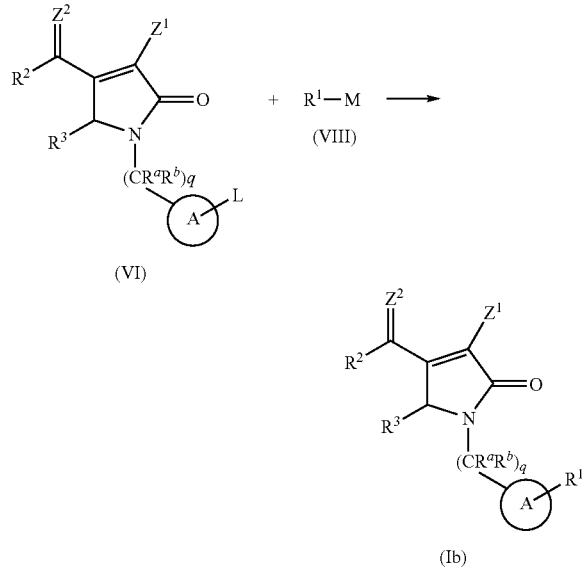

(Ib)

wherein, one of L and M is trialkyltin (e.g., $-SnBu_3$, etc.) and the other is halogen or $-OSO_2(C_sF_{2s+1})$ wherein s is an integer 1 to 4 and all other variants are as defined above.

As shown, the compound of the invention represented by the general formula (Ib) may be prepared by Stille coupling of compound (VI) with compound (VIII) in an appropriate solvent in the presence of a catalyst.

In this reaction, compound (VIII) can be used in an amount of one equivalent or more, preferably 1 to 3 equivalent, in respect of compound (VI).

Catalyst can be used include tris(dibenzylideneacetone)dipalladium(0), palladium acetate (II), dichlorobis(triphenylphosphine)palladium(II) or tetrakis(triphenylphosphine) palladium(II), etc., and may be used in an amount of 0.001 equivalent or more, preferably 0.01 to 1 equivalent, in respect of compound (VI). Optionally, phosphine ligand such as tri-tert-butylphosphine, 2-(di-tert-butylphosphino)biphenyl, 2-(dicyclohexyl-phosphino)biphenyl, triphenylphosphine, tris(2-furyl)phosphine, etc. may be added in twice molar amounts in respect of the catalyst.

Solvent that may be used includes aromatic hydrocarbons (e.g., toluene, benzene, xylene, etc.), saturated hydrocarbons (e.g., cyclohexane, hexanes, etc.), ethers (e.g., tetrahydrofuran, diethyl ether, dioxane, dimethoxyethane, etc.), N,N-dimethylformamide and mixture thereof, etc.

The temperature for such reaction may be $-10°$ C. to $180°$ C., preferably $20°$ C. to $120°$ C., optionally under microwave radiation. Although reaction time depends on the compound, such reaction may be conducted for 10 minutes to 80 hours.

Optionally, desired compound (Ib) thus obtained may be purified according to conventional methods (e.g., column chromatography, recrystallization, etc.).

[Route 5]

[Chemical Formula 25]

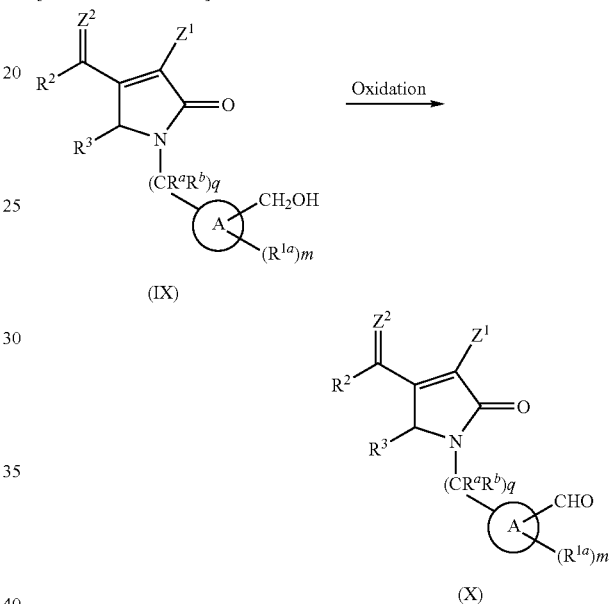

wherein all other variants are as defined above.

As shown, the compound of the invention represented by the general formula (X) may be prepared by the reaction of the compound (IX) in an appropriate solvent, in the presence of an oxidizing agent.

Oxidizing agent that may be used includes manganese dioxide, 2-iodoxybenzoic acid, etc., and may be used in an amount of one equivalent or more, preferably 1 to 1.5 equivalent, in respect of compound (IX).

Solvent that may be used includes aromatic hydrocarbons (e.g., toluene, benzene, xylene, etc.), saturated hydrocarbons (e.g., cyclohexane, hexanes, etc.), halogenated hydrocarbons (e.g., dichloromethane, 1,2-dichloroethane, etc.), ethers (e.g., tetrahydrofuran, dioxane, etc.), ketones (e.g., acetone, methylethyl ketone, etc.), nitriles (e.g., acetonitrile, etc.) and mixture thereof, etc.

The temperature for such reaction may be $-10°$ C. to $150°$ C., preferably $20°$ C. to $100°$ C. Although reaction time depends on the compound, such reaction may be conducted for 10 minutes to 80 hours.

The compound (IX) obtained may be used in the next step as a crude product or after purification according to conventional methods (e.g., column chromatography, recrystallization, etc.).

[Route 5 (continued)]

[Chemical Formula 26]

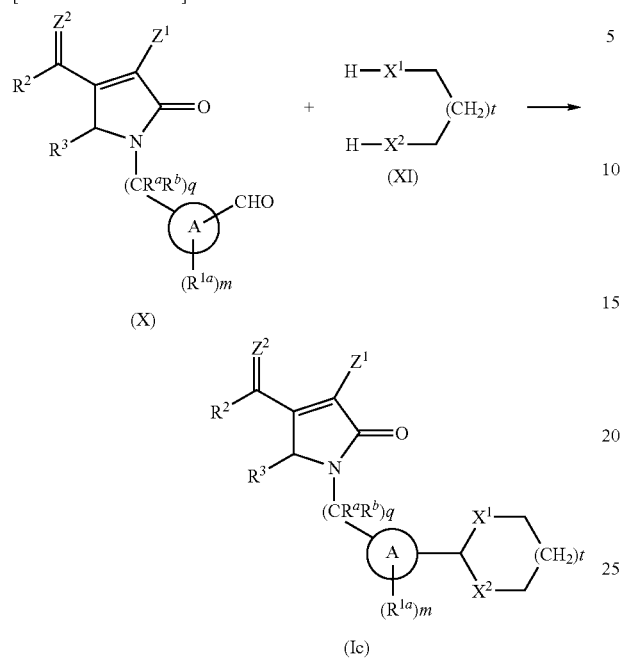

wherein, t is an integer 0 to 3; $X^1$ and $X^2$ are independently $NR^8$, O or S; $R^8$ is hydrogen or lower alkyl; all other variables are as defined above.

As shown, the compound of the invention represented by the general formula (Ic) may be prepared by the reaction of compound (X) and compound (XI) without solvent or in an appropriate solvent, in the presence or absence of an acid.

In this reaction, compound (XI) can be used in an amount of one equivalent or more, preferably 1 to 3 equivalent, in respect of compound (X).

Acid that may be used includes p-toluenesulfonic acid, sulfuric acid, p-toluenesulfonic acid pyridinium salt, etc.

Solvent that may be used includes aromatic hydrocarbons (e.g., toluene, benzene, xylene, etc.), saturated hydrocarbons (e.g., cyclohexane, hexanes, etc.), and mixture thereof.

The temperature for such reaction may be −10° C. to 170° C., preferably 20° C. to 150° C. Reaction time depends on the compound, such reaction may be conducted for 10 minutes to 80 hours.

Optionally, desired compound (Ic) thus obtained may be purified according to conventional methods (e.g., column chromatography, recrystallization, etc.).

[Route 6]

[Chemical Formula 27]

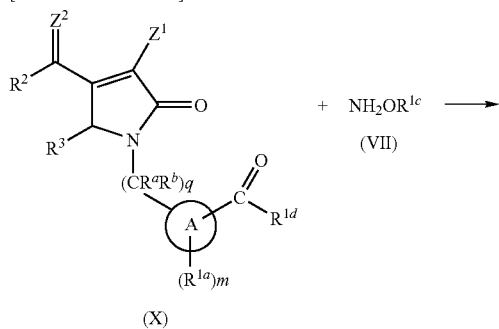

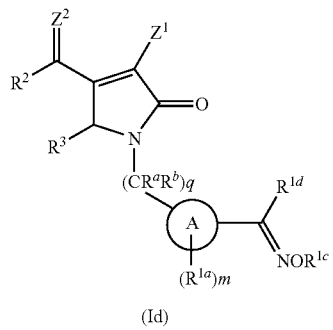

wherein all variables are as defined above.

As shown, the compound of the invention represented by the general formula (Id) may be prepared by the reaction of compound (X) and compound (XII) or a salt thereof in an appropriate solvent. The compound (XII) or a salt thereof can be used in an amount of 1 to 4 equivalent, preferably 1 to 2.5 equivalent, in respect of compound (X).

Salts of compound (XII) include mineral acid salts such as hydrochloride, sulfate, etc. Such salt is neutralized with a base when it is used in the reaction.

Base that may be used includes sodium acetate, amines (pyridinium, etc.), etc., and can be used in an amount of 1 to 3 equivalent, preferably 1 to 2 equivalent, in respect of the salt of compound (XI).

Solvent that may be used includes aromatic hydrocarbons (e.g., toluene, benzene, xylene, etc.), halogenated hydrocarbons (e.g., chloroform, 1,2-dichloroethane, etc.), ethers (e.g., tetrahydrofuran, dioxane, etc.), alcohols (e.g., methanol, enthanol, n-propanol, iso-propanol, etc.), water and mixture thereof, etc.

Reaction temperature is 0° C. to 150° C., preferably 20° C. to 120° C.

Reaction time is generally from about 10 minutes to 24 hours.

Optionally, desired compound (Id) thus obtained may be purified according to conventional methods (e.g., column chromatography, recrystallization, etc.).

[Chemical Formula 28]

[Route 7]

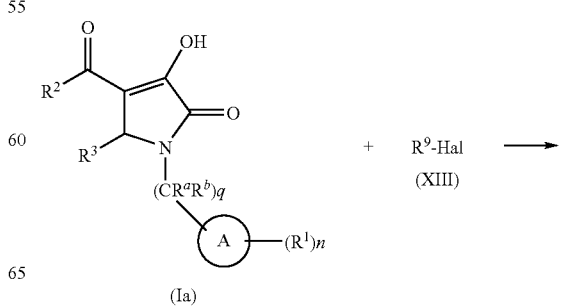

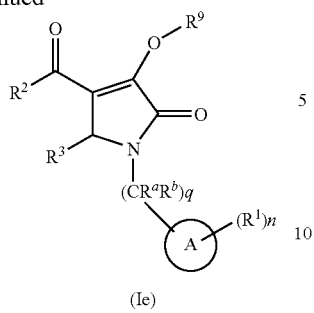

(Ie)

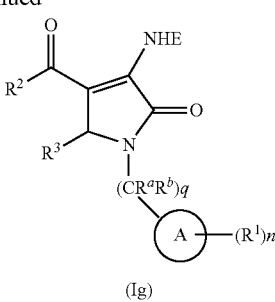

(Ig)

wherein, Hal is halogen; $R^9$ is a hydroxy protecting group; all other variables are as defined above.

As shown, the compound of the invention represented by the general formula (Ie) may be prepared by the reaction of the compound (Ia) and the compound (XIII) in an appropriate solvent in the presence of a base. The compound (XII) can be used in an amount of 1 to 4 equivalent, preferably 1 to 2.5 equivalent, in respect of compound (Ia).

Base that may be used includes amines, etc. (triethylamine, pyridinium, etc.) and can be used in an amount of 1 to 3 equivalent, preferably 1 to 2 equivalent, in respect of the salt of compound (Ia).

Solvent that may be used includes aromatic hydrocarbons (e.g., toluene, benzene, xylene, etc.), halogenated hydrocarbons (e.g., chloroform, 1,2-dichloroethane, etc.), ethers (e.g., tetrahydrofuran, dioxane, etc.), N,N-dimethylformamide, dimethylsulfoxide and mixture thereof, etc.

Reaction temperature is −20° C. to 150° C., preferably 0° C. to 120° C.

Reaction time is generally from about 10 minutes to 24 hours.

Optionally, desired compound (Ie) thus obtained may be purified according to conventional methods (e.g., column chromatography, recrystallization, etc.).

wherein the variables are as defined above.

As shown, the compound of the invention represented by the general formula (If) or (Ig) may be prepared by the reaction of the compound (Ia) with an amine or a salt thereof in an appropriate solvent. The amine and salt thereof can be used in an amount of 1 to 4 equivalent, preferably 1 to 2.5 equivalent, in respect of compound (Ia).

Salts of the hydroxylamine include mineral acid salts such as hydrochloride, sulfate, etc. Such salt is neutralized with a base when it is used in the reaction.

Base that may be used includes sodium acetate, amines, etc. (pyridinium, etc.) and can be used in an amount of 1 to 3 equivalent, preferably 1 to 2 equivalent, in respect of salt of the amine.

Solvent that may be used includes hydrocarbons (e.g., benzene, toluene, xylene, etc.), halogenated hydrocarbons (e.g., chloroform, 1,2-dichloroethane, etc.), ethers (e.g., tetrahydrofuran, dioxane, etc.), alcohols (e.g., methanol, enthanol, n-propanol, iso-propanol, etc.), water and mixture thereof, etc.

Reaction temperature is 0° C. to 150° C., preferably 20° C. to 120° C.

Reaction time is generally 15 minutes to 24 hours.

Optionally, desired compound (If) or (Ig) thus obtained may be purified according to conventional methods (e.g., column chromatography, recrystallization, etc.).

[Route 8]

[Chemical Formula 29]

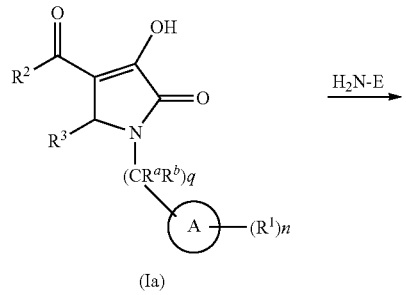

[Route 9]

[Chemical Formula 30]

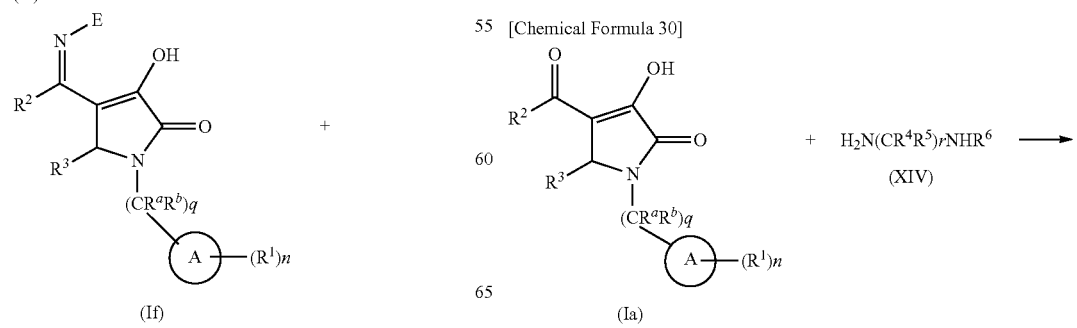

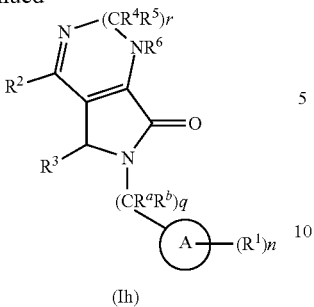

(Ih)

wherein all variables are as defined above.

As shown, the compound of the invention represented by the general formula (Ih) may be prepared by the reaction of compound (Ia) and compound (XIV) in an appropriate solvent. The compound (XIV) can be used in an amount of 1 to 4 equivalent, preferably 1 to 2.5 equivalent, in respect of compound (Ia).

Solvent that may be used includes acetic acid, hydrocarbons (e.g., benzene, toluene, xylene, etc.), ethers (e.g., tetrahydrofuran, dioxane, etc.), alcohols (e.g., methanol, enthanol, n-propanol, iso-propanol, etc.) and mixture thereof, etc.

Reaction temperature is 0° C. to 150° C., preferably 20° C. to 130° C.

Reaction time is generally from about 10 minutes to 24 hours.

Optionally, desired compound (Ih) thus obtained may be purified according to conventional methods (e.g., column chromatography, recrystallization, etc.).

The compounds of the invention can form salts with pharmaceutically acceptable acids or bases, such as salts with an inorganic acid such as hydrochloric acid, sulfuric acid, nitric acid, phosphoric acid, hydrofluoric acid, hydrobromic acid, etc.; salts with an organic acid such as formic acid, acetic acid, oxalic acid, succinic acid, maleic acid, tartaric acid, lactic acid, citric acid, fumaric acid, etc.; salts with an organic base such as ammonium, trimethyl ammonium, triethyl ammonium, etc.; salts with an alkali metal such as sodium, potassium, etc.; salts with an alkali earth metal such as calcium, magnesium, etc.

Also, the compounds of the invention and pharmaceutically acceptable salts thereof as described above can be prepared in a form of solvate (preferably hydrate) thereof. Such solvate includes solvates with an organic solvent and/or water. Any number of solvent molecule can be coordinated to form such solvate.

The compound (I) of the invention is not limited to certain isomer, and thus, all possible isomers and racemates are encompassed by the invention. Also, the invention is intended to encompass tautomers as shown below.

[Chemical Formula 31]

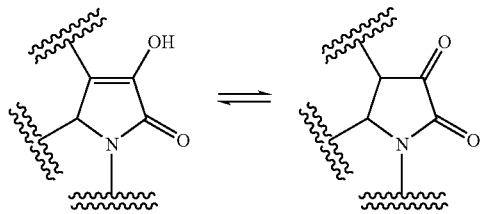

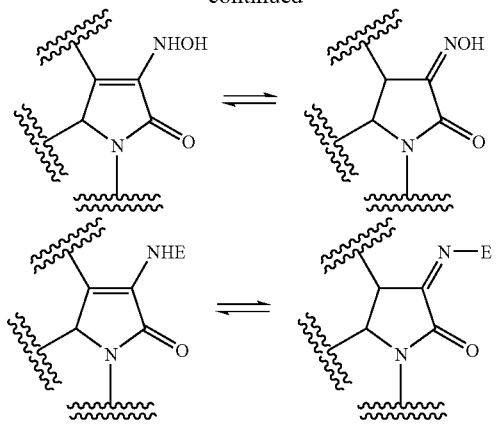

The compound of the invention may be isolated enantiomer having certain configuration or a mixture thereof. For example, the compound of the invention can be isolated enantiomer having a certain configuration at position 5 of the pyrrolidinone ring or a mixture of such enantiomers. One skilled in the art can readily isolate an enantiomer having such certain configuration using conventional techniques such as recrystallization, enzyme reaction, chromatography, etc.

The compound of the invention represented above by the general formula (I) has an antagonizing action on $P2X_3$ and/or $P2X_{2/3}$ receptor, and therefore, is useful as a therapeutic agent for diseases associated with a $P2X_3$ and/or $P2X_{2/3}$ receptor. Since $P2X_3$ and/or $P2X_{2/3}$ receptor is believed to associate with pain and diseases in urinary system (Nature 407, 26, 1011-1015 (2000), Nature, Vol. 407, No. 26, 1015-1017 (2000), Non-Patent Document 1, Non-Patent Document 2, etc.), the compound of the invention is useful in the treatment of, alleviation of symptoms or prevention of diseases, such as for example, pain associated with rheumatoid arthritis, pain associated with osteoarthritis, headache, migraine, orofacial pain, toothache, glossagra, pain associated with temporomandibular arthrosis, trigeminal neuralgia, shoulder pain, pain associated with hernia of intervertebral disk, pain associated with cervical spondylosis deformans, pain associated with spinal canal stenosis, pain associated with thoracic outlet syndrome, pain associated with traumatic brachial plexus injury syndrome, pain associated with shoulder-hand syndrome, pain associated with whiplash injury, chest pain, abdominal pain, colic pain, pain associated with cholelithiasis, pain associated with pancreatitis, pain associated with urinary calculosis, pain associated with irritable bowel syndrome, lumbar backache, sciatica, pain associated with bone fracture, pain associated with osteoporosis, joint pain, pain associated with gout, pain associated with cauda equina syndrome, pain associated with ankylosing spondylitis, sore muscle, pain associated with painful spasm, pain associated with myofascial pain syndrome, pain associated with fibromyalgia syndrome, pain associated with arteriosclerosis obliterans, pain associated with Buerger's disease, pain associated with Raynaud's phenomenon, pain associated with zoster, causalgic pain, pain associated with entrapment neuropathy, pain associated with carpal canal syndrome, pain associated with diabetes, pain associated with Guillain-Barre syndrome, pain associated with Hansen's disease, pain associated with drug therapy, pain associated with radiation therapy, pain associated with cord injury, pain associated with syringomyelia, pain associated with stroke, thalamic pain, pain associated with deafferentation, sympathetically-maintained pain, pain associated with ABC syndrome, pain associated with multiple sclerosis, pain associated with skin disease, cancer pain, postoperative pain, pain associated with injury, pain associated with gangrene, pain associated with somatoform disorder, pain associated with somatization disorder, pain associated with depression, pain associated with Parkinson's disease, knee joint pain, pain associated with arthritis, neuropathic pain such as menstrual pain, intermenstrual pain, labor pain, etc., inflammatory pain, nociceptive pain, psychogenic pain, and overactive bladder, incontinence, pollakiuria, urinary urgency, cystatrophia, prostatic hypertrophy, prostatitis, prostate pain, detrusor hyperreflesxia, dysuria, nervous pollakiuria, chronic prostatitis, chronic cystitis, etc.

The compound of the invention can be a drug with reduced side-effect such as effect on motor function because it has a high affinity for ATP receptor, especially $P2X_3$ receptor, and also has high subtype selectivity and high selectivity for other receptors. Also, the compound of the invention is advantageous because of its high stability and high oral absorptivity, good bioavailability, low clearance, long half-life, prolonged duration of action, and/or low activity of hepatic enzyme inhibition, etc.

In another embodiment, the invention provides a pharmaceutical composition comprising an effective amount of the compound of the invention, in combination with a pharmaceutically acceptable carrier.

For use of the compound of the invention as a medicament, a pharmaceutical composition can be prepared according to conventional methods, using pharmaceutically acceptable carriers well known in the art, such as excipients, binders, disintegrants, lubricants, colourants, flavors, surfactants, etc.

For the pharmaceutical composition of the invention to be administered in the treatment of mammals including human, an appropriate unit dosage form may be selected depending on the purpose of the treatment and the route of administration. Specifically, such unit dosage form includes oral formulations such as tablet, coated tablet, powder, granule, capsule, liquid, pill, suspension, emulsion, etc., and parenteral formulations such as injectable solution, suppository, ointment, patch, aerosol, etc. Such unit dosage form can be formulated according to methods well known in the art.

The amount of the compound in a formulation can be varied depending on its dosage form, route for administration, dosing regimen, etc.

Means for administration of the pharmaceutical composition may be selected depending on dosage form, age, sex, body weight, severity of the disease, and other factors, etc., and route for administration can be selected from various routes such as oral, subcutaneous, transdermal, rectal, intranasal, buccal, etc.

Dose of the compound of the invention in a pharmaceutical composition of the invention can be determined depending on the choice of route for administration, age, sex, body weight, severity of the disease, the compound to be administered, and other factors, etc., and can be generally from 0.05 to 1000 mg/kg/day, preferably from 0.1 to 10 mg/kg/day, for oral administration to adults. For parenteral administration, dose can be varied widely depending on its route but generally from 0.005 to 100 mg/kg/day, preferably from 0.01 to 1 mg/kg/day. Such pharmaceutical composition of the invention may be administered once a day or in several times at a divided dosage in a day.

Preferred embodiments of the compound of the invention are represented by the formula (a) to (f):

[Chemical Formula 32]

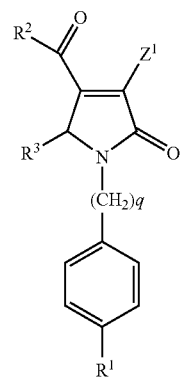

(a)

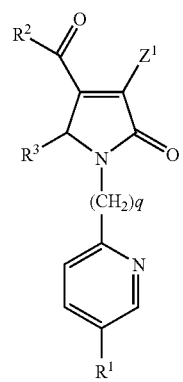

(b)

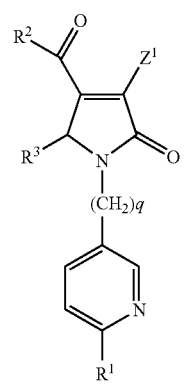

(c)

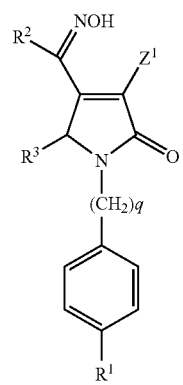

(d)

(e)

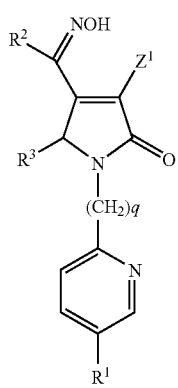

(f)

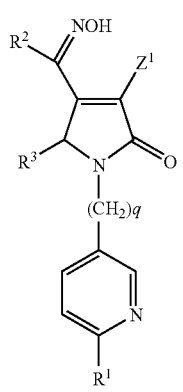

(q = 0 or 1)

TABLE 1

| | $Z^1$ |
|---|---|
| ZA | OH |
| ZB | OAc |
| ZC | NHOH |

TABLE 2

| | $R^1$ |
|---|---|
| R1A | COOEt |
| R1B | $CF_3$ |
| R1C | $OCF_3$ |
| R1D | $SCF_3$ |
| R1E | Ac |
| R1F | Br |
| R1G | 2- or 5-oxazolyl |
| R1H | isoxazolyl-3-yl |
| R1I | 3-Me-isoxazolyl-5-yl |
| R1J | 5-Me-isoxazolyl-3-yl |
| R1K | 1,2,4-oxadiazol-3-yl |
| R1L | 1,3,4-oxadiazolyl-2-yl |
| R1M | 5-Me-1,2,4-oxadiazol-3-yl |
| R1N | 3-Me-1,2,4-oxadiazol-5-yl |
| R1O | C(Me)=NOMe |
| R1P | CH=NOMe |
| R1Q | 2-oxazolinyl |
| R1R | 2-thiazolinyl |
| R1S | 1,3-dioxolan-2-yl |

TABLE 3

| | $R^2$ |
|---|---|
| R2A | iPr |
| R2B | nBu |
| R2C | tBu |
| R2D | cBu |
| R2E | cHex |
| R2F | Ph |
| R2G | 4-Cl or F-Ph |
| R2H | 4-$NO_2$-Ph |
| R2I | 4-$CF_3$-Ph |
| R2J | 4-$Me_2$N-Ph |
| R2K | 2- or 3-thyenyl |
| R2L | 3-pyridyl |
| R2M | 6-MeO-3-pyridyl |
| R2N | 2- or 3- or 4-MeO-Ph |

TABLE 4

| | $R^3$ |
|---|---|
| R3A | iPr |
| R3B | $Et_2$CH |
| R3C | $Pr_2$CH |
| R3D | $nBu_2$CH |
| R3E | Pr(Me)CH |
| R3F | Ph(Me)CH |
| R3G | cPent |
| R3H | cHex |
| R3I | Ph |
| R3J | 2-Cl-Ph |
| R3K | 2- or 3- or 4-Me-Ph |
| R3L | 2- or 3- or 4-MeO-Ph |
| R3M | 2- or 3- or 4-F-Ph |
| R3N | 3- or 4-Cl-Ph |
| R3O | 2-pyridyl |
| R3P | 4-piperidinyl |
| R3Q | 1-Ac-4-piperidinyl |
| R3R | tetrahydropyran-4-yl | wherein
Ac is acetyl, Me is methyl, Et is ethyl, Pr is propyl, iPr is isopropyl, nBu is n-butyl, tBu is t-butyl, cBu is cyclobutyl, cPent is cyclopentyl, cHex is cyclohexyl, Ph is phenyl; and the combination of $Z^1$, $R^1$, $R^2$ and $R^3$, i.e., ($Z^1$, $R^1$, $R^2$, $R^3$), is any one of the following combinations:
(Z1,R1,R2,R3)=(ZA,R1A,R2A,R3A), (ZA,R1A,R2A,R3B), (ZA,R1A,R2A,R3C),
(ZA,R1A,R2A,R3D), (ZA,R1A,R2A,R3E), (ZA,R1A,R2A,R3F),
(ZA,R1A,R2A,R3H), (ZA,R1A,R2A,R3I),
(ZA,R1A,R2A,R3J), (ZA,R1A,R2A,R3K), (ZA,R1A,R2A,R3L),
(ZA,R1A,R2A,R3M), (ZA,R1A,R2A,R3N), (ZA,R1A,R2A,R3O),
(ZA,R1A,R2A,R3P), (ZA,R1A,R2A,R3O), (ZA,R1A,R2A,R3R),
(ZA,R1A,R2B,R3A), (ZA,R1A,R2B,R3B), (ZA,R1A,R2B,R3C),
(ZA,R1A,R2B,R3E), (ZA,R1A,R2B,R3F),
(ZA,R1A,R2B,R3G), (ZA,R1A,R2B,R3H), (ZA,R1A,R2B,R3I),
(ZA,R1A,R2B,R3J), (ZA,R1A,R2B,R3K), (ZA,R1A,R2B,R3L),
(ZA,R1A,R2B,R3M), (ZA,R1A,R2B,R3N), (ZA,R1A,R2B,R3O),
(ZA,R1A,R2B,R3P), (ZA,R1A,R2B,R3O), (ZA,R1A,R2B,R3R),
(ZA,R1A,R2C,R3B), (ZA,R1A,R2C,R3C),
(ZA,R1A,R2C,R3D), (ZA,R1A,R2C,R3E), (ZA,R1A,R2C,R3F), (ZA,R1A,R2C,R3G), (ZA,R1A,R2C,R3H), (ZA,R1A,R2C,R3I),
(ZA,R1A,R2C,R3J), (ZA,R1A,R2C,R3K), (ZA,R1A,R2C,R3L),
(ZA,R1A,R2C,R3M), (ZA,R1A,R2C,R3N), (ZA,R1A,R2C,R3O),
(ZA,R1A,R2C,R3P), (ZA,R1A,R2C,R3Q), (ZA,R1A,R2C,R3R),
(ZA,R1A,R2D,R3A), (ZA,R1A,R2D,R3B), (ZA,R1A,R2D,R3C),
(ZA,R1A,R2D,R3D), (ZA,R1A,R2D,R3E), (ZA,R1A,R2D,R3F),
(ZA,R1A,R2D,R3G), (ZA,R1A,R2D,R3H), (ZA,R1A,R2D,R3I),
(ZA,R1A,R2D,R3J), (ZA,R1A,R2D,R3K), (ZA,R1A,R2D,R3L),
(ZA,R1A,R2D,R3M), (ZA,R1A,R2D,R3N), (ZA,R1A,R2D,R3O),
(ZA,R1A,R2D,R3P), (ZA,R1A,R2D,R3Q), (ZA,R1A,R2D,R3R),
(ZA,R1A,R2E,R3A), (ZA,R1A,R2E,R3B), (ZA,R1A,R2E,R3C),
(ZA,R1A,R2E,R3D), (ZA,R1A,R2E,R3E), (ZA,R1A,R2E,R3F),
(ZA,R1A,R2E,R3G), (ZA,R1A,R2E,R3H), (ZA,R1A,R2E,R3I),
(ZA,R1A,R2E,R3J), (ZA,R1A,R2E,R3K), (ZA,R1A,R2E,R3L),
(ZA,R1A,R2E,R3M), (ZA,R1A,R2E,R3N), (ZA,R1A,R2E,R3O),
(ZA,R1A,R2E,R3P), (ZA,R1A,R2E,R3Q), (ZA,R1A,R2E,R3R),
(ZA,R1A,R2F,R3A), (ZA,R1A,R2F,R3B), (ZA,R1A,R2F,R3C),
(ZA,R1A,R2F,R3D), (ZA,R1A,R2F,R3E), (ZA,R1A,R2F,R3F),
(ZA,R1A,R2F,R3G), (ZA,R1A,R2F,R3H), (ZA,R1A,R2F,R3I),
(ZA,R1A,R2F,R3J), (ZA,R1A,R2F,R3K), (ZA,R1A,R2F,R3L),
(ZA,R1A,R2F,R3M), (ZA,R1A,R2F,R3N), (ZA,R1A,R2F,R3O),
(ZA,R1A,R2F,R3P), (ZA,R1A,R2F,R3Q), (ZA,R1A,R2F,R3R),
(ZA,R1A,R2G,R3A), (ZA,R1A,R2G,R3B), (ZA,R1A,R2G,R3C),
(ZA,R1A,R2G,R3D), (ZA,R1A,R2G,R3E), (ZA,R1A,R2G,R3F),
(ZA,R1A,R2G,R3G), (ZA,R1A,R2G,R3H), (ZA,R1A,R2G,R3I),
(ZA,R1A,R2G,R3J), (ZA,R1A,R2G,R3K), (ZA,R1A,R2G,R3L),
(ZA,R1A,R2G,R3M), (ZA,R1A,R2G,R3N), (ZA,R1A,R2G,R3O),
(ZA,R1A,R2G,R3P), (ZA,R1A,R2G,R3Q), (ZA,R1A,R2G,R3R),
(ZA,R1A,R2H,R3A), (ZA,R1A,R2H,R3B), (ZA,R1A,R2H,R3C),
(ZA,R1A,R2H,R3D), (ZA,R1A,R2H,R3E), (ZA,R1A,R2H,R3F),
(ZA,R1A,R2H,R3G), (ZA,R1A,R2H,R3H), (ZA,R1A,R2H,R3I),
(ZA,R1A,R2H,R3J), (ZA,R1A,R2H,R3K), (ZA,R1A,R2H,R3L),
(ZA,R1A,R2H,R3M), (ZA,R1A,R2H,R3N), (ZA,R1A,R2H,R3O),
(ZA,R1A,R2H,R3P), (ZA,R1A,R2H,R3Q), (ZA,R1A,R2H,R3R),
(ZA,R1A,R2I,R3A), (ZA,R1A,R2I,R3B), (ZA,R1A,R2I,R3C), (ZA,R1A,R2I,R3D),
(ZA,R1A,R2I,R3E), (ZA,R1A,R2I,R3F), (ZA,R1A,R2I,R3G), (ZA,R1A,R2I,R3H),
(ZA,R1A,R2I,R3I), (ZA,R1A,R2I,R3J), (ZA,R1A,R2I,R3K), (ZA,R1A,R2I,R3L),
(ZA,R1A,R2I,R3M), (ZA,R1A,R2I,R3N), (ZA,R1A,R2I,R3O), (ZA,R1A,R2I,R3P),
(ZA,R1A,R2I,R3Q), (ZA,R1A,R2I,R3R), (ZA,R1A,R2J,R3A),
(ZA,R1A,R2J,R3B), (ZA,R1A,R2J,R3C), (ZA,R1A,R2J,R3D),
(ZA,R1A,R2J,R3E), (ZA,R1A,R2J,R3F), (ZA,R1A,R2J,R3G),
(ZA,R1A,R2J,R3H), (ZA,R1A,R2J,R3I), (ZA,R1A,R2J,R3J),
(ZA,R1A,R2J,R3K), (ZA,R1A,R2J,R3L), (ZA,R1A,R2J,R3M),
(ZA,R1A,R2J,R3N), (ZA,R1A,R2J,R3O), (ZA,R1A,R2J,R3P),
(ZA,R1A,R2J,R3Q), (ZA,R1A,R2J,R3R), (ZA,R1A,R2K,R3A),
(ZA,R1A,R2K,R3B), (ZA,R1A,R2K,R3C), (ZA,R1A,R2K,R3D),
(ZA,R1A,R2K,R3E), (ZA,R1A,R2K,R3F), (ZA,R1A,R2K,R3G),
(ZA,R1A,R2K,R3H), (ZA,R1A,R2K,R3I), (ZA,R1A,R2K,R3J),
(ZA,R1A,R2K,R3K), (ZA,R1A,R2K,R3L), (ZA,R1A,R2K,R3M),
(ZA,R1A,R2K,R3N), (ZA,R1A,R2K,R3O), (ZA,R1A,R2K,R3P),
(ZA,R1A,R2K,R3Q), (ZA,R1A,R2K,R3R), (ZA,R1A,R2L,R3A),
(ZA,R1A,R2L,R3B), (ZA,R1A,R2L,R3C), (ZA,R1A,R2L,R3D),
(ZA,R1A,R2L,R3E), (ZA,R1A,R2L,R3F), (ZA,R1A,R2L,R3G),
(ZA,R1A,R2L,R3H), (ZA,R1A,R2L,R3I), (ZA,R1A,R2L,R3J),
(ZA,R1A,R2L,R3K), (ZA,R1A,R2L,R3L), (ZA,R1A,R2L,R3M),
(ZA,R1A,R2L,R3N), (ZA,R1A,R2L,R3O), (ZA,R1A,R2L,R3P),
(ZA,R1A,R2L,R3Q), (ZA,R1A,R2L,R3R), (ZA,R1A,R2M,R3A),
(ZA,R1A,R2M,R3B), (ZA,R1A,R2M,R3C), (ZA,R1A,R2M,R3D),
(ZA,R1A,R2M,R3E), (ZA,R1A,R2M,R3F), (ZA,R1A,R2M,R3G),
(ZA,R1A,R2M,R3H), (ZA,R1A,R2M,R3I), (ZA,R1A,R2M,R3J),
(ZA,R1A,R2M,R3K), (ZA,R1A,R2M,R3L), (ZA,R1A,R2M,R3M),
(ZA,R1A,R2M,R3N), (ZA,R1A,R2M,R3O), (ZA,R1A,R2M,R3P),
(ZA,R1A,R2M,R3Q), (ZA,R1A,R2M,R3R), (ZA,R1A,R2N,R3A),
(ZA,R1A,R2N,R3B), (ZA,R1A,R2N,R3C), (ZA,R1A,R2N,R3D),
(ZA,R1A,R2N,R3E), (ZA,R1A,R2N,R3F), (ZA,R1A,R2N,R3G),
(ZA,R1A,R2N,R3H), (ZA,R1A,R2N,R3I), (ZA,R1A,R2N,R3J), (ZA,R1A,R2N,R3K), (ZA,R1A,R2N,R3L), (ZA,R1A,R2N,R3M),
(ZA,R1A,R2N,R3N), (ZA,R1A,R2N,R3O), (ZA,R1A,R2N,R3P),
(ZA,R1A,R2N,R3Q), (ZA,R1A,R2N,R3R), (ZA,R1B,R2A,R3A),
(ZA,R1B,R2A,R3B), (ZA,R1B,R2A,R3C), (ZA,R1B,R2A,R3D),
(ZA,R1B,R2A,R3E), (ZA,R1B,R2A,R3F), (ZA,R1B,R2A,R3G),
(ZA,R1B,R2A,R3H), (ZA,R1B,R2A,R3I), (ZA,R1B,R2A,R3J),
(ZA,R1B,R2A,R3K), (ZA,R1B,R2A,R3L), (ZA,R1B,R2A,R3M),
(ZA,R1B,R2A,R3N), (ZA,R1B,R2A,R3O), (ZA,R1B,R2A,R3P),
(ZA,R1B,R2A,R3Q), (ZA,R1B,R2A,R3R), (ZA,R1B,R2B,R3A),
(ZA,R1B,R2B,R3B), (ZA,R1B,R2B,R3C), (ZA,R1B,R2B,R3D),
(ZA,R1B,R2B,R3E), (ZA,R1B,R2B,R3F), (ZA,R1B,R2B,R3G),
(ZA,R1B,R2B,R3H), (ZA,R1B,R2B,R3I), (ZA,R1B,R2B,R3J),
(ZA,R1B,R2B,R3K), (ZA,R1B,R2B,R3L), (ZA,R1B,R2B,R3M),
(ZA,R1B,R2B,R3N), (ZA,R1B,R2B,R3O), (ZA,R1B,R2B,R3P),
(ZA,R1B,R2B,R3Q), (ZA,R1B,R2B,R3R), (ZA,R1B,R2C,R3A),
(ZA,R1B,R2C,R3B), (ZA,R1B,R2C,R3C), (ZA,R1B,R2C,R3D),
(ZA,R1B,R2C,R3E), (ZA,R1B,R2C,R3F), (ZA,R1B,R2C,R3G),
(ZA,R1B,R2C,R3H), (ZA,R1B,R2C,R3I), (ZA,R1B,R2C,R3J),
(ZA,R1B,R2C,R3K), (ZA,R1B,R2C,R3L), (ZA,R1B,R2C,R3M),
(ZA,R1B,R2C,R3N), (ZA,R1B,R2C,R3O), (ZA,R1B,R2C,R3P),
(ZA,R1B,R2C,R3Q), (ZA,R1B,R2C,R3R), (ZA,R1B,R2D,R3A),
(ZA,R1B,R2D,R3B), (ZA,R1B,R2D,R3C), (ZA,R1B,R2D,R3D),
(ZA,R1B,R2D,R3E), (ZA,R1B,R2D,R3F), (ZA,R1B,R2D,R3G),
(ZA,R1B,R2D,R3H), (ZA,R1B,R2D,R3I), (ZA,R1B,R2D,R3J),
(ZA,R1B,R2D,R3K), (ZA,R1B,R2D,R3L), (ZA,R1B,R2D,R3M),
(ZA,R1B,R2D,R3N), (ZA,R1B,R2D,R3O), (ZA,R1B,R2D,R3P),
(ZA,R1B,R2D,R3Q), (ZA,R1B,R2D,R3R), (ZA,R1B,R2E,R3A),
(ZA,R1B,R2E,R3B), (ZA,R1B,R2E,R3C), (ZA,R1B,R2E,R3D),
(ZA,R1B,R2E,R3E), (ZA,R1B,R2E,R3F), (ZA,R1B,R2E,R3G),
(ZA,R1B,R2E,R3H), (ZA,R1B,R2E,R3I), (ZA,R1B,R2E,R3J),
(ZA,R1B,R2E,R3K), (ZA,R1B,R2E,R3L), (ZA,R1B,R2E,R3M),
(ZA,R1B,R2E,R3N), (ZA,R1B,R2E,R3O), (ZA,R1B,R2E,R3P),
(ZA,R1B,R2E,R3Q), (ZA,R1B,R2E,R3R), (ZA,R1B,R2F,R3A),
(ZA,R1B,R2F,R3B), (ZA,R1B,R2F,R3C), (ZA,R1B,R2F,R3D),
(ZA,R1B,R2F,R3E), (ZA,R1B,R2F,R3F), (ZA,R1B,R2F,R3G),
(ZA,R1B,R2F,R3H), (ZA,R1B,R2F,R3I), (ZA,R1B,R2F,R3J),
(ZA,R1B,R2F,R3K), (ZA,R1B,R2F,R3L), (ZA,R1B,R2F,R3M),
(ZA,R1B,R2F,R3N), (ZA,R1B,R2F,R3O), (ZA,R1B,R2F,R3P),
(ZA,R1B,R2F,R3Q), (ZA,R1B,R2F,R3R), (ZA,R1B,R2G,R3A),
(ZA,R1B,R2G,R3B), (ZA,R1B,R2G,R3C), (ZA,R1B,R2G,R3D),
(ZA,R1B,R2G,R3E), (ZA,R1B,R2G,R3F), (ZA,R1B,R2G,R3G),
(ZA,R1B,R2G,R3H), (ZA,R1B,R2G,R3I), (ZA,R1B,R2G,R3J),
(ZA,R1B,R2G,R3K), (ZA,R1B,R2G,R3L), (ZA,R1B,R2G,R3M),
(ZA,R1B,R2G,R3N), (ZA,R1B,R2G,R3O), (ZA,R1B,R2G,R3P),
(ZA,R1B,R2G,R3Q), (ZA,R1B,R2G,R3R), (ZA,R1B,R2H,R3A),
(ZA,R1B,R2H,R3B), (ZA,R1B,R2H,R3C), (ZA,R1B,R2H,R3D),
(ZA,R1B,R2H,R3E), (ZA,R1B,R2H,R3F), (ZA,R1B,R2H,R3G),
(ZA,R1B,R2H,R3H), (ZA,R1B,R2H,R3I), (ZA,R1B,R2H,R3J),
(ZA,R1B,R2H,R3K), (ZA,R1B,R2H,R3L), (ZA,R1B,R2H,R3M),
(ZA,R1B,R2H,R3N), (ZA,R1B,R2H,R3O), (ZA,R1B,R2H,R3P),
(ZA,R1B,R2H,R3Q), (ZA,R1B,R2H,R3R), (ZA,R1B,R2I,R3A),
(ZA,R1B,R2I,R3B), (ZA,R1B,R2I,R3C), (ZA,R1B,R2I,R3D), (ZA,R1B,R2I,R3E),
(ZA,R1B,R2I,R3F), (ZA,R1B,R2I,R3G), (ZA,R1B,R2I,R3H), (ZA,R1B,R2I,R3I),
(ZA,R1B,R2I,R3J), (ZA,R1B,R2I,R3K), (ZA,R1B,R2I,R3L), (ZA,R1B,R2I,R3M),
(ZA,R1B,R2I,R3N), (ZA,R1B,R2I,R3O), (ZA,R1B,R2I,R3P), (ZA,R1B,R2I,R3Q),
(ZA,R1B,R2I,R3R), (ZA,R1B,R2J,R3A), (ZA,R1B,R2J,R3B),
(ZA,R1B,R2J,R3D), (ZA,R1B,R2J,R3E),
(ZA,R1B,R2J,R3F), (ZA,R1B,R2J,R3G), (ZA,R1B,R2J,R3H),
(ZA,R1B,R2J,R3I), (ZA,R1B,R2J,R3J), (ZA,R1B,R2J,R3K),
(ZA,R1B,R2J,R3L), (ZA,R1B,R2J,R3M), (ZA,R1B,R2J,R3N),
(ZA,R1B,R2J,R3O), (ZA,R1B,R2J,R3P), (ZA,R1B,R2J,R3Q),
(ZA,R1B,R2K,R3A), (ZA,R1B,R2K,R3B),
(ZA,R1B,R2K,R3C), (ZA,R1B,R2K,R3D), (ZA,R1B,R2K,R3E),
(ZA,R1B,R2K,R3F), (ZA,R1B,R2K,R3G), (ZA,R1B,R2K,R3H),
(ZA,R1B,R2K,R3I), (ZA,R1B,R2K,R3J), (ZA,R1B,R2K,R3K),
(ZA,R1B,R2K,R3L), (ZA,R1B,R2K,R3M), (ZA,R1B,R2K,R3N),
(ZA,R1B,R2K,R3P), (ZA,R1B,R2K,R3Q),
(ZA,R1B,R2K,R3R), (ZA,R1B,R2L,R3A), (ZA,R1B,R2L,R3B), (ZA,R1B,R2L,R3C), (ZA,R1B,R2L,R3D), (ZA,R1B,R2L,R3E),
(ZA,R1B,R2L,R3F), (ZA,R1B,R2L,R3G), (ZA,R1B,R2L,R3H),
(ZA,R1B,R2L,R3I), (ZA,R1B,R2L,R3J), (ZA,R1B,R2L,R3K),
(ZA,R1B,R2L,R3M), (ZA,R1B,R2L,R3N),
(ZA,R1B,R2L,R3O), (ZA,R1B,R2L,R3P), (ZA,R1B,R2L,R3Q),
(ZA,R1B,R2L,R3R), (ZA,R1B,R2M,R3A), (ZA,R1B,R2M,R3B),
(ZA,R1B,R2M,R3C), (ZA,R1B,R2M,R3D), (ZA,R1B,R2M,R3E),
(ZA,R1B,R2M,R3F), (ZA,R1B,R2M,R3G), (ZA,R1B,R2M,R3H),
(ZA,R1B,R2M,R3I), (ZA,R1B,R2M,R3J), (ZA,R1B,R2M,R3K),
(ZA,R1B,R2M,R3L), (ZA,R1B,R2M,R3M), (ZA,R1B,R2M,R3N),
(ZA,R1B,R2M,R3O), (ZA,R1B,R2M,R3P), (ZA,R1B,R2M,R3Q),
(ZA,R1B,R2M,R3R), (ZA,R1B,R2N,R3A), (ZA,R1B,R2N,R3B),
(ZA,R1B,R2N,R3C), (ZA,R1B,R2N,R3D), (ZA,R1B,R2N,R3E),
(ZA,R1B,R2N,R3F), (ZA,R1B,R2N,R3G), (ZA,R1B,R2N,R3H),
(ZA,R1B,R2N,R3I), (ZA,R1B,R2N,R3J), (ZA,R1B,R2N,R3K),
(ZA,R1B,R2N,R3L), (ZA,R1B,R2N,R3M), (ZA,R1B,R2N,R3N),
(ZA,R1B,R2N,R3O), (ZA,R1B,R2N,R3P), (ZA,R1B,R2N,R3Q),
(ZA,R1B,R2N,R3R), (ZA,R1C,R2A,R3A), (ZA,R1C,R2A,R3B),
(ZA,R1C,R2A,R3C), (ZA,R1C,R2A,R3D), (ZA,R1C,R2A,R3E),
(ZA,R1C,R2A,R3F), (ZA,R1C,R2A,R3G), (ZA,R1C,R2A,R3H),
(ZA,R1C,R2A,R3I), (ZA,R1C,R2A,R3J), (ZA,R1C,R2A,R3K),
(ZA,R1C,R2A,R3L), (ZA,R1C,R2A,R3M), (ZA,R1C,R2A,R3N),
(ZA,R1C,R2A,R3O), (ZA,R1C,R2A,R3P), (ZA,R1C,R2A,R3Q),
(ZA,R1C,R2A,R3R), (ZA,R1C,R2B,R3A), (ZA,R1C,R2B,R3B),
(ZA,R1C,R2B,R3C), (ZA,R1C,R2B,R3D), (ZA,R1C,R2B,R3E),
(ZA,R1C,R2B,R3F), (ZA,R1C,R2B,R3G), (ZA,R1C,R2B,R3H),
(ZA,R1C,R2B,R3I), (ZA,R1C,R2B,R3J), (ZA,R1C,R2B,R3K),
(ZA,R1C,R2B,R3L), (ZA,R1C,R2B,R3M), (ZA,R1C,R2B,R3N),
(ZA,R1C,R2B,R3O), (ZA,R1C,R2B,R3P), (ZA,R1C,R2B,R3Q),
(ZA,R1C,R2B,R3R), (ZA,R1C,R2C,R3A), (ZA,R1C,R2C,R3B),
(ZA,R1C,R2C,R3C), (ZA,R1C,R2C,R3D), (ZA,R1C,R2C,R3E),
(ZA,R1C,R2C,R3F), (ZA,R1C,R2C,R3G), (ZA,R1C,R2C,R3H),
(ZA,R1C,R2C,R3I), (ZA,R1C,R2C,R3J), (ZA,R1C,R2C,R3K),
(ZA,R1C,R2C,R3L), (ZA,R1C,R2C,R3M), (ZA,R1C,R2C,R3N),
(ZA,R1C,R2C,R3O), (ZA,R1C,R2C,R3P), (ZA,R1C,R2C,R3Q),
(ZA,R1C,R2C,R3R), (ZA,R1C,R2D,R3A), (ZA,R1C,R2D,R3B),
(ZA,R1C,R2D,R3C), (ZA,R1C,R2D,R3D), (ZA,R1C,R2D,R3E),
(ZA,R1C,R2D,R3F), (ZA,R1C,R2D,R3G), (ZA,R1C,R2D,R3H),
(ZA,R1C,R2D,R3I), (ZA,R1C,R2D,R3J), (ZA,R1C,R2D,R3K),
(ZA,R1C,R2D,R3L), (ZA,R1C,R2D,R3M), (ZA,R1C,R2D,R3N),
(ZA,R1C,R2D,R3O), (ZA,R1C,R2D,R3P), (ZA,R1C,R2D,R3Q),
(ZA,R1C,R2D,R3R), (ZA,R1C,R2E,R3A), (ZA,R1C,R2E,R3B),
(ZA,R1C,R2E,R3C), (ZA,R1C,R2E,R3D), (ZA,R1C,R2E,R3E),
(ZA,R1C,R2E,R3F), (ZA,R1C,R2E,R3G), (ZA,R1C,R2E,R3H),
(ZA,R1C,R2E,R3I), (ZA,R1C,R2E,R3J), (ZA,R1C,R2E,R3K),
(ZA,R1C,R2E,R3L), (ZA,R1C,R2E,R3M), (ZA,R1C,R2E,R3N),
(ZA,R1C,R2E,R3O), (ZA,R1C,R2E,R3P), (ZA,R1C,R2E,R3Q),
(ZA,R1C,R2E,R3R), (ZA,R1C,R2F,R3A), (ZA,R1C,R2F,R3B),
(ZA,R1C,R2F,R3C), (ZA,R1C,R2F,R3D), (ZA,R1C,R2F,R3E),
(ZA,R1C,R2F,R3F), (ZA,R1C,R2F,R3G), (ZA,R1C,R2F,R3H),
(ZA,R1C,R2F,R3I), (ZA,R1C,R2F,R3J), (ZA,R1C,R2F,R3K),
(ZA,R1C,R2F,R3L), (ZA,R1C,R2F,R3M), (ZA,R1C,R2F,R3N),
(ZA,R1C,R2F,R3O), (ZA,R1C,R2F,R3P), (ZA,R1C,R2F,R3Q),
(ZA,R1C,R2F,R3R), (ZA,R1C,R2G,R3A), (ZA,R1C,R2G,R3B),
(ZA,R1C,R2G,R3C), (ZA,R1C,R2G,R3D), (ZA,R1C,R2G,R3E),
(ZA,R1C,R2G,R3F), (ZA,R1C,R2G,R3G), (ZA,R1C,R2G,R3H),
(ZA,R1C,R2G,R3I), (ZA,R1C,R2G,R3J), (ZA,R1C,R2G,R3K),
(ZA,R1C,R2G,R3L), (ZA,R1C,R2G,R3M), (ZA,R1C,R2G,R3N),
(ZA,R1C,R2G,R3O), (ZA,R1C,R2G,R3P), (ZA,R1C,R2G,R3Q),
(ZA,R1C,R2G,R3R), (ZA,R1C,R2H,R3A), (ZA,R1C,R2H,R3B),
(ZA,R1C,R2H,R3C), (ZA,R1C,R2H,R3D), (ZA,R1C,R2H,R3E),
(ZA,R1C,R2H,R3F), (ZA,R1C,R2H,R3G), (ZA,R1C,R2H,R3H),
(ZA,R1C,R2H,R3I), (ZA,R1C,R2H,R3J), (ZA,R1C,R2H,R3K),
(ZA,R1C,R2H,R3L), (ZA,R1C,R2H,R3M), (ZA,R1C,R2H,R3N),
(ZA,R1C,R2H,R3O), (ZA,R1C,R2H,R3P), (ZA,R1C,R2H,R3Q),
(ZA,R1C,R2H,R3R), (ZA,R1C,R2I,R3A), (ZA,R1C,R2I,R3B),
(ZA,R1C,R2I,R3C), (ZA,R1C,R2I,R3D), (ZA,R1C,R2I,R3E), (ZA,R1C,R2I,R3F), (ZA,R1C,R2I,R3G), (ZA,R1C,R2I,R3H), (ZA,R1C,R2I,R3I), (ZA,R1C,R2I,R3J),
(ZA,R1C,R2I,R3K), (ZA,R1C,R2I,R3L), (ZA,R1C,R2I,R3M), (ZA,R1C,R2I,R3N),
(ZA,R1C,R2I,R3O), (ZA,R1C,R2I,R3P), (ZA,R1C,R2I,R3Q), (ZA,R1C,R2I,R3R),
(ZA,R1C,R2J,R3A), (ZA,R1C,R2J,R3B), (ZA,R1C,R2J,R3C),
(ZA,R1C,R2J,R3D), (ZA,R1C,R2J,R3E), (ZA,R1C,R2J,R3F),
(ZA,R1C,R2J,R3G), (ZA,R1C,R2J,R3H), (ZA,R1C,R2J,R3I),
(ZA,R1C,R2J,R3J), (ZA,R1C,R2J,R3K), (ZA,R1C,R2J,R3L),
(ZA,R1C,R2J,R3M), (ZA,R1C,R2J,R3N), (ZA,R1C,R2J,R3O),
(ZA,R1C,R2J,R3P), (ZA,R1C,R2J,R3Q), (ZA,R1C,R2J,R3R),
(ZA,R1C,R2K,R3A), (ZA,R1C,R2K,R3B), (ZA,R1C,R2K,R3C),
(ZA,R1C,R2K,R3D), (ZA,R1C,R2K,R3E), (ZA,R1C,R2K,R3F),
(ZA,R1C,R2K,R3G), (ZA,R1C,R2K,R3H), (ZA,R1C,R2K,R3I),
(ZA,R1C,R2K,R3J), (ZA,R1C,R2K,R3K), (ZA,R1C,R2K,R3L),
(ZA,R1C,R2K,R3M), (ZA,R1C,R2K,R3N), (ZA,R1C,R2K,R3O),
(ZA,R1C,R2K,R3P), (ZA,R1C,R2K,R3Q), (ZA,R1C,R2K,R3R),
(ZA,R1C,R2L,R3A), (ZA,R1C,R2L,R3B), (ZA,R1C,R2L,R3C),
(ZA,R1C,R2L,R3D), (ZA,R1C,R2L,R3E), (ZA,R1C,R2L,R3F),
(ZA,R1C,R2L,R3G), (ZA,R1C,R2L,R3H), (ZA,R1C,R2L,R3I),
(ZA,R1C,R2L,R3J), (ZA,R1C,R2L,R3K), (ZA,R1C,R2L,R3L),
(ZA,R1C,R2L,R3M), (ZA,R1C,R2L,R3N), (ZA,R1C,R2L,R3O),
(ZA,R1C,R2L,R3P), (ZA,R1C,R2L,R3Q), (ZA,R1C,R2L,R3R),
(ZA,R1C,R2M,R3A), (ZA,R1C,R2M,R3B), (ZA,R1C,R2M,R3C),
(ZA,R1C,R2M,R3D), (ZA,R1C,R2M,R3E), (ZA,R1C,R2M,R3F),
(ZA,R1C,R2M,R3G), (ZA,R1C,R2M,R3H), (ZA,R1C,R2M,R3I),
(ZA,R1C,R2M,R3J), (ZA,R1C,R2M,R3K), (ZA,R1C,R2M,R3L),
(ZA,R1C,R2M,R3M), (ZA,R1C,R2M,R3N), (ZA,R1C,R2M,R3O),
(ZA,R1C,R2M,R3P), (ZA,R1C,R2M,R3Q), (ZA,R1C,R2M,R3R),
(ZA,R1C,R2N,R3A), (ZA,R1C,R2N,R3B), (ZA,R1C,R2N,R3C),
(ZA,R1C,R2N,R3D), (ZA,R1C,R2N,R3E), (ZA,R1C,R2N,R3F),
(ZA,R1C,R2N,R3G), (ZA,R1C,R2N,R3H), (ZA,R1C,R2N,R3I),
(ZA,R1C,R2N,R3J), (ZA,R1C,R2N,R3K), (ZA,R1C,R2N,R3L),
(ZA,R1C,R2N,R3M), (ZA,R1C,R2N,R3N), (ZA,R1C,R2N,R3O),
(ZA,R1C,R2N,R3P), (ZA,R1C,R2N,R3Q), (ZA,R1C,R2N,R3R),
(ZA,R1D,R2A,R3A), (ZA,R1D,R2A,R3B), (ZA,R1D,R2A,R3C),
(ZA,R1D,R2A,R3D), (ZA,R1D,R2A,R3E), (ZA,R1D,R2A,R3F),
(ZA,R1D,R2A,R3G), (ZA,R1D,R2A,R3H), (ZA,R1D,R2A,R3I),
(ZA,R1D,R2A,R3J), (ZA,R1D,R2A,R3K), (ZA,R1D,R2A,R3L),
(ZA,R1D,R2A,R3M), (ZA,R1D,R2A,R3N), (ZA,R1D,R2A,R3O),
(ZA,R1D,R2A,R3P), (ZA,R1D,R2A,R3Q), (ZA,R1D,R2A,R3R),
(ZA,R1D,R2B,R3A), (ZA,R1D,R2B,R3B), (ZA,R1D,R2B,R3C),
(ZA,R1D,R2B,R3D), (ZA,R1D,R2B,R3E), (ZA,R1D,R2B,R3F),
(ZA,R1D,R2B,R3G), (ZA,R1D,R2B,R3H), (ZA,R1D,R2B,R3I),
(ZA,R1D,R2B,R3J), (ZA,R1D,R2B,R3K), (ZA,R1D,R2B,R3L),
(ZA,R1D,R2B,R3M), (ZA,R1D,R2B,R3N), (ZA,R1D,R2B,R3O),
(ZA,R1D,R2B,R3P), (ZA,R1D,R2B,R3Q), (ZA,R1D,R2B,R3R),
(ZA,R1D,R2C,R3A), (ZA,R1D,R2C,R3B), (ZA,R1D,R2C,R3C),
(ZA,R1D,R2C,R3D), (ZA,R1D,R2C,R3E), (ZA,R1D,R2C,R3F),
(ZA,R1D,R2C,R3G), (ZA,R1D,R2C,R3H), (ZA,R1D,R2C,R3I),
(ZA,R1D,R2C,R3J), (ZA,R1D,R2C,R3K), (ZA,R1D,R2C,R3L),
(ZA,R1D,R2C,R3M), (ZA,R1D,R2C,R3N), (ZA,R1D,R2C,R3O),
(ZA,R1D,R2C,R3P), (ZA,R1D,R2C,R3Q), (ZA,R1D,R2C,R3R),
(ZA,R1D,R2D,R3A), (ZA,R1D,R2D,R3B), (ZA,R1D,R2D,R3C),
(ZA,R1D,R2D,R3D), (ZA,R1D,R2D,R3E), (ZA,R1D,R2D,R3F),
(ZA,R1D,R2D,R3G), (ZA,R1D,R2D,R3H), (ZA,R1D,R2D,R3I),
(ZA,R1D,R2D,R3J), (ZA,R1D,R2D,R3K), (ZA,R1D,R2D,R3L),
(ZA,R1D,R2D,R3M), (ZA,R1D,R2D,R3N), (ZA,R1D,R2D,R3O),
(ZA,R1D,R2D,R3P), (ZA,R1D,R2D,R3Q), (ZA,R1D,R2D,R3R),
(ZA,R1D,R2E,R3A), (ZA,R1D,R2E,R3B), (ZA,R1D,R2E,R3C),
(ZA,R1D,R2E,R3D), (ZA,R1D,R2E,R3E), (ZA,R1D,R2E,R3F),
(ZA,R1D,R2E,R3G), (ZA,R1D,R2E,R3H), (ZA,R1D,R2E,R3I),
(ZA,R1D,R2E,R3J), (ZA,R1D,R2E,R3K), (ZA,R1D,R2E,R3L),
(ZA,R1D,R2E,R3M), (ZA,R1D,R2E,R3N), (ZA,R1D,R2E,R3O),
(ZA,R1D,R2E,R3P), (ZA,R1D,R2E,R3Q), (ZA,R1D,R2E,R3R),
(ZA,R1D,R2F,R3A), (ZA,R1D,R2F,R3B), (ZA,R1D,R2F,R3C),
(ZA,R1D,R2F,R3D), (ZA,R1D,R2F,R3E), (ZA,R1D,R2F,R3F),
(ZA,R1D,R2F,R3G), (ZA,R1D,R2F,R3H), (ZA,R1D,R2F,R3I), (ZA,R1D,R2F,R3J), (ZA,R1D,R2F,R3K), (ZA,R1D,R2F,R3L),
(ZA,R1D,R2F,R3M), (ZA,R1D,R2F,R3N), (ZA,R1D,R2F,R3O),
(ZA,R1D,R2F,R3P), (ZA,R1D,R2F,R3Q), (ZA,R1D,R2F,R3R),
(ZA,R1D,R2G,R3A), (ZA,R1D,R2G,R3B), (ZA,R1D,R2G,R3C),
(ZA,R1D,R2G,R3D), (ZA,R1D,R2G,R3E), (ZA,R1D,R2G,R3F),
(ZA,R1D,R2G,R3G), (ZA,R1D,R2G,R3H), (ZA,R1D,R2G,R3I),
(ZA,R1D,R2G,R3J), (ZA,R1D,R2G,R3K), (ZA,R1D,R2G,R3L),
(ZA,R1D,R2G,R3M), (ZA,R1D,R2G,R3N), (ZA,R1D,R2G,R3O),
(ZA,R1D,R2G,R3P), (ZA,R1D,R2G,R3Q), (ZA,R1D,R2G,R3R),
(ZA,R1D,R2H,R3A), (ZA,R1D,R2H,R3B), (ZA,R1D,R2H,R3C),
(ZA,R1D,R2H,R3D), (ZA,R1D,R2H,R3E), (ZA,R1D,R2H,R3F),
(ZA,R1D,R2H,R3G), (ZA,R1D,R2H,R3H), (ZA,R1D,R2H,R3I),
(ZA,R1D,R2H,R3J), (ZA,R1D,R2H,R3K), (ZA,R1D,R2H,R3L),
(ZA,R1D,R2H,R3M), (ZA,R1D,R2H,R3N), (ZA,R1D,R2H,R3O),
(ZA,R1D,R2H,R3P), (ZA,R1D,R2H,R3Q), (ZA,R1D,R2H,R3R),
(ZA,R1D,R2I,R3A), (ZA,R1D,R2I,R3B), (ZA,R1D,R2I,R3C),
(ZA,R1D,R2I,R3D), (ZA,R1D,R2I,R3E), (ZA,R1D,R2I,R3F),
(ZA,R1D,R2I,R3G), (ZA,R1D,R2I,R3H), (ZA,R1D,R2I,R3I), (ZA,R1D,R2I,R3J),
(ZA,R1D,R2I,R3K), (ZA,R1D,R2I,R3L), (ZA,R1D,R2I,R3M),
(ZA,R1D,R2I,R3N), (ZA,R1D,R2I,R3O), (ZA,R1D,R2I,R3P),
(ZA,R1D,R2I,R3Q), (ZA,R1D,R2I,R3R), (ZA,R1D,R2J,R3A),
(ZA,R1D,R2J,R3B), (ZA,R1D,R2J,R3C), (ZA,R1D,R2J,R3D),
(ZA,R1D,R2J,R3E), (ZA,R1D,R2J,R3F), (ZA,R1D,R2J,R3G),
(ZA,R1D,R2J,R3H), (ZA,R1D,R2J,R3I), (ZA,R1D,R2J,R3J),
(ZA,R1D,R2J,R3K), (ZA,R1D,R2J,R3L), (ZA,R1D,R2J,R3M),
(ZA,R1D,R2J,R3N), (ZA,R1D,R2J,R3O), (ZA,R1D,R2J,R3P),
(ZA,R1D,R2J,R3Q), (ZA,R1D,R2J,R3R), (ZA,R1D,R2K,R3A),
(ZA,R1D,R2K,R3B), (ZA,R1D,R2K,R3C), (ZA,R1D,R2K,R3D),
(ZA,R1D,R2K,R3E), (ZA,R1D,R2K,R3F), (ZA,R1D,R2K,R3G),
(ZA,R1D,R2K,R3H), (ZA,R1D,R2K,R3I), (ZA,R1D,R2K,R3J),
(ZA,R1D,R2K,R3K), (ZA,R1D,R2K,R3L), (ZA,R1D,R2K,R3M),
(ZA,R1D,R2K,R3N), (ZA,R1D,R2K,R3O), (ZA,R1D,R2K,R3P),
(ZA,R1D,R2K,R3Q), (ZA,R1D,R2K,R3R), (ZA,R1D,R2L,R3A),
(ZA,R1D,R2L,R3B), (ZA,R1D,R2L,R3C), (ZA,R1D,R2L,R3D),
(ZA,R1D,R2L,R3E), (ZA,R1D,R2L,R3F), (ZA,R1D,R2L,R3G),
(ZA,R1D,R2L,R3H), (ZA,R1D,R2L,R3I), (ZA,R1D,R2L,R3J),
(ZA,R1D,R2L,R3K), (ZA,R1D,R2L,R3L), (ZA,R1D,R2L,R3M),
(ZA,R1D,R2L,R3N), (ZA,R1D,R2L,R3O), (ZA,R1D,R2L,R3P),
(ZA,R1D,R2L,R3Q), (ZA,R1D,R2L,R3R), (ZA,R1D,R2M,R3A),
(ZA,R1D,R2M,R3B), (ZA,R1D,R2M,R3C), (ZA,R1D,R2M,R3D),
(ZA,R1D,R2M,R3E), (ZA,R1D,R2M,R3F), (ZA,R1D,R2M,R3G),
(ZA,R1D,R2M,R3H), (ZA,R1D,R2M,R3I), (ZA,R1D,R2M,R3J),
(ZA,R1D,R2M,R3K), (ZA,R1D,R2M,R3L), (ZA,R1D,R2M,R3M),
(ZA,R1D,R2M,R3N), (ZA,R1D,R2M,R3O), (ZA,R1D,R2M,R3P),
(ZA,R1D,R2M,R3Q), (ZA,R1D,R2M,R3R), (ZA,R1D,R2N,R3A),
(ZA,R1D,R2N,R3B), (ZA,R1D,R2N,R3C), (ZA,R1D,R2N,R3D),
(ZA,R1D,R2N,R3E), (ZA,R1D,R2N,R3F), (ZA,R1D,R2N,R3G),
(ZA,R1D,R2N,R3H), (ZA,R1D,R2N,R3I), (ZA,R1D,R2N,R3J),
(ZA,R1D,R2N,R3K), (ZA,R1D,R2N,R3L), (ZA,R1D,R2N,R3M),
(ZA,R1D,R2N,R3N), (ZA,R1D,R2N,R3O), (ZA,R1D,R2N,R3P),
(ZA,R1D,R2N,R3Q), (ZA,R1D,R2N,R3R), (ZA,R1E,R2A,R3A),
(ZA,R1E,R2A,R3B), (ZA,R1E,R2A,R3C), (ZA,R1E,R2A,R3D),
(ZA,R1E,R2A,R3E), (ZA,R1E,R2A,R3F), (ZA,R1E,R2A,R3G),
(ZA,R1E,R2A,R3H), (ZA,R1E,R2A,R3I), (ZA,R1E,R2A,R3J),
(ZA,R1E,R2A,R3K), (ZA,R1E,R2A,R3L), (ZA,R1E,R2A,R3M),
(ZA,R1E,R2A,R3N), (ZA,R1E,R2A,R3O), (ZA,R1E,R2A,R3P),
(ZA,R1E,R2A,R3Q), (ZA,R1E,R2A,R3R), (ZA,R1E,R2B,R3A),
(ZA,R1E,R2B,R3B), (ZA,R1E,R2B,R3C), (ZA,R1E,R2B,R3D),
(ZA,R1E,R2B,R3E), (ZA,R1E,R2B,R3F), (ZA,R1E,R2B,R3G),
(ZA,R1E,R2B,R3H), (ZA,R1E,R2B,R3I), (ZA,R1E,R2B,R3J),
(ZA,R1E,R2B,R3K), (ZA,R1E,R2B,R3L), (ZA,R1E,R2B,R3M),
(ZA,R1E,R2B,R3N), (ZA,R1E,R2B,R3O), (ZA,R1E,R2B,R3P),
(ZA,R1E,R2B,R3Q), (ZA,R1E,R2B,R3R), (ZA,R1E,R2C,R3A),
(ZA,R1E,R2C,R3B), (ZA,R1E,R2C,R3C), (ZA,R1E,R2C,R3D),
(ZA,R1E,R2C,R3E), (ZA,R1E,R2C,R3F), (ZA,R1E,R2C,R3G),
(ZA,R1E,R2C,R3H), (ZA,R1E,R2C,R3I), (ZA,R1E,R2C,R3J), (ZA,R1E,R2C,R3K), (ZA,R1E,R2C,R3L), (ZA,R1E,R2C,R3M),
(ZA,R1E,R2C,R3N), (ZA,R1E,R2C,R3O), (ZA,R1E,R2C,R3P),
(ZA,R1E,R2C,R3Q), (ZA,R1E,R2C,R3R), (ZA,R1E,R2D,R3A),
(ZA,R1E,R2D,R3B), (ZA,R1E,R2D,R3C), (ZA,R1E,R2D,R3D),
(ZA,R1E,R2D,R3E), (ZA,R1E,R2D,R3F), (ZA,R1E,R2D,R3G),
(ZA,R1E,R2D,R3H), (ZA,R1E,R2D,R3I), (ZA,R1E,R2D,R3J),
(ZA,R1E,R2D,R3K), (ZA,R1E,R2D,R3L), (ZA,R1E,R2D,R3M),
(ZA,R1E,R2D,R3N), (ZA,R1E,R2D,R3O), (ZA,R1E,R2D,R3P),
(ZA,R1E,R2D,R3Q), (ZA,R1E,R2D,R3R), (ZA,R1E,R2E,R3A),
(ZA,R1E,R2E,R3B), (ZA,R1E,R2E,R3C), (ZA,R1E,R2E,R3D),
(ZA,R1E,R2E,R3E), (ZA,R1E,R2E,R3F), (ZA,R1E,R2E,R3G),
(ZA,R1E,R2E,R3H), (ZA,R1E,R2E,R3I), (ZA,R1E,R2E,R3J),
(ZA,R1E,R2E,R3K), (ZA,R1E,R2E,R3L), (ZA,R1E,R2E,R3M),
(ZA,R1E,R2E,R3N), (ZA,R1E,R2E,R3O), (ZA,R1E,R2E,R3P),
(ZA,R1E,R2E,R3Q), (ZA,R1E,R2E,R3R), (ZA,R1E,R2F,R3A),
(ZA,R1E,R2F,R3B), (ZA,R1E,R2F,R3C), (ZA,R1E,R2F,R3D),
(ZA,R1E,R2F,R3E), (ZA,R1E,R2F,R3F), (ZA,R1E,R2F,R3G),
(ZA,R1E,R2F,R3H), (ZA,R1E,R2F,R3I), (ZA,R1E,R2F,R3J),
(ZA,R1E,R2F,R3K), (ZA,R1E,R2F,R3L), (ZA,R1E,R2F,R3M),
(ZA,R1E,R2F,R3N), (ZA,R1E,R2F,R3O), (ZA,R1E,R2F,R3P),
(ZA,R1E,R2F,R3Q), (ZA,R1E,R2F,R3R), (ZA,R1E,R2G,R3A),
(ZA,R1E,R2G,R3B), (ZA,R1E,R2G,R3C), (ZA,R1E,R2G,R3D),
(ZA,R1E,R2G,R3E), (ZA,R1E,R2G,R3F), (ZA,R1E,R2G,R3G),
(ZA,R1E,R2G,R3H), (ZA,R1E,R2G,R3I), (ZA,R1E,R2G,R3J),
(ZA,R1E,R2G,R3K), (ZA,R1E,R2G,R3L), (ZA,R1E,R2G,R3M),
(ZA,R1E,R2G,R3N), (ZA,R1E,R2G,R3O), (ZA,R1E,R2G,R3P),
(ZA,R1E,R2G,R3Q), (ZA,R1E,R2G,R3R), (ZA,R1E,R2H,R3A),
(ZA,R1E,R2H,R3B), (ZA,R1E,R2H,R3C), (ZA,R1E,R2H,R3D),
(ZA,R1E,R2H,R3E), (ZA,R1E,R2H,R3F), (ZA,R1E,R2H,R3G),
(ZA,R1E,R2H,R3H), (ZA,R1E,R2H,R3I), (ZA,R1E,R2H,R3J),
(ZA,R1E,R2H,R3K), (ZA,R1E,R2H,R3L), (ZA,R1E,R2H,R3M),
(ZA,R1E,R2H,R3N), (ZA,R1E,R2H,R3O), (ZA,R1E,R2H,R3P),
(ZA,R1E,R2H,R3Q), (ZA,R1E,R2H,R3R), (ZA,R1E,R2I,R3A),
(ZA,R1E,R2I,R3B), (ZA,R1E,R2I,R3C), (ZA,R1E,R2I,R3D), (ZA,R1E,R2I,R3E),
(ZA,R1E,R2I,R3F), (ZA,R1E,R2I,R3G), (ZA,R1E,R2I,R3H), (ZA,R1E,R2I,R3I),
(ZA,R1E,R2I,R3J), (ZA,R1E,R2I,R3K), (ZA,R1E,R2I,R3L), (ZA,R1E,R2I,R3M),
(ZA,R1E,R2I,R3N), (ZA,R1E,R2I,R3O), (ZA,R1E,R2I,R3P), (ZA,R1E,R2I,R3Q),
(ZA,R1E,R2I,R3R), (ZA,R1E,R2J,R3A), (ZA,R1E,R2J,R3B),
(ZA,R1E,R2J,R3C), (ZA,R1E,R2J,R3D), (ZA,R1E,R2J,R3E),
(ZA,R1E,R2J,R3G), (ZA,R1E,R2J,R3H),
(ZA,R1E,R2J,R3I), (ZA,R1E,R2J,R3J), (ZA,R1E,R2J,R3K),
(ZA,R1E,R2J,R3L), (ZA,R1E,R2J,R3M), (ZA,R1E,R2J,R3N),
(ZA,R1E,R2J,R3O), (ZA,R1E,R2J,R3P), (ZA,R1E,R2J,R3Q),
(ZA,R1E,R2J,R3R), (ZA,R1E,R2K,R3A), (ZA,R1E,R2K,R3B),
(ZA,R1E,R2K,R3D), (ZA,R1E,R2K,R3E),
(ZA,R1E,R2K,R3F), (ZA,R1E,R2K,R3G), (ZA,R1E,R2K,R3H),
(ZA,R1E,R2K,R3I), (ZA,R1E,R2K,R3J), (ZA,R1E,R2K,R3K),
(ZA,R1E,R2K,R3L), (ZA,R1E,R2K,R3M), (ZA,R1E,R2K,R3N),
(ZA,R1E,R2K,R3O), (ZA,R1E,R2K,R3P), (ZA,R1E,R2K,R3Q),
(ZA,R1E,R2L,R3A), (ZA,R1E,R2L,R3B),
(ZA,R1E,R2L,R3C), (ZA,R1E,R2L,R3D), (ZA,R1E,R2L,R3E),
(ZA,R1E,R2L,R3F), (ZA,R1E,R2L,R3G), (ZA,R1E,R2L,R3H),
(ZA,R1E,R2L,R3I), (ZA,R1E,R2L,R3J), (ZA,R1E,R2L,R3K),
(ZA,R1E,R2L,R3L), (ZA,R1E,R2L,R3M), (ZA,R1E,R2L,R3N),
(ZA,R1E,R2L,R3O), (ZA,R1E,R2L,R3P_, (ZA,R1E,R2L,R3Q),
(ZA,R1E,R2L,R3R), (ZA,R1E,R2M,R3A), (ZA,R1E,R2M,R3B),
(ZA,R1E,R2M,R3C), (ZA,R1E,R2M,R3D), (ZA,R1E,R2M,R3E),
(ZA,R1E,R2M,R3F), (ZA,R1E,R2M,R3G), (ZA,R1E,R2M,R3H),
(ZA,R1E,R2M,R3I), (ZA,R1E,R2M,R3J), (ZA,R1E,R2M,R3K),
(ZA,R1E,R2M,R3L), (ZA,R1E,R2M,R3M), (ZA,R1E,R2M,R3N),
(ZA,R1E,R2M,R3O), (ZA,R1E,R2M,R3P), (ZA,R1E,R2M,R3Q),
(ZA,R1E,R2M,R3R), (ZA,R1E,R2N,R3A), (ZA,R1E,R2N,R3B),
(ZA,R1E,R2N,R3C), (ZA,R1E,R2N,R3D), (ZA,R1E,R2N,R3E),
(ZA,R1E,R2N,R3F), (ZA,R1E,R2N,R3G), (ZA,R1E,R2N,R3H),
(ZA,R1E,R2N,R3I), (ZA,R1E,R2N,R3J), (ZA,R1E,R2N,R3K),
(ZA,R1E,R2N,R3L), (ZA,R1E,R2N,R3M), (ZA,R1E,R2N,R3N),
(ZA,R1E,R2N,R3O), (ZA,R1E,R2N,R3P), (ZA,R1E,R2N,R3Q),
(ZA,R1E,R2N,R3R), (ZA,R1F,R2A,R3A), (ZA,R1F,R2A,R3B), (ZA,R1F,R2A,R3C), (ZA,R1F,R2A,R3D), (ZA,R1F,R2A,R3E),
(ZA,R1F,R2A,R3F), (ZA,R1F,R2A,R3G), (ZA,R1F,R2A,R3H),
(ZA,R1F,R2A,R3I), (ZA,R1F,R2A,R3J), (ZA,R1F,R2A,R3K),
(ZA,R1F,R2A,R3L), (ZA,R1F,R2A,R3M), (ZA,R1F,R2A,R3N),
(ZA,R1F,R2A,R3O), (ZA,R1F,R2A,R3P), (ZA,R1F,R2A,R3Q),
(ZA,R1F,R2A,R3R), (ZA,R1F,R2B,R3A), (ZA,R1F,R2B,R3B),
(ZA,R1F,R2B,R3C), (ZA,R1F,R2B,R3D), (ZA,R1F,R2B,R3E),
(ZA,R1F,R2B,R3F), (ZA,R1F,R2B,R3G), (ZA,R1F,R2B,R3H),
(ZA,R1F,R2B,R3I), (ZA,R1F,R2B,R3J), (ZA,R1F,R2B,R3K),
(ZA,R1F,R2B,R3L), (ZA,R1F,R2B,R3M), (ZA,R1F,R2B,R3N),
(ZA,R1F,R2B,R3O), (ZA,R1F,R2B,R3P), (ZA,R1F,R2B,R3Q),
(ZA,R1F,R2B,R3R), (ZA,R1F,R2C,R3A), (ZA,R1F,R2C,R3B),
(ZA,R1F,R2C,R3C), (ZA,R1F,R2C,R3D), (ZA,R1F,R2C,R3E),
(ZA,R1F,R2C,R3F), (ZA,R1F,R2C,R3G), (ZA,R1F,R2C,R3H),
(ZA,R1F,R2C,R3I), (ZA,R1F,R2C,R3J), (ZA,R1F,R2C,R3K),
(ZA,R1F,R2C,R3L), (ZA,R1F,R2C,R3M), (ZA,R1F,R2C,R3N),
(ZA,R1F,R2C,R3O), (ZA,R1F,R2C,R3P), (ZA,R1F,R2C,R3Q),
(ZA,R1F,R2C,R3R), (ZA,R1F,R2D,R3A), (ZA,R1F,R2D,R3B),
(ZA,R1F,R2D,R3C), (ZA,R1F,R2D,R3D), (ZA,R1F,R2D,R3E),
(ZA,R1F,R2D,R3F), (ZA,R1F,R2D,R3G), (ZA,R1F,R2D,R3H),
(ZA,R1F,R2D,R3I), (ZA,R1F,R2D,R3J), (ZA,R1F,R2D,R3K),
(ZA,R1F,R2D,R3L), (ZA,R1F,R2D,R3M), (ZA,R1F,R2D,R3N),
(ZA,R1F,R2D,R3O), (ZA,R1F,R2D,R3P), (ZA,R1F,R2D,R3Q),
(ZA,R1F,R2D,R3R), (ZA,R1F,R2E,R3A), (ZA,R1F,R2E,R3B),
(ZA,R1F,R2E,R3C), (ZA,R1F,R2E,R3D), (ZA,R1F,R2E,R3E),
(ZA,R1F,R2E,R3F), (ZA,R1F,R2E,R3G), (ZA,R1F,R2E,R3H),
(ZA,R1F,R2E,R3I), (ZA,R1F,R2E,R3J), (ZA,R1F,R2E,R3K),
(ZA,R1F,R2E,R3L), (ZA,R1F,R2E,R3M), (ZA,R1F,R2E,R3N),
(ZA,R1F,R2E,R3O), (ZA,R1F,R2E,R3P), (ZA,R1F,R2E,R3Q),
(ZA,R1F,R2E,R3R), (ZA,R1F,R2F,R3A), (ZA,R1F,R2F,R3B),
(ZA,R1F,R2F,R3C), (ZA,R1F,R2F,R3D), (ZA,R1F,R2F,R3E),
(ZA,R1F,R2F,R3F), (ZA,R1F,R2F,R3G), (ZA,R1F,R2F,R3H),
(ZA,R1F,R2F,R3I), (ZA,R1F,R2F,R3J), (ZA,R1F,R2F,R3K), (ZA,R1F,R2F,R3L),
(ZA,R1F,R2F,R3M), (ZA,R1F,R2F,R3N), (ZA,R1F,R2F,R3O),
(ZA,R1F,R2F,R3P), (ZA,R1F,R2F,R3Q), (ZA,R1F,R2F,R3R),
(ZA,R1F,R2G,R3A), (ZA,R1F,R2G,R3B), (ZA,R1F,R2G,R3C),
(ZA,R1F,R2G,R3D), (ZA,R1F,R2G,R3E), (ZA,R1F,R2G,R3F),
(ZA,R1F,R2G,R3G), (ZA,R1F,R2G,R3H), (ZA,R1F,R2G,R3I),
(ZA,R1F,R2G,R3J), (ZA,R1F,R2G,R3K), (ZA,R1F,R2G,R3L),
(ZA,R1F,R2G,R3M), (ZA,R1F,R2G,R3N), (ZA,R1F,R2G,R3O),
(ZA,R1F,R2G,R3P), (ZA,R1F,R2G,R3Q), (ZA,R1F,R2G,R3R),
(ZA,R1F,R2H,R3A), (ZA,R1F,R2H,R3B), (ZA,R1F,R2H,R3C),
(ZA,R1F,R2H,R3D), (ZA,R1F,R2H,R3E), (ZA,R1F,R2H,R3F),
(ZA,R1F,R2H,R3G), (ZA,R1F,R2H,R3H), (ZA,R1F,R2H,R3I),
(ZA,R1F,R2H,R3J), (ZA,R1F,R2H,R3K), (ZA,R1F,R2H,R3L),
(ZA,R1F,R2H,R3M), (ZA,R1F,R2H,R3N), (ZA,R1F,R2H,R3O),
(ZA,R1F,R2H,R3P), (ZA,R1F,R2H,R3Q), (ZA,R1F,R2H,R3R),
(ZA,R1F,R2I,R3A), (ZA,R1F,R2I,R3B), (ZA,R1F,R2I,R3C), (ZA,R1F,R2I,R3D),
(ZA,R1F,R2I,R3E), (ZA,R1F,R2I,R3F), (ZA,R1F,R2I,R3G), (ZA,R1F,R2I,R3H),
(ZA,R1F,R2I,R3I), (ZA,R1F,R2I,R3J), (ZA,R1F,R2I,R3K), (ZA,R1F,R2I,R3L),
(ZA,R1F,R2I,R3M), (ZA,R1F,R2I,R3N), (ZA,R1F,R2I,R3O), (ZA,R1F,R2I,R3P),
(ZA,R1F,R2I,R3Q), (ZA,R1F,R2I,R3R), (ZA,R1F,R2J,R3A), (ZA,R1F,R2J,R3B),
(ZA,R1F,R2J,R3C), (ZA,R1F,R2J,R3D), (ZA,R1F,R2J,R3E),
(ZA,R1F,R2J,R3F), (ZA,R1F,R2J,R3G), (ZA,R1F,R2J,R3H),
(ZA,R1F,R2J,R3I), (ZA,R1F,R2J,R3J), (ZA,R1F,R2J,R3K), (ZA,R1F,R2J,R3L),
(ZA,R1F,R2J,R3M), (ZA,R1F,R2J,R3N), (ZA,R1F,R2J,R3O),
(ZA,R1F,R2J,R3P), (ZA,R1F,R2J,R3Q), (ZA,R1F,R2J,R3R),
(ZA,R1F,R2K,R3A), (ZA,R1F,R2K,R3B), (ZA,R1F,R2K,R3C),
(ZA,R1F,R2K,R3D), (ZA,R1F,R2K,R3E), (ZA,R1F,R2K,R3F),
(ZA,R1F,R2K,R3G), (ZA,R1F,R2K,R3H), (ZA,R1F,R2K,R3I),
(ZA,R1F,R2K,R3J), (ZA,R1F,R2K,R3K), (ZA,R1F,R2K,R3L),
(ZA,R1F,R2K,R3M), (ZA,R1F,R2K,R3N), (ZA,R1F,R2K,R3O),
(ZA,R1F,R2K,R3P), (ZA,R1F,R2K,R3Q), (ZA,R1F,R2K,R3R),
(ZA,R1F,R2L,R3A), (ZA,R1F,R2L,R3B), (ZA,R1F,R2L,R3C),
(ZA,R1F,R2L,R3D), (ZA,R1F,R2L,R3E), (ZA,R1F,R2L,R3F),
(ZA,R1F,R2L,R3G), (ZA,R1F,R2L,R3H), (ZA,R1F,R2L,R3I), (ZA,R1F,R2L,R3J), (ZA,R1F,R2L,R3K), (ZA,R1F,R2L,R3L),
(ZA,R1F,R2L,R3M), (ZA,R1F,R2L,R3N), (ZA,R1F,R2L,R3O),
(ZA,R1F,R2L,R3P), (ZA,R1F,R2L,R3Q), (ZA,R1F,R2L,R3R),
(ZA,R1F,R2M,R3A), (ZA,R1F,R2M,R3B), (ZA,R1F,R2M,R3C),
(ZA,R1F,R2M,R3D), (ZA,R1F,R2M,R3E), (ZA,R1F,R2M,R3F),
(ZA,R1F,R2M,R3G), (ZA,R1F,R2M,R3H), (ZA,R1F,R2M,R3I),
(ZA,R1F,R2M,R3J), (ZA,R1F,R2M,R3K), (ZA,R1F,R2M,R3L),
(ZA,R1F,R2M,R3M), (ZA,R1F,R2M,R3N), (ZA,R1F,R2M,R3O),
(ZA,R1F,R2M,R3P), (ZA,R1F,R2M,R3Q), (ZA,R1F,R2M,R3R),
(ZA,R1F,R2N,R3A), (ZA,R1F,R2N,R3B), (ZA,R1F,R2N,R3C),
(ZA,R1F,R2N,R3D), (ZA,R1F,R2N,R3E), (ZA,R1F,R2N,R3F),
(ZA,R1F,R2N,R3G), (ZA,R1F,R2N,R3H), (ZA,R1F,R2N,R3I),
(ZA,R1F,R2N,R3J), (ZA,R1F,R2N,R3K), (ZA,R1F,R2N,R3L),
(ZA,R1F,R2N,R3M), (ZA,R1F,R2N,R3N), (ZA,R1F,R2N,R3O),
(ZA,R1F,R2N,R3P), (ZA,R1F,R2N,R3Q), (ZA,R1F,R2N,R3R),
(ZA,R1G,R2A,R3A), (ZA,R1G,R2A,R3B), (ZA,R1G,R2A,R3C),
(ZA,R1G,R2A,R3D), (ZA,R1G,R2A,R3E), (ZA,R1G,R2A,R3F),
(ZA,R1G,R2A,R3G), (ZA,R1G,R2A,R3H), (ZA,R1G,R2A,R3I),
(ZA,R1G,R2A,R3J), (ZA,R1G,R2A,R3K), (ZA,R1G,R2A,R3L),
(ZA,R1G,R2A,R3M), (ZA,R1G,R2A,R3N), (ZA,R1G,R2A,R3O),
(ZA,R1G,R2A,R3P), (ZA,R1G,R2A,R3Q), (ZA,R1G,R2A,R3R),
(ZA,R1G,R2B,R3A), (ZA,R1G,R2B,R3B), (ZA,R1G,R2B,R3C),
(ZA,R1G,R2B,R3D), (ZA,R1G,R2B,R3E), (ZA,R1G,R2B,R3F),
(ZA,R1G,R2B,R3G), (ZA,R1G,R2B,R3H), (ZA,R1G,R2B,R3I),
(ZA,R1G,R2B,R3J), (ZA,R1G,R2B,R3K), (ZA,R1G,R2B,R3L),
(ZA,R1G,R2B,R3M), (ZA,R1G,R2B,R3N), (ZA,R1G,R2B,R3O),
(ZA,R1G,R2B,R3P), (ZA,R1G,R2B,R3Q), (ZA,R1G,R2B,R3R),
(ZA,R1G,R2C,R3A), (ZA,R1G,R2C,R3B), (ZA,R1G,R2C,R3C),
(ZA,R1G,R2C,R3D), (ZA,R1G,R2C,R3E), (ZA,R1G,R2C,R3F),
(ZA,R1G,R2C,R3G), (ZA,R1G,R2C,R3H), (ZA,R1G,R2C,R3I),
(ZA,R1G,R2C,R3J), (ZA,R1G,R2C,R3K), (ZA,R1G,R2C,R3L),
(ZA,R1G,R2C,R3M), (ZA,R1G,R2C,R3N), (ZA,R1G,R2C,R3O),
(ZA,R1G,R2C,R3P), (ZA,R1G,R2C,R3Q), (ZA,R1G,R2C,R3R),
(ZA,R1G,R2D,R3A), (ZA,R1G,R2D,R3B), (ZA,R1G,R2D,R3C),
(ZA,R1G,R2D,R3D), (ZA,R1G,R2D,R3E), (ZA,R1G,R2D,R3F),
(ZA,R1G,R2D,R3G), (ZA,R1G,R2D,R3H), (ZA,R1G,R2D,R3I),
(ZA,R1G,R2D,R3J), (ZA,R1G,R2D,R3K), (ZA,R1G,R2D,R3L),
(ZA,R1G,R2D,R3M), (ZA,R1G,R2D,R3N), (ZA,R1G,R2D,R3O),
(ZA,R1G,R2D,R3P), (ZA,R1G,R2D,R3Q), (ZA,R1G,R2D,R3R),
(ZA,R1G,R2E,R3A), (ZA,R1G,R2E,R3B), (ZA,R1G,R2E,R3C),
(ZA,R1G,R2E,R3D), (ZA,R1G,R2E,R3E), (ZA,R1G,R2E,R3F),
(ZA,R1G,R2E,R3G), (ZA,R1G,R2E,R3H), (ZA,R1G,R2E,R3I),
(ZA,R1G,R2E,R3J), (ZA,R1G,R2E,R3K), (ZA,R1G,R2E,R3L),
(ZA,R1G,R2E,R3M), (ZA,R1G,R2E,R3N), (ZA,R1G,R2E,R3O),
(ZA,R1G,R2E,R3P), (ZA,R1G,R2E,R3Q), (ZA,R1G,R2E,R3R),
(ZA,R1G,R2F,R3A), (ZA,R1G,R2F,R3B), (ZA,R1G,R2F,R3C),
(ZA,R1G,R2F,R3D), (ZA,R1G,R2F,R3E), (ZA,R1G,R2F,R3F),
(ZA,R1G,R2F,R3G), (ZA,R1G,R2F,R3H), (ZA,R1G,R2F,R3I),
(ZA,R1G,R2F,R3J), (ZA,R1G,R2F,R3K), (ZA,R1G,R2F,R3L),
(ZA,R1G,R2F,R3M), (ZA,R1G,R2F,R3N), (ZA,R1G,R2F,R3O),
(ZA,R1G,R2F,R3P), (ZA,R1G,R2F,R3Q), (ZA,R1G,R2F,R3R),
(ZA,R1G,R2G,R3A), (ZA,R1G,R2G,R3B), (ZA,R1G,R2G,R3C),
(ZA,R1G,R2G,R3D), (ZA,R1G,R2G,R3E), (ZA,R1G,R2G,R3F),
(ZA,R1G,R2G,R3G), (ZA,R1G,R2G,R3H), (ZA,R1G,R2G,R3I),
(ZA,R1G,R2G,R3J), (ZA,R1G,R2G,R3K), (ZA,R1G,R2G,R3L),
(ZA,R1G,R2G,R3M), (ZA,R1G,R2G,R3N), (ZA,R1G,R2G,R3O),
(ZA,R1G,R2G,R3P), (ZA,R1G,R2G,R3Q), (ZA,R1G,R2G,R3R),
(ZA,R1G,R2H,R3A), (ZA,R1G,R2H,R3B), (ZA,R1G,R2H,R3C),
(ZA,R1G,R2H,R3D), (ZA,R1G,R2H,R3E), (ZA,R1G,R2H,R3F),
(ZA,R1G,R2H,R3G), (ZA,R1G,R2H,R3H), (ZA,R1G,R2H,R3I),
(ZA,R1G,R2H,R3J), (ZA,R1G,R2H,R3K), (ZA,R1G,R2H,R3L),
(ZA,R1G,R2H,R3M), (ZA,R1G,R2H,R3N), (ZA,R1G,R2H,R3O),
(ZA,R1G,R2H,R3P), (ZA,R1G,R2H,R3Q), (ZA,R1G,R2H,R3R),
(ZA,R1G,R2I,R3A), (ZA,R1G,R2I,R3B), (ZA,R1G,R2I,R3C),
(ZA,R1G,R2I,R3D), (ZA,R1G,R2I,R3E), (ZA,R1G,R2I,R3F),
(ZA,R1G,R2I,R3G), (ZA,R1G,R2I,R3H), (ZA,R1G,R2I,R3I), (ZA,R1G,R2I,R3J), (ZA,R1G,R2I,R3K), (ZA,R1G,R2I,R3L), (ZA,R1G,R2I,R3M),
(ZA,R1G,R2I,R3N), (ZA,R1G,R2I,R3O), (ZA,R1G,R2I,R3P),
(ZA,R1G,R2I,R3Q), (ZA,R1G,R2I,R3R), (ZA,R1G,R2J,R3A),
(ZA,R1G,R2J,R3B), (ZA,R1G,R2J,R3C), (ZA,R1G,R2J,R3D),
(ZA,R1G,R2J,R3F), (ZA,R1G,R2J,R3G),
(ZA,R1G,R2J,R3H), (ZA,R1G,R2J,R3I), (ZA,R1G,R2J,R3J),
(ZA,R1G,R2J,R3K), (ZA,R1G,R2J,R3L), (ZA,R1G,R2J,R3M),
(ZA,R1G,R2J,R3N), (ZA,R1G,R2J,R3O), (ZA,R1G,R2J,R3P),
(ZA,R1G,R2J,R3Q), (ZA,R1G,R2J,R3R), (ZA,R1G,R2K,R3A),
(ZA,R1G,R2K,R3C), (ZA,R1G,R2K,R3D),
(ZA,R1G,R2K,R3E), (ZA,R1G,R2K,R3F), (ZA,R1G,R2K,R3G),
(ZA,R1G,R2K,R3H), (ZA,R1G,R2K,R3I), (ZA,R1G,R2K,R3J),
(ZA,R1G,R2K,R3K), (ZA,R1G,R2K,R3L), (ZA,R1G,R2K,R3M),
(ZA,R1G,R2K,R3N), (ZA,R1G,R2K,R3O), (ZA,R1G,R2K,R3P),
(ZA,R1G,R2K,R3R), (ZA,R1G,R2L,R3A),
(ZA,R1G,R2L,R3B), (ZA,R1G,R2L,R3C), (ZA,R1G,R2L,R3D),
(ZA,R1G,R2L,R3E), (ZA,R1G,R2L,R3F), (ZA,R1G,R2L,R3G),
(ZA,R1G,R2L,R3H), (ZA,R1G,R2L,R3I), (ZA,R1G,R2L,R3J),
(ZA,R1G,R2L,R3K), (ZA,R1G,R2L,R3L), (ZA,R1G,R2L,R3M),
(ZA,R1G,R2L,R3O), (ZA,R1G,R2L,R3P),
(ZA,R1G,R2L,R3Q), (ZA,R1G,R2L,R3R), (ZA,R1G,R2M,R3A),
(ZA,R1G,R2M,R3B), (ZA,R1G,R2M,R3C), (ZA,R1G,R2M,R3D),
(ZA,R1G,R2M,R3E), (ZA,R1G,R2M,R3F), (ZA,R1G,R2M,R3G),
(ZA,R1G,R2M,R3H), (ZA,R1G,R2M,R3I), (ZA,R1G,R2M,R3J),
(ZA,R1G,R2M,R3L), (ZA,R1G,R2M,R3M),
(ZA,R1G,R2M,R3N), (ZA,R1G,R2M,R3O), (ZA,R1G,R2M,R3P),
(ZA,R1G,R2M,R3Q), (ZA,R1G,R2M,R3R), (ZA,R1G,R2N,R3A),
(ZA,R1G,R2N,R3B), (ZA,R1G,R2N,R3C), (ZA,R1G,R2N,R3D),
(ZA,R1G,R2N,R3E), (ZA,R1G,R2N,R3F), (ZA,R1G,R2N,R3G),
(ZA,R1G,R2N,R3H), (ZA,R1G,R2N,R3I), (ZA,R1G,R2N,R3J),
(ZA,R1G,R2N,R3K), (ZA,R1G,R2N,R3L), (ZA,R1G,R2N,R3M),
(ZA,R1G,R2N,R3N), (ZA,R1G,R2N,R3O), (ZA,R1G,R2N,R3P),
(ZA,R1G,R2N,R3Q), (ZA,R1G,R2N,R3R), (ZA,R1H,R2A,R3A),
(ZA,R1H,R2A,R3B), (ZA,R1H,R2A,R3C), (ZA,R1H,R2A,R3D),
(ZA,R1H,R2A,R3E), (ZA,R1H,R2A,R3F), (ZA,R1H,R2A,R3G),
(ZA,R1H,R2A,R3H), (ZA,R1H,R2A,R3I), (ZA,R1H,R2A,R3J),
(ZA,R1H,R2A,R3K), (ZA,R1H,R2A,R3L), (ZA,R1H,R2A,R3M),
(ZA,R1H,R2A,R3N), (ZA,R1H,R2A,R3O), (ZA,R1H,R2A,R3P),
(ZA,R1H,R2A,R3Q), (ZA,R1H,R2A,R3R), (ZA,R1H,R2B,R3A),
(ZA,R1H,R2B,R3B), (ZA,R1H,R2B,R3C), (ZA,R1H,R2B,R3D),
(ZA,R1H,R2B,R3E), (ZA,R1H,R2B,R3F), (ZA,R1H,R2B,R3G),
(ZA,R1H,R2B,R3H), (ZA,R1H,R2B,R3I), (ZA,R1H,R2B,R3J),
(ZA,R1H,R2B,R3K), (ZA,R1H,R2B,R3L), (ZA,R1H,R2B,R3M),
(ZA,R1H,R2B,R3N), (ZA,R1H,R2B,R3O), (ZA,R1H,R2B,R3P),
(ZA,R1H,R2B,R3Q), (ZA,R1H,R2B,R3R), (ZA,R1H,R2C,R3A),
(ZA,R1H,R2C,R3B), (ZA,R1H,R2C,R3C), (ZA,R1H,R2C,R3D),
(ZA,R1H,R2C,R3E), (ZA,R1H,R2C,R3F), (ZA,R1H,R2C,R3G),
(ZA,R1H,R2C,R3H), (ZA,R1H,R2C,R3I), (ZA,R1H,R2C,R3J),
(ZA,R1H,R2C,R3K), (ZA,R1H,R2C,R3L), (ZA,R1H,R2C,R3M),
(ZA,R1H,R2C,R3N), (ZA,R1H,R2C,R3O), (ZA,R1H,R2C,R3P),
(ZA,R1H,R2C,R3Q), (ZA,R1H,R2C,R3R), (ZA,R1H,R2D,R3A),
(ZA,R1H,R2D,R3B), (ZA,R1H,R2D,R3C), (ZA,R1H,R2D,R3D),
(ZA,R1H,R2D,R3E), (ZA,R1H,R2D,R3F), (ZA,R1H,R2D,R3G),
(ZA,R1H,R2D,R3H), (ZA,R1H,R2D,R3I), (ZA,R1H,R2D,R3J),
(ZA,R1H,R2D,R3K), (ZA,R1H,R2D,R3L), (ZA,R1H,R2D,R3M),
(ZA,R1H,R2D,R3N), (ZA,R1H,R2D,R3O), (ZA,R1H,R2D,R3P),
(ZA,R1H,R2D,R3Q), (ZA,R1H,R2D,R3R), (ZA,R1H,R2E,R3A),
(ZA,R1H,R2E,R3B), (ZA,R1H,R2E,R3C), (ZA,R1H,R2E,R3D),
(ZA,R1H,R2E,R3E), (ZA,R1H,R2E,R3F), (ZA,R1H,R2E,R3G),
(ZA,R1H,R2E,R3H), (ZA,R1H,R2E,R3I), (ZA,R1H,R2E,R3J),
(ZA,R1H,R2E,R3K), (ZA,R1H,R2E,R3L), (ZA,R1H,R2E,R3M),
(ZA,R1H,R2E,R3N), (ZA,R1H,R2E,R3O), (ZA,R1H,R2E,R3P),
(ZA,R1H,R2E,R3Q), (ZA,R1H,R2E,R3R), (ZA,R1H,R2F,R3A),
(ZA,R1H,R2F,R3B), (ZA,R1H,R2F,R3C), (ZA,R1H,R2F,R3D),
(ZA,R1H,R2F,R3E), (ZA,R1H,R2F,R3F), (ZA,R1H,R2F,R3G),
(ZA,R1H,R2F,R3H), (ZA,R1H,R2F,R3I), (ZA,R1H,R2F,R3J),
(ZA,R1H,R2F,R3K), (ZA,R1H,R2F,R3L), (ZA,R1H,R2F,R3M),
(ZA,R1H,R2F,R3N), (ZA,R1H,R2F,R3O), (ZA,R1H,R2F,R3P),
(ZA,R1H,R2F,R3Q), (ZA,R1H,R2F,R3R), (ZA,R1H,R2G,R3A), (ZA,R1H,R2G,R3B), (ZA,R1H,R2G,R3C), (ZA,R1H,R2G,R3D),
(ZA,R1H,R2G,R3E), (ZA,R1H,R2G,R3F), (ZA,R1H,R2G,R3G),
(ZA,R1H,R2G,R3H), (ZA,R1H,R2G,R3I), (ZA,R1H,R2G,R3J),
(ZA,R1H,R2G,R3K), (ZA,R1H,R2G,R3L), (ZA,R1H,R2G,R3M),
(ZA,R1H,R2G,R3N), (ZA,R1H,R2G,R3O), (ZA,R1H,R2G,R3P),
(ZA,R1H,R2G,R3Q), (ZA,R1H,R2G,R3R), (ZA,R1H,R2H,R3A),
(ZA,R1H,R2H,R3B), (ZA,R1H,R2H,R3C), (ZA,R1H,R2H,R3D),
(ZA,R1H,R2H,R3E), (ZA,R1H,R2H,R3F), (ZA,R1H,R2H,R3G),
(ZA,R1H,R2H,R3H), (ZA,R1H,R2H,R3I), (ZA,R1H,R2H,R3J),
(ZA,R1H,R2H,R3K), (ZA,R1H,R2H,R3L), (ZA,R1H,R2H,R3M),
(ZA,R1H,R2H,R3N), (ZA,R1H,R2H,R3O), (ZA,R1H,R2H,R3P),
(ZA,R1H,R2H,R3Q), (ZA,R1H,R2H,R3R), (ZA,R1H,R2I,R3A),
(ZA,R1H,R2I,R3B), (ZA,R1H,R2I,R3C), (ZA,R1H,R2I,R3D),
(ZA,R1H,R2I,R3E), (ZA,R1H,R2I,R3F), (ZA,R1H,R2I,R3G),
(ZA,R1H,R2I,R3H), (ZA,R1H,R2I,R3I), (ZA,R1H,R2I,R3J), (ZA,R1H,R2I,R3K),
(ZA,R1H,R2I,R3L), (ZA,R1H,R2I,R3M), (ZA,R1H,R2I,R3N),
(ZA,R1H,R2I,R3O), (ZA,R1H,R2I,R3P), (ZA,R1H,R2I,R3Q),
(ZA,R1H,R2I,R3R), (ZA,R1H,R2J,R3A), (ZA,R1H,R2J,R3B),
(ZA,R1H,R2J,R3C), (ZA,R1H,R2J,R3D), (ZA,R1H,R2J,R3E),
(ZA,R1H,R2J,R3F), (ZA,R1H,R2J,R3G), (ZA,R1H,R2J,R3H),
(ZA,R1H,R2J,R3J), (ZA,R1H,R2J,R3K),
(ZA,R1H,R2J,R3L), (ZA,R1H,R2J,R3M), (ZA,R1H,R2J,R3N),
(ZA,R1H,R2J,R3O), (ZA,R1H,R2J,R3P), (ZA,R1H,R2J,R3Q),
(ZA,R1H,R2J,R3R), (ZA,R1H,R2K,R3A), (ZA,R1H,R2K,R3B),
(ZA,R1H,R2K,R3C), (ZA,R1H,R2K,R3D), (ZA,R1H,R2K,R3E),
(ZA,R1H,R2K,R3G), (ZA,R1H,R2K,R3H),
(ZA,R1H,R2K,R3I), (ZA,R1H,R2K,R3J), (ZA,R1H,R2K,R3K),
(ZA,R1H,R2K,R3L), (ZA,R1H,R2K,R3M), (ZA,R1H,R2K,R3N),
(ZA,R1H,R2K,R3O), (ZA,R1H,R2K,R3P), (ZA,R1H,R2K,R3Q),
(ZA,R1H,R2K,R3R), (ZA,R1H,R2L,R3A), (ZA,R1H,R2L,R3B),
(ZA,R1H,R2L,R3C), (ZA,R1H,R2L,R3D), (ZA,R1H,R2L,R3E),
(ZA,R1H,R2L,R3F), (ZA,R1H,R2L,R3G), (ZA,R1H,R2L,R3H),
(ZA,R1H,R2L,R3I), (ZA,R1H,R2L,R3J), (ZA,R1H,R2L,R3K),
(ZA,R1H,R2L,R3L), (ZA,R1H,R2L,R3M), (ZA,R1H,R2L,R3N),
(ZA,R1H,R2L,R3O), (ZA,R1H,R2L,R3P), (ZA,R1H,R2L,R3Q),
(ZA,R1H,R2M,R3A), (ZA,R1H,R2M,R3B),
(ZA,R1H,R2M,R3C), (ZA,R1H,R2M,R3D), (ZA,R1H,R2M,R3E),
(ZA,R1H,R2M,R3F), (ZA,R1H,R2M,R3G), (ZA,R1H,R2M,R3H),
(ZA,R1H,R2M,R3I), (ZA,R1H,R2M,R3J), (ZA,R1H,R2M,R3K),
(ZA,R1H,R2M,R3L), (ZA,R1H,R2M,R3M), (ZA,R1H,R2M,R3N),
(ZA,R1H,R2M,R3P), (ZA,R1H,R2M,R3Q),
(ZA,R1H,R2M,R3R), (ZA,R1H,R2N,R3A), (ZA,R1H,R2N,R3B),
(ZA,R1H,R2N,R3C), (ZA,R1H,R2N,R3D), (ZA,R1H,R2N,R3E),
(ZA,R1H,R2N,R3F), (ZA,R1H,R2N,R3G), (ZA,R1H,R2N,R3H),
(ZA,R1H,R2N,R3I), (ZA,R1H,R2N,R3J), (ZA,R1H,R2N,R3K),
(ZA,R1H,R2N,R3M), (ZA,R1H,R2N,R3N),
(ZA,R1H,R2N,R3O), (ZA,R1H,R2N,R3P), (ZA,R1H,R2N,R3Q),
(ZA,R1H,R2N,R3R), (ZA,R1H,R2A,R3A), (ZA,R1H,R2A,R3B),
(ZA,R1H,R2A,R3C), (ZA,R1H,R2A,R3D), (ZA,R1H,R2A,R3E), (ZA,R1H,R2A,R3F),
(ZA,R1H,R2A,R3G), (ZA,R1H,R2A,R3H), (ZA,R1H,R2A,R3I), (ZA,R1H,R2A,R3J),
(ZA,R1H,R2A,R3K), (ZA,R1H,R2A,R3L), (ZA,R1H,R2A,R3M), (ZA,R1H,R2A,R3N),
(ZA,R1H,R2A,R3O), (ZA,R1H,R2A,R3P), (ZA,R1H,R2A,R3Q), (ZA,R1H,R2A,R3R),
(ZA,R1H,R2B,R3A), (ZA,R1H,R2B,R3B), (ZA,R1H,R2B,R3C), (ZA,R1H,R2B,R3D),
(ZA,R1H,R2B,R3E), (ZA,R1H,R2B,R3F), (ZA,R1H,R2B,R3G), (ZA,R1H,R2B,R3H),
(ZA,R1I,R2B,R3I), (ZA,R1H,R2B,R3J), (ZA,R1H,R2B,R3K), (ZA,R1H,R2B,R3L),
(ZA,R1H,R2B,R3M), (ZA,R1H,R2B,R3N), (ZA,R1H,R2B,R3O), (ZA,R1H,R2B,R3P),
(ZA,R1H,R2B,R3Q), (ZA,R1H,R2B,R3R), (ZA,R1H,R2C,R3A), (ZA,R1H,R2C,R3B),
(ZA,R1H,R2C,R3C), (ZA,R1H,R2C,R3D), (ZA,R1H,R2C,R3E), (ZA,R1H,R2C,R3F),
(ZA,R1H,R2C,R3G), (ZA,R1H,R2C,R3H), (ZA,R1H,R2C,R3I), (ZA,R1H,R2C,R3J),
(ZA,R1H,R2C,R3K), (ZA,R1H,R2C,R3L), (ZA,R1H,R2C,R3M), (ZA,R1H,R2C,R3N),
(ZA,R1H,R2C,R3O), (ZA,R1I,R2C,R3P), (ZA,R1H,R2C,R3Q), (ZA,R1H,R2C,R3R),
(ZA,R1H,R2D,R3A), (ZA,R1H,R2D,R3B), (ZA,R1H,R2D,R3C),
(ZA,R1H,R2D,R3D), (ZA,R1H,R2D,R3E), (ZA,R1H,R2D,R3F),
(ZA,R1H,R2D,R3G), (ZA,R1H,R2D,R3H), (ZA,R1H,R2D,R3I), (ZA,R1H,R2D,R3J),
(ZA,R1I,R2D,R3K), (ZA,R1H,R2D,R3L), (ZA,R1H,R2D,R3M),
(ZA,R1H,R2D,R3N), (ZA,R1H,R2D,R3O), (ZA,R1H,R2D,R3P),
(ZA,R1H,R2D,R3Q), (ZA,R1H,R2D,R3R), (ZA,R1H,R2E,R3A), (ZA,R1H,R2E,R3B),
(ZA,R1H,R2E,R3C), (ZA,R1H,R2E,R3D), (ZA,R1H,R2E,R3E), (ZA,R1H,R2E,R3F),
(ZA,R1H,R2E,R3G), (ZA,R1H,R2E,R3H), (ZA,R1H,R2E,R3I), (ZA,R1H,R2E,R3J), (ZA,R1H,R2E,R3K), (ZA,R1H,R2E,R3L), (ZA,R1H,R2E, R3M), (ZA,R1H,R2E,R3N),
(ZA,R1H,R2E,R3O), (ZA,R1H,R2E,R3P), (ZA,R1H,R2E, R3Q), (ZA,R1H,R2E,R3R),
(ZA,R1H,R2F,R3A), (ZA,R1H,R2F,R3B), (ZA,R1H,R2F, R3C), (ZA,R1H,R2F,R3D),
(ZA,R1H,R2F,R3E), (ZA,R1H,R2F,R3F), (ZA,R1H,R2F, R3G), (ZA,R1H,R2F,R3H),
(ZA,R1H,R2F,R3I), (ZA,R1H,R2F,R3J), (ZA,R1H,R2F, R3K), (ZA,R1H,R2F,R3L),
(ZA,R1H,R2F,R3M), (ZA,R1H,R2F,R3N), (ZA,R1H,R2F, R3O), (ZA,R1H,R2F,R3P),
(ZA,R1H,R2F,R3Q), (ZA,R1H,R2F,R3R), (ZA,R1H,R2G, R3A), (ZA,R1H,R2G,R3B),
(ZA,R1H,R2G,R3C), (ZA,R1H,R2G,R3D), (ZA,R1H,R2G, R3E),
(ZA,R1H,R2G,R3F), (ZA,R1H,R2G,R3G), (ZA,R1H,R2G, R3H), (ZA,R1H,R2G,R3I),
(ZA,R1H,R2G,R3J), (ZA,R1H,R2G,R3K), (ZA,R1H,R2G, R3L), (ZA,R1H,R2G,R3M),
(ZA,R1H,R2G,R3N), (ZA,R1H,R2G,R3O), (ZA,R1H,R2G, R3P),
(ZA,R1H,R2G,R3Q), (ZA,R1H,R2G,R3R), (ZA,R1H,R2H, R3A),
(ZA,R1H,R2H,R3B), (ZA,R1H,R2H,R3C), (ZA,R1H,R2H, R3D),
(ZA,R1H,R2H,R3E), (ZA,R1I,R2H,R3F), (ZA,R1H,R2H, R3G),
(ZA,R1H,R2H,R3H), (ZA,R1H,R2H,R3I), (ZA,R1H,R2H, R3J), (ZA,R1H,R2H,R3K),
(ZA,R1H,R2H,R3L), (ZA,R1H,R2H,R3M), (ZA,R1H,R2H, R3N),
(ZA,R1H,R2H,R3O), (ZA,R1H,R2H,R3P), (ZA,R1H,R2H, R3Q),
(ZA,R1H,R2H,R3R), (ZA,R1H,R2I,R3A), (ZA,R1H,R2I, R3B), (ZA,R1H,R2I,R3C),
(ZA,R1H,R2I,R3D), (ZA,R1H,R2I,R3E), (ZA,R1H,R2I, R3F), (ZA,R1H,R2I,R3G),
(ZA,R1H,R2I,R3H), (ZA,R1H,R2I,R3I), (ZA,R1H,R2I, R3J), (ZA,R1H,R2I,R3K),
(ZA,R1H,R2I,R3L), (ZA,R1H,R2I,R3M), (ZA,R1H,R2I, R3N), (ZA,R1H,R2I,R3O),
(ZA,R1H,R2I,R3P), (ZA,R1H,R2I,R3Q), (ZA,R1H,R2I, R3R), (ZA,R1H,R2J,R3A),
(ZA,R1H,R2J,R3B), (ZA,R1H,R2J,R3C), (ZA,R1H,R2J, R3D), (ZA,R1H,R2J,R3E),
(ZA,R1H,R2J,R3F), (ZA,R1H,R2J,R3G), (ZA,R1H,R2J, R3H), (ZA,R1H,R2J,R3I),
(ZA,R1H,R2J,R3J), (ZA,R1H,R2J,R3K), (ZA,R1H,R2J, R3L), (ZA,R1H,R2J,R3M),
(ZA,R1H,R2J,R3N), (ZA,R1H,R2J,R3O), (ZA,R1H,R2J, R3P), (ZA,R1H,R2J,R3Q),
(ZA,R1H,R2J,R3R), (ZA,R1H,R2K,R3A), (ZA,R1H,R2K, R3B), (ZA,R1H,R2K,R3C),
(ZA,R1H,R2K,R3D), (ZA,R1H,R2K,R3E), (ZA,R1H,R2K, R3F), (ZA,R1H,R2K,R3G),
(ZA,R1H,R2K,R3H), (ZA,R1H,R2K,R3I), (ZA,R1H,R2K, R3J), (ZA,R1H,R2K,R3K),
(ZA,R1H,R2K,R3L), (ZA,R1H,R2K,R3M), (ZA,R1H,R2K, R3N), (ZA,R1H,R2K,R3O),
(ZA,R1H,R2K,R3P), (ZA,R1H,R2K,R3Q), (ZA,R1H,R2K, R3R), (ZA,R1H,R2L,R3A),
(ZA,R1H,R2L,R3B), (ZA,R1H,R2L,R3C), (ZA,R1H,R2L, R3D), (ZA,R1H,R2L,R3E),
(ZA,R1H,R2L,R3F), (ZA,R1H,R2L,R3G), (ZA,R1H,R2L, R3H), (ZA,R1H,R2L,R3I),
(ZA,R1H,R2L,R3J), (ZA,R1H,R2L,R3K), (ZA,R1H,R2L, R3L), (ZA,R1H,R2L,R3M),
(ZA,R1H,R2L,R3N), (ZA,R1H,R2L,R3O), (ZA,R1H,R2L, R3P), (ZA,R1H,R2L,R3Q),
(ZA,R1H,R2L,R3R), (ZA,R1H,R2M,R3A), (ZA,R1H,R2M, R3B),
(ZA,R1H,R2M,R3C), (ZA,R1H,R2M,R3D), (ZA,R1H, R2M,R3E),
(ZA,R1H,R2M,R3F), (ZA,R1H,R2M,R3G), (ZA,R1H, R2M,R3H),
(ZA,R1H,R2M,R3I), (ZA,R1H,R2M,R3J), (ZA,R1H,R2M, R3K), (ZA,R1H,R2M,R3L),
(ZA,R1H,R2M,R3M), (ZA,R1H,R2M,R3N), (ZA,R1H, R2M,R3O),
(ZA,R1H,R2M,R3P), (ZA,R1H,R2M,R3Q), (ZA,R1H, R2M,R3R),
(ZA,R1H,R2N,R3A), (ZA,R1H,R2N,R3B), (ZA,R1H,R2N, R3C), (ZA,R1H,R2N,R3D),
(ZA,R1H,R2N,R3E), (ZA,R1H,R2N,R3F), (ZA,R1H,R2N, R3G), (ZA,R1H,R2N,R3H),
(ZA,R1H,R2N,R3I), (ZA,R1H,R2N,R3J), (ZA,R1H,R2N, R3K), (ZA,R1H,R2N,R3L),
(ZA,R1H,R2N,R3M), (ZA,R1H,R2N,R3N), (ZA,R1H,R2N, R3O), (ZA,R1H,R2N,R3P),
(ZA,R1H,R2N,R3Q), (ZA,R1H,R2N,R3R), (ZA,R1J,R2A, R3A),
(ZA,R1J,R2A,R3C), (ZA,R1J,R2A,R3D),
(ZA,R1J,R2A,R3E), (ZA,R1J,R2A,R3F), (ZA,R1J,R2A, R3G),
(ZA,R1J,R2A,R3H), (ZA,R1J,R2A,R3I), (ZA,R1J,R2A, R3J),
(ZA,R1J,R2A,R3K), (ZA,R1J,R2A,R3L), (ZA,R1J,R2A, R3M),
(ZA,R1J,R2A,R3N), (ZA,R1J,R2A,R3O), (ZA,R1J,R2A, R3P),
(ZA,R1J,R2A,R3R), (ZA,R1J,R2B,R3A),
(ZA,R1J,R2B,R3B), (ZA,R1J,R2B,R3C), (ZA,R1J,R2B, R3D),
(ZA,R1J,R2B,R3E), (ZA,R1J,R2B,R3F), (ZA,R1J,R2B, R3G),
(ZA,R1J,R2B,R3H), (ZA,R1J,R2B,R3I), (ZA,R1J,R2B, R3J),
(ZA,R1J,R2B,R3K), (ZA,R1J,R2B,R3L), (ZA,R1J,R2B, R3M),
(ZA,R1J,R2B,R3O), (ZA,R1J,R2B,R3P),
(ZA,R1J,R2B,R3Q), (ZA,R1J,R2B,R3R), (ZA,R1J,R2C, R3A),
(ZA,R1J,R2C,R3B), (ZA,R1J,R2C,R3C), (ZA,R1J,R2C, R3D),
(ZA,R1J,R2C,R3E), (ZA,R1J,R2C,R3F), (ZA,R1J,R2C, R3G),
(ZA,R1J,R2C,R3H), (ZA,R1J,R2C,R3I), (ZA,R1J,R2C, R3J),
(ZA,R1J,R2C,R3L), (ZA,R1J,R2C,R3M),
(ZA,R1J,R2C,R3N), (ZA,R1J,R2C,R3O), (ZA,R1J,R2C, R3P),
(ZA,R1J,R2C,R3Q), (ZA,R1J,R2C,R3R), (ZA,R1J,R2D, R3A),
(ZA,R1J,R2D,R3B), (ZA,R1J,R2D,R3C), (ZA,R1J,R2D, R3D),
(ZA,R1J,R2D,R3E), (ZA,R1J,R2D,R3F), (ZA,R1J,R2D, R3G),
(ZA,R1J,R2D,R3H), (ZA,R1J,R2D,R3I),
(ZA,R1J,R2D,R3K), (ZA,R1J,R2D,R3L), (ZA,R1J,R2D, R3M),
(ZA,R1J,R2D,R3N), (ZA,R1J,R2D,R3O), (ZA,R1J,R2D, R3P), (ZA,R1J,R2D,R3Q), (ZA,R1J,R2D,R3R), (ZA,R1J,R2E,R3A),
(ZA,R1J,R2E,R3B), (ZA,R1J,R2E,R3C), (ZA,R1J,R2E,R3D),
(ZA,R1J,R2E,R3E), (ZA,R1J,R2E,R3F), (ZA,R1J,R2E,R3G),
(ZA,R1J,R2E,R3H), (ZA,R1J,R2E,R3I), (ZA,R1J,R2E,R3J),
(ZA,R1J,R2E,R3K), (ZA,R1J,R2E,R3L), (ZA,R1J,R2E,R3M),
(ZA,R1J,R2E,R3N), (ZA,R1J,R2E,R3O), (ZA,R1J,R2E,R3P),
(ZA,R1J,R2E,R3Q), (ZA,R1J,R2E,R3R), (ZA,R1J,R2F,R3A),
(ZA,R1J,R2F,R3B), (ZA,R1J,R2F,R3C), (ZA,R1J,R2F,R3D),
(ZA,R1J,R2F,R3E), (ZA,R1J,R2F,R3F), (ZA,R1J,R2F,R3G),
(ZA,R1J,R2F,R3H), (ZA,R1J,R2F,R3I), (ZA,R1J,R2F,R3J), (ZA,R1J,R2F,R3K),
(ZA,R1J,R2F,R3L), (ZA,R1J,R2F,R3M), (ZA,R1J,R2F,R3N),
(ZA,R1J,R2F,R3O), (ZA,R1J,R2F,R3P), (ZA,R1J,R2F,R3Q),
(ZA,R1J,R2F,R3R), (ZA,R1J,R2G,R3A), (ZA,R1J,R2G,R3B),
(ZA,R1J,R2G,R3C), (ZA,R1J,R2G,R3D), (ZA,R1J,R2G,R3E),
(ZA,R1J,R2G,R3F), (ZA,R1J,R2G,R3G), (ZA,R1J,R2G,R3H),
(ZA,R1J,R2G,R3I), (ZA,R1J,R2G,R3J), (ZA,R1J,R2G,R3K),
(ZA,R1J,R2G,R3L), (ZA,R1J,R2G,R3M), (ZA,R1J,R2G,R3N),
(ZA,R1J,R2G,R3O), (ZA,R1J,R2G,R3P), (ZA,R1J,R2G,R3Q),
(ZA,R1J,R2G,R3R), (ZA,R1J,R2H,R3A), (ZA,R1J,R2H,R3B),
(ZA,R1J,R2H,R3C), (ZA,R1J,R2H,R3D), (ZA,R1J,R2H,R3E),
(ZA,R1J,R2H,R3F), (ZA,R1J,R2H,R3G), (ZA,R1J,R2H,R3H),
(ZA,R1J,R2H,R3I), (ZA,R1J,R2H,R3J), (ZA,R1J,R2H,R3K),
(ZA,R1J,R2H,R3L), (ZA,R1J,R2H,R3M), (ZA,R1J,R2H,R3N),
(ZA,R1J,R2H,R3O), (ZA,R1J,R2H,R3P), (ZA,R1J,R2H,R3Q),
(ZA,R1J,R2H,R3R), (ZA,R1J,R2I,R3A), (ZA,R1J,R2I,R3B), (ZA,R1J,R2I,R3C),
(ZA,R1J,R2I,R3D), (ZA,R1J,R2I,R3E), (ZA,R1J,R2I,R3F), (ZA,R1J,R2I,R3G),
(ZA,R1J,R2I,R3H), (ZA,R1J,R2I,R3I), (ZA,R1J,R2I,R3J), (ZA,R1J,R2I,R3K),
(ZA,R1J,R2I,R3L), (ZA,R1J,R2I,R3M), (ZA,R1J,R2I,R3N), (ZA,R1J,R2I,R3O),
(ZA,R1J,R2I,R3P), (ZA,R1J,R2I,R3Q), (ZA,R1J,R2I,R3R), (ZA,R1J,R2J,R3A),
(ZA,R1J,R2J,R3B), (ZA,R1J,R2J,R3C), (ZA,R1J,R2J,R3D),
(ZA,R1J,R2J,R3E), (ZA,R1J,R2J,R3F), (ZA,R1J,R2J,R3G),
(ZA,R1J,R2J,R3H), (ZA,R1J,R2J,R3I), (ZA,R1J,R2J,R3J), (ZA,R1J,R2J,R3K),
(ZA,R1J,R2J,R3L), (ZA,R1J,R2J,R3M), (ZA,R1J,R2J,R3N),
(ZA,R1J,R2J,R3O), (ZA,R1J,R2J,R3P), (ZA,R1J,R2J,R3Q),
(ZA,R1J,R2J,R3R), (ZA,R1J,R2K,R3A), (ZA,R1J,R2K,R3B),
(ZA,R1J,R2K,R3C), (ZA,R1J,R2K,R3D), (ZA,R1J,R2K,R3E),
(ZA,R1J,R2K,R3F), (ZA,R1J,R2K,R3G), (ZA,R1J,R2K,R3H),
(ZA,R1J,R2K,R3I), (ZA,R1J,R2K,R3J), (ZA,R1J,R2K,R3K),
(ZA,R1J,R2K,R3L), (ZA,R1J,R2K,R3M), (ZA,R1J,R2K,R3N),
(ZA,R1J,R2K,R3O), (ZA,R1J,R2K,R3P), (ZA,R1J,R2K,R3Q),
(ZA,R1J,R2K,R3R), (ZA,R1J,R2L,R3A), (ZA,R1J,R2L,R3B),
(ZA,R1J,R2L,R3C), (ZA,R1J,R2L,R3D), (ZA,R1J,R2L,R3E),
(ZA,R1J,R2L,R3F), (ZA,R1J,R2L,R3G), (ZA,R1J,R2L,R3H), (ZA,R1J,R2L,R3I),
(ZA,R1J,R2L,R3J), (ZA,R1J,R2L,R3K), (ZA,R1J,R2L,R3L),
(ZA,R1J,R2L,R3M), (ZA,R1J,R2L,R3N), (ZA,R1J,R2L,R3O),
(ZA,R1J,R2L,R3P), (ZA,R1J,R2L,R3Q), (ZA,R1J,R2L,R3R),
(ZA,R1J,R2M,R3A), (ZA,R1J,R2M,R3B), (ZA,R1J,R2M,R3C),
(ZA,R1J,R2M,R3E), (ZA,R1J,R2M,R3F),
(ZA,R1J,R2M,R3G), (ZA,R1J,R2M,R3H), (ZA,R1J,R2M,R3I),
(ZA,R1J,R2M,R3J), (ZA,R1J,R2M,R3K), (ZA,R1J,R2M,R3L),
(ZA,R1J,R2M,R3M), (ZA,R1J,R2M,R3N), (ZA,R1J,R2M,R3O),
(ZA,R1J,R2M,R3P), (ZA,R1J,R2M,R3Q), (ZA,R1J,R2M,R3R),
(ZA,R1J,R2N,R3B), (ZA,R1J,R2N,R3C),
(ZA,R1J,R2N,R3D), (ZA,R1J,R2N,R3E), (ZA,R1J,R2N,R3F),
(ZA,R1J,R2N,R3G), (ZA,R1J,R2N,R3H), (ZA,R1J,R2N,R3I),
(ZA,R1J,R2N,R3J), (ZA,R1J,R2N,R3K), (ZA,R1J,R2N,R3L),
(ZA,R1J,R2N,R3M), (ZA,R1J,R2N,R3N), (ZA,R1J,R2N,R3O),
(ZA,R1J,R2N,R3Q), (ZA,R1J,R2N,R3R),
(ZA,R1K,R2A,R3A), (ZA,R1K,R2A,R3B), (ZA,R1K,R2A,R3C),
(ZA,R1K,R2A,R3D), (ZA,R1K,R2A,R3E), (ZA,R1K,R2A,R3F),
(ZA,R1K,R2A,R3G), (ZA,R1K,R2A,R3H), (ZA,R1K,R2A,R3I),
(ZA,R1K,R2A,R3J), (ZA,R1K,R2A,R3K), (ZA,R1K,R2A,R3L),
(ZA,R1K,R2A,R3N), (ZA,R1K,R2A,R3O),
(ZA,R1K,R2A,R3P), (ZA,R1K,R2A,R3Q), (ZA,R1K,R2A,R3R),
(ZA,R1K,R2B,R3A), (ZA,R1K,R2B,R3B), (ZA,R1K,R2B,R3C),
(ZA,R1K,R2B,R3D), (ZA,R1K,R2B,R3E), (ZA,R1K,R2B,R3F),
(ZA,R1K,R2B,R3G), (ZA,R1K,R2B,R3H), (ZA,R1K,R2B,R3I),
(ZA,R1K,R2B,R3J), (ZA,R1K,R2B,R3K), (ZA,R1K,R2B,R3L), (ZA,R1K,R2B,R3M), (ZA,R1K,R2B,R3N), (ZA,R1K,R2B,R3O),
(ZA,R1K,R2B,R3P), (ZA,R1K,R2B,R3Q), (ZA,R1K,R2B,R3R),
(ZA,R1K,R2C,R3A), (ZA,R1K,R2C,R3B), (ZA,R1K,R2C,R3C),
(ZA,R1K,R2C,R3D), (ZA,R1K,R2C,R3E), (ZA,R1K,R2C,R3F),
(ZA,R1K,R2C,R3G), (ZA,R1K,R2C,R3H), (ZA,R1K,R2C,R3I),
(ZA,R1K,R2C,R3J), (ZA,R1K,R2C,R3K), (ZA,R1K,R2C,R3L),
(ZA,R1K,R2C,R3M), (ZA,R1K,R2C,R3N), (ZA,R1K,R2C,R3O),
(ZA,R1K,R2C,R3P), (ZA,R1K,R2C,R3Q), (ZA,R1K,R2C,R3R),
(ZA,R1K,R2D,R3A), (ZA,R1K,R2D,R3B), (ZA,R1K,R2D,R3C),
(ZA,R1K,R2D,R3D), (ZA,R1K,R2D,R3E), (ZA,R1K,R2D,R3F),
(ZA,R1K,R2D,R3G), (ZA,R1K,R2D,R3H), (ZA,R1K,R2D,R3I),
(ZA,R1K,R2D,R3J), (ZA,R1K,R2D,R3K), (ZA,R1K,R2D,R3L),
(ZA,R1K,R2D,R3M), (ZA,R1K,R2D,R3N), (ZA,R1K,R2D,R3O),
(ZA,R1K,R2D,R3P), (ZA,R1K,R2D,R3Q), (ZA,R1K,R2D,R3R),
(ZA,R1K,R2E,R3A), (ZA,R1K,R2E,R3B), (ZA,R1K,R2E,R3C),
(ZA,R1K,R2E,R3D), (ZA,R1K,R2E,R3E), (ZA,R1K,R2E,R3F),
(ZA,R1K,R2E,R3G), (ZA,R1K,R2E,R3H), (ZA,R1K,R2E,R3I),
(ZA,R1K,R2E,R3J), (ZA,R1K,R2E,R3K), (ZA,R1K,R2E,R3L),
(ZA,R1K,R2E,R3M), (ZA,R1K,R2E,R3N), (ZA,R1K,R2E,R3O),
(ZA,R1K,R2E,R3P), (ZA,R1K,R2E,R3Q), (ZA,R1K,R2E,R3R),
(ZA,R1K,R2F,R3A), (ZA,R1K,R2F,R3B), (ZA,R1K,R2F,R3C),
(ZA,R1K,R2F,R3D), (ZA,R1K,R2F,R3E), (ZA,R1K,R2F,R3F),
(ZA,R1K,R2F,R3G), (ZA,R1K,R2F,R3H), (ZA,R1K,R2F,R3I),
(ZA,R1K,R2F,R3J), (ZA,R1K,R2F,R3K), (ZA,R1K,R2F,R3L),
(ZA,R1K,R2F,R3M), (ZA,R1K,R2F,R3N), (ZA,R1K,R2F,R3O),
(ZA,R1K,R2F,R3P), (ZA,R1K,R2F,R3Q), (ZA,R1K,R2F,R3R),
(ZA,R1K,R2G,R3A), (ZA,R1K,R2G,R3B), (ZA,R1K,R2G,R3C),
(ZA,R1K,R2G,R3D), (ZA,R1K,R2G,R3E), (ZA,R1K,R2G,R3F),
(ZA,R1K,R2G,R3G), (ZA,R1K,R2G,R3H), (ZA,R1K,R2G,R3I),
(ZA,R1K,R2G,R3J), (ZA,R1K,R2G,R3K), (ZA,R1K,R2G,R3L),
(ZA,R1K,R2G,R3M), (ZA,R1K,R2G,R3N), (ZA,R1K,R2G,R3O),
(ZA,R1K,R2G,R3P), (ZA,R1K,R2G,R3Q), (ZA,R1K,R2G,R3R),
(ZA,R1K,R2H,R3A), (ZA,R1K,R2H,R3B), (ZA,R1K,R2H,R3C),
(ZA,R1K,R2H,R3D), (ZA,R1K,R2H,R3E), (ZA,R1K,R2H,R3F),
(ZA,R1K,R2H,R3G), (ZA,R1K,R2H,R3H), (ZA,R1K,R2H,R3I),
(ZA,R1K,R2H,R3J), (ZA,R1K,R2H,R3K), (ZA,R1K,R2H,R3L),
(ZA,R1K,R2H,R3M), (ZA,R1K,R2H,R3N), (ZA,R1K,R2H,R3O),
(ZA,R1K,R2H,R3P), (ZA,R1K,R2H,R3Q), (ZA,R1K,R2H,R3R),
(ZA,R1K,R2I,R3A), (ZA,R1K,R2I,R3B), (ZA,R1K,R2I,R3C), (ZA,R1K,R2I,R3D),
(ZA,R1K,R2I,R3E), (ZA,R1K,R2I,R3F), (ZA,R1K,R2I,R3G), (ZA,R1K,R2I,R3H),
(ZA,R1K,R2I,R3I), (ZA,R1K,R2I,R3J), (ZA,R1K,R2I,R3K), (ZA,R1K,R2I,R3L),
(ZA,R1K,R2I,R3M), (ZA,R1K,R2I,R3N), (ZA,R1K,R2I,R3O), (ZA,R1K,R2I,R3P),
(ZA,R1K,R2I,R3Q), (ZA,R1K,R2I,R3R), (ZA,R1K,R2J,R3A),
(ZA,R1K,R2J,R3B), (ZA,R1K,R2J,R3C), (ZA,R1K,R2J,R3D),
(ZA,R1K,R2J,R3F), (ZA,R1K,R2J,R3G),
(ZA,R1K,R2J,R3H), (ZA,R1K,R2J,R3I), (ZA,R1K,R2J,R3J),
(ZA,R1K,R2J,R3K), (ZA,R1K,R2J,R3L), (ZA,R1K,R2J,R3M),
(ZA,R1K,R2J,R3N), (ZA,R1K,R2J,R3O), (ZA,R1K,R2J,R3P),
(ZA,R1K,R2J,R3Q), (ZA,R1K,R2J,R3R), (ZA,R1K,R2K,R3A),
(ZA,R1K,R2K,R3C), (ZA,R1K,R2K,R3D),
(ZA,R1K,R2K,R3E), (ZA,R1K,R2K,R3F), (ZA,R1K,R2K,R3G),
(ZA,R1K,R2K,R3H), (ZA,R1K,R2K,R3I), (ZA,R1K,R2K,R3J),
(ZA,R1K,R2K,R3K), (ZA,R1K,R2K,R3L), (ZA,R1K,R2K,R3M),
(ZA,R1K,R2K,R3N), (ZA,R1K,R2K,R3O), (ZA,R1K,R2K,R3P),
(ZA,R1K,R2K,R3R), (ZA,R1K,R2L,R3A),
(ZA,R1K,R2L,R3B), (ZA,R1K,R2L,R3C), (ZA,R1K,R2L,R3D),
(ZA,R1K,R2L,R3E), (ZA,R1K,R2L,R3F), (ZA,R1K,R2L,R3G),
(ZA,R1K,R2L,R3H), (ZA,R1K,R2L,R3I), (ZA,R1K,R2L,R3J),
(ZA,R1K,R2L,R3K), (ZA,R1K,R2L,R3L), (ZA,R1K,R2L,R3M),
(ZA,R1K,R2L,R3O), (ZA,R1K,R2L,R3P),
(ZA,R1K,R2L,R3Q), (ZA,R1K,R2L,R3R), (ZA,R1K,R2M,R3A),
(ZA,R1K,R2M,R3B), (ZA,R1K,R2M,R3C), (ZA,R1K,R2M,R3D),
(ZA,R1K,R2M,R3E), (ZA,R1K,R2M,R3F), (ZA,R1K,R2M,R3G),
(ZA,R1K,R2M,R3H), (ZA,R1K,R2M,R3I), (ZA,R1K,R2M,R3J),
(ZA,R1K,R2M,R3L), (ZA,R1K,R2M,R3M),
(ZA,R1K,R2M,R3N), (ZA,R1K,R2M,R3O), (ZA,R1K,R2M,R3P),
(ZA,R1K,R2M,R3Q), (ZA,R1K,R2M,R3R), (ZA,R1K,R2N,R3A),
(ZA,R1K,R2N,R3B), (ZA,R1K,R2N,R3C), (ZA,R1K,R2N,R3D),
(ZA,R1K,R2N,R3E), (ZA,R1K,R2N,R3F), (ZA,R1K,R2N,R3G), (ZA,R1K,R2N,R3H), (ZA,R1K,R2N,R3I), (ZA,R1K,R2N,R3J),
(ZA,R1K,R2N,R3K), (ZA,R1K,R2N,R3L), (ZA,R1K,R2N,R3M),
(ZA,R1K,R2N,R3N), (ZA,R1K,R2N,R3O), (ZA,R1K,R2N,R3P),
(ZA,R1K,R2N,R3Q), (ZA,R1K,R2N,R3R), (ZA,R1L,R2A,R3A),
(ZA,R1L,R2A,R3B), (ZA,R1L,R2A,R3C), (ZA,R1L,R2A,R3D),
(ZA,R1L,R2A,R3E), (ZA,R1L,R2A,R3F), (ZA,R1L,R2A,R3G),
(ZA,R1L,R2A,R3H), (ZA,R1L,R2A,R3I), (ZA,R1L,R2A,R3J),
(ZA,R1L,R2A,R3K), (ZA,R1L,R2A,R3L), (ZA,R1L,R2A,R3M),
(ZA,R1L,R2A,R3N), (ZA,R1L,R2A,R3O), (ZA,R1L,R2A,R3P),
(ZA,R1L,R2A,R3Q), (ZA,R1L,R2A,R3R), (ZA,R1L,R2B,R3A),
(ZA,R1L,R2B,R3B), (ZA,R1L,R2B,R3C), (ZA,R1L,R2B,R3D),
(ZA,R1L,R2B,R3E), (ZA,R1L,R2B,R3F), (ZA,R1L,R2B,R3G),
(ZA,R1L,R2B,R3H), (ZA,R1L,R2B,R3I), (ZA,R1L,R2B,R3J),
(ZA,R1L,R2B,R3K), (ZA,R1L,R2B,R3L), (ZA,R1L,R2B,R3M),
(ZA,R1L,R2B,R3N), (ZA,R1L,R2B,R3O), (ZA,R1L,R2B,R3P),
(ZA,R1L,R2B,R3Q), (ZA,R1L,R2B,R3R), (ZA,R1L,R2C,R3A),
(ZA,R1L,R2C,R3B), (ZA,R1L,R2C,R3C), (ZA,R1L,R2C,R3D),
(ZA,R1L,R2C,R3E), (ZA,R1L,R2C,R3F), (ZA,R1L,R2C,R3G),
(ZA,R1L,R2C,R3H), (ZA,R1L,R2C,R3I), (ZA,R1L,R2C,R3J),
(ZA,R1L,R2C,R3K), (ZA,R1L,R2C,R3L), (ZA,R1L,R2C,R3M),
(ZA,R1L,R2C,R3N), (ZA,R1L,R2C,R3O), (ZA,R1L,R2C,R3P),
(ZA,R1L,R2C,R3Q), (ZA,R1L,R2C,R3R), (ZA,R1L,R2D,R3A),
(ZA,R1L,R2D,R3B), (ZA,R1L,R2D,R3C), (ZA,R1L,R2D,R3D),
(ZA,R1L,R2D,R3E), (ZA,R1L,R2D,R3F), (ZA,R1L,R2D,R3G),
(ZA,R1L,R2D,R3H), (ZA,R1L,R2D,R3I), (ZA,R1L,R2D,R3J),
(ZA,R1L,R2D,R3K), (ZA,R1L,R2D,R3L), (ZA,R1L,R2D,R3M),
(ZA,R1L,R2D,R3N), (ZA,R1L,R2D,R3O), (ZA,R1L,R2D,R3P),
(ZA,R1L,R2D,R3Q), (ZA,R1L,R2D,R3R), (ZA,R1L,R2E,R3A),
(ZA,R1L,R2E,R3B), (ZA,R1L,R2E,R3C), (ZA,R1L,R2E,R3D),
(ZA,R1L,R2E,R3E), (ZA,R1L,R2E,R3F), (ZA,R1L,R2E,R3G),
(ZA,R1L,R2E,R3H), (ZA,R1L,R2E,R3I), (ZA,R1L,R2E,R3J),
(ZA,R1L,R2E,R3K), (ZA,R1L,R2E,R3L), (ZA,R1L,R2E,R3M),
(ZA,R1L,R2E,R3N), (ZA,R1L,R2E,R3O), (ZA,R1L,R2E,R3P),
(ZA,R1L,R2E,R3Q), (ZA,R1L,R2E,R3R), (ZA,R1L,R2F,R3A),
(ZA,R1L,R2F,R3B), (ZA,R1L,R2F,R3C), (ZA,R1L,R2F,R3D),
(ZA,R1L,R2F,R3E), (ZA,R1L,R2F,R3F), (ZA,R1L,R2F,R3G),
(ZA,R1L,R2F,R3H), (ZA,R1L,R2F,R3I), (ZA,R1L,R2F,R3J), (ZA,R1L,R2F,R3K),
(ZA,R1L,R2F,R3L), (ZA,R1L,R2F,R3M), (ZA,R1L,R2F,R3N),
(ZA,R1L,R2F,R3O), (ZA,R1L,R2F,R3P), (ZA,R1L,R2F,R3Q),
(ZA,R1L,R2F,R3R), (ZA,R1L,R2G,R3A), (ZA,R1L,R2G,R3B),
(ZA,R1L,R2G,R3C), (ZA,R1L,R2G,R3D), (ZA,R1L,R2G,R3E),
(ZA,R1L,R2G,R3F), (ZA,R1L,R2G,R3G), (ZA,R1L,R2G,R3H),
(ZA,R1L,R2G,R3I), (ZA,R1L,R2G,R3J), (ZA,R1L,R2G,R3K),
(ZA,R1L,R2G,R3L), (ZA,R1L,R2G,R3M), (ZA,R1L,R2G,R3N),
(ZA,R1L,R2G,R3O), (ZA,R1L,R2G,R3P), (ZA,R1L,R2G,R3Q),
(ZA,R1L,R2G,R3R), (ZA,R1L,R2H,R3A), (ZA,R1L,R2H,R3B),
(ZA,R1L,R2H,R3C), (ZA,R1L,R2H,R3D), (ZA,R1L,R2H,R3E),
(ZA,R1L,R2H,R3F), (ZA,R1L,R2H,R3G), (ZA,R1L,R2H,R3H),
(ZA,R1L,R2H,R3I), (ZA,R1L,R2H,R3J), (ZA,R1L,R2H,R3K),
(ZA,R1L,R2H,R3L), (ZA,R1L,R2H,R3M), (ZA,R1L,R2H,R3N),
(ZA,R1L,R2H,R3O), (ZA,R1L,R2H,R3P), (ZA,R1L,R2H,R3Q),
(ZA,R1L,R2H,R3R), (ZA,R1L,R21,R3A), (ZA,R1L,R2I,R3B), (ZA,R1L,R2I,R3C),
(ZA,R1L,R2I,R3D), (ZA,R1L,R2I,R3E), (ZA,R1L,R2I,R3F), (ZA,R1L,R2I,R3G),
(ZA,R1L,R2I,R3H), (ZA,R1L,R2I,R3I), (ZA,R1L,R2I,R3J), (ZA,R1L,R2I,R3K),
(ZA,R1L,R2I,R3L), (ZA,R1L,R2I,R3M), (ZA,R1L,R2I,R3N), (ZA,R1L,R2I,R3O),
(ZA,R1L,R2I,R3P), (ZA,R1L,R2I,R3Q), (ZA,R1L,R2I,R3R), (ZA,R1L,R2J,R3A),
(ZA,R1L,R2J,R3B), (ZA,R1L,R2J,R3C), (ZA,R1L,R2J,R3D),
(ZA,R1L,R2J,R3E), (ZA,R1L,R2J,R3F), (ZA,R1L,R2J,R3G),
(ZA,R1L,R2J,R3H), (ZA,R1L,R2J,R3I), (ZA,R1L,R2J,R3J), (ZA,R1L,R2J,R3K),
(ZA,R1L,R2J,R3L), (ZA,R1L,R2J,R3M), (ZA,R1L,R2J,R3N),
(ZA,R1L,R2J,R3P), (ZA,R1L,R2J,R3Q),
(ZA,R1L,R2J,R3R), (ZA,R1L,R2K,R3A), (ZA,R1L,R2K,R3B),
(ZA,R1L,R2K,R3C), (ZA,R1L,R2K,R3D), (ZA,R1L,R2K,R3E),
(ZA,R1L,R2K,R3F), (ZA,R1L,R2K,R3G), (ZA,R1L,R2K,R3H),
(ZA,R1L,R2K,R3I), (ZA,R1L,R2K,R3J), (ZA,R1L,R2K,R3K),
(ZA,R1L,R2K,R3M), (ZA,R1L,R2K,R3N),
(ZA,R1L,R2K,R3O), (ZA,R1L,R2K,R3P), (ZA,R1L,R2K,R3Q), (ZA,R1L,R2K,R3R), (ZA,R1L,R2L,R3A), (ZA,R1L,R2L,R3B),
(ZA,R1L,R2L,R3C), (ZA,R1L,R2L,R3D), (ZA,R1L,R2L,R3E),
(ZA,R1L,R2L,R3F), (ZA,R1L,R2L,R3G), (ZA,R1L,R2L,R3H), (ZA,R1L,R2L,R3I),
(ZA,R1L,R2L,R3J), (ZA,R1L,R2L,R3K), (ZA,R1L,R2L,R3L),
(ZA,R1L,R2L,R3M), (ZA,R1L,R2L,R3N), (ZA,R1L,R2L,R3O),
(ZA,R1L,R2L,R3P), (ZA,R1L,R2L,R3Q), (ZA,R1L,R2L,R3R),
(ZA,R1L,R2M,R3A), (ZA,R1L,R2M,R3B), (ZA,R1L,R2M,R3C), (ZA,R1L,R2M,R3D), (ZA,R1L,R2M,R3E), (ZA,R1L,R2M,R3F), (ZA,R1L,R2M,R3G), (ZA,R1L,R2M,R3H), (ZA,R1L,R2M,R3I),
(ZA,R1L,R2M,R3J), (ZA,R1L,R2M,R3K), (ZA,R1L,R2M,R3L),
(ZA,R1L,R2M,R3M), (ZA,R1L,R2M,R3N), (ZA,R1L,R2M,R3O),
(ZA,R1L,R2M,R3P), (ZA,R1L,R2M,R3Q), (ZA,R1L,R2M,R3R),
(ZA,R1L,R2N,R3A), (ZA,R1L,R2N,R3B), (ZA,R1L,R2N,R3C),
(ZA,R1L,R2N,R3D), (ZA,R1L,R2N,R3E), (ZA,R1L,R2N,R3F),
(ZA,R1L,R2N,R3G), (ZA,R1L,R2N,R3H), (ZA,R1L,R2N,R3I),
(ZA,R1L,R2N,R3J), (ZA,R1L,R2N,R3K), (ZA,R1L,R2N,R3L),
(ZA,R1L,R2N,R3M), (ZA,R1L,R2N,R3N), (ZA,R1L,R2N,R3O),
(ZA,R1L,R2N,R3P), (ZA,R1L,R2N,R3Q), (ZA,R1L,R2N,R3R),
(ZA,R1M,R2A,R3A), (ZA,R1M,R2A,R3B), (ZA,R1M,R2A,R3C),
(ZA,R1M,R2A,R3D), (ZA,R1M,R2A,R3E), (ZA,R1M,R2A,R3F),
(ZA,R1M,R2A,R3G), (ZA,R1M,R2A,R3H), (ZA,R1M,R2A,R3I),
(ZA,R1M,R2A,R3J), (ZA,R1M,R2A,R3K), (ZA,R1M,R2A,R3L),
(ZA,R1M,R2A,R3M), (ZA,R1M,R2A,R3N), (ZA,R1M,R2A,R3O),
(ZA,R1M,R2A,R3P), (ZA,R1M,R2A,R3Q), (ZA,R1M,R2A,R3R),
(ZA,R1M,R2B,R3A), (ZA,R1M,R2B,R3B), (ZA,R1M,R2B,R3C),
(ZA,R1M,R2B,R3D), (ZA,R1M,R2B,R3E), (ZA,R1M,R2B,R3F),
(ZA,R1M,R2B,R3G), (ZA,R1M,R2B,R3H), (ZA,R1M,R2B,R3I),
(ZA,R1M,R2B,R3J), (ZA,R1M,R2B,R3K), (ZA,R1M,R2B,R3L),
(ZA,R1M,R2B,R3M), (ZA,R1M,R2B,R3N), (ZA,R1M,R2B,R3O),
(ZA,R1M,R2B,R3P), (ZA,R1M,R2B,R3Q), (ZA,R1M,R2B,R3R),
(ZA,R1M,R2C,R3A), (ZA,R1M,R2C,R3B), (ZA,R1M,R2C,R3C),
(ZA,R1M,R2C,R3D), (ZA,R1M,R2C,R3E), (ZA,R1M,R2C,R3F),
(ZA,R1M,R2C,R3G), (ZA,R1M,R2C,R3H), (ZA,R1M,R2C,R3I),
(ZA,R1M,R2C,R3J), (ZA,R1M,R2C,R3K), (ZA,R1M,R2C,R3L),
(ZA,R1M,R2C,R3M), (ZA,R1M,R2C,R3N), (ZA,R1M,R2C,R3O),
(ZA,R1M,R2C,R3P), (ZA,R1M,R2C,R3Q), (ZA,R1M,R2C,R3R),
(ZA,R1M,R2D,R3A), (ZA,R1M,R2D,R3B), (ZA,R1M,R2D,R3C),
(ZA,R1M,R2D,R3D), (ZA,R1M,R2D,R3E), (ZA,R1M,R2D,R3F),
(ZA,R1M,R2D,R3G), (ZA,R1M,R2D,R3H), (ZA,R1M,R2D,R3I),
(ZA,R1M,R2D,R3J), (ZA,R1M,R2D,R3K), (ZA,R1M,R2D,R3L),
(ZA,R1M,R2D,R3M), (ZA,R1M,R2D,R3N), (ZA,R1M,R2D,R3O),
(ZA,R1M,R2D,R3P), (ZA,R1M,R2D,R3Q), (ZA,R1M,R2D,R3R),
(ZA,R1M,R2E,R3A), (ZA,R1M,R2E,R3B), (ZA,R1M,R2E,R3C),
(ZA,R1M,R2E,R3D), (ZA,R1M,R2E,R3E), (ZA,R1M,R2E,R3F),
(ZA,R1M,R2E,R3G), (ZA,R1M,R2E,R3H), (ZA,R1M,R2E,R3I),
(ZA,R1M,R2E,R3J), (ZA,R1M,R2E,R3K), (ZA,R1M,R2E,R3L),
(ZA,R1M,R2E,R3M), (ZA,R1M,R2E,R3N), (ZA,R1M,R2E,R3O),
(ZA,R1M,R2E,R3P), (ZA,R1M,R2E,R3Q), (ZA,R1M,R2E,R3R),
(ZA,R1M,R2F,R3A), (ZA,R1M,R2F,R3B), (ZA,R1M,R2F,R3C),
(ZA,R1M,R2F,R3D), (ZA,R1M,R2F,R3E), (ZA,R1M,R2F,R3F),
(ZA,R1M,R2F,R3G), (ZA,R1M,R2F,R3H), (ZA,R1M,R2F,R3I),
(ZA,R1M,R2F,R3J), (ZA,R1M,R2F,R3K), (ZA,R1M,R2F,R3L),
(ZA,R1M,R2F,R3M), (ZA,R1M,R2F,R3N), (ZA,R1M,R2F,R3O),
(ZA,R1M,R2F,R3P), (ZA,R1M,R2F,R3Q), (ZA,R1M,R2F,R3R),
(ZA,R1M,R2G,R3A), (ZA,R1M,R2G,R3B), (ZA,R1M,R2G,R3C),
(ZA,R1M,R2G,R3D), (ZA,R1M,R2G,R3E), (ZA,R1M,R2G,R3F),
(ZA,R1M,R2G,R3G), (ZA,R1M,R2G,R3H), (ZA,R1M,R2G,R3I),
(ZA,R1M,R2G,R3J), (ZA,R1M,R2G,R3K), (ZA,R1M,R2G,R3L),
(ZA,R1M,R2G,R3M), (ZA,R1M,R2G,R3N), (ZA,R1M,R2G,R3O),
(ZA,R1M,R2G,R3P), (ZA,R1M,R2G,R3Q), (ZA,R1M,R2G,R3R),
(ZA,R1M,R2H,R3A), (ZA,R1M,R2H,R3B), (ZA,R1M,R2H,R3C),
(ZA,R1M,R2H,R3D), (ZA,R1M,R2H,R3E), (ZA,R1M,R2H,R3F),
(ZA,R1M,R2H,R3G), (ZA,R1M,R2H,R3H), (ZA,R1M,R2H,R3I),
(ZA,R1M,R2H,R3J), (ZA,R1M,R2H,R3K), (ZA,R1M,R2H,R3L),
(ZA,R1M,R2H,R3M), (ZA,R1M,R2H,R3N), (ZA,R1M,R2H,R3O),
(ZA,R1M,R2H,R3P), (ZA,R1M,R2H,R3Q), (ZA,R1M,R2H,R3R),
(ZA,R1M,R2I,R3A), (ZA,R1M,R21,R3B), (ZA,R1M,R21,R3C), (ZA,R1M,R2I,R3D), (ZA,R1M,R2I,R3E), (ZA,R1M,R2I,R3F),
(ZA,R1M,R2I,R3G), (ZA,R1M,R2I,R3H), (ZA,R1M,R2I,R3I),
(ZA,R1M,R2I,R3J), (ZA,R1M,R2I,R3K), (ZA,R1M,R2I,R3L),
(ZA,R1M,R2I,R3M), (ZA,R1M,R2I,R3N), (ZA,R1M,R2I,R3O),
(ZA,R1M,R2I,R3P), (ZA,R1M,R2I,R3Q), (ZA,R1M,R2I,R3R),
(ZA,R1M,R2J,R3A), (ZA,R1M,R2J,R3B), (ZA,R1M,R2J,R3C),
(ZA,R1M,R2J,R3D), (ZA,R1M,R2J,R3E), (ZA,R1M,R2J,R3F),
(ZA,R1M,R2J,R3G), (ZA,R1M,R2J,R3H), (ZA,R1M,R2J,R3I),
(ZA,R1M,R2J,R3J), (ZA,R1M,R2J,R3K), (ZA,R1M,R2J,R3L),
(ZA,R1M,R2J,R3M), (ZA,R1M,R2J,R3N), (ZA,R1M,R2J,R3O),
(ZA,R1M,R2J,R3P), (ZA,R1M,R2J,R3Q), (ZA,R1M,R2J,R3R),
(ZA,R1M,R2K,R3A), (ZA,R1M,R2K,R3B), (ZA,R1M,R2K,R3C),
(ZA,R1M,R2K,R3D), (ZA,R1M,R2K,R3E), (ZA,R1M,R2K,R3F),
(ZA,R1M,R2K,R3G), (ZA,R1M,R2K,R3H), (ZA,R1M,R2K,R3I),
(ZA,R1M,R2K,R3J),(ZA,R1M,R2K,R3K),(ZA,R1M,R2K,R3L),
(ZA,R1M,R2K,R3M), (ZA,R1M,R2K,R3N), (ZA,R1M,R2K,R3O),
(ZA,R1M,R2K,R3P), (ZA,R1M,R2K,R3Q), (ZA,R1M,R2K,R3R),
(ZA,R1M,R2L,R3A), (ZA,R1M,R2L,R3B), (ZA,R1M,R2L,R3C),
(ZA,R1M,R2L,R3D), (ZA,R1M,R2L,R3E), (ZA,R1M,R2L,R3F),
(ZA,R1M,R2L,R3G),(ZA,R1M,R2L,R3H),(ZA,R1M,R2L,R3I),
(ZA,R1M,R2L,R3J), (ZA,R1M,R2L,R3K), (ZA,R1M,R2L,R3L),
(ZA,R1M,R2L,R3M), (ZA,R1M,R2L,R3N), (ZA,R1M,R2L,R3O),
(ZA,R1M,R2L,R3P), (ZA,R1M,R2L,R3Q), (ZA,R1M,R2L,R3R),
(ZA,R1M,R2M,R3A), (ZA,R1M,R2M,R3B), (ZA,R1M,R2M,R3C),
(ZA,R1M,R2M,R3D), (ZA,R1M,R2M,R3E), (ZA,R1M,R2M,R3F),
(ZA,R1M,R2M,R3G), (ZA,R1M,R2M,R3H), (ZA,R1M,R2M,R3I),
(ZA,R1M,R2M,R3J), (ZA,R1M,R2M,R3K), (ZA,R1M,R2M,R3L),
(ZA,R1M,R2M,R3M), (ZA,R1M,R2M,R3N), (ZA,R1M,R2M,R3O),
(ZA,R1M,R2M,R3P), (ZA,R1M,R2M,R3Q), (ZA,R1M,R2M,R3R),
(ZA,R1M,R2N,R3A), (ZA,R1M,R2N,R3B), (ZA,R1M,R2N,R3C),
(ZA,R1M,R2N,R3D), (ZA,R1M,R2N,R3E), (ZA,R1M,R2N,R3F),
(ZA,R1M,R2N,R3G), (ZA,R1M,R2N,R3H), (ZA,R1M,R2N,R3I),
(ZA,R1M,R2N,R3J),(ZA,R1M,R2N,R3K),(ZA,R1M,R2N,R3L),
(ZA,R1M,R2N,R3M), (ZA,R1M,R2N,R3N), (ZA,R1M,R2N,R3O),
(ZA,R1M,R2N,R3P), (ZA,R1M,R2N,R3Q), (ZA,R1M,R2N,R3R),
(ZA,R1N,R2A,R3A), (ZA,R1N,R2A,R3B), (ZA,R1N,R2A,R3C),
(ZA,R1N,R2A,R3D), (ZA,R1N,R2A,R3E), (ZA,R1N,R2A,R3F),
(ZA,R1N,R2A,R3G), (ZA,R1N,R2A,R3H), (ZA,R1N,R2A,R3I),
(ZA,R1N,R2A,R3J), (ZA,R1N,R2A,R3K), (ZA,R1N,R2A,R3L),
(ZA,R1N,R2A,R3M),(ZA,R1N,R2A,R3N),(ZA,R1N,R2A,R3O),
(ZA,R1N,R2A,R3P), (ZA,R1N,R2A,R3Q), (ZA,R1N,R2A,R3R),
(ZA,R1N,R2B,R3A), (ZA,R1N,R2B,R3B), (ZA,R1N,R2B,R3C),
(ZA,R1N,R2B,R3D), (ZA,R1N,R2B,R3E), (ZA,R1N,R2B,R3F),
(ZA,R1N,R2B,R3G), (ZA,R1N,R2B,R3H), (ZA,R1N,R2B,R3I),
(ZA,R1N,R2B,R3J), (ZA,R1N,R2B,R3K), (ZA,R1N,R2B,R3L),
(ZA,R1N,R2B,R3M), (ZA,R1N,R2B,R3N), (ZA,R1N,R2B,R3O),
(ZA,R1N,R2B,R3P), (ZA,R1N,R2B,R3Q), (ZA,R1N,R2B,R3R),
(ZA,R1N,R2C,R3A), (ZA,R1N,R2C,R3B), (ZA,R1N,R2C,R3C),
(ZA,R1N,R2C,R3D), (ZA,R1N,R2C,R3E), (ZA,R1N,R2C,R3F),
(ZA,R1N,R2C,R3G), (ZA,R1N,R2C,R3H), (ZA,R1N,R2C,R3I),
(ZA,R1N,R2C,R3J), (ZA,R1N,R2C,R3K), (ZA,R1N,R2C,R3L),
(ZA,R1N,R2C,R3M), (ZA,R1N,R2C,R3N), (ZA,R1N,R2C,R3O),
(ZA,R1N,R2C,R3P), (ZA,R1N,R2C,R3Q), (ZA,R1N,R2C,R3R),
(ZA,R1N,R2D,R3A), (ZA,R1N,R2D,R3B), (ZA,R1N,R2D,R3C),
(ZA,R1N,R2D,R3D), (ZA,R1N,R2D,R3E), (ZA,R1N,R2D,R3F),
(ZA,R1N,R2D,R3G), (ZA,R1N,R2D,R3H), (ZA,R1N,R2D,R3I),
(ZA,R1N,R2D,R3J), (ZA,R1N,R2D,R3K), (ZA,R1N,R2D,R3L),
(ZA,R1N,R2D,R3M),(ZA,R1N,R2D,R3N),(ZA,R1N,R2D,R3O),
(ZA,R1N,R2D,R3P), (ZA,R1N,R2D,R3Q), (ZA,R1N,R2D,R3R),
(ZA,R1N,R2E,R3A), (ZA,R1N,R2E,R3B), (ZA,R1N,R2E,R3C),
(ZA,R1N,R2E,R3D), (ZA,R1N,R2E,R3E), (ZA,R1N,R2E,R3F),
(ZA,R1N,R2E,R3G), (ZA,R1N,R2E,R3H), (ZA,R1N,R2E,R3I),
(ZA,R1N,R2E,R3J), (ZA,R1N,R2E,R3K), (ZA,R1N,R2E,R3L),
(ZA,R1N,R2E,R3M), (ZA,R1N,R2E,R3N), (ZA,R1N,R2E,R3O),
(ZA,R1N,R2E,R3P), (ZA,R1N,R2E,R3Q), (ZA,R1N,R2E,R3R),
(ZA,R1N,R2F,R3A), (ZA,R1N,R2F,R3B), (ZA,R1N,R2F,R3C), (ZA,R1N,R2F,R3D), (ZA,R1N,R2F,R3E), (ZA,R1N,R2F,R3F),
(ZA,R1N,R2F,R3G), (ZA,R1N,R2F,R3H), (ZA,R1N,R2F,R3I),
(ZA,R1N,R2F,R3J), (ZA,R1N,R2F,R3K), (ZA,R1N,R2F,R3L),
(ZA,R1N,R2F,R3M), (ZA,R1N,R2F,R3N), (ZA,R1N,R2F,R3O),
(ZA,R1N,R2F,R3P), (ZA,R1N,R2F,R3Q), (ZA,R1N,R2F,R3R),
(ZA,R1N,R2G,R3A), (ZA,R1N,R2G,R3B), (ZA,R1N,R2G,R3C),
(ZA,R1N,R2G,R3D), (ZA,R1N,R2G,R3E), (ZA,R1N,R2G,R3F),
(ZA,R1N,R2G,R3G), (ZA,R1N,R2G,R3H), (ZA,R1N,R2G,R3I),
(ZA,R1N,R2G,R3J), (ZA,R1N,R2G,R3K), (ZA,R1N,R2G,R3L),
(ZA,R1N,R2G,R3M), (ZA,R1N,R2G,R3N), (ZA,R1N,R2G,R3O),
(ZA,R1N,R2G,R3P), (ZA,R1N,R2G,R3Q), (ZA,R1N,R2G,R3R),
(ZA,R1N,R2H,R3A), (ZA,R1N,R2H,R3B), (ZA,R1N,R2H,R3C),
(ZA,R1N,R2H,R3D), (ZA,R1N,R2H,R3E), (ZA,R1N,R2H,R3F),
(ZA,R1N,R2H,R3G), (ZA,R1N,R2H,R3H), (ZA,R1N,R2H,R3I),
(ZA,R1N,R2H,R3J), (ZA,R1N,R2H,R3K), (ZA,R1N,R2H,R3L),
(ZA,R1N,R2H,R3M), (ZA,R1N,R2H,R3N), (ZA,R1N,R2H,R3O),
(ZA,R1N,R2H,R3P), (ZA,R1N,R2H,R3Q), (ZA,R1N,R2H,R3R),
(ZA,R1N,R2I,R3A), (ZA,R1N,R2I,R3B), (ZA,R1N,R2I,R3C), (ZA,R1N,R2I,R3D),
(ZA,R1N,R2I,R3E), (ZA,R1N,R2I,R3F), (ZA,R1N,R2I,R3G), (ZA,R1N,R2I,R3H),
(ZA,R1N,R2I,R3I), (ZA,R1N,R2I,R3J), (ZA,R1N,R2I,R3K), (ZA,R1N,R2I,R3L),
(ZA,R1N,R2I,R3M), (ZA,R1N,R2I,R3N), (ZA,R1N,R2I,R3O), (ZA,R1N,R2I,R3P),
(ZA,R1N,R2I,R3Q), (ZA,R1N,R2I,R3R), (ZA,R1N,R2J,R3A),
(ZA,R1N,R2J,R3B), (ZA,R1N,R2J,R3C), (ZA,R1N,R2J,R3D),
(ZA,R1N,R2J,R3E), (ZA,R1N,R2J,R3F), (ZA,R1N,R2J,R3G),
(ZA,R1N,R2J,R3H), (ZA,R1N,R2J,R3I), (ZA,R1N,R2J,R3J),
(ZA,R1N,R2J,R3L), (ZA,R1N,R2J,R3M),
(ZA,R1N,R2J,R3N), (ZA,R1N,R2J,R3O), (ZA,R1N,R2J,R3P),
(ZA,R1N,R2J,R3Q), (ZA,R1N,R2J,R3R), (ZA,R1N,R2K,R3A),
(ZA,R1N,R2K,R3B), (ZA,R1N,R2K,R3C), (ZA,R1N,R2K,R3D),
(ZA,R1N,R2K,R3E), (ZA,R1N,R2K,R3F), (ZA,R1N,R2K,R3G),
(ZA,R1N,R2K,R3I), (ZA,R1N,R2K,R3J),
(ZA,R1N,R2K,R3K), (ZA,R1N,R2K,R3L), (ZA,R1N,R2K,R3M),
(ZA,R1N,R2K,R3N), (ZA,R1N,R2K,R3O), (ZA,R1N,R2K,R3P),
(ZA,R1N,R2K,R3Q), (ZA,R1N,R2K,R3R), (ZA,R1N,R2L,R3A),
(ZA,R1N,R2L,R3B), (ZA,R1N,R2L,R3C), (ZA,R1N,R2L,R3D),
(ZA,R1N,R2L,R3F), (ZA,R1N,R2L,R3G),
(ZA,R1N,R2L,R3H), (ZA,R1N,R2L,R3I), (ZA,R1N,R2L,R3J),
(ZA,R1N,R2L,R3K), (ZA,R1N,R2L,R3L), (ZA,R1N,R2L,R3M),
(ZA,R1N,R2L,R3N), (ZA,R1N,R2L,R3O), (ZA,R1N,R2L,R3P),
(ZA,R1N,R2L,R3Q), (ZA,R1N,R2L,R3R), (ZA,R1N,R2M,R3A),
(ZA,R1N,R2M,R3C), (ZA,R1N,R2M,R3D),
(ZA,R1N,R2M,R3E), (ZA,R1N,R2M,R3F), (ZA,R1N,R2M,R3G),
(ZA,R1N,R2M,R3H), (ZA,R1N,R2M,R3I), (ZA,R1N,R2M,R3J),
(ZA,R1N,R2M,R3K), (ZA,R1N,R2M,R3L), (ZA,R1N,R2M,R3M),
(ZA,R1N,R2M,R3N), (ZA,R1N,R2M,R3O), (ZA,R1N,R2M,R3P),
(ZA,R1N,R2M,R3Q), (ZA,R1N,R2M,R3R), (ZA,R1N,R2N,R3A),
(ZA,R1N,R2N,R3B), (ZA,R1N,R2N,R3C), (ZA,R1N,R2N,R3D),
(ZA,R1N,R2N,R3E), (ZA,R1N,R2N,R3F), (ZA,R1N,R2N,R3G),
(ZA,R1N,R2N,R3H), (ZA,R1N,R2N,R3I), (ZA,R1N,R2N,R3J),
(ZA,R1N,R2N,R3K), (ZA,R1N,R2N,R3L), (ZA,R1N,R2N,R3M),
(ZA,R1N,R2N,R3N), (ZA,R1N,R2N,R3O), (ZA,R1N,R2N,R3P),
(ZA,R1N,R2N,R3Q), (ZA,R1N,R2N,R3R), (ZA,R1O,R2A,R3A),
(ZA,R1O,R2A,R3B), (ZA,R1O,R2A,R3C), (ZA,R1O,R2A,R3D),
(ZA,R1O,R2A,R3E), (ZA,R1O,R2A,R3F), (ZA,R1O,R2A,R3G),
(ZA,R1O,R2A,R3H), (ZA,R1O,R2A,R3I), (ZA,R1O,R2A,R3J),
(ZA,R1O,R2A,R3K), (ZA,R1O,R2A,R3L), (ZA,R1O,R2A,R3M),
(ZA,R1O,R2A,R3N), (ZA,R1O,R2A,R3O), (ZA,R1O,R2A,R3P),
(ZA,R1O,R2A,R3Q), (ZA,R1O,R2A,R3R), (ZA,R1O,R2B,R3A),
(ZA,R1O,R2B,R3B), (ZA,R1O,R2B,R3C), (ZA,R1O,R2B,R3D),
(ZA,R1O,R2B,R3E), (ZA,R1O,R2B,R3F), (ZA,R1O,R2B,R3G),
(ZA,R1O,R2B,R3H), (ZA,R1O,R2B,R3I), (ZA,R1O,R2B,R3J),
(ZA,R1O,R2B,R3K), (ZA,R1O,R2B,R3L), (ZA,R1O,R2B,R3M),
(ZA,R1O,R2B,R3N), (ZA,R1O,R2B,R3O), (ZA,R1O,R2B,R3P),
(ZA,R1O,R2B,R3Q), (ZA,R1O,R2B,R3R), (ZA,R1O,R2C,R3A),
(ZA,R1O,R2C,R3B), (ZA,R1O,R2C,R3C), (ZA,R1O,R2C,R3D),
(ZA,R1O,R2C,R3E), (ZA,R1O,R2C,R3F), (ZA,R1O,R2C,R3G),
(ZA,R1O,R2C,R3H), (ZA,R1O,R2C,R3I), (ZA,R1O,R2C,R3J),
(ZA,R1O,R2C,R3K), (ZA,R1O,R2C,R3L), (ZA,R1O,R2C,R3M), (ZA,R1O,R2C,R3N), (ZA,R1O,R2C,R3O), (ZA,R1O,R2C,R3P),
(ZA,R1O,R2C,R3Q), (ZA,R1O,R2C,R3R), (ZA,R1O,R2D,R3A),
(ZA,R1O,R2D,R3B), (ZA,R1O,R2D,R3C), (ZA,R1O,R2D,R3D),
(ZA,R1O,R2D,R3E), (ZA,R1O,R2D,R3F), (ZA,R1O,R2D,R3G),
(ZA,R1O,R2D,R3H), (ZA,R1O,R2D,R3I), (ZA,R1O,R2D,R3J),
(ZA,R1O,R2D,R3K), (ZA,R1O,R2D,R3L), (ZA,R1O,R2D,R3M),
(ZA,R1O,R2D,R3N), (ZA,R1O,R2D,R3O), (ZA,R1O,R2D,R3P),
(ZA,R1O,R2D,R3Q), (ZA,R1O,R2D,R3R), (ZA,R1O,R2E,R3A),
(ZA,R1O,R2E,R3B), (ZA,R1O,R2E,R3C), (ZA,R1O,R2E,R3D),
(ZA,R1O,R2E,R3E), (ZA,R1O,R2E,R3F), (ZA,R1O,R2E,R3G),
(ZA,R1O,R2E,R3H), (ZA,R1O,R2E,R3I), (ZA,R1O,R2E,R3J),
(ZA,R1O,R2E,R3K), (ZA,R1O,R2E,R3L), (ZA,R1O,R2E,R3M),
(ZA,R1O,R2E,R3N), (ZA,R1O,R2E,R3O), (ZA,R1O,R2E,R3P),
(ZA,R1O,R2E,R3Q), (ZA,R1O,R2E,R3R), (ZA,R1O,R2F,R3A),
(ZA,R1O,R2F,R3B), (ZA,R1O,R2F,R3C), (ZA,R1O,R2F,R3D),
(ZA,R1O,R2F,R3E), (ZA,R1O,R2F,R3F), (ZA,R1O,R2F,R3G),
(ZA,R1O,R2F,R3H), (ZA,R1O,R2F,R3I), (ZA,R1O,R2F,R3J),
(ZA,R1O,R2F,R3K), (ZA,R1O,R2F,R3L), (ZA,R1O,R2F,R3M),
(ZA,R1O,R2F,R3N), (ZA,R1O,R2F,R3O), (ZA,R1O,R2F,R3P),
(ZA,R1O,R2F,R3Q), (ZA,R1O,R2F,R3R), (ZA,R1O,R2G,R3A),
(ZA,R1O,R2G,R3B), (ZA,R1O,R2G,R3C), (ZA,R1O,R2G,R3D),
(ZA,R1O,R2G,R3E), (ZA,R1O,R2G,R3F), (ZA,R1O,R2G,R3G),
(ZA,R1O,R2G,R3H), (ZA,R1O,R2G,R3I), (ZA,R1O,R2G,R3J),
(ZA,R1O,R2G,R3K), (ZA,R1O,R2G,R3L), (ZA,R1O,R2G,R3M),
(ZA,R1O,R2G,R3N), (ZA,R1O,R2G,R3O), (ZA,R1O,R2G,R3P),
(ZA,R1O,R2G,R3Q), (ZA,R1O,R2G,R3R), (ZA,R1O,R2H,R3A),
(ZA,R1O,R2H,R3B), (ZA,R1O,R2H,R3C), (ZA,R1O,R2H,R3D),
(ZA,R1O,R2H,R3E), (ZA,R1O,R2H,R3F), (ZA,R1O,R2H,R3G),
(ZA,R1O,R2H,R3H), (ZA,R1O,R2H,R3I), (ZA,R1O,R2H,R3J),
(ZA,R1O,R2H,R3K), (ZA,R1O,R2H,R3L), (ZA,R1O,R2H,R3M),
(ZA,R1O,R2H,R3N), (ZA,R1O,R2H,R3O), (ZA,R1O,R2H,R3P),
(ZA,R1O,R2H,R3Q), (ZA,R1O,R2H,R3R), (ZA,R1O,R2I,R3A),
(ZA,R1O,R2I,R3B), (ZA,R1O,R2I,R3C), (ZA,R1O,R2I,R3D),
(ZA,R1O,R2I,R3E), (ZA,R1O,R2I,R3F), (ZA,R1O,R2I,R3G),
(ZA,R1O,R2I,R3H), (ZA,R1O,R2I,R3I), (ZA,R1O,R2I,R3J), (ZA,R1O,R2I,R3K),
(ZA,R1O,R2I,R3L), (ZA,R1O,R2I,R3M), (ZA,R1O,R2I,R3N),
(ZA,R1O,R2I,R3O), (ZA,R1O,R2I,R3P), (ZA,R1O,R2I,R3Q),
(ZA,R1O,R2J,R3A), (ZA,R1O,R2J,R3B),
(ZA,R1O,R2J,R3C), (ZA,R1O,R2J,R3D), (ZA,R1O,R2J,R3E),
(ZA,R1O,R2J,R3F), (ZA,R1O,R2J,R3G), (ZA,R1O,R2J,R3H),
(ZA,R1O,R2J,R3I), (ZA,R1O,R2J,R3J), (ZA,R1O,R2J,R3K),
(ZA,R1O,R2J,R3L), (ZA,R1O,R2J,R3M), (ZA,R1O,R2J,R3N),
(ZA,R1O,R2J,R3P), (ZA,R1O,R2J,R3Q),
(ZA,R1O,R2J,R3R), (ZA,R1O,R2K,R3A), (ZA,R1O,R2K,R3B),
(ZA,R1O,R2K,R3C), (ZA,R1O,R2K,R3D), (ZA,R1O,R2K,R3E),
(ZA,R1O,R2K,R3F), (ZA,R1O,R2K,R3G), (ZA,R1O,R2K,R3H),
(ZA,R1O,R2K,R3I), (ZA,R1O,R2K,R3J), (ZA,R1O,R2K,R3K),
(ZA,R1O,R2K,R3L), (ZA,R1O,R2K,R3M), (ZA,R1O,R2K,R3N),
(ZA,R1O,R2K,R3O), (ZA,R1O,R2K,R3P), (ZA,R1O,R2K,R3Q),
(ZA,R1O,R2K,R3R), (ZA,R1O,R2L,R3A), (ZA,R1O,R2L,R3B),
(ZA,R1O,R2L,R3C), (ZA,R1O,R2L,R3D), (ZA,R1O,R2L,R3E),
(ZA,R1O,R2L,R3F), (ZA,R1O,R2L,R3G), (ZA,R1O,R2L,R3H),
(ZA,R1O,R2L,R3I), (ZA,R1O,R2L,R3J), (ZA,R1O,R2L,R3K),
(ZA,R1O,R2L,R3L), (ZA,R1O,R2L,R3M), (ZA,R1O,R2L,R3N),
(ZA,R1O,R2L,R3O), (ZA,R1O,R2L,R3P), (ZA,R1O,R2L,R3Q),
(ZA,R1O,R2L,R3R), (ZA,R1O,R2M,R3A), (ZA,R1O,R2M,R3B),
(ZA,R1O,R2M,R3C), (ZA,R1O,R2M,R3D), (ZA,R1O,R2M,R3E),
(ZA,R1O,R2M,R3F), (ZA,R1O,R2M,R3G), (ZA,R1O,R2M,R3H),
(ZA,R1O,R2M,R3I), (ZA,R1O,R2M,R3J), (ZA,R1O,R2M,R3K),
(ZA,R1O,R2M,R3L), (ZA,R1O,R2M,R3M), (ZA,R1O,R2M,R3N),
(ZA,R1O,R2M,R3O), (ZA,R1O,R2M,R3P), (ZA,R1O,R2M,R3Q),
(ZA,R1O,R2M,R3R), (ZA,R1O,R2N,R3A), (ZA,R1O,R2N,R3B),
(ZA,R1O,R2N,R3C), (ZA,R1O,R2N,R3D), (ZA,R1O,R2N,R3E),
(ZA,R1O,R2N,R3F), (ZA,R1O,R2N,R3G), (ZA,R1O,R2N,R3H),
(ZA,R1O,R2N,R3I), (ZA,R1O,R2N,R3J), (ZA,R1O,R2N,R3K),
(ZA,R1O,R2N,R3L), (ZA,R1O,R2N,R3M), (ZA,R1O,R2N,R3N),
(ZA,R1O,R2N,R3O), (ZA,R1O,R2N,R3P), (ZA,R1O,R2N,R3Q), (ZA,R1O,R2N,R3R), (ZA,R1P,R2A,R3A), (ZA,R1P,R2A,R3B),
(ZA,R1P,R2A,R3C), (ZA,R1P,R2A,R3D), (ZA,R1P,R2A,R3E),
(ZA,R1P,R2A,R3F), (ZA,R1P,R2A,R3G), (ZA,R1P,R2A,R3H),
(ZA,R1P,R2A,R3I), (ZA,R1P,R2A,R3J), (ZA,R1P,R2A,R3K),
(ZA,R1P,R2A,R3L), (ZA,R1P,R2A,R3M), (ZA,R1P,R2A,R3N),
(ZA,R1P,R2A,R3O), (ZA,R1P,R2A,R3P), (ZA,R1P,R2A,R3Q),
(ZA,R1P,R2A,R3R), (ZA,R1P,R2B,R3A), (ZA,R1P,R2B,R3B),
(ZA,R1P,R2B,R3C), (ZA,R1P,R2B,R3D), (ZA,R1P,R2B,R3E),
(ZA,R1P,R2B,R3F), (ZA,R1P,R2B,R3G), (ZA,R1P,R2B,R3H),
(ZA,R1P,R2B,R3I), (ZA,R1P,R2B,R3J), (ZA,R1P,R2B,R3K),
(ZA,R1P,R2B,R3L), (ZA,R1P,R2B,R3M), (ZA,R1P,R2B,R3N),
(ZA,R1P,R2B,R3O), (ZA,R1P,R2B,R3P), (ZA,R1P,R2B,R3Q),
(ZA,R1P,R2B,R3R), (ZA,R1P,R2C,R3A), (ZA,R1P,R2C,R3B),
(ZA,R1P,R2C,R3C), (ZA,R1P,R2C,R3D), (ZA,R1P,R2C,R3E),
(ZA,R1P,R2C,R3F), (ZA,R1P,R2C,R3G), (ZA,R1P,R2C,R3H),
(ZA,R1P,R2C,R3I), (ZA,R1P,R2C,R3J), (ZA,R1P,R2C,R3K),
(ZA,R1P,R2C,R3L), (ZA,R1P,R2C,R3M), (ZA,R1P,R2C,R3N),
(ZA,R1P,R2C,R3O), (ZA,R1P,R2C,R3P), (ZA,R1P,R2C,R3Q),
(ZA,R1P,R2C,R3R), (ZA,R1P,R2D,R3A), (ZA,R1P,R2D,R3B),
(ZA,R1P,R2D,R3C), (ZA,R1P,R2D,R3D), (ZA,R1P,R2D,R3E),
(ZA,R1P,R2D,R3F), (ZA,R1P,R2D,R3G), (ZA,R1P,R2D,R3H),
(ZA,R1P,R2D,R3I), (ZA,R1P,R2D,R3J), (ZA,R1P,R2D,R3K),
(ZA,R1P,R2D,R3L), (ZA,R1P,R2D,R3M), (ZA,R1P,R2D,R3N),
(ZA,R1P,R2D,R3O), (ZA,R1P,R2D,R3P), (ZA,R1P,R2D,R3Q),
(ZA,R1P,R2D,R3R), (ZA,R1P,R2E,R3A), (ZA,R1P,R2E,R3B),
(ZA,R1P,R2E,R3C), (ZA,R1P,R2E,R3D), (ZA,R1P,R2E,R3E),
(ZA,R1P,R2E,R3F), (ZA,R1P,R2E,R3G), (ZA,R1P,R2E,R3H),
(ZA,R1P,R2E,R3I), (ZA,R1P,R2E,R3J), (ZA,R1P,R2E,R3K),
(ZA,R1P,R2E,R3L), (ZA,R1P,R2E,R3M), (ZA,R1P,R2E,R3N),
(ZA,R1P,R2E,R3O), (ZA,R1P,R2E,R3P), (ZA,R1P,R2E,R3Q),
(ZA,R1P,R2E,R3R), (ZA,R1P,R2F,R3A), (ZA,R1P,R2F,R3B),
(ZA,R1P,R2F,R3C), (ZA,R1P,R2F,R3D), (ZA,R1P,R2F,R3E),
(ZA,R1P,R2F,R3F), (ZA,R1P,R2F,R3G), (ZA,R1P,R2F,R3H),
(ZA,R1P,R2F,R3I), (ZA,R1P,R2F,R3J), (ZA,R1P,R2F,R3K), (ZA,R1P,R2F,R3L),
(ZA,R1P,R2F,R3M), (ZA,R1P,R2F,R3N), (ZA,R1P,R2F,R3O),
(ZA,R1P,R2F,R3P), (ZA,R1P,R2F,R3Q), (ZA,R1P,R2F,R3R),
(ZA,R1P,R2G,R3A), (ZA,R1P,R2G,R3B), (ZA,R1P,R2G,R3C),
(ZA,R1P,R2G,R3D), (ZA,R1P,R2G,R3E), (ZA,R1P,R2G,R3F),
(ZA,R1P,R2G,R3G), (ZA,R1P,R2G,R3H), (ZA,R1P,R2G,R3I),
(ZA,R1P,R2G,R3J), (ZA,R1P,R2G,R3K), (ZA,R1P,R2G,R3L),
(ZA,R1P,R2G,R3M), (ZA,R1P,R2G,R3N), (ZA,R1P,R2G,R3O),
(ZA,R1P,R2G,R3P), (ZA,R1P,R2G,R3Q), (ZA,R1P,R2G,R3R),
(ZA,R1P,R2H,R3A), (ZA,R1P,R2H,R3B), (ZA,R1P,R2H,R3C),
(ZA,R1P,R2H,R3D), (ZA,R1P,R2H,R3E), (ZA,R1P,R2H,R3F),
(ZA,R1P,R2H,R3G), (ZA,R1P,R2H,R3H), (ZA,R1P,R2H,R3I),
(ZA,R1P,R2H,R3J), (ZA,R1P,R2H,R3K), (ZA,R1P,R2H,R3L),
(ZA,R1P,R2H,R3M), (ZA,R1P,R2H,R3N), (ZA,R1P,R2H,R3O),
(ZA,R1P,R2H,R3P), (ZA,R1P,R2H,R3Q), (ZA,R1P,R2H,R3R),
(ZA,R1P,R2I,R3A), (ZA,R1P,R2I,R3B), (ZA,R1P,R2I,R3C), (ZA,R1P,R2I,R3D),
(ZA,R1P,R2I,R3E), (ZA,R1P,R2I,R3F), (ZA,R1P,R2I,R3G), (ZA,R1P,R2I,R3H),
(ZA,R1P,R2I,R3I), (ZA,R1P,R2I,R3J), (ZA,R1P,R2I,R3K), (ZA,R1P,R2I,R3L),
(ZA,R1P,R2I,R3M), (ZA,R1P,R2I,R3N), (ZA,R1P,R2I,R3O), (ZA,R1P,R2I,R3P),
(ZA,R1P,R2I,R3Q), (ZA,R1P,R2I,R3R), (ZA,R1P,R2J,R3A), (ZA,R1P,R2J,R3B),
(ZA,R1P,R2J,R3C), (ZA,R1P,R2J,R3D), (ZA,R1P,R2J,R3E),
(ZA,R1P,R2J,R3F), (ZA,R1P,R2J,R3G), (ZA,R1P,R2J,R3H),
(ZA,R1P,R2J,R3I), (ZA,R1P,R2J,R3J), (ZA,R1P,R2J,R3K), (ZA,R1P,R2J,R3L),
(ZA,R1P,R2J,R3M), (ZA,R1P,R2J,R3N), (ZA,R1P,R2J,R3O),
(ZA,R1P,R2J,R3P), (ZA,R1P,R2J,R3Q), (ZA,R1P,R2J,R3R),
(ZA,R1P,R2K,R3A), (ZA,R1P,R2K,R3B), (ZA,R1P,R2K,R3C),
(ZA,R1P,R2K,R3D), (ZA,R1P,R2K,R3E), (ZA,R1P,R2K,R3F),
(ZA,R1P,R2K,R3G), (ZA,R1P,R2K,R3H), (ZA,R1P,R2K,R3I),
(ZA,R1P,R2K,R3J), (ZA,R1P,R2K,R3K), (ZA,R1P,R2K,R3L),
(ZA,R1P,R2K,R3M), (ZA,R1P,R2K,R3N), (ZA,R1P,R2K,R3O),
(ZA,R1P,R2K,R3P), (ZA,R1P,R2K,R3Q), (ZA,R1P,R2K,R3R),
(ZA,R1P,R2L,R3A), (ZA,R1P,R2L,R3B), (ZA,R1P,R2L,R3C),
(ZA,R1P,R2L,R3D), (ZA,R1P,R2L,R3E), (ZA,R1P,R2L,R3F), (ZA,R1P,R2L,R3G), (ZA,R1P,R2L,R3H), (ZA,R1P,R2L,R3I), (ZA,R1P,R2L,R3J),
(ZA,R1P,R2L,R3K), (ZA,R1P,R2L,R3L), (ZA,R1P,R2L,R3M),
(ZA,R1P,R2L,R3N), (ZA,R1P,R2L,R3O), (ZA,R1P,R2L,R3P),
(ZA,R1P,R2L,R3Q), (ZA,R1P,R2L,R3R), (ZA,R1P,R2M,R3A),
(ZA,R1P,R2M,R3C), (ZA,R1P,R2M,R3D),
(ZA,R1P,R2M,R3E), (ZA,R1P,R2M,R3F), (ZA,R1P,R2M,R3G),
(ZA,R1P,R2M,R3H), (ZA,R1P,R2M,R3I), (ZA,R1P,R2M,R3J),
(ZA,R1P,R2M,R3K), (ZA,R1P,R2M,R3L), (ZA,R1P,R2M,R3M),
(ZA,R1P,R2M,R3N), (ZA,R1P,R2M,R3O), (ZA,R1P,R2M,R3P),
(ZA,R1P,R2M,R3R), (ZA,R1P,R2N,R3A),
(ZA,R1P,R2N,R3B), (ZA,R1P,R2N,R3C), (ZA,R1P,R2N,R3D),
(ZA,R1P,R2N,R3E), (ZA,R1P,R2N,R3F), (ZA,R1P,R2N,R3G),
(ZA,R1P,R2N,R3H), (ZA,R1P,R2N,R3I), (ZA,R1P,R2N,R3J),
(ZA,R1P,R2N,R3K), (ZA,R1P,R2N,R3L), (ZA,R1P,R2N,R3M),
(ZA,R1P,R2N,R3O), (ZA,R1P,R2N,R3P),
(ZA,R1P,R2N,R3Q), (ZA,R1P,R2N,R3R), (ZA,R1Q,R2A,R3A),
(ZA,R1Q,R2A,R3B), (ZA,R1Q,R2A,R3C), (ZA,R1Q,R2A,R3D),
(ZA,R1Q,R2A,R3E), (ZA,R1Q,R2A,R3F), (ZA,R1Q,R2A,R3G),
(ZA,R1Q,R2A,R3H), (ZA,R1Q,R2A,R3I), (ZA,R1Q,R2A,R3J),
(ZA,R1Q,R2A,R3K), (ZA,R1Q,R2A,R3L), (ZA,R1Q,R2A,R3M),
(ZA,R1Q,R2A,R3N), (ZA,R1Q,R2A,R3O), (ZA,R1Q,R2A,R3P),
(ZA,R1Q,R2A,R3Q), (ZA,R1Q,R2A,R3R), (ZA,R1Q,R2B,R3A)
(ZA,R1Q,R2B,R3B), (ZA,R1Q,R2B,R3C), (ZA,R1Q,R2B,R3D),
(ZA,R1Q,R2B,R3E), (ZA,R1Q,R2B,R3F), (ZA,R1Q,R2B,R3G),
(ZA,R1Q,R2B,R3H), (ZA,R1Q,R2B,R3I), (ZA,R1Q,R2B,R3J),
(ZA,R1Q,R2B,R3K), (ZA,R1Q,R2B,R3L), (ZA,R1Q,R2B,R3M),
(ZA,R1Q,R2B,R3N), (ZA,R1Q,R2B,R3O), (ZA,R1Q,R2B,R3P),
(ZA,R1Q,R2B,R3H), (ZA,R1Q,R2B,R3I), (ZA,R1Q,R2B,R3J),
(ZA,R1Q,R2B,R3K), (ZA,R1Q,R2B,R3L), (ZA,R1Q,R2B,R3M),
(ZA,R1Q,R2B,R3N), (ZA,R1Q,R2B,R3O), (ZA,R1Q,R2B,R3P),
(ZA,R1Q,R2B,R3Q), (ZA,R1Q,R2B,R3R), (ZA,R1Q,R2B,R3A),
(ZA,R1Q,R2C,R3B), (ZA,R1Q,R2C,R3C), (ZA,R1Q,R2C,R3D),
(ZA,R1Q,R2C,R3E), (ZA,R1Q,R2C,R3F), (ZA,R1Q,R2C,R3G),
(ZA,R1Q,R2C,R3H), (ZA,R1Q,R2C,R3I), (ZA,R1Q,R2C,R3J),
(ZA,R1Q,R2C,R3K), (ZA,R1Q,R2C,R3L), (ZA,R1Q,R2C,R3M),
(ZA,R1Q,R2C,R3N), (ZA,R1Q,R2C,R3O), (ZA,R1Q,R2C,R3P),
(ZA,R1Q,R2C,R3Q), (ZA,R1Q,R2C,R3R), (ZA,R1Q,R2C,R3A),
(ZA,R1Q,R2C,R3B), (ZA,R1Q,R2C,R3C), (ZA,R1Q,R2C,R3D),
(ZA,R1Q,R2D,R3E), (ZA,R1Q,R2D,R3F), (ZA,R1Q,R2D,R3G),
(ZA,R1Q,R2D,R3H), (ZA,R1Q,R2D,R3I), (ZA,R1Q,R2D,R3J),
(ZA,R1Q,R2D,R3K), (ZA,R1Q,R2D,R3L), (ZA,R1Q,R2D,R3M),
(ZA,R1Q,R2D,R3N), (ZA,R1Q,R2D,R3O), (ZA,R1Q,R2D,R3P),
(ZA,R1Q,R2D,R3Q), (ZA,R1Q,R2D,R3R), (ZA,R1Q,R2E,R3A),
(ZA,R1Q,R2E,R3B), (ZA,R1Q,R2E,R3C), (ZA,R1Q,R2E,R3D),
(ZA,R1Q,R2E,R3E), (ZA,R1Q,R2E,R3F), (ZA,R1Q,R2E,R3G),
(ZA,R1Q,R2E,R3H), (ZA,R1Q,R2E,R3I), (ZA,R1Q,R2E,R3J),
(ZA,R1Q,R2E,R3K), (ZA,R1Q,R2E,R3L), (ZA,R1Q,R2E,R3M),
(ZA,R1Q,R2E,R3N), (ZA,R1Q,R2E,R3O), (ZA,R1Q,R2E,R3P),
(ZA,R1Q,R2E,R3Q), (ZA,R1Q,R2E,R3R), (ZA,R1Q,R2E,R3A),
(ZA,R1Q,R2F,R3B), (ZA,R1Q,R2F,R3C), (ZA,R1Q,R2F,R3D),
(ZA,R1Q,R2F,R3E), (ZA,R1Q,R2F,R3F), (ZA,R1Q,R2F,R3G),
(ZA,R1Q,R2F,R3H), (ZA,R1Q,R2F,R3I), (ZA,R1Q,R2F,R3J),
(ZA,R1Q,R2F,R3K), (ZA,R1Q,R2F,R3L), (ZA,R1Q,R2F,R3M),
(ZA,R1Q,R2F,R3N), (ZA,R1Q,R2F,R3O), (ZA,R1Q,R2F,R3P),
(ZA,R1Q,R2F,R3Q), (ZA,R1Q,R2F,R3R), (ZA,R1Q,R2F,R3A),
(ZA,R1Q,R2G,R3B), (ZA,R1Q,R2G,R3C), (ZA,R1Q,R2G,R3D),
(ZA,R1Q,R2G,R3E), (ZA,R1Q,R2G,R3F), (ZA,R1Q,R2G,R3G),
(ZA,R1Q,R2G,R3H), (ZA,R1Q,R2G,R3I), (ZA,R1Q,R2G,R3J),
(ZA,R1Q,R2G,R3K), (ZA,R1Q,R2G,R3L), (ZA,R1Q,R2G,R3M),
(ZA,R1Q,R2G,R3N), (ZA,R1Q,R2G,R3O), (ZA,R1Q,R2G,R3P),
(ZA,R1Q,R2G,R3Q), (ZA,R1Q,R2G,R3R), (ZA,R1Q,R2G,R3A),
(ZA,R1Q,R2H,R3B), (ZA,R1Q,R2H,R3C), (ZA,R1Q,R2H,R3D),
(ZA,R1Q,R2H,R3E), (ZA,R1Q,R2H,R3F), (ZA,R1Q,R2H,R3G),
(ZA,R1Q,R2H,R3H), (ZA,R1Q,R2H,R3I), (ZA,R1Q,R2H,R3J),
(ZA,R1Q,R2H,R3K), (ZA,R1Q,R2H,R3L), (ZA,R1Q,R2H,R3M),
(ZA,R1Q,R2H,R3N), (ZA,R1Q,R2H,R3O), (ZA,R1Q,R2H,R3P),
(ZA,R1Q,R2H,R3Q), (ZA,R1Q,R2H,R3R), (ZA,R1Q,R2H,R3A),
(ZA,R1Q,R2I,R3B), (ZA,R1Q,R2I,R3C), (ZA,R1Q,R2I,R3D), (ZA,R1Q,R2I,R3E), (ZA,R1Q,R2I,R3F), (ZA,R1Q,R2I,R3G),
(ZA,R1Q,R2I,R3H), (ZA,R1Q,R2I,R3I), (ZA,R1Q,R2I,R3J), (ZA,R1Q,R2I,R3K),
(ZA,R1Q,R2I,R3L), (ZA,R1Q,R2I,R3M), (ZA,R1Q,R2I,R3N),
(ZA,R1Q,R2I,R3O), (ZA,R1Q,R2I,R3P), (ZA,R1Q,R2I,R3Q),
(ZA,R1Q,R2I,R3R), (ZA,R1Q,R2J,R3A), (ZA,R1Q,R2J,R3B),
(ZA,R1Q,R2J,R3C), (ZA,R1Q,R2J,R3D), (ZA,R1Q,R2J,R3E),
(ZA,R1Q,R2J,R3F), (ZA,R1Q,R2J,R3G), (ZA,R1Q,R2J,R3H),
(ZA,R1Q,R2J,R3I), (ZA,R1Q,R2J,R3J), (ZA,R1Q,R2J,R3K),
(ZA,R1Q,R2J,R3L), (ZA,R1Q,R2J,R3M), (ZA,R1Q,R2J,R3N),
(ZA,R1Q,R2J,R3O), (ZA,R1Q,R2J,R3P), (ZA,R1Q,R2J,R3Q),
(ZA,R1Q,R2J,R3R), (ZA,R1Q,R2K,R3A), (ZA,R1Q,R2K,R3B),
(ZA,R1Q,R2K,R3C), (ZA,R1Q,R2K,R3D), (ZA,R1Q,R2K,R3E),
(ZA,R1Q,R2K,R3F), (ZA,R1Q,R2K,R3G), (ZA,R1Q,R2K,R3H),
(ZA,R1Q,R2K,R3I), (ZA,R1Q,R2K,R3J), (ZA,R1Q,R2K,R3K),
(ZA,R1Q,R2K,R3L), (ZA,R1Q,R2K,R3M), (ZA,R1Q,R2K,R3N),
(ZA,R1Q,R2K,R3O), (ZA,R1Q,R2K,R3P), (ZA,R1Q,R2K,R3Q),
(ZA,R1Q,R2K,R3R), (ZA,R1Q,R2L,R3A), (ZA,R1Q,R2L,R3B),
(ZA,R1Q,R2L,R3C), (ZA,R1Q,R2L,R3D), (ZA,R1Q,R2L,R3E),
(ZA,R1Q,R2L,R3F), (ZA,R1Q,R2L,R3G), (ZA,R1Q,R2L,R3H),
(ZA,R1Q,R2L,R3I), (ZA,R1Q,R2L,R3J), (ZA,R1Q,R2L,R3K),
(ZA,R1Q,R2L,R3L), (ZA,R1Q,R2L,R3M), (ZA,R1Q,R2L,R3N),
(ZA,R1Q,R2L,R3O), (ZA,R1Q,R2L,R3P), (ZA,R1Q,R2L,R3Q),
(ZA,R1Q,R2L,R3R), (ZA,R1Q,R2M,R3A), (ZA,R1Q,R2M,R3B),
(ZA,R1Q,R2M,R3C), (ZA,R1Q,R2M,R3D), (ZA,R1Q,R2M,R3E),
(ZA,R1Q,R2M,R3F), (ZA,R1Q,R2M,R3G), (ZA,R1Q,R2M,R3H),
(ZA,R1Q,R2M,R3I), (ZA,R1Q,R2M,R3J), (ZA,R1Q,R2M,R3K),
(ZA,R1Q,R2M,R3L), (ZA,R1Q,R2M,R3M), (ZA,R1Q,R2M,R3N),
(ZA,R1Q,R2M,R3O), (ZA,R1Q,R2M,R3P), (ZA,R1Q,R2M,R3Q),
(ZA,R1Q,R2M,R3R), (ZA,R1Q,R2N,R3A), (ZA,R1Q,R2N,R3B),
(ZA,R1Q,R2N,R3C), (ZA,R1Q,R2N,R3D), (ZA,R1Q,R2N,R3E),
(ZA,R1Q,R2N,R3F), (ZA,R1Q,R2N,R3G), (ZA,R1Q,R2N,R3H),
(ZA,R1Q,R2N,R3I), (ZA,R1Q,R2N,R3J), (ZA,R1Q,R2N,R3K),
(ZA,R1Q,R2N,R3L), (ZA,R1Q,R2N,R3M), (ZA,R1Q,R2N,R3N),
(ZA,R1Q,R2N,R3O), (ZA,R1Q,R2N,R3P), (ZA,R1Q,R2N,R3Q),
(ZA,R1Q,R2N,R3R), (ZA,R1R,R2A,R3A), (ZA,R1R,R2A,R3B),
(ZA,R1R,R2A,R3C), (ZA,R1R,R2A,R3D), (ZA,R1R,R2A,R3E),
(ZA,R1R,R2A,R3F), (ZA,R1R,R2A,R3G), (ZA,R1R,R2A,R3H),
(ZA,R1R,R2A,R3I), (ZA,R1R,R2A,R3J), (ZA,R1R,R2A,R3K),
(ZA,R1R,R2A,R3L), (ZA,R1R,R2A,R3M), (ZA,R1R,R2A,R3N),
(ZA,R1R,R2A,R3O), (ZA,R1R,R2A,R3P), (ZA,R1R,R2A,R3Q),
(ZA,R1R,R2A,R3R), (ZA,R1R,R2B,R3A), (ZA,R1R,R2B,R3B),
(ZA,R1R,R2B,R3C), (ZA,R1R,R2B,R3D), (ZA,R1R,R2B,R3E),
(ZA,R1R,R2B,R3F), (ZA,R1R,R2B,R3G), (ZA,R1R,R2B,R3H),
(ZA,R1R,R2B,R3I), (ZA,R1R,R2B,R3J), (ZA,R1R,R2B,R3K),
(ZA,R1R,R2B,R3L), (ZA,R1R,R2B,R3M), (ZA,R1R,R2B,R3N),
(ZA,R1R,R2B,R3O), (ZA,R1R,R2B,R3P), (ZA,R1R,R2B,R3Q),
(ZA,R1R,R2B,R3R), (ZA,R1R,R2C,R3A), (ZA,R1R,R2C,R3B),
(ZA,R1R,R2C,R3C), (ZA,R1R,R2C,R3D), (ZA,R1R,R2C,R3E),
(ZA,R1R,R2C,R3F), (ZA,R1R,R2C,R3G), (ZA,R1R,R2C,R3H),
(ZA,R1R,R2C,R3I), (ZA,R1R,R2C,R3J), (ZA,R1R,R2C,R3K),
(ZA,R1R,R2C,R3L), (ZA,R1R,R2C,R3M), (ZA,R1R,R2C,R3N),
(ZA,R1R,R2C,R3O), (ZA,R1R,R2C,R3P), (ZA,R1R,R2C,R3Q),
(ZA,R1R,R2C,R3R), (ZA,R1R,R2D,R3A), (ZA,R1R,R2D,R3B),
(ZA,R1R,R2D,R3C), (ZA,R1R,R2D,R3D), (ZA,R1R,R2D,R3E),
(ZA,R1R,R2D,R3F), (ZA,R1R,R2D,R3G), (ZA,R1R,R2D,R3H),
(ZA,R1R,R2D,R3I), (ZA,R1R,R2D,R3J), (ZA,R1R,R2D,R3K),
(ZA,R1R,R2D,R3L), (ZA,R1R,R2D,R3M), (ZA,R1R,R2D,R3N),
(ZA,R1R,R2D,R3O), (ZA,R1R,R2D,R3P), (ZA,R1R,R2D,R3Q),
(ZA,R1R,R2D,R3R), (ZA,R1R,R2E,R3A), (ZA,R1R,R2E,R3B),
(ZA,R1R,R2E,R3C), (ZA,R1R,R2E,R3D), (ZA,R1R,R2E,R3E),
(ZA,R1R,R2E,R3F), (ZA,R1R,R2E,R3G), (ZA,R1R,R2E,R3H),
(ZA,R1R,R2E,R3I), (ZA,R1R,R2E,R3J), (ZA,R1R,R2E,R3K),
(ZA,R1R,R2E,R3L), (ZA,R1R,R2E,R3M), (ZA,R1R,R2E,R3N),
(ZA,R1R,R2E,R3O), (ZA,R1R,R2E,R3P), (ZA,R1R,R2E,R3Q),
(ZA,R1R,R2E,R3R), (ZA,R1R,R2F,R3A), (ZA,R1R,R2F,R3B),
(ZA,R1R,R2F,R3C), (ZA,R1R,R2F,R3D), (ZA,R1R,R2F,R3E), (ZA,R1R,R2F,R3F), (ZA,R1R,R2F,R3G), (ZA,R1R,R2F,R3H),
(ZA,R1R,R2F,R3I), (ZA,R1R,R2F,R3J), (ZA,R1R,R2F,R3K),
(ZA,R1R,R2F,R3L), (ZA,R1R,R2F,R3M), (ZA,R1R,R2F,R3N),
(ZA,R1R,R2F,R3O), (ZA,R1R,R2F,R3P), (ZA,R1R,R2F,R3Q),
(ZA,R1R,R2F,R3R), (ZA,R1R,R2G,R3A), (ZA,R1R,R2G,R3B),
(ZA,R1R,R2G,R3C), (ZA,R1R,R2G,R3D), (ZA,R1R,R2G,R3E),
(ZA,R1R,R2G,R3F), (ZA,R1R,R2G,R3G), (ZA,R1R,R2G,R3H),
(ZA,R1R,R2G,R3I), (ZA,R1R,R2G,R3J), (ZA,R1R,R2G,R3K),
(ZA,R1R,R2G,R3L), (ZA,R1R,R2G,R3M), (ZA,R1R,R2G,R3N),
(ZA,R1R,R2G,R3O), (ZA,R1R,R2G,R3P), (ZA,R1R,R2G,R3Q),
(ZA,R1R,R2G,R3R), (ZA,R1R,R2H,R3A), (ZA,R1R,R2H,R3B),
(ZA,R1R,R2H,R3C), (ZA,R1R,R2H,R3D), (ZA,R1R,R2H,R3E),
(ZA,R1R,R2H,R3F), (ZA,R1R,R2H,R3G), (ZA,R1R,R2H,R3H),
(ZA,R1R,R2H,R3I), (ZA,R1R,R2H,R3J), (ZA,R1R,R2H,R3K),
(ZA,R1R,R2H,R3L), (ZA,R1R,R2H,R3M), (ZA,R1R,R2H,R3N),
(ZA,R1R,R2H,R3O), (ZA,R1R,R2H,R3P), (ZA,R1R,R2H,R3Q),
(ZA,R1R,R2H,R3R), (ZA,R1R,R2I,R3A), (ZA,R1R,R2I,R3B),
(ZA,R1R,R2I,R3C), (ZA,R1R,R2I,R3D), (ZA,R1R,R2I,R3E), (ZA,R1R,R2I,R3F),
(ZA,R1R,R2I,R3G), (ZA,R1R,R2I,R3H), (ZA,R1R,R2I,R3I), (ZA,R1R,R2I,R3J),
(ZA,R1R,R2I,R3K), (ZA,R1R,R2I,R3L), (ZA,R1R,R2I,R3M), (ZA,R1R,R2I,R3N),
(ZA,R1R,R2I,R3O), (ZA,R1R,R2I,R3P), (ZA,R1R,R2I,R3Q), (ZA,R1R,R2I,R3R),
(ZA,R1R,R2J,R3A), (ZA,R1R,R2J,R3B), (ZA,R1R,R2J,R3C),
(ZA,R1R,R2J,R3D), (ZA,R1R,R2J,R3E), (ZA,R1R,R2J,R3F),
(ZA,R1R,R2J,R3H), (ZA,R1R,R2J,R3I),
(ZA,R1R,R2J,R3J), (ZA,R1R,R2J,R3K), (ZA,R1R,R2J,R3L),
(ZA,R1R,R2J,R3M), (ZA,R1R,R2J,R3N), (ZA,R1R,R2J,R3O),
(ZA,R1R,R2J,R3P), (ZA,R1R,R2J,R3Q), (ZA,R1R,R2J,R3R),
(ZA,R1R,R2K,R3A), (ZA,R1R,R2K,R3B), (ZA,R1R,R2K,R3C),
(ZA,R1R,R2K,R3D), (ZA,R1R,R2K,R3E), (ZA,R1R,R2K,R3F),
(ZA,R1R,R2K,R3G), (ZA,R1R,R2K,R3H), (ZA,R1R,R2K,R3I),
(ZA,R1R,R2K,R3J), (ZA,R1R,R2K,R3K), (ZA,R1R,R2K,R3L),
(ZA,R1R,R2K,R3M), (ZA,R1R,R2K,R3N), (ZA,R1R,R2K,R3O),
(ZA,R1R,R2K,R3P), (ZA,R1R,R2K,R3Q), (ZA,R1R,R2K,R3R),
(ZA,R1R,R2L,R3A), (ZA,R1R,R2L,R3B), (ZA,R1R,R2L,R3C),
(ZA,R1R,R2L,R3D), (ZA,R1R,R2L,R3E), (ZA,R1R,R2L,R3F),
(ZA,R1R,R2L,R3G), (ZA,R1R,R2L,R3H), (ZA,R1R,R2L,R3I),
(ZA,R1R,R2L,R3J), (ZA,R1R,R2L,R3K), (ZA,R1R,R2L,R3L),
(ZA,R1R,R2L,R3M), (ZA,R1R,R2L,R3N), (ZA,R1R,R2L,R3O),
(ZA,R1R,R2L,R3P), (ZA,R1R,R2L,R3Q), (ZA,R1R,R2L,R3R),
(ZA,R1R,R2M,R3A), (ZA,R1R,R2M,R3B), (ZA,R1R,R2M,R3C),
(ZA,R1R,R2M,R3D), (ZA,R1R,R2M,R3E), (ZA,R1R,R2M,R3F),
(ZA,R1R,R2M,R3G), (ZA,R1R,R2M,R3H), (ZA,R1R,R2M,R3I),
(ZA,R1R,R2M,R3J), (ZA,R1R,R2M,R3K), (ZA,R1R,R2M,R3L),
(ZA,R1R,R2M,R3M), (ZA,R1R,R2M,R3N), (ZA,R1R,R2M,R3O),
(ZA,R1R,R2M,R3P), (ZA,R1R,R2M,R3Q), (ZA,R1R,R2M,R3R),
(ZA,R1R,R2N,R3A), (ZA,R1R,R2N,R3B), (ZA,R1R,R2N,R3C),
(ZA,R1R,R2N,R3D), (ZA,R1R,R2N,R3E), (ZA,R1R,R2N,R3F),
(ZA,R1R,R2N,R3G), (ZA,R1R,R2N,R3H), (ZA,R1R,R2N,R3I),
(ZA,R1R,R2N,R3J), (ZA,R1R,R2N,R3K), (ZA,R1R,R2N,R3L),
(ZA,R1R,R2N,R3M), (ZA,R1R,R2N,R3N), (ZA,R1R,R2N,R3O),
(ZA,R1R,R2N,R3P), (ZA,R1R,R2N,R3Q), (ZA,R1R,R2N,R3R),
(ZA,R1S,R2A,R3A), (ZA,R1S,R2A,R3B), (ZA,R1S,R2A,R3C),
(ZA,R1S,R2A,R3D), (ZA,R1S,R2A,R3E), (ZA,R1S,R2A,R3F),
(ZA,R1S,R2A,R3G), (ZA,R1S,R2A,R3H), (ZA,R1S,R2A,R3I),
(ZA,R1S,R2A,R3J), (ZA,R1S,R2A,R3K), (ZA,R1S,R2A,R3L),
(ZA,R1S,R2A,R3M), (ZA,R1S,R2A,R3N), (ZA,R1S,R2A,R3O),
(ZA,R1S,R2A,R3P), (ZA,R1S,R2A,R3Q), (ZA,R1S,R2A,R3R),
(ZA,R1S,R2B,R3A), (ZA,R1S,R2B,R3B), (ZA,R1S,R2B,R3C),
(ZA,R1S,R2B,R3D), (ZA,R1S,R2B,R3E), (ZA,R1S,R2B,R3F),
(ZA,R1S,R2B,R3G), (ZA,R1S,R2B,R3H), (ZA,R1S,R2B,R3I),
(ZA,R1S,R2B,R3J), (ZA,R1S,R2B,R3K), (ZA,R1S,R2B,R3L),
(ZA,R1S,R2B,R3M), (ZA,R1S,R2B,R3N), (ZA,R1S,R2B,R3O),
(ZA,R1S,R2B,R3P), (ZA,R1S,R2B,R3Q), (ZA,R1S,R2B,R3R),
(ZA,R1S,R2C,R3A), (ZA,R1S,R2C,R3B), (ZA,R1S,R2C,R3C),
(ZA,R1S,R2C,R3D), (ZA,R1S,R2C,R3E), (ZA,R1S,R2C,R3F),
(ZA,R1S,R2C,R3G), (ZA,R1S,R2C,R3H), (ZA,R1S,R2C,R3I),
(ZA,R1S,R2C,R3J), (ZA,R1S,R2C,R3K), (ZA,R1S,R2C,R3L), (ZA,R1S,R2C,R3M), (ZA,R1S,R2C,R3N), (ZA,R1S,R2C,R3O),
(ZA,R1S,R2C,R3P), (ZA,R1S,R2C,R3Q), (ZA,R1S,R2C,R3R),
(ZA,R1S,R2D,R3A), (ZA,R1S,R2D,R3B), (ZA,R1S,R2D,R3C),
(ZA,R1S,R2D,R3D), (ZA,R1S,R2D,R3E), (ZA,R1S,R2D,R3F),
(ZA,R1S,R2D,R3G), (ZA,R1S,R2D,R3H), (ZA,R1S,R2D,R3I),
(ZA,R1S,R2D,R3J), (ZA,R1S,R2D,R3K), (ZA,R1S,R2D,R3L),
(ZA,R1S,R2D,R3M), (ZA,R1S,R2D,R3N), (ZA,R1S,R2D,R3O),
(ZA,R1S,R2D,R3P), (ZA,R1S,R2D,R3Q), (ZA,R1S,R2D,R3R),
(ZA,R1S,R2E,R3A), (ZA,R1S,R2E,R3B), (ZA,R1S,R2E,R3C),
(ZA,R1S,R2E,R3D), (ZA,R1S,R2E,R3E), (ZA,R1S,R2E,R3F),
(ZA,R1S,R2E,R3G), (ZA,R1S,R2E,R3H), (ZA,R1S,R2E,R3I),
(ZA,R1S,R2E,R3J), (ZA,R1S,R2E,R3K), (ZA,R1S,R2E,R3L),
(ZA,R1S,R2E,R3M), (ZA,R1S,R2E,R3N), (ZA,R1S,R2E,R3O),
(ZA,R1S,R2E,R3P), (ZA,R1S,R2E,R3Q), (ZA,R1S,R2E,R3R),
(ZA,R1S,R2F,R3A), (ZA,R1S,R2F,R3B), (ZA,R1S,R2F,R3C),
(ZA,R1S,R2F,R3D), (ZA,R1S,R2F,R3E), (ZA,R1S,R2F,R3F),
(ZA,R1S,R2F,R3G), (ZA,R1S,R2F,R3H), (ZA,R1S,R2F,R3I),
(ZA,R1S,R2F,R3J), (ZA,R1S,R2F,R3K), (ZA,R1S,R2F,R3L),
(ZA,R1S,R2F,R3M), (ZA,R1S,R2F,R3N), (ZA,R1S,R2F,R3O),
(ZA,R1S,R2F,R3P), (ZA,R1S,R2F,R3Q), (ZA,R1S,R2F,R3R),
(ZA,R1S,R2G,R3A), (ZA,R1S,R2G,R3B), (ZA,R1S,R2G,R3C),
(ZA,R1S,R2G,R3D), (ZA,R1S,R2G,R3E), (ZA,R1S,R2G,R3F),
(ZA,R1S,R2G,R3G), (ZA,R1S,R2G,R3H), (ZA,R1S,R2G,R3I),
(ZA,R1S,R2G,R3J), (ZA,R1S,R2G,R3K), (ZA,R1S,R2G,R3L),
(ZA,R1S,R2G,R3M), (ZA,R1S,R2G,R3N), (ZA,R1S,R2G,R3O),
(ZA,R1S,R2G,R3P), (ZA,R1S,R2G,R3Q), (ZA,R1S,R2G,R3R),
(ZA,R1S,R2H,R3A), (ZA,R1S,R2H,R3B), (ZA,R1S,R2H,R3C),
(ZA,R1S,R2H,R3D), (ZA,R1S,R2H,R3E), (ZA,R1S,R2H,R3F),
(ZA,R1S,R2H,R3G), (ZA,R1S,R2H,R3H), (ZA,R1S,R2H,R3I),
(ZA,R1S,R2H,R3J), (ZA,R1S,R2H,R3K), (ZA,R1S,R2H,R3L),
(ZA,R1S,R2H,R3M), (ZA,R1S,R2H,R3N), (ZA,R1S,R2H,R3O),
(ZA,R1S,R2H,R3P), (ZA,R1S,R2H,R3Q), (ZA,R1S,R2H,R3R),
(ZA,R1S,R2I,R3A), (ZA,R1S,R2I,R3B), (ZA,R1S,R2I,R3C), (ZA,R1S,R2I,R3D),
(ZA,R1S,R2I,R3E), (ZA,R1S,R2I,R3F), (ZA,R1S,R2I,R3G), (ZA,R1S,R2I,R3H),
(ZA,R1S,R2I,R3I), (ZA,R1S,R2I,R3J), (ZA,R1S,R2I,R3K), (ZA,R1S,R2I,R3L),
(ZA,R1S,R2I,R3M), (ZA,R1S,R2I,R3N), (ZA,R1S,R2I,R3O), (ZA,R1S,R2I,R3P),
(ZA,R1S,R2I,R3Q), (ZA,R1S,R2I,R3R), (ZA,R1S,R2J,R3A),
(ZA,R1S,R2J,R3B), (ZA,R1S,R2J,R3C), (ZA,R1S,R2J,R3D),
(ZA,R1S,R2J,R3E), (ZA,R1S,R2J,R3F), (ZA,R1S,R2J,R3G),
(ZA,R1S,R2J,R3H), (ZA,R1S,R2J,R3I), (ZA,R1S,R2J,R3J),
(ZA,R1S,R2J,R3K), (ZA,R1S,R2J,R3L), (ZA,R1S,R2J,R3M),
(ZA,R1S,R2J,R3O), (ZA,R1S,R2J,R3P),
(ZA,R1S,R2J,R3Q), (ZA,R1S,R2J,R3R), (ZA,R1S,R2K,R3A),
(ZA,R1S,R2K,R3B), (ZA,R1S,R2K,R3C), (ZA,R1S,R2K,R3D),
(ZA,R1S,R2K,R3E), (ZA,R1S,R2K,R3F), (ZA,R1S,R2K,R3G),
(ZA,R1S,R2K,R3H), (ZA,R1S,R2K,R3I), (ZA,R1S,R2K,R3J),
(ZA,R1S,R2K,R3L), (ZA,R1S,R2K,R3M),
(ZA,R1S,R2K,R3N), (ZA,R1S,R2K,R3O), (ZA,R1S,R2K,R3P),
(ZA,R1S,R2K,R3Q), (ZA,R1S,R2K,R3R), (ZA,R1S,R2L,R3A),
(ZA,R1S,R2L,R3B), (ZA,R1S,R2L,R3C), (ZA,R1S,R2L,R3D),
(ZA,R1S,R2L,R3E), (ZA,R1S,R2L,R3F), (ZA,R1S,R2L,R3G),
(ZA,R1S,R2L,R3I), (ZA,R1S,R2L,R3J),
(ZA,R1S,R2L,R3K), (ZA,R1S,R2L,R3L), (ZA,R1S,R2L,R3M),
(ZA,R1S,R2L,R3N), (ZA,R1S,R2L,R3O), (ZA,R1S,R2L,R3P),
(ZA,R1S,R2L,R3Q), (ZA,R1S,R2L,R3R), (ZA,R1S,R2M,R3A),
(ZA,R1S,R2M,R3B), (ZA,R1S,R2M,R3C), (ZA,R1S,R2M,R3D),
(ZA,R1S,R2M,R3F), (ZA,R1S,R2M,R3G),
(ZA,R1S,R2M,R3H), (ZA,R1S,R2M,R3I), (ZA,R1S,R2M,R3J),
(ZA,R1S,R2M,R3K), (ZA,R1S,R2M,R3L), (ZA,R1S,R2M,R3M),
(ZA,R1S,R2M,R3N), (ZA,R1S,R2M,R3O), (ZA,R1S,R2M,R3P),
(ZA,R1S,R2M,R3Q), (ZA,R1S,R2M,R3R), (ZA,R1S,R2N,R3A),
(ZA,R1S,R2N,R3C), (ZA,R1S,R2N,R3D),
(ZA,R1S,R2N,R3E), (ZA,R1S,R2N,R3F), (ZA,R1S,R2N,R3G),
(ZA,R1S,R2N,R3H), (ZA,R1S,R2N,R3I), (ZA,R1S,R2N,R3J),
(ZA,R1S,R2N,R3K), (ZA,R1S,R2N,R3L), (ZA,R1S,R2N,R3M),
(ZA,R1S,R2N,R3N), (ZA,R1S,R2N,R3O), (ZA,R1S,R2N,R3P),
(ZA,R1S,R2N,R3Q), (ZA,R1S,R2N,R3R), (ZA,R1S,R2N,R3A),
(ZB,R1A,R2A,R3B), (ZB,R1A,R2A,R3C), (ZB,R1A,R2A,R3D),
(ZB,R1A,R2A,R3E), (ZB,R1A,R2A,R3F), (ZB,R1A,R2A,R3G), (ZB,R1A,R2A,R3H), (ZB,R1A,R2A,R3I), (ZB,R1A,R2A,R3J),
(ZB,R1A,R2A,R3K), (ZB,R1A,R2A,R3L), (ZB,R1A,R2A,R3M),
(ZB,R1A,R2A,R3N), (ZB,R1A,R2A,R3O), (ZB,R1A,R2A,R3P),
(ZB,R1A,R2A,R3Q), (ZB,R1A,R2A,R3R), (ZB,R1A,R2B,R3A),
(ZB,R1A,R2B,R3B), (ZB,R1A,R2B,R3C), (ZB,R1A,R2B,R3D),
(ZB,R1A,R2B,R3E), (ZB,R1A,R2B,R3F), (ZB,R1A,R2B,R3G),
(ZB,R1A,R2B,R3H), (ZB,R1A,R2B,R3I), (ZB,R1A,R2B,R3J),
(ZB,R1A,R2B,R3K), (ZB,R1A,R2B,R3L), (ZB,R1A,R2B,R3M),
(ZB,R1A,R2B,R3N), (ZB,R1A,R2B,R3O), (ZB,R1A,R2B,R3P),
(ZB,R1A,R2B,R3Q), (ZB,R1A,R2B,R3R), (ZB,R1A,R2C,R3A),
(ZB,R1A,R2C,R3B), (ZB,R1A,R2C,R3C), (ZB,R1A,R2C,R3D),
(ZB,R1A,R2C,R3E), (ZB,R1A,R2C,R3F), (ZB,R1A,R2C,R3G),
(ZB,R1A,R2C,R3H), (ZB,R1A,R2C,R3I), (ZB,R1A,R2C,R3J),
(ZB,R1A,R2C,R3K), (ZB,R1A,R2C,R3L), (ZB,R1A,R2C,R3M),
(ZB,R1A,R2C,R3N), (ZB,R1A,R2C,R3O), (ZB,R1A,R2C,R3P),
(ZB,R1A,R2C,R3Q), (ZB,R1A,R2C,R3R), (ZB,R1A,R2D,R3A),
(ZB,R1A,R2D,R3B), (ZB,R1A,R2D,R3C), (ZB,R1A,R2D,R3D),
(ZB,R1A,R2D,R3E), (ZB,R1A,R2D,R3F), (ZB,R1A,R2D,R3G),
(ZB,R1A,R2D,R3H), (ZB,R1A,R2D,R3I), (ZB,R1A,R2D,R3J),
(ZB,R1A,R2D,R3K), (ZB,R1A,R2D,R3L), (ZB,R1A,R2D,R3M),
(ZB,R1A,R2D,R3N), (ZB,R1A,R2D,R3O), (ZB,R1A,R2D,R3P),
(ZB,R1A,R2D,R3Q), (ZB,R1A,R2D,R3R), (ZB,R1A,R2E,R3A),
(ZB,R1A,R2E,R3B), (ZB,R1A,R2E,R3C), (ZB,R1A,R2E,R3D),
(ZB,R1A,R2E,R3E), (ZB,R1A,R2E,R3F), (ZB,R1A,R2E,R3G),
(ZB,R1A,R2E,R3H), (ZB,R1A,R2E,R3I), (ZB,R1A,R2E,R3J),
(ZB,R1A,R2E,R3K), (ZB,R1A,R2E,R3L), (ZB,R1A,R2E,R3M),
(ZB,R1A,R2E,R3N), (ZB,R1A,R2E,R3O), (ZB,R1A,R2E,R3P),
(ZB,R1A,R2E,R3Q), (ZB,R1A,R2E,R3R), (ZB,R1A,R2F,R3A),
(ZB,R1A,R2F,R3B), (ZB,R1A,R2F,R3C), (ZB,R1A,R2F,R3D),
(ZB,R1A,R2F,R3E), (ZB,R1A,R2F,R3F), (ZB,R1A,R2F,R3G),
(ZB,R1A,R2F,R3H), (ZB,R1A,R2F,R3I), (ZB,R1A,R2F,R3J),
(ZB,R1A,R2F,R3K), (ZB,R1A,R2F,R3L), (ZB,R1A,R2F,R3M),
(ZB,R1A,R2F,R3N), (ZB,R1A,R2F,R3O), (ZB,R1A,R2F,R3P),
(ZB,R1A,R2F,R3Q), (ZB,R1A,R2F,R3R), (ZB,R1A,R2G,R3A),
(ZB,R1A,R2G,R3B), (ZB,R1A,R2G,R3C), (ZB,R1A,R2G,R3D),
(ZB,R1A,R2G,R3E), (ZB,R1A,R2G,R3F), (ZB,R1A,R2G,R3G),
(ZB,R1A,R2G,R3H), (ZB,R1A,R2G,R3I), (ZB,R1A,R2G,R3J),
(ZB,R1A,R2G,R3K), (ZB,R1A,R2G,R3L), (ZB,R1A,R2G,R3M),
(ZB,R1A,R2G,R3N), (ZB,R1A,R2G,R3O), (ZB,R1A,R2G,R3P),
(ZB,R1A,R2G,R3Q), (ZB,R1A,R2G,R3R), (ZB,R1A,R2H,R3A),
(ZB,R1A,R2H,R3B), (ZB,R1A,R2H,R3C), (ZB,R1A,R2H,R3D),
(ZB,R1A,R2H,R3E), (ZB,R1A,R2H,R3F), (ZB,R1A,R2H,R3G),
(ZB,R1A,R2H,R3H), (ZB,R1A,R2H,R3I), (ZB,R1A,R2H,R3J),
(ZB,R1A,R2H,R3K), (ZB,R1A,R2H,R3L), (ZB,R1A,R2H,R3M),
(ZB,R1A,R2H,R3N), (ZB,R1A,R2H,R3O), (ZB,R1A,R2H,R3P),
(ZB,R1A,R2H,R3Q), (ZB,R1A,R2H,R3R), (ZB,R1A,R2I,R3A),
(ZB,R1A,R2I,R3B), (ZB,R1A,R2I,R3C), (ZB,R1A,R2I,R3D), (ZB,R1A,R2I,R3E),
(ZB,R1A,R2I,R3F), (ZB,R1A,R2I,R3G), (ZB,R1A,R2I,R3H), (ZB,R1A,R2I,R3I),
(ZB,R1A,R2I,R3J), (ZB,R1A,R2I,R3K), (ZB,R1A,R2I,R3L), (ZB,R1A,R2I,R3M),
(ZB,R1A,R2I,R3N), (ZB,R1A,R2I,R3O), (ZB,R1A,R2I,R3P), (ZB,R1A,R2I,R3Q),
(ZB,R1A,R2I,R3R), (ZB,R1A,R2J,R3A), (ZB,R1A,R2J,R3B),
(ZB,R1A,R2J,R3C), (ZB,R1A,R2J,R3D), (ZB,R1A,R2J,R3E),
(ZB,R1A,R2J,R3G), (ZB,R1A,R2J,R3H),
(ZB,R1A,R2J,R3I), (ZB,R1A,R2J,R3J), (ZB,R1A,R2J,R3K),
(ZB,R1A,R2J,R3L), (ZB,R1A,R2J,R3M), (ZB,R1A,R2J,R3N),
(ZB,R1A,R2J,R3O), (ZB,R1A,R2J,R3P), (ZB,R1A,R2J,R3Q),
(ZB,R1A,R2J,R3R), (ZB,R1A,R2K,R3A), (ZB,R1A,R2K,R3B),
(ZB,R1A,R2K,R3D), (ZB,R1A,R2K,R3E),
(ZB,R1A,R2K,R3F), (ZB,R1A,R2K,R3G), (ZB,R1A,R2K,R3H),
(ZB,R1A,R2K,R3I), (ZB,R1A,R2K,R3J), (ZB,R1A,R2K,R3K),
(ZB,R1A,R2K,R3L), (ZB,R1A,R2K,R3M), (ZB,R1A,R2K,R3N),
(ZB,R1A,R2K,R3O), (ZB,R1A,R2K,R3P), (ZB,R1A,R2K,R3Q),
(ZB,R1A,R2L,R3A), (ZB,R1A,R2L,R3B),
(ZB,R1A,R2L,R3C), (ZB,R1A,R2L,R3D), (ZB,R1A,R2L,R3E),
(ZB,R1A,R2L,R3F), (ZB,R1A,R2L,R3G), (ZB,R1A,R2L,R3H),
(ZB,R1A,R2L,R3I), (ZB,R1A,R2L,R3J), (ZB,R1A,R2L,R3K),
(ZB,R1A,R2L,R3L), (ZB,R1A,R2L,R3M), (ZB,R1A,R2L,R3N),
(ZB,R1A,R2L,R3O), (ZB,R1A,R2L,R3P), (ZB,R1A,R2L,R3Q), (ZB,R1A,R2L,R3R), (ZB,R1A,R2M,R3A), (ZB,R1A,R2M,R3B),
(ZB,R1A,R2M,R3C), (ZB,R1A,R2M,R3D), (ZB,R1A,R2M,R3E),
(ZB,R1A,R2M,R3F), (ZB,R1A,R2M,R3G), (ZB,R1A,R2M,R3H),
(ZB,R1A,R2M,R3I), (ZB,R1A,R2M,R3J), (ZB,R1A,R2M,R3K),
(ZB,R1A,R2M,R3L), (ZB,R1A,R2M,R3M), (ZB,R1A,R2M,R3N),
(ZB,R1A,R2M,R3O), (ZB,R1A,R2M,R3P), (ZB,R1A,R2M,R3Q),
(ZB,R1A,R2M,R3R), (ZB,R1A,R2N,R3A), (ZB,R1A,R2N,R3B),
(ZB,R1A,R2N,R3C), (ZB,R1A,R2N,R3D), (ZB,R1A,R2N,R3E),
(ZB,R1A,R2N,R3F), (ZB,R1A,R2N,R3G), (ZB,R1A,R2N,R3H),
(ZB,R1A,R2N,R3I), (ZB,R1A,R2N,R3J), (ZB,R1A,R2N,R3K),
(ZB,R1A,R2N,R3L), (ZB,R1A,R2N,R3M), (ZB,R1A,R2N,R3N),
(ZB,R1A,R2N,R3O), (ZB,R1A,R2N,R3P), (ZB,R1A,R2N,R3Q),
(ZB,R1A,R2N,R3R), (ZB,R1B,R2A,R3A), (ZB,R1B,R2A,R3B),
(ZB,R1B,R2A,R3C), (ZB,R1B,R2A,R3D), (ZB,R1B,R2A,R3E),
(ZB,R1B,R2A,R3F), (ZB,R1B,R2A,R3G), (ZB,R1B,R2A,R3H),
(ZB,R1B,R2A,R3I), (ZB,R1B,R2A,R3J), (ZB,R1B,R2A,R3K),
(ZB,R1B,R2A,R3L), (ZB,R1B,R2A,R3M), (ZB,R1B,R2A,R3N),
(ZB,R1B,R2A,R3O), (ZB,R1B,R2A,R3P), (ZB,R1B,R2A,R3Q),
(ZB,R1B,R2A,R3R), (ZB,R1B,R2B,R3A), (ZB,R1B,R2B,R3B),
(ZB,R1B,R2B,R3C), (ZB,R1B,R2B,R3D), (ZB,R1B,R2B,R3E),
(ZB,R1B,R2B,R3F), (ZB,R1B,R2B,R3G), (ZB,R1B,R2B,R3H),
(ZB,R1B,R2B,R3I), (ZB,R1B,R2B,R3J), (ZB,R1B,R2B,R3K),
(ZB,R1B,R2B,R3L), (ZB,R1B,R2B,R3M), (ZB,R1B,R2B,R3N),
(ZB,R1B,R2B,R3O), (ZB,R1B,R2B,R3P), (ZB,R1B,R2B,R3Q),
(ZB,R1B,R2B,R3R), (ZB,R1B,R2C,R3A), (ZB,R1B,R2C,R3B),
(ZB,R1B,R2C,R3C), (ZB,R1B,R2C,R3D), (ZB,R1B,R2C,R3E),
(ZB,R1B,R2C,R3F), (ZB,R1B,R2C,R3G), (ZB,R1B,R2C,R3H),
(ZB,R1B,R2C,R3I), (ZB,R1B,R2C,R3J), (ZB,R1B,R2C,R3K),
(ZB,R1B,R2C,R3L), (ZB,R1B,R2C,R3M), (ZB,R1B,R2C,R3N),
(ZB,R1B,R2C,R3O), (ZB,R1B,R2C,R3P), (ZB,R1B,R2C,R3Q),
(ZB,R1B,R2C,R3R), (ZB,R1B,R2D,R3A), (ZB,R1B,R2D,R3B),
(ZB,R1B,R2D,R3C), (ZB,R1B,R2D,R3D), (ZB,R1B,R2D,R3E),
(ZB,R1B,R2D,R3F), (ZB,R1B,R2D,R3G), (ZB,R1B,R2D,R3H),
(ZB,R1B,R2D,R3I), (ZB,R1B,R2D,R3J), (ZB,R1B,R2D,R3K),
(ZB,R1B,R2D,R3L), (ZB,R1B,R2D,R3M), (ZB,R1B,R2D,R3N),
(ZB,R1B,R2D,R3O), (ZB,R1B,R2D,R3P), (ZB,R1B,R2D,R3Q),
(ZB,R1B,R2D,R3R), (ZB,R1B,R2E,R3A), (ZB,R1B,R2E,R3B),
(ZB,R1B,R2E,R3C), (ZB,R1B,R2E,R3D), (ZB,R1B,R2E,R3E),
(ZB,R1B,R2E,R3F), (ZB,R1B,R2E,R3G), (ZB,R1B,R2E,R3H),
(ZB,R1B,R2E,R3I), (ZB,R1B,R2E,R3J), (ZB,R1B,R2E,R3K),
(ZB,R1B,R2E,R3L), (ZB,R1B,R2E,R3M), (ZB,R1B,R2E,R3N),
(ZB,R1B,R2E,R3O), (ZB,R1B,R2E,R3P), (ZB,R1B,R2E,R3Q),
(ZB,R1B,R2E,R3R), (ZB,R1B,R2F,R3A), (ZB,R1B,R2F,R3B),
(ZB,R1B,R2F,R3C), (ZB,R1B,R2F,R3D), (ZB,R1B,R2F,R3E),
(ZB,R1B,R2F,R3F), (ZB,R1B,R2F,R3G), (ZB,R1B,R2F,R3H),
(ZB,R1B,R2F,R3I), (ZB,R1B,R2F,R3J), (ZB,R1B,R2F,R3K),
(ZB,R1B,R2F,R3L), (ZB,R1B,R2F,R3M), (ZB,R1B,R2F,R3N),
(ZB,R1B,R2F,R3O), (ZB,R1B,R2F,R3P), (ZB,R1B,R2F,R3Q),
(ZB,R1B,R2F,R3R), (ZB,R1B,R2G,R3A), (ZB,R1B,R2G,R3B),
(ZB,R1B,R2G,R3C), (ZB,R1B,R2G,R3D), (ZB,R1B,R2G,R3E),
(ZB,R1B,R2G,R3F), (ZB,R1B,R2G,R3G), (ZB,R1B,R2G,R3H),
(ZB,R1B,R2G,R3I), (ZB,R1B,R2G,R3J), (ZB,R1B,R2G,R3K),
(ZB,R1B,R2G,R3L), (ZB,R1B,R2G,R3M), (ZB,R1B,R2G,R3N),
(ZB,R1B,R2G,R3O), (ZB,R1B,R2G,R3P), (ZB,R1B,R2G,R3Q),
(ZB,R1B,R2G,R3R), (ZB,R1B,R2H,R3A), (ZB,R1B,R2H,R3B),
(ZB,R1B,R2H,R3C), (ZB,R1B,R2H,R3D), (ZB,R1B,R2H,R3E),
(ZB,R1B,R2H,R3F), (ZB,R1B,R2H,R3G), (ZB,R1B,R2H,R3H),
(ZB,R1B,R2H,R3I), (ZB,R1B,R2H,R3J), (ZB,R1B,R2H,R3K),
(ZB,R1B,R2H,R3L), (ZB,R1B,R2H,R3M), (ZB,R1B,R2H,R3N),
(ZB,R1B,R2H,R3O), (ZB,R1B,R2H,R3P), (ZB,R1B,R2H,R3Q),
(ZB,R1B,R2H,R3R), (ZB,R1B,R21,R3A), (ZB,R1B,R2I,R3B),
(ZB,R1B,R2I,R3C), (ZB,R1B,R2I,R3D), (ZB,R1B,R2I,R3E),
(ZB,R1B,R2I,R3F), (ZB,R1B,R2I,R3G), (ZB,R1B,R2I,R3H), (ZB,R1B,R2I,R3I),
(ZB,R1B,R2I,R3J), (ZB,R1B,R2I,R3K), (ZB,R1B,R2I,R3L), (ZB,R1B,R2I,R3M),
(ZB,R1B,R2I,R3N), (ZB,R1B,R2I,R3O), (ZB,R1B,R2I,R3P),
(ZB,R1B,R2I,R3Q), (ZB,R1B,R2I,R3R), (ZB,R1B,R2J,R3A), (ZB,R1B,R2J,R3B), (ZB,R1B,R2J,R3C), (ZB,R1B,R2J,R3D),
(ZB,R1B,R2J,R3E), (ZB,R1B,R2J,R3F), (ZB,R1B,R2J,R3G),
(ZB,R1B,R2J,R3H), (ZB,R1B,R2J,R3I), (ZB,R1B,R2J,R3J),
(ZB,R1B,R2J,R3K), (ZB,R1B,R2J,R3L), (ZB,R1B,R2J,R3M),
(ZB,R1B,R2J,R3N), (ZB,R1B,R2J,R3O), (ZB,R1B,R2J,R3P),
(ZB,R1B,R2J,R3Q), (ZB,R1B,R2J,R3R), (ZB,R1B,R2K,R3A),
(ZB,R1B,R2K,R3B), (ZB,R1B,R2K,R3C), (ZB,R1B,R2K,R3D),
(ZB,R1B,R2K,R3E), (ZB,R1B,R2K,R3F), (ZB,R1B,R2K,R3G),
(ZB,R1B,R2K,R3H), (ZB,R1B,R2K,R3I), (ZB,R1B,R2K,R3J),
(ZB,R1B,R2K,R3K), (ZB,R1B,R2K,R3L), (ZB,R1B,R2K,R3M),
(ZB,R1B,R2K,R3N), (ZB,R1B,R2K,R3O), (ZB,R1B,R2K,R3P),
(ZB,R1B,R2K,R3Q), (ZB,R1B,R2K,R3R), (ZB,R1B,R2L,R3A),
(ZB,R1B,R2L,R3B), (ZB,R1B,R2L,R3C), (ZB,R1B,R2L,R3D),
(ZB,R1B,R2L,R3E), (ZB,R1B,R2L,R3F), (ZB,R1B,R2L,R3G),
(ZB,R1B,R2L,R3H), (ZB,R1B,R2L,R3I), (ZB,R1B,R2L,R3J),
(ZB,R1B,R2L,R3K), (ZB,R1B,R2L,R3L), (ZB,R1B,R2L,R3M),
(ZB,R1B,R2L,R3N), (ZB,R1B,R2L,R3O), (ZB,R1B,R2L,R3P),
(ZB,R1B,R2L,R3Q), (ZB,R1B,R2L,R3R), (ZB,R1B,R2M,R3A),
(ZB,R1B,R2M,R3B), (ZB,R1B,R2M,R3C), (ZB,R1B,R2M,R3D),
(ZB,R1B,R2M,R3E), (ZB,R1B,R2M,R3F), (ZB,R1B,R2M,R3G),
(ZB,R1B,R2M,R3H), (ZB,R1B,R2M,R3I), (ZB,R1B,R2M,R3J),
(ZB,R1B,R2M,R3K), (ZB,R1B,R2M,R3L), (ZB,R1B,R2M,R3M),
(ZB,R1B,R2M,R3N), (ZB,R1B,R2M,R3O), (ZB,R1B,R2M,R3P),
(ZB,R1B,R2M,R3Q), (ZB,R1B,R2M,R3R), (ZB,R1B,R2N,R3A),
(ZB,R1B,R2N,R3B), (ZB,R1B,R2N,R3C), (ZB,R1B,R2N,R3D),
(ZB,R1B,R2N,R3E), (ZB,R1B,R2N,R3F), (ZB,R1B,R2N,R3G),
(ZB,R1B,R2N,R3H), (ZB,R1B,R2N,R3I), (ZB,R1B,R2N,R3J),
(ZB,R1B,R2N,R3K), (ZB,R1B,R2N,R3L), (ZB,R1B,R2N,R3M),
(ZB,R1B,R2N,R3N), (ZB,R1B,R2N,R3O), (ZB,R1B,R2N,R3P),
(ZB,R1B,R2N,R3Q), (ZB,R1B,R2N,R3R), (ZB,R1C,R2A,R3A),
(ZB,R1C,R2A,R3B), (ZB,R1C,R2A,R3C), (ZB,R1C,R2A,R3D),
(ZB,R1C,R2A,R3E), (ZB,R1C,R2A,R3F), (ZB,R1C,R2A,R3G),
(ZB,R1C,R2A,R3H), (ZB,R1C,R2A,R3I), (ZB,R1C,R2A,R3J),
(ZB,R1C,R2A,R3K), (ZB,R1C,R2A,R3L), (ZB,R1C,R2A,R3M),
(ZB,R1C,R2A,R3N), (ZB,R1C,R2A,R3O), (ZB,R1C,R2A,R3P),
(ZB,R1C,R2A,R3Q), (ZB,R1C,R2A,R3R), (ZB,R1C,R2B,R3A),
(ZB,R1C,R2B,R3B), (ZB,R1C,R2B,R3C), (ZB,R1C,R2B,R3D),
(ZB,R1C,R2B,R3E), (ZB,R1C,R2B,R3F), (ZB,R1C,R2B,R3G),
(ZB,R1C,R2B,R3H), (ZB,R1C,R2B,R3I), (ZB,R1C,R2B,R3J),
(ZB,R1C,R2B,R3K), (ZB,R1C,R2B,R3L), (ZB,R1C,R2B,R3M),
(ZB,R1C,R2B,R3N), (ZB,R1C,R2B,R3O), (ZB,R1C,R2B,R3P),
(ZB,R1C,R2B,R3Q), (ZB,R1C,R2B,R3R), (ZB,R1C,R2C,R3A),
(ZB,R1C,R2C,R3B), (ZB,R1C,R2C,R3C), (ZB,R1C,R2C,R3D),
(ZB,R1C,R2C,R3E), (ZB,R1C,R2C,R3F), (ZB,R1C,R2C,R3G),
(ZB,R1C,R2C,R3H), (ZB,R1C,R2C,R3I), (ZB,R1C,R2C,R3J),
(ZB,R1C,R2C,R3K), (ZB,R1C,R2C,R3L), (ZB,R1C,R2C,R3M),
(ZB,R1C,R2C,R3N), (ZB,R1C,R2C,R3O), (ZB,R1C,R2C,R3P),
(ZB,R1C,R2C,R3Q), (ZB,R1C,R2C,R3R), (ZB,R1C,R2D,R3A),
(ZB,R1C,R2D,R3B), (ZB,R1C,R2D,R3C), (ZB,R1C,R2D,R3D),
(ZB,R1C,R2D,R3E), (ZB,R1C,R2D,R3F), (ZB,R1C,R2D,R3G),
(ZB,R1C,R2D,R3H), (ZB,R1C,R2D,R3I), (ZB,R1C,R2D,R3J),
(ZB,R1C,R2D,R3K), (ZB,R1C,R2D,R3L), (ZB,R1C,R2D,R3M),
(ZB,R1C,R2D,R3N), (ZB,R1C,R2D,R3O), (ZB,R1C,R2D,R3P),
(ZB,R1C,R2D,R3Q), (ZB,R1C,R2D,R3R), (ZB,R1C,R2E,R3A),
(ZB,R1C,R2E,R3B), (ZB,R1C,R2E,R3C), (ZB,R1C,R2E,R3D),
(ZB,R1C,R2E,R3E), (ZB,R1C,R2E,R3F), (ZB,R1C,R2E,R3G),
(ZB,R1C,R2E,R3H), (ZB,R1C,R2E,R3I), (ZB,R1C,R2E,R3J),
(ZB,R1C,R2E,R3K), (ZB,R1C,R2E,R3L), (ZB,R1C,R2E,R3M),
(ZB,R1C,R2E,R3N), (ZB,R1C,R2E,R3O), (ZB,R1C,R2E,R3P),
(ZB,R1C,R2E,R3Q), (ZB,R1C,R2E,R3R), (ZB,R1C,R2F,R3A),
(ZB,R1C,R2F,R3B), (ZB,R1C,R2F,R3C), (ZB,R1C,R2F,R3D),
(ZB,R1C,R2F,R3E), (ZB,R1C,R2F,R3F), (ZB,R1C,R2F,R3G),
(ZB,R1C,R2F,R3H), (ZB,R1C,R2F,R3I), (ZB,R1C,R2F,R3J),
(ZB,R1C,R2F,R3K), (ZB,R1C,R2F,R3L), (ZB,R1C,R2F,R3M),
(ZB,R1C,R2F,R3N), (ZB,R1C,R2F,R3O), (ZB,R1C,R2F,R3P),
(ZB,R1C,R2F,R3Q), (ZB,R1C,R2F,R3R), (ZB,R1C,R2G,R3A), (ZB,R1C,R2G,R3B), (ZB,R1C,R2G,R3C), (ZB,R1C,R2G,R3D),
(ZB,R1C,R2G,R3E), (ZB,R1C,R2G,R3F), (ZB,R1C,R2G,R3G),
(ZB,R1C,R2G,R3H), (ZB,R1C,R2G,R3I), (ZB,R1C,R2G,R3J),
(ZB,R1C,R2G,R3K), (ZB,R1C,R2G,R3L), (ZB,R1C,R2G,R3M),
(ZB,R1C,R2G,R3N), (ZB,R1C,R2G,R3O), (ZB,R1C,R2G,R3P),
(ZB,R1C,R2G,R3Q), (ZB,R1C,R2G,R3R), (ZB,R1C,R2H,R3A),
(ZB,R1C,R2H,R3B), (ZB,R1C,R2H,R3C), (ZB,R1C,R2H,R3D),
(ZB,R1C,R2H,R3E), (ZB,R1C,R2H,R3F), (ZB,R1C,R2H,R3G),
(ZB,R1C,R2H,R3H), (ZB,R1C,R2H,R3I), (ZB,R1C,R2H,R3J),
(ZB,R1C,R2H,R3K), (ZB,R1C,R2H,R3L), (ZB,R1C,R2H,R3M),
(ZB,R1C,R2H,R3N), (ZB,R1C,R2H,R3O), (ZB,R1C,R2H,R3P),
(ZB,R1C,R2H,R3Q), (ZB,R1C,R2H,R3R), (ZB,R1C,R2I,R3A),
(ZB,R1C,R2I,R3B), (ZB,R1C,R2I,R3C), (ZB,R1C,R2I,R3D),
(ZB,R1C,R2I,R3E), (ZB,R1C,R2I,R3F), (ZB,R1C,R2I,R3G),
(ZB,R1C,R2I,R3H), (ZB,R1C,R2I,R3I), (ZB,R1C,R2I,R3J), (ZB,R1C,R2I,R3K),
(ZB,R1C,R2I,R3L), (ZB,R1C,R2I,R3M), (ZB,R1C,R2I,R3N),
(ZB,R1C,R2I,R3O), (ZB,R1C,R2I,R3P), (ZB,R1C,R2I,R3Q),
(ZB,R1C,R2J,R3A), (ZB,R1C,R2J,R3B),
(ZB,R1C,R2J,R3C), (ZB,R1C,R2J,R3D), (ZB,R1C,R2J,R3E),
(ZB,R1C,R2J,R3F), (ZB,R1C,R2J,R3G), (ZB,R1C,R2J,R3H),
(ZB,R1C,R2J,R3I), (ZB,R1C,R2J,R3J), (ZB,R1C,R2J,R3K),
(ZB,R1C,R2J,R3L), (ZB,R1C,R2J,R3M), (ZB,R1C,R2J,R3N),
(ZB,R1C,R2J,R3P), (ZB,R1C,R2J,R3Q),
(ZB,R1C,R2J,R3R), (ZB,R1C,R2K,R3A), (ZB,R1C,R2K,R3B),
(ZB,R1C,R2K,R3C), (ZB,R1C,R2K,R3D), (ZB,R1C,R2K,R3E),
(ZB,R1C,R2K,R3F), (ZB,R1C,R2K,R3G), (ZB,R1C,R2K,R3H),
(ZB,R1C,R2K,R3I), (ZB,R1C,R2K,R3J), (ZB,R1C,R2K,R3K),
(ZB,R1C,R2K,R3M), (ZB,R1C,R2K,R3N),
(ZB,R1C,R2K,R3O), (ZB,R1C,R2K,R3P), (ZB,R1C,R2K,R3Q),
(ZB,R1C,R2K,R3R), (ZB,R1C,R2L,R3A), (ZB,R1C,R2L,R3B),
(ZB,R1C,R2L,R3C), (ZB,R1C,R2L,R3D), (ZB,R1C,R2L,R3E),
(ZB,R1C,R2L,R3F), (ZB,R1C,R2L,R3G), (ZB,R1C,R2L,R3H),
(ZB,R1C,R2L,R3J), (ZB,R1C,R2L,R3K),
(ZB,R1C,R2L,R3L), (ZB,R1C,R2L,R3M), (ZB,R1C,R2L,R3N), 6(ZB,R1C,R2L,R3O), (ZB,R1C,R2L,R3P), (ZB,R1C,R2L,R3Q),
(ZB,R1C,R2L,R3R), (ZB,R1C,R2M,R3A), (ZB,R1C,R2M,R3B),
(ZB,R1C,R2M,R3C), (ZB,R1C,R2M,R3D), (ZB,R1C,R2M,R3E),
(ZB,R1C,R2M,R3G), (ZB,R1C,R2M,R3H),
(ZB,R1C,R2M,R3I), (ZB,R1C,R2M,R3J), (ZB,R1C,R2M,R3K),
(ZB,R1C,R2M,R3L), (ZB,R1C,R2M,R3M), (ZB,R1C,R2M,R3N),
(ZB,R1C,R2M,R3O), (ZB,R1C,R2M,R3P), (ZB,R1C,R2M,R3Q),
(ZB,R1C,R2M,R3R), (ZB,R1C,R2N,R3A), (ZB,R1C,R2N,R3B),
(ZB,R1C,R2N,R3C), (ZB,R1C,R2N,R3D), (ZB,R1C,R2N,R3E),
(ZB,R1C,R2N,R3F), (ZB,R1C,R2N,R3G), (ZB,R1C,R2N,R3H),
(ZB,R1C,R2N,R3I), (ZB,R1C,R2N,R3J), (ZB,R1C,R2N,R3K),
(ZB,R1C,R2N,R3L), (ZB,R1C,R2N,R3M), (ZB,R1C,R2N,R3N),
(ZB,R1C,R2N,R3O), (ZB,R1C,R2N,R3P), (ZB,R1C,R2N,R3Q),
(ZB,R1C,R2N,R3R), (ZB,R1D,R2A,R3A), (ZB,R1D,R2A,R3B),
(ZB,R1D,R2A,R3C), (ZB,R1D,R2A,R3D), (ZB,R1D,R2A,R3E),
(ZB,R1D,R2A,R3F), (ZB,R1D,R2A,R3G), (ZB,R1D,R2A,R3H),
(ZB,R1D,R2A,R3I), (ZB,R1D,R2A,R3J), (ZB,R1D,R2A,R3K),
(ZB,R1D,R2A,R3L), (ZB,R1D,R2A,R3M), (ZB,R1D,R2A,R3N),
(ZB,R1D,R2A,R3O), (ZB,R1D,R2A,R3P), (ZB,R1D,R2A,R3Q),
(ZB,R1D,R2A,R3R), (ZB,R1D,R2B,R3A), (ZB,R1D,R2B,R3B),
(ZB,R1D,R2B,R3C), (ZB,R1D,R2B,R3D), (ZB,R1D,R2B,R3E),
(ZB,R1D,R2B,R3F), (ZB,R1D,R2B,R3G), (ZB,R1D,R2B,R3H),
(ZB,R1D,R2B,R3I), (ZB,R1D,R2B,R3J), (ZB,R1D,R2B,R3K),
(ZB,R1D,R2B,R3L), (ZB,R1D,R2B,R3M), (ZB,R1D,R2B,R3N),
(ZB,R1D,R2B,R3O), (ZB,R1D,R2B,R3P), (ZB,R1D,R2B,R3Q),
(ZB,R1D,R2B,R3R), (ZB,R1D,R2C,R3A), (ZB,R1D,R2C,R3B),
(ZB,R1D,R2C,R3C), (ZB,R1D,R2C,R3D), (ZB,R1D,R2C,R3E),
(ZB,R1D,R2C,R3F), (ZB,R1D,R2C,R3G), (ZB,R1D,R2C,R3H),
(ZB,R1D,R2C,R3I), (ZB,R1D,R2C,R3J), (ZB,R1D,R2C,R3K),
(ZB,R1D,R2C,R3L), (ZB,R1D,R2C,R3M), (ZB,R1D,R2C,R3N),
(ZB,R1D,R2C,R3O), (ZB,R1D,R2C,R3P), (ZB,R1D,R2C,R3Q),
(ZB,R1D,R2C,R3R), (ZB,R1D,R2D,R3A), (ZB,R1D,R2D,R3B),
(ZB,R1D,R2D,R3C), (ZB,R1D,R2D,R3D), (ZB,R1D,R2D,R3E),
(ZB,R1D,R2D,R3F), (ZB,R1D,R2D,R3G), (ZB,R1D,R2D,R3H),
(ZB,R1D,R2D,R3I), (ZB,R1D,R2D,R3J), (ZB,R1D,R2D,R3K),
(ZB,R1D,R2D,R3L), (ZB,R1D,R2D,R3M), (ZB,R1D,R2D,R3N), (ZB,R1D,R2D,R3O), (ZB,R1D,R2D,R3P), (ZB,R1D,R2D,R3Q),
(ZB,R1D,R2D,R3R), (ZB,R1D,R2E,R3A), (ZB,R1D,R2E,R3B),
(ZB,R1D,R2E,R3C), (ZB,R1D,R2E,R3D), (ZB,R1D,R2E,R3E),
(ZB,R1D,R2E,R3F), (ZB,R1D,R2E,R3G), (ZB,R1D,R2E,R3H),
(ZB,R1D,R2E,R3I), (ZB,R1D,R2E,R3J), (ZB,R1D,R2E,R3K),
(ZB,R1D,R2E,R3L), (ZB,R1D,R2E,R3M), (ZB,R1D,R2E,R3N),
(ZB,R1D,R2E,R3O), (ZB,R1D,R2E,R3P), (ZB,R1D,R2E,R3Q),
(ZB,R1D,R2E,R3R), (ZB,R1D,R2F,R3A), (ZB,R1D,R2F,R3B),
(ZB,R1D,R2F,R3C), (ZB,R1D,R2F,R3D), (ZB,R1D,R2F,R3E),
(ZB,R1D,R2F,R3F), (ZB,R1D,R2F,R3G), (ZB,R1D,R2F,R3H),
(ZB,R1D,R2F,R3I), (ZB,R1D,R2F,R3J), (ZB,R1D,R2F,R3K),
(ZB,R1D,R2F,R3L), (ZB,R1D,R2F,R3M), (ZB,R1D,R2F,R3N),
(ZB,R1D,R2F,R3O), (ZB,R1D,R2F,R3P), (ZB,R1D,R2F,R3Q),
(ZB,R1D,R2F,R3R), (ZB,R1D,R2G,R3A), (ZB,R1D,R2G,R3B),
(ZB,R1D,R2G,R3C), (ZB,R1D,R2G,R3D), (ZB,R1D,R2G,R3E),
(ZB,R1D,R2G,R3F), (ZB,R1D,R2G,R3G), (ZB,R1D,R2G,R3H),
(ZB,R1D,R2G,R3I), (ZB,R1D,R2G,R3J), (ZB,R1D,R2G,R3K),
(ZB,R1D,R2G,R3L), (ZB,R1D,R2G,R3M), (ZB,R1D,R2G,R3N),
(ZB,R1D,R2G,R3O), (ZB,R1D,R2G,R3P), (ZB,R1D,R2G,R3Q),
(ZB,R1D,R2G,R3R), (ZB,R1D,R2H,R3A), (ZB,R1D,R2H,R3B),
(ZB,R1D,R2H,R3C), (ZB,R1D,R2H,R3D), (ZB,R1D,R2H,R3E),
(ZB,R1D,R2H,R3F), (ZB,R1D,R2H,R3G), (ZB,R1D,R2H,R3H),
(ZB,R1D,R2H,R3I), (ZB,R1D,R2H,R3J), (ZB,R1D,R2H,R3K),
(ZB,R1D,R2H,R3L), (ZB,R1D,R2H,R3M), (ZB,R1D,R2H,R3N),
(ZB,R1D,R2H,R3O), (ZB,R1D,R2H,R3P), (ZB,R1D,R2H,R3Q),
(ZB,R1D,R2H,R3R), (ZB,R1D,R2I,R3A), (ZB,R1D,R2I,R3B),
(ZB,R1D,R2I,R3C), (ZB,R1D,R2I,R3D), (ZB,R1D,R2I,R3E),
(ZB,R1D,R2I,R3F), (ZB,R1D,R2I,R3G), (ZB,R1D,R2I,R3H), (ZB,R1D,R2I,R3I),
(ZB,R1D,R2I,R3J), (ZB,R1D,R2I,R3K), (ZB,R1D,R2I,R3L),
(ZB,R1D,R2I,R3M), (ZB,R1D,R2I,R3N), (ZB,R1D,R2I,R3O),
(ZB,R1D,R2I,R3P), (ZB,R1D,R2I,R3Q), (ZB,R1D,R2I,R3R),
(ZB,R1D,R2J,R3A), (ZB,R1D,R2J,R3B), (ZB,R1D,R2J,R3C),
(ZB,R1D,R2J,R3D), (ZB,R1D,R2J,R3E), (ZB,R1D,R2J,R3F),
(ZB,R1D,R2J,R3G), (ZB,R1D,R2J,R3H), (ZB,R1D,R2J,R3I),
(ZB,R1D,R2J,R3J), (ZB,R1D,R2J,R3K), (ZB,R1D,R2J,R3L),
(ZB,R1D,R2J,R3M), (ZB,R1D,R2J,R3N), (ZB,R1D,R2J,R3O),
(ZB,R1D,R2J,R3P), (ZB,R1D,R2J,R3Q), (ZB,R1D,R2J,R3R),
(ZB,R1D,R2K,R3A), (ZB,R1D,R2K,R3B), (ZB,R1D,R2K,R3C),
(ZB,R1D,R2K,R3D), (ZB,R1D,R2K,R3E), (ZB,R1D,R2K,R3F),
(ZB,R1D,R2K,R3G), (ZB,R1D,R2K,R3H), (ZB,R1D,R2K,R3I),
(ZB,R1D,R2K,R3J), (ZB,R1D,R2K,R3K), (ZB,R1D,R2K,R3L),
(ZB,R1D,R2K,R3M), (ZB,R1D,R2K,R3N), (ZB,R1D,R2K,R3O),
(ZB,R1D,R2K,R3P), (ZB,R1D,R2K,R3Q), (ZB,R1D,R2K,R3R),
(ZB,R1D,R2L,R3A), (ZB,R1D,R2L,R3B), (ZB,R1D,R2L,R3C),
(ZB,R1D,R2L,R3D), (ZB,R1D,R2L,R3E), (ZB,R1D,R2L,R3F),
(ZB,R1D,R2L,R3G), (ZB,R1D,R2L,R3H), (ZB,R1D,R2L,R3I),
(ZB,R1D,R2L,R3J), (ZB,R1D,R2L,R3K), (ZB,R1D,R2L,R3L),
(ZB,R1D,R2L,R3M), (ZB,R1D,R2L,R3N), (ZB,R1D,R2L,R3O),
(ZB,R1D,R2L,R3P), (ZB,R1D,R2L,R3Q), (ZB,R1D,R2L,R3R),
(ZB,R1D,R2M,R3A), (ZB,R1D,R2M,R3B), (ZB,R1D,R2M,R3C),
(ZB,R1D,R2M,R3D), (ZB,R1D,R2M,R3E), (ZB,R1D,R2M,R3F),
(ZB,R1D,R2M,R3G), (ZB,R1D,R2M,R3H), (ZB,R1D,R2M,R3I),
(ZB,R1D,R2M,R3J), (ZB,R1D,R2M,R3K), (ZB,R1D,R2M,R3L),
(ZB,R1D,R2M,R3M), (ZB,R1D,R2M,R3N), (ZB,R1D,R2M,R3O),
(ZB,R1D,R2M,R3P), (ZB,R1D,R2M,R3Q), (ZB,R1D,R2M,R3R),
(ZB,R1D,R2N,R3A), (ZB,R1D,R2N,R3B), (ZB,R1D,R2N,R3C),
(ZB,R1D,R2N,R3D), (ZB,R1D,R2N,R3E), (ZB,R1D,R2N,R3F),
(ZB,R1D,R2N,R3G), (ZB,R1D,R2N,R3H), (ZB,R1D,R2N,R3I),
(ZB,R1D,R2N,R3J), (ZB,R1D,R2N,R3K), (ZB,R1D,R2N,R3L),
(ZB,R1D,R2N,R3M), (ZB,R1D,R2N,R3N), (ZB,R1D,R2N,R3O),
(ZB,R1D,R2N,R3P), (ZB,R1D,R2N,R3Q), (ZB,R1D,R2N,R3R),
(ZB,R1E,R2A,R3A), (ZB,R1E,R2A,R3B), (ZB,R1E,R2A,R3C),
(ZB,R1E,R2A,R3D), (ZB,R1E,R2A,R3E), (ZB,R1E,R2A,R3F),
(ZB,R1E,R2A,R3G), (ZB,R1E,R2A,R3H), (ZB,R1E,R2A,R3I),
(ZB,R1E,R2A,R3J), (ZB,R1E,R2A,R3K), (ZB,R1E,R2A,R3L),
(ZB,R1E,R2A,R3M), (ZB,R1E,R2A,R3N), (ZB,R1E,R2A,R3O), (ZB,R1E,R2A,R3P), (ZB,R1E,R2A,R3Q), (ZB,R1E,R2A,R3R),
(ZB,R1E,R2B,R3A), (ZB,R1E,R2B,R3B), (ZB,R1E,R2B,R3C),
(ZB,R1E,R2B,R3D), (ZB,R1E,R2B,R3E), (ZB,R1E,R2B,R3F),
(ZB,R1E,R2B,R3G), (ZB,R1E,R2B,R3H), (ZB,R1E,R2B,R3I),
(ZB,R1E,R2B,R3J), (ZB,R1E,R2B,R3K), (ZB,R1E,R2B,R3L),
(ZB,R1E,R2B,R3M), (ZB,R1E,R2B,R3N), (ZB,R1E,R2B,R3O),
(ZB,R1E,R2B,R3P), (ZB,R1E,R2B,R3Q), (ZB,R1E,R2B,R3R),
(ZB,R1E,R2C,R3A), (ZB,R1E,R2C,R3B), (ZB,R1E,R2C,R3C),
(ZB,R1E,R2C,R3D), (ZB,R1E,R2C,R3E), (ZB,R1E,R2C,R3F),
(ZB,R1E,R2C,R3G), (ZB,R1E,R2C,R3H), (ZB,R1E,R2C,R3I),
(ZB,R1E,R2C,R3J), (ZB,R1E,R2C,R3K), (ZB,R1E,R2C,R3L),
(ZB,R1E,R2C,R3M), (ZB,R1E,R2C,R3N), (ZB,R1E,R2C,R3O),
(ZB,R1E,R2C,R3P), (ZB,R1E,R2C,R3Q), (ZB,R1E,R2C,R3R),
(ZB,R1E,R2D,R3A), (ZB,R1E,R2D,R3B), (ZB,R1E,R2D,R3C),
(ZB,R1E,R2D,R3D), (ZB,R1E,R2D,R3E), (ZB,R1E,R2D,R3F),
(ZB,R1E,R2D,R3G), (ZB,R1E,R2D,R3H), (ZB,R1E,R2D,R3I),
(ZB,R1E,R2D,R3J), (ZB,R1E,R2D,R3K), (ZB,R1E,R2D,R3L),
(ZB,R1E,R2D,R3M), (ZB,R1E,R2D,R3N), (ZB,R1E,R2D,R3O),
(ZB,R1E,R2D,R3P), (ZB,R1E,R2D,R3Q), (ZB,R1E,R2D,R3R),
(ZB,R1E,R2E,R3A), (ZB,R1E,R2E,R3B), (ZB,R1E,R2E,R3C),
(ZB,R1E,R2E,R3D), (ZB,R1E,R2E,R3E), (ZB,R1E,R2E,R3F),
(ZB,R1E,R2E,R3G), (ZB,R1E,R2E,R3H), (ZB,R1E,R2E,R3I),
(ZB,R1E,R2E,R3J), (ZB,R1E,R2E,R3K), (ZB,R1E,R2E,R3L),
(ZB,R1E,R2E,R3M), (ZB,R1E,R2E,R3N), (ZB,R1E,R2E,R3O),
(ZB,R1E,R2E,R3P), (ZB,R1E,R2E,R3Q), (ZB,R1E,R2E,R3R),
(ZB,R1E,R2F,R3A), (ZB,R1E,R2F,R3B), (ZB,R1E,R2F,R3C),
(ZB,R1E,R2F,R3D), (ZB,R1E,R2F,R3E), (ZB,R1E,R2F,R3F),
(ZB,R1E,R2F,R3G), (ZB,R1E,R2F,R3H), (ZB,R1E,R2F,R3I),
(ZB,R1E,R2F,R3J), (ZB,R1E,R2F,R3K), (ZB,R1E,R2F,R3L),
(ZB,R1E,R2F,R3M), (ZB,R1E,R2F,R3N), (ZB,R1E,R2F,R3O),
(ZB,R1E,R2F,R3P), (ZB,R1E,R2F,R3Q), (ZB,R1E,R2F,R3R),
(ZB,R1E,R2G,R3A), (ZB,R1E,R2G,R3B), (ZB,R1E,R2G,R3C),
(ZB,R1E,R2G,R3D), (ZB,R1E,R2G,R3E), (ZB,R1E,R2G,R3F),
(ZB,R1E,R2G,R3G), (ZB,R1E,R2G,R3H), (ZB,R1E,R2G,R3I),
(ZB,R1E,R2G,R3J), (ZB,R1E,R2G,R3K), (ZB,R1E,R2G,R3L),
(ZB,R1E,R2G,R3M), (ZB,R1E,R2G,R3N), (ZB,R1E,R2G,R3O),
(ZB,R1E,R2G,R3P), (ZB,R1E,R2G,R3Q), (ZB,R1E,R2G,R3R),
(ZB,R1E,R2H,R3A), (ZB,R1E,R2H,R3B), (ZB,R1E,R2H,R3C),
(ZB,R1E,R2H,R3D), (ZB,R1E,R2H,R3E), (ZB,R1E,R2H,R3F),
(ZB,R1E,R2H,R3G), (ZB,R1E,R2H,R3H), (ZB,R1E,R2H,R3I),
(ZB,R1E,R2H,R3J), (ZB,R1E,R2H,R3K), (ZB,R1E,R2H,R3L),
(ZB,R1E,R2H,R3M), (ZB,R1E,R2H,R3N), (ZB,R1E,R2H,R3O),
(ZB,R1E,R2H,R3P), (ZB,R1E,R2H,R3Q), (ZB,R1E,R2H,R3R),
(ZB,R1E,R2I,R3A), (ZB,R1E,R2I,R3B), (ZB,R1E,R2I,R3C), (ZB,R1E,R2I,R3D),
(ZB,R1E,R2I,R3E), (ZB,R1E,R2I,R3F), (ZB,R1E,R2I,R3G), (ZB,R1E,R2I,R3H),
(ZB,R1E,R2I,R3I), (ZB,R1E,R2I,R3J), (ZB,R1E,R2I,R3K), (ZB,R1E,R2I,R3L),
(ZB,R1E,R2I,R3M), (ZB,R1E,R2I,R3N), (ZB,R1E,R2I,R3O),
(ZB,R1E,R2I,R3P), (ZB,R1E,R2I,R3Q), (ZB,R1E,R2I,R3R),
(ZB,R1E,R2J,R3A), (ZB,R1E,R2J,R3B), (ZB,R1E,R2J,R3C),
(ZB,R1E,R2J,R3D), (ZB,R1E,R2J,R3E), (ZB,R1E,R2J,R3F),
(ZB,R1E,R2J,R3G), (ZB,R1E,R2J,R3H), (ZB,R1E,R2J,R3I),
(ZB,R1E,R2J,R3J), (ZB,R1E,R2J,R3K), (ZB,R1E,R2J,R3L),
(ZB,R1E,R2J,R3M), (ZB,R1E,R2J,R3N), (ZB,R1E,R2J,R3O),
(ZB,R1E,R2J,R3P), (ZB,R1E,R2J,R3Q), (ZB,R1E,R2J,R3R),
(ZB,R1E,R2K,R3A), (ZB,R1E,R2K,R3B), (ZB,R1E,R2K,R3C),
(ZB,R1E,R2K,R3D), (ZB,R1E,R2K,R3E), (ZB,R1E,R2K,R3F),
(ZB,R1E,R2K,R3G), (ZB,R1E,R2K,R3H), (ZB,R1E,R2K,R3I),
(ZB,R1E,R2K,R3J), (ZB,R1E,R2K,R3K), (ZB,R1E,R2K,R3L),
(ZB,R1E,R2K,R3M), (ZB,R1E,R2K,R3N), (ZB,R1E,R2K,R3O),
(ZB,R1E,R2K,R3P), (ZB,R1E,R2K,R3Q), (ZB,R1E,R2K,R3R),
(ZB,R1E,R2L,R3A), (ZB,R1E,R2L,R3B), (ZB,R1E,R2L,R3C),
(ZB,R1E,R2L,R3D), (ZB,R1E,R2L,R3E), (ZB,R1E,R2L,R3F),
(ZB,R1E,R2L,R3G), (ZB,R1E,R2L,R3H), (ZB,R1E,R2L,R3I),
(ZB,R1E,R2L,R3J), (ZB,R1E,R2L,R3K), (ZB,R1E,R2L,R3L),
(ZB,R1E,R2L,R3M), (ZB,R1E,R2L,R3N), (ZB,R1E,R2L,R3O),
(ZB,R1E,R2L,R3P), (ZB,R1E,R2L,R3Q), (ZB,R1E,R2L,R3R), (ZB,R1E,R2M,R3A), (ZB,R1E,R2M,R3B), (ZB,R1E,R2M,R3C),
(ZB,R1E,R2M,R3D), (ZB,R1E,R2M,R3E), (ZB,R1E,R2M,R3F),
(ZB,R1E,R2M,R3G), (ZB,R1E,R2M,R3H), (ZB,R1E,R2M,R3I),
(ZB,R1E,R2M,R3J), (ZB,R1E,R2M,R3K), (ZB,R1E,R2M,R3L),
(ZB,R1E,R2M,R3M), (ZB,R1E,R2M,R3N), (ZB,R1E,R2M,R3O),
(ZB,R1E,R2M,R3P), (ZB,R1E,R2M,R3Q), (ZB,R1E,R2M,R3R),
(ZB,R1E,R2N,R3A), (ZB,R1E,R2N,R3B), (ZB,R1E,R2N,R3C),
(ZB,R1E,R2N,R3D), (ZB,R1E,R2N,R3E), (ZB,R1E,R2N,R3F),
(ZB,R1E,R2N,R3G), (ZB,R1E,R2N,R3H), (ZB,R1E,R2N,R3I),
(ZB,R1E,R2N,R3J), (ZB,R1E,R2N,R3K), (ZB,R1E,R2N,R3L),
(ZB,R1E,R2N,R3M), (ZB,R1E,R2N,R3N), (ZB,R1E,R2N,R3O),
(ZB,R1E,R2N,R3P), (ZB,R1E,R2N,R3Q), (ZB,R1E,R2N,R3R),
(ZB,R1F,R2A,R3A), (ZB,R1F,R2A,R3B), (ZB,R1F,R2A,R3C),
(ZB,R1F,R2A,R3D), (ZB,R1F,R2A,R3E), (ZB,R1F,R2A,R3F),
(ZB,R1F,R2A,R3G), (ZB,R1F,R2A,R3H), (ZB,R1F,R2A,R3I),
(ZB,R1F,R2A,R3J), (ZB,R1F,R2A,R3K), (ZB,R1F,R2A,R3L),
(ZB,R1F,R2A,R3M), (ZB,R1F,R2A,R3N), (ZB,R1F,R2A,R3O),
(ZB,R1F,R2A,R3P), (ZB,R1F,R2A,R3Q), (ZB,R1F,R2A,R3R),
(ZB,R1F,R2B,R3A), (ZB,R1F,R2B,R3B), (ZB,R1F,R2B,R3C),
(ZB,R1F,R2B,R3D), (ZB,R1F,R2B,R3E), (ZB,R1F,R2B,R3F),
(ZB,R1F,R2B,R3G), (ZB,R1F,R2B,R3H), (ZB,R1F,R2B,R3I),
(ZB,R1F,R2B,R3J), (ZB,R1F,R2B,R3K), (ZB,R1F,R2B,R3L),
(ZB,R1F,R2B,R3M), (ZB,R1F,R2B,R3N), (ZB,R1F,R2B,R3O),
(ZB,R1F,R2B,R3P), (ZB,R1F,R2B,R3Q), (ZB,R1F,R2B,R3R),
(ZB,R1F,R2C,R3A), (ZB,R1F,R2C,R3B), (ZB,R1F,R2C,R3C),
(ZB,R1F,R2C,R3D), (ZB,R1F,R2C,R3E), (ZB,R1F,R2C,R3F),
(ZB,R1F,R2C,R3G), (ZB,R1F,R2C,R3H), (ZB,R1F,R2C,R3I),
(ZB,R1F,R2C,R3J), (ZB,R1F,R2C,R3K), (ZB,R1F,R2C,R3L),
(ZB,R1F,R2C,R3M), (ZB,R1F,R2C,R3N), (ZB,R1F,R2C,R3O),
(ZB,R1F,R2C,R3P), (ZB,R1F,R2C,R3Q), (ZB,R1F,R2C,R3R),
(ZB,R1F,R2D,R3A), (ZB,R1F,R2D,R3B), (ZB,R1F,R2D,R3C),
(ZB,R1F,R2D,R3D), (ZB,R1F,R2D,R3E), (ZB,R1F,R2D,R3F),
(ZB,R1F,R2D,R3G), (ZB,R1F,R2D,R3H), (ZB,R1F,R2D,R3I),
(ZB,R1F,R2D,R3J), (ZB,R1F,R2D,R3K), (ZB,R1F,R2D,R3L),
(ZB,R1F,R2D,R3M), (ZB,R1F,R2D,R3N), (ZB,R1F,R2D,R3O),
(ZB,R1F,R2D,R3P), (ZB,R1F,R2D,R3Q), (ZB,R1F,R2D,R3R),
(ZB,R1F,R2E,R3A), (ZB,R1F,R2E,R3B), (ZB,R1F,R2E,R3C),
(ZB,R1F,R2E,R3D), (ZB,R1F,R2E,R3E), (ZB,R1F,R2E,R3F),
(ZB,R1F,R2E,R3G), (ZB,R1F,R2E,R3H), (ZB,R1F,R2E,R3I),
(ZB,R1F,R2E,R3J), (ZB,R1F,R2E,R3K), (ZB,R1F,R2E,R3L),
(ZB,R1F,R2E,R3M), (ZB,R1F,R2E,R3N), (ZB,R1F,R2E,R3O),
(ZB,R1F,R2E,R3P), (ZB,R1F,R2E,R3Q), (ZB,R1F,R2E,R3R),
(ZB,R1F,R2F,R3A), (ZB,R1F,R2F,R3B), (ZB,R1F,R2F,R3C),
(ZB,R1F,R2F,R3D), (ZB,R1F,R2F,R3E), (ZB,R1F,R2F,R3F),
(ZB,R1F,R2F,R3G), (ZB,R1F,R2F,R3H), (ZB,R1F,R2F,R3I),
(ZB,R1F,R2F,R3J), (ZB,R1F,R2F,R3K), (ZB,R1F,R2F,R3L),
(ZB,R1F,R2F,R3M), (ZB,R1F,R2F,R3N), (ZB,R1F,R2F,R3O),
(ZB,R1F,R2F,R3P), (ZB,R1F,R2F,R3Q), (ZB,R1F,R2F,R3R),
(ZB,R1F,R2G,R3A), (ZB,R1F,R2G,R3B), (ZB,R1F,R2G,R3C),
(ZB,R1F,R2G,R3D), (ZB,R1F,R2G,R3E), (ZB,R1F,R2G,R3F),
(ZB,R1F,R2G,R3G), (ZB,R1F,R2G,R3H), (ZB,R1F,R2G,R3I),
(ZB,R1F,R2G,R3J), (ZB,R1F,R2G,R3K), (ZB,R1F,R2G,R3L),
(ZB,R1F,R2G,R3M), (ZB,R1F,R2G,R3N), (ZB,R1F,R2G,R3O),
(ZB,R1F,R2G,R3P), (ZB,R1F,R2G,R3Q), (ZB,R1F,R2G,R3R),
(ZB,R1F,R2H,R3A), (ZB,R1F,R2H,R3B), (ZB,R1F,R2H,R3C),
(ZB,R1F,R2H,R3D), (ZB,R1F,R2H,R3E), (ZB,R1F,R2H,R3F),
(ZB,R1F,R2H,R3G), (ZB,R1F,R2H,R3H), (ZB,R1F,R2H,R3I),
(ZB,R1F,R2H,R3J), (ZB,R1F,R2H,R3K), (ZB,R1F,R2H,R3L),
(ZB,R1F,R2H,R3M), (ZB,R1F,R2H,R3N), (ZB,R1F,R2H,R3O),
(ZB,R1F,R2H,R3P), (ZB,R1F,R2H,R3Q), (ZB,R1F,R2H,R3R),
(ZB,R1F,R2I,R3A), (ZB,R1F,R2I,R3B), (ZB,R1F,R2I,R3C), (ZB,R1F,R2I,R3D),
(ZB,R1F,R2I,R3E), (ZB,R1F,R2I,R3F), (ZB,R1F,R2I,R3G), (ZB,R1F,R2I,R3H),
(ZB,R1F,R2I,R3I), (ZB,R1F,R2I,R3J), (ZB,R1F,R2I,R3K), (ZB,R1F,R2I,R3L),
(ZB,R1F,R2I,R3M), (ZB,R1F,R2I,R3N), (ZB,R1F,R2I,R3O), (ZB,R1F,R2I,R3P),
(ZB,R1F,R2I,R3Q), (ZB,R1F,R2I,R3R), (ZB,R1F,R2J,R3A),
(ZB,R1F,R2J,R3C), (ZB,R1F,R2J,R3D),
(ZB,R1F,R2J,R3E), (ZB,R1F,R2J,R3F), (ZB,R1F,R2J,R3G), (ZB,R1F,R2J,R3H), (ZB,R1F,R2J,R3I), (ZB,R1F,R2J,R3J),
(ZB,R1F,R2J,R3K), (ZB,R1F,R2J,R3L), (ZB,R1F,R2J,R3M),
(ZB,R1F,R2J,R3N), (ZB,R1F,R2J,R3O), (ZB,R1F,R2J,R3P),
(ZB,R1F,R2J,R3R), (ZB,R1F,R2K,R3A),
(ZB,R1F,R2K,R3B), (ZB,R1F,R2K,R3C), (ZB,R1F,R2K,R3D),
(ZB,R1F,R2K,R3E), (ZB,R1F,R2K,R3F), (ZB,R1F,R2K,R3G),
(ZB,R1F,R2K,R3H), (ZB,R1F,R2K,R3I), (ZB,R1F,R2K,R3J),
(ZB,R1F,R2K,R3K), (ZB,R1F,R2K,R3L), (ZB,R1F,R2K,R3M),
(ZB,R1F,R2K,R3O), (ZB,R1F,R2K,R3P),
(ZB,R1F,R2K,R3Q), (ZB,R1F,R2K,R3R), (ZB,R1F,R2L,R3A),
(ZB,R1F,R2L,R3B), (ZB,R1F,R2L,R3C), (ZB,R1F,R2L,R3D),
(ZB,R1F,R2L,R3E), (ZB,R1F,R2L,R3F), (ZB,R1F,R2L,R3G),
(ZB,R1F,R2L,R3H), (ZB,R1F,R2L,R3I), (ZB,R1F,R2L,R3J),
(ZB,R1F,R2L,R3L), (ZB,R1F,R2L,R3M),
(ZB,R1F,R2L,R3N), (ZB,R1F,R2L,R3O), (ZB,R1F,R2L,R3P),
(ZB,R1F,R2L,R3Q), (ZB,R1F,R2L,R3R), (ZB,R1F,R2M,R3A),
(ZB,R1F,R2M,R3B), (ZB,R1F,R2M,R3C), (ZB,R1F,R2M,R3D),
(ZB,R1F,R2M,R3E), (ZB,R1F,R2M,R3F), (ZB,R1F,R2M,R3G),
(ZB,R1F,R2M,R3H), (ZB,R1F,R2M,R3I), (ZB,R1F,R2M,R3J),
(ZB,R1F,R2M,R3K), (ZB,R1F,R2M,R3L), (ZB,R1F,R2M,R3M),
(ZB,R1F,R2M,R3N), (ZB,R1F,R2M,R3O), (ZB,R1F,R2M,R3P),
(ZB,R1F,R2M,R3Q), (ZB,R1F,R2M,R3R), (ZB,R1F,R2N,R3A),
(ZB,R1F,R2N,R3B), (ZB,R1F,R2N,R3C), (ZB,R1F,R2N,R3D),
(ZB,R1F,R2N,R3E), (ZB,R1F,R2N,R3F), (ZB,R1F,R2N,R3G),
(ZB,R1F,R2N,R3H), (ZB,R1F,R2N,R3I), (ZB,R1F,R2N,R3J),
(ZB,R1F,R2N,R3K), (ZB,R1F,R2N,R3L), (ZB,R1F,R2N,R3M),
(ZB,R1F,R2N,R3N), (ZB,R1F,R2N,R3O), (ZB,R1F,R2N,R3P),
(ZB,R1F,R2N,R3Q), (ZB,R1F,R2N,R3R), (ZB,R1G,R2A,R3A),
(ZB,R1G,R2A,R3B), (ZB,R1G,R2A,R3C), (ZB,R1G,R2A,R3D),
(ZB,R1G,R2A,R3E), (ZB,R1G,R2A,R3F), (ZB,R1G,R2A,R3G),
(ZB,R1G,R2A,R3H), (ZB,R1G,R2A,R3I), (ZB,R1G,R2A,R3J),
(ZB,R1G,R2A,R3K), (ZB,R1G,R2A,R3L), (ZB,R1G,R2A,R3M),
(ZB,R1G,R2A,R3N), (ZB,R1G,R2A,R3O), (ZB,R1G,R2A,R3P),
(ZB,R1G,R2A,R3Q), (ZB,R1G,R2A,R3R), (ZB,R1G,R2B,R3A),
(ZB,R1G,R2B,R3B), (ZB,R1G,R2B,R3C), (ZB,R1G,R2B,R3D),
(ZB,R1G,R2B,R3E), (ZB,R1G,R2B,R3F), (ZB,R1G,R2B,R3G),
(ZB,R1G,R2B,R3H), (ZB,R1G,R2B,R3I), (ZB,R1G,R2B,R3J),
(ZB,R1G,R2B,R3K), (ZB,R1G,R2B,R3L), (ZB,R1G,R2B,R3M),
(ZB,R1G,R2B,R3N), (ZB,R1G,R2B,R3O), (ZB,R1G,R2B,R3P),
(ZB,R1G,R2B,R3Q), (ZB,R1G,R2B,R3R), (ZB,R1G,R2C,R3A),
(ZB,R1G,R2C,R3B), (ZB,R1G,R2C,R3C), (ZB,R1G,R2C,R3D),
(ZB,R1G,R2C,R3E), (ZB,R1G,R2C,R3F), (ZB,R1G,R2C,R3G),
(ZB,R1G,R2C,R3H), (ZB,R1G,R2C,R3I), (ZB,R1G,R2C,R3J),
(ZB,R1G,R2C,R3K), (ZB,R1G,R2C,R3L), (ZB,R1G,R2C,R3M),
(ZB,R1G,R2C,R3N), (ZB,R1G,R2C,R3O), (ZB,R1G,R2C,R3P),
(ZB,R1G,R2C,R3Q), (ZB,R1G,R2C,R3R), (ZB,R1G,R2D,R3A),
(ZB,R1G,R2D,R3B), (ZB,R1G,R2D,R3C), (ZB,R1G,R2D,R3D),
(ZB,R1G,R2D,R3E), (ZB,R1G,R2D,R3F), (ZB,R1G,R2D,R3G),
(ZB,R1G,R2D,R3H), (ZB,R1G,R2D,R3I), (ZB,R1G,R2D,R3J),
(ZB,R1G,R2D,R3K), (ZB,R1G,R2D,R3L), (ZB,R1G,R2D,R3M),
(ZB,R1G,R2D,R3N), (ZB,R1G,R2D,R3O), (ZB,R1G,R2D,R3P),
(ZB,R1G,R2D,R3Q), (ZB,R1G,R2D,R3R), (ZB,R1G,R2E,R3A),
(ZB,R1G,R2E,R3B), (ZB,R1G,R2E,R3C), (ZB,R1G,R2E,R3D),
(ZB,R1G,R2E,R3E), (ZB,R1G,R2E,R3F), (ZB,R1G,R2E,R3G),
(ZB,R1G,R2E,R3H), (ZB,R1G,R2E,R3I), (ZB,R1G,R2E,R3J),
(ZB,R1G,R2E,R3K), (ZB,R1G,R2E,R3L), (ZB,R1G,R2E,R3M),
(ZB,R1G,R2E,R3N), (ZB,R1G,R2E,R3O), (ZB,R1G,R2E,R3P),
(ZB,R1G,R2E,R3Q), (ZB,R1G,R2E,R3R), (ZB,R1G,R2F,R3A),
(ZB,R1G,R2F,R3B), (ZB,R1G,R2F,R3C), (ZB,R1G,R2F,R3D),
(ZB,R1G,R2F,R3E), (ZB,R1G,R2F,R3F), (ZB,R1G,R2F,R3G),
(ZB,R1G,R2F,R3H), (ZB,R1G,R2F,R3I), (ZB,R1G,R2F,R3J),
(ZB,R1G,R2F,R3K), (ZB,R1G,R2F,R3L), (ZB,R1G,R2F,R3M),
(ZB,R1G,R2F,R3N), (ZB,R1G,R2F,R3O), (ZB,R1G,R2F,R3P),
(ZB,R1G,R2F,R3Q), (ZB,R1G,R2F,R3R), (ZB,R1G,R2G,R3A),
(ZB,R1G,R2G,R3B), (ZB,R1G,R2G,R3C), (ZB,R1G,R2G,R3D),
(ZB,R1G,R2G,R3E), (ZB,R1G,R2G,R3F), (ZB,R1G,R2G,R3G),
(ZB,R1G,R2G,R3H), (ZB,R1G,R2G,R3I), (ZB,R1G,R2G,R3J),
(ZB,R1G,R2G,R3K), (ZB,R1G,R2G,R3L), (ZB,R1G,R2G,R3M), (ZB,R1G,R2G,R3N), (ZB,R1G,R2G,R3O), (ZB,R1G,R2G,R3P),
(ZB,R1G,R2G,R3Q), (ZB,R1G,R2G,R3R), (ZB,R1G,R2H,R3A),
(ZB,R1G,R2H,R3B), (ZB,R1G,R2H,R3C), (ZB,R1G,R2H,R3D),
(ZB,R1G,R2H,R3E), (ZB,R1G,R2H,R3F), (ZB,R1G,R2H,R3G),
(ZB,R1G,R2H,R3H), (ZB,R1G,R2H,R3I), (ZB,R1G,R2H,R3J),
(ZB,R1G,R2H,R3K), (ZB,R1G,R2H,R3L), (ZB,R1G,R2H,R3M),
(ZB,R1G,R2H,R3N), (ZB,R1G,R2H,R3O), (ZB,R1G,R2H,R3P),
(ZB,R1G,R2H,R3Q), (ZB,R1G,R2H,R3R), (ZB,R1G,R2I,R3A),
(ZB,R1G,R2I,R3B), (ZB,R1G,R2I,R3C), (ZB,R1G,R2I,R3D),
(ZB,R1G,R2I,R3E), (ZB,R1G,R2I,R3F), (ZB,R1G,R2I,R3G),
(ZB,R1G,R2I,R3H), (ZB,R1G,R2I,R3I), (ZB,R1G,R2I,R3J), (ZB,R1G,R2I,R3K),
(ZB,R1G,R2I,R3L), (ZB,R1G,R2I,R3M), (ZB,R1G,R2I,R3N),
(ZB,R1G,R2I,R3O), (ZB,R1G,R2I,R3P), (ZB,R1G,R2I,R3Q),
(ZB,R1G,R2I,R3R), (ZB,R1G,R2J,R3A), (ZB,R1G,R2J,R3B),
(ZB,R1G,R2J,R3C), (ZB,R1G,R2J,R3D), (ZB,R1G,R2J,R3E),
(ZB,R1G,R2J,R3G), (ZB,R1G,R2J,R3H),
(ZB,R1G,R2J,R3I), (ZB,R1G,R2J,R3J), (ZB,R1G,R2J,R3K),
(ZB,R1G,R2J,R3L), (ZB,R1G,R2J,R3M), (ZB,R1G,R2J,R3N),
(ZB,R1G,R2J,R3O), (ZB,R1G,R2J,R3P), (ZB,R1G,R2J,R3Q),
(ZB,R1G,R2J,R3R), (ZB,R1G,R2K,R3A), (ZB,R1G,R2K,R3B),
(ZB,R1G,R2K,R3C), (ZB,R1G,R2K,R3D), (ZB,R1G,R2K,R3E),
(ZB,R1G,R2K,R3F), (ZB,R1G,R2K,R3G), (ZB,R1G,R2K,R3H),
(ZB,R1G,R2K,R3I), (ZB,R1G,R2K,R3J), (ZB,R1G,R2K,R3K),
(ZB,R1G,R2K,R3L), (ZB,R1G,R2K,R3M), (ZB,R1G,R2K,R3N),
(ZB,R1G,R2K,R3O), (ZB,R1G,R2K,R3P), (ZB,R1G,R2K,R3Q),
(ZB,R1G,R2K,R3R), (ZB,R1G,R2L,R3A), (ZB,R1G,R2L,R3B),
(ZB,R1G,R2L,R3C), (ZB,R1G,R2L,R3D), (ZB,R1G,R2L,R3E),
(ZB,R1G,R2L,R3F), (ZB,R1G,R2L,R3G), (ZB,R1G,R2L,R3H),
(ZB,R1G,R2L,R3I), (ZB,R1G,R2L,R3J), (ZB,R1G,R2L,R3K),
(ZB,R1G,R2L,R3L), (ZB,R1G,R2L,R3M), (ZB,R1G,R2L,R3N),
(ZB,R1G,R2L,R3O), (ZB,R1G,R2L,R3P), (ZB,R1G,R2L,R3Q),
(ZB,R1G,R2L,R3R), (ZB,R1G,R2M,R3A), (ZB,R1G,R2M,R3B),
(ZB,R1G,R2M,R3C), (ZB,R1G,R2M,R3D), (ZB,R1G,R2M,R3E),
(ZB,R1G,R2M,R3F), (ZB,R1G,R2M,R3G), (ZB,R1G,R2M,R3H),
(ZB,R1G,R2M,R3I), (ZB,R1G,R2M,R3J), (ZB,R1G,R2M,R3K),
(ZB,R1G,R2M,R3L), (ZB,R1G,R2M,R3M), (ZB,R1G,R2M,R3N),
(ZB,R1G,R2M,R3O), (ZB,R1G,R2M,R3P), (ZB,R1G,R2M,R3Q),
(ZB,R1G,R2M,R3R), (ZB,R1G,R2N,R3A), (ZB,R1G,R2N,R3B),
(ZB,R1G,R2N,R3C), (ZB,R1G,R2N,R3D), (ZB,R1G,R2N,R3E),
(ZB,R1G,R2N,R3F), (ZB,R1G,R2N,R3G), (ZB,R1G,R2N,R3H),
(ZB,R1G,R2N,R3I), (ZB,R1G,R2N,R3J), (ZB,R1G,R2N,R3K),
(ZB,R1G,R2N,R3L), (ZB,R1G,R2N,R3M), (ZB,R1G,R2N,R3N),
(ZB,R1G,R2N,R3O), (ZB,R1G,R2N,R3P), (ZB,R1G,R2N,R3Q),
(ZB,R1G,R2N,R3R), (ZB,R1H,R2A,R3A), (ZB,R1H,R2A,R3B),
(ZB,R1H,R2A,R3C), (ZB,R1H,R2A,R3D), (ZB,R1H,R2A,R3E),
(ZB,R1H,R2A,R3F), (ZB,R1H,R2A,R3G), (ZB,R1H,R2A,R3H),
(ZB,R1H,R2A,R3I), (ZB,R1H,R2A,R3J), (ZB,R1H,R2A,R3K),
(ZB,R1H,R2A,R3L), (ZB,R1H,R2A,R3M), (ZB,R1H,R2A,R3N),
(ZB,R1H,R2A,R3O), (ZB,R1H,R2A,R3P), (ZB,R1H,R2A,R3Q),
(ZB,R1H,R2A,R3R), (ZB,R1H,R2B,R3A), (ZB,R1H,R2B,R3B),
(ZB,R1H,R2B,R3C), (ZB,R1H,R2B,R3D), (ZB,R1H,R2B,R3E),
(ZB,R1H,R2B,R3F), (ZB,R1H,R2B,R3G), (ZB,R1H,R2B,R3H),
(ZB,R1H,R2B,R3I), (ZB,R1H,R2B,R3J), (ZB,R1H,R2B,R3K),
(ZB,R1H,R2B,R3L), (ZB,R1H,R2B,R3M), (ZB,R1H,R2B,R3N),
(ZB,R1H,R2B,R3O), (ZB,R1H,R2B,R3P), (ZB,R1H,R2B,R3Q),
(ZB,R1H,R2B,R3R), (ZB,R1H,R2C,R3A), (ZB,R1H,R2C,R3B),
(ZB,R1H,R2C,R3C), (ZB,R1H,R2C,R3D), (ZB,R1H,R2C,R3E),
(ZB,R1H,R2C,R3F), (ZB,R1H,R2C,R3G), (ZB,R1H,R2C,R3H),
(ZB,R1H,R2C,R3I), (ZB,R1H,R2C,R3J), (ZB,R1H,R2C,R3K),
(ZB,R1H,R2C,R3L), (ZB,R1H,R2C,R3M), (ZB,R1H,R2C,R3N),
(ZB,R1H,R2C,R3O), (ZB,R1H,R2C,R3P), (ZB,R1H,R2C,R3Q),
(ZB,R1H,R2C,R3R), (ZB,R1H,R2D,R3A), (ZB,R1H,R2D,R3B),
(ZB,R1H,R2D,R3C), (ZB,R1H,R2D,R3D), (ZB,R1H,R2D,R3E),
(ZB,R1H,R2D,R3F), (ZB,R1H,R2D,R3G), (ZB,R1H,R2D,R3H),
(ZB,R1H,R2D,R3I), (ZB,R1H,R2D,R3J), (ZB,R1H,R2D,R3K),
(ZB,R1H,R2D,R3L), (ZB,R1H,R2D,R3M), (ZB,R1H,R2D,R3N),
(ZB,R1H,R2D,R3O), (ZB,R1H,R2D,R3P), (ZB,R1H,R2D,R3Q), (ZB,R1H,R2D,R3R), (ZB,R1H,R2E,R3A), (ZB,R1H,R2E,R3B),
(ZB,R1H,R2E,R3C), (ZB,R1H,R2E,R3D), (ZB,R1H,R2E,R3E),
(ZB,R1H,R2E,R3F), (ZB,R1H,R2E,R3G), (ZB,R1H,R2E,R3H),
(ZB,R1H,R2E,R3I), (ZB,R1H,R2E,R3J), (ZB,R1H,R2E,R3K),
(ZB,R1H,R2E,R3L), (ZB,R1H,R2E,R3M), (ZB,R1H,R2E,R3N),
(ZB,R1H,R2E,R3O), (ZB,R1H,R2E,R3P), (ZB,R1H,R2E,R3Q),
(ZB,R1H,R2E,R3R), (ZB,R1H,R2F,R3A), (ZB,R1H,R2F,R3B),
(ZB,R1H,R2F,R3C), (ZB,R1H,R2F,R3D), (ZB,R1H,R2F,R3E),
(ZB,R1H,R2F,R3F), (ZB,R1H,R2F,R3G), (ZB,R1H,R2F,R3H),
(ZB,R1H,R2F,R3I), (ZB,R1H,R2F,R3J), (ZB,R1H,R2F,R3K),
(ZB,R1H,R2F,R3L), (ZB,R1H,R2F,R3M), (ZB,R1H,R2F,R3N),
(ZB,R1H,R2F,R3O), (ZB,R1H,R2F,R3P), (ZB,R1H,R2F,R3Q),
(ZB,R1H,R2F,R3R), (ZB,R1H,R2G,R3A), (ZB,R1H,R2G,R3B),
(ZB,R1H,R2G,R3C), (ZB,R1H,R2G,R3D), (ZB,R1H,R2G,R3E),
(ZB,R1H,R2G,R3F), (ZB,R1H,R2G,R3G), (ZB,R1H,R2G,R3H),
(ZB,R1H,R2G,R3I), (ZB,R1H,R2G,R3J), (ZB,R1H,R2G,R3K),
(ZB,R1H,R2G,R3L), (ZB,R1H,R2G,R3M), (ZB,R1H,R2G,R3N),
(ZB,R1H,R2G,R3O), (ZB,R1H,R2G,R3P), (ZB,R1H,R2G,R3Q),
(ZB,R1H,R2G,R3R), (ZB,R1H,R2H,R3A), (ZB,R1H,R2H,R3B),
(ZB,R1H,R2H,R3C), (ZB,R1H,R2H,R3D), (ZB,R1H,R2H,R3E),
(ZB,R1H,R2H,R3F), (ZB,R1H,R2H,R3G), (ZB,R1H,R2H,R3H),
(ZB,R1H,R2H,R3I), (ZB,R1H,R2H,R3J), (ZB,R1H,R2H,R3K),
(ZB,R1H,R2H,R3L), (ZB,R1H,R2H,R3M), (ZB,R1H,R2H,R3N),
(ZB,R1H,R2H,R3O), (ZB,R1H,R2H,R3P), (ZB,R1H,R2H,R3Q),
(ZB,R1H,R2H,R3R), (ZB,R1H,R2I,R3A), (ZB,R1H,R2I,R3B),
(ZB,R1H,R2I,R3C), (ZB,R1H,R2I,R3D), (ZB,R1H,R2I,R3E),
(ZB,R1H,R2I,R3F), (ZB,R1H,R2I,R3G), (ZB,R1H,R2I,R3H), (ZB,R1H,R2I,R3I),
(ZB,R1H,R2I,R3J), (ZB,R1H,R2I,R3K), (ZB,R1H,R2I,R3L),
(ZB,R1H,R2I,R3M), (ZB,R1H,R2I,R3N), (ZB,R1H,R2I,R3O),
(ZB,R1H,R2I,R3P), (ZB,R1H,R2I,R3Q), (ZB,R1H,R2I,R3R),
(ZB,R1H,R2J,R3A), (ZB,R1H,R2J,R3B), (ZB,R1H,R2J,R3C),
(ZB,R1H,R2J,R3D), (ZB,R1H,R2J,R3E), (ZB,R1H,R2J,R3F),
(ZB,R1H,R2J,R3G), (ZB,R1H,R2J,R3H), (ZB,R1H,R2J,R3I),
(ZB,R1H,R2J,R3J), (ZB,R1H,R2J,R3K), (ZB,R1H,R2J,R3L),
(ZB,R1H,R2J,R3M), (ZB,R1H,R2J,R3N), (ZB,R1H,R2J,R3O),
(ZB,R1H,R2J,R3P), (ZB,R1H,R2J,R3Q), (ZB,R1H,R2J,R3R),
(ZB,R1H,R2K,R3A), (ZB,R1H,R2K,R3B), (ZB,R1H,R2K,R3C),
(ZB,R1H,R2K,R3D), (ZB,R1H,R2K,R3E), (ZB,R1H,R2K,R3F),
(ZB,R1H,R2K,R3G), (ZB,R1H,R2K,R3H), (ZB,R1H,R2K,R3I),
(ZB,R1H,R2K,R3J), (ZB,R1H,R2K,R3K), (ZB,R1H,R2K,R3L),
(ZB,R1H,R2K,R3M), (ZB,R1H,R2K,R3N), (ZB,R1H,R2K,R3O),
(ZB,R1H,R2K,R3P), (ZB,R1H,R2K,R3Q), (ZB,R1H,R2K,R3R),
(ZB,R1H,R2L,R3A), (ZB,R1H,R2L,R3B), (ZB,R1H,R2L,R3C),
(ZB,R1H,R2L,R3D), (ZB,R1H,R2L,R3E), (ZB,R1H,R2L,R3F),
(ZB,R1H,R2L,R3G), (ZB,R1H,R2L,R3H), (ZB,R1H,R2L,R3I),
(ZB,R1H,R2L,R3J), (ZB,R1H,R2L,R3K), (ZB,R1H,R2L,R3L),
(ZB,R1H,R2L,R3M), (ZB,R1H,R2L,R3N), (ZB,R1H,R2L,R3O),
(ZB,R1H,R2L,R3P), (ZB,R1H,R2L,R3Q), (ZB,R1H,R2L,R3R),
(ZB,R1H,R2M,R3A), (ZB,R1H,R2M,R3B), (ZB,R1H,R2M,R3C),
(ZB,R1H,R2M,R3D), (ZB,R1H,R2M,R3E), (ZB,R1H,R2M,R3F),
(ZB,R1H,R2M,R3G), (ZB,R1H,R2M,R3H), (ZB,R1H,R2M,R3I),
(ZB,R1H,R2M,R3J), (ZB,R1H,R2M,R3K), (ZB,R1H,R2M,R3L),
(ZB,R1H,R2M,R3M), (ZB,R1H,R2M,R3N), (ZB,R1H,R2M,R3O),
(ZB,R1H,R2M,R3P), (ZB,R1H,R2M,R3Q), (ZB,R1H,R2M,R3R),
(ZB,R1H,R2N,R3A), (ZB,R1H,R2N,R3B), (ZB,R1H,R2N,R3C),
(ZB,R1H,R2N,R3D), (ZB,R1H,R2N,R3E), (ZB,R1H,R2N,R3F),
(ZB,R1H,R2N,R3G), (ZB,R1H,R2N,R3H), (ZB,R1H,R2N,R3I),
(ZB,R1H,R2N,R3J), (ZB,R1H,R2N,R3K), (ZB,R1H,R2N,R3L),
(ZB,R1H,R2N,R3M), (ZB,R1H,R2N,R3N), (ZB,R1H,R2N,R3O),
(ZB,R1H,R2N,R3P), (ZB,R1H,R2N,R3Q), (ZB,R1H,R2N,R3R),
(ZB,R1H,R2A,R3A), (ZB,R1H,R2A,R3B), (ZB,R1H,R2A,R3C), (ZB,R1H,R2A,R3D),
(ZB,R1H,R2A,R3E), (ZB,R1H,R2A,R3F), (ZB,R1H,R2A,R3G), (ZB,R1H,R2A,R3H),
(ZB,R1H,R2A,R3I), (ZB,R1H,R2A,R3J), (ZB,R1H,R2A,R3K), (ZB,R1H,R2A,R3L),
(ZB,R1H,R2A,R3M), (ZB,R1H,R2A,R3N), (ZB,R1H,R2A,R3O), (ZB,R1H,R2A,R3P),
(ZB,R1H,R2A,R3Q), (ZB,R1H,R2A,R3R), (ZB,R1H,R2B,R3A), (ZB,R1H,R2B,R3B),
(ZB,R1H,R2B,R3C), (ZB,R1H,R2B,R3D), (ZB,R1H,R2B,R3E), (ZB,R1H,R2B,R3F), (ZB,R1H,R2B,R3G), (ZB,R1H,R2B,R3H), (ZB,R1H,R2B,R3I),
(ZB,R1H,R2B,R3J), (ZB,R1H,R2B,R3K), (ZB,R1H,R2B,R3L), (ZB,R1H,R2B,R3M),
(ZB,R1H,R2B,R3N), (ZB,R1H,R2B,R3O), (ZB,R1H,R2B,R3P),
(ZB,R1H,R2B,R3Q), (ZB,R1I,R2B,R3R), (ZB,R1I,R2C,R3A),
(ZB,R1H,R2C,R3B), (ZB,R1H,R2C,R3C), (ZB,R1H,R2C,R3D),
(ZB,R1H,R2C,R3E), (ZB,R1I,R2C,R3F), (ZB,R1H,R2C,R3G),
(ZB,R1H,R2C,R3H), (ZB,R1H,R2C,R3I), (ZB,R1H,R2C,R3J), (ZB,R1H,R2C,R3K),
(ZB,R1H,R2C,R3L), (ZB,R1H,R2C,R3M), (ZB,R1H,R2C,R3N),
(ZB,R1H,R2C,R3O), (ZB,R1H,R2C,R3P), (ZB,R1H,R2C,R3Q),
(ZB,R1H,R2C,R3R), (ZB,R1H,R2D,R3A), (ZB,R1J,R2D,R3B),
(ZB,R1H,R2D,R3C), (ZB,R1H,R2D,R3D), (ZB,R1H,R2D,R3E),
(ZB,R1H,R2D,R3F), (ZB,R1H,R2D,R3G), (ZB,R1H,R2D,R3H), (ZB,R1H,R2D,R3I),
(ZB,R1H,R2D,R3J), (ZB,R1H,R2D,R3K), (ZB,R1H,R2D,R3L),
(ZB,R1I,R2D,R3M), (ZB,R1H,R2D,R3N), (ZB,R1H,R2D,R3O),
(ZB,R1H,R2D,R3P), (ZB,R1H,R2D,R3Q), (ZB,R1H,R2D,R3R),
(ZB,R1H,R2E,R3A), (ZB,R1H,R2E,R3B), (ZB,R1H,R2E,R3C), (ZB,R1I,R2E,R3D),
(ZB,R1H,R2E,R3E), (ZB,R1H,R2E,R3F), (ZB,R1H,R2E,R3G), (ZB,R1H,R2E,R3H),
(ZB,R1H,R2E,R3I), (ZB,R1H,R2E,R3J), (ZB,R1H,R2E,R3K), (ZB,R1H,R2E,R3L),
(ZB,R1H,R2E,R3M), (ZB,R1H,R2E,R3N), (ZB,R1H,R2E,R3O),
(ZB,R1H,R2E,R3P), (ZB,R1H,R2E,R3Q), (ZB,R1H,R2E,R3R), (ZB,R1H,R2F,R3A),
(ZB,R1H,R2F,R3B), (ZB,R1H,R2F,R3C), (ZB,R1H,R2F,R3D), (ZB,R1H,R2F,R3E),
(ZB,R1H,R2F,R3F), (ZB,R1H,R2F,R3G), (ZB,R1H,R2F,R3H), (ZB,R1H,R2F,R3I),
(ZB,R1H,R2F,R3J), (ZB,R1H,R2F,R3K), (ZB,R1H,R2F,R3L), (ZB,R1H,R2F,R3M),
(ZB,R1H,R2F,R3N), (ZB,R1H,R2F,R3O), (ZB,R1H,R2F,R3P), (ZB,R1H,R2F,R3Q),
(ZB,R1H,R2F,R3R), (ZB,R1H,R2G,R3A), (ZB,R1H,R2G,R3B),
(ZB,R1H,R2G,R3C), (ZB,R1H,R2G,R3D), (ZB,R1H,R2G,R3E),
(ZB,R1H,R2G,R3F), (ZB,R1H,R2G,R3G), (ZB,R1H,R2G,R3H), (ZB,R1H,R2G,R3I),
(ZB,R1H,R2G,R3J), (ZB,R1H,R2G,R3K), (ZB,R1H,R2G,R3L),
(ZB,R1H,R2G,R3M), (ZB,R1H,R2G,R3N), (ZB,R1H,R2G,R3O),
(ZB,R1H,R2G,R3P), (ZB,R1H,R2G,R3Q), (ZB,R1H,R2G,R3R),
(ZB,R1H,R2H,R3A), (ZB,R1H,R2H,R3B), (ZB,R1H,R2H,R3C),
(ZB,R1H,R2H,R3D), (ZB,R1H,R2H,R3E), (ZB,R1H,R2H,R3F),
(ZB,R1H,R2H,R3G), (ZB,R1H,R2H,R3H), (ZB,R1H,R2H,R3I), (ZB,R1H,R2H,R3J),
(ZB,R1H,R2H,R3K), (ZB,R1H,R2H,R3L), (ZB,R1H,R2H,R3M),
(ZB,R1H,R2H,R3N), (ZB,R1H,R2H,R3O), (ZB,R1H,R2H,R3P),
(ZB,R1H,R2H,R3Q), (ZB,R1H,R2H,R3R), (ZB,R1H,R2I,R3A), (ZB,R1H,R2I,R3B),
(ZB,R1H,R2I,R3C), (ZB,R1H,R2I,R3D), (ZB,R1H,R2I,R3E), (ZB,R1H,R2I,R3F),
(ZB,R1H,R2I,R3G), (ZB,R1H,R2I,R3H), (ZB,R1H,R2I,R3I), (ZB,R1H,R2I,R3J),
(ZB,R1H,R2I,R3K), (ZB,R1H,R2I,R3L), (ZB,R1H,R2I,R3M), (ZB,R1H,R2I,R3N),
(ZB,R1H,R2I,R3O), (ZB,R1H,R2I,R3P), (ZB,R1H,R2I,R3Q), (ZB,R1H,R2I,R3R),
(ZB,R1H,R2J,R3A), (ZB,R1H,R2J,R3B), (ZB,R1H,R2J,R3C), (ZB,R1H,R2J,R3D),
(ZB,R1H,R2J,R3E), (ZB,R1H,R2J,R3F), (ZB,R1H,R2J,R3G), (ZB,R1H,R2J,R3H),
(ZB,R1H,R2J,R3I), (ZB,R1H,R2J,R3J), (ZB,R1H,R2J,R3K), (ZB,R1H,R2J,R3L),
(ZB,R1H,R2J,R3M), (ZB,R1H,R2J,R3N), (ZB,R1H,R2J,R3O), (ZB,R1H,R2J,R3P),
(ZB,R1H,R2J,R3Q), (ZB,R1H,R2J,R3R), (ZB,R1H,R2K,R3A), (ZB,R1H,R2K,R3B),
(ZB,R1H,R2K,R3C), (ZB,R1H,R2K,R3D), (ZB,R1H,R2K,R3E), (ZB,R1H,R2K,R3F),
(ZB,R1H,R2K,R3G), (ZB,R1H,R2K,R3H), (ZB,R1H,R2K,R3I), (ZB,R1H,R2K,R3J),
(ZB,R1H,R2K,R3K), (ZB,R1H,R2K,R3L), (ZB,R1H,R2K,R3M),
(ZB,R1H,R2K,R3N), (ZB,R1H,R2K,R3O), (ZB,R1H,R2K,R3P), (ZB,R1H,R2K,R3Q),
(ZB,R1H,R2K,R3R), (ZB,R1H,R2L,R3A), (ZB,R1H,R2L,R3B), (ZB,R1H,R2L,R3C),
(ZB,R1H,R2L,R3D), (ZB,R1H,R2L,R3E), (ZB,R1H,R2L,R3F), (ZB,R1H,R2L,R3G),
(ZB,R1H,R2L,R3H), (ZB,R1H,R2L,R3I), (ZB,R1H,R2L,R3J), (ZB,R1H,R2L,R3K),
(ZB,R1H,R2L,R3L), (ZB,R1H,R2L,R3M), (ZB,R1H,R2L,R3N), (ZB,R1H,R2L,R3O),
(ZB,R1H,R2L,R3P), (ZB,R1H,R2L,R3Q), (ZB,R1H,R2L,R3R), (ZB,R1H,R2M,R3A),
(ZB,R1H,R2M,R3B), (ZB,R1H,R2M,R3C), (ZB,R1H,R2M,R3D),
(ZB,R1H,R2M,R3E), (ZB,R1H,R2M,R3F), (ZB,R1H,R2M,R3G),
(ZB,R1H,R2M,R3H), (ZB,R1H,R2M,R3I), (ZB,R1H,R2M,R3J),
(ZB,R1H,R2M,R3K), (ZB,R1H,R2M,R3L), (ZB,R1H,R2M,R3M),
(ZB,R1H,R2M,R3N), (ZB,R1H,R2M,R3O), (ZB,R1H,R2M,R3P),
(ZB,R1H,R2M,R3Q), (ZB,R1H,R2M,R3R), (ZB,R1H,R2N,R3A),
(ZB,R1H,R2N,R3B), (ZB,R1H,R2N,R3C), (ZB,R1H,R2N,R3D),
(ZB,R1H,R2N,R3E), (ZB,R1H,R2N,R3F), (ZB,R1H,R2N,R3G),
(ZB,R1H,R2N,R3H), (ZB,R1H,R2N,R3I), (ZB,R1H,R2N,R3J), (ZB,R1H,R2N,R3K),
(ZB,R1H,R2N,R3L), (ZB,R1I,R2N,R3M), (ZB,R1H,R2N,R3N),
(ZB,R1H,R2N,R3O), (ZB,R1H,R2N,R3P), (ZB,R1H,R2N,R3Q),
(ZB,R1H,R2N,R3R), (ZB,R1J,R2A,R3A), (ZB,R1J,R2A,R3B), (ZB,R1J,R2A,R3C), (ZB,R1J,R2A,R3D), (ZB,R1J,R2A, R3E),
(ZB,R1J,R2A,R3F), (ZB,R1J,R2A,R3G), (ZB,R1J,R2A, R3H),
(ZB,R1J,R2A,R3I), (ZB,R1J,R2A,R3J), (ZB,R1J,R2A, R3K),
(ZB,R1J,R2A,R3L), (ZB,R1J,R2A,R3M), (ZB,R1J,R2A, R3N),
(ZB,R1J,R2A,R3O), (ZB,R1J,R2A,R3P), (ZB,R1J,R2A, R3Q),
(ZB,R1J,R2A,R3R), (ZB,R1J,R2B,R3A), (ZB,R1J,R2B, R3B),
(ZB,R1J,R2B,R3C), (ZB,R1J,R2B,R3D), (ZB,R1J,R2B, R3E),
(ZB,R1J,R2B,R3F), (ZB,R1J,R2B,R3G), (ZB,R1J,R2B, R3H),
(ZB,R1J,R2B,R3I), (ZB,R1J,R2B,R3J), (ZB,R1J,R2B, R3K),
(ZB,R1J,R2B,R3L), (ZB,R1J,R2B,R3M), (ZB,R1J,R2B, R3N),
(ZB,R1J,R2B,R3O), (ZB,R1J,R2B,R3P), (ZB,R1J,R2B, R3Q),
(ZB,R1J,R2B,R3R), (ZB,R1J,R2C,R3A), (ZB,R1J,R2C, R3B),
(ZB,R1J,R2C,R3C), (ZB,R1J,R2C,R3D), (ZB,R1J,R2C, R3E),
(ZB,R1J,R2C,R3F), (ZB,R1J,R2C,R3G), (ZB,R1J,R2C, R3H),
(ZB,R1J,R2C,R3I), (ZB,R1J,R2C,R3J), (ZB,R1J,R2C, R3K),
(ZB,R1J,R2C,R3L), (ZB,R1J,R2C,R3M), (ZB,R1J,R2C, R3N),
(ZB,R1J,R2C,R3O), (ZB,R1J,R2C,R3P), (ZB,R1J,R2C, R3Q),
(ZB,R1J,R2C,R3R), (ZB,R1J,R2D,R3A), (ZB,R1J,R2D, R3B),
(ZB,R1J,R2D,R3C), (ZB,R1J,R2D,R3D), (ZB,R1J,R2D, R3E),
(ZB,R1J,R2D,R3F), (ZB,R1J,R2D,R3G), (ZB,R1J,R2D, R3H),
(ZB,R1J,R2D,R3I), (ZB,R1J,R2D,R3J), (ZB,R1J,R2D, R3K),
(ZB,R1J,R2D,R3L), (ZB,R1J,R2D,R3M), (ZB,R1J,R2D, R3N),
(ZB,R1J,R2D,R3O), (ZB,R1J,R2D,R3P), (ZB,R1J,R2D, R3Q),
(ZB,R1J,R2D,R3R), (ZB,R1J,R2E,R3A), (ZB,R1J,R2E, R3B),
(ZB,R1J,R2E,R3C), (ZB,R1J,R2E,R3D), (ZB,R1J,R2E, R3E),
(ZB,R1J,R2E,R3F), (ZB,R1J,R2E,R3G), (ZB,R1J,R2E, R3H),
(ZB,R1J,R2E,R3I), (ZB,R1J,R2E,R3J), (ZB,R1J,R2E, R3K),
(ZB,R1J,R2E,R3L), (ZB,R1J,R2E,R3M), (ZB,R1J,R2E, R3N),
(ZB,R1J,R2E,R3O), (ZB,R1J,R2E,R3P), (ZB,R1J,R2E, R3Q),
(ZB,R1J,R2E,R3R), (ZB,R1J,R2F,R3A), (ZB,R1J,R2F, R3B),
(ZB,R1J,R2F,R3C), (ZB,R1J,R2F,R3D), (ZB,R1J,R2F, R3E),
(ZB,R1J,R2F,R3F), (ZB,R1J,R2F,R3G), (ZB,R1J,R2F, R3H),
(ZB,R1J,R2F,R3I), (ZB,R1J,R2F,R3J), (ZB,R1J,R2F,R3K),
(ZB,R1J,R2F,R3L), (ZB,R1J,R2F,R3M), (ZB,R1J,R2F, R3N),
(ZB,R1J,R2F,R3O), (ZB,R1J,R2F,R3P), (ZB,R1J,R2F, R3Q),
(ZB,R1J,R2F,R3R), (ZB,R1J,R2G,R3A), (ZB,R1J,R2G, R3B),
(ZB,R1J,R2G,R3C), (ZB,R1J,R2G,R3D), (ZB,R1J,R2G, R3E),
(ZB,R1J,R2G,R3F), (ZB,R1J,R2G,R3G), (ZB,R1J,R2G, R3H),
(ZB,R1J,R2G,R3I), (ZB,R1J,R2G,R3J), (ZB,R1J,R2G, R3K),
(ZB,R1J,R2G,R3L), (ZB,R1J,R2G,R3M), (ZB,R1J,R2G, R3N),
(ZB,R1J,R2G,R3O), (ZB,R1J,R2G,R3P), (ZB,R1J,R2G, R3Q),
(ZB,R1J,R2G,R3R), (ZB,R1J,R2H,R3A), (ZB,R1J,R2H, R3B),
(ZB,R1J,R2H,R3C), (ZB,R1J,R2H,R3D), (ZB,R1J,R2H, R3E),
(ZB,R1J,R2H,R3F), (ZB,R1J,R2H,R3G), (ZB,R1J,R2H, R3H),
(ZB,R1J,R2H,R3I), (ZB,R1J,R2H,R3J), (ZB,R1J,R2H, R3K),
(ZB,R1J,R2H,R3L), (ZB,R1J,R2H,R3M), (ZB,R1J,R2H, R3N),
(ZB,R1J,R2H,R3O), (ZB,R1J,R2H,R3P), (ZB,R1J,R2H, R3Q),
(ZB,R1J,R2H,R3R), (ZB,R1J,R2I,R3A), (ZB,R1J,R2I, R3B), (ZB,R1J,R2I,R3C),
(ZB,R1J,R2I,R3D), (ZB,R1J,R2I,R3E), (ZB,R1J,R2I,R3F), (ZB,R1J,R2I,R3G),
(ZB,R1J,R2I,R3H), (ZB,R1J,R2I,R3I), (ZB,R1J,R2I,R3J), (ZB,R1J,R2I,R3K),
(ZB,R1J,R2I,R3L), (ZB,R1J,R2I,R3M), (ZB,R1J,R2I, R3N), (ZB,R1J,R2I,R3O),
(ZB,R1J,R2I,R3P), (ZB,R1J,R2I,R3Q), (ZB,R1J,R2I,R3R), (ZB,R1J,R2J,R3A),
(ZB,R1J,R2J,R3B), (ZB,R1J,R2J,R3C), (ZB,R1J,R2J, R3D),
(ZB,R1J,R2J,R3E), (ZB,R1J,R2J,R3F), (ZB,R1J,R2J,R3G), (ZB,R1J,R2J,R3H), (ZB,R1J,R2J,R3I), (ZB,R1J,R2J,R3J), (ZB,R1J,R2J,R3K), (ZB,R1J,R2J,R3L), (ZB,R1J,R2J, R3M),
(ZB,R1J,R2J,R3O), (ZB,R1J,R2J,R3P),
(ZB,R1J,R2J,R3Q), (ZB,R1J,R2J,R3R), (ZB,R1J,R2K, R3A),
(ZB,R1J,R2K,R3B), (ZB,R1J,R2K,R3C), (ZB,R1J,R2K, R3D),
(ZB,R1J,R2K,R3E), (ZB,R1J,R2K,R3F), (ZB,R1J,R2K, R3G),
(ZB,R1J,R2K,R3H), (ZB,R1J,R2K,R3I), (ZB,R1J,R2K, R3J),
(ZB,R1J,R2K,R3L), (ZB,R1J,R2K,R3M),
(ZB,R1J,R2K,R3N), (ZB,R1J,R2K,R3O), (ZB,R1J,R2K, R3P),
(ZB,R1J,R2K,R3Q), (ZB,R1J,R2K,R3R), (ZB,R1J,R2L, R3A),
(ZB,R1J,R2L,R3B), (ZB,R1J,R2L,R3C), (ZB,R1J,R2L, R3D),
(ZB,R1J,R2L,R3E), (ZB,R1J,R2L,R3F), (ZB,R1J,R2L, R3G),
(ZB,R1J,R2L,R3H), (ZB,R1J,R2L,R3I), (ZB,R1J,R2L, R3J),
(ZB,R1J,R2L,R3K), (ZB,R1J,R2L,R3L), (ZB,R1J,R2L, R3M),
(ZB,R1J,R2L,R3N), (ZB,R1J,R2L,R3O), (ZB,R1J,R2L, R3P), (ZB,R1J,R2L,R3Q), (ZB,R1J,R2L,R3R), (ZB,R1J,R2M,R3A),
(ZB,R1J,R2M,R3B), (ZB,R1J,R2M,R3C), (ZB,R1J,R2M,R3D),
(ZB,R1J,R2M,R3E), (ZB,R1J,R2M,R3F), (ZB,R1J,R2M,R3G),
(ZB,R1J,R2M,R3H), (ZB,R1J,R2M,R3I), (ZB,R1J,R2M,R3J),
(ZB,R1J,R2M,R3K), (ZB,R1J,R2M,R3L), (ZB,R1J,R2M,R3M),
(ZB,R1J,R2M,R3N), (ZB,R1J,R2M,R3O), (ZB,R1J,R2M,R3P),
(ZB,R1J,R2M,R3Q), (ZB,R1J,R2M,R3R), (ZB,R1J,R2N,R3A),
(ZB,R1J,R2N,R3B), (ZB,R1J,R2N,R3C), (ZB,R1J,R2N,R3D),
(ZB,R1J,R2N,R3E), (ZB,R1J,R2N,R3F), (ZB,R1J,R2N,R3G),
(ZB,R1J,R2N,R3H), (ZB,R1J,R2N,R3I), (ZB,R1J,R2N,R3J),
(ZB,R1J,R2N,R3K), (ZB,R1J,R2N,R3L), (ZB,R1J,R2N,R3M),
(ZB,R1J,R2N,R3N), (ZB,R1J,R2N,R3O), (ZB,R1J,R2N,R3P),
(ZB,R1J,R2N,R3Q), (ZB,R1J,R2N,R3R), (ZB,R1K,R2A,R3A),
(ZB,R1K,R2A,R3B), (ZB,R1K,R2A,R3C), (ZB,R1K,R2A,R3D),
(ZB,R1K,R2A,R3E), (ZB,R1K,R2A,R3F), (ZB,R1K,R2A,R3G),
(ZB,R1K,R2A,R3H), (ZB,R1K,R2A,R3I), (ZB,R1K,R2A,R3J),
(ZB,R1K,R2A,R3K), (ZB,R1K,R2A,R3L), (ZB,R1K,R2A,R3M),
(ZB,R1K,R2A,R3N), (ZB,R1K,R2A,R3O), (ZB,R1K,R2A,R3P),
(ZB,R1K,R2A,R3Q), (ZB,R1K,R2A,R3R), (ZB,R1K,R2B,R3A),
(ZB,R1K,R2B,R3B), (ZB,R1K,R2B,R3C), (ZB,R1K,R2B,R3D),
(ZB,R1K,R2B,R3E), (ZB,R1K,R2B,R3F), (ZB,R1K,R2B,R3G),
(ZB,R1K,R2B,R3H), (ZB,R1K,R2B,R3I), (ZB,R1K,R2B,R3J),
(ZB,R1K,R2B,R3K), (ZB,R1K,R2B,R3L), (ZB,R1K,R2B,R3M),
(ZB,R1K,R2B,R3N), (ZB,R1K,R2B,R3O), (ZB,R1K,R2B,R3P),
(ZB,R1K,R2B,R3Q), (ZB,R1K,R2B,R3R), (ZB,R1K,R2C,R3A),
(ZB,R1K,R2C,R3B), (ZB,R1K,R2C,R3C), (ZB,R1K,R2C,R3D),
(ZB,R1K,R2C,R3E), (ZB,R1K,R2C,R3F), (ZB,R1K,R2C,R3G),
(ZB,R1K,R2C,R3H), (ZB,R1K,R2C,R3I), (ZB,R1K,R2C,R3J),
(ZB,R1K,R2C,R3K), (ZB,R1K,R2C,R3L), (ZB,R1K,R2C,R3M),
(ZB,R1K,R2C,R3N), (ZB,R1K,R2C,R3O), (ZB,R1K,R2C,R3P),
(ZB,R1K,R2C,R3Q), (ZB,R1K,R2C,R3R), (ZB,R1K,R2D,R3A),
(ZB,R1K,R2D,R3B), (ZB,R1K,R2D,R3C), (ZB,R1K,R2D,R3D),
(ZB,R1K,R2D,R3E), (ZB,R1K,R2D,R3F), (ZB,R1K,R2D,R3G),
(ZB,R1K,R2D,R3H), (ZB,R1K,R2D,R3I), (ZB,R1K,R2D,R3J),
(ZB,R1K,R2D,R3K), (ZB,R1K,R2D,R3L), (ZB,R1K,R2D,R3M),
(ZB,R1K,R2D,R3N), (ZB,R1K,R2D,R3O), (ZB,R1K,R2D,R3P),
(ZB,R1K,R2D,R3Q), (ZB,R1K,R2D,R3R), (ZB,R1K,R2E,R3A),
(ZB,R1K,R2E,R3B), (ZB,R1K,R2E,R3C), (ZB,R1K,R2E,R3D),
(ZB,R1K,R2E,R3E), (ZB,R1K,R2E,R3F), (ZB,R1K,R2E,R3G),
(ZB,R1K,R2E,R3H), (ZB,R1K,R2E,R3I), (ZB,R1K,R2E,R3J),
(ZB,R1K,R2E,R3K), (ZB,R1K,R2E,R3L), (ZB,R1K,R2E,R3M),
(ZB,R1K,R2E,R3N), (ZB,R1K,R2E,R3O), (ZB,R1K,R2E,R3P),
(ZB,R1K,R2E,R3Q), (ZB,R1K,R2E,R3R), (ZB,R1K,R2F,R3A),
(ZB,R1K,R2F,R3B), (ZB,R1K,R2F,R3C), (ZB,R1K,R2F,R3D),
(ZB,R1K,R2F,R3E), (ZB,R1K,R2F,R3F), (ZB,R1K,R2F,R3G),
(ZB,R1K,R2F,R3H), (ZB,R1K,R2F,R3I), (ZB,R1K,R2F,R3J),
(ZB,R1K,R2F,R3K), (ZB,R1K,R2F,R3L), (ZB,R1K,R2F,R3M),
(ZB,R1K,R2F,R3N), (ZB,R1K,R2F,R3O), (ZB,R1K,R2F,R3P),
(ZB,R1K,R2F,R3Q), (ZB,R1K,R2F,R3R), (ZB,R1K,R2G,R3A),
(ZB,R1K,R2G,R3B), (ZB,R1K,R2G,R3C), (ZB,R1K,R2G,R3D),
(ZB,R1K,R2G,R3E), (ZB,R1K,R2G,R3F), (ZB,R1K,R2G,R3G),
(ZB,R1K,R2G,R3H), (ZB,R1K,R2G,R3I), (ZB,R1K,R2G,R3J),
(ZB,R1K,R2G,R3K), (ZB,R1K,R2G,R3L), (ZB,R1K,R2G,R3M),
(ZB,R1K,R2G,R3N), (ZB,R1K,R2G,R3O), (ZB,R1K,R2G,R3P),
(ZB,R1K,R2G,R3Q), (ZB,R1K,R2G,R3R), (ZB,R1K,R2H,R3A),
(ZB,R1K,R2H,R3B), (ZB,R1K,R2H,R3C), (ZB,R1K,R2H,R3D),
(ZB,R1K,R2H,R3E), (ZB,R1K,R2H,R3F), (ZB,R1K,R2H,R3G),
(ZB,R1K,R2H,R3H), (ZB,R1K,R2H,R3I), (ZB,R1K,R2H,R3J),
(ZB,R1K,R2H,R3K), (ZB,R1K,R2H,R3L), (ZB,R1K,R2H,R3M),
(ZB,R1K,R2H,R3N), (ZB,R1K,R2H,R3O), (ZB,R1K,R2H,R3P),
(ZB,R1K,R2H,R3Q), (ZB,R1K,R2H,R3R), (ZB,R1K,R2I,R3A),
(ZB,R1K,R2I,R3B), (ZB,R1K,R2I,R3C), (ZB,R1K,R2I,R3D),
(ZB,R1K,R2I,R3E), (ZB,R1K,R2I,R3F), (ZB,R1K,R2I,R3G), (ZB,R1K,R2I,R3H),
(ZB,R1K,R2I,R3I), (ZB,R1K,R2I,R3J), (ZB,R1K,R2I,R3K), (ZB,R1K,R2I,R3L),
(ZB,R1K,R2I,R3M), (ZB,R1K,R2I,R3N), (ZB,R1K,R2I,R3O),
(ZB,R1K,R2I,R3P), (ZB,R1K,R2I,R3Q), (ZB,R1K,R2I,R3R), (ZB,R1K,R2J,R3A), (ZB,R1K,R2J,R3B), (ZB,R1K,R2J,R3C),
(ZB,R1K,R2J,R3D), (ZB,R1K,R2J,R3E), (ZB,R1K,R2J,R3F),
(ZB,R1K,R2J,R3G), (ZB,R1K,R2J,R3H), (ZB,R1K,R2J,R3I),
(ZB,R1K,R2J,R3J), (ZB,R1K,R2J,R3K), (ZB,R1K,R2J,R3L),
(ZB,R1K,R2J,R3M), (ZB,R1K,R2J,R3N), (ZB,R1K,R2J,R3O),
(ZB,R1K,R2J,R3P), (ZB,R1K,R2J,R3Q), (ZB,R1K,R2J,R3R),
(ZB,R1K,R2K,R3A), (ZB,R1K,R2K,R3B), (ZB,R1K,R2K,R3C),
(ZB,R1K,R2K,R3D), (ZB,R1K,R2K,R3E), (ZB,R1K,R2K,R3F),
(ZB,R1K,R2K,R3G), (ZB,R1K,R2K,R3H), (ZB,R1K,R2K,R3I),
(ZB,R1K,R2K,R3J), (ZB,R1K,R2K,R3K), (ZB,R1K,R2K,R3L),
(ZB,R1K,R2K,R3M), (ZB,R1K,R2K,R3N), (ZB,R1K,R2K,R3O),
(ZB,R1K,R2K,R3P), (ZB,R1K,R2K,R3Q), (ZB,R1K,R2K,R3R),
(ZB,R1K,R2L,R3A), (ZB,R1K,R2L,R3B), (ZB,R1K,R2L,R3C),
(ZB,R1K,R2L,R3D), (ZB,R1K,R2L,R3E), (ZB,R1K,R2L,R3F),
(ZB,R1K,R2L,R3G), (ZB,R1K,R2L,R3H), (ZB,R1K,R2L,R3I),
(ZB,R1K,R2L,R3J), (ZB,R1K,R2L,R3K), (ZB,R1K,R2L,R3L),
(ZB,R1K,R2L,R3M), (ZB,R1K,R2L,R3N), (ZB,R1K,R2L,R3O),
(ZB,R1K,R2L,R3P), (ZB,R1K,R2L,R3Q), (ZB,R1K,R2L,R3R),
(ZB,R1K,R2M,R3A), (ZB,R1K,R2M,R3B), (ZB,R1K,R2M,R3C),
(ZB,R1K,R2M,R3D), (ZB,R1K,R2M,R3E), (ZB,R1K,R2M,R3F),
(ZB,R1K,R2M,R3G), (ZB,R1K,R2M,R3H), (ZB,R1K,R2M,R3I),
(ZB,R1K,R2M,R3J), (ZB,R1K,R2M,R3K), (ZB,R1K,R2M,R3L),
(ZB,R1K,R2M,R3M), (ZB,R1K,R2M,R3N), (ZB,R1K,R2M,R3O),
(ZB,R1K,R2M,R3P), (ZB,R1K,R2M,R3Q), (ZB,R1K,R2M,R3R),
(ZB,R1K,R2N,R3A), (ZB,R1K,R2N,R3B), (ZB,R1K,R2N,R3C),
(ZB,R1K,R2N,R3D), (ZB,R1K,R2N,R3E), (ZB,R1K,R2N,R3F),
(ZB,R1K,R2N,R3G), (ZB,R1K,R2N,R3H), (ZB,R1K,R2N,R3I),
(ZB,R1K,R2N,R3J), (ZB,R1K,R2N,R3K), (ZB,R1K,R2N,R3L),
(ZB,R1K,R2N,R3M), (ZB,R1K,R2N,R3N), (ZB,R1K,R2N,R3O),
(ZB,R1K,R2N,R3P), (ZB,R1K,R2N,R3Q), (ZB,R1K,R2N,R3R),
(ZB,R1L,R2A,R3A), (ZB,R1L,R2A,R3B), (ZB,R1L,R2A,R3C),
(ZB,R1L,R2A,R3D), (ZB,R1L,R2A,R3E), (ZB,R1L,R2A,R3F),
(ZB,R1L,R2A,R3G), (ZB,R1L,R2A,R3H), (ZB,R1L,R2A,R3I),
(ZB,R1L,R2A,R3J), (ZB,R1L,R2A,R3K), (ZB,R1L,R2A,R3L),
(ZB,R1L,R2A,R3M), (ZB,R1L,R2A,R3N), (ZB,R1L,R2A,R3O),
(ZB,R1L,R2A,R3P), (ZB,R1L,R2A,R3Q), (ZB,R1L,R2A,R3R),
(ZB,R1L,R2B,R3A), (ZB,R1L,R2B,R3B), (ZB,R1L,R2B,R3C),
(ZB,R1L,R2B,R3D), (ZB,R1L,R2B,R3E), (ZB,R1L,R2B,R3F),
(ZB,R1L,R2B,R3G), (ZB,R1L,R2B,R3H), (ZB,R1L,R2B,R3I),
(ZB,R1L,R2B,R3J), (ZB,R1L,R2B,R3K), (ZB,R1L,R2B,R3L),
(ZB,R1L,R2B,R3M), (ZB,R1L,R2B,R3N), (ZB,R1L,R2B,R3O),
(ZB,R1L,R2B,R3P), (ZB,R1L,R2B,R3Q), (ZB,R1L,R2B,R3R),
(ZB,R1L,R2C,R3A), (ZB,R1L,R2C,R3B), (ZB,R1L,R2C,R3C),
(ZB,R1L,R2C,R3D), (ZB,R1L,R2C,R3E), (ZB,R1L,R2C,R3F),
(ZB,R1L,R2C,R3G), (ZB,R1L,R2C,R3H), (ZB,R1L,R2C,R3I),
(ZB,R1L,R2C,R3J), (ZB,R1L,R2C,R3K), (ZB,R1L,R2C,R3L),
(ZB,R1L,R2C,R3M), (ZB,R1L,R2C,R3N), (ZB,R1L,R2C,R3O),
(ZB,R1L,R2C,R3P), (ZB,R1L,R2C,R3Q), (ZB,R1L,R2C,R3R),
(ZB,R1L,R2D,R3A), (ZB,R1L,R2D,R3B), (ZB,R1L,R2D,R3C),
(ZB,R1L,R2D,R3D), (ZB,R1L,R2D,R3E), (ZB,R1L,R2D,R3F),
(ZB,R1L,R2D,R3G), (ZB,R1L,R2D,R3H), (ZB,R1L,R2D,R3I),
(ZB,R1L,R2D,R3J), (ZB,R1L,R2D,R3K), (ZB,R1L,R2D,R3L),
(ZB,R1L,R2D,R3M), (ZB,R1L,R2D,R3N), (ZB,R1L,R2D,R3O),
(ZB,R1L,R2D,R3P), (ZB,R1L,R2D,R3Q), (ZB,R1L,R2D,R3R),
(ZB,R1L,R2E,R3A), (ZB,R1L,R2E,R3B), (ZB,R1L,R2E,R3C),
(ZB,R1L,R2E,R3D), (ZB,R1L,R2E,R3E), (ZB,R1L,R2E,R3F),
(ZB,R1L,R2E,R3G), (ZB,R1L,R2E,R3H), (ZB,R1L,R2E,R3I),
(ZB,R1L,R2E,R3J), (ZB,R1L,R2E,R3K), (ZB,R1L,R2E,R3L),
(ZB,R1L,R2E,R3M), (ZB,R1L,R2E,R3N), (ZB,R1L,R2E,R3O),
(ZB,R1L,R2E,R3P), (ZB,R1L,R2E,R3Q), (ZB,R1L,R2E,R3R),
(ZB,R1L,R2F,R3A), (ZB,R1L,R2F,R3B), (ZB,R1L,R2F,R3C),
(ZB,R1L,R2F,R3D), (ZB,R1L,R2F,R3E), (ZB,R1L,R2F,R3F),
(ZB,R1L,R2F,R3G), (ZB,R1L,R2F,R3H), (ZB,R1L,R2F,R3I),
(ZB,R1L,R2F,R3J), (ZB,R1L,R2F,R3K), (ZB,R1L,R2F,R3L),
(ZB,R1L,R2F,R3M), (ZB,R1L,R2F,R3N), (ZB,R1L,R2F,R3O),
(ZB,R1L,R2F,R3P), (ZB,R1L,R2F,R3Q), (ZB,R1L,R2F,R3R), (ZB,R1L,R2G,R3A), (ZB,R1L,R2G,R3B), (ZB,R1L,R2G,R3C),
(ZB,R1L,R2G,R3D), (ZB,R1L,R2G,R3E), (ZB,R1L,R2G,R3F),
(ZB,R1L,R2G,R3G), (ZB,R1L,R2G,R3H), (ZB,R1L,R2G,R3I),
(ZB,R1L,R2G,R3J), (ZB,R1L,R2G,R3K), (ZB,R1L,R2G,R3L),
(ZB,R1L,R2G,R3M), (ZB,R1L,R2G,R3N), (ZB,R1L,R2G,R3O),
(ZB,R1L,R2G,R3P), (ZB,R1L,R2G,R3Q), (ZB,R1L,R2G,R3R),
(ZB,R1L,R2H,R3A), (ZB,R1L,R2H,R3B), (ZB,R1L,R2H,R3C),
(ZB,R1L,R2H,R3D), (ZB,R1L,R2H,R3E), (ZB,R1L,R2H,R3F),
(ZB,R1L,R2H,R3G), (ZB,R1L,R2H,R3H), (ZB,R1L,R2H,R3I),
(ZB,R1L,R2H,R3J), (ZB,R1L,R2H,R3K), (ZB,R1L,R2H,R3L),
(ZB,R1L,R2H,R3M), (ZB,R1L,R2H,R3N), (ZB,R1L,R2H,R3O),
(ZB,R1L,R2H,R3P), (ZB,R1L,R2H,R3Q), (ZB,R1L,R2H,R3R),
(ZB,R1L,R2I,R3A), (ZB,R1L,R2I,R3B), (ZB,R1L,R2I,R3C), (ZB,R1L,R2I,R3D),
(ZB,R1L,R2I,R3E), (ZB,R1L,R2I,R3F), (ZB,R1L,R2I,R3G), (ZB,R1L,R2I,R3H),
(ZB,R1L,R2I,R3I), (ZB,R1L,R2I,R3J), (ZB,R1L,R2I,R3K), (ZB,R1L,R2I,R3L),
(ZB,R1L,R2I,R3M), (ZB,R1L,R2I,R3N), (ZB,R1L,R2I,R3O), (ZB,R1L,R2I,R3P),
(ZB,R1L,R2I,R3Q), (ZB,R1L,R2I,R3R), (ZB,R1L,R2J,R3A),
(ZB,R1L,R2J,R3B), (ZB,R1L,R2J,R3C), (ZB,R1L,R2J,R3D),
(ZB,R1L,R2J,R3E), (ZB,R1L,R2J,R3F), (ZB,R1L,R2J,R3G),
(ZB,R1L,R2J,R3H), (ZB,R1L,R2J,R3I), (ZB,R1L,R2J,R3J),
(ZB,R1L,R2J,R3L), (ZB,R1L,R2J,R3M),
(ZB,R1L,R2J,R3N), (ZB,R1L,R2J,R3O), (ZB,R1L,R2J,R3P),
(ZB,R1L,R2J,R3Q), (ZB,R1L,R2J,R3R), (ZB,R1L,R2K,R3A),
(ZB,R1L,R2K,R3B), (ZB,R1L,R2K,R3C), (ZB,R1L,R2K,R3D),
(ZB,R1L,R2K,R3E), (ZB,R1L,R2K,R3F), (ZB,R1L,R2K,R3G),
(ZB,R1L,R2K,R3I), (ZB,R1L,R2K,R3J),
(ZB,R1L,R2K,R3K), (ZB,R1L,R2K,R3L), (ZB,R1L,R2K,R3M),
(ZB,R1L,R2K,R3N), (ZB,R1L,R2K,R3O), (ZB,R1L,R2K,R3P),
(ZB,R1L,R2K,R3Q), (ZB,R1L,R2K,R3R), (ZB,R1L,R2L,R3A),
(ZB,R1L,R2L,R3B), (ZB,R1L,R2L,R3C), (ZB,R1L,R2L,R3D),
(ZB,R1L,R2L,R3F), (ZB,R1L,R2L,R3G),
(ZB,R1L,R2L,R3H), (ZB,R1L,R2L,R3I), (ZB,R1L,R2L,R3J),
(ZB,R1L,R2L,R3K), (ZB,R1L,R2L,R3L), (ZB,R1L,R2L,R3M),
(ZB,R1L,R2L,R3N), (ZB,R1L,R2L,R3O), (ZB,R1L,R2L,R3P),
(ZB,R1L,R2L,R3Q), (ZB,R1L,R2L,R3R), (ZB,R1L,R2M,R3A),
(ZB,R1L,R2M,R3C), (ZB,R1L,R2M,R3D),
(ZB,R1L,R2M,R3E), (ZB,R1L,R2M,R3F), (ZB,R1L,R2M,R3G),
(ZB,R1L,R2M,R3H), (ZB,R1L,R2M,R3I), (ZB,R1L,R2M,R3J),
(ZB,R1L,R2M,R3K), (ZB,R1L,R2M,R3L), (ZB,R1L,R2M,R3M),
(ZB,R1L,R2M,R3N), (ZB,R1L,R2M,R3O), (ZB,R1L,R2M,R3P),
(ZB,R1L,R2M,R3Q), (ZB,R1L,R2M,R3R), (ZB,R1L,R2M,R3A),
(ZB,R1L,R2N,R3B), (ZB,R1L,R2N,R3C), (ZB,R1L,R2N,R3D),
(ZB,R1L,R2N,R3E), (ZB,R1L,R2N,R3F), (ZB,R1L,R2N,R3G),
(ZB,R1L,R2N,R3H), (ZB,R1L,R2N,R3I), (ZB,R1L,R2N,R3J),
(ZB,R1L,R2N,R3K), (ZB,R1L,R2N,R3L), (ZB,R1L,R2N,R3M),
(ZB,R1L,R2N,R3N), (ZB,R1L,R2N,R3O), (ZB,R1L,R2N,R3P),
(ZB,R1L,R2N,R3Q), (ZB,R1L,R2N,R3R), (ZB,R1M,R2A,R3A),
(ZB,R1M,R2A,R3B), (ZB,R1M,R2A,R3C), (ZB,R1M,R2A,R3D),
(ZB,R1M,R2A,R3E), (ZB,R1M,R2A,R3F), (ZB,R1M,R2A,R3G),
(ZB,R1M,R2A,R3H), (ZB,R1M,R2A,R3I), (ZB,R1M,R2A,R3J),
(ZB,R1M,R2A,R3K), (ZB,R1M,R2A,R3L), (ZB,R1M,R2A,R3M),
(ZB,R1M,R2A,R3N), (ZB,R1M,R2A,R3O), (ZB,R1M,R2A,R3P),
(ZB,R1M,R2A,R3Q), (ZB,R1M,R2A,R3R), (ZB,R1M,R2B,R3A),
(ZB,R1M,R2B,R3B), (ZB,R1M,R2B,R3C), (ZB,R1M,R2B,R3D),
(ZB,R1M,R2B,R3E), (ZB,R1M,R2B,R3F), (ZB,R1M,R2B,R3G),
(ZB,R1M,R2B,R3H), (ZB,R1M,R2B,R3I), (ZB,R1M,R2B,R3J),
(ZB,R1M,R2B,R3K), (ZB,R1M,R2B,R3L), (ZB,R1M,R2B,R3M),
(ZB,R1M,R2B,R3N), (ZB,R1M,R2B,R3O), (ZB,R1M,R2B,R3P),
(ZB,R1M,R2B,R3Q), (ZB,R1M,R2B,R3R), (ZB,R1M,R2C,R3A),
(ZB,R1M,R2C,R3B), (ZB,R1M,R2C,R3C), (ZB,R1M,R2C,R3D),
(ZB,R1M,R2C,R3E), (ZB,R1M,R2C,R3F), (ZB,R1M,R2C,R3G),
(ZB,R1M,R2C,R3H), (ZB,R1M,R2C,R3I), (ZB,R1M,R2C,R3J),
(ZB,R1M,R2C,R3K), (ZB,R1M,R2C,R3L), (ZB,R1M,R2C,R3M),
(ZB,R1M,R2C,R3N), (ZB,R1M,R2C,R3O), (ZB,R1M,R2C,R3P),
(ZB,R1M,R2C,R3Q), (ZB,R1M,R2C,R3R), (ZB,R1M,R2D,R3A),
(ZB,R1M,R2D,R3B), (ZB,R1M,R2D,R3C), (ZB,R1M,R2D,R3D),
(ZB,R1M,R2D,R3E), (ZB,R1M,R2D,R3F), (ZB,R1M,R2D,R3G),
(ZB,R1M,R2D,R3H), (ZB,R1M,R2D,R3I), (ZB,R1M,R2D,R3J),
(ZB,R1M,R2D,R3K), (ZB,R1M,R2D,R3L), (ZB,R1M,R2D,R3M), (ZB,R1M,R2D,R3N), (ZB,R1M,R2D,R3O), (ZB,R1M,R2D,R3P),
(ZB,R1M,R2D,R3Q), (ZB,R1M,R2D,R3R), (ZB,R1M,R2E,R3A),
(ZB,R1M,R2E,R3B), (ZB,R1M,R2E,R3C), (ZB,R1M,R2E,R3D),
(ZB,R1M,R2E,R3E), (ZB,R1M,R2E,R3F), (ZB,R1M,R2E,R3G),
(ZB,R1M,R2E,R3H), (ZB,R1M,R2E,R3I), (ZB,R1M,R2E,R3J),
(ZB,R1M,R2E,R3K), (ZB,R1M,R2E,R3L), (ZB,R1M,R2E,R3M),
(ZB,R1M,R2E,R3N), (ZB,R1M,R2E,R3O), (ZB,R1M,R2E,R3P),
(ZB,R1M,R2E,R3Q), (ZB,R1M,R2E,R3R), (ZB,R1M,R2F,R3A),
(ZB,R1M,R2F,R3B), (ZB,R1M,R2F,R3C), (ZB,R1M,R2F,R3D),
(ZB,R1M,R2F,R3E), (ZB,R1M,R2F,R3F), (ZB,R1M,R2F,R3G),
(ZB,R1M,R2F,R3H), (ZB,R1M,R2F,R3I), (ZB,R1M,R2F,R3J),
(ZB,R1M,R2F,R3K), (ZB,R1M,R2F,R3L), (ZB,R1M,R2F,R3M),
(ZB,R1M,R2F,R3N), (ZB,R1M,R2F,R3O), (ZB,R1M,R2F,R3P),
(ZB,R1M,R2F,R3Q), (ZB,R1M,R2F,R3R), (ZB,R1M,R2G,R3A),
(ZB,R1M,R2G,R3B), (ZB,R1M,R2G,R3C), (ZB,R1M,R2G,R3D),
(ZB,R1M,R2G,R3E), (ZB,R1M,R2G,R3F), (ZB,R1M,R2G,R3G),
(ZB,R1M,R2G,R3H), (ZB,R1M,R2G,R3I), (ZB,R1M,R2G,R3J),
(ZB,R1M,R2G,R3K), (ZB,R1M,R2G,R3L), (ZB,R1M,R2G,R3M),
(ZB,R1M,R2G,R3N), (ZB,R1M,R2G,R3O), (ZB,R1M,R2G,R3P),
(ZB,R1M,R2G,R3Q), (ZB,R1M,R2G,R3R), (ZB,R1M,R2H,R3A),
(ZB,R1M,R2H,R3B), (ZB,R1M,R2H,R3C), (ZB,R1M,R2H,R3D),
(ZB,R1M,R2H,R3E), (ZB,R1M,R2H,R3F), (ZB,R1M,R2H,R3G),
(ZB,R1M,R2H,R3H), (ZB,R1M,R2H,R3I), (ZB,R1M,R2H,R3J),
(ZB,R1M,R2H,R3K), (ZB,R1M,R2H,R3L), (ZB,R1M,R2H,R3M),
(ZB,R1M,R2H,R3N), (ZB,R1M,R2H,R3O), (ZB,R1M,R2H,R3P),
(ZB,R1M,R2H,R3Q), (ZB,R1M,R2H,R3R), (ZB,R1M,R2I,R3A),
(ZB,R1M,R2I,R3B), (ZB,R1M,R2I,R3C), (ZB,R1M,R2I,R3D),
(ZB,R1M,R2I,R3E), (ZB,R1M,R2I,R3F), (ZB,R1M,R2I,R3G),
(ZB,R1M,R2I,R3H), (ZB,R1M,R2I,R3I), (ZB,R1M,R2I,R3J),
(ZB,R1M,R2I,R3K), (ZB,R1M,R2I,R3L), (ZB,R1M,R2I,R3M),
(ZB,R1M,R2I,R3N), (ZB,R1M,R2I,R3O), (ZB,R1M,R2I,R3P),
(ZB,R1M,R2I,R3Q), (ZB,R1M,R2I,R3R), (ZB,R1M,R2J,R3A),
(ZB,R1M,R2J,R3B), (ZB,R1M,R2J,R3C), (ZB,R1M,R2J,R3D),
(ZB,R1M,R2J,R3E), (ZB,R1M,R2J,R3F), (ZB,R1M,R2J,R3G),
(ZB,R1M,R2J,R3H), (ZB,R1M,R2J,R3I), (ZB,R1M,R2J,R3J),
(ZB,R1M,R2J,R3K), (ZB,R1M,R2J,R3L), (ZB,R1M,R2J,R3M),
(ZB,R1M,R2J,R3N), (ZB,R1M,R2J,R3O), (ZB,R1M,R2J,R3P),
(ZB,R1M,R2J,R3Q), (ZB,R1M,R2J,R3R), (ZB,R1M,R2K,R3A),
(ZB,R1M,R2K,R3B), (ZB,R1M,R2K,R3C), (ZB,R1M,R2K,R3D),
(ZB,R1M,R2K,R3E), (ZB,R1M,R2K,R3F), (ZB,R1M,R2K,R3G),
(ZB,R1M,R2K,R3H), (ZB,R1M,R2K,R3I), (ZB,R1M,R2K,R3J),
(ZB,R1M,R2K,R3K), (ZB,R1M,R2K,R3L), (ZB,R1M,R2K,R3M),
(ZB,R1M,R2K,R3N), (ZB,R1M,R2K,R3O), (ZB,R1M,R2K,R3P),
(ZB,R1M,R2K,R3Q), (ZB,R1M,R2K,R3R), (ZB,R1M,R2L,R3A),
(ZB,R1M,R2L,R3B), (ZB,R1M,R2L,R3C), (ZB,R1M,R2L,R3D),
(ZB,R1M,R2L,R3E), (ZB,R1M,R2L,R3F), (ZB,R1M,R2L,R3G),
(ZB,R1M,R2L,R3H), (ZB,R1M,R2L,R3I), (ZB,R1M,R2L,R3J),
(ZB,R1M,R2L,R3K), (ZB,R1M,R2L,R3L), (ZB,R1M,R2L,R3M),
(ZB,R1M,R2L,R3N), (ZB,R1M,R2L,R3O), (ZB,R1M,R2L,R3P),
(ZB,R1M,R2L,R3Q), (ZB,R1M,R2L,R3R), (ZB,R1M,R2M,R3A),
(ZB,R1M,R2M,R3B), (ZB,R1M,R2M,R3C), (ZB,R1M,R2M,R3D),
(ZB,R1M,R2M,R3E), (ZB,R1M,R2M,R3F), (ZB,R1M,R2M,R3G),
(ZB,R1M,R2M,R3H), (ZB,R1M,R2M,R3I), (ZB,R1M,R2M,R3J),
(ZB,R1M,R2M,R3K), (ZB,R1M,R2M,R3L), (ZB,R1M,R2M,R3M),
(ZB,R1M,R2M,R3N), (ZB,R1M,R2M,R3O), (ZB,R1M,R2M,R3P),
(ZB,R1M,R2M,R3Q), (ZB,R1M,R2M,R3R), (ZB,R1M,R2N,R3A),
(ZB,R1M,R2M,R3B), (ZB,R1M,R2M,R3C), (ZB,R1M,R2N,R3D),
(ZB,R1M,R2N,R3E), (ZB,R1M,R2N,R3F), (ZB,R1M,R2N,R3G),
(ZB,R1M,R2N,R3H), (ZB,R1M,R2N,R3I), (ZB,R1M,R2N,R3J),
(ZB,R1M,R2N,R3K), (ZB,R1M,R2N,R3L), (ZB,R1M,R2N,R3M),
(ZB,R1M,R2N,R3N), (ZB,R1M,R2N,R3O), (ZB,R1M,R2N,R3P),
(ZB,R1M,R2M,R3Q), (ZB,R1M,R2M,R3R), (ZB,R1M,R2A,R3A),
(ZB,R1N,R2A,R3B), (ZB,R1N,R2A,R3C), (ZB,R1N,R2A,R3D),
(ZB,R1N,R2A,R3E), (ZB,R1N,R2A,R3F), (ZB,R1N,R2A,R3G),
(ZB,R1N,R2A,R3H), (ZB,R1N,R2A,R3I), (ZB,R1N,R2A,R3J),
(ZB,R1N,R2A,R3K), (ZB,R1N,R2A,R3L), (ZB,R1N,R2A,R3M), (ZB,R1M,R2N,R3N), (ZB,R1M,R2N,R3R), (ZB,R1N,R2A,R3P),
(ZB,R1N,R2A,R3Q), (ZB,R1N,R2A,R3R), (ZB,R1N,R2B,R3A),
(ZB,R1N,R2B,R3B), (ZB,R1N,R2B,R3C), (ZB,R1N,R2B,R3D),
(ZB,R1N,R2B,R3E), (ZB,R1N,R2B,R3F), (ZB,R1N,R2B,R3G),
(ZB,R1N,R2B,R3H), (ZB,R1N,R2B,R3I), (ZB,R1N,R2B,R3J),
(ZB,R1N,R2B,R3K), (ZB,R1N,R2B,R3L), (ZB,R1N,R2B,R3M),
(ZB,R1N,R2B,R3N), (ZB,R1N,R2B,R3O), (ZB,R1N,R2B,R3P),
(ZB,R1N,R2B,R3Q), (ZB,R1N,R2B,R3R), (ZB,R1N,R2C,R3A),
(ZB,R1N,R2C,R3B), (ZB,R1N,R2C,R3C), (ZB,R1N,R2C,R3D),
(ZB,R1N,R2C,R3E), (ZB,R1N,R2C,R3F), (ZB,R1N,R2C,R3G),
(ZB,R1N,R2C,R3H), (ZB,R1N,R2C,R3I), (ZB,R1N,R2C,R3J),
(ZB,R1N,R2C,R3K), (ZB,R1N,R2C,R3L), (ZB,R1N,R2C,R3M),
(ZB,R1N,R2C,R3N), (ZB,R1N,R2C,R3O), (ZB,R1N,R2C,R3P),
(ZB,R1N,R2C,R3Q), (ZB,R1N,R2C,R3R), (ZB,R1N,R2D,R3A),
(ZB,R1N,R2D,R3B), (ZB,R1N,R2D,R3C), (ZB,R1N,R2D,R3D),
(ZB,R1N,R2D,R3E), (ZB,R1N,R2D,R3F), (ZB,R1N,R2D,R3G),
(ZB,R1N,R2D,R3H), (ZB,R1N,R2D,R3I), (ZB,R1N,R2D,R3J),
(ZB,R1N,R2D,R3K), (ZB,R1N,R2D,R3L), (ZB,R1N,R2D,R3M),
(ZB,R1N,R2D,R3N), (ZB,R1N,R2D,R3O), (ZB,R1N,R2D,R3P),
(ZB,R1N,R2D,R3Q), (ZB,R1N,R2D,R3R), (ZB,R1N,R2E,R3A),
(ZB,R1N,R2E,R3B), (ZB,R1N,R2E,R3C), (ZB,R1N,R2E,R3D),
(ZB,R1N,R2E,R3E), (ZB,R1N,R2E,R3F), (ZB,R1N,R2E,R3G),
(ZB,R1N,R2E,R3H), (ZB,R1N,R2E,R3I), (ZB,R1N,R2E,R3J),
(ZB,R1N,R2E,R3K), (ZB,R1N,R2E,R3L), (ZB,R1N,R2E,R3M),
(ZB,R1N,R2E,R3N), (ZB,R1N,R2E,R3O), (ZB,R1N,R2E,R3P),
(ZB,R1N,R2E,R3Q), (ZB,R1N,R2E,R3R), (ZB,R1N,R2F,R3A),
(ZB,R1N,R2F,R3B), (ZB,R1N,R2F,R3C), (ZB,R1N,R2F,R3D),
(ZB,R1N,R2F,R3E), (ZB,R1N,R2F,R3F), (ZB,R1N,R2F,R3G),
(ZB,R1N,R2F,R3H), (ZB,R1N,R2F,R3I), (ZB,R1N,R2F,R3J),
(ZB,R1N,R2F,R3K), (ZB,R1N,R2F,R3L), (ZB,R1N,R2F,R3M),
(ZB,R1N,R2F,R3N), (ZB,R1N,R2F,R3O), (ZB,R1N,R2F,R3P),
(ZB,R1N,R2F,R3Q), (ZB,R1N,R2F,R3R), (ZB,R1N,R2G,R3A),
(ZB,R1N,R2G,R3B), (ZB,R1N,R2G,R3C), (ZB,R1N,R2G,R3D),
(ZB,R1N,R2G,R3E), (ZB,R1N,R2G,R3F), (ZB,R1N,R2G,R3G),
(ZB,R1N,R2G,R3H), (ZB,R1N,R2G,R3I), (ZB,R1N,R2G,R3J),
(ZB,R1N,R2G,R3K), (ZB,R1N,R2G,R3L), (ZB,R1N,R2G,R3M),
(ZB,R1N,R2G,R3N), (ZB,R1N,R2G,R3O), (ZB,R1N,R2G,R3P),
(ZB,R1N,R2G,R3Q), (ZB,R1N,R2G,R3R), (ZB,R1N,R2H,R3A),
(ZB,R1N,R2H,R3B), (ZB,R1N,R2H,R3C), (ZB,R1N,R2H,R3D),
(ZB,R1N,R2H,R3E), (ZB,R1N,R2H,R3F), (ZB,R1N,R2H,R3G),
(ZB,R1N,R2H,R3H), (ZB,R1N,R2H,R3I), (ZB,R1N,R2H,R3J),
(ZB,R1N,R2H,R3K), (ZB,R1N,R2H,R3L), (ZB,R1N,R2H,R3M),
(ZB,R1N,R2H,R3N), (ZB,R1N,R2H,R3O), (ZB,R1N,R2H,R3P),
(ZB,R1N,R2H,R3Q), (ZB,R1N,R2H,R3R), (ZB,R1N,R2I,R3A),
(ZB,R1N,R2I,R3B), (ZB,R1N,R2I,R3C), (ZB,R1N,R2I,R3D),
(ZB,R1N,R2I,R3E), (ZB,R1N,R2I,R3F), (ZB,R1N,R2I,R3G),
(ZB,R1N,R2I,R3H), (ZB,R1N,R2I,R3I), (ZB,R1N,R2I,R3J), (ZB,R1N,R2I,R3K),
(ZB,R1N,R2I,R3L), (ZB,R1N,R2I,R3M), (ZB,R1N,R2I,R3N),
(ZB,R1N,R2I,R3O), (ZB,R1N,R2I,R3P), (ZB,R1N,R2I,R3Q),
(ZB,R1N,R2I,R3R), (ZB,R1N,R2J,R3A), (ZB,R1N,R2J,R3B),
(ZB,R1N,R2J,R3C), (ZB,R1N,R2J,R3D), (ZB,R1N,R2J,R3E),
(ZB,R1N,R2J,R3F), (ZB,R1N,R2J,R3G), (ZB,R1N,R2J,R3H),
(ZB,R1N,R2J,R3I), (ZB,R1N,R2J,R3J), (ZB,R1N,R2J,R3K),
(ZB,R1N,R2J,R3L), (ZB,R1N,R2J,R3M), (ZB,R1N,R2J,R3N),
(ZB,R1N,R2J,R3O), (ZB,R1N,R2J,R3P), (ZB,R1N,R2J,R3Q),
(ZB,R1N,R2J,R3R), (ZB,R1N,R2K,R3A), (ZB,R1N,R2K,R3B),
(ZB,R1N,R2K,R3C), (ZB,R1N,R2K,R3D), (ZB,R1N,R2K,R3E),
(ZB,R1N,R2K,R3F), (ZB,R1N,R2K,R3G), (ZB,R1N,R2K,R3H),
(ZB,R1N,R2K,R3I), (ZB,R1N,R2K,R3J), (ZB,R1N,R2K,R3K),
(ZB,R1N,R2K,R3L), (ZB,R1N,R2K,R3M), (ZB,R1N,R2K,R3N),
(ZB,R1N,R2K,R3O), (ZB,R1N,R2K,R3P), (ZB,R1N,R2K,R3Q),
(ZB,R1N,R2K,R3R), (ZB,R1N,R2L,R3A), (ZB,R1N,R2L,R3B),
(ZB,R1N,R2L,R3C), (ZB,R1N,R2L,R3D), (ZB,R1N,R2L,R3E),
(ZB,R1N,R2L,R3F), (ZB,R1N,R2L,R3G), (ZB,R1N,R2L,R3H),
(ZB,R1N,R2L,R3I), (ZB,R1N,R2L,R3J), (ZB,R1N,R2L,R3K),
(ZB,R1N,R2L,R3L), (ZB,R1N,R2L,R3M), (ZB,R1N,R2L,R3N), (ZB,R1N,R2L,R3O), (ZB,R1N,R2L,R3P), (ZB,R1N,R2L,R3Q),
(ZB,R1N,R2L,R3R), (ZB,R1N,R2M,R3A), (ZB,R1N,R2M,R3B),
(ZB,R1N,R2M,R3C), (ZB,R1N,R2M,R3D), (ZB,R1N,R2M,R3E),
(ZB,R1N,R2M,R3F), (ZB,R1N,R2M,R3G), (ZB,R1N,R2M,R3H),
(ZB,R1N,R2M,R3I), (ZB,R1N,R2M,R3J), (ZB,R1N,R2M,R3K),
(ZB,R1N,R2M,R3L), (ZB,R1N,R2M,R3M), (ZB,R1N,R2M,R3N),
(ZB,R1N,R2M,R3O), (ZB,R1N,R2M,R3P), (ZB,R1N,R2M,R3Q),
(ZB,R1N,R2M,R3R), (ZB,R1N,R2N,R3A), (ZB,R1N,R2N,R3B),
(ZB,R1N,R2N,R3C), (ZB,R1N,R2N,R3D), (ZB,R1N,R2N,R3E),
(ZB,R1N,R2N,R3F), (ZB,R1N,R2N,R3G), (ZB,R1N,R2N,R3H),
(ZB,R1N,R2N,R3I), (ZB,R1N,R2N,R3J), (ZB,R1N,R2N,R3K),
(ZB,R1N,R2N,R3L), (ZB,R1N,R2N,R3M), (ZB,R1N,R2N,R3N),
(ZB,R1N,R2N,R3O), (ZB,R1N,R2N,R3P), (ZB,R1N,R2N,R3Q),
(ZB,R1N,R2N,R3R), (ZB,R1O,R2A,R3A), (ZB,R1O,R2A,R3B),
(ZB,R1O,R2A,R3C), (ZB,R1O,R2A,R3D), (ZB,R1O,R2A,R3E),
(ZB,R1O,R2A,R3F), (ZB,R1O,R2A,R3G), (ZB,R1O,R2A,R3H),
(ZB,R1O,R2A,R3I), (ZB,R1O,R2A,R3J), (ZB,R1O,R2A,R3K),
(ZB,R1O,R2A,R3L), (ZB,R1O,R2A,R3M), (ZB,R1O,R2A,R3N),
(ZB,R1O,R2A,R3O), (ZB,R1O,R2A,R3P), (ZB,R1O,R2A,R3Q),
(ZB,R1O,R2A,R3R), (ZB,R1O,R2B,R3A), (ZB,R1O,R2B,R3B),
(ZB,R1O,R2B,R3C), (ZB,R1O,R2B,R3D), (ZB,R1O,R2B,R3E),
(ZB,R1O,R2B,R3F), (ZB,R1O,R2B,R3G), (ZB,R1O,R2B,R3H),
(ZB,R1O,R2B,R3I), (ZB,R1O,R2B,R3J), (ZB,R1O,R2B,R3K),
(ZB,R1O,R2B,R3L), (ZB,R1O,R2B,R3M), (ZB,R1O,R2B,R3N),
(ZB,R1O,R2B,R3O), (ZB,R1O,R2B,R3P), (ZB,R1O,R2B,R3Q),
(ZB,R1O,R2B,R3R), (ZB,R1O,R2C,R3A), (ZB,R1O,R2C,R3B),
(ZB,R1O,R2C,R3C), (ZB,R1O,R2C,R3D), (ZB,R1O,R2C,R3E),
(ZB,R1O,R2C,R3F), (ZB,R1O,R2C,R3G), (ZB,R1O,R2C,R3H),
(ZB,R1O,R2C,R3I), (ZB,R1O,R2C,R3J), (ZB,R1O,R2C,R3K),
(ZB,R1O,R2C,R3L), (ZB,R1O,R2C,R3M), (ZB,R1O,R2C,R3N),
(ZB,R1O,R2C,R3O), (ZB,R1O,R2C,R3P), (ZB,R1O,R2C,R3Q),
(ZB,R1O,R2C,R3R), (ZB,R1O,R2D,R3A), (ZB,R1O,R2D,R3B),
(ZB,R1O,R2D,R3C), (ZB,R1O,R2D,R3D), (ZB,R1O,R2D,R3E),
(ZB,R1O,R2D,R3F), (ZB,R1O,R2D,R3G), (ZB,R1O,R2D,R3H),
(ZB,R1O,R2D,R3I), (ZB,R1O,R2D,R3J), (ZB,R1O,R2D,R3K),
(ZB,R1O,R2D,R3L), (ZB,R1O,R2D,R3M), (ZB,R1O,R2D,R3N),
(ZB,R1O,R2D,R3O), (ZB,R1O,R2D,R3P), (ZB,R1O,R2D,R3Q),
(ZB,R1O,R2D,R3R), (ZB,R1O,R2E,R3A), (ZB,R1O,R2E,R3B),
(ZB,R1O,R2E,R3C), (ZB,R1O,R2E,R3D), (ZB,R1O,R2E,R3E),
(ZB,R1O,R2E,R3F), (ZB,R1O,R2E,R3G), (ZB,R1O,R2E,R3H),
(ZB,R1O,R2E,R3I), (ZB,R1O,R2E,R3J), (ZB,R1O,R2E,R3K),
(ZB,R1O,R2E,R3L), (ZB,R1O,R2E,R3M), (ZB,R1O,R2E,R3N),
(ZB,R1O,R2E,R3O), (ZB,R1O,R2E,R3P), (ZB,R1O,R2E,R3Q),
(ZB,R1O,R2E,R3R), (ZB,R1O,R2F,R3A), (ZB,R1O,R2F,R3B),
(ZB,R1O,R2F,R3C), (ZB,R1O,R2F,R3D), (ZB,R1O,R2F,R3E),
(ZB,R1O,R2F,R3F), (ZB,R1O,R2F,R3G), (ZB,R1O,R2F,R3H),
(ZB,R1O,R2F,R3I), (ZB,R1O,R2F,R3J), (ZB,R1O,R2F,R3K),
(ZB,R1O,R2F,R3L), (ZB,R1O,R2F,R3M), (ZB,R1O,R2F,R3N),
(ZB,R1O,R2F,R3O), (ZB,R1O,R2F,R3P), (ZB,R1O,R2F,R3Q),
(ZB,R1O,R2F,R3R), (ZB,R1O,R2G,R3A), (ZB,R1O,R2G,R3B),
(ZB,R1O,R2G,R3C), (ZB,R1O,R2G,R3D), (ZB,R1O,R2G,R3E),
(ZB,R1O,R2G,R3F), (ZB,R1O,R2G,R3G), (ZB,R1O,R2G,R3H),
(ZB,R1O,R2G,R3I), (ZB,R1O,R2G,R3J), (ZB,R1O,R2G,R3K),
(ZB,R1O,R2G,R3L), (ZB,R1O,R2G,R3M), (ZB,R1O,R2G,R3N),
(ZB,R1O,R2G,R3O), (ZB,R1O,R2G,R3P), (ZB,R1O,R2G,R3Q),
(ZB,R1O,R2G,R3R), (ZB,R1O,R2H,R3A), (ZB,R1O,R2H,R3B),
(ZB,R1O,R2H,R3C), (ZB,R1O,R2H,R3D), (ZB,R1O,R2H,R3E),
(ZB,R1O,R2H,R3F), (ZB,R1O,R2H,R3G), (ZB,R1O,R2H,R3H),
(ZB,R1O,R2H,R3I), (ZB,R1O,R2H,R3J), (ZB,R1O,R2H,R3K),
(ZB,R1O,R2H,R3L), (ZB,R1O,R2H,R3M), (ZB,R1O,R2H,R3N),
(ZB,R1O,R2H,R3O), (ZB,R1O,R2H,R3P), (ZB,R1O,R2H,R3Q),
(ZB,R1O,R2H,R3R), (ZB,R1O,R2I,R3A), (ZB,R1O,R2I,R3B),
(ZB,R1O,R2I,R3C), (ZB,R1O,R2I,R3D), (ZB,R1O,R2I,R3E),
(ZB,R1O,R2I,R3F), (ZB,R1O,R2I,R3G), (ZB,R1O,R2I,R3H), (ZB,R1O,R2I,R3I),
(ZB,R1O,R2I,R3J), (ZB,R1O,R2I,R3K), (ZB,R1O,R2I,R3L),
(ZB,R1O,R2I,R3M), (ZB,R1O,R2I,R3N), (ZB,R1O,R2I,R3O), (ZB,R1O,R2I,R3P), (ZB,R1O,R2I,R3Q), (ZB,R1O,R2I,R3R),
(ZB,R1O,R2J,R3A), (ZB,R1O,R2J,R3B), (ZB,R1O,R2J,R3C),
(ZB,R1O,R2J,R3D), (ZB,R1O,R2J,R3E), (ZB,R1O,R2J,R3F),
(ZB,R1O,R2J,R3H), (ZB,R1O,R2J,R3I),
(ZB,R1O,R2J,R3J), (ZB,R1O,R2J,R3K), (ZB,R1O,R2J,R3L),
(ZB,R1O,R2J,R3M), (ZB,R1O,R2J,R3N), (ZB,R1O,R2J,R3O),
(ZB,R1O,R2J,R3P), (ZB,R1O,R2J,R3Q), (ZB,R1O,R2J,R3R),
(ZB,R1O,R2K,R3A), (ZB,R1O,R2K,R3B), (ZB,R1O,R2K,R3C),
(ZB,R1O,R2K,R3D), (ZB,R1O,R2K,R3E), (ZB,R1O,R2K,R3F),
(ZB,R1O,R2K,R3G), (ZB,R1O,R2K,R3H), (ZB,R1O,R2K,R3I),
(ZB,R1O,R2K,R3J), (ZB,R1O,R2K,R3K), (ZB,R1O,R2K,R3L),
(ZB,R1O,R2K,R3M), (ZB,R1O,R2K,R3N), (ZB,R1O,R2K,R3O),
(ZB,R1O,R2K,R3P), (ZB,R1O,R2K,R3Q), (ZB,R1O,R2K,R3R),
(ZB,R1O,R2L,R3A), (ZB,R1O,R2L,R3B), (ZB,R1O,R2L,R3C),
(ZB,R1O,R2L,R3D), (ZB,R1O,R2L,R3E), (ZB,R1O,R2L,R3F),
(ZB,R1O,R2L,R3G), (ZB,R1O,R2L,R3H), (ZB,R1O,R2L,R3I),
(ZB,R1O,R2L,R3J), (ZB,R1O,R2L,R3K), (ZB,R1O,R2L,R3L),
(ZB,R1O,R2L,R3M), (ZB,R1O,R2L,R3N), (ZB,R1O,R2L,R3O),
(ZB,R1O,R2L,R3P), (ZB,R1O,R2L,R3Q), (ZB,R1O,R2L,R3R),
(ZB,R1O,R2M,R3A), (ZB,R1O,R2M,R3B), (ZB,R1O,R2M,R3C),
(ZB,R1O,R2M,R3D), (ZB,R1O,R2M,R3E), (ZB,R1O,R2M,R3F),
(ZB,R1O,R2M,R3G), (ZB,R1O,R2M,R3H), (ZB,R1O,R2M,R3I),
(ZB,R1O,R2M,R3J), (ZB,R1O,R2M,R3K), (ZB,R1O,R2M,R3L),
(ZB,R1O,R2M,R3M), (ZB,R1O,R2M,R3N), (ZB,R1O,R2M,R3O),
(ZB,R1O,R2M,R3P), (ZB,R1O,R2M,R3Q), (ZB,R1O,R2M,R3R),
(ZB,R1O,R2N,R3A), (ZB,R1O,R2N,R3B), (ZB,R1O,R2N,R3C),
(ZB,R1O,R2N,R3D), (ZB,R1O,R2N,R3E), (ZB,R1O,R2N,R3F),
(ZB,R1O,R2N,R3G), (ZB,R1O,R2N,R3H), (ZB,R1O,R2N,R3I),
(ZB,R1O,R2N,R3J), (ZB,R1O,R2N,R3K), (ZB,R1O,R2N,R3L),
(ZB,R1O,R2N,R3M), (ZB,R1O,R2N,R3N), (ZB,R1O,R2N,R3O),
(ZB,R1O,R2N,R3P), (ZB,R1O,R2N,R3Q), (ZB,R1O,R2N,R3R),
(ZB,R1P,R2A,R3A), (ZB,R1P,R2A,R3B), (ZB,R1P,R2A,R3C),
(ZB,R1P,R2A,R3D), (ZB,R1P,R2A,R3E), (ZB,R1P,R2A,R3F),
(ZB,R1P,R2A,R3G), (ZB,R1P,R2A,R3H), (ZB,R1P,R2A,R3I),
(ZB,R1P,R2A,R3J), (ZB,R1P,R2A,R3K), (ZB,R1P,R2A,R3L),
(ZB,R1P,R2A,R3M), (ZB,R1P,R2A,R3N), (ZB,R1P,R2A,R3O),
(ZB,R1P,R2A,R3P), (ZB,R1P,R2A,R3Q), (ZB,R1P,R2A,R3R),
(ZB,R1P,R2B,R3A), (ZB,R1P,R2B,R3B), (ZB,R1P,R2B,R3C),
(ZB,R1P,R2B,R3D), (ZB,R1P,R2B,R3E), (ZB,R1P,R2B,R3F),
(ZB,R1P,R2B,R3G), (ZB,R1P,R2B,R3H), (ZB,R1P,R2B,R3I),
(ZB,R1P,R2B,R3J), (ZB,R1P,R2B,R3K), (ZB,R1P,R2B,R3L),
(ZB,R1P,R2B,R3M), (ZB,R1P,R2B,R3N), (ZB,R1P,R2B,R3O),
(ZB,R1P,R2B,R3P), (ZB,R1P,R2B,R3Q), (ZB,R1P,R2B,R3R),
(ZB,R1P,R2C,R3A), (ZB,R1P,R2C,R3B), (ZB,R1P,R2C,R3C),
(ZB,R1P,R2C,R3D), (ZB,R1P,R2C,R3E), (ZB,R1P,R2C,R3F),
(ZB,R1P,R2C,R3G), (ZB,R1P,R2C,R3H), (ZB,R1P,R2C,R3I),
(ZB,R1P,R2C,R3J), (ZB,R1P,R2C,R3K), (ZB,R1P,R2C,R3L),
(ZB,R1P,R2C,R3M), (ZB,R1P,R2C,R3N), (ZB,R1P,R2C,R3O),
(ZB,R1P,R2C,R3P), (ZB,R1P,R2C,R3Q), (ZB,R1P,R2C,R3R),
(ZB,R1P,R2D,R3A), (ZB,R1P,R2D,R3B), (ZB,R1P,R2D,R3C),
(ZB,R1P,R2D,R3D), (ZB,R1P,R2D,R3E), (ZB,R1P,R2D,R3F),
(ZB,R1P,R2D,R3G), (ZB,R1P,R2D,R3H), (ZB,R1P,R2D,R3I),
(ZB,R1P,R2D,R3J), (ZB,R1P,R2D,R3K), (ZB,R1P,R2D,R3L),
(ZB,R1P,R2D,R3M), (ZB,R1P,R2D,R3N), (ZB,R1P,R2D,R3O),
(ZB,R1P,R2D,R3P), (ZB,R1P,R2D,R3Q), (ZB,R1P,R2D,R3R),
(ZB,R1P,R2E,R3A), (ZB,R1P,R2E,R3B), (ZB,R1P,R2E,R3C),
(ZB,R1P,R2E,R3D), (ZB,R1P,R2E,R3E), (ZB,R1P,R2E,R3F),
(ZB,R1P,R2E,R3G), (ZB,R1P,R2E,R3H), (ZB,R1P,R2E,R3I),
(ZB,R1P,R2E,R3J), (ZB,R1P,R2E,R3K), (ZB,R1P,R2E,R3L),
(ZB,R1P,R2E,R3M), (ZB,R1P,R2E,R3N), (ZB,R1P,R2E,R3O),
(ZB,R1P,R2E,R3P), (ZB,R1P,R2E,R3Q), (ZB,R1P,R2E,R3R),
(ZB,R1P,R2F,R3A), (ZB,R1P,R2F,R3B), (ZB,R1P,R2F,R3C),
(ZB,R1P,R2F,R3D), (ZB,R1P,R2F,R3E), (ZB,R1P,R2F,R3F),
(ZB,R1P,R2F,R3H), (ZB,R1P,R2F,R3I),
(ZB,R1P,R2F,R3J), (ZB,R1P,R2F,R3K), (ZB,R1P,R2F,R3L),
(ZB,R1P,R2F,R3M), (ZB,R1P,R2F,R3N), (ZB,R1P,R2F,R3O),
(ZB,R1P,R2F,R3P), (ZB,R1P,R2F,R3Q), (ZB,R1P,R2F,R3R),
(ZB,R1P,R2G,R3A), (ZB,R1P,R2G,R3B), (ZB,R1P,R2G,R3C), (ZB,R1P,R2G,R3D)(ZB,R1P,R2G,R3E), (ZB,R1P,R2G,R3F),
(ZB,R1P,R2G,R3G), (ZB,R1P,R2G,R3H), (ZB,R1P,R2G,R3I),
(ZB,R1P,R2G,R3J), (ZB,R1P,R2G,R3K), (ZB,R1P,R2G,R3L),
(ZB,R1P,R2G,R3M), (ZB,R1P,R2G,R3N), (ZB,R1P,R2G,R3O),
(ZB,R1P,R2G,R3P), (ZB,R1P,R2G,R3Q), (ZB,R1P,R2G,R3R),
(ZB,R1P,R2H,R3A), (ZB,R1P,R2H,R3B), (ZB,R1P,R2H,R3C),
(ZB,R1P,R2H,R3D), (ZB,R1P,R2H,R3E), (ZB,R1P,R2H,R3F),
(ZB,R1P,R2H,R3G), (ZB,R1P,R2H,R3H), (ZB,R1P,R2H,R3I),
(ZB,R1P,R2H,R3J), (ZB,R1P,R2H,R3K), (ZB,R1P,R2H,R3L),
(ZB,R1P,R2H,R3M), (ZB,R1P,R2H,R3N), (ZB,R1P,R2H,R3O),
(ZB,R1P,R2H,R3P), (ZB,R1P,R2H,R3Q), (ZB,R1P,R2H,R3R),
(ZB,R1P,R2I,R3A), (ZB,R1P,R2I,R3B), (ZB,R1P,R2I,R3C), (ZB,R1P,R2I,R3D),
(ZB,R1P,R2I,R3E), (ZB,R1P,R2I,R3F), (ZB,R1P,R2I,R3G), (ZB,R1P,R2I,R3H),
(ZB,R1P,R2I,R3I), (ZB,R1P,R2I,R3J), (ZB,R1P,R2I,R3K), (ZB,R1P,R2I,R3L),
(ZB,R1P,R2I,R3M), (ZB,R1P,R2I,R3N), (ZB,R1P,R2I,R3O), (ZB,R1P,R2I,R3P),
(ZB,R1P,R2I,R3Q), (ZB,R1P,R2I,R3R), (ZB,R1P,R2J,R3A),
(ZB,R1P,R2J,R3B), (ZB,R1P,R2J,R3C), (ZB,R1P,R2J,R3D),
(ZB,R1P,R2J,R3E), (ZB,R1P,R2J,R3F), (ZB,R1P,R2J,R3G),
(ZB,R1P,R2J,R3H), (ZB,R1P,R2J,R3I), (ZB,R1P,R2J,R3J),
(ZB,R1P,R2J,R3K), (ZB,R1P,R2J,R3L), (ZB,R1P,R2J,R3M),
(ZB,R1P,R2J,R3N), (ZB,R1P,R2J,R3O), (ZB,R1P,R2J,R3P),
(ZB,R1P,R2J,R3Q), (ZB,R1P,R2J,R3R), (ZB,R1P,R2K,R3A),
(ZB,R1P,R2K,R3B), (ZB,R1P,R2K,R3C), (ZB,R1P,R2K,R3D),
(ZB,R1P,R2K,R3E), (ZB,R1P,R2K,R3F), (ZB,R1P,R2K,R3G),
(ZB,R1P,R2K,R3H), (ZB,R1P,R2K,R3I), (ZB,R1P,R2K,R3J),
(ZB,R1P,R2K,R3K), (ZB,R1P,R2K,R3L), (ZB,R1P,R2K,R3M),
(ZB,R1P,R2K,R3N), (ZB,R1P,R2K,R3O), (ZB,R1P,R2K,R3P),
(ZB,R1P,R2K,R3Q), (ZB,R1P,R2K,R3R), (ZB,R1P,R2L,R3A),
(ZB,R1P,R2L,R3B), (ZB,R1P,R2L,R3C), (ZB,R1P,R2L,R3D),
(ZB,R1P,R2L,R3E), (ZB,R1P,R2L,R3F), (ZB,R1P,R2L,R3G),
(ZB,R1P,R2L,R3H), (ZB,R1P,R2L,R3I), (ZB,R1P,R2L,R3J),
(ZB,R1P,R2L,R3K), (ZB,R1P,R2L,R3L), (ZB,R1P,R2L,R3M),
(ZB,R1P,R2L,R3N), (ZB,R1P,R2L,R3O), (ZB,R1P,R2L,R3P),
(ZB,R1P,R2L,R3Q), (ZB,R1P,R2L,R3R), (ZB,R1P,R2M,R3A),
(ZB,R1P,R2M,R3B), (ZB,R1P,R2M,R3C), (ZB,R1P,R2M,R3D),
(ZB,R1P,R2M,R3E), (ZB,R1P,R2M,R3F), (ZB,R1P,R2M,R3G),
(ZB,R1P,R2M,R3H), (ZB,R1P,R2M,R3I), (ZB,R1P,R2M,R3J),
(ZB,R1P,R2M,R3K), (ZB,R1P,R2M,R3L), (ZB,R1P,R2M,R3M),
(ZB,R1P,R2M,R3N), (ZB,R1P,R2M,R3O), (ZB,R1P,R2M,R3P),
(ZB,R1P,R2M,R3Q), (ZB,R1P,R2M,R3R), (ZB,R1P,R2N,R3A),
(ZB,R1P,R2N,R3B), (ZB,R1P,R2N,R3C), (ZB,R1P,R2N,R3D),
(ZB,R1P,R2N,R3E), (ZB,R1P,R2N,R3F), (ZB,R1P,R2N,R3G),
(ZB,R1P,R2N,R3H), (ZB,R1P,R2N,R3I), (ZB,R1P,R2N,R3J),
(ZB,R1P,R2N,R3K), (ZB,R1P,R2N,R3L), (ZB,R1P,R2N,R3M),
(ZB,R1P,R2N,R3N), (ZB,R1P,R2N,R3O), (ZB,R1P,R2N,R3P),
(ZB,R1P,R2N,R3Q), (ZB,R1P,R2N,R3R), (ZB,R1Q,R2A,R3A),
(ZB,R1Q,R2A,R3B), (ZB,R1Q,R2A,R3C), (ZB,R1Q,R2A,R3D),
(ZB,R1Q,R2A,R3E), (ZB,R1Q,R2A,R3F), (ZB,R1Q,R2A,R3G),
(ZB,R1Q,R2A,R3H), (ZB,R1Q,R2A,R3I), (ZB,R1Q,R2A,R3J),
(ZB,R1Q,R2A,R3K), (ZB,R1Q,R2A,R3L), (ZB,R1Q,R2A,R3M),
(ZB,R1Q,R2A,R3N), (ZB,R1Q,R2A,R3O), (ZB,R1Q,R2A,R3P),
(ZB,R1Q,R2A,R3Q), (ZB,R1Q,R2A,R3R), (ZB,R1Q,R2B,R3A),
(ZB,R1Q,R2B,R3B), (ZB,R1Q,R2B,R3C), (ZB,R1Q,R2B,R3D),
(ZB,R1Q,R2B,R3E), (ZB,R1Q,R2B,R3F), (ZB,R1Q,R2B,R3G),
(ZB,R1Q,R2B,R3H), (ZB,R1Q,R2B,R3I), (ZB,R1Q,R2B,R3J),
(ZB,R1Q,R2B,R3K), (ZB,R1Q,R2B,R3L), (ZB,R1Q,R2B,R3M),
(ZB,R1Q,R2B,R3N), (ZB,R1Q,R2B,R3O), (ZB,R1Q,R2B,R3P),
(ZB,R1Q,R2B,R3Q), (ZB,R1Q,R2B,R3R), (ZB,R1Q,R2C,R3A),
(ZB,R1Q,R2C,R3B), (ZB,R1Q,R2C,R3C), (ZB,R1Q,R2C,R3D),
(ZB,R1Q,R2C,R3E), (ZB,R1Q,R2C,R3F), (ZB,R1Q,R2C,R3G),
(ZB,R1Q,R2C,R3H), (ZB,R1Q,R2C,R3I), (ZB,R1Q,R2C,R3J),
(ZB,R1Q,R2C,R3K), (ZB,R1Q,R2C,R3L), (ZB,R1Q,R2C,R3M),
(ZB,R1Q,R2C,R3N), (ZB,R1Q,R2C,R3O), (ZB,R1Q,R2C,R3P),
(ZB,R1Q,R2C,R3Q), (ZB,R1Q,R2C,R3R), (ZB,R1Q,R2D,R3A),
(ZB,R1Q,R2D,R3B), (ZB,R1Q,R2D,R3C), (ZB,R1Q,R2D,R3D),
(ZB,R1Q,R2D,R3E), (ZB,R1Q,R2D,R3F), (ZB,R1Q,R2D,R3G),
(ZB,R1Q,R2D,R3H), (ZB,R1Q,R2D,R3I), (ZB,R1Q,R2D,R3J), (ZB,R1Q,R2D,R3K), (ZB,R1Q,R2D,R3L), (ZB,R1Q,R2D,R3M),
(ZB,R1Q,R2D,R3N), (ZB,R1Q,R2D,R3O), (ZB,R1Q,R2D,R3P),
(ZB,R1Q,R2D,R3Q), (ZB,R1Q,R2D,R3R), (ZB,R1Q,R2E,R3A),
(ZB,R1Q,R2E,R3B), (ZB,R1Q,R2E,R3C), (ZB,R1Q,R2E,R3D),
(ZB,R1Q,R2E,R3E), (ZB,R1Q,R2E,R3F), (ZB,R1Q,R2E,R3G),
(ZB,R1Q,R2E,R3H), (ZB,R1Q,R2E,R3I), (ZB,R1Q,R2E,R3J),
(ZB,R1Q,R2E,R3K), (ZB,R1Q,R2E,R3L), (ZB,R1Q,R2E,R3M),
(ZB,R1Q,R2E,R3N), (ZB,R1Q,R2E,R3O), (ZB,R1Q,R2E,R3P),
(ZB,R1Q,R2E,R3Q), (ZB,R1Q,R2E,R3R), (ZB,R1Q,R2F,R3A),
(ZB,R1Q,R2F,R3B), (ZB,R1Q,R2F,R3C), (ZB,R1Q,R2F,R3D),
(ZB,R1Q,R2F,R3E), (ZB,R1Q,R2F,R3F), (ZB,R1Q,R2F,R3G),
(ZB,R1Q,R2F,R3H), (ZB,R1Q,R2F,R3I), (ZB,R1Q,R2F,R3J),
(ZB,R1Q,R2F,R3K), (ZB,R1Q,R2F,R3L), (ZB,R1Q,R2F,R3M),
(ZB,R1Q,R2F,R3N), (ZB,R1Q,R2F,R3O), (ZB,R1Q,R2F,R3P),
(ZB,R1Q,R2F,R3Q), (ZB,R1Q,R2F,R3R), (ZB,R1Q,R2G,R3A),
(ZB,R1Q,R2G,R3B), (ZB,R1Q,R2G,R3C), (ZB,R1Q,R2G,R3D),
(ZB,R1Q,R2G,R3E), (ZB,R1Q,R2G,R3F), (ZB,R1Q,R2G,R3G),
(ZB,R1Q,R2G,R3H), (ZB,R1Q,R2G,R3I), (ZB,R1Q,R2G,R3J),
(ZB,R1Q,R2G,R3K), (ZB,R1Q,R2G,R3L), (ZB,R1Q,R2G,R3M),
(ZB,R1Q,R2G,R3N), (ZB,R1Q,R2G,R3O), (ZB,R1Q,R2G,R3P),
(ZB,R1Q,R2G,R3Q), (ZB,R1Q,R2G,R3R), (ZB,R1Q,R2H,R3A),
(ZB,R1Q,R2H,R3B), (ZB,R1Q,R2H,R3C), (ZB,R1Q,R2H,R3D),
(ZB,R1Q,R2H,R3E), (ZB,R1Q,R2H,R3F), (ZB,R1Q,R2H,R3G),
(ZB,R1Q,R2H,R3H), (ZB,R1Q,R2H,R3I), (ZB,R1Q,R2H,R3J),
(ZB,R1Q,R2H,R3K), (ZB,R1Q,R2H,R3L), (ZB,R1Q,R2H,R3M),
(ZB,R1Q,R2H,R3N), (ZB,R1Q,R2H,R3O), (ZB,R1Q,R2H,R3P),
(ZB,R1Q,R2H,R3Q), (ZB,R1Q,R2H,R3R), (ZB,R1Q,R2I,R3A),
(ZB,R1Q,R2I,R3B), (ZB,R1Q,R2I,R3C), (ZB,R1Q,R2I,R3D),
(ZB,R1Q,R2I,R3E), (ZB,R1Q,R2I,R3F), (ZB,R1Q,R2I,R3G),
(ZB,R1Q,R2I,R3H), (ZB,R1Q,R2I,R3I), (ZB,R1Q,R2I,R3J), (ZB,R1Q,R2I,R3K),
(ZB,R1Q,R2I,R3L), (ZB,R1Q,R2I,R3M), (ZB,R1Q,R2I,R3N),
(ZB,R1Q,R2I,R3O), (ZB,R1Q,R2I,R3P), (ZB,R1Q,R2I,R3Q),
(ZB,R1Q,R2I,R3R), (ZB,R1Q,R2J,R3A), (ZB,R1Q,R2J,R3B),
(ZB,R1Q,R2J,R3C), (ZB,R1Q,R2J,R3D), (ZB,R1Q,R2J,R3E),
(ZB,R1Q,R2J,R3F), (ZB,R1Q,R2J,R3G), (ZB,R1Q,R2J,R3H),
(ZB,R1Q,R2J,R3I), (ZB,R1Q,R2J,R3J), (ZB,R1Q,R2J,R3K),
(ZB,R1Q,R2J,R3L), (ZB,R1Q,R2J,R3M), (ZB,R1Q,R2J,R3N),
(ZB,R1Q,R2J,R3O), (ZB,R1Q,R2J,R3P), (ZB,R1Q,R2J,R3Q),
(ZB,R1Q,R2J,R3R), (ZB,R1Q,R2K,R3A), (ZB,R1Q,R2K,R3B),
(ZB,R1Q,R2K,R3C), (ZB,R1Q,R2K,R3D), (ZB,R1Q,R2K,R3E),
(ZB,R1Q,R2K,R3F), (ZB,R1Q,R2K,R3G), (ZB,R1Q,R2K,R3H),
(ZB,R1Q,R2K,R3I), (ZB,R1Q,R2K,R3J), (ZB,R1Q,R2K,R3K),
(ZB,R1Q,R2K,R3L), (ZB,R1Q,R2K,R3M), (ZB,R1Q,R2K,R3N),
(ZB,R1Q,R2K,R3O), (ZB,R1Q,R2K,R3P), (ZB,R1Q,R2K,R3Q),
(ZB,R1Q,R2K,R3R), (ZB,R1Q,R2L,R3A), (ZB,R1Q,R2L,R3B),
(ZB,R1Q,R2L,R3C), (ZB,R1Q,R2L,R3D), (ZB,R1Q,R2L,R3E),
(ZB,R1Q,R2L,R3F), (ZB,R1Q,R2L,R3G), (ZB,R1Q,R2L,R3H),
(ZB,R1Q,R2L,R3I), (ZB,R1Q,R2L,R3J), (ZB,R1Q,R2L,R3K),
(ZB,R1Q,R2L,R3L), (ZB,R1Q,R2L,R3M), (ZB,R1Q,R2L,R3N),
(ZB,R1Q,R2L,R3O), (ZB,R1Q,R2L,R3P), (ZB,R1Q,R2L,R3Q),
(ZB,R1Q,R2L,R3R), (ZB,R1Q,R2M,R3A), (ZB,R1Q,R2M,R3B),
(ZB,R1Q,R2M,R3C), (ZB,R1Q,R2M,R3D), (ZB,R1Q,R2M,R3E),
(ZB,R1Q,R2M,R3F), (ZB,R1Q,R2M,R3G), (ZB,R1Q,R2M,R3H),
(ZB,R1Q,R2M,R3I), (ZB,R1Q,R2M,R3J), (ZB,R1Q,R2M,R3K),
(ZB,R1Q,R2M,R3L), (ZB,R1Q,R2M,R3M), (ZB,R1Q,R2M,R3N),
(ZB,R1Q,R2M,R3O), (ZB,R1Q,R2M,R3P), (ZB,R1Q,R2M,R3Q),
(ZB,R1Q,R2M,R3R), (ZB,R1Q,R2N,R3A), (ZB,R1Q,R2N,R3B),
(ZB,R1Q,R2N,R3F), (ZB,R1Q,R2N,R3G), (ZB,R1Q,R2N,R3H),
(ZB,R1Q,R2N,R3I), (ZB,R1Q,R2N,R3J), (ZB,R1Q,R2N,R3K),
(ZB,R1Q,R2N,R3L), (ZB,R1Q,R2N,R3M), (ZB,R1Q,R2N,R3N),
(ZB,R1Q,R2N,R3O), (ZB,R1Q,R2N,R3P), (ZB,R1Q,R2N,R3Q),
(ZB,R1Q,R2N,R3R), (ZB,R1R,R2A,R3A), (ZB,R1R,R2A,R3B),
(ZB,R1R,R2A,R3C), (ZB,R1R,R2A,R3D), (ZB,R1R,R2A,R3E),
(ZB,R1R,R2A,R3F), (ZB,R1R,R2A,R3G), (ZB,R1R,R2A,R3H),
(ZB,R1R,R2A,R3I), (ZB,R1R,R2A,R3J), (ZB,R1R,R2A,R3K),
(ZB,R1R,R2A,R3L), (ZB,R1R,R2A,R3M), (ZB,R1R,R2A,R3N), (ZB,R1R,R2A,R3O), (ZB,R1R,R2A,R3P), (ZB,R1R,R2A,R3Q),
(ZB,R1R,R2A,R3R), (ZB,R1R,R2B,R3A), (ZB,R1R,R2B,R3B),
(ZB,R1R,R2B,R3C), (ZB,R1R,R2B,R3D), (ZB,R1R,R2B,R3E),
(ZB,R1R,R2B,R3F), (ZB,R1R,R2B,R3G), (ZB,R1R,R2B,R3H),
(ZB,R1R,R2B,R3I), (ZB,R1R,R2B,R3J), (ZB,R1R,R2B,R3K),
(ZB,R1R,R2B,R3L), (ZB,R1R,R2B,R3M), (ZB,R1R,R2B,R3N),
(ZB,R1R,R2B,R3O), (ZB,R1R,R2B,R3P), (ZB,R1R,R2B,R3Q),
(ZB,R1R,R2B,R3R), (ZB,R1R,R2C,R3A), (ZB,R1R,R2C,R3B),
(ZB,R1R,R2C,R3C), (ZB,R1R,R2C,R3D), (ZB,R1R,R2C,R3E),
(ZB,R1R,R2C,R3F), (ZB,R1R,R2C,R3G), (ZB,R1R,R2C,R3H),
(ZB,R1R,R2C,R3I), (ZB,R1R,R2C,R3J), (ZB,R1R,R2C,R3K),
(ZB,R1R,R2C,R3L), (ZB,R1R,R2C,R3M), (ZB,R1R,R2C,R3N),
(ZB,R1R,R2C,R3O), (ZB,R1R,R2C,R3P), (ZB,R1R,R2C,R3Q),
(ZB,R1R,R2C,R3R), (ZB,R1R,R2D,R3A), (ZB,R1R,R2D,R3B),
(ZB,R1R,R2D,R3C), (ZB,R1R,R2D,R3D), (ZB,R1R,R2D,R3E),
(ZB,R1R,R2D,R3F), (ZB,R1R,R2D,R3G), (ZB,R1R,R2D,R3H),
(ZB,R1R,R2D,R3I), (ZB,R1R,R2D,R3J), (ZB,R1R,R2D,R3K),
(ZB,R1R,R2D,R3L), (ZB,R1R,R2D,R3M), (ZB,R1R,R2D,R3N),
(ZB,R1R,R2D,R3O), (ZB,R1R,R2D,R3P), (ZB,R1R,R2D,R3Q),
(ZB,R1R,R2D,R3R), (ZB,R1R,R2E,R3A), (ZB,R1R,R2E,R3B),
(ZB,R1R,R2E,R3C), (ZB,R1R,R2E,R3D), (ZB,R1R,R2E,R3E),
(ZB,R1R,R2E,R3F), (ZB,R1R,R2E,R3G), (ZB,R1R,R2E,R3H),
(ZB,R1R,R2E,R3I), (ZB,R1R,R2E,R3J), (ZB,R1R,R2E,R3K),
(ZB,R1R,R2E,R3L), (ZB,R1R,R2E,R3M), (ZB,R1R,R2E,R3N),
(ZB,R1R,R2E,R3O), (ZB,R1R,R2E,R3P), (ZB,R1R,R2E,R3Q),
(ZB,R1R,R2E,R3R), (ZB,R1R,R2F,R3A), (ZB,R1R,R2F,R3B),
(ZB,R1R,R2F,R3C), (ZB,R1R,R2F,R3D), (ZB,R1R,R2F,R3E),
(ZB,R1R,R2F,R3F), (ZB,R1R,R2F,R3G), (ZB,R1R,R2F,R3H),
(ZB,R1R,R2F,R3I), (ZB,R1R,R2F,R3J), (ZB,R1R,R2F,R3K),
(ZB,R1R,R2F,R3L), (ZB,R1R,R2F,R3M), (ZB,R1R,R2F,R3N),
(ZB,R1R,R2F,R3O), (ZB,R1R,R2F,R3P), (ZB,R1R,R2F,R3Q),
(ZB,R1R,R2F,R3R), (ZB,R1R,R2G,R3A), (ZB,R1R,R2G,R3B),
(ZB,R1R,R2G,R3C), (ZB,R1R,R2G,R3D), (ZB,R1R,R2G,R3E),
(ZB,R1R,R2G,R3F), (ZB,R1R,R2G,R3G), (ZB,R1R,R2G,R3H),
(ZB,R1R,R2G,R3I), (ZB,R1R,R2G,R3J), (ZB,R1R,R2G,R3K),
(ZB,R1R,R2G,R3L), (ZB,R1R,R2G,R3M), (ZB,R1R,R2G,R3N),
(ZB,R1R,R2G,R3O), (ZB,R1R,R2G,R3P), (ZB,R1R,R2G,R3Q),
(ZB,R1R,R2G,R3R), (ZB,R1R,R2H,R3A), (ZB,R1R,R2H,R3B),
(ZB,R1R,R2H,R3C), (ZB,R1R,R2H,R3D), (ZB,R1R,R2H,R3E),
(ZB,R1R,R2H,R3F), (ZB,R1R,R2H,R3G), (ZB,R1R,R2H,R3H),
(ZB,R1R,R2H,R3I), (ZB,R1R,R2H,R3J), (ZB,R1R,R2H,R3K),
(ZB,R1R,R2H,R3L), (ZB,R1R,R2H,R3M), (ZB,R1R,R2H,R3N),
(ZB,R1R,R2H,R3O), (ZB,R1R,R2H,R3P), (ZB,R1R,R2H,R3Q),
(ZB,R1R,R2H,R3R), (ZB,R1R,R2I,R3A), (ZB,R1R,R2I,R3B),
(ZB,R1R,R2I,R3C), (ZB,R1R,R2I,R3D), (ZB,R1R,R2I,R3E), (ZB,R1R,R2I,R3F),
(ZB,R1R,R2I,R3G), (ZB,R1R,R2I,R3H), (ZB,R1R,R2I,R3I), (ZB,R1R,R2I,R3J),
(ZB,R1R,R2I,R3K), (ZB,R1R,R2I,R3L), (ZB,R1R,R2I,R3M),
(ZB,R1R,R2I,R3N), (ZB,R1R,R2I,R3O), (ZB,R1R,R2I,R3P), (ZB,R1R,R2I,R3Q),
(ZB,R1R,R2I,R3R), (ZB,R1R,R2J,R3A), (ZB,R1R,R2J,R3B),
(ZB,R1R,R2J,R3C), (ZB,R1R,R2J,R3D), (ZB,R1R,R2J,R3E),
(ZB,R1R,R2J,R3F), (ZB,R1R,R2J,R3G), (ZB,R1R,R2J,R3H),
(ZB,R1R,R2J,R3J), (ZB,R1R,R2J,R3K),
(ZB,R1R,R2J,R3L), (ZB,R1R,R2J,R3M), (ZB,R1R,R2J,R3N),
(ZB,R1R,R2J,R3O), (ZB,R1R,R2J,R3P), (ZB,R1R,R2J,R3Q),
(ZB,R1R,R2J,R3R), (ZB,R1R,R2K,R3A), (ZB,R1R,R2K,R3B),
(ZB,R1R,R2K,R3C), (ZB,R1R,R2K,R3D), (ZB,R1R,R2K,R3E),
(ZB,R1R,R2K,R3G), (ZB,R1R,R2K,R3H),
(ZB,R1R,R2K,R3I), (ZB,R1R,R2K,R3J), (ZB,R1R,R2K,R3K),
(ZB,R1R,R2K,R3L), (ZB,R1R,R2K,R3M), (ZB,R1R,R2K,R3N),
(ZB,R1R,R2K,R3O), (ZB,R1R,R2K,R3P), (ZB,R1R,R2K,R3Q),
(ZB,R1R,R2K,R3R), (ZB,R1R,R2L,R3A), (ZB,R1R,R2L,R3B),
(ZB,R1R,R2L,R3C), (ZB,R1R,R2L,R3D), (ZB,R1R,R2L,R3E),
(ZB,R1R,R2L,R3F), (ZB,R1R,R2L,R3G), (ZB,R1R,R2L,R3H),
(ZB,R1R,R2L,R3I), (ZB,R1R,R2L,R3J), (ZB,R1R,R2L,R3K),
(ZB,R1R,R2L,R3L), (ZB,R1R,R2L,R3M), (ZB,R1R,R2L,R3N),
(ZB,R1R,R2L,R3O), (ZB,R1R,R2L,R3P), (ZB,R1R,R2L,R3Q),
(ZB,R1R,R2L,R3R), (ZB,R1R,R2M,R3A), (ZB,R1R,R2M,R3B), (ZB,R1R,R2M,R3C), (ZB,R1R,R2M,R3D), (ZB,R1R,R2M,R3E),
(ZB,R1R,R2M,R3F), (ZB,R1R,R2M,R3G), (ZB,R1R,R2M,R3H),
(ZB,R1R,R2M,R3I), (ZB,R1R,R2M,R3J), (ZB,R1R,R2M,R3K),
(ZB,R1R,R2M,R3L), (ZB,R1R,R2M,R3M), (ZB,R1R,R2M,R3N),
(ZB,R1R,R2M,R3O), (ZB,R1R,R2M,R3P), (ZB,R1R,R2M,R3Q),
(ZB,R1R,R2M,R3R), (ZB,R1R,R2N,R3A), (ZB,R1R,R2N,R3B),
(ZB,R1R,R2N,R3C), (ZB,R1R,R2N,R3D), (ZB,R1R,R2N,R3E),
(ZB,R1R,R2N,R3F), (ZB,R1R,R2N,R3G), (ZB,R1R,R2N,R3H),
(ZB,R1R,R2N,R3I), (ZB,R1R,R2N,R3J), (ZB,R1R,R2N,R3K),
(ZB,R1R,R2N,R3L), (ZB,R1R,R2N,R3M), (ZB,R1R,R2N,R3N),
(ZB,R1R,R2N,R3O), (ZB,R1R,R2N,R3P), (ZB,R1R,R2N,R3Q),
(ZB,R1R,R2N,R3R), (ZB,R1S,R2A,R3A), (ZB,R1S,R2A,R3B),
(ZB,R1S,R2A,R3C), (ZB,R1S,R2A,R3D), (ZB,R1S,R2A,R3E),
(ZB,R1S,R2A,R3F), (ZB,R1S,R2A,R3G), (ZB,R1S,R2A,R3H),
(ZB,R1S,R2A,R3I), (ZB,R1S,R2A,R3J), (ZB,R1S,R2A,R3K),
(ZB,R1S,R2A,R3L), (ZB,R1S,R2A,R3M), (ZB,R1S,R2A,R3N),
(ZB,R1S,R2A,R3O), (ZB,R1S,R2A,R3P), (ZB,R1S,R2A,R3Q),
(ZB,R1S,R2A,R3R), (ZB,R1S,R2B,R3A), (ZB,R1S,R2B,R3B),
(ZB,R1S,R2B,R3C), (ZB,R1S,R2B,R3D), (ZB,R1S,R2B,R3E),
(ZB,R1S,R2B,R3F), (ZB,R1S,R2B,R3G), (ZB,R1S,R2B,R3H),
(ZB,R1S,R2B,R3I), (ZB,R1S,R2B,R3J), (ZB,R1S,R2B,R3K),
(ZB,R1S,R2B,R3L), (ZB,R1S,R2B,R3M), (ZB,R1S,R2B,R3N),
(ZB,R1S,R2B,R3O), (ZB,R1S,R2B,R3P), (ZB,R1S,R2B,R3Q),
(ZB,R1S,R2B,R3R), (ZB,R1S,R2C,R3A), (ZB,R1S,R2C,R3B),
(ZB,R1S,R2C,R3C), (ZB,R1S,R2C,R3D), (ZB,R1S,R2C,R3E),
(ZB,R1S,R2C,R3F), (ZB,R1S,R2C,R3G), (ZB,R1S,R2C,R3H),
(ZB,R1S,R2C,R3I), (ZB,R1S,R2C,R3J), (ZB,R1S,R2C,R3K),
(ZB,R1S,R2C,R3L), (ZB,R1S,R2C,R3M), (ZB,R1S,R2C,R3N),
(ZB,R1S,R2C,R3O), (ZB,R1S,R2C,R3P), (ZB,R1S,R2C,R3Q),
(ZB,R1S,R2C,R3R), (ZB,R1S,R2D,R3A), (ZB,R1S,R2D,R3B),
(ZB,R1S,R2D,R3C), (ZB,R1S,R2D,R3D), (ZB,R1S,R2D,R3E),
(ZB,R1S,R2D,R3F), (ZB,R1S,R2D,R3G), (ZB,R1S,R2D,R3H),
(ZB,R1S,R2D,R3I), (ZB,R1S,R2D,R3J), (ZB,R1S,R2D,R3K),
(ZB,R1S,R2D,R3L), (ZB,R1S,R2D,R3M), (ZB,R1S,R2D,R3N),
(ZB,R1S,R2D,R3O), (ZB,R1S,R2D,R3P), (ZB,R1S,R2D,R3Q),
(ZB,R1S,R2D,R3R), (ZB,R1S,R2E,R3A), (ZB,R1S,R2E,R3B),
(ZB,R1S,R2E,R3C), (ZB,R1S,R2E,R3D), (ZB,R1S,R2E,R3E),
(ZB,R1S,R2E,R3F), (ZB,R1S,R2E,R3G), (ZB,R1S,R2E,R3H),
(ZB,R1S,R2E,R3I), (ZB,R1S,R2E,R3J), (ZB,R1S,R2E,R3K),
(ZB,R1S,R2E,R3L), (ZB,R1S,R2E,R3M), (ZB,R1S,R2E,R3N),
(ZB,R1S,R2E,R3O), (ZB,R1S,R2E,R3P), (ZB,R1S,R2E,R3Q),
(ZB,R1S,R2E,R3R), (ZB,R1S,R2F,R3A), (ZB,R1S,R2F,R3B),
(ZB,R1S,R2F,R3C), (ZB,R1S,R2F,R3D), (ZB,R1S,R2F,R3E),
(ZB,R1S,R2F,R3F), (ZB,R1S,R2F,R3G), (ZB,R1S,R2F,R3H),
(ZB,R1S,R2F,R3I), (ZB,R1S,R2F,R3J), (ZB,R1S,R2F,R3K),
(ZB,R1S,R2F,R3L), (ZB,R1S,R2F,R3M), (ZB,R1S,R2F,R3N),
(ZB,R1S,R2F,R3O), (ZB,R1S,R2F,R3P), (ZB,R1S,R2F,R3Q),
(ZB,R1S,R2F,R3R), (ZB,R1S,R2G,R3A), (ZB,R1S,R2G,R3B),
(ZB,R1S,R2G,R3C), (ZB,R1S,R2G,R3D), (ZB,R1S,R2G,R3E),
(ZB,R1S,R2G,R3F), (ZB,R1S,R2G,R3G), (ZB,R1S,R2G,R3H),
(ZB,R1S,R2G,R3I), (ZB,R1S,R2G,R3J), (ZB,R1S,R2G,R3K),
(ZB,R1S,R2G,R3L), (ZB,R1S,R2G,R3M), (ZB,R1S,R2G,R3N),
(ZB,R1S,R2G,R3O), (ZB,R1S,R2G,R3P), (ZB,R1S,R2G,R3Q)
(ZB,R1S,R2G,R3R), (ZB,R1S,R2H,R3A), (ZB,R1S,R2H,R3B),
(ZB,R1S,R2H,R3C), (ZB,R1S,R2H,R3D), (ZB,R1S,R2H,R3E),
(ZB,R1S,R2H,R3F), (ZB,R1S,R2H,R3G), (ZB,R1S,R2H,R3H),
(ZB,R1S,R2H,R3I), (ZB,R1S,R2H,R3J), (ZB,R1S,R2H,R3K),
(ZB,R1S,R2H,R3L), (ZB,R1S,R2H,R3M), (ZB,R1S,R2H,R3N),
(ZB,R1S,R2H,R3O), (ZB,R1S,R2H,R3P), (ZB,R1S,R2H,R3Q),
(ZB,R1S,R2H,R3R), (ZB,R1S,R2I,R3A), (ZB,R1S,R2I,R3B),
(ZB,R1S,R2I,R3C), (ZB,R1S,R2I,R3D), (ZB,R1S,R2I,R3E), (ZB,R1S,R2I,R3F),
(ZB,R1S,R2I,R3G), (ZB,R1S,R2I,R3H), (ZB,R1S,R2I,R3I), (ZB,R1S,R2I,R3J),
(ZB,R1S,R2I,R3K), (ZB,R1S,R2I,R3L), (ZB,R1S,R2I,R3M), (ZB,R1S,R2I,R3N),
(ZB,R1S,R2I,R3O), (ZB,R1S,R2I,R3P), (ZB,R1S,R2I,R3Q), (ZB,R1S,R2I,R3R),
(ZB,R1S,R2J,R3A), (ZB,R1S,R2J,R3B), (ZB,R1S,R2J,R3C),
(ZB,R1S,R2J,R3D), (ZB,R1S,R2J,R3E), (ZB,R1S,R2J,R3F), (ZB,R1S,R2J,R3G), (ZB,R1S,R2J,R3H), (ZB,R1S,R2J,R3I),
(ZB,R1S,R2J,R3J), (ZB,R1S,R2J,R3K), (ZB,R1S,R2J,R3L),
(ZB,R1S,R2J,R3M), (ZB,R1S,R2J,R3N), (ZB,R1S,R2J,R3O),
(ZB,R1S,R2J,R3P), (ZB,R1S,R2J,R3Q), (ZB,R1S,R2J,R3R),
(ZB,R1S,R2K,R3A), (ZB,R1S,R2K,R3B), (ZB,R1S,R2K,R3C),
(ZB,R1S,R2K,R3D), (ZB,R1S,R2K,R3E), (ZB,R1S,R2K,R3F),
(ZB,R1S,R2K,R3G), (ZB,R1S,R2K,R3H), (ZB,R1S,R2K,R3I),
(ZB,R1S,R2K,R3J), (ZB,R1S,R2K,R3K), (ZB,R1S,R2K,R3L),
(ZB,R1S,R2K,R3M), (ZB,R1S,R2K,R3N), (ZB,R1S,R2K,R3O),
(ZB,R1S,R2K,R3P), (ZB,R1S,R2K,R3Q), (ZB,R1S,R2K,R3R),
(ZB,R1S,R2L,R3A), (ZB,R1S,R2L,R3B), (ZB,R1S,R2L,R3C),
(ZB,R1S,R2L,R3D), (ZB,R1S,R2L,R3E), (ZB,R1S,R2L,R3F),
(ZB,R1S,R2L,R3G), (ZB,R1S,R2L,R3H), (ZB,R1S,R2L,R3I),
(ZB,R1S,R2L,R3J), (ZB,R1S,R2L,R3K), (ZB,R1S,R2L,R3L),
(ZB,R1S,R2L,R3M), (ZB,R1S,R2L,R3N), (ZB,R1S,R2L,R3O),
(ZB,R1S,R2L,R3P), (ZB,R1S,R2L,R3Q), (ZB,R1S,R2L,R3R),
(ZB,R1S,R2M,R3A), (ZB,R1S,R2M,R3B), (ZB,R1S,R2M,R3C),
(ZB,R1S,R2M,R3D), (ZB,R1S,R2M,R3E), (ZB,R1S,R2M,R3F),
(ZB,R1S,R2M,R3G), (ZB,R1S,R2M,R3H), (ZB,R1S,R2M,R3I),
(ZB,R1S,R2M,R3J), (ZB,R1S,R2M,R3K), (ZB,R1S,R2M,R3L),
(ZB,R1S,R2M,R3M), (ZB,R1S,R2M,R3N), (ZB,R1S,R2M,R3O),
(ZB,R1S,R2M,R3P), (ZB,R1S,R2M,R3Q), (ZB,R1S,R2M,R3R),
(ZB,R1S,R2N,R3A), (ZB,R1S,R2N,R3B), (ZB,R1S,R2N,R3C),
(ZB,R1S,R2N,R3D), (ZB,R1S,R2N,R3E), (ZB,R1S,R2N,R3F),
(ZB,R1S,R2N,R3G), (ZB,R1S,R2N,R3H), (ZB,R1S,R2N,R3I),
(ZB,R1S,R2N,R3J), (ZB,R1S,R2N,R3K), (ZB,R1S,R2N,R3L),
(ZB,R1S,R2N,R3M), (ZB,R1S,R2N,R3N), (ZB,R1S,R2N,R3O),
(ZB,R1S,R2N,R3P), (ZB,R1S,R2N,R3Q), (ZB,R1S,R2N,R3R),
(ZC,R1A,R2A,R3A), (ZC,R1A,R2A,R3B), (ZC,R1A,R2A,R3C),
(ZC,R1A,R2A,R3D), (ZC,R1A,R2A,R3E), (ZC,R1A,R2A,R3F),
(ZC,R1A,R2A,R3G), (ZC,R1A,R2A,R3H), (ZC,R1A,R2A,R3I),
(ZC,R1A,R2A,R3J), (ZC,R1A,R2A,R3K), (ZC,R1A,R2A,R3L),
(ZC,R1A,R2A,R3M), (ZC,R1A,R2A,R3N), (ZC,R1A,R2A,R3O),
(ZC,R1A,R2A,R3P), (ZC,R1A,R2A,R3Q), (ZC,R1A,R2A,R3R),
(ZC,R1A,R2B,R3A), (ZC,R1A,R2B,R3B), (ZC,R1A,R2B,R3C),
(ZC,R1A,R2B,R3D), (ZC,R1A,R2B,R3E), (ZC,R1A,R2B,R3F),
(ZC,R1A,R2B,R3G), (ZC,R1A,R2B,R3H), (ZC,R1A,R2B,R3I),
(ZC,R1A,R2B,R3J), (ZC,R1A,R2B,R3K), (ZC,R1A,R2B,R3L),
(ZC,R1A,R2B,R3M), (ZC,R1A,R2B,R3N), (ZC,R1A,R2B,R3O),
(ZC,R1A,R2B,R3P), (ZC,R1A,R2B,R3Q), (ZC,R1A,R2B,R3R),
(ZC,R1A,R2C,R3A), (ZC,R1A,R2C,R3B), (ZC,R1A,R2C,R3C),
(ZC,R1A,R2C,R3D), (ZC,R1A,R2C,R3E), (ZC,R1A,R2C,R3F),
(ZC,R1A,R2C,R3G), (ZC,R1A,R2C,R3H), (ZC,R1A,R2C,R3I),
(ZC,R1A,R2C,R3J), (ZC,R1A,R2C,R3K), (ZC,R1A,R2C,R3L),
(ZC,R1A,R2C,R3M), (ZC,R1A,R2C,R3N), (ZC,R1A,R2C,R3O),
(ZC,R1A,R2C,R3P), (ZC,R1A,R2C,R3Q), (ZC,R1A,R2C,R3R),
(ZC,R1A,R2D,R3A), (ZC,R1A,R2D,R3B), (ZC,R1A,R2D,R3C),
(ZC,R1A,R2D,R3D), (ZC,R1A,R2D,R3E), (ZC,R1A,R2D,R3F),
(ZC,R1A,R2D,R3G), (ZC,R1A,R2D,R3H), (ZC,R1A,R2D,R3I),
(ZC,R1A,R2D,R3J), (ZC,R1A,R2D,R3K), (ZC,R1A,R2D,R3L),
(ZC,R1A,R2D,R3M), (ZC,R1A,R2D,R3N), (ZC,R1A,R2D,R3O),
(ZC,R1A,R2D,R3P), (ZC,R1A,R2D,R3Q), (ZC,R1A,R2D,R3R),
(ZC,R1A,R2E,R3A), (ZC,R1A,R2E,R3B), (ZC,R1A,R2E,R3C),
(ZC,R1A,R2E,R3D), (ZC,R1A,R2E,R3E), (ZC,R1A,R2E,R3F),
(ZC,R1A,R2E,R3G), (ZC,R1A,R2E,R3H), (ZC,R1A,R2E,R3I),
(ZC,R1A,R2E,R3J), (ZC,R1A,R2E,R3K), (ZC,R1A,R2E,R3L),
(ZC,R1A,R2E,R3M), (ZC,R1A,R2E,R3N), (ZC,R1A,R2E,R3O),
(ZC,R1A,R2E,R3P), (ZC,R1A,R2E,R3Q), (ZC,R1A,R2E,R3R),
(ZC,R1A,R2F,R3A), (ZC,R1A,R2F,R3B), (ZC,R1A,R2F,R3C),
(ZC,R1A,R2F,R3D), (ZC,R1A,R2F,R3E), (ZC,R1A,R2F,R3F),
(ZC,R1A,R2F,R3G), (ZC,R1A,R2F,R3H), (ZC,R1A,R2F,R3I),
(ZC,R1A,R2F,R3J), (ZC,R1A,R2F,R3K), (ZC,R1A,R2F,R3L),
(ZC,R1A,R2F,R3M), (ZC,R1A,R2F,R3N), (ZC,R1A,R2F,R3O),
(ZC,R1A,R2F,R3P), (ZC,R1A,R2F,R3Q), (ZC,R1A,R2F,R3R),
(ZC,R1A,R2G,R3A), (ZC,R1A,R2G,R3B), (ZC,R1A,R2G,R3C),
(ZC,R1A,R2G,R3D), (ZC,R1A,R2G,R3E), (ZC,R1A,R2G,R3F), (ZC,R1A,R2G,R3G), (ZC,R1A,R2G,R3H), (ZC,R1A,R2G,R3I),
(ZC,R1A,R2G,R3J), (ZC,R1A,R2G,R3K), (ZC,R1A,R2G,R3L),
(ZC,R1A,R2G,R3M), (ZC,R1A,R2G,R3N), (ZC,R1A,R2G,R3O),
(ZC,R1A,R2G,R3P), (ZC,R1A,R2G,R3Q), (ZC,R1A,R2G,R3R),
(ZC,R1A,R2H,R3A), (ZC,R1A,R2H,R3B), (ZC,R1A,R2H,R3C),
(ZC,R1A,R2H,R3D), (ZC,R1A,R2H,R3E), (ZC,R1A,R2H,R3F),
(ZC,R1A,R2H,R3G), (ZC,R1A,R2H,R3H), (ZC,R1A,R2H,R3I),
(ZC,R1A,R2H,R3J), (ZC,R1A,R2H,R3K), (ZC,R1A,R2H,R3L),
(ZC,R1A,R2H,R3M), (ZC,R1A,R2H,R3N), (ZC,R1A,R2H,R3O),
(ZC,R1A,R2H,R3P), (ZC,R1A,R2H,R3Q), (ZC,R1A,R2H,R3R),
(ZC,R1A,R2I,R3A), (ZC,R1A,R2I,R3B), (ZC,R1A,R2I,R3C), (ZC,R1A,R2I,R3D),
(ZC,R1A,R2I,R3E), (ZC,R1A,R2I,R3F), (ZC,R1A,R2I,R3G), (ZC,R1A,R2I,R3H),
(ZC,R1A,R2I,R3I), (ZC,R1A,R2I,R3J), (ZC,R1A,R2I,R3K), (ZC,R1A,R2I,R3L),
(ZC,R1A,R2I,R3M), (ZC,R1A,R2I,R3N), (ZC,R1A,R2I,R3O), (ZC,R1A,R2I,R3P),
(ZC,R1A,R2I,R3Q), (ZC,R1A,R2I,R3R), (ZC,R1A,R2J,R3A),
(ZC,R1A,R2J,R3B), (ZC,R1A,R2J,R3C), (ZC,R1A,R2J,R3D),
(ZC,R1A,R2J,R3E), (ZC,R1A,R2J,R3F), (ZC,R1A,R2J,R3G),
(ZC,R1A,R2J,R3I), (ZC,R1A,R2J,R3J),
(ZC,R1A,R2J,R3K), (ZC,R1A,R2J,R3L), (ZC,R1A,R2J,R3M),
(ZC,R1A,R2J,R3N), (ZC,R1A,R2J,R3O), (ZC,R1A,R2J,R3P),
(ZC,R1A,R2J,R3Q), (ZC,R1A,R2J,R3R), (ZC,R1A,R2K,R3A),
(ZC,R1A,R2K,R3B), (ZC,R1A,R2K,R3C), (ZC,R1A,R2K,R3D),
(ZC,R1A,R2K,R3F), (ZC,R1A,R2K,R3G),
(ZC,R1A,R2K,R3H), (ZC,R1A,R2K,R3I), (ZC,R1A,R2K,R3J),
(ZC,R1A,R2K,R3K), (ZC,R1A,R2K,R3L), (ZC,R1A,R2K,R3M),
(ZC,R1A,R2K,R3N), (ZC,R1A,R2K,R3O), (ZC,R1A,R2K,R3P),
(ZC,R1A,R2K,R3Q), (ZC,R1A,R2K,R3R), (ZC,R1A,R2L,R3A),
(ZC,R1A,R2L,R3C), (ZC,R1A,R2L,R3D),
(ZC,R1A,R2L,R3E), (ZC,R1A,R2L,R3F), (ZC,R1A,R2L,R3G),
(ZC,R1A,R2L,R3H), (ZC,R1A,R2L,R3I), (ZC,R1A,R2L,R3J),
(ZC,R1A,R2L,R3K), (ZC,R1A,R2L,R3L), (ZC,R1A,R2L,R3M),
(ZC,R1A,R2L,R3N), (ZC,R1A,R2L,R3O), (ZC,R1A,R2L,R3P),
(ZC,R1A,R2L,R3R), (ZC,R1A,R2M,R3A),
(ZC,R1A,R2M,R3B), (ZC,R1A,R2M,R3C), (ZC,R1A,R2M,R3D),
(ZC,R1A,R2M,R3E), (ZC,R1A,R2M,R3F), (ZC,R1A,R2M,R3G),
(ZC,R1A,R2M,R3H), (ZC,R1A,R2M,R3I), (ZC,R1A,R2M,R3J),
(ZC,R1A,R2M,R3K), (ZC,R1A,R2M,R3L), (ZC,R1A,R2M,R3M),
(ZC,R1A,R2M,R3N), (ZC,R1A,R2M,R3O), (ZC,R1A,R2M,R3P),
(ZC,R1A,R2M,R3Q), (ZC,R1A,R2M,R3R), (ZC,R1A,R2N,R3A),
(ZC,R1A,R2N,R3B), (ZC,R1A,R2N,R3C), (ZC,R1A,R2N,R3D),
(ZC,R1A,R2N,R3E), (ZC,R1A,R2N,R3F), (ZC,R1A,R2N,R3G),
(ZC,R1A,R2N,R3H), (ZC,R1A,R2N,R3I), (ZC,R1A,R2N,R3J),
(ZC,R1A,R2N,R3K), (ZC,R1A,R2N,R3L), (ZC,R1A,R2N,R3M),
(ZC,R1A,R2N,R3N), (ZC,R1A,R2N,R3O), (ZC,R1A,R2N,R3P),
(ZC,R1A,R2N,R3Q), (ZC,R1A,R2N,R3R), (ZC,R1B,R2A,R3A),
(ZC,R1B,R2A,R3B), (ZC,R1B,R2A,R3C), (ZC,R1B,R2A,R3D),
(ZC,R1B,R2A,R3E), (ZC,R1B,R2A,R3F), (ZC,R1B,R2A,R3G),
(ZC,R1B,R2A,R3H), (ZC,R1B,R2A,R3I), (ZC,R1B,R2A,R3J),
(ZC,R1B,R2A,R3K), (ZC,R1B,R2A,R3L), (ZC,R1B,R2A,R3M),
(ZC,R1B,R2A,R3N), (ZC,R1B,R2A,R3O), (ZC,R1B,R2A,R3P),
(ZC,R1B,R2A,R3Q), (ZC,R1B,R2A,R3R), (ZC,R1B,R2B,R3A),
(ZC,R1B,R2B,R3B), (ZC,R1B,R2B,R3C), (ZC,R1B,R2B,R3D),
(ZC,R1B,R2B,R3E), (ZC,R1B,R2B,R3F), (ZC,R1B,R2B,R3G),
(ZC,R1B,R2B,R3H), (ZC,R1B,R2B,R3I), (ZC,R1B,R2B,R3J),
(ZC,R1B,R2B,R3K), (ZC,R1B,R2B,R3L), (ZC,R1B,R2B,R3M),
(ZC,R1B,R2B,R3N), (ZC,R1B,R2B,R3O), (ZC,R1B,R2B,R3P),
(ZC,R1B,R2B,R3Q), (ZC,R1B,R2B,R3R), (ZC,R1B,R2C,R3A),
(ZC,R1B,R2C,R3B), (ZC,R1B,R2C,R3C), (ZC,R1B,R2C,R3D),
(ZC,R1B,R2C,R3E), (ZC,R1B,R2C,R3F), (ZC,R1B,R2C,R3G),
(ZC,R1B,R2C,R3H), (ZC,R1B,R2C,R3I), (ZC,R1B,R2C,R3J),
(ZC,R1B,R2C,R3K), (ZC,R1B,R2C,R3L), (ZC,R1B,R2C,R3M),
(ZC,R1B,R2C,R3N), (ZC,R1B,R2C,R3O), (ZC,R1B,R2C,R3P),
(ZC,R1B,R2C,R3Q), (ZC,R1B,R2C,R3R), (ZC,R1B,R2D,R3A),
(ZC,R1B,R2D,R3B), (ZC,R1B,R2D,R3C), (ZC,R1B,R2D,R3D),
(ZC,R1B,R2D,R3E), (ZC,R1B,R2D,R3F), (ZC,R1B,R2D,R3G),
(ZC,R1B,R2D,R3H), (ZC,R1B,R2D,R3I), (ZC,R1B,R2D,R3J),
(ZC,R1B,R2D,R3K), (ZC,R1B,R2D,R3L), (ZC,R1B,R2D,R3M),
(ZC,R1B,R2D,R3N), (ZC,R1B,R2D,R3O), (ZC,R1B,R2D,R3P), (ZC,R1B,R2D,R3Q), (ZC,R1B,R2D,R3R), (ZC,R1B,R2E,R3A),
(ZC,R1B,R2E,R3B), (ZC,R1B,R2E,R3C), (ZC,R1B,R2E,R3D),
(ZC,R1B,R2E,R3E), (ZC,R1B,R2E,R3F), (ZC,R1B,R2E,R3G),
(ZC,R1B,R2E,R3H), (ZC,R1B,R2E,R3I), (ZC,R1B,R2E,R3J),
(ZC,R1B,R2E,R3K), (ZC,R1B,R2E,R3L), (ZC,R1B,R2E,R3M),
(ZC,R1B,R2E,R3N), (ZC,R1B,R2E,R3O), (ZC,R1B,R2E,R3P),
(ZC,R1B,R2E,R3Q), (ZC,R1B,R2E,R3R), (ZC,R1B,R2F,R3A),
(ZC,R1B,R2F,R3B), (ZC,R1B,R2F,R3C), (ZC,R1B,R2F,R3D),
(ZC,R1B,R2F,R3E), (ZC,R1B,R2F,R3F), (ZC,R1B,R2F,R3G),
(ZC,R1B,R2F,R3H), (ZC,R1B,R2F,R3I), (ZC,R1B,R2F,R3J),
(ZC,R1B,R2F,R3K), (ZC,R1B,R2F,R3L), (ZC,R1B,R2F,R3M),
(ZC,R1B,R2F,R3N), (ZC,R1B,R2F,R3O), (ZC,R1B,R2F,R3P),
(ZC,R1B,R2F,R3Q), (ZC,R1B,R2F,R3R), (ZC,R1B,R2G,R3A),
(ZC,R1B,R2G,R3B), (ZC,R1B,R2G,R3C), (ZC,R1B,R2G,R3D),
(ZC,R1B,R2G,R3E), (ZC,R1B,R2G,R3F), (ZC,R1B,R2G,R3G),
(ZC,R1B,R2G,R3H), (ZC,R1B,R2G,R3I), (ZC,R1B,R2G,R3J),
(ZC,R1B,R2G,R3K), (ZC,R1B,R2G,R3L), (ZC,R1B,R2G,R3M),
(ZC,R1B,R2G,R3N), (ZC,R1B,R2G,R3O), (ZC,R1B,R2G,R3P),
(ZC,R1B,R2G,R3Q), (ZC,R1B,R2G,R3R), (ZC,R1B,R2H,R3A),
(ZC,R1B,R2H,R3B), (ZC,R1B,R2H,R3C), (ZC,R1B,R2H,R3D),
(ZC,R1B,R2H,R3E), (ZC,R1B,R2H,R3F), (ZC,R1B,R2H,R3G),
(ZC,R1B,R2H,R3H), (ZC,R1B,R2H,R3I), (ZC,R1B,R2H,R3J),
(ZC,R1B,R2H,R3K), (ZC,R1B,R2H,R3L), (ZC,R1B,R2H,R3M),
(ZC,R1B,R2H,R3N), (ZC,R1B,R2H,R3O), (ZC,R1B,R2H,R3P),
(ZC,R1B,R2H,R3Q), (ZC,R1B,R2H,R3R), (ZC,R1B,R2I,R3A),
(ZC,R1B,R2I,R3B), (ZC,R1B,R2I,R3C), (ZC,R1B,R2I,R3D),
(ZC,R1B,R2I,R3E), (ZC,R1B,R2I,R3F), (ZC,R1B,R2I,R3G),
(ZC,R1B,R2I,R3H), (ZC,R1B,R2I,R3I), (ZC,R1B,R2I,R3J), (ZC,R1B,R2I,R3K),
(ZC,R1B,R2I,R3L), (ZC,R1B,R2I,R3M), (ZC,R1B,R2I,R3N),
(ZC,R1B,R2I,R3P), (ZC,R1B,R2I,R3Q),
(ZC,R1B,R2I,R3R), (ZC,R1B,R2J,R3A), (ZC,R1B,R2J,R3B),
(ZC,R1B,R2J,R3C), (ZC,R1B,R2J,R3D), (ZC,R1B,R2J,R3E),
(ZC,R1B,R2J,R3F), (ZC,R1B,R2J,R3G), (ZC,R1B,R2J,R3H),
(ZC,R1B,R2J,R3I), (ZC,R1B,R2J,R3J), (ZC,R1B,R2J,R3K),
(ZC,R1B,R2J,R3L), (ZC,R1B,R2J,R3M), (ZC,R1B,R2J,R3N),
(ZC,R1B,R2J,R3O), (ZC,R1B,R2J,R3P), (ZC,R1B,R2J,R3Q),
(ZC,R1B,R2J,R3R), (ZC,R1B,R2K,R3A), (ZC,R1B,R2K,R3B),
(ZC,R1B,R2K,R3C), (ZC,R1B,R2K,R3D), (ZC,R1B,R2K,R3E),
(ZC,R1B,R2K,R3F), (ZC,R1B,R2K,R3G), (ZC,R1B,R2K,R3H),
(ZC,R1B,R2K,R3I), (ZC,R1B,R2K,R3J), (ZC,R1B,R2K,R3K),
(ZC,R1B,R2K,R3L), (ZC,R1B,R2K,R3M), (ZC,R1B,R2K,R3N),
(ZC,R1B,R2K,R3O), (ZC,R1B,R2K,R3P), (ZC,R1B,R2K,R3Q),
(ZC,R1B,R2K,R3R), (ZC,R1B,R2L,R3A), (ZC,R1B,R2L,R3B),
(ZC,R1B,R2L,R3C), (ZC,R1B,R2L,R3D), (ZC,R1B,R2L,R3E),
(ZC,R1B,R2L,R3F), (ZC,R1B,R2L,R3G), (ZC,R1B,R2L,R3H),
(ZC,R1B,R2L,R3I), (ZC,R1B,R2L,R3J), (ZC,R1B,R2L,R3K),
(ZC,R1B,R2L,R3L), (ZC,R1B,R2L,R3M), (ZC,R1B,R2L,R3N),
(ZC,R1B,R2L,R3O), (ZC,R1B,R2L,R3P), (ZC,R1B,R2L,R3Q),
(ZC,R1B,R2L,R3R), (ZC,R1B,R2M,R3A), (ZC,R1B,R2M,R3B),
(ZC,R1B,R2M,R3C), (ZC,R1B,R2M,R3D), (ZC,R1B,R2M,R3E),
(ZC,R1B,R2M,R3F), (ZC,R1B,R2M,R3G), (ZC,R1B,R2M,R3H),
(ZC,R1B,R2M,R3I), (ZC,R1B,R2M,R3J), (ZC,R1B,R2M,R3K),
(ZC,R1B,R2M,R3L), (ZC,R1B,R2M,R3M), (ZC,R1B,R2M,R3N),
(ZC,R1B,R2M,R3O), (ZC,R1B,R2M,R3P), (ZC,R1B,R2M,R3Q),
(ZC,R1B,R2M,R3R), (ZC,R1B,R2N,R3A), (ZC,R1B,R2N,R3B),
(ZC,R1B,R2N,R3C), (ZC,R1B,R2N,R3D), (ZC,R1B,R2N,R3E),
(ZC,R1B,R2N,R3F), (ZC,R1B,R2N,R3G), (ZC,R1B,R2N,R3H),
(ZC,R1B,R2N,R3I), (ZC,R1B,R2N,R3J), (ZC,R1B,R2N,R3K),
(ZC,R1B,R2N,R3L), (ZC,R1B,R2N,R3M), (ZC,R1B,R2N,R3N),
(ZC,R1B,R2N,R3O), (ZC,R1B,R2N,R3P), (ZC,R1B,R2N,R3Q),
(ZC,R1B,R2N,R3R), (ZC,R1C,R2A,R3A), (ZC,R1C,R2A,R3B),
(ZC,R1C,R2A,R3C), (ZC,R1C,R2A,R3D), (ZC,R1C,R2A,R3E),
(ZC,R1C,R2A,R3F), (ZC,R1C,R2A,R3G), (ZC,R1C,R2A,R3H),
(ZC,R1C,R2A,R3I), (ZC,R1C,R2A,R3J), (ZC,R1C,R2A,R3K),
(ZC,R1C,R2A,R3L), (ZC,R1C,R2A,R3M), (ZC,R1C,R2A,R3N),
(ZC,R1C,R2A,R3O), (ZC,R1C,R2A,R3P), (ZC,R1C,R2A,R3Q),
(ZC,R1C,R2A,R3R), (ZC,R1C,R2B,R3A), (ZC,R1C,R2B,R3B), (ZC,R1C,R2B,R3C), (ZC,R1C,R2B,R3D), (ZC,R1C,R2B,R3E),
(ZC,R1C,R2B,R3F), (ZC,R1C,R2B,R3G), (ZC,R1C,R2B,R3H),
(ZC,R1C,R2B,R3I), (ZC,R1C,R2B,R3J), (ZC,R1C,R2B,R3K),
(ZC,R1C,R2B,R3L), (ZC,R1C,R2B,R3M), (ZC,R1C,R2B,R3N),
(ZC,R1C,R2B,R3O), (ZC,R1C,R2B,R3P), (ZC,R1C,R2B,R3Q),
(ZC,R1C,R2B,R3R), (ZC,R1C,R2C,R3A), (ZC,R1C,R2C,R3B),
(ZC,R1C,R2C,R3C), (ZC,R1C,R2C,R3D), (ZC,R1C,R2C,R3E),
(ZC,R1C,R2C,R3F), (ZC,R1C,R2C,R3G), (ZC,R1C,R2C,R3H),
(ZC,R1C,R2C,R3I), (ZC,R1C,R2C,R3J), (ZC,R1C,R2C,R3K),
(ZC,R1C,R2C,R3L), (ZC,R1C,R2C,R3M), (ZC,R1C,R2C,R3N),
(ZC,R1C,R2C,R3O), (ZC,R1C,R2C,R3P), (ZC,R1C,R2C,R3Q),
(ZC,R1C,R2C,R3R), (ZC,R1C,R2D,R3A), (ZC,R1C,R2D,R3B),
(ZC,R1C,R2D,R3C), (ZC,R1C,R2D,R3D), (ZC,R1C,R2D,R3E),
(ZC,R1C,R2D,R3F), (ZC,R1C,R2D,R3G), (ZC,R1C,R2D,R3H),
(ZC,R1C,R2D,R3I), (ZC,R1C,R2D,R3J), (ZC,R1C,R2D,R3K),
(ZC,R1C,R2D,R3L), (ZC,R1C,R2D,R3M), (ZC,R1C,R2D,R3N),
(ZC,R1C,R2D,R3O), (ZC,R1C,R2D,R3P), (ZC,R1C,R2D,R3Q),
(ZC,R1C,R2D,R3R), (ZC,R1C,R2E,R3A), (ZC,R1C,R2E,R3B),
(ZC,R1C,R2E,R3C), (ZC,R1C,R2E,R3D), (ZC,R1C,R2E,R3E),
(ZC,R1C,R2E,R3F), (ZC,R1C,R2E,R3G), (ZC,R1C,R2E,R3H),
(ZC,R1C,R2E,R3I), (ZC,R1C,R2E,R3J), (ZC,R1C,R2E,R3K),
(ZC,R1C,R2E,R3L), (ZC,R1C,R2E,R3M), (ZC,R1C,R2E,R3N),
(ZC,R1C,R2E,R3O), (ZC,R1C,R2E,R3P), (ZC,R1C,R2E,R3Q),
(ZC,R1C,R2E,R3R), (ZC,R1C,R2F,R3A), (ZC,R1C,R2F,R3B),
(ZC,R1C,R2F,R3C), (ZC,R1C,R2F,R3D), (ZC,R1C,R2F,R3E),
(ZC,R1C,R2F,R3F), (ZC,R1C,R2F,R3G), (ZC,R1C,R2F,R3H),
(ZC,R1C,R2F,R3I), (ZC,R1C,R2F,R3J), (ZC,R1C,R2F,R3K),
(ZC,R1C,R2F,R3L), (ZC,R1C,R2F,R3M), (ZC,R1C,R2F,R3N),
(ZC,R1C,R2F,R3O), (ZC,R1C,R2F,R3P), (ZC,R1C,R2F,R3Q),
(ZC,R1C,R2F,R3R), (ZC,R1C,R2G,R3A), (ZC,R1C,R2G,R3B),
(ZC,R1C,R2G,R3C), (ZC,R1C,R2G,R3D), (ZC,R1C,R2G,R3E),
(ZC,R1C,R2G,R3F), (ZC,R1C,R2G,R3G), (ZC,R1C,R2G,R3H),
(ZC,R1C,R2G,R3I), (ZC,R1C,R2G,R3J), (ZC,R1C,R2G,R3K),
(ZC,R1C,R2G,R3L), (ZC,R1C,R2G,R3M), (ZC,R1C,R2G,R3N),
(ZC,R1C,R2G,R3O), (ZC,R1C,R2G,R3P), (ZC,R1C,R2G,R3Q),
(ZC,R1C,R2G,R3R), (ZC,R1C,R2H,R3A), (ZC,R1C,R2H,R3B),
(ZC,R1C,R2H,R3C), (ZC,R1C,R2H,R3D), (ZC,R1C,R2H,R3E),
(ZC,R1C,R2H,R3F), (ZC,R1C,R2H,R3G), (ZC,R1C,R2H,R3H),
(ZC,R1C,R2H,R3I), (ZC,R1C,R2H,R3J), (ZC,R1C,R2H,R3K),
(ZC,R1C,R2H,R3L), (ZC,R1C,R2H,R3M), (ZC,R1C,R2H,R3N),
(ZC,R1C,R2H,R3O), (ZC,R1C,R2H,R3P), (ZC,R1C,R2H,R3Q),
(ZC,R1C,R2H,R3R), (ZC,R1C,R2I,R3A), (ZC,R1C,R2I,R3B),
(ZC,R1C,R2I,R3C), (ZC,R1C,R2I,R3D), (ZC,R1C,R2I,R3E),
(ZC,R1C,R2I,R3F), (ZC,R1C,R2I,R3G), (ZC,R1C,R2I,R3H), (ZC,R1C,R2I,R3I),
(ZC,R1C,R2I,R3J), (ZC,R1C,R2I,R3K), (ZC,R1C,R2I,R3L), (ZC,R1C,R2I,R3M),
(ZC,R1C,R2I,R3N), (ZC,R1C,R2I,R3O), (ZC,R1C,R2I,R3P),
(ZC,R1C,R2I,R3Q), (ZC,R1C,R2I,R3R), (ZC,R1C,R2J,R3A),
(ZC,R1C,R2J,R3B), (ZC,R1C,R2J,R3C), (ZC,R1C,R2J,R3D),
(ZC,R1C,R2J,R3E), (ZC,R1C,R2J,R3F), (ZC,R1C,R2J,R3G),
(ZC,R1C,R2J,R3H), (ZC,R1C,R2J,R3I), (ZC,R1C,R2J,R3J),
(ZC,R1C,R2J,R3K), (ZC,R1C,R2J,R3L), (ZC,R1C,R2J,R3M),
(ZC,R1C,R2J,R3N), (ZC,R1C,R2J,R3O), (ZC,R1C,R2J,R3P),
(ZC,R1C,R2J,R3Q), (ZC,R1C,R2J,R3R), (ZC,R1C,R2K,R3A),
(ZC,R1C,R2K,R3B), (ZC,R1C,R2K,R3C), (ZC,R1C,R2K,R3D),
(ZC,R1C,R2K,R3E), (ZC,R1C,R2K,R3F), (ZC,R1C,R2K,R3G),
(ZC,R1C,R2K,R3H), (ZC,R1C,R2K,R3I), (ZC,R1C,R2K,R3J),
(ZC,R1C,R2K,R3K), (ZC,R1C,R2K,R3L), (ZC,R1C,R2K,R3M),
(ZC,R1C,R2K,R3N), (ZC,R1C,R2K,R3O), (ZC,R1C,R2K,R3P),
(ZC,R1C,R2K,R3Q), (ZC,R1C,R2K,R3R), (ZC,R1C,R2L,R3A),
(ZC,R1C,R2L,R3B), (ZC,R1C,R2L,R3C), (ZC,R1C,R2L,R3D),
(ZC,R1C,R2L,R3E), (ZC,R1C,R2L,R3F), (ZC,R1C,R2L,R3G),
(ZC,R1C,R2L,R3H), (ZC,R1C,R2L,R3I), (ZC,R1C,R2L,R3J),
(ZC,R1C,R2L,R3K), (ZC,R1C,R2L,R3L), (ZC,R1C,R2L,R3M),
(ZC,R1C,R2L,R3N), (ZC,R1C,R2L,R3O), (ZC,R1C,R2L,R3P),
(ZC,R1C,R2L,R3Q), (ZC,R1C,R2L,R3R), (ZC,R1C,R2M,R3A),
(ZC,R1C,R2M,R3B), (ZC,R1C,R2M,R3C), (ZC,R1C,R2M,R3D), (ZC,R1C,R2M,R3E), (ZC,R1C,R2M,R3F), (ZC,R1C,R2M, R3G),
(ZC,R1C,R2M,R3H), (ZC,R1C,R2M,R3I), (ZC,R1C,R2M, R3J),
(ZC,R1C,R2M,R3K), (ZC,R1C,R2M,R3L), (ZC,R1C,R2M, R3M),
(ZC,R1C,R2M,R3N), (ZC,R1C,R2M,R3O), (ZC,R1C,R2M, R3P),
(ZC,R1C,R2M,R3Q), (ZC,R1C,R2M,R3R), (ZC,R1C,R2N, R3A),
(ZC,R1C,R2N,R3B), (ZC,R1C,R2N,R3C), (ZC,R1C,R2N, R3D),
(ZC,R1C,R2N,R3E), (ZC,R1C,R2N,R3F), (ZC,R1C,R2N, R3G),
(ZC,R1C,R2N,R3H), (ZC,R1C,R2N,R3I), (ZC,R1C,R2N, R3J),
(ZC,R1C,R2N,R3K), (ZC,R1C,R2N,R3L), (ZC,R1C,R2N, R3M),
(ZC,R1C,R2N,R3N), (ZC,R1C,R2N,R3O), (ZC,R1C,R2N, R3P),
(ZC,R1C,R2N,R3Q), (ZC,R1C,R2N,R3R), (ZC,R1D,R2A, R3A),
(ZC,R1D,R2A,R3B), (ZC,R1D,R2A,R3C), (ZC,R1D,R2A, R3D),
(ZC,R1D,R2A,R3E), (ZC,R1D,R2A,R3F), (ZC,R1D,R2A, R3G),
(ZC,R1D,R2A,R3H), (ZC,R1D,R2A,R3I), (ZC,R1D,R2A, R3J),
(ZC,R1D,R2A,R3K), (ZC,R1D,R2A,R3L), (ZC,R1D,R2A, R3M),
(ZC,R1D,R2A,R3N), (ZC,R1D,R2A,R3O), (ZC,R1D,R2A, R3P),
(ZC,R1D,R2A,R3Q), (ZC,R1D,R2A,R3R), (ZC,R1D,R2B, R3A),
(ZC,R1D,R2B,R3B), (ZC,R1D,R2B,R3C), (ZC,R1D,R2B, R3D),
(ZC,R1D,R2B,R3E), (ZC,R1D,R2B,R3F), (ZC,R1D,R2B, R3G),
(ZC,R1D,R2B,R3H), (ZC,R1D,R2B,R3I), (ZC,R1D,R2B, R3J),
(ZC,R1D,R2B,R3K), (ZC,R1D,R2B,R3L), (ZC,R1D,R2B, R3M),
(ZC,R1D,R2B,R3N), (ZC,R1D,R2B,R3O), (ZC,R1D,R2B, R3P),
(ZC,R1D,R2B,R3Q), (ZC,R1D,R2B,R3R), (ZC,R1D,R2C, R3A),
(ZC,R1D,R2C,R3B), (ZC,R1D,R2C,R3C), (ZC,R1D,R2C, R3D),
(ZC,R1D,R2C,R3E), (ZC,R1D,R2C,R3F), (ZC,R1D,R2C, R3G),
(ZC,R1D,R2C,R3H), (ZC,R1D,R2C,R3I), (ZC,R1D,R2C, R3J),
(ZC,R1D,R2C,R3K), (ZC,R1D,R2C,R3L), (ZC,R1D,R2C, R3M),
(ZC,R1D,R2C,R3N), (ZC,R1D,R2C,R3O), (ZC,R1D,R2C, R3P),
(ZC,R1D,R2C,R3Q), (ZC,R1D,R2C,R3R), (ZC,R1D,R2D, R3A),
(ZC,R1D,R2D,R3B), (ZC,R1D,R2D,R3C), (ZC,R1D,R2D, R3D),
(ZC,R1D,R2D,R3E), (ZC,R1D,R2D,R3F), (ZC,R1D,R2D, R3G),
(ZC,R1D,R2D,R3H), (ZC,R1D,R2D,R3I), (ZC,R1D,R2D, R3J),
(ZC,R1D,R2D,R3K), (ZC,R1D,R2D,R3L), (ZC,R1D,R2D, R3M),
(ZC,R1D,R2D,R3N), (ZC,R1D,R2D,R3O), (ZC,R1D,R2D, R3P),
(ZC,R1D,R2D,R3Q), (ZC,R1D,R2D,R3R), (ZC,R1D,R2E, R3A),
(ZC,R1D,R2E,R3B), (ZC,R1D,R2E,R3C), (ZC,R1D,R2E, R3D),
(ZC,R1D,R2E,R3E), (ZC,R1D,R2E,R3F), (ZC,R1D,R2E, R3G),
(ZC,R1D,R2E,R3H), (ZC,R1D,R2E,R3I), (ZC,R1D,R2E, R3J),
(ZC,R1D,R2E,R3K), (ZC,R1D,R2E,R3L), (ZC,R1D,R2E, R3M),
(ZC,R1D,R2E,R3N), (ZC,R1D,R2E,R3O), (ZC,R1D,R2E, R3P),
(ZC,R1D,R2E,R3Q), (ZC,R1D,R2E,R3R), (ZC,R1D,R2F, R3A),
(ZC,R1D,R2F,R3B), (ZC,R1D,R2F,R3C), (ZC,R1D,R2F, R3D),
(ZC,R1D,R2F,R3E), (ZC,R1D,R2F,R3F), (ZC,R1D,R2F, R3G),
(ZC,R1D,R2F,R3H), (ZC,R1D,R2F,R3I), (ZC,R1D,R2F, R3J),
(ZC,R1D,R2F,R3K), (ZC,R1D,R2F,R3L), (ZC,R1D,R2F, R3M),
(ZC,R1D,R2F,R3N), (ZC,R1D,R2F,R3O), (ZC,R1D,R2F, R3P),
(ZC,R1D,R2F,R3Q), (ZC,R1D,R2F,R3R), (ZC,R1D,R2G, R3A),
(ZC,R1D,R2G,R3B), (ZC,R1D,R2G,R3C), (ZC,R1D,R2G, R3D),
(ZC,R1D,R2G,R3E), (ZC,R1D,R2G,R3F), (ZC,R1D,R2G, R3G),
(ZC,R1D,R2G,R3H), (ZC,R1D,R2G,R3I), (ZC,R1D,R2G, R3J),
(ZC,R1D,R2G,R3K), (ZC,R1D,R2G,R3L), (ZC,R1D,R2G, R3M),
(ZC,R1D,R2G,R3N), (ZC,R1D,R2G,R3O), (ZC,R1D,R2G, R3P),
(ZC,R1D,R2G,R3Q), (ZC,R1D,R2G,R3R), (ZC,R1D,R2H, R3A),
(ZC,R1D,R2H,R3B), (ZC,R1D,R2H,R3C), (ZC,R1D,R2H, R3D),
(ZC,R1D,R2H,R3E), (ZC,R1D,R2H,R3F), (ZC,R1D,R2H, R3G),
(ZC,R1D,R2H,R3H), (ZC,R1D,R2H,R3I), (ZC,R1D,R2H, R3J),
(ZC,R1D,R2H,R3K), (ZC,R1D,R2H,R3L), (ZC,R1D,R2H, R3M),
(ZC,R1D,R2H,R3N), (ZC,R1D,R2H,R3O), (ZC,R1D,R2H, R3P),
(ZC,R1D,R2H,R3Q), (ZC,R1D,R2H,R3R), (ZC,R1D,R2I, R3A),
(ZC,R1D,R2I,R3B), (ZC,R1D,R2I,R3C), (ZC,R1D,R2I, R3D),
(ZC,R1D,R2I,R3E), (ZC,R1D,R2I,R3F), (ZC,R1D,R2I, R3G),
(ZC,R1D,R2I,R3H), (ZC,R1D,R2I,R3I), (ZC,R1D,R2I, R3J), (ZC,R1D,R2I,R3K),
(ZC,R1D,R2I,R3L), (ZC,R1D,R2I,R3M), (ZC,R1D,R2I, R3N),
(ZC,R1D,R2I,R3O), (ZC,R1D,R2I,R3P), (ZC,R1D,R2I, R3Q),
(ZC,R1D,R2I,R3R), (ZC,R1D,R2J,R3A), (ZC,R1D,R2J, R3B),
(ZC,R1D,R2J,R3C), (ZC,R1D,R2J,R3D), (ZC,R1D,R2J, R3E), (ZC,R1D,R2J,R3F), (ZC,R1D,R2J,R3G), (ZC,R1D,R2J,R3H),
(ZC,R1D,R2J,R3I), (ZC,R1D,R2J,R3J), (ZC,R1D,R2J,R3K),
(ZC,R1D,R2J,R3L), (ZC,R1D,R2J,R3M), (ZC,R1D,R2J,R3N),
(ZC,R1D,R2J,R3O), (ZC,R1D,R2J,R3P), (ZC,R1D,R2J,R3Q),
(ZC,R1D,R2J,R3R), (ZC,R1D,R2K,R3A), (ZC,R1D,R2K,R3B),
(ZC,R1D,R2K,R3C), (ZC,R1D,R2K,R3D), (ZC,R1D,R2K,R3E),
(ZC,R1D,R2K,R3F), (ZC,R1D,R2K,R3G), (ZC,R1D,R2K,R3H),
(ZC,R1D,R2K,R3I), (ZC,R1D,R2K,R3J), (ZC,R1D,R2K,R3K),
(ZC,R1D,R2K,R3L), (ZC,R1D,R2K,R3M), (ZC,R1D,R2K,R3N),
(ZC,R1D,R2K,R3O), (ZC,R1D,R2K,R3P), (ZC,R1D,R2K,R3Q),
(ZC,R1D,R2K,R3R), (ZC,R1D,R2L,R3A), (ZC,R1D,R2L,R3B),
(ZC,R1D,R2L,R3C), (ZC,R1D,R2L,R3D), (ZC,R1D,R2L,R3E),
(ZC,R1D,R2L,R3F), (ZC,R1D,R2L,R3G), (ZC,R1D,R2L,R3H),
(ZC,R1D,R2L,R3I), (ZC,R1D,R2L,R3J), (ZC,R1D,R2L,R3K),
(ZC,R1D,R2L,R3L), (ZC,R1D,R2L,R3M), (ZC,R1D,R2L,R3N),
(ZC,R1D,R2L,R3O), (ZC,R1D,R2L,R3P), (ZC,R1D,R2L,R3Q),
(ZC,R1D,R2L,R3R), (ZC,R1D,R2M,R3A), (ZC,R1D,R2M,R3B),
(ZC,R1D,R2M,R3C), (ZC,R1D,R2M,R3D), (ZC,R1D,R2M,R3E),
(ZC,R1D,R2M,R3F), (ZC,R1D,R2M,R3G), (ZC,R1D,R2M,R3H),
(ZC,R1D,R2M,R3I), (ZC,R1D,R2M,R3J), (ZC,R1D,R2M,R3K),
(ZC,R1D,R2M,R3L), (ZC,R1D,R2M,R3M), (ZC,R1D,R2M,R3N),
(ZC,R1D,R2M,R3O), (ZC,R1D,R2M,R3P), (ZC,R1D,R2M,R3Q),
(ZC,R1D,R2M,R3R), (ZC,R1D,R2N,R3A), (ZC,R1D,R2N,R3B),
(ZC,R1D,R2N,R3C), (ZC,R1D,R2N,R3D), (ZC,R1D,R2N,R3E),
(ZC,R1D,R2N,R3F), (ZC,R1D,R2N,R3G), (ZC,R1D,R2N,R3H),
(ZC,R1D,R2N,R3I), (ZC,R1D,R2N,R3J), (ZC,R1D,R2N,R3K),
(ZC,R1D,R2N,R3L), (ZC,R1D,R2N,R3M), (ZC,R1D,R2N,R3N),
(ZC,R1D,R2N,R3O), (ZC,R1D,R2N,R3P), (ZC,R1D,R2N,R3Q),
(ZC,R1D,R2N,R3R), (ZC,R1E,R2A,R3A), (ZC,R1E,R2A,R3B),
(ZC,R1E,R2A,R3C), (ZC,R1E,R2A,R3D), (ZC,R1E,R2A,R3E),
(ZC,R1E,R2A,R3F), (ZC,R1E,R2A,R3G), (ZC,R1E,R2A,R3H),
(ZC,R1E,R2A,R3I), (ZC,R1E,R2A,R3J), (ZC,R1E,R2A,R3K),
(ZC,R1E,R2A,R3L), (ZC,R1E,R2A,R3M), (ZC,R1E,R2A,R3N),
(ZC,R1E,R2A,R3O), (ZC,R1E,R2A,R3P), (ZC,R1E,R2A,R3Q),
(ZC,R1E,R2A,R3R), (ZC,R1E,R2B,R3A), (ZC,R1E,R2B,R3B),
(ZC,R1E,R2B,R3C), (ZC,R1E,R2B,R3D), (ZC,R1E,R2B,R3E),
(ZC,R1E,R2B,R3F), (ZC,R1E,R2B,R3G), (ZC,R1E,R2B,R3H),
(ZC,R1E,R2B,R3I), (ZC,R1E,R2B,R3J), (ZC,R1E,R2B,R3K),
(ZC,R1E,R2B,R3L), (ZC,R1E,R2B,R3M), (ZC,R1E,R2B,R3N),
(ZC,R1E,R2B,R3O), (ZC,R1E,R2B,R3P), (ZC,R1E,R2B,R3Q),
(ZC,R1E,R2B,R3R), (ZC,R1E,R2C,R3A), (ZC,R1E,R2C,R3B),
(ZC,R1E,R2C,R3C), (ZC,R1E,R2C,R3D), (ZC,R1E,R2C,R3E),
(ZC,R1E,R2C,R3F), (ZC,R1E,R2C,R3G), (ZC,R1E,R2C,R3H),
(ZC,R1E,R2C,R3I), (ZC,R1E,R2C,R3J), (ZC,R1E,R2C,R3K),
(ZC,R1E,R2C,R3L), (ZC,R1E,R2C,R3M), (ZC,R1E,R2C,R3N),
(ZC,R1E,R2C,R3O), (ZC,R1E,R2C,R3P), (ZC,R1E,R2C,R3Q),
(ZC,R1E,R2C,R3R), (ZC,R1E,R2D,R3A), (ZC,R1E,R2D,R3B),
(ZC,R1E,R2D,R3C), (ZC,R1E,R2D,R3D), (ZC,R1E,R2D,R3E),
(ZC,R1E,R2D,R3F), (ZC,R1E,R2D,R3G), (ZC,R1E,R2D,R3H),
(ZC,R1E,R2D,R3I), (ZC,R1E,R2D,R3J), (ZC,R1E,R2D,R3K),
(ZC,R1E,R2D,R3L), (ZC,R1E,R2D,R3M), (ZC,R1E,R2D,R3N),
(ZC,R1E,R2D,R3O), (ZC,R1E,R2D,R3P), (ZC,R1E,R2D,R3Q),
(ZC,R1E,R2D,R3R), (ZC,R1E,R2E,R3A), (ZC,R1E,R2E,R3B),
(ZC,R1E,R2E,R3C), (ZC,R1E,R2E,R3D), (ZC,R1E,R2E,R3E),
(ZC,R1E,R2E,R3F), (ZC,R1E,R2E,R3G), (ZC,R1E,R2E,R3H),
(ZC,R1E,R2E,R3I), (ZC,R1E,R2E,R3J), (ZC,R1E,R2E,R3K),
(ZC,R1E,R2E,R3L), (ZC,R1E,R2E,R3M), (ZC,R1E,R2E,R3N),
(ZC,R1E,R2E,R3O), (ZC,R1E,R2E,R3P), (ZC,R1E,R2E,R3Q),
(ZC,R1E,R2E,R3R), (ZC,R1E,R2F,R3A), (ZC,R1E,R2F,R3B),
(ZC,R1E,R2F,R3C), (ZC,R1E,R2F,R3D), (ZC,R1E,R2F,R3E),
(ZC,R1E,R2F,R3F), (ZC,R1E,R2F,R3G), (ZC,R1E,R2F,R3H),
(ZC,R1E,R2F,R3I), (ZC,R1E,R2F,R3J), (ZC,R1E,R2F,R3K),
(ZC,R1E,R2F,R3L), (ZC,R1E,R2F,R3M), (ZC,R1E,R2F,R3N),
(ZC,R1E,R2F,R3O), (ZC,R1E,R2F,R3P), (ZC,R1E,R2F,R3Q),
(ZC,R1E,R2F,R3R), (ZC,R1E,R2G,R3A), (ZC,R1E,R2G,R3B),
(ZC,R1E,R2G,R3C), (ZC,R1E,R2G,R3D), (ZC,R1E,R2G,R3E), (ZC,R1E,R2G,R3F), (ZC,R1E,R2G,R3G), (ZC,R1E,R2G,R3H),
(ZC,R1E,R2G,R3I), (ZC,R1E,R2G,R3J), (ZC,R1E,R2G,R3K),
(ZC,R1E,R2G,R3L), (ZC,R1E,R2G,R3M), (ZC,R1E,R2G,R3N),
(ZC,R1E,R2G,R3O), (ZC,R1E,R2G,R3P), (ZC,R1E,R2G,R3Q),
(ZC,R1E,R2G,R3R), (ZC,R1E,R2H,R3A), (ZC,R1E,R2H,R3B),
(ZC,R1E,R2H,R3C), (ZC,R1E,R2H,R3D), (ZC,R1E,R2H,R3E),
(ZC,R1E,R2H,R3F), (ZC,R1E,R2H,R3G), (ZC,R1E,R2H,R3H),
(ZC,R1E,R2H,R3I), (ZC,R1E,R2H,R3J), (ZC,R1E,R2H,R3K),
(ZC,R1E,R2H,R3L), (ZC,R1E,R2H,R3M), (ZC,R1E,R2H,R3N),
(ZC,R1E,R2H,R3O), (ZC,R1E,R2H,R3P), (ZC,R1E,R2H,R3Q),
(ZC,R1E,R2H,R3R), (ZC,R1E,R2I,R3A), (ZC,R1E,R2I,R3B),
(ZC,R1E,R2I,R3C), (ZC,R1E,R2I,R3D), (ZC,R1E,R2I,R3E), (ZC,R1E,R2I,R3F),
(ZC,R1E,R2I,R3G), (ZC,R1E,R2I,R3H), (ZC,R1E,R2I,R3I), (ZC,R1E,R2I,R3J),
(ZC,R1E,R2I,R3K), (ZC,R1E,R2I,R3L), (ZC,R1E,R2I,R3M),
(ZC,R1E,R2I,R3N), (ZC,R1E,R2I,R3O), (ZC,R1E,R2I,R3P), (ZC,R1E,R2I,R3Q),
(ZC,R1E,R2I,R3R), (ZC,R1E,R2J,R3A), (ZC,R1E,R2J,R3B),
(ZC,R1E,R2J,R3C), (ZC,R1E,R2J,R3D), (ZC,R1E,R2J,R3E),
(ZC,R1E,R2J,R3F), (ZC,R1E,R2J,R3G), (ZC,R1E,R2J,R3H),
(ZC,R1E,R2J,R3I), (ZC,R1E,R2J,R3J), (ZC,R1E,R2J,R3K),
(ZC,R1E,R2J,R3L), (ZC,R1E,R2J,R3M), (ZC,R1E,R2J,R3N),
(ZC,R1E,R2J,R3O), (ZC,R1E,R2J,R3P), (ZC,R1E,R2J,R3Q),
(ZC,R1E,R2J,R3R), (ZC,R1E,R2K,R3A), (ZC,R1E,R2K,R3B),
(ZC,R1E,R2K,R3C), (ZC,R1E,R2K,R3D), (ZC,R1E,R2K,R3E),
(ZC,R1E,R2K,R3F), (ZC,R1E,R2K,R3G), (ZC,R1E,R2K,R3H),
(ZC,R1E,R2K,R3I), (ZC,R1E,R2K,R3J), (ZC,R1E,R2K,R3K),
(ZC,R1E,R2K,R3L), (ZC,R1E,R2K,R3M), (ZC,R1E,R2K,R3N),
(ZC,R1E,R2K,R3O), (ZC,R1E,R2K,R3P), (ZC,R1E,R2K,R3Q),
(ZC,R1E,R2K,R3R), (ZC,R1E,R2L,R3A), (ZC,R1E,R2L,R3B),
(ZC,R1E,R2L,R3C), (ZC,R1E,R2L,R3D), (ZC,R1E,R2L,R3E),
(ZC,R1E,R2L,R3F), (ZC,R1E,R2L,R3G), (ZC,R1E,R2L,R3H),
(ZC,R1E,R2L,R3I), (ZC,R1E,R2L,R3J), (ZC,R1E,R2L,R3K),
(ZC,R1E,R2L,R3L), (ZC,R1E,R2L,R3M), (ZC,R1E,R2L,R3N),
(ZC,R1E,R2L,R3O), (ZC,R1E,R2L,R3P), (ZC,R1E,R2L,R3Q),
(ZC,R1E,R2L,R3R), (ZC,R1E,R2M,R3A), (ZC,R1E,R2M,R3B),
(ZC,R1E,R2M,R3C), (ZC,R1E,R2M,R3D), (ZC,R1E,R2M,R3E),
(ZC,R1E,R2M,R3F), (ZC,R1E,R2M,R3G), (ZC,R1E,R2M,R3H),
(ZC,R1E,R2M,R3I), (ZC,R1E,R2M,R3J), (ZC,R1E,R2M,R3K),
(ZC,R1E,R2M,R3L), (ZC,R1E,R2M,R3M), (ZC,R1E,R2M,R3N),
(ZC,R1E,R2M,R3O), (ZC,R1E,R2M,R3P), (ZC,R1E,R2M,R3Q),
(ZC,R1E,R2M,R3R), (ZC,R1E,R2N,R3A), (ZC,R1E,R2N,R3B),
(ZC,R1E,R2N,R3C), (ZC,R1E,R2N,R3D), (ZC,R1E,R2N,R3E),
(ZC,R1E,R2N,R3F), (ZC,R1E,R2N,R3G), (ZC,R1E,R2N,R3H),
(ZC,R1E,R2N,R3I), (ZC,R1E,R2N,R3J), (ZC,R1E,R2N,R3K),
(ZC,R1E,R2N,R3L), (ZC,R1E,R2N,R3M), (ZC,R1E,R2N,R3N),
(ZC,R1E,R2N,R3O), (ZC,R1E,R2N,R3P), (ZC,R1E,R2N,R3Q),
(ZC,R1E,R2N,R3R), (ZC,R1F,R2A,R3A), (ZC,R1F,R2A,R3B),
(ZC,R1F,R2A,R3C), (ZC,R1F,R2A,R3D), (ZC,R1F,R2A,R3E),
(ZC,R1F,R2A,R3F), (ZC,R1F,R2A,R3G), (ZC,R1F,R2A,R3H),
(ZC,R1F,R2A,R3I), (ZC,R1F,R2A,R3J), (ZC,R1F,R2A,R3K),
(ZC,R1F,R2A,R3L), (ZC,R1F,R2A,R3M), (ZC,R1F,R2A,R3N),
(ZC,R1F,R2A,R3O), (ZC,R1F,R2A,R3P), (ZC,R1F,R2A,R3Q),
(ZC,R1F,R2A,R3R), (ZC,R1F,R2B,R3A), (ZC,R1F,R2B,R3B),
(ZC,R1F,R2B,R3C), (ZC,R1F,R2B,R3D), (ZC,R1F,R2B,R3E),
(ZC,R1F,R2B,R3F), (ZC,R1F,R2B,R3G), (ZC,R1F,R2B,R3H),
(ZC,R1F,R2B,R3L), (ZC,R1F,R2B,R3M), (ZC,R1F,R2B,R3N),
(ZC,R1F,R2B,R3L), (ZC,R1F,R2B,R3M), (ZC,R1F,R2B,R3N),
(ZC,R1F,R2B,R3O), (ZC,R1F,R2B,R3P), (ZC,R1F,R2B,R3Q),
(ZC,R1F,R2B,R3R), (ZC,R1F,R2C,R3A), (ZC,R1F,R2C,R3B),
(ZC,R1F,R2C,R3C), (ZC,R1F,R2C,R3D), (ZC,R1F,R2C,R3E),
(ZC,R1F,R2C,R3F), (ZC,R1F,R2C,R3G), (ZC,R1F,R2C,R3H),
(ZC,R1F,R2C,R3I), (ZC,R1F,R2C,R3J), (ZC,R1F,R2C,R3K),
(ZC,R1F,R2C,R3L), (ZC,R1F,R2C,R3M), (ZC,R1F,R2C,R3N),
(ZC,R1F,R2C,R3O), (ZC,R1F,R2C,R3P), (ZC,R1F,R2C,R3Q),
(ZC,R1F,R2C,R3R), (ZC,R1F,R2D,R3A), (ZC,R1F,R2D,R3B),
(ZC,R1F,R2D,R3C), (ZC,R1F,R2D,R3D), (ZC,R1F,R2D,R3E),
(ZC,R1F,R2D,R3F), (ZC,R1F,R2D,R3G), (ZC,R1F,R2D,R3H), (ZC,R1F,R2D,R3I), (ZC,R1F,R2D,R3J), (ZC,R1F,R2D,R3K),
(ZC,R1F,R2D,R3L), (ZC,R1F,R2D,R3M), (ZC,R1F,R2D,R3N),
(ZC,R1F,R2D,R3O), (ZC,R1F,R2D,R3P), (ZC,R1F,R2D,R3Q),
(ZC,R1F,R2D,R3R), (ZC,R1F,R2E,R3A), (ZC,R1F,R2E,R3B),
(ZC,R1F,R2E,R3C), (ZC,R1F,R2E,R3D), (ZC,R1F,R2E,R3E),
(ZC,R1F,R2E,R3F), (ZC,R1F,R2E,R3G), (ZC,R1F,R2E,R3H),
(ZC,R1F,R2E,R3I), (ZC,R1F,R2E,R3J), (ZC,R1F,R2E,R3K),
(ZC,R1F,R2E,R3L), (ZC,R1F,R2E,R3M), (ZC,R1F,R2E,R3N),
(ZC,R1F,R2E,R3O), (ZC,R1F,R2E,R3P), (ZC,R1F,R2E,R3Q),
(ZC,R1F,R2E,R3R), (ZC,R1F,R2F,R3A), (ZC,R1F,R2F,R3B),
(ZC,R1F,R2F,R3C), (ZC,R1F,R2F,R3D), (ZC,R1F,R2F,R3E),
(ZC,R1F,R2F,R3F), (ZC,R1F,R2F,R3G), (ZC,R1F,R2F,R3H),
(ZC,R1F,R2F,R3I), (ZC,R1F,R2F,R3J), (ZC,R1F,R2F,R3K),
(ZC,R1F,R2F,R3L), (ZC,R1F,R2F,R3M), (ZC,R1F,R2F,R3N),
(ZC,R1F,R2F,R3O), (ZC,R1F,R2F,R3P), (ZC,R1F,R2F,R3Q),
(ZC,R1F,R2F,R3R), (ZC,R1F,R2G,R3A), (ZC,R1F,R2G,R3B),
(ZC,R1F,R2G,R3C), (ZC,R1F,R2G,R3D), (ZC,R1F,R2G,R3E),
(ZC,R1F,R2G,R3F), (ZC,R1F,R2G,R3G), (ZC,R1F,R2G,R3H),
(ZC,R1F,R2G,R3I), (ZC,R1F,R2G,R3J), (ZC,R1F,R2G,R3K),
(ZC,R1F,R2G,R3L), (ZC,R1F,R2G,R3M), (ZC,R1F,R2G,R3N),
(ZC,R1F,R2G,R3O), (ZC,R1F,R2G,R3P), (ZC,R1F,R2G,R3Q),
(ZC,R1F,R2G,R3R), (ZC,R1F,R2H,R3A), (ZC,R1F,R2H,R3B),
(ZC,R1F,R2H,R3C), (ZC,R1F,R2H,R3D), (ZC,R1F,R2H,R3E),
(ZC,R1F,R2H,R3F), (ZC,R1F,R2H,R3G), (ZC,R1F,R2H,R3H),
(ZC,R1F,R2H,R3I), (ZC,R1F,R2H,R3J), (ZC,R1F,R2H,R3K),
(ZC,R1F,R2H,R3L), (ZC,R1F,R2H,R3M), (ZC,R1F,R2H,R3N),
(ZC,R1F,R2H,R3O), (ZC,R1F,R2H,R3P), (ZC,R1F,R2H,R3Q),
(ZC,R1F,R2H,R3R), (ZC,R1F,R2I,R3A), (ZC,R1F,R2I,R3B),
(ZC,R1F,R2I,R3C), (ZC,R1F,R2I,R3D), (ZC,R1F,R2I,R3E), (ZC,R1F,R2I,R3F),
(ZC,R1F,R2I,R3G), (ZC,R1F,R2I,R3H), (ZC,R1F,R2I,R3I), (ZC,R1F,R2I,R3J),
(ZC,R1F,R2I,R3K), (ZC,R1F,R2I,R3L), (ZC,R1F,R2I,R3M), (ZC,R1F,R2I,R3N),
(ZC,R1F,R2I,R3O), (ZC,R1F,R2I,R3P), (ZC,R1F,R2I,R3Q), (ZC,R1F,R2I,R3R),
(ZC,R1F,R2J,R3A), (ZC,R1F,R2J,R3B), (ZC,R1F,R2J,R3C),
(ZC,R1F,R2J,R3D), (ZC,R1F,R2J,R3E), (ZC,R1F,R2J,R3F),
(ZC,R1F,R2J,R3G), (ZC,R1F,R2J,R3H), (ZC,R1F,R2J,R3I),
(ZC,R1F,R2J,R3J), (ZC,R1F,R2J,R3K), (ZC,R1F,R2J,R3L),
(ZC,R1F,R2J,R3M), (ZC,R1F,R2J,R3N), (ZC,R1F,R2J,R3O),
(ZC,R1F,R2J,R3P), (ZC,R1F,R2J,R3Q), (ZC,R1F,R2J,R3R),
(ZC,R1F,R2K,R3A), (ZC,R1F,R2K,R3B), (ZC,R1F,R2K,R3C),
(ZC,R1F,R2K,R3D), (ZC,R1F,R2K,R3E), (ZC,R1F,R2K,R3F),
(ZC,R1F,R2K,R3G), (ZC,R1F,R2K,R3H), (ZC,R1F,R2K,R3I),
(ZC,R1F,R2K,R3J), (ZC,R1F,R2K,R3K), (ZC,R1F,R2K,R3L),
(ZC,R1F,R2K,R3M), (ZC,R1F,R2K,R3N), (ZC,R1F,R2K,R3O),
(ZC,R1F,R2J,R3P), (ZC,R1F,R2K,R3Q), (ZC,R1F,R2K,R3R),
(ZC,R1F,R2L,R3A), (ZC,R1F,R2L,R3B), (ZC,R1F,R2L,R3C),
(ZC,R1F,R2L,R3D), (ZC,R1F,R2L,R3E), (ZC,R1F,R2L,R3F),
(ZC,R1F,R2L,R3G), (ZC,R1F,R2L,R3H), (ZC,R1F,R2L,R3I),
(ZC,R1F,R2L,R3J), (ZC,R1F,R2L,R3K), (ZC,R1F,R2L,R3L),
(ZC,R1F,R2L,R3M), (ZC,R1F,R2L,R3N), (ZC,R1F,R2L,R3O),
(ZC,R1F,R2L,R3P), (ZC,R1F,R2L,R3Q), (ZC,R1F,R2L,R3R),
(ZC,R1F,R2M,R3A), (ZC,R1F,R2M,R3B), (ZC,R1F,R2M,R3C),
(ZC,R1F,R2M,R3D), (ZC,R1F,R2M,R3E), (ZC,R1F,R2M,R3F),
(ZC,R1F,R2M,R3G), (ZC,R1F,R2M,R3H), (ZC,R1F,R2M,R3I),
(ZC,R1F,R2M,R3J), (ZC,R1F,R2M,R3K), (ZC,R1F,R2M,R3L),
(ZC,R1F,R2M,R3M), (ZC,R1F,R2M,R3N), (ZC,R1F,R2M,R3O),
(ZC,R1F,R2M,R3P), (ZC,R1F,R2M,R3Q), (ZC,R1F,R2M,R3R),
(ZC,R1F,R2N,R3A), (ZC,R1F,R2N,R3B), (ZC,R1F,R2N,R3C),
(ZC,R1F,R2N,R3D), (ZC,R1F,R2N,R3E), (ZC,R1F,R2N,R3F),
(ZC,R1F,R2N,R3G), (ZC,R1F,R2N,R3H), (ZC,R1F,R2N,R3I),
(ZC,R1F,R2N,R3J), (ZC,R1F,R2N,R3K), (ZC,R1F,R2N,R3L),
(ZC,R1F,R2N,R3M), (ZC,R1F,R2N,R3N), (ZC,R1F,R2N,R3O),
(ZC,R1F,R2N,R3P), (ZC,R1F,R2N,R3Q), (ZC,R1F,R2N,R3R),
(ZC,R1G,R2A,R3A), (ZC,R1G,R2A,R3B), (ZC,R1G,R2A,R3C),
(ZC,R1G,R2A,R3D), (ZC,R1G,R2A,R3E), (ZC,R1G,R2A,R3F),
(ZC,R1G,R2A,R3G), (ZC,R1G,R2A,R3H), (ZC,R1G,R2A,R3I),
(ZC,R1G,R2A,R3J), (ZC,R1G,R2A,R3K), (ZC,R1G,R2A,R3L),
(ZC,R1G,R2A,R3M), (ZC,R1G,R2A,R3N), (ZC,R1G,R2A,R3O),
(ZC,R1G,R2A,R3P), (ZC,R1G,R2A,R3Q), (ZC,R1G,R2A,R3R), (ZC,R1G,R2B,R3A), (ZC,R1G,R2B,R3B), (ZC,R1G,R2B,R3C),
(ZC,R1G,R2B,R3D), (ZC,R1G,R2B,R3E), (ZC,R1G,R2B,R3F),
(ZC,R1G,R2B,R3G), (ZC,R1G,R2B,R3H), (ZC,R1G,R2B,R3I),
(ZC,R1G,R2B,R3J), (ZC,R1G,R2B,R3K), (ZC,R1G,R2B,R3L),
(ZC,R1G,R2B,R3M), (ZC,R1G,R2B,R3N), (ZC,R1G,R2B,R3O),
(ZC,R1G,R2B,R3P), (ZC,R1G,R2B,R3Q), (ZC,R1G,R2B,R3R),
(ZC,R1G,R2C,R3A), (ZC,R1G,R2C,R3B), (ZC,R1G,R2C,R3C),
(ZC,R1G,R2C,R3D), (ZC,R1G,R2C,R3E), (ZC,R1G,R2C,R3F),
(ZC,R1G,R2C,R3G), (ZC,R1G,R2C,R3H), (ZC,R1G,R2C,R3I),
(ZC,R1G,R2C,R3J), (ZC,R1G,R2C,R3K), (ZC,R1G,R2C,R3L),
(ZC,R1G,R2C,R3M), (ZC,R1G,R2C,R3N), (ZC,R1G,R2C,R3O),
(ZC,R1G,R2C,R3P), (ZC,R1G,R2C,R3Q), (ZC,R1G,R2C,R3R),
(ZC,R1G,R2D,R3A), (ZC,R1G,R2D,R3B), (ZC,R1G,R2D,R3C),
(ZC,R1G,R2D,R3D), (ZC,R1G,R2D,R3E), (ZC,R1G,R2D,R3F),
(ZC,R1G,R2D,R3G), (ZC,R1G,R2D,R3H), (ZC,R1G,R2D,R3I),
(ZC,R1G,R2D,R3J), (ZC,R1G,R2D,R3K), (ZC,R1G,R2D,R3L),
(ZC,R1G,R2D,R3M), (ZC,R1G,R2D,R3N), (ZC,R1G,R2D,R3O),
(ZC,R1G,R2D,R3P), (ZC,R1G,R2D,R3Q), (ZC,R1G,R2D,R3R),
(ZC,R1G,R2E,R3A), (ZC,R1G,R2E,R3B), (ZC,R1G,R2E,R3C),
(ZC,R1G,R2E,R3D), (ZC,R1G,R2E,R3E), (ZC,R1G,R2E,R3F),
(ZC,R1G,R2E,R3G), (ZC,R1G,R2E,R3H), (ZC,R1G,R2E,R3I),
(ZC,R1G,R2E,R3J), (ZC,R1G,R2E,R3K), (ZC,R1G,R2E,R3L),
(ZC,R1G,R2E,R3M), (ZC,R1G,R2E,R3N), (ZC,R1G,R2E,R3O),
(ZC,R1G,R2E,R3P), (ZC,R1G,R2E,R3Q), (ZC,R1G,R2E,R3R),
(ZC,R1G,R2F,R3A), (ZC,R1G,R2F,R3B), (ZC,R1G,R2F,R3C),
(ZC,R1G,R2F,R3D), (ZC,R1G,R2F,R3E), (ZC,R1G,R2F,R3F),
(ZC,R1G,R2F,R3G), (ZC,R1G,R2F,R3H), (ZC,R1G,R2F,R3I),
(ZC,R1G,R2F,R3J), (ZC,R1G,R2F,R3K), (ZC,R1G,R2F,R3L),
(ZC,R1G,R2F,R3M), (ZC,R1G,R2F,R3N), (ZC,R1G,R2F,R3O),
(ZC,R1G,R2F,R3P), (ZC,R1G,R2F,R3Q), (ZC,R1G,R2F,R3R),
(ZC,R1G,R2G,R3A), (ZC,R1G,R2G,R3B), (ZC,R1G,R2G,R3C),
(ZC,R1G,R2G,R3D), (ZC,R1G,R2G,R3E), (ZC,R1G,R2G,R3F),
(ZC,R1G,R2G,R3G), (ZC,R1G,R2G,R3H), (ZC,R1G,R2G,R3I),
(ZC,R1G,R2G,R3J), (ZC,R1G,R2G,R3K), (ZC,R1G,R2G,R3L),
(ZC,R1G,R2G,R3M), (ZC,R1G,R2G,R3N), (ZC,R1G,R2G,R3O),
(ZC,R1G,R2G,R3P), (ZC,R1G,R2G,R3Q), (ZC,R1G,R2G,R3R),
(ZC,R1G,R2H,R3A), (ZC,R1G,R2H,R3B), (ZC,R1G,R2H,R3C),
(ZC,R1G,R2H,R3D), (ZC,R1G,R2H,R3E), (ZC,R1G,R2H,R3F),
(ZC,R1G,R2H,R3G), (ZC,R1G,R2H,R3H), (ZC,R1G,R2H,R3I),
(ZC,R1G,R2H,R3J), (ZC,R1G,R2H,R3K), (ZC,R1G,R2H,R3L),
(ZC,R1G,R2H,R3M), (ZC,R1G,R2H,R3N), (ZC,R1G,R2H,R3O),
(ZC,R1G,R2H,R3P), (ZC,R1G,R2H,R3Q), (ZC,R1G,R2H,R3R),
(ZC,R1G,R2I,R3A), (ZC,R1G,R2I,R3B), (ZC,R1G,R2I,R3C),
(ZC,R1G,R2I,R3D), (ZC,R1G,R2I,R3E), (ZC,R1G,R2I,R3F),
(ZC,R1G,R2I,R3G), (ZC,R1G,R2I,R3H), (ZC,R1G,R2I,R3I), (ZC,R1G,R2I,R3J),
(ZC,R1G,R2I,R3K), (ZC,R1G,R2I,R3L), (ZC,R1G,R2I,R3M),
(ZC,R1G,R2I,R3N), (ZC,R1G,R2I,R3O), (ZC,R1G,R2I,R3P),
(ZC,R1G,R2I,R3Q), (ZC,R1G,R2I,R3R), (ZC,R1G,R2J,R3A),
(ZC,R1G,R2J,R3B), (ZC,R1G,R2J,R3C), (ZC,R1G,R2J,R3D),
(ZC,R1G,R2J,R3E), (ZC,R1G,R2J,R3F), (ZC,R1G,R2J,R3G),
(ZC,R1G,R2J,R3H), (ZC,R1G,R2J,R3I), (ZC,R1G,R2J,R3J),
(ZC,R1G,R2J,R3K), (ZC,R1G,R2J,R3L), (ZC,R1G,R2J,R3M),
(ZC,R1G,R2J,R3N), (ZC,R1G,R2J,R3O), (ZC,R1G,R2J,R3P),
(ZC,R1G,R2J,R3Q), (ZC,R1G,R2J,R3R), (ZC,R1G,R2K,R3A),
(ZC,R1G,R2K,R3B), (ZC,R1G,R2K,R3C), (ZC,R1G,R2K,R3D),
(ZC,R1G,R2K,R3E), (ZC,R1G,R2K,R3F), (ZC,R1G,R2K,R3G),
(ZC,R1G,R2K,R3H), (ZC,R1G,R2K,R3I), (ZC,R1G,R2K,R3J),
(ZC,R1G,R2K,R3K), (ZC,R1G,R2K,R3L), (ZC,R1G,R2K,R3M),
(ZC,R1G,R2K,R3N), (ZC,R1G,R2K,R3O), (ZC,R1G,R2K,R3P),
(ZC,R1G,R2K,R3Q), (ZC,R1G,R2K,R3R), (ZC,R1G,R2L,R3A),
(ZC,R1G,R2L,R3B), (ZC,R1G,R2L,R3C), (ZC,R1G,R2L,R3D),
(ZC,R1G,R2L,R3E), (ZC,R1G,R2L,R3F), (ZC,R1G,R2L,R3G),
(ZC,R1G,R2L,R3H), (2C,R1G,R2L,R3I), (ZC,R1G,R2L,R3J),
(ZC,R1G,R2L,R3K), (ZC,R1G,R2L,R3L), (ZC,R1G,R2L,R3M),
(ZC,R1G,R2L,R3N), (ZC,R1G,R2L,R3O), (ZC,R1G,R2L,R3P),
(ZC,R1G,R2L,R3Q), (ZC,R1G,R2L,R3R), (ZC,R1G,R2M,R3A), (ZC,R1G,R2M,R3B), (ZC,R1G,R2M,R3C), (ZC,R1G,R2M,R3D),
(ZC,R1G,R2M,R3E), (ZC,R1G,R2M,R3F), (ZC,R1G,R2M,R3G),
(ZC,R1G,R2M,R3H), (ZC,R1G,R2M,R3I), (ZC,R1G,R2M,R3J),
(ZC,R1G,R2M,R3K), (ZC,R1G,R2M,R3L), (ZC,R1G,R2M,R3M),
(ZC,R1G,R2M,R3N), (ZC,R1G,R2M,R3O), (ZC,R1G,R2M,R3P),
(ZC,R1G,R2M,R3Q), (ZC,R1G,R2M,R3R), (ZC,R1G,R2N,R3A),
(ZC,R1G,R2N,R3B), (ZC,R1G,R2N,R3C), (ZC,R1G,R2N,R3D),
(ZC,R1G,R2N,R3E), (ZC,R1G,R2N,R3F), (ZC,R1G,R2N,R3G),
(ZC,R1G,R2N,R3H), (ZC,R1G,R2N,R3I), (ZC,R1G,R2N,R3J),
(ZC,R1G,R2N,R3K), (ZC,R1G,R2N,R3L), (ZC,R1G,R2N,R3M),
(ZC,R1G,R2N,R3N), (ZC,R1G,R2N,R3O), (ZC,R1G,R2N,R3P),
(ZC,R1G,R2N,R3Q), (ZC,R1G,R2N,R3R), (ZC,R1H,R2A,R3A),
(ZC,R1H,R2A,R3B), (ZC,R1H,R2A,R3C), (ZC,R1H,R2A,R3D),
(ZC,R1H,R2A,R3E), (ZC,R1H,R2A,R3F), (ZC,R1H,R2A,R3G),
(ZC,R1H,R2A,R3H), (ZC,R1H,R2A,R3I), (ZC,R1H,R2A,R3J),
(ZC,R1H,R2A,R3K), (ZC,R1H,R2A,R3L), (ZC,R1H,R2A,R3M),
(ZC,R1H,R2A,R3N), (ZC,R1H,R2A,R3O), (ZC,R1H,R2A,R3P),
(ZC,R1H,R2A,R3Q), (ZC,R1H,R2A,R3R), (ZC,R1H,R2B,R3A),
(ZC,R1H,R2B,R3B), (ZC,R1H,R2B,R3C), (ZC,R1H,R2B,R3D),
(ZC,R1H,R2B,R3E), (ZC,R1H,R2B,R3F), (ZC,R1H,R2B,R3G),
(ZC,R1H,R2B,R3H), (ZC,R1H,R2B,R3I), (ZC,R1H,R2B,R3J),
(ZC,R1H,R2B,R3K), (ZC,R1H,R2B,R3L), (ZC,R1H,R2B,R3M),
(ZC,R1H,R2B,R3N), (ZC,R1H,R2B,R3O), (ZC,R1H,R2B,R3P),
(ZC,R1H,R2B,R3Q), (ZC,R1H,R2B,R3R), (ZC,R1H,R2C,R3A),
(ZC,R1H,R2C,R3B), (ZC,R1H,R2C,R3C), (ZC,R1H,R2C,R3D),
(ZC,R1H,R2C,R3E), (ZC,R1H,R2C,R3F), (ZC,R1H,R2C,R3G),
(ZC,R1H,R2C,R3H), (ZC,R1H,R2C,R3I), (ZC,R1H,R2C,R3J),
(ZC,R1H,R2C,R3K), (ZC,R1H,R2C,R3L), (ZC,R1H,R2C,R3M),
(ZC,R1H,R2C,R3N), (ZC,R1H,R2C,R3O), (ZC,R1H,R2C,R3P),
(ZC,R1H,R2C,R3Q), (ZC,R1H,R2C,R3R), (ZC,R1H,R2D,R3A),
(ZC,R1H,R2D,R3B), (ZC,R1H,R2D,R3C), (ZC,R1H,R2D,R3D),
(ZC,R1H,R2D,R3E), (ZC,R1H,R2D,R3F), (ZC,R1H,R2D,R3G),
(ZC,R1H,R2D,R3H), (ZC,R1H,R2D,R3I), (ZC,R1H,R2D,R3J),
(ZC,R1H,R2D,R3K), (ZC,R1H,R2D,R3L), (ZC,R1H,R2D,R3M),
(ZC,R1H,R2D,R3N), (ZC,R1H,R2D,R3O), (ZC,R1H,R2D,R3P),
(ZC,R1H,R2D,R3Q), (ZC,R1H,R2D,R3R), (ZC,R1H,R2E,R3A),
(ZC,R1H,R2E,R3B), (ZC,R1H,R2E,R3C), (ZC,R1H,R2E,R3D),
(ZC,R1H,R2E,R3E), (ZC,R1H,R2E,R3F), (ZC,R1H,R2E,R3G),
(ZC,R1H,R2E,R3H), (ZC,R1H,R2E,R3I), (ZC,R1H,R2E,R3J),
(ZC,R1H,R2E,R3K), (ZC,R1H,R2E,R3L), (ZC,R1H,R2E,R3M),
(ZC,R1H,R2E,R3N), (ZC,R1H,R2E,R3O), (ZC,R1H,R2E,R3P),
(ZC,R1H,R2E,R3Q), (ZC,R1H,R2E,R3R), (ZC,R1H,R2F,R3A),
(ZC,R1H,R2F,R3B), (ZC,R1H,R2F,R3C), (ZC,R1H,R2F,R3D),
(ZC,R1H,R2F,R3E), (ZC,R1H,R2F,R3F), (ZC,R1H,R2F,R3G),
(ZC,R1H,R2F,R3H), (ZC,R1H,R2F,R3I), (ZC,R1H,R2F,R3J),
(ZC,R1H,R2F,R3K), (ZC,R1H,R2F,R3L), (ZC,R1H,R2F,R3M),
(ZC,R1H,R2F,R3N), (ZC,R1H,R2F,R3O), (ZC,R1H,R2F,R3P),
(ZC,R1H,R2F,R3Q), (ZC,R1H,R2F,R3R), (ZC,R1H,R2G,R3A),
(ZC,R1H,R2G,R3B), (ZC,R1H,R2G,R3C), (ZC,R1H,R2G,R3D),
(ZC,R1H,R2G,R3E), (ZC,R1H,R2G,R3F), (ZC,R1H,R2G,R3G),
(ZC,R1H,R2G,R3H), (ZC,R1H,R2G,R3I), (ZC,R1H,R2G,R3J),
(ZC,R1H,R2G,R3K), (ZC,R1H,R2G,R3L), (ZC,R1H,R2G,R3M),
(ZC,R1H,R2G,R3N), (ZC,R1H,R2G,R3O), (ZC,R1H,R2G,R3P),
(ZC,R1H,R2G,R3Q), (ZC,R1H,R2G,R3R), (ZC,R1H,R2H,R3A),
(ZC,R1H,R2H,R3B), (ZC,R1H,R2H,R3C), (ZC,R1H,R2H,R3D),
(ZC,R1H,R2H,R3E), (ZC,R1H,R2H,R3F), (ZC,R1H,R2H,R3G),
(ZC,R1H,R2H,R3H), (ZC,R1H,R2H,R3I), (ZC,R1H,R2H,R3J),
(ZC,R1H,R2H,R3K), (ZC,R1H,R2H,R3L), (ZC,R1H,R2H,R3M),
(ZC,R1H,R2H,R3N), (ZC,R1H,R2H,R3O), (ZC,R1H,R2H,R3P),
(ZC,R1H,R2H,R3Q), (ZC,R1H,R2H,R3R), (ZC,R1H,R2I,R3A),
(ZC,R1H,R2I,R3B), (ZC,R1H,R2I,R3C), (ZC,R1H,R2I,R3D),
(ZC,R1H,R2I,R3E), (ZC,R1H,R2I,R3F), (ZC,R1H,R2I,R3G),
(ZC,R1H,R2I,R3H), (ZC,R1H,R2I,R3I), (ZC,R1H,R2I,R3J), (ZC,R1H,R2I,R3K),
(ZC,R1H,R2I,R3L), (ZC,R1H,R2I,R3M), (ZC,R1H,R2I,R3N),
(ZC,R1H,R2I,R3O), (ZC,R1H,R2I,R3P), (ZC,R1H,R2I,R3Q),
(ZC,R1H,R2I,R3R), (ZC,R1H,R2J,R3A), (ZC,R1H,R2J,R3B), (ZC,R1H,R2J,R3C), (ZC,R1H,R2J,R3D), (ZC,R1H,R2J,R3E),
(ZC,R1H,R2J,R3F), (ZC,R1H,R2J,R3G), (ZC,R1H,R2J,R3H),
(ZC,R1H,R2J,R3I), (ZC,R1H,R2J,R3J), (ZC,R1H,R2J,R3K),
(ZC,R1H,R2J,R3L), (ZC,R1H,R2J,R3M), (ZC,R1H,R2J,R3N),
(ZC,R1H,R2J,R3O), (ZC,R1H,R2J,R3P), (ZC,R1H,R2J,R3Q),
(ZC,R1H,R2J,R3R), (ZC,R1H,R2K,R3A), (ZC,R1H,R2K,R3B),
(ZC,R1H,R2K,R3C), (ZC,R1H,R2K,R3D), (ZC,R1H,R2K,R3E),
(ZC,R1H,R2K,R3F), (ZC,R1H,R2K,R3G), (ZC,R1H,R2K,R3H),
(ZC,R1H,R2K,R3I), (ZC,R1H,R2K,R3J), (ZC,R1H,R2K,R3K),
(ZC,R1H,R2K,R3L), (ZC,R1H,R2K,R3M), (ZC,R1H,R2K,R3N),
(ZC,R1H,R2K,R3O), (ZC,R1H,R2K,R3P), (ZC,R1H,R2K,R3Q),
(ZC,R1H,R2K,R3R), (ZC,R1H,R2L,R3A), (ZC,R1H,R2L,R3B),
(ZC,R1H,R2L,R3C), (ZC,R1H,R2L,R3D), (ZC,R1H,R2L,R3E),
(ZC,R1H,R2L,R3F), (ZC,R1H,R2L,R3G), (ZC,R1H,R2L,R3H),
(ZC,R1H,R2L,R3I), (ZC,R1H,R2L,R3J), (ZC,R1H,R2L,R3K),
(ZC,R1H,R2L,R3L), (ZC,R1H,R2L,R3M), (ZC,R1H,R2L,R3N),
(ZC,R1H,R2L,R3O), (ZC,R1H,R2L,R3P), (ZC,R1H,R2L,R3Q),
(ZC,R1H,R2L,R3R), (ZC,R1H,R2M,R3A), (ZC,R1H,R2M,R3B),
(ZC,R1H,R2M,R3C), (ZC,R1H,R2M,R3D), (ZC,R1H,R2M,R3E),
(ZC,R1H,R2M,R3F), (ZC,R1H,R2M,R3G), (ZC,R1H,R2M,R3H),
(ZC,R1H,R2M,R3I), (ZC,R1H,R2M,R3J), (ZC,R1H,R2M,R3K),
(ZC,R1H,R2M,R3L), (ZC,R1H,R2M,R3M), (ZC,R1H,R2M,R3N),
(ZC,R1H,R2M,R3O), (ZC,R1H,R2M,R3P), (ZC,R1H,R2M,R3Q),
(ZC,R1H,R2M,R3R), (ZC,R1H,R2N,R3A), (ZC,R1H,R2N,R3B),
(ZC,R1H,R2N,R3C), (ZC,R1H,R2N,R3D), (ZC,R1H,R2N,R3E),
(ZC,R1H,R2N,R3F), (ZC,R1H,R2N,R3G), (ZC,R1H,R2N,R3H),
(ZC,R1H,R2N,R3I), (ZC,R1H,R2N,R3J), (ZC,R1H,R2N,R3K),
(ZC,R1H,R2N,R3L), (ZC,R1H,R2N,R3M), (ZC,R1H,R2N,R3N),
(ZC,R1H,R2N,R3O), (ZC,R1H,R2N,R3P), (ZC,R1H,R2N,R3Q),
(ZC,R1H,R2N,R3R), (ZC,R1H,R2A,R3A), (ZC,R1H,R2A,R3B),
(ZC,R1H,R2A,R3C), (ZC,R1H,R2A,R3D), (ZC,R1H,R2A,R3E), (ZC,R1H,R2A,R3F),
(ZC,R1H,R2A,R3G), (ZC,R1H,R2A,R3H), (ZC,R1H,R2A,R3I), (ZC,R1H,R2A,R3J),
(ZC,R1H,R2A,R3K), (ZC,R1H,R2A,R3L), (ZC,R1H,R2A,R3M), (ZC,R1H,R2A,R3N),
(ZC,R1H,R2A,R3O), (ZC,R1H,R2A,R3P), (ZC,R1H,R2A,R3Q), (ZC,R1H,R2A,R3R),
(ZC,R1H,R2B,R3A), (ZC,R1H,R2B,R3B), (ZC,R1H,R2B,R3C),
(ZC,R1H,R2B,R3D), (ZC,R1H,R2B,R3E), (ZC,R1H,R2B,R3F),
(ZC,R1H,R2B,R3G), (ZC,R1H,R2B,R3H), (ZC,R1H,R2B,R3I), (ZC,R1H,R2B,R3J),
(ZC,R1I,R2B,R3K), (ZC,R1I,R2B,R3L), (ZC,R1H,R2B,R3M),
(ZC,R1H,R2B,R3N), (ZC,R1H,R2B,R3O), (ZC,R1H,R2B,R3P),
(ZC,R1H,R2B,R3Q), (ZC,R1H,R2B,R3R), (ZC,R1H,R2C,R3A),
(ZC,R1H,R2C,R3B), (ZC,R1H,R2C,R3C), (ZC,R1H,R2C,R3D),
(ZC,R1H,R2C,R3E), (ZC,R1H,R2C,R3F), (ZC,R1H,R2C,R3G),
(ZC,R1H,R2C,R3H), (ZC,R1H,R2C,R3I), (ZC,R1H,R2C,R3J), (ZC,R1H,R2C,R3K),
(ZC,R1H,R2C,R3L), (ZC,R1H,R2C,R3M), (ZC,R1H,R2C,R3N),
(ZC,R1H,R2C,R3O), (ZC,R1H,R2C,R3P), (ZC,R1H,R2C,R3Q),
(ZC,R1I,R2C,R3R), (ZC,R1H,R2D,R3A), (ZC,R1H,R2D,R3B),
(ZC,R1H,R2D,R3C), (ZC,R1H,R2D,R3D), (ZC,R1H,R2D,R3E),
(ZC,R1H,R2D,R3F), (ZC,R1H,R2D,R3G), (ZC,R1H,R2D,R3H), (ZC,R1H,R2D,R3I),
(ZC,R1H,R2D,R3J), (ZC,R1H,R2D,R3K), (ZC,R1H,R2D,R3L),
(ZC,R1H,R2D,R3M), (ZC,R1H,R2D,R3N), (ZC,R1H,R2D,R3O),
(ZC,R1H,R2D,R3P), (ZC,R1H,R2D,R3Q), (ZC,R1H,R2D,R3R),
(ZC,R1H,R2E,R3A), (ZC,R1H,R2E,R3B), (ZC,R1H,R2E,R3C), (ZC,R1H,R2E,R3D),
(ZC,R1H,R2E,R3E), (ZC,R1H,R2E,R3F), (ZC,R1H,R2E,R3G), (ZC,R1H,R2E,R3H),
(ZC,R1H,R2E,R3I), (ZC,R1H,R2E,R3J), (ZC,R1H,R2E,R3K), (ZC,R1H,R2E,R3L),
(ZC,R1H,R2E,R3M), (ZC,R1H,R2E,R3N), (ZC,R1H,R2E,R3O),
(ZC,R1H,R2E,R3P), (ZC,R1H,R2E,R3Q), (ZC,R1H,R2E,R3R), (ZC,R1H,R2F,R3A),
(ZC,R1H,R2F,R3B), (ZC,R1H,R2F,R3C), (ZC,R1H,R2F,R3D), (ZC,R1H,R2F,R3E),
(ZC,R1H,R2F,R3F), (ZC,R1H,R2F,R3G), (ZC,R1H,R2F,R3H), (ZC,R1H,R2F,R3I),
(ZC,R1H,R2F,R3J), (ZC,R1H,R2F,R3K), (ZC,R1H,R2F,R3L), (ZC,R1H,R2F,R3M),
(ZC,R1H,R2F,R3N), (ZC,R1H,R2F,R3O), (ZC,R1H,R2F,R3P), (ZC,R1H,R2F,R3Q),
(ZC,R1H,R2F,R3R), (ZC,R1H,R2G,R3A), (ZC,R1H,R2G,R3B),
(ZC,R1H,R2G,R3C), (ZC,R1H,R2G,R3D), (ZC,R1H,R2G,R3E),
(ZC,R1H,R2G,R3F), (ZC,R1H,R2G,R3G), (ZC,R1H,R2G,R3H), (ZC,R1H,R2G,R3I),
(ZC,R1H,R2G,R3J), (ZC,R1H,R2G,R3K), (ZC,R1H,R2G,R3L),
(ZC,R1H,R2G,R3M), (ZC,R1H,R2G,R3N), (ZC,R1H,R2G,R3O),
(ZC,R1H,R2G,R3P), (ZC,R1H,R2G,R3Q), (ZC,R1I,R2G,R3R), (ZC,R1H,R2H,R3A), (ZC,R1H,R2H,R3B), (ZC,R1H,R2H,R3C),
(ZC,R1H,R2H,R3D), (ZC,R1H,R2H,R3E), (ZC,R1H,R2H,R3F),
(ZC,R1H,R2H,R3G), (ZC,R1H,R2H,R3H), (ZC,R1H,R2H,R3I), (ZC,R1H,R2H,R3J),
(ZC,R1H,R2H,R3K), (ZC,R1H,R2H,R3L), (ZC,R1H,R2H,R3M),
(ZC,R1H,R2H,R3N), (ZC,R1H,R2H,R3O), (ZC,R1H,R2H,R3P),
(ZC,R1H,R2H,R3Q), (ZC,R1H,R2H,R3R), (ZC,R1H,R2I,R3A), (ZC,R1H,R2I,R3B),
(ZC,R1H,R2I,R3C), (ZC,R1H,R2I,R3D), (ZC,R1H,R2I,R3E), (ZC,R1H,R2I,R3F),
(ZC,R1H,R2I,R3G), (ZC,R1H,R2I,R3H), (ZC,R1H,R2I,R3I), (ZC,R1H,R2I,R3J),
(ZC,R1H,R2I,R3K), (ZC,R1H,R2I,R3L), (ZC,R1H,R2I,R3M), (ZC,R1H,R2I,R3N),
(ZC,R1H,R2I,R3O), (ZC,R1H,R2I,R3P), (ZC,R1H,R2I,R3Q), (ZC,R1H,R2I,R3R),
(ZC,R1H,R2J,R3A), (ZC,R1H,R2J,R3B), (ZC,R1H,R2J,R3C), (ZC,R1H,R2J,R3D),
(ZC,R1H,R2J,R3E), (ZC,R1H,R2J,R3F), (ZC,R1H,R2J,R3G), (ZC,R1H,R2J,R3H),
(ZC,R1H,R2J,R3I), (ZC,R1H,R2J,R3J), (ZC,R1H,R2J,R3K), (ZC,R1H,R2J,R3L),
(ZC,R1H,R2J,R3M), (ZC,R1H,R2J,R3N), (ZC,R1H,R2J,R3O), (ZC,R1H,R2J,R3P),
(ZC,R1H,R2J,R3Q), (ZC,R1H,R2J,R3R), (ZC,R1H,R2K,R3A), (ZC,R1H,R2K,R3B),
(ZC,R1H,R2K,R3C), (ZC,R1H,R2K,R3D), (ZC,R1H,R2K,R3E), (ZC,R1H,R2K,R3F),
(ZC,R1H,R2K,R3G), (ZC,R1H,R2K,R3H), (ZC,R1H,R2K,R3I), (ZC,R1H,R2K,R3J),
(ZC,R1H,R2K,R3K), (ZC,R1H,R2K,R3L), (ZC,R1H,R2K,R3M),
(ZC,R1H,R2K,R3N), (ZC,R1H,R2K,R3O), (ZC,R1H,R2K,R3P), (ZC,R1H,R2K,R3Q),
(ZC,R1H,R2K,R3R), (ZC,R1H,R2L,R3A), (ZC,R1H,R2L,R3B), (ZC,R1H,R2L,R3C),
(ZC,R1H,R2L,R3D), (ZC,R1H,R2L,R3E), (ZC,R1H,R2L,R3F), (ZC,R1H,R2L,R3G),
(ZC,R1H,R2L,R3H), (ZC,R1H,R2L,R3I), (ZC,R1H,R2L,R3J), (ZC,R1H,R2L,R3K),
(ZC,R1H,R2L,R3L), (ZC,R1H,R2L,R3M), (ZC,R1H,R2L,R3N), (ZC,R1H,R2L,R3O),
(ZC,R1H,R2L,R3P), (ZC,R1H,R2L,R3Q), (ZC,R1H,R2L,R3R), (ZC,R1H,R2M,R3A),
(ZC,R1H,R2M,R3B), (ZC,R1H,R2M,R3C), (ZC,R1H,R2M,R3D),
(ZC,R1H,R2M,R3E), (ZC,R1H,R2M,R3F), (ZC,R1H,R2M,R3G),
(ZC,R1H,R2M,R3H), (ZC,R1I,R2M,R3I), (ZC,R1H,R2M,R3J),
(ZC,R1H,R2M,R3K), (ZC,R1H,R2M,R3L), (ZC,R1H,R2M,R3M),
(ZC,R1H,R2M,R3N), (ZC,R1H,R2M,R3O), (ZC,R1H,R2M,R3P),
(ZC,R1H,R2M,R3Q), (ZC,R1H,R2M,R3R), (ZC,R1H,R2N,R3A),
(ZC,R1H,R2N,R3B), (ZC,R1H,R2N,R3C), (ZC,R1H,R2N,R3D),
(ZC,R1H,R2N,R3E), (ZC,R1H,R2N,R3F), (ZC,R1H,R2N,R3G),
(ZC,R1H,R2N,R3H), (ZC,R1H,R2N,R3I), (ZC,R1H,R2N,R3J), (ZC,R1H,R2N,R3K),
(ZC,R1I,R2N,R3L), (ZC,R1H,R2N,R3M), (ZC,R1H,R2N,R3N),
(ZC,R1H,R2N,R3O), (ZC,R1H,R2N,R3P), (ZC,R1H,R2N,R3Q),
(ZC,R1H,R2N,R3R), (ZC,R1J,R2A,R3A), (ZC,R1J,R2A,R3B),
(ZC,R1J,R2A,R3C), (ZC,R1J,R2A,R3D), (ZC,R1J,R2A,R3E),
(ZC,R1J,R2A,R3F), (ZC,R1J,R2A,R3G), (ZC,R1J,R2A,R3H),
(ZC,R1J,R2A,R3I), (ZC,R1J,R2A,R3J), (ZC,R1J,R2A,R3K),
(ZC,R1J,R2A,R3L), (ZC,R1J,R2A,R3M), (ZC,R1J,R2A,R3N),
(ZC,R1J,R2A,R3O), (ZC,R1J,R2A,R3P), (ZC,R1J,R2A,R3Q),
(ZC,R1J,R2A,R3R), (ZC,R1J,R2B,R3A), (ZC,R1J,R2B,R3B),
(ZC,R1J,R2B,R3C), (ZC,R1J,R2B,R3D), (ZC,R1J,R2B,R3E),
(ZC,R1J,R2B,R3F), (ZC,R1J,R2B,R3G), (ZC,R1J,R2B,R3H),
(ZC,R1J,R2B,R3I), (ZC,R1J,R2B,R3J), (ZC,R1J,R2B,R3K),
(ZC,R1J,R2B,R3L), (ZC,R1J,R2B,R3M), (ZC,R1J,R2B,R3N),
(ZC,R1J,R2B,R3O), (ZC,R1J,R2B,R3P), (ZC,R1J,R2B,R3Q),
(ZC,R1J,R2B,R3R), (ZC,R1J,R2C,R3A), (ZC,R1J,R2C,R3B),
(ZC,R1J,R2C,R3C), (ZC,R1J,R2C,R3D), (ZC,R1J,R2C,R3E),
(ZC,R1J,R2C,R3F), (ZC,R1J,R2C,R3G), (ZC,R1J,R2C,R3H),
(ZC,R1J,R2C,R3I), (ZC,R1J,R2C,R3J), (ZC,R1J,R2C,R3K),
(ZC,R1J,R2C,R3L), (ZC,R1J,R2C,R3M), (ZC,R1J,R2C,R3N),
(ZC,R1J,R2C,R3O), (ZC,R1J,R2C,R3P), (ZC,R1J,R2C,R3Q),
(ZC,R1J,R2C,R3R), (ZC,R1J,R2D,R3A), (ZC,R1J,R2D,R3B),
(ZC,R1J,R2D,R3C), (ZC,R1J,R2D,R3D), (ZC,R1J,R2D,R3E),
(ZC,R1J,R2D,R3F), (ZC,R1J,R2D,R3G), (ZC,R1J,R2D,R3H),
(ZC,R1J,R2D,R3I), (ZC,R1J,R2D,R3J), (ZC,R1J,R2D,R3K),
(ZC,R1J,R2D,R3L), (ZC,R1J,R2D,R3M), (ZC,R1J,R2D,R3N),
(ZC,R1J,R2D,R3O), (ZC,R1J,R2D,R3P), (ZC,R1J,R2D,R3Q),
(ZC,R1J,R2D,R3R), (ZC,R1J,R2E,R3A), (ZC,R1J,R2E,R3B),
(ZC,R1J,R2E,R3C), (ZC,R1J,R2E,R3D), (ZC,R1J,R2E,R3E),
(ZC,R1J,R2E,R3F), (ZC,R1J,R2E,R3G), (ZC,R1J,R2E,R3H),
(ZC,R1J,R2E,R3I), (ZC,R1J,R2E,R3J), (ZC,R1J,R2E,R3K),
(ZC,R1J,R2E,R3L), (ZC,R1J,R2E,R3M), (ZC,R1J,R2E,R3N),
(ZC,R1J,R2E,R3O), (ZC,R1J,R2E,R3P), (ZC,R1J,R2E,R3Q),
(ZC,R1J,R2E,R3R), (ZC,R1J,R2F,R3A), (ZC,R1J,R2F,R3B), (ZC,R1J,R2F,R3C), (ZC,R1J,R2F,R3D), (ZC,R1J,R2F,R3E),
(ZC,R1J,R2F,R3F), (ZC,R1J,R2F,R3G), (ZC,R1J,R2F,R3H),
(ZC,R1J,R2F,R3I), (ZC,R1J,R2F,R3J), (ZC,R1J,R2F,R3K),
(ZC,R1J,R2F,R3L), (ZC,R1J,R2F,R3M), (ZC,R1J,R2F,R3N),
(ZC,R1J,R2F,R3O), (ZC,R1J,R2F,R3P), (ZC,R1J,R2F,R3Q),
(ZC,R1J,R2F,R3R), (ZC,R1J,R2G,R3A), (ZC,R1J,R2G,R3B),
(ZC,R1J,R2G,R3C), (ZC,R1J,R2G,R3D), (ZC,R1J,R2G,R3E),
(ZC,R1J,R2G,R3F), (ZC,R1J,R2G,R3G), (ZC,R1J,R2G,R3H),
(ZC,R1J,R2G,R3I), (ZC,R1J,R2G,R3J), (ZC,R1J,R2G,R3K),
(ZC,R1J,R2G,R3L), (ZC,R1J,R2G,R3M), (ZC,R1J,R2G,R3N),
(ZC,R1J,R2G,R3O), (ZC,R1J,R2G,R3P), (ZC,R1J,R2G,R3Q),
(ZC,R1J,R2G,R3R), (ZC,R1J,R2H,R3A), (ZC,R1J,R2H,R3B),
(ZC,R1J,R2H,R3C), (ZC,R1J,R2H,R3D), (ZC,R1J,R2H,R3E),
(ZC,R1J,R2H,R3F), (ZC,R1J,R2H,R3G), (ZC,R1J,R2H,R3H),
(ZC,R1J,R2H,R3I), (ZC,R1J,R2H,R3J), (ZC,R1J,R2H,R3K),
(ZC,R1J,R2H,R3L), (ZC,R1J,R2H,R3M), (ZC,R1J,R2H,R3N),
(ZC,R1J,R2H,R3O), (ZC,R1J,R2H,R3P), (ZC,R1J,R2H,R3Q),
(ZC,R1J,R2H,R3R), (ZC,R1J,R2I,R3A), (ZC,R1J,R2I,R3B), (ZC,R1J,R2I,R3C),
(ZC,R1J,R2I,R3D), (ZC,R1J,R2I,R3E), (ZC,R1J,R2I,R3F), (ZC,R1J,R2I,R3G),
(ZC,R1J,R2I,R3H), (ZC,R1J,R2I,R3I), (ZC,R1J,R2I,R3J), (ZC,R1J,R2I,R3K),
(ZC,R1J,R2I,R3L), (ZC,R1J,R2I,R3M), (ZC,R1J,R2I,R3N), (ZC,R1J,R2I,R3O),
(ZC,R1J,R2I,R3P), (ZC,R1J,R2I,R3Q), (ZC,R1J,R2I,R3R), (ZC,R1J,R2J,R3A),
(ZC,R1J,R2J,R3B), (ZC,R1J,R2J,R3C), (ZC,R1J,R2J,R3D),
(ZC,R1J,R2J,R3E), (ZC,R1J,R2J,R3F), (ZC,R1J,R2J,R3G),
(ZC,R1J,R2J,R3H), (ZC,R1J,R2J,R3I), (ZC,R1J,R2J,R3J),
(ZC,R1J,R2J,R3K), (ZC,R1J,R2J,R3L), (ZC,R1J,R2J,R3M),
(ZC,R1J,R2J,R3N), (ZC,R1J,R2J,R3O), (ZC,R1J,R2J,R3P),
(ZC,R1J,R2J,R3Q), (ZC,R1J,R2J,R3R), (ZC,R1J,R2K,R3A),
(ZC,R1J,R2K,R3B), (ZC,R1J,R2K,R3C), (ZC,R1J,R2K,R3D),
(ZC,R1J,R2K,R3E), (ZC,R1J,R2K,R3F), (ZC,R1J,R2K,R3G),
(ZC,R1J,R2K,R3H), (ZC,R1J,R2K,R3I), (ZC,R1J,R2K,R3J),
(ZC,R1J,R2K,R3K), (ZC,R1J,R2K,R3L), (ZC,R1J,R2K,R3M),
(ZC,R1J,R2K,R3N), (ZC,R1J,R2K,R3O), (ZC,R1J,R2K,R3P),
(ZC,R1J,R2K,R3Q), (ZC,R1J,R2K,R3R), (ZC,R1J,R2L,R3A),
(ZC,R1J,R2L,R3B), (ZC,R1J,R2L,R3C), (ZC,R1J,R2L,R3D),
(ZC,R1J,R2L,R3E), (ZC,R1J,R2L,R3F), (ZC,R1J,R2L,R3G),
(ZC,R1J,R2L,R3H), (ZC,R1J,R2L,R3I), (ZC,R1J,R2L,R3J),
(ZC,R1J,R2L,R3K), (ZC,R1J,R2L,R3L), (ZC,R1J,R2L,R3M),
(ZC,R1J,R2L,R3N), (ZC,R1J,R2L,R3O), (ZC,R1J,R2L,R3P),
(ZC,R1J,R2L,R3Q), (ZC,R1J,R2L,R3R), (ZC,R1J,R2M,R3A),
(ZC,R1J,R2M,R3B), (ZC,R1J,R2M,R3C), (ZC,R1J,R2M,R3D),
(ZC,R1J,R2M,R3E), (ZC,R1J,R2M,R3F), (ZC,R1J,R2M,R3G),
(ZC,R1J,R2M,R3H), (ZC,R1J,R2M,R3I), (ZC,R1J,R2M,R3J),
(ZC,R1J,R2M,R3K), (ZC,R1J,R2M,R3L), (ZC,R1J,R2M,R3M),
(ZC,R1J,R2M,R3N), (ZC,R1J,R2M,R3O), (ZC,R1J,R2M,R3P),
(ZC,R1J,R2M,R3Q), (ZC,R1J,R2M,R3R), (ZC,R1J,R2N,R3A),
(ZC,R1J,R2N,R3B), (ZC,R1J,R2N,R3C), (ZC,R1J,R2N,R3D),
(ZC,R1J,R2N,R3E), (ZC,R1J,R2N,R3F), (ZC,R1J,R2N,R3G),
(ZC,R1J,R2N,R3H), (ZC,R1J,R2N,R3I), (ZC,R1J,R2N,R3J),
(ZC,R1J,R2N,R3K), (ZC,R1J,R2N,R3L), (ZC,R1J,R2N,R3M),
(ZC,R1J,R2N,R3N), (ZC,R1J,R2N,R3O), (ZC,R1J,R2N,R3P),
(ZC,R1J,R2N,R3Q), (ZC,R1J,R2N,R3R), (ZC,R1K,R2A,R3A),
(ZC,R1K,R2A,R3B), (ZC,R1K,R2A,R3C), (ZC,R1K,R2A,R3D),
(ZC,R1K,R2A,R3E), (ZC,R1K,R2A,R3F), (ZC,R1K,R2A,R3G),
(ZC,R1K,R2A,R3H), (ZC,R1K,R2A,R3I), (ZC,R1K,R2A,R3J),
(ZC,R1K,R2A,R3K), (ZC,R1K,R2A,R3L), (ZC,R1K,R2A,R3M),
(ZC,R1K,R2A,R3N), (ZC,R1K,R2A,R3O), (ZC,R1K,R2A,R3P),
(ZC,R1K,R2A,R3Q), (ZC,R1K,R2A,R3R), (ZC,R1K,R2B,R3A),
(ZC,R1K,R2B,R3B), (ZC,R1K,R2B,R3C), (ZC,R1K,R2B,R3D),
(ZC,R1K,R2B,R3E), (ZC,R1K,R2B,R3F), (ZC,R1K,R2B,R3G),
(ZC,R1K,R2B,R3H), (ZC,R1K,R2B,R3I), (ZC,R1K,R2B,R3J),
(ZC,R1K,R2B,R3K), (ZC,R1K,R2B,R3L), (ZC,R1K,R2B,R3M),
(ZC,R1K,R2B,R3N), (ZC,R1K,R2B,R3O), (ZC,R1K,R2B,R3P),
(ZC,R1K,R2B,R3Q), (ZC,R1K,R2B,R3R), (ZC,R1K,R2C,R3A),
(ZC,R1K,R2C,R3B), (ZC,R1K,R2C,R3C), (ZC,R1K,R2C,R3D),
(ZC,R1K,R2C,R3E), (ZC,R1K,R2C,R3F), (ZC,R1K,R2C,R3G),
(ZC,R1K,R2C,R3H), (ZC,R1K,R2C,R3I), (ZC,R1K,R2C,R3J),
(ZC,R1K,R2C,R3K), (ZC,R1K,R2C,R3L), (ZC,R1K,R2C,R3M), (ZC,R1K,R2C,R3N), (ZC,R1K,R2C,R3O), (ZC,R1K,R2C,R3P),
(ZC,R1K,R2C,R3Q), (ZC,R1K,R2C,R3R), (ZC,R1K,R2D,R3A),
(ZC,R1K,R2D,R3B), (ZC,R1K,R2D,R3C), (ZC,R1K,R2D,R3D),
(ZC,R1K,R2D,R3E), (ZC,R1K,R2D,R3F), (ZC,R1K,R2D,R3G),
(ZC,R1K,R2D,R3H), (ZC,R1K,R2D,R3I), (ZC,R1K,R2D,R3J),
(ZC,R1K,R2D,R3K), (ZC,R1K,R2D,R3L), (ZC,R1K,R2D,R3M),
(ZC,R1K,R2D,R3N), (ZC,R1K,R2D,R3O), (ZC,R1K,R2D,R3P),
(ZC,R1K,R2D,R3Q), (ZC,R1K,R2D,R3R), (ZC,R1K,R2E,R3A),
(ZC,R1K,R2E,R3B), (ZC,R1K,R2E,R3C), (ZC,R1K,R2E,R3D),
(ZC,R1K,R2E,R3E), (ZC,R1K,R2E,R3F), (ZC,R1K,R2E,R3G),
(ZC,R1K,R2E,R3H), (ZC,R1K,R2E,R3I), (ZC,R1K,R2E,R3J),
(ZC,R1K,R2E,R3K), (ZC,R1K,R2E,R3L), (ZC,R1K,R2E,R3M),
(ZC,R1K,R2E,R3N), (ZC,R1K,R2E,R3O), (ZC,R1K,R2E,R3P),
(ZC,R1K,R2E,R3Q), (ZC,R1K,R2E,R3R), (ZC,R1K,R2F,R3A),
(ZC,R1K,R2F,R3B), (ZC,R1K,R2F,R3C), (ZC,R1K,R2F,R3D),
(ZC,R1K,R2F,R3E), (ZC,R1K,R2F,R3F), (ZC,R1K,R2F,R3G),
(ZC,R1K,R2F,R3H), (ZC,R1K,R2F,R3I), (ZC,R1K,R2F,R3J),
(ZC,R1K,R2F,R3K), (ZC,R1K,R2F,R3L), (ZC,R1K,R2F,R3M),
(ZC,R1K,R2F,R3N), (ZC,R1K,R2F,R3O), (ZC,R1K,R2F,R3P),
(ZC,R1K,R2F,R3Q), (ZC,R1K,R2F,R3R), (ZC,R1K,R2G,R3A),
(ZC,R1K,R2G,R3B), (ZC,R1K,R2G,R3C), (ZC,R1K,R2G,R3D),
(ZC,R1K,R2G,R3E), (ZC,R1K,R2G,R3F), (ZC,R1K,R2G,R3G),
(ZC,R1K,R2G,R3H), (ZC,R1K,R2G,R3I), (ZC,R1K,R2G,R3J),
(ZC,R1K,R2G,R3K), (ZC,R1K,R2G,R3L), (ZC,R1K,R2G,R3M),
(ZC,R1K,R2G,R3N), (ZC,R1K,R2G,R3O), (ZC,R1K,R2G,R3P),
(ZC,R1K,R2G,R3Q), (ZC,R1K,R2G,R3R), (ZC,R1K,R2H,R3A),
(ZC,R1K,R2H,R3B), (ZC,R1K,R2H,R3C), (ZC,R1K,R2H,R3D),
(ZC,R1K,R2H,R3E), (ZC,R1K,R2H,R3F), (ZC,R1K,R2H,R3G),
(ZC,R1K,R2H,R3H), (ZC,R1K,R2H,R3I), (ZC,R1K,R2H,R3J),
(ZC,R1K,R2H,R3K), (ZC,R1K,R2H,R3L), (ZC,R1K,R2H,R3M),
(ZC,R1K,R2H,R3N), (ZC,R1K,R2H,R3O), (ZC,R1K,R2H,R3P),
(ZC,R1K,R2H,R3Q), (ZC,R1K,R2H,R3R), (ZC,R1K,R2I,R3A),
(ZC,R1K,R2I,R3B), (ZC,R1K,R2I,R3C), (ZC,R1K,R2I,R3D),
(ZC,R1K,R2I,R3E), (ZC,R1K,R2I,R3F), (ZC,R1K,R2I,R3G), (ZC,R1K,R2I,R3H),
(ZC,R1K,R2I,R3I), (ZC,R1K,R2I,R3J), (ZC,R1K,R2I,R3K), (ZC,R1K,R2I,R3L),
(ZC,R1K,R2I,R3M), (ZC,R1K,R2I,R3N), (ZC,R1K,R2I,R3O),
(ZC,R1K,R2I,R3P), (ZC,R1K,R2I,R3Q), (ZC,R1K,R2I,R3R),
(ZC,R1K,R2J,R3A), (ZC,R1K,R2J,R3B), (ZC,R1K,R2J,R3C),
(ZC,R1K,R2J,R3D), (ZC,R1K,R2J,R3E), (ZC,R1K,R2J,R3F),
(ZC,R1K,R2J,R3G), (ZC,R1K,R2J,R3H), (ZC,R1K,R2J,R3I),
(ZC,R1K,R2J,R3J), (ZC,R1K,R2J,R3K), (ZC,R1K,R2J,R3L),
(ZC,R1K,R2J,R3M), (ZC,R1K,R2J,R3N), (ZC,R1K,R2J,R3O),
(ZC,R1K,R2J,R3P), (ZC,R1K,R2J,R3Q), (ZC,R1K,R2J,R3R),
(ZC,R1K,R2K,R3A), (ZC,R1K,R2K,R3B), (ZC,R1K,R2K,R3C),
(ZC,R1K,R2K,R3D), (ZC,R1K,R2K,R3E), (ZC,R1K,R2K,R3F),
(ZC,R1K,R2K,R3G), (ZC,R1K,R2K,R3H), (ZC,R1K,R2K,R3I),
(ZC,R1K,R2K,R3J), (ZC,R1K,R2K,R3K), (ZC,R1K,R2K,R3L),
(ZC,R1K,R2K,R3M), (ZC,R1K,R2K,R3N), (ZC,R1K,R2K,R3O),
(ZC,R1K,R2K,R3P), (ZC,R1K,R2K,R3Q), (ZC,R1K,R2K,R3R),
(ZC,R1K,R2L,R3A), (ZC,R1K,R2L,R3B), (ZC,R1K,R2L,R3C),
(ZC,R1K,R2L,R3D), (ZC,R1K,R2L,R3E), (ZC,R1K,R2L,R3F),
(ZC,R1K,R2L,R3G), (ZC,R1K,R2L,R3H), (ZC,R1K,R2L,R3I),
(ZC,R1K,R2L,R3J), (ZC,R1K,R2L,R3K), (ZC,R1K,R2L,R3L),
(ZC,R1K,R2L,R3M), (ZC,R1K,R2L,R3N), (ZC,R1K,R2L,R3O),
(ZC,R1K,R2L,R3P), (ZC,R1K,R2L,R3Q), (ZC,R1K,R2L,R3R),
(ZC,R1K,R2M,R3A), (ZC,R1K,R2M,R3B), (ZC,R1K,R2M,R3C),
(ZC,R1K,R2M,R3D), (ZC,R1K,R2M,R3E), (ZC,R1K,R2M,R3F),
(ZC,R1K,R2M,R3G), (ZC,R1K,R2M,R3H), (ZC,R1K,R2M,R3I),
(ZC,R1K,R2M,R3J), (ZC,R1K,R2M,R3K), (ZC,R1K,R2M,R3L),
(ZC,R1K,R2M,R3M), (ZC,R1K,R2M,R3N), (ZC,R1K,R2M,R3O),
(ZC,R1K,R2M,R3P), (ZC,R1K,R2M,R3Q), (ZC,R1K,R2M,R3R),
(ZC,R1K,R2N,R3A), (ZC,R1K,R2N,R3B), (ZC,R1K,R2N,R3C),
(ZC,R1K,R2N,R3D), (ZC,R1K,R2N,R3E), (ZC,R1K,R2N,R3F),
(ZC,R1K,R2N,R3G), (ZC,R1K,R2N,R3H), (ZC,R1K,R2N,R3I),
(ZC,R1K,R2N,R3J), (ZC,R1K,R2N,R3K), (ZC,R1K,R2N,R3L),
(ZC,R1K,R2N,R3M), (ZC,R1K,R2N,R3N), (ZC,R1K,R2N,R3O), (ZC,R1K,R2N,R3P), (ZC,R1K,R2N,R3Q), (ZC,R1K,R2N,R3R),
(ZC,R1L,R2A,R3A), (ZC,R1L,R2A,R3B), (ZC,R1L,R2A,R3C),
(ZC,R1L,R2A,R3D), (ZC,R1L,R2A,R3E), (ZC,R1L,R2A,R3F),
(ZC,R1L,R2A,R3G), (ZC,R1L,R2A,R3H), (ZC,R1L,R2A,R3I),
(ZC,R1L,R2A,R3J), (ZC,R1L,R2A,R3K), (ZC,R1L,R2A,R3L),
(ZC,R1L,R2A,R3M), (ZC,R1L,R2A,R3N), (ZC,R1L,R2A,R3O),
(ZC,R1L,R2A,R3P), (ZC,R1L,R2A,R3Q), (ZC,R1L,R2A,R3R),
(ZC,R1L,R2B,R3A), (ZC,R1L,R2B,R3B), (ZC,R1L,R2B,R3C),
(ZC,R1L,R2B,R3D), (ZC,R1L,R2B,R3E), (ZC,R1L,R2B,R3F),
(ZC,R1L,R2B,R3G), (ZC,R1L,R2B,R3H), (ZC,R1L,R2B,R3I),
(ZC,R1L,R2B,R3J), (ZC,R1L,R2B,R3K), (ZC,R1L,R2B,R3L),
(ZC,R1L,R2B,R3M), (ZC,R1L,R2B,R3N), (ZC,R1L,R2B,R3O),
(ZC,R1L,R2B,R3P), (ZC,R1L,R2B,R3Q), (ZC,R1L,R2B,R3R),
(ZC,R1L,R2C,R3A), (ZC,R1L,R2C,R3B), (ZC,R1L,R2C,R3C),
(ZC,R1L,R2C,R3D), (ZC,R1L,R2C,R3E), (ZC,R1L,R2C,R3F),
(ZC,R1L,R2C,R3G), (ZC,R1L,R2C,R3H), (ZC,R1L,R2C,R3I),
(ZC,R1L,R2C,R3J), (ZC,R1L,R2C,R3K), (ZC,R1L,R2C,R3L),
(ZC,R1L,R2C,R3M), (ZC,R1L,R2C,R3N), (ZC,R1L,R2C,R3O),
(ZC,R1L,R2C,R3P), (ZC,R1L,R2C,R3Q), (ZC,R1L,R2C,R3R),
(ZC,R1L,R2D,R3A), (ZC,R1L,R2D,R3B), (ZC,R1L,R2D,R3C),
(ZC,R1L,R2D,R3D), (ZC,R1L,R2D,R3E), (ZC,R1L,R2D,R3F),
(ZC,R1L,R2D,R3G), (ZC,R1L,R2D,R3H), (ZC,R1L,R2D,R3I),
(ZC,R1L,R2D,R3J), (ZC,R1L,R2D,R3K), (ZC,R1L,R2D,R3L),
(ZC,R1L,R2D,R3M), (ZC,R1L,R2D,R3N), (ZC,R1L,R2D,R3O),
(ZC,R1L,R2D,R3P), (ZC,R1L,R2D,R3Q), (ZC,R1L,R2D,R3R),
(ZC,R1L,R2E,R3A), (ZC,R1L,R2E,R3B), (ZC,R1L,R2E,R3C),
(ZC,R1L,R2E,R3D), (ZC,R1L,R2E,R3E), (ZC,R1L,R2E,R3F),
(ZC,R1L,R2E,R3G), (ZC,R1L,R2E,R3H), (ZC,R1L,R2E,R3I),
(ZC,R1L,R2E,R3J), (ZC,R1L,R2E,R3K), (ZC,R1L,R2E,R3L),
(ZC,R1L,R2E,R3M), (ZC,R1L,R2E,R3N), (ZC,R1L,R2E,R3O),
(ZC,R1L,R2E,R3P), (ZC,R1L,R2E,R3Q), (ZC,R1L,R2E,R3R),
(ZC,R1L,R2F,R3A), (ZC,R1L,R2F,R3B), (ZC,R1L,R2F,R3C),
(ZC,R1L,R2F,R3D), (ZC,R1L,R2F,R3E), (ZC,R1L,R2F,R3F),
(ZC,R1L,R2F,R3G), (ZC,R1L,R2F,R3H), (ZC,R1L,R2F,R3I),
(ZC,R1L,R2F,R3J), (ZC,R1L,R2F,R3K), (ZC,R1L,R2F,R3L),
(ZC,R1L,R2F,R3M), (ZC,R1L,R2F,R3N), (ZC,R1L,R2F,R3O),
(ZC,R1L,R2F,R3P), (ZC,R1L,R2F,R3Q), (ZC,R1L,R2F,R3R),
(ZC,R1L,R2G,R3A), (ZC,R1L,R2G,R3B), (ZC,R1L,R2G,R3C),
(ZC,R1L,R2G,R3D), (ZC,R1L,R2G,R3E), (ZC,R1L,R2G,R3F),
(ZC,R1L,R2G,R3G), (ZC,R1L,R2G,R3H), (ZC,R1L,R2G,R3I),
(ZC,R1L,R2G,R3J), (ZC,R1L,R2G,R3K), (ZC,R1L,R2G,R3L),
(ZC,R1L,R2G,R3M), (ZC,R1L,R2G,R3N), (ZC,R1L,R2G,R3O),
(ZC,R1L,R2G,R3P), (ZC,R1L,R2G,R3Q), (ZC,R1L,R2G,R3R),
(ZC,R1L,R2H,R3A), (ZC,R1L,R2H,R3B), (ZC,R1L,R2H,R3C),
(ZC,R1L,R2H,R3D), (ZC,R1L,R2H,R3E), (ZC,R1L,R2H,R3F),
(ZC,R1L,R2H,R3G), (ZC,R1L,R2H,R3H), (ZC,R1L,R2H,R3I),
(ZC,R1L,R2H,R3J), (ZC,R1L,R2H,R3K), (ZC,R1L,R2H,R3L),
(ZC,R1L,R2H,R3M), (ZC,R1L,R2H,R3N), (ZC,R1L,R2H,R3O),
(ZC,R1L,R2H,R3P), (ZC,R1L,R2H,R3Q), (ZC,R1L,R2H,R3R),
(ZC,R1L,R2I,R3A), (ZC,R1L,R2I,R3B), (ZC,R1L,R2I,R3C), (ZC,R1L,R2I,R3D),
(ZC,R1L,R2I,R3E), (ZC,R1L,R2I,R3F), (ZC,R1L,R2I,R3G), (ZC,R1L,R2I,R3H),
(ZC,R1L,R2I,R3I), (ZC,R1L,R2I,R3J), (ZC,R1L,R2I,R3K), (ZC,R1L,R2I,R3L),
(ZC,R1L,R2I,R3M), (ZC,R1L,R2I,R3N), (ZC,R1L,R2I,R3O), (ZC,R1L,R2I,R3P),
(ZC,R1L,R2I,R3Q), (ZC,R1L,R2I,R3R), (ZC,R1L,R2J,R3A),
(ZC,R1L,R2J,R3B), (ZC,R1L,R2J,R3C), (ZC,R1L,R2J,R3D),
(ZC,R1L,R2J,R3E), (ZC,R1L,R2J,R3F), (ZC,R1L,R2J,R3G),
(ZC,R1L,R2J,R3H), (ZC,R1L,R2J,R3I), (ZC,R1L,R2J,R3J),
(ZC,R1L,R2J,R3K), (ZC,R1L,R2J,R3L), (ZC,R1L,R2J,R3M),
(ZC,R1L,R2J,R3N), (ZC,R1L,R2J,R3O), (ZC,R1L,R2J,R3P),
(ZC,R1L,R2J,R3Q), (ZC,R1L,R2J,R3R), (ZC,R1L,R2K,R3A),
(ZC,R1L,R2K,R3B), (ZC,R1L,R2K,R3C), (ZC,R1L,R2K,R3D),
(ZC,R1L,R2K,R3E), (ZC,R1L,R2K,R3F), (ZC,R1L,R2K,R3G),
(ZC,R1L,R2K,R3H), (ZC,R1L,R2K,R3I), (ZC,R1L,R2K,R3J),
(ZC,R1L,R2K,R3K), (ZC,R1L,R2K,R3L), (ZC,R1L,R2K,R3M),
(ZC,R1L,R2K,R3N), (ZC,R1L,R2K,R3O), (ZC,R1L,R2K,R3P),
(ZC,R1L,R2K,R3Q), (ZC,R1L,R2K,R3R), (ZC,R1L,R2L,R3A), (ZC,R1L,R2L,R3B), (ZC,R1L,R2L,R3C), (ZC,R1L,R2L,R3D),
(ZC,R1L,R2L,R3E), (ZC,R1L,R2L,R3F), (ZC,R1L,R2L,R3G),
(ZC,R1L,R2L,R3H), (ZC,R1L,R2L,R3I), (ZC,R1L,R2L,R3J),
(ZC,R1L,R2L,R3K), (ZC,R1L,R2L,R3L), (ZC,R1L,R2L,R3M),
(ZC,R1L,R2L,R3N), (ZC,R1L,R2L,R3O), (ZC,R1L,R2L,R3P),
(ZC,R1L,R2L,R3Q), (ZC,R1L,R2L,R3R), (ZC,R1L,R2M,R3A),
(ZC,R1L,R2M,R3B), (ZC,R1L,R2M,R3C), (ZC,R1L,R2M,R3D),
(ZC,R1L,R2M,R3E), (ZC,R1L,R2M,R3F), (ZC,R1L,R2M,R3G),
(ZC,R1L,R2M,R3H), (ZC,R1L,R2M,R3I), (ZC,R1L,R2M,R3J),
(ZC,R1L,R2M,R3K), (ZC,R1L,R2M,R3L), (ZC,R1L,R2M,R3M),
(ZC,R1L,R2M,R3N), (ZC,R1L,R2M,R3O), (ZC,R1L,R2M,R3P),
(ZC,R1L,R2M,R3Q), (ZC,R1L,R2M,R3R), (ZC,R1L,R2N,R3A),
(ZC,R1L,R2N,R3B), (ZC,R1L,R2N,R3C), (ZC,R1L,R2N,R3D),
(ZC,R1L,R2N,R3E), (ZC,R1L,R2N,R3F), (ZC,R1L,R2N,R3G),
(ZC,R1L,R2N,R3H), (ZC,R1L,R2N,R3I), (ZC,R1L,R2N,R3J),
(ZC,R1L,R2N,R3K), (ZC,R1L,R2N,R3L), (ZC,R1L,R2N,R3M),
(ZC,R1L,R2N,R3N), (ZC,R1L,R2N,R3O), (ZC,R1L,R2N,R3P),
(ZC,R1L,R2N,R3Q), (ZC,R1L,R2N,R3R), (ZC,R1M,R2A,R3A),
(ZC,R1M,R2A,R3B), (ZC,R1M,R2A,R3C), (ZC,R1M,R2A,R3D),
(ZC,R1M,R2A,R3E), (ZC,R1M,R2A,R3F), (ZC,R1M,R2A,R3G),
(ZC,R1M,R2A,R3H), (ZC,R1M,R2A,R3I), (ZC,R1M,R2A,R3J),
(ZC,R1M,R2A,R3K), (ZC,R1M,R2A,R3L), (ZC,R1M,R2A,R3M),
(ZC,R1M,R2A,R3N), (ZC,R1M,R2A,R3O), (ZC,R1M,R2A,R3P),
(ZC,R1M,R2A,R3Q), (ZC,R1M,R2A,R3R), (ZC,R1M,R2B,R3A),
(ZC,R1M,R2B,R3B), (ZC,R1M,R2B,R3C), (ZC,R1M,R2B,R3D),
(ZC,R1M,R2B,R3E), (ZC,R1M,R2B,R3F), (ZC,R1M,R2B,R3G),
(ZC,R1M,R2B,R3H), (ZC,R1M,R2B,R3I), (ZC,R1M,R2B,R3J),
(ZC,R1M,R2B,R3K), (ZC,R1M,R2B,R3L), (ZC,R1M,R2B,R3M),
(ZC,R1M,R2B,R3N), (ZC,R1M,R2B,R3O), (ZC,R1M,R2B,R3P),
(ZC,R1M,R2B,R3Q), (ZC,R1M,R2B,R3R), (ZC,R1M,R2C,R3A),
(ZC,R1M,R2C,R3B), (ZC,R1M,R2C,R3C), (ZC,R1M,R2C,R3D),
(ZC,R1M,R2C,R3E), (ZC,R1M,R2C,R3F), (ZC,R1M,R2C,R3G),
(ZC,R1M,R2C,R3H), (ZC,R1M,R2C,R3I), (ZC,R1M,R2C,R3J),
(ZC,R1M,R2C,R3K), (ZC,R1M,R2C,R3L), (ZC,R1M,R2C,R3M),
(ZC,R1M,R2C,R3N), (ZC,R1M,R2C,R3O), (ZC,R1M,R2C,R3P),
(ZC,R1M,R2C,R3Q), (ZC,R1M,R2C,R3R), (ZC,R1M,R2D,R3A),
(ZC,R1M,R2D,R3B), (ZC,R1M,R2D,R3C), (ZC,R1M,R2D,R3D),
(ZC,R1M,R2D,R3E), (ZC,R1M,R2D,R3F), (ZC,R1M,R2D,R3G),
(ZC,R1M,R2D,R3H), (ZC,R1M,R2D,R3I), (ZC,R1M,R2D,R3J),
(ZC,R1M,R2D,R3K), (ZC,R1M,R2D,R3L), (ZC,R1M,R2D,R3M),
(ZC,R1M,R2D,R3N), (ZC,R1M,R2D,R3O), (ZC,R1M,R2D,R3P),
(ZC,R1M,R2D,R3Q), (ZC,R1M,R2D,R3R), (ZC,R1M,R2E,R3A),
(ZC,R1M,R2E,R3B), (ZC,R1M,R2E,R3C), (ZC,R1M,R2E,R3D),
(ZC,R1M,R2E,R3E), (ZC,R1M,R2E,R3F), (ZC,R1M,R2E,R3G),
(ZC,R1M,R2E,R3H), (ZC,R1M,R2E,R3I), (ZC,R1M,R2E,R3J),
(ZC,R1M,R2E,R3K), (ZC,R1M,R2E,R3L), (ZC,R1M,R2E,R3M),
(ZC,R1M,R2E,R3N), (ZC,R1M,R2E,R3O), (ZC,R1M,R2E,R3P),
(ZC,R1M,R2E,R3Q), (ZC,R1M,R2E,R3R), (ZC,R1M,R2F,R3A),
(ZC,R1M,R2F,R3B), (ZC,R1M,R2F,R3C), (ZC,R1M,R2F,R3D),
(ZC,R1M,R2F,R3E), (ZC,R1M,R2F,R3F), (ZC,R1M,R2F,R3G),
(ZC,R1M,R2F,R3H), (ZC,R1M,R2F,R3I), (ZC,R1M,R2F,R3J),
(ZC,R1M,R2F,R3K), (ZC,R1M,R2F,R3L), (ZC,R1M,R2F,R3M),
(ZC,R1M,R2F,R3N), (ZC,R1M,R2F,R3O), (ZC,R1M,R2F,R3P),
(ZC,R1M,R2F,R3Q), (ZC,R1M,R2F,R3R), (ZC,R1M,R2G,R3A),
(ZC,R1M,R2G,R3B), (ZC,R1M,R2G,R3C), (ZC,R1M,R2G,R3D),
(ZC,R1M,R2G,R3E), (ZC,R1M,R2G,R3F), (ZC,R1M,R2G,R3G),
(ZC,R1M,R2G,R3H), (ZC,R1M,R2G,R3I), (ZC,R1M,R2G,R3J),
(ZC,R1M,R2G,R3K), (ZC,R1M,R2G,R3L), (ZC,R1M,R2G,R3M),
(ZC,R1M,R2G,R3N), (ZC,R1M,R2G,R3O), (ZC,R1M,R2G,R3P),
(ZC,R1M,R2G,R3Q), (ZC,R1M,R2G,R3R), (ZC,R1M,R2H,R3A),
(ZC,R1M,R2H,R3B), (ZC,R1M,R2H,R3C), (ZC,R1M,R2H,R3D),
(ZC,R1M,R2H,R3E), (ZC,R1M,R2H,R3F), (ZC,R1M,R2H,R3G),
(ZC,R1M,R2H,R3H), (ZC,R1M,R2H,R3I), (ZC,R1M,R2H,R3J),
(ZC,R1M,R2H,R3K), (ZC,R1M,R2H,R3L), (ZC,R1M,R2H,R3M),
(ZC,R1M,R2H,R3N), (ZC,R1M,R2H,R3O), (ZC,R1M,R2H,R3P),
(ZC,R1M,R2H,R3Q), (ZC,R1M,R2H,R3R), (ZC,R1M,R2I,R3A), (ZC,R1M,R2I,R3B), (ZC,R1M,R2I,R3C), (ZC,R1M,R2I,R3D),
(ZC,R1M,R2I,R3E), (ZC,R1M,R2I,R3F), (ZC,R1M,R2I,R3G),
(ZC,R1M,R2I,R3H), (ZC,R1M,R2I,R3I), (ZC,R1M,R2I,R3J),
(ZC,R1M,R2I,R3K), (ZC,R1M,R2I,R3L), (ZC,R1M,R2I,R3M),
(ZC,R1M,R2I,R3N), (ZC,R1M,R2I,R3O), (ZC,R1M,R2I,R3P),
(ZC,R1M,R2I,R3Q), (ZC,R1M,R2I,R3R), (ZC,R1M,R2J,R3A),
(ZC,R1M,R2J,R3B), (ZC,R1M,R2J,R3C), (ZC,R1M,R2J,R3D),
(ZC,R1M,R2J,R3E), (ZC,R1M,R2J,R3F), (ZC,R1M,R2J,R3G),
(ZC,R1M,R2J,R3H), (ZC,R1M,R2J,R3I), (ZC,R1M,R2J,R3J),
(ZC,R1M,R2J,R3K), (ZC,R1M,R2J,R3L), (ZC,R1M,R2J,R3M),
(ZC,R1M,R2J,R3N), (ZC,R1M,R2J,R3O), (ZC,R1M,R2J,R3P),
(ZC,R1M,R2J,R3Q), (ZC,R1M,R2J,R3R), (ZC,R1M,R2K,R3A),
(ZC,R1M,R2K,R3B), (ZC,R1M,R2K,R3C), (ZC,R1M,R2K,R3D),
(ZC,R1M,R2K,R3E), (ZC,R1M,R2K,R3F), (ZC,R1M,R2K,R3G),
(ZC,R1M,R2K,R3H), (ZC,R1M,R2K,R3I), (ZC,R1M,R2K,R3J),
(ZC,R1M,R2K,R3K), (ZC,R1M,R2K,R3L), (ZC,R1M,R2K,R3M),
(ZC,R1M,R2K,R3N), (ZC,R1M,R2K,R3O), (ZC,R1M,R2K,R3P),
(ZC,R1M,R2K,R3Q), (ZC,R1M,R2K,R3R), (ZC,R1M,R2L,R3A),
(ZC,R1M,R2L,R3B), (ZC,R1M,R2L,R3C), (ZC,R1M,R2L,R3D),
(ZC,R1M,R2L,R3E), (ZC,R1M,R2L,R3F), (ZC,R1M,R2L,R3G),
(ZC,R1M,R2L,R3H), (ZC,R1M,R2L,R3I), (ZC,R1M,R2L,R3J),
(ZC,R1M,R2L,R3K), (ZC,R1M,R2L,R3L), (ZC,R1M,R2L,R3M),
(ZC,R1M,R2L,R3N), (ZC,R1M,R2L,R3O), (ZC,R1M,R2L,R3P),
(ZC,R1M,R2L,R3Q), (ZC,R1M,R2L,R3R), (ZC,R1M,R2M,R3A),
(ZC,R1M,R2M,R3B), (ZC,R1M,R2M,R3C), (ZC,R1M,R2M,R3D),
(ZC,R1M,R2M,R3E), (ZC,R1M,R2M,R3F), (ZC,R1M,R2M,R3G),
(ZC,R1M,R2M,R3H), (ZC,R1M,R2M,R3I), (ZC,R1M,R2M,R3J),
(ZC,R1M,R2M,R3K), (ZC,R1M,R2M,R3L), (ZC,R1M,R2M,R3M),
(ZC,R1M,R2M,R3N), (ZC,R1M,R2M,R3O), (ZC,R1M,R2M,R3P),
(ZC,R1M,R2M,R3Q), (ZC,R1M,R2M,R3R), (ZC,R1M,R2N,R3A),
(ZC,R1M,R2N,R3B), (ZC,R1M,R2N,R3C), (ZC,R1M,R2N,R3D),
(ZC,R1M,R2N,R3E), (ZC,R1M,R2N,R3F), (ZC,R1M,R2N,R3G),
(ZC,R1M,R2N,R3H), (ZC,R1M,R2N,R3I), (ZC,R1M,R2N,R3J),
(ZC,R1M,R2N,R3K), (ZC,R1M,R2N,R3L), (ZC,R1M,R2N,R3M),
(ZC,R1M,R2N,R3N), (ZC,R1M,R2N,R3O), (ZC,R1M,R2N,R3P),
(ZC,R1M,R2N,R3Q), (ZC,R1M,R2N,R3R), (ZC,R1N,R2A,R3A),
(ZC,R1N,R2A,R3B), (ZC,R1N,R2A,R3C), (ZC,R1N,R2A,R3D),
(ZC,R1N,R2A,R3E), (ZC,R1N,R2A,R3F), (ZC,R1N,R2A,R3G),
(ZC,R1N,R2A,R3H), (ZC,R1N,R2A,R3I), (ZC,R1N,R2A,R3J),
(ZC,R1N,R2A,R3K), (ZC,R1N,R2A,R3L), (ZC,R1N,R2A,R3M),
(ZC,R1N,R2A,R3N), (ZC,R1N,R2A,R3O), (ZC,R1N,R2A,R3P),
(ZC,R1N,R2A,R3Q), (ZC,R1N,R2A,R3R), (ZC,R1N,R2B,R3A),
(ZC,R1N,R2B,R3B), (ZC,R1N,R2B,R3C), (ZC,R1N,R2B,R3D),
(ZC,R1N,R2B,R3E), (ZC,R1N,R2B,R3F), (ZC,R1N,R2B,R3G),
(ZC,R1N,R2B,R3H), (ZC,R1N,R2B,R3I), (ZC,R1N,R2B,R3J),
(ZC,R1N,R2B,R3K), (ZC,R1N,R2B,R3L), (ZC,R1N,R2B,R3M),
(ZC,R1N,R2B,R3N), (ZC,R1N,R2B,R3O), (ZC,R1N,R2B,R3P),
(ZC,R1N,R2B,R3Q), (ZC,R1N,R2B,R3R), (ZC,R1N,R2C,R3A),
(ZC,R1N,R2C,R3B), (ZC,R1N,R2C,R3C), (ZC,R1N,R2C,R3D),
(ZC,R1N,R2C,R3E), (ZC,R1N,R2C,R3F), (ZC,R1N,R2C,R3G),
(ZC,R1N,R2C,R3H), (ZC,R1N,R2C,R3I), (ZC,R1N,R2C,R3J),
(ZC,R1N,R2C,R3K), (ZC,R1N,R2C,R3L), (ZC,R1N,R2C,R3M),
(ZC,R1N,R2C,R3N), (ZC,R1N,R2C,R3O), (ZC,R1N,R2C,R3P),
(ZC,R1N,R2C,R3Q), (ZC,R1N,R2C,R3R), (ZC,R1N,R2D,R3A),
(ZC,R1N,R2D,R3B), (ZC,R1N,R2D,R3C), (ZC,R1N,R2D,R3D),
(ZC,R1N,R2D,R3E), (ZC,R1N,R2D,R3F), (ZC,R1N,R2D,R3G),
(ZC,R1N,R2D,R3H), (ZC,R1N,R2D,R3I), (ZC,R1N,R2D,R3J),
(ZC,R1N,R2D,R3K), (ZC,R1N,R2D,R3L), (ZC,R1N,R2D,R3M),
(ZC,R1N,R2D,R3N), (ZC,R1N,R2D,R3O), (ZC,R1N,R2D,R3P),
(ZC,R1N,R2D,R3Q), (ZC,R1N,R2D,R3R), (ZC,R1N,R2E,R3A),
(ZC,R1N,R2E,R3B), (ZC,R1N,R2E,R3C), (ZC,R1N,R2E,R3D),
(ZC,R1N,R2E,R3E), (ZC,R1N,R2E,R3F), (ZC,R1N,R2E,R3G),
(ZC,R1N,R2E,R3H), (ZC,R1N,R2E,R3I), (ZC,R1N,R2E,R3J),
(ZC,R1N,R2E,R3K), (ZC,R1N,R2E,R3L), (ZC,R1N,R2E,R3M),
(ZC,R1N,R2E,R3N), (ZC,R1N,R2E,R3O), (ZC,R1N,R2E,R3P),
(ZC,R1N,R2E,R3Q), (ZC,R1N,R2E,R3R), (ZC,R1N,R2F,R3A), (ZC,R1N,R2F,R3B), (ZC,R1N,R2F,R3C), (ZC,R1N,R2F,R3D),
(ZC,R1N,R2F,R3E), (ZC,R1N,R2F,R3F), (ZC,R1N,R2F,R3G),
(ZC,R1N,R2F,R3H), (ZC,R1N,R2F,R3I), (ZC,R1N,R2F,R3J),
(ZC,R1N,R2F,R3K), (ZC,R1N,R2F,R3L), (ZC,R1N,R2F,R3M),
(ZC,R1N,R2F,R3N), (ZC,R1N,R2F,R3O), (ZC,R1N,R2F,R3P),
(ZC,R1N,R2F,R3Q), (ZC,R1N,R2F,R3R), (ZC,R1N,R2G,R3A),
(ZC,R1N,R2G,R3B), (ZC,R1N,R2G,R3C), (ZC,R1N,R2G,R3D),
(ZC,R1N,R2G,R3E), (ZC,R1N,R2G,R3F), (ZC,R1N,R2G,R3G),
(ZC,R1N,R2G,R3H), (ZC,R1N,R2G,R3I), (ZC,R1N,R2G,R3J),
(ZC,R1N,R2G,R3K), (ZC,R1N,R2G,R3L), (ZC,R1N,R2G,R3M),
(ZC,R1N,R2G,R3N), (ZC,R1N,R2G,R3O), (ZC,R1N,R2G,R3P),
(ZC,R1N,R2G,R3Q), (ZC,R1N,R2G,R3R), (ZC,R1N,R2H,R3A),
(ZC,R1N,R2H,R3B), (ZC,R1N,R2H,R3C), (ZC,R1N,R2H,R3D),
(ZC,R1N,R2H,R3E), (ZC,R1N,R2H,R3F), (ZC,R1N,R2H,R3G),
(ZC,R1N,R2H,R3H), (ZC,R1N,R2H,R3I), (ZC,R1N,R2H,R3J),
(ZC,R1N,R2H,R3K), (ZC,R1N,R2H,R3L), (ZC,R1N,R2H,R3M),
(ZC,R1N,R2H,R3N), (ZC,R1N,R2H,R3O), (ZC,R1N,R2H,R3P),
(ZC,R1N,R2H,R3Q), (ZC,R1N,R2H,R3R), (ZC,R1N,R2I,R3A),
(ZC,R1N,R2I,R3B), (ZC,R1N,R2I,R3C), (ZC,R1N,R2I,R3D),
(ZC,R1N,R2I,R3E), (ZC,R1N,R2I,R3F), (ZC,R1N,R2I,R3G),
(ZC,R1N,R2I,R3H), (ZC,R1N,R2I,R3I), (ZC,R1N,R2I,R3J), (ZC,R1N,R2I,R3K),
(ZC,R1N,R2I,R3L), (ZC,R1N,R2I,R3M), (ZC,R1N,R2I,R3N),
(ZC,R1N,R2I,R3O), (ZC,R1N,R2I,R3P), (ZC,R1N,R2I,R3Q),
(ZC,R1N,R2I,R3R), (ZC,R1N,R2J,R3A), (ZC,R1N,R2J,R3B),
(ZC,R1N,R2J,R3C), (ZC,R1N,R2J,R3D), (ZC,R1N,R2J,R3E),
(ZC,R1N,R2J,R3F), (ZC,R1N,R2J,R3G), (ZC,R1N,R2J,R3H),
(ZC,R1N,R2J,R3I), (ZC,R1N,R2J,R3J), (ZC,R1N,R2J,R3K),
(ZC,R1N,R2J,R3L), (ZC,R1N,R2J,R3M), (ZC,R1N,R2J,R3N),
(ZC,R1N,R2J,R3O), (ZC,R1N,R2J,R3P), (ZC,R1N,R2J,R3Q),
(ZC,R1N,R2J,R3R), (ZC,R1N,R2K,R3A), (ZC,R1N,R2K,R3B),
(ZC,R1N,R2K,R3C), (ZC,R1N,R2K,R3D), (ZC,R1N,R2K,R3E),
(ZC,R1N,R2K,R3F), (ZC,R1N,R2K,R3G), (ZC,R1N,R2K,R3H),
(ZC,R1N,R2K,R3I), (ZC,R1N,R2K,R3J), (ZC,R1N,R2K,R3K),
(ZC,R1N,R2K,R3L), (ZC,R1N,R2K,R3M), (ZC,R1N,R2K,R3N),
(ZC,R1N,R2K,R3O), (ZC,R1N,R2K,R3P), (ZC,R1N,R2K,R3Q),
(ZC,R1N,R2K,R3R), (ZC,R1N,R2L,R3A), (ZC,R1N,R2L,R3B),
(ZC,R1N,R2L,R3C), (ZC,R1N,R2L,R3D), (ZC,R1N,R2L,R3E),
(ZC,R1N,R2L,R3F), (ZC,R1N,R2L,R3G), (ZC,R1N,R2L,R3H),
(ZC,R1N,R2L,R3I), (ZC,R1N,R2L,R3J), (ZC,R1N, R2L,R3K),
(ZC,R1N,R2L,R3L), (ZC,R1N,R2L,R3M), (ZC,R1N,R2L,R3N),
(ZC,R1N,R2L,R3O), (ZC,R1N,R2L,R3P), (ZC,R1N,R2L,R3Q),
(ZC,R1N,R2L,R3R), (ZC,R1N,R2M,R3A), (ZC,R1N,R2M,R3B),
(ZC,R1N,R2M,R3C), (ZC,R1N,R2M,R3D), (ZC,R1N,R2M,R3E),
(ZC,R1N,R2M,R3F), (ZC,R1N,R2M,R3G), (ZC,R1N,R2M,R3H),
(ZC,R1N,R2M,R3I), (ZC,R1N,R2M,R3J), (ZC,R1N,R2M,R3K),
(ZC,R1N,R2M,R3L), (ZC,R1N,R2M,R3M), (ZC,R1N,R2M,R3N),
(ZC,R1N,R2M,R3O), (ZC,R1N,R2M,R3P), (ZC,R1N,R2M,R3Q),
(ZC,R1N,R2M,R3R), (ZC,R1N,R2N,R3A), (ZC,R1N,R2N,R3B),
(ZC,R1N,R2N,R3C), (ZC,R1N,R2N,R3D), (ZC,R1N,R2N,R3E),
(ZC,R1N,R2N,R3F), (ZC,R1N,R2N,R3G), (ZC,R1N,R2N,R3H),
(ZC,R1N,R2N,R3I), (ZC,R1N,R2N,R3J), (ZC,R1N,R2N,R3K),
(ZC,R1N,R2N,R3L), (ZC,R1N,R2N,R3M), (ZC,R1N,R2N,R3N),
(ZC,R1N,R2N,R3O), (ZC,R1N,R2N,R3P), (ZC,R1N,R2N,R3Q),
(ZC,R1N,R2N,R3R), (ZC,R1O,R2A,R3A), (ZC,R1O,R2A,R3B),
(ZC,R1O,R2A,R3C), (ZC,R1O,R2A,R3D), (ZC,R1O,R2A,R3E),
(ZC,R1O,R2A,R3F), (ZC,R1O,R2A,R3G), (ZC,R1O,R2A,R3H),
(ZC,R1O,R2A,R3I), (ZC,R1O,R2A,R3J), (ZC,R1O,R2A,R3K),
(ZC,R1O,R2A,R3L), (ZC,R1O,R2A,R3M), (ZC,R1O,R2A,R3N),
(ZC,R1O,R2A,R3O), (ZC,R1O,R2A,R3P), (ZC,R1O,R2A,R3Q),
(ZC,R1O,R2A,R3R), (ZC,R1O,R2B,R3A), (ZC,R1O,R2B,R3B),
(ZC,R1O,R2B,R3C), (ZC,R1O,R2B,R3D), (ZC,R1O,R2B,R3E),
(ZC,R1O,R2B,R3F), (ZC,R1O,R2B,R3G), (ZC,R1O,R2B,R3H),
(ZC,R1O,R2B,R3I), (ZC,R1O,R2B,R3J), (ZC,R1O,R2B,R3K),
(ZC,R1O,R2B,R3L), (ZC,R1O,R2B,R3M), (ZC,R1O,R2B,R3N),
(ZC,R1O,R2B,R3O), (ZC,R1O,R2B,R3P), (ZC,R1O,R2B,R3Q),
(ZC,R1O,R2B,R3R), (ZC,R1O,R2C,R3A), (ZC,R1O,R2C,R3B), (ZC,R1O,R2C,R3C), (ZC,R1O,R2C,R3D), (ZC,R1O,R2C,R3E),
(ZC,R1O,R2C,R3F), (ZC,R1O,R2C,R3G), (ZC,R1O,R2C,R3H),
(ZC,R1O,R2C,R3I), (ZC,R1O,R2C,R3J), (ZC,R1O,R2C,R3K),
(ZC,R1O,R2C,R3L), (ZC,R1O,R2C,R3M), (ZC,R1O,R2C,R3N),
(ZC,R1O,R2C,R3O), (ZC,R1O,R2C,R3P), (ZC,R1O,R2C,R3Q),
(ZC,R1O,R2C,R3R), (ZC,R1O,R2D,R3A), (ZC,R1O,R2D,R3B),
(ZC,R1O,R2D,R3C), (ZC,R1O,R2D,R3D), (ZC,R1O,R2D,R3E),
(ZC,R1O,R2D,R3F), (ZC,R1O,R2D,R3G), (ZC,R1O,R2D,R3H),
(ZC,R1O,R2D,R3I), (ZC,R1O,R2D,R3J), (ZC,R1O,R2D,R3K),
(ZC,R1O,R2D,R3L), (ZC,R1O,R2D,R3M), (ZC,R1O,R2D,R3N),
(ZC,R1O,R2D,R3O), (ZC,R1O,R2D,R3P), (ZC,R1O,R2D,R3Q),
(ZC,R1O,R2D,R3R), (ZC,R1O,R2E,R3A), (ZC,R1O,R2E,R3B),
(ZC,R1O,R2E,R3C), (ZC,R1O,R2E,R3D), (ZC,R1O,R2E,R3E),
(ZC,R1O,R2E,R3F), (ZC,R1O,R2E,R3G), (ZC,R1O,R2E,R3H),
(ZC,R1O,R2E,R3I), (ZC,R1O,R2E,R3J), (ZC,R1O,R2E,R3K),
(ZC,R1O,R2E,R3L), (ZC,R1O,R2E,R3M), (ZC,R1O,R2E,R3N),
(ZC,R1O,R2E,R3O), (ZC,R1O,R2E,R3P), (ZC,R1O,R2E,R3Q),
(ZC,R1O,R2E,R3R), (ZC,R1O,R2F,R3A), (ZC,R1O,R2F,R3B),
(ZC,R1O,R2F,R3C), (ZC,R1O,R2F,R3D), (ZC,R1O,R2F,R3E),
(ZC,R1O,R2F,R3F), (ZC,R1O,R2F,R3G), (ZC,R1O,R2F,R3H),
(ZC,R1O,R2F,R3I), (ZC,R1O,R2F,R3J), (ZC,R1O,R2F,R3K),
(ZC,R1O,R2F,R3L), (ZC,R1O,R2F,R3M), (ZC,R1O,R2F,R3N),
(ZC,R1O,R2F,R3O), (ZC,R1O,R2F,R3P), (ZC,R1O,R2F,R3Q),
(ZC,R1O,R2F,R3R), (ZC,R1O,R2G,R3A), (ZC,R1O,R2G,R3B),
(ZC,R1O,R2G,R3C), (ZC,R1O,R2G,R3D), (ZC,R1O,R2G,R3E),
(ZC,R1O,R2G,R3F), (ZC,R1O,R2G,R3G), (ZC,R1O,R2G,R3H),
(ZC,R1O,R2G,R3I), (ZC,R1O,R2G,R3J), (ZC,R1O,R2G,R3K),
(ZC,R1O,R2G,R3L), (ZC,R1O,R2G,R3M), (ZC,R1O,R2G,R3N),
(ZC,R1O,R2G,R3O), (ZC,R1O,R2G,R3P), (ZC,R1O,R2G,R3Q),
(ZC,R1O,R2G,R3R), (ZC,R1O,R2H,R3A), (ZC,R1O,R2H,R3B),
(ZC,R1O,R2H,R3C), (ZC,R1O,R2H,R3D), (ZC,R1O,R2H,R3E),
(ZC,R1O,R2H,R3F), (ZC,R1O,R2H,R3G), (ZC,R1O,R2H,R3H),
(ZC,R1O,R2H,R3I), (ZC,R1O,R2H,R3J), (ZC,R1O,R2H,R3K),
(ZC,R1O,R2H,R3L), (ZC,R1O,R2H,R3M), (ZC,R1O,R2H,R3N),
(ZC,R1O,R2H,R3O), (ZC,R1O,R2H,R3P), (ZC,R1O,R2H,R3Q),
(ZC,R1O,R2H,R3R), (ZC,R1O,R2I,R3A), (ZC,R1O,R2I,R3B),
(ZC,R1O,R2I,R3C), (ZC,R1O,R2I,R3D), (ZC,R1O,R2I,R3E),
(ZC,R1O,R2I,R3F), (ZC,R1O,R2I,R3G), (ZC,R1O,R2I,R3H), (ZC,R1O,R2I,R3I),
(ZC,R1O,R2I,R3J), (ZC,R1O,R2I,R3K), (ZC,R1O,R2I,R3L),
(ZC,R1O,R2I,R3M), (ZC,R1O,R2I,R3N), (ZC,R1O,R2I,R3O),
(ZC,R1O,R2I,R3P), (ZC,R1O,R2I,R3Q), (ZC,R1O,R2I,R3R),
(ZC,R1O,R2J,R3A), (ZC,R1O,R2J,R3B), (ZC,R1O,R2J,R3C),
(ZC,R1O,R2J,R3D), (ZC,R1O,R2J,R3E), (ZC,R1O,R2J,R3F),
(ZC,R1O,R2J,R3G), (ZC,R1O,R2J,R3H), (ZC,R1O,R2J,R3I),
(ZC,R1O,R2J,R3J), (ZC,R1O,R2J,R3K), (ZC,R1O,R2J,R3L),
(ZC,R1O,R2J,R3M), (ZC,R1O,R2J,R3N), (ZC,R1O,R2J,R3O),
(ZC,R1O,R2J,R3P), (ZC,R1O,R2J,R3Q), (ZC,R1O,R2J,R3R),
(ZC,R1O,R2K,R3A), (ZC,R1O,R2K,R3B), (ZC,R1O,R2K,R3C),
(ZC,R1O,R2K,R3D), (ZC,R1O,R2K,R3E), (ZC,R1O,R2K,R3F),
(ZC,R1O,R2K,R3G), (ZC,R1O,R2K,R3H), (ZC,R1O,R2K,R3I),
(ZC,R1O,R2K,R3J), (ZC,R1O,R2K,R3K), (ZC,R1O,R2K,R3L),
(ZC,R1O,R2K,R3M), (ZC,R1O,R2K,R3N), (ZC,R1O,R2K,R3O),
(ZC,R1O,R2K,R3P), (ZC,R1O,R2K,R3Q), (ZC,R1O,R2K,R3R),
(ZC,R1O,R2L,R3A), (ZC,R1O,R2L,R3B), (ZC,R1O,R2L,R3C),
(ZC,R1O,R2L,R3D), (ZC,R1O,R2L,R3E), (ZC,R1O,R2L,R3F),
(ZC,R1O,R2L,R3G), (ZC,R1O,R2L,R3H), (ZC,R1O,R2L,R3I),
(ZC,R1O,R2L,R3J), (ZC,R1O,R2L,R3K), (ZC,R1O,R2L,R3L),
(ZC,R1O,R2L,R3M), (ZC,R1O,R2L,R3N), (ZC,R1O,R2L,R3O),
(ZC,R1O,R2L,R3P), (ZC,R1O,R2L,R3Q), (ZC,R1O,R2L,R3R),
(ZC,R1O,R2M,R3A), (ZC,R1O,R2M,R3B), (ZC,R1O,R2M,R3C),
(ZC,R1O,R2M,R3D), (ZC,R1O,R2M,R3E), (ZC,R1O,R2M,R3F),
(ZC,R1O,R2M,R3G), (ZC,R1O,R2M,R3H), (ZC,R1O,R2M,R3I),
(ZC,R1O,R2M,R3J), (ZC,R1O,R2M,R3K), (ZC,R1O,R2M,R3L),
(ZC,R1O,R2M,R3M), (ZC,R1O,R2M,R3N), (ZC,R1O,R2M,R3O)
(ZC,R1O,R2M,R3P), (ZC,R1O,R2M,R3Q), (ZC,R1O,R2M,R3R),
(ZC,R1O,R2N,R3A), (ZC,R1O,R2N,R3B), (ZC,R1O,R2N,R3C), (ZC,R1O,R2N,R3D), (ZC,R1O,R2N,R3E), (ZC,R1O,R2N,R3F),
(ZC,R1O,R2N,R3G), (ZC,R1O,R2N,R3H), (ZC,R1O,R2N,R3I),
(ZC,R1O,R2N,R3J), (ZC,R1O,R2N,R3K), (ZC,R1O,R2N,R3L),
(ZC,R1O,R2N,R3M), (ZC,R1O,R2N,R3N), (ZC,R1O,R2N,R3O),
(ZC,R1O,R2N,R3P), (ZC,R1O,R2N,R3Q), (ZC,R1O,R2N,R3R),
(ZC,R1P,R2A,R3A), (ZC,R1P,R2A,R3B), (ZC,R1P,R2A,R3C),
(ZC,R1P,R2A,R3D), (ZC,R1P,R2A,R3E), (ZC,R1P,R2A,R3F),
(ZC,R1P,R2A,R3G), (ZC,R1P,R2A,R3H), (ZC,R1P,R2A,R3I),
(ZC,R1P,R2A,R3J), (ZC,R1P,R2A,R3K), (ZC,R1P,R2A,R3L),
(ZC,R1P,R2A,R3M), (ZC,R1P,R2A,R3N), (ZC,R1P,R2A,R3O),
(ZC,R1P,R2A,R3P), (ZC,R1P,R2A,R3Q), (ZC,R1P,R2A,R3R),
(ZC,R1P,R2B,R3A), (ZC,R1P,R2B,R3B), (ZC,R1P,R2B,R3C),
(ZC,R1P,R2B,R3D), (ZC,R1P,R2B,R3E), (ZC,R1P,R2B,R3F),
(ZC,R1P,R2B,R3G), (ZC,R1P,R2B,R3H), (ZC,R1P,R2B,R3I),
(ZC,R1P,R2B,R3J), (ZC,R1P,R2B,R3K), (ZC,R1P,R2B,R3L),
(ZC,R1P,R2B,R3M), (ZC,R1P,R2B,R3N), (ZC,R1P,R2B,R3O),
(ZC,R1P,R2B,R3P), (ZC,R1P,R2B,R3Q), (ZC,R1P,R2B,R3R),
(ZC,R1P,R2C,R3A), (ZC,R1P,R2C,R3B), (ZC,R1P,R2C,R3C),
(ZC,R1P,R2C,R3D), (ZC,R1P,R2C,R3E), (ZC,R1P,R2C,R3F),
(ZC,R1P,R2C,R3G), (ZC,R1P,R2C,R3H), (ZC,R1P,R2C,R3I),
(ZC,R1P,R2C,R3J), (ZC,R1P,R2C,R3K), (ZC,R1P,R2C,R3L),
(ZC,R1P,R2C,R3M), (ZC,R1P,R2C,R3N), (ZC,R1P,R2C,R3O),
(ZC,R1P,R2C,R3P), (ZC,R1P,R2C,R3Q), (ZC,R1P,R2C,R3R),
(ZC,R1P,R2D,R3A), (ZC,R1P,R2D,R3B), (ZC,R1P,R2D,R3C),
(ZC,R1P,R2D,R3D), (ZC,R1P,R2D,R3E), (ZC,R1P,R2D,R3F),
(ZC,R1P,R2D,R3G), (ZC,R1P,R2D,R3H), (ZC,R1P,R2D,R3I),
(ZC,R1P,R2D,R3J), (ZC,R1P,R2D,R3K), (ZC,R1P,R2D,R3L),
(ZC,R1P,R2D,R3M), (ZC,R1P,R2D,R3N), (ZC,R1P,R2D,R3O),
(ZC,R1P,R2D,R3P), (ZC,R1P,R2D,R3Q), (ZC,R1P,R2D,R3R),
(ZC,R1P,R2E,R3A), (ZC,R1P,R2E,R3B), (ZC,R1P,R2E,R3C),
(ZC,R1P,R2E,R3D), (ZC,R1P,R2E,R3E), (ZC,R1P,R2E,R3F),
(ZC,R1P,R2E,R3G), (ZC,R1P,R2E,R3H), (ZC,R1P,R2E,R3I),
(ZC,R1P,R2E,R3J), (ZC,R1P,R2E,R3K), (ZC,R1P,R2E,R3L),
(ZC,R1P,R2E,R3M), (ZC,R1P,R2E,R3N), (ZC,R1P,R2E,R3O),
(ZC,R1P,R2E,R3P), (ZC,R1P,R2E,R3Q), (ZC,R1P,R2E,R3R),
(ZC,R1P,R2F,R3A), (ZC,R1P,R2F,R3B), (ZC,R1P,R2F,R3C),
(ZC,R1P,R2F,R3D), (ZC,R1P,R2F,R3E), (ZC,R1P,R2F,R3F),
(ZC,R1P,R2F,R3G), (ZC,R1P,R2F,R3H), (ZC,R1P,R2F,R3I),
(ZC,R1P,R2F,R3J), (ZC,R1P,R2F,R3K), (ZC,R1P,R2F,R3L),
(ZC,R1P,R2F,R3M), (ZC,R1P,R2F,R3N), (ZC,R1P,R2F,R3O),
(ZC,R1P,R2F,R3P), (ZC,R1P,R2F,R3Q), (ZC,R1P,R2F,R3R),
(ZC,R1P,R2G,R3A), (ZC,R1P,R2G,R3B), (ZC,R1P,R2G,R3C),
(ZC,R1P,R2G,R3D), (ZC,R1P,R2G,R3E), (ZC,R1P,R2G,R3F),
(ZC,R1P,R2G,R3G), (ZC,R1P,R2G,R3H), (ZC,R1P,R2G,R3I),
(ZC,R1P,R2G,R3J), (ZC,R1P,R2G,R3K), (ZC,R1P,R2G,R3L),
(ZC,R1P,R2G,R3M), (ZC,R1P,R2G,R3N), (ZC,R1P,R2G,R3O),
(ZC,R1P,R2G,R3P), (ZC,R1P,R2G,R3Q), (ZC,R1P,R2G,R3R),
(ZC,R1P,R2H,R3A), (ZC,R1P,R2H,R3B), (ZC,R1P,R2H,R3C),
(ZC,R1P,R2H,R3D), (ZC,R1P,R2H,R3E), (ZC,R1P,R2H,R3F),
(ZC,R1P,R2H,R3G), (ZC,R1P,R2H,R3H), (ZC,R1P,R2H,R3I),
(ZC,R1P,R2H,R3J), (ZC,R1P,R2H,R3K), (ZC,R1P,R2H,R3L),
(ZC,R1P,R2H,R3M), (ZC,R1P,R2H,R3N), (ZC,R1P,R2H,R3O),
(ZC,R1P,R2H,R3P), (ZC,R1P,R2H,R3Q), (ZC,R1P,R2H,R3R),
(ZC,R1P,R2I,R3A), (ZC,R1P,R2I,R3B), (ZC,R1P,R2I,R3C), (ZC,R1P,R2I,R3D),
(ZC,R1P,R2I,R3E), (ZC,R1P,R2I,R3F), (ZC,R1P,R2I,R3G), (ZC,R1P,R2I,R3H),
(ZC,R1P,R2I,R3I), (ZC,R1P,R2I,R3J), (ZC,R1P,R2I,R3K), (ZC,R1P,R2I,R3L),
(ZC,R1P,R2I,R3M), (ZC,R1P,R2I,R3N), (ZC,R1P,R2I,R3O), (ZC,R1P,R2I,R3P),
(ZC,R1P,R2I,R3Q), (ZC,R1P,R2I,R3R), (ZC,R1P,R2J,R3A),
(ZC,R1P,R2J,R3B), (ZC,R1P,R2J,R3C), (ZC,R1P,R2J,R3D),
(ZC,R1P,R2J,R3E), (ZC,R1P,R2J,R3F), (ZC,R1P,R2J,R3G),
(ZC,R1P,R2J,R3H), (ZC,R1P,R2J,R3I), (ZC,R1P,R2J,R3J),
(ZC,R1P,R2J,R3K), (ZC,R1P,R2J,R3L), (ZC,R1P,R2J,R3M),
(ZC,R1P,R2J,R3N), (ZC,R1P,R2J,R3O), (ZC,R1P,R2J,R3P),
(ZC,R1P,R2J,R3Q), (ZC,R1P,R2J,R3R), (ZC,R1P,R2K,R3A),
(ZC,R1P,R2K,R3B), (ZC,R1P,R2K,R3C), (ZC,R1P,R2K,R3D),
(ZC,R1P,R2K,R3E), (ZC,R1P,R2K,R3F), (ZC,R1P,R2K,R3G),
(ZC,R1P,R2K,R3H), (ZC,R1P,R2K,R3I), (ZC,R1P,R2K,R3J), (ZC,R1P,R2K,R3K), (ZC,R1P,R2K,R3L), (ZC,R1P,R2K, R3M),
(ZC,R1P,R2K,R3N), (ZC,R1P,R2K,R3O), (ZC,R1P,R2K, R3P),
(ZC,R1P,R2K,R3Q), (ZC,R1P,R2K,R3R), (ZC,R1P,R2L, R3A),
(ZC,R1P,R2L,R3B), (ZC,R1P,R2L,R3C), (ZC,R1P,R2L, R3D),
(ZC,R1P,R2L,R3E), (ZC,R1P,R2L,R3F), (ZC,R1P,R2L, R3G),
(ZC,R1P,R2L,R3H), (ZC,R1P,R2L,R3I), (ZC,R1P,R2L, R3J),
(ZC,R1P,R2L,R3K), (ZC,R1P,R2L,R3L), (ZC,R1P,R2L, R3M),
(ZC,R1P,R2L,R3N), (ZC,R1P,R2L,R3O), (ZC,R1P,R2L, R3P),
(ZC,R1P,R2L,R3Q), (ZC,R1P,R2L,R3R), (ZC,R1P,R2M, R3A),
(ZC,R1P,R2M,R3B), (ZC,R1P,R2M,R3C), (ZC,R1P,R2M, R3D),
(ZC,R1P,R2M,R3E), (ZC,R1P,R2M,R3F), (ZC,R1P,R2M, R3G),
(ZC,R1P,R2M,R3H), (ZC,R1P,R2M,R3I), (ZC,R1P,R2M, R3J),
(ZC,R1P,R2M,R3K), (ZC,R1P,R2M,R3L), (ZC,R1P,R2M, R3M),
(ZC,R1P,R2M,R3N), (ZC,R1P,R2M,R3O), (ZC,R1P,R2M, R3P),
(ZC,R1P,R2M,R3Q), (ZC,R1P,R2M,R3R), (ZC,R1P,R2N, R3A),
(ZC,R1P,R2N,R3B), (ZC,R1P,R2N,R3C), (ZC,R1P,R2N, R3D),
(ZC,R1P,R2N,R3E), (ZC,R1P,R2N,R3F), (ZC,R1P,R2N, R3G),
(ZC,R1P,R2N,R3H), (ZC,R1P,R2N,R3I), (ZC,R1P,R2N, R3J),
(ZC,R1P,R2N,R3K), (ZC,R1P,R2N,R3L), (ZC,R1P,R2N, R3M),
(ZC,R1P,R2N,R3N), (ZC,R1P,R2N,R3O), (ZC,R1P,R2N, R3P),
(ZC,R1P,R2N,R3Q), (ZC,R1P,R2N,R3R), (ZC,R1Q,R2A, R3A),
(ZC,R1Q,R2A,R3B), (ZC,R1Q,R2A,R3C), (ZC,R1Q,R2A, R3D),
(ZC,R1Q,R2A,R3E), (ZC,R1Q,R2A,R3F), (ZC,R1Q,R2A, R3G),
(ZC,R1Q,R2A,R3H), (ZC,R1Q,R2A,R3I), (ZC,R1Q,R2A, R3J),
(ZC,R1Q,R2A,R3K), (ZC,R1Q,R2A,R3L), (ZC,R1Q,R2A, R3M),
(ZC,R1Q,R2A,R3N), (ZC,R1Q,R2A,R3O), (ZC,R1Q,R2A, R3P),
(ZC,R1Q,R2A,R3Q), (ZC,R1Q,R2A,R3R), (ZC,R1Q,R2B, R3A),
(ZC,R1Q,R2B,R3B), (ZC,R1Q,R2B,R3C), (ZC,R1Q,R2B, R3D),
(ZC,R1Q,R2B,R3E), (ZC,R1Q,R2B,R3F), (ZC,R1Q,R2B, R3G),
(ZC,R1Q,R2B,R3H), (ZC,R1Q,R2B,R3I), (ZC,R1Q,R2B, R3J),
(ZC,R1Q,R2B,R3K), (ZC,R1Q,R2B,R3L), (ZC,R1Q,R2B, R3M),
(ZC,R1Q,R2B,R3N), (ZC,R1Q,R2B,R3O), (ZC,R1Q,R2B, R3P),
(ZC,R1Q,R2B,R3Q), (ZC,R1Q,R2B,R3R), (ZC,R1Q,R2C, R3A),
(ZC,R1Q,R2C,R3B), (ZC,R1Q,R2C,R3C), (ZC,R1Q,R2C, R3D),
(ZC,R1Q,R2C,R3E), (ZC,R1Q,R2C,R3F), (ZC,R1Q,R2C, R3G),
(ZC,R1Q,R2C,R3H), (ZC,R1Q,R2C,R3I), (ZC,R1Q,R2C, R3J),
(ZC,R1Q,R2C,R3K), (ZC,R1Q,R2C,R3L), (ZC,R1Q,R2C, R3M),
(ZC,R1Q,R2C,R3N), (ZC,R1Q,R2C,R3O), (ZC,R1Q,R2C, R3P),
(ZC,R1Q,R2C,R3Q), (ZC,R1Q,R2C,R3R), (ZC,R1Q,R2D, R3A),
(ZC,R1Q,R2D,R3B), (ZC,R1Q,R2D,R3C), (ZC,R1Q,R2D, R3D),
(ZC,R1Q,R2D,R3E), (ZC,R1Q,R2D,R3F), (ZC,R1Q,R2D, R3G),
(ZC,R1Q,R2D,R3H), (ZC,R1Q,R2D,R3I), (ZC,R1Q,R2D, R3J),
(ZC,R1Q,R2D,R3K), (ZC,R1Q,R2D,R3L), (ZC,R1Q,R2D, R3M),
(ZC,R1Q,R2D,R3N), (ZC,R1Q,R2D,R3O), (ZC,R1Q,R2D, R3P),
(ZC,R1Q,R2D,R3Q), (ZC,R1Q,R2D,R3R), (ZC,R1Q,R2E, R3A),
(ZC,R1Q,R2E,R3B), (ZC,R1Q,R2E,R3C), (ZC,R1Q,R2E, R3D),
(ZC,R1Q,R2E,R3E), (ZC,R1Q,R2E,R3F), (ZC,R1Q,R2E, R3G),
(ZC,R1Q,R2E,R3H), (ZC,R1Q,R2E,R3I), (ZC,R1Q,R2E, R3J),
(ZC,R1Q,R2E,R3K), (ZC,R1Q,R2E,R3L), (ZC,R1Q,R2E, R3M),
(ZC,R1Q,R2E,R3N), (ZC,R1Q,R2E,R3O), (ZC,R1Q,R2E, R3P),
(ZC,R1Q,R2E,R3Q), (ZC,R1Q,R2E,R3R), (ZC,R1Q,R2F, R3A),
(ZC,R1Q,R2F,R3B), (ZC,R1Q,R2F,R3C), (ZC,R1Q,R2F, R3D),
(ZC,R1Q,R2F,R3E), (ZC,R1Q,R2F,R3F), (ZC,R1Q,R2F, R3G),
(ZC,R1Q,R2F,R3H), (ZC,R1Q,R2F,R3I), (ZC,R1Q,R2F, R3J),
(ZC,R1Q,R2F,R3K), (ZC,R1Q,R2F,R3L), (ZC,R1Q,R2F, R3M),
(ZC,R1Q,R2F,R3N), (ZC,R1Q,R2F,R3O), (ZC,R1Q,R2F, R3P),
(ZC,R1Q,R2F,R3Q), (ZC,R1Q,R2F,R3R), (ZC,R1Q,R2G, R3A),
(ZC,R1Q,R2G,R3B), (ZC,R1Q,R2G,R3C), (ZC,R1Q,R2G, R3D),
(ZC,R1Q,R2G,R3E), (ZC,R1Q,R2G,R3F), (ZC,R1Q,R2G, R3G),
(ZC,R1Q,R2G,R3H), (ZC,R1Q,R2G,R3I), (ZC,R1Q,R2G, R3J),
(ZC,R1Q,R2G,R3K), (ZC,R1Q,R2G,R3L), (ZC,R1Q,R2G, R3M),
(ZC,R1Q,R2G,R3N), (ZC,R1Q,R2G,R3O), (ZC,R1Q,R2G, R3P),
(ZC,R1Q,R2G,R3Q), (ZC,R1Q,R2G,R3R), (ZC,R1Q,R2H, R3A),
(ZC,R1Q,R2H,R3B), (ZC,R1Q,R2H,R3C), (ZC,R1Q,R2H, R3D),
(ZC,R1Q,R2H,R3E), (ZC,R1Q,R2H,R3F), (ZC,R1Q,R2H, R3G),
(ZC,R1Q,R2H,R3H), (ZC,R1Q,R2H,R3I), (ZC,R1Q,R2H, R3J), (ZC,R1Q,R2H,R3K), (ZC,R1Q,R2H,R3L), (ZC,R1Q,R2H,R3M),
(ZC,R1Q,R2H,R3N), (ZC,R1Q,R2H,R3O), (ZC,R1Q,R2H,R3P),
(ZC,R1Q,R2H,R3Q), (ZC,R1Q,R2H,R3R), (ZC,R1Q,R2I,R3A),
(ZC,R1Q,R2I,R3B), (ZC,R1Q,R2I,R3C), (ZC,R1Q,R2I,R3D),
(ZC,R1Q,R2I,R3E), (ZC,R1Q,R2I,R3F), (ZC,R1Q,R2I,R3G),
(ZC,R1Q,R2I,R3H), (ZC,R1Q,R2I,R3I), (ZC,R1Q,R2I,R3J), (ZC,R1Q,R2I,R3K),
(ZC,R1Q,R2I,R3L), (ZC,R1Q,R2I,R3M), (ZC,R1Q,R2I,R3N),
(ZC,R1Q,R2I,R3O), (ZC,R1Q,R2I,R3P), (ZC,R1Q,R2I,R3Q),
(ZC,R1Q,R2I,R3R), (ZC,R1Q,R2J,R3A), (ZC,R1Q,R2J,R3B),
(ZC,R1Q,R2J,R3C), (ZC,R1Q,R2J,R3D), (ZC,R1Q,R2J,R3E),
(ZC,R1Q,R2J,R3F), (ZC,R1Q,R2J,R3G), (ZC,R1Q,R2J,R3H),
(ZC,R1Q,R2J,R3I), (ZC,R1Q,R2J,R3J), (ZC,R1Q,R2J,R3K),
(ZC,R1Q,R2J,R3L), (ZC,R1Q,R2J,R3M), (ZC,R1Q,R2J,R3N),
(ZC,R1Q,R2J,R3O), (ZC,R1Q,R2J,R3P), (ZC,R1Q,R2J,R3Q),
(ZC,R1Q,R2J,R3R), (ZC,R1Q,R2K,R3A), (ZC,R1Q,R2K,R3B),
(ZC,R1Q,R2K,R3C), (ZC,R1Q,R2K,R3D), (ZC,R1Q,R2K,R3E),
(ZC,R1Q,R2K,R3F), (ZC,R1Q,R2K,R3G), (ZC,R1Q,R2K,R3H),
(ZC,R1Q,R2K,R3I), (ZC,R1Q,R2K,R3J), (ZC,R1Q,R2K,R3K),
(ZC,R1Q,R2K,R3L), (ZC,R1Q,R2K,R3M), (ZC,R1Q,R2K,R3N),
(ZC,R1Q,R2K,R3O), (ZC,R1Q,R2K,R3P), (ZC,R1Q,R2K,R3Q),
(ZC,R1Q,R2K,R3R), (ZC,R1Q,R2L,R3A), (ZC,R1Q,R2L,R3B),
(ZC,R1Q,R2L,R3C), (ZC,R1Q,R2L,R3D), (ZC,R1Q,R2L,R3E),
(ZC,R1Q,R2L,R3F), (ZC,R1Q,R2L,R3G), (ZC,R1Q,R2L,R3H),
(ZC,R1Q,R2L,R3I), (ZC,R1Q,R2L,R3J), (ZC,R1Q,R2L,R3K),
(ZC,R1Q,R2L,R3L), (ZC,R1Q,R2L,R3M), (ZC,R1Q,R2L,R3N),
(ZC,R1Q,R2L,R3O), (ZC,R1Q,R2L,R3P), (ZC,R1Q,R2L,R3Q),
(ZC,R1Q,R2L,R3R), (ZC,R1Q,R2M,R3A), (ZC,R1Q,R2M,R3B),
(ZC,R1Q,R2M,R3C), (ZC,R1Q,R2M,R3D), (ZC,R1Q,R2M,R3E),
(ZC,R1Q,R2M,R3F), (ZC,R1Q,R2M,R3G), (ZC,R1Q,R2M,R3H),
(ZC,R1Q,R2M,R3I), (ZC,R1Q,R2M,R3J), (ZC,R1Q,R2M,R3K),
(ZC,R1Q,R2M,R3L), (ZC,R1Q,R2M,R3M), (ZC,R1Q,R2M,R3N),
(ZC,R1Q,R2M,R3O), (ZC,R1Q,R2M,R3P), (ZC,R1Q,R2M,R3Q),
(ZC,R1Q,R2M,R3R), (ZC,R1Q,R2N,R3A), (ZC,R1Q,R2N,R3B),
(ZC,R1Q,R2N,R3C), (ZC,R1Q,R2N,R3D), (ZC,R1Q,R2N,R3E),
(ZC,R1Q,R2N,R3F), (ZC,R1Q,R2N,R3G), (ZC,R1Q,R2N,R3H),
(ZC,R1Q,R2N,R3I), (ZC,R1Q,R2N,R3J), (ZC,R1Q,R2N,R3K),
(ZC,R1Q,R2N,R3L), (ZC,R1Q,R2N,R3M), (ZC,R1Q,R2N,R3N),
(ZC,R1Q,R2N,R3O), (ZC,R1Q,R2N,R3P), (ZC,R1Q,R2N,R3Q),
(ZC,R1Q,R2N,R3R), (ZC,R1R,R2A,R3A), (ZC,R1R,R2A,R3B),
(ZC,R1R,R2A,R3C), (ZC,R1R,R2A,R3D), (ZC,R1R,R2A,R3E),
(ZC,R1R,R2A,R3F), (ZC,R1R,R2A,R3G), (ZC,R1R,R2A,R3H),
(ZC,R1R,R2A,R3I), (ZC,R1R,R2A,R3J), (ZC,R1R,R2A,R3K),
(ZC,R1R,R2A,R3L), (ZC,R1R,R2A,R3M), (ZC,R1R,R2A,R3N),
(ZC,R1R,R2A,R3O), (ZC,R1R,R2A,R3P), (ZC,R1R,R2A,R3Q),
(ZC,R1R,R2A,R3R), (ZC,R1R,R2B,R3A), (ZC,R1R,R2B,R3B),
(ZC,R1R,R2B,R3C), (ZC,R1R,R2B,R3D), (ZC,R1R,R2B,R3E),
(ZC,R1R,R2B,R3F), (ZC,R1R,R2B,R3G), (ZC,R1R,R2B,R3H),
(ZC,R1R,R2B,R3I), (ZC,R1R,R2B,R3J), (ZC,R1R,R2B,R3K),
(ZC,R1R,R2B,R3L), (ZC,R1R,R2B,R3M), (ZC,R1R,R2B,R3N),
(ZC,R1R,R2B,R3O), (ZC,R1R,R2B,R3P), (ZC,R1R,R2B,R3Q),
(ZC,R1R,R2B,R3R), (ZC,R1R,R2C,R3A), (ZC,R1R,R2C,R3B),
(ZC,R1R,R2C,R3C), (ZC,R1R,R2C,R3D), (ZC,R1R,R2C,R3E),
(ZC,R1R,R2C,R3F), (ZC,R1R,R2C,R3G), (ZC,R1R,R2C,R3H),
(ZC,R1R,R2C,R3I), (ZC,R1R,R2C,R3J), (ZC,R1R,R2C,R3K),
(ZC,R1R,R2C,R3L), (ZC,R1R,R2C,R3M), (ZC,R1R,R2C,R3N),
(ZC,R1R,R2C,R3O), (ZC,R1R,R2C,R3P), (ZC,R1R,R2C,R3Q),
(ZC,R1R,R2C,R3R), (ZC,R1R,R2D,R3A), (ZC,R1R,R2D,R3B),
(ZC,R1R,R2D,R3C), (ZC,R1R,R2D,R3D), (ZC,R1R,R2D,R3E),
(ZC,R1R,R2D,R3F), (ZC,R1R,R2D,R3G), (ZC,R1R,R2D,R3H),
(ZC,R1R,R2D,R3I), (ZC,R1R,R2D,R3J), (ZC,R1R,R2D,R3K),
(ZC,R1R,R2D,R3L), (ZC,R1R,R2D,R3M), (ZC,R1R,R2D,R3N),
(ZC,R1R,R2D,R3O), (ZC,R1R,R2D,R3P), (ZC,R1R,R2D,R3Q),
(ZC,R1R,R2D,R3R), (ZC,R1R,R2E,R3A), (ZC,R1R,R2E,R3B),
(ZC,R1R,R2E,R3C), (ZC,R1R,R2E,R3D), (ZC,R1R,R2E,R3E),
(ZC,R1R,R2E,R3F), (ZC,R1R,R2E,R3G), (ZC,R1R,R2E,R3H),
(ZC,R1R,R2E,R3I), (ZC,R1R,R2E,R3J), (ZC,R1R,R2E,R3K), (ZC,R1R,R2E,R3L), (ZC,R1R,R2E,R3M), (ZC,R1R,R2E,R3N),
(ZC,R1R,R2E,R3O), (ZC,R1R,R2E,R3P), (ZC,R1R,R2E,R3Q),
(ZC,R1R,R2E,R3R), (ZC,R1R,R2F,R3A), (ZC,R1R,R2F,R3B),
(ZC,R1R,R2F,R3C), (ZC,R1R,R2F,R3D), (ZC,R1R,R2F,R3E),
(ZC,R1R,R2F,R3F), (ZC,R1R,R2F,R3G), (ZC,R1R,R2F,R3H),
(ZC,R1R,R2F,R3I), (ZC,R1R,R2F,R3J), (ZC,R1R,R2F,R3K),
(ZC,R1R,R2F,R3L), (ZC,R1R,R2F,R3M), (ZC,R1R,R2F,R3N),
(ZC,R1R,R2F,R3O), (ZC,R1R,R2F,R3P), (ZC,R1R,R2F,R3Q),
(ZC,R1R,R2F,R3R), (ZC,R1R,R2G,R3A), (ZC,R1R,R2G,R3B),
(ZC,R1R,R2G,R3C), (ZC,R1R,R2G,R3D), (ZC,R1R,R2G,R3E),
(ZC,R1R,R2G,R3F), (ZC,R1R,R2G,R3G), (ZC,R1R,R2G,R3H),
(ZC,R1R,R2G,R3I), (ZC,R1R,R2G,R3J), (ZC,R1R,R2G,R3K),
(ZC,R1R,R2G,R3L), (ZC,R1R,R2G,R3M), (ZC,R1R,R2G,R3N),
(ZC,R1R,R2G,R3O), (ZC,R1R,R2G,R3P), (ZC,R1R,R2G,R3Q),
(ZC,R1R,R2G,R3R), (ZC,R1R,R2H,R3A), (ZC,R1R,R2H,R3B),
(ZC,R1R,R2H,R3C), (ZC,R1R,R2H,R3D), (ZC,R1R,R2H,R3E),
(ZC,R1R,R2H,R3F), (ZC,R1R,R2H,R3G), (ZC,R1R,R2H,R3H),
(ZC,R1R,R2H,R3I), (ZC,R1R,R2H,R3J), (ZC,R1R,R2H,R3K),
(ZC,R1R,R2H,R3L), (ZC,R1R,R2H,R3M), (ZC,R1R,R2H,R3N),
(ZC,R1R,R2H,R3O), (ZC,R1R,R2H,R3P), (ZC,R1R,R2H,R3Q),
(ZC,R1R,R2H,R3R), (ZC,R1R,R2I,R3A), (ZC,R1R,R2I,R3B),
(ZC,R1R,R2I,R3C), (ZC,R1R,R2I,R3D), (ZC,R1R,R2I,R3E), (ZC,R1R,R2I,R3F),
(ZC,R1R,R2I,R3G), (ZC,R1R,R2I,R3H), (ZC,R1R,R2I,R3I), (ZC,R1R,R2I,R3J),
(ZC,R1R,R2I,R3K), (ZC,R1R,R2I,R3L), (ZC,R1R,R2I,R3M),
(ZC,R1R,R2I,R3N), (ZC,R1R,R2I,R3O), (ZC,R1R,R2I,R3P), (ZC,R1R,R2I,R3Q),
(ZC,R1R,R2I,R3R), (ZC,R1R,R2J,R3A), (ZC,R1R,R2J,R3B),
(ZC,R1R,R2J,R3C), (ZC,R1R,R2J,R3D), (ZC,R1R,R2J,R3E),
(ZC,R1R,R2J,R3F), (ZC,R1R,R2J,R3G), (ZC,R1R,R2J,R3H),
(ZC,R1R,R2J,R3I), (ZC,R1R,R2J,R3J), (ZC,R1R,R2J,R3K),
(ZC,R1R,R2J,R3L), (ZC,R1R,R2J,R3M), (ZC,R1R,R2J,R3N),
(ZC,R1R,R2J,R3O), (ZC,R1R,R2J,R3P), (ZC,R1R,R2J,R3Q),
(ZC,R1R,R2J,R3R), (ZC,R1R,R2K,R3A), (ZC,R1R,R2K,R3B),
(ZC,R1R,R2K,R3C), (ZC,R1R,R2K,R3D), (ZC,R1R,R2K,R3E),
(ZC,R1R,R2K,R3F), (ZC,R1R,R2K,R3G), (ZC,R1R,R2K,R3H),
(ZC,R1R,R2K,R3I), (ZC,R1R,R2K,R3J), (ZC,R1R,R2K,R3K),
(ZC,R1R,R2K,R3L), (ZC,R1R,R2K,R3M), (ZC,R1R,R2K,R3N),
(ZC,R1R,R2K,R3O), (ZC,R1R,R2K,R3P), (ZC,R1R,R2K,R3Q),
(ZC,R1R,R2K,R3R), (ZC,R1R,R2L,R3A), (ZC,R1R,R2L,R3B),
(ZC,R1R,R2L,R3C), (ZC,R1R,R2L,R3D), (ZC,R1R,R2L,R3E),
(ZC,R1R,R2L,R3F), (ZC,R1R,R2L,R3G), (ZC,R1R,R2L,R3H),
(ZC,R1R,R2L,R3I), (ZC,R1R,R2L,R3J), (ZC,R1R,R2L,R3K),
(ZC,R1R,R2L,R3L), (ZC,R1R,R2L,R3M), (ZC,R1R,R2L,R3N),
(ZC,R1R,R2L,R3O), (ZC,R1R,R2L,R3P), (ZC,R1R,R2L,R3Q),
(ZC,R1R,R2L,R3R), (ZC,R1R,R2M,R3A), (ZC,R1R,R2M,R3B),
(ZC,R1R,R2M,R3C), (ZC,R1R,R2M,R3D), (ZC,R1R,R2M,R3E),
(ZC,R1R,R2M,R3F), (ZC,R1R,R2M,R3G), (ZC,R1R,R2M,R3H),
(ZC,R1R,R2M,R3I), (ZC,R1R,R2M,R3J), (ZC,R1R,R2M,R3K),
(ZC,R1R,R2M,R3L), (ZC,R1R,R2M,R3M), (ZC,R1R,R2M,R3N),
(ZC,R1R,R2M,R3O), (ZC,R1R,R2M,R3P), (ZC,R1R,R2M,R3Q),
(ZC,R1R,R2M,R3R), (ZC,R1R,R2N,R3A), (ZC,R1R,R2N,R3B),
(ZC,R1R,R2N,R3C), (ZC,R1R,R2N,R3D), (ZC,R1R,R2N,R3E),
(ZC,R1R,R2N,R3F), (ZC,R1R,R2N,R3G), (ZC,R1R,R2N,R3H),
(ZC,R1R,R2N,R3I), (ZC,R1R,R2N,R3J), (ZC,R1R,R2N,R3K),
(ZC,R1R,R2N,R3L), (ZC,R1R,R2N,R3M), (ZC,R1R,R2N,R3N),
(ZC,R1R,R2N,R3O), (ZC,R1R,R2N,R3P), (ZC,R1R,R2N,R3Q),
(ZC,R1R,R2N,R3R), (ZC,R1S,R2A,R3A), (ZC,R1S,R2A,R3B),
(ZC,R1S,R2A,R3C), (ZC,R1S,R2A,R3D), (ZC,R1S,R2A,R3E),
(ZC,R1S,R2A,R3F), (ZC,R1S,R2A,R3G), (ZC,R1S,R2A,R3H),
(ZC,R1S,R2A,R3I), (ZC,R1S,R2A,R3J), (ZC,R1S,R2A,R3K),
(ZC,R1S,R2A,R3L), (ZC,R1S,R2A,R3M), (ZC,R1S,R2A,R3N),
(ZC,R1S,R2A,R3O), (ZC,R1S,R2A,R3P), (ZC,R1S,R2A,R3Q),
(ZC,R1S,R2A,R3R), (ZC,R1S,R2B,R3A), (ZC,R1S,R2B,R3B),
(ZC,R1S,R2B,R3C), (ZC,R1S,R2B,R3D), (ZC,R1S,R2B,R3E),
(ZC,R1S,R2B,R3F), (ZC,R1S,R2B,R3G), (ZC,R1S,R2B,R3H),
(ZC,R1S,R2B,R3I), (ZC,R1S,R2B,R3J), (ZC,R1S,R2B,R3K),
(ZC,R1S,R2B,R3L), (ZC,R1S,R2B,R3M), (ZC,R1S,R2B,R3N), (ZC,R1S,R2B,R3O), (ZC,R1S,R2B,R3P), (ZC,R1S,R2B,R3Q),
(ZC,R1S,R2B,R3R), (ZC,R1S,R2C,R3A), (ZC,R1S,R2C,R3B),
(ZC,R1S,R2C,R3C), (ZC,R1S,R2C,R3D), (ZC,R1S,R2C,R3E),
(ZC,R1S,R2C,R3F), (ZC,R1S,R2C,R3G), (ZC,R1S,R2C,R3H),
(ZC,R1S,R2C,R3I), (ZC,R1S,R2C,R3J), (ZC,R1S,R2C,R3K),
(ZC,R1S,R2C,R3L), (ZC,R1S,R2C,R3M), (ZC,R1S,R2C,R3N),
(ZC,R1S,R2C,R3O), (ZC,R1S,R2C,R3P), (ZC,R1S,R2C,R3Q),
(ZC,R1S,R2C,R3R), (ZC,R1S,R2D,R3A), (ZC,R1S,R2D,R3B),
(ZC,R1S,R2D,R3C), (ZC,R1S,R2D,R3D), (ZC,R1S,R2D,R3E),
(ZC,R1S,R2D,R3F), (ZC,R1S,R2D,R3G), (ZC,R1S,R2D,R3H),
(ZC,R1S,R2D,R3I), (ZC,R1S,R2D,R3J), (ZC,R1S,R2D,R3K),
(ZC,R1S,R2D,R3L), (ZC,R1S,R2D,R3M), (ZC,R1S,R2D,R3N),
(ZC,R1S,R2D,R3O), (ZC,R1S,R2D,R3P), (ZC,R1S,R2D,R3Q),
(ZC,R1S,R2D,R3R), (ZC,R1S,R2E,R3A), (ZC,R1S,R2E,R3B),
(ZC,R1S,R2E,R3C), (ZC,R1S,R2E,R3D), (ZC,R1S,R2E,R3E),
(ZC,R1S,R2E,R3F), (ZC,R1S,R2E,R3G), (ZC,R1S,R2E,R3H),
(ZC,R1S,R2E,R3I), (ZC,R1S,R2E,R3J), (ZC,R1S,R2E,R3K),
(ZC,R1S,R2E,R3L), (ZC,R1S,R2E,R3M), (ZC,R1S,R2E,R3N),
(ZC,R1S,R2E,R3O), (ZC,R1S,R2E,R3P), (ZC,R1S,R2E,R3Q),
(ZC,R1S,R2E,R3R), (ZC,R1S,R2F,R3A), (ZC,R1S,R2F,R3B),
(ZC,R1S,R2F,R3C), (ZC,R1S,R2F,R3D), (ZC,R1S,R2F,R3E),
(ZC,R1S,R2F,R3F), (ZC,R1S,R2F,R3G), (ZC,R1S,R2F,R3H),
(ZC,R1S,R2F,R3I), (ZC,R1S,R2F,R3J), (ZC,R1S,R2F,R3K),
(ZC,R1S,R2F,R3L), (ZC,R1S,R2F,R3M), (ZC,R1S,R2F,R3N),
(ZC,R1S,R2F,R3O), (ZC,R1S,R2F,R3P), (ZC,R1S,R2F,R3Q),
(ZC,R1S,R2F,R3R), (ZC,R1S,R2G,R3A), (ZC,R1S,R2G,R3B),
(ZC,R1S,R2G,R3C), (ZC,R1S,R2G,R3D), (ZC,R1S,R2G,R3E),
(ZC,R1S,R2G,R3F), (ZC,R1S,R2G,R3G), (ZC,R1S,R2G,R3H),
(ZC,R1S,R2G,R3I), (ZC,R1S,R2G,R3J), (ZC,R1S,R2G,R3K),
(ZC,R1S,R2G,R3L), (ZC,R1S,R2G,R3M), (ZC,R1S,R2G,R3N),
(ZC,R1S,R2G,R3O), (ZC,R1S,R2G,R3P), (ZC,R1S,R2G,R3Q),
(ZC,R1S,R2G,R3R), (ZC,R1S,R2H,R3A), (ZC,R1S,R2H,R3B),
(ZC,R1S,R2H,R3C), (ZC,R1S,R2H,R3D), (ZC,R1S,R2H,R3E),
(ZC,R1S,R2H,R3F), (ZC,R1S,R2H,R3G), (ZC,R1S,R2H,R3H),
(ZC,R1S,R2H,R3I), (ZC,R1S,R2H,R3J), (ZC,R1S,R2H,R3K),
(ZC,R1S,R2H,R3L), (ZC,R1S,R2H,R3M), (ZC,R1S,R2H,R3N),
(ZC,R1S,R2H,R3O), (ZC,R1S,R2H,R3P), (ZC,R1S,R2H,R3Q),
(ZC,R1S,R2H,R3R), (ZC,R1S,R2I,R3A), (ZC,R1S,R2I,R3B),
(ZC,R1S,R2I,R3C), (ZC,R1S,R2I,R3D), (ZC,R1S,R2I,R3E), (ZC,R1S,R2I,R3F),
(ZC,R1S,R2I,R3G), (ZC,R1S,R2I,R3H), (ZC,R1S,R2I,R3I), (ZC,R1S,R2I,R3J),
(ZC,R1S,R2I,R3K), (ZC,R1S,R2I,R3L), (ZC,R1S,R2I,R3M), (ZC,R1S,R2I,R3N),
(ZC,R1S,R2I,R3O), (ZC,R1S,R2I,R3P), (ZC,R1S,R2I,R3Q), (ZC,R1S,R2I,R3R),
(ZC,R1S,R2J,R3A), (ZC,R1S,R2J,R3B), (ZC,R1S,R2J,R3C),
(ZC,R1S,R2J,R3D), (ZC,R1S,R2J,R3E), (ZC,R1S,R2J,R3F),
(ZC,R1S,R2J,R3G), (ZC,R1S,R2J,R3H), (ZC,R1S,R2J,R3I),
(ZC,R1S,R2J,R3J), (ZC,R1S,R2J,R3K), (ZC,R1S,R2J,R3L),
(ZC,R1S,R2J,R3M), (ZC,R1S,R2J,R3N), (ZC,R1S,R2J,R3O),
(ZC,R1S,R2J,R3P), (ZC,R1S,R2J,R3Q), (ZC,R1S,R2J,R3R),
(ZC,R1S,R2K,R3A), (ZC,R1S,R2K,R3B), (ZC,R1S,R2K,R3C),
(ZC,R1S,R2K,R3D), (ZC,R1S,R2K,R3E), (ZC,R1S,R2K,R3F),
(ZC,R1S,R2K,R3G), (ZC,R1S,R2K,R3H), (ZC,R1S,R2K,R3I),
(ZC,R1S,R2K,R3J), (ZC,R1S,R2K,R3K), (ZC,R1S,R2K,R3L),
(ZC,R1S,R2K,R3M), (ZC,R1S,R2K,R3N), (ZC,R1S,R2K,R3O),
(ZC,R1S,R2K,R3P), (ZC,R1S,R2K,R3Q), (ZC,R1S,R2K,R3R),
(ZC,R1S,R2L,R3A), (ZC,R1S,R2L,R3B), (ZC,R1S,R2L,R3C),
(ZC,R1S,R2L,R3D), (ZC,R1S,R2L,R3E), (ZC,R1S,R2L,R3F),
(ZC,R1S,R2L,R3G), (ZC,R1S,R2L,R3H), (ZC,R1S,R2L,R3I),
(ZC,R1S,R2L,R3J), (ZC,R1S,R2L,R3K), (ZC,R1S,R2L,R3L),
(ZC,R1S,R2L,R3M), (ZC,R1S,R2L,R3N), (ZC,R1S,R2L,R3O),
(ZC,R1S,R2L,R3P), (ZC,R1S,R2L,R3Q), (ZC,R1S,R2L,R3R),
(ZC,R1S,R2M,R3A), (ZC,R1S,R2M,R3B), (ZC,R1S,R2M,R3C),
(ZC,R1S,R2M,R3D), (ZC,R1S,R2M,R3E), (ZC,R1S,R2M,R3F),
(ZC,R1S,R2M,R3G), (ZC,R1S,R2M,R3H), (ZC,R1S,R2M,R3I),
(ZC,R1S,R2M,R3J), (ZC,R1S,R2M,R3K), (ZC,R1S,R2M,R3L),
(ZC,R1S,R2M,R3M), (ZC,R1S,R2M,R3N), (ZC,R1S,R2M,R3O),
(ZC,R1S,R2M,R3P), (ZC,R1S,R2M,R3Q), (ZC,R1S,R2M,R3R), (ZC,R1S,R2N,R3A), (ZC,R1S,R2N,R3B), (ZC,R1S,R2N,R3C),
(ZC,R1S,R2N,R3D), (ZC,R1S,R2N,R3E), (ZC,R1S,R2N,R3F),
(ZC,R1S,R2N,R3G), (ZC,R1S,R2N,R3H), (ZC,R1S,R2N,R3I),
(ZC,R1S,R2N,R3J), (ZC,R1S,R2N,R3K), (ZC,R1S,R2N,R3L),
(ZC,R1S,R2N,R3M), (ZC,R1S,R2N,R3N), (ZC,R1S,R2N,R3O),
(ZC,R1S,R2N,R3P), (ZC,R1S,R2N,R3Q), and (ZC,R1S,R2N,R3R).

Another preferred embodiments of the compound of the invention are represented by the formula (g) to (n):

[Chemical Formula 33]

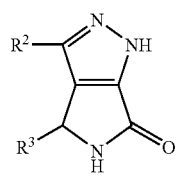
(g)

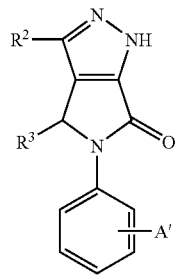
(h)

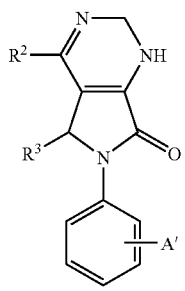
(i)

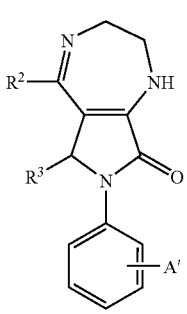
(j)

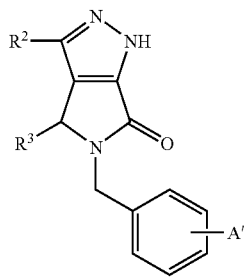
(k)

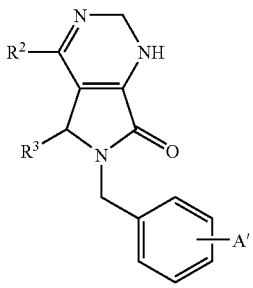
(m)

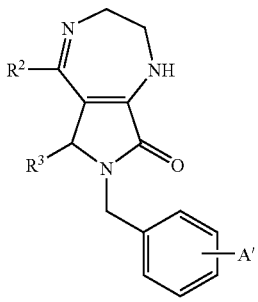
(n)

TABLE 5

| | $R^2$ |
|---|---|
| R2O | iPr |
| R2P | tBu |
| R2Q | cHex |
| R2R | Ph |
| R2S | 4-OMe-Ph |
| R2T | 3-pyridyl |
| R2U | thyenyl |

TABLE 6

| | $R^3$ |
|---|---|
| R3S | iPr |
| R3T | tBu |
| R3U | cHex |
| R3V | Ph |
| R3W | 2-Cl-Ph |
| R3X | 2-pyridyl |

TABLE 7

| | A' |
|---|---|
| | (in Formulae (h), (i), (j), (k), (m) and (n) only) |
| A1 | 2- or 3- or 4-COOEt |
| A2 | 2- or 3- or 4-$CF_3$ |

TABLE 7-continued

| | A' (in Formulae (h), (i), (j), (k), (m) and (n) only) |
|---|---|
| A3 | 2- or 3- or 4-OCF$_3$ |
| A4 | 2- or 3- or 4-SCF$_3$ |
| A5 | 2- or 3- or 4-isoxazolyl-3-yl |
| A6 | 2- or 3- or 4-CH=NOH |
| A7 | 2- or 3- or 4-CH=NOMe | wherein
Me is methyl, Et is ethyl, iPr is isopropyl, tBu is t-butyl, cHex is cyclohexyl, Ph is phenyl; and
the combination of R$^2$, R$^3$ and A', i.e., (R$^2$, R$^3$, A'), is any one of the following combinations:
(R2,R3,A')=(R2O,R3S,A1), (R2O,R3S,A2), (R2O,R3S, A3), (R2O,R3S,A4),
(R2O,R3S,A5), (R2O,R3S,A6), (R2O,R3S,A7), (R2O,R3T, A1), (R2O,R3T,A2),
(R2O,R3T,A3), (R2O,R3T,A4), (R2O,R3T,A5), (R2O,R3T, A6), (R2O,R3T,A7),
(R2O,R3U,A1), (R2O,R3U,A2), (R2O,R3U,A3), (R2O, R3U,A4), (R2O,R3U,A5),
(R2O,R3U,A6), (R2O,R3U,A7), (R2O,R3V,A1), (R2O, R3V,A2), (R2O,R3V,A3),
(R2O,R3V,A4), (R2O,R3V,A5), (R2O,R3V,A6), (R2O,R3V, A7), (R2O,R3W,A1),
(R2O,R3W,A2), (R2O,R3W,A3), (R2O,R3W,A4), (R2O, R3W,A5),
(R2O,R3W,A6), (R2O,R3W,A7), (R2O,R3X,A1), (R2O, R3X,A2), (R2O,R3X,A3),
(R2O,R3X,A4), (R2O,R3X,A5), (R2O,R3X,A6), (R2O, R3X,A7), (R2P,R3S,A1),
(R2P,R3S,A2), (R2P,R3S,A3), (R2P,R3S,A4), (R2P,R3S, A5), (R2P,R3S,A6),
(R2P,R3S,A7), (R2P,R3T,A1), (R2P,R3T,A2), (R2P,R3T, A3), (R2P,R3T,A4),
(R2P,R3T,A5), (R2P,R3T,A6), (R2P,R3T,A7), (R2P,R3U, A1), (R2P,R3U,A2),
(R2P,R3U,A3), (R2P,R3U,A4), (R2P,R3U,A5), (R2P,R3U, A6), (R2P,R3U,A7),
(R2P,R3V,A1), (R2P,R3V,A2), (R2P,R3V,A3), (R2P,R3V, A4), (R2P,R3V,A5),
(R2P,R3V,A6), (R2P,R3V,A7), (R2P,R3W,A1), (R2P,R3W, A2), (R2P,R3W,A3),
(R2P,R3W,A4), (R2P,R3W,A5), (R2P,R3W,A6), (R2P,R3W, A7), (R2P,R3X,A1),
(R2P,R3X,A2), (R2P,R3X,A3), (R2P,R3X,A4), (R2P,R3X, A5), (R2P,R3X,A6),
(R2P,R3X,A7), (R2Q,R3S,A1), (R2Q,R3S,A2), (R2Q,R3S, A3), (R2Q,R3S,A4),
(R2Q,R3S,A5), (R2Q,R3S,A6), (R2Q,R3S,A7), (R2Q,R3T, A1), (R2Q,R3T,A2),
(R2Q,R3T,A3), (R2Q,R3T,A4), (R2Q,R3T,A5), (R2Q,R3T, A6), (R2Q,R3T,A7),
(R2Q,R3U,A1), (R2Q,R3U,A2), (R2Q,R3U,A3), (R2Q, R3U,A4), (R2Q,R3U,A5),
(R2Q,R3U,A6), (R2Q,R3U,A7), (R2Q,R3V,A1), (R2Q, R3V,A2), (R2Q,R3V,A3),
(R2Q,R3V,A4), (R2Q,R3V,A5), (R2Q,R3V,A6), (R2Q,R3V, A7), (R2Q,R3W,A1),
(R2Q,R3W,A2), (R2Q,R3W,A3), (R2Q,R3W,A4), (R2Q, R3W,A5),
(R2Q,R3W,A6), (R2Q,R3W,A7), (R2Q,R3X,A1), (R2Q, R3X,A2), (R2Q,R3X,A3),
(R2Q,R3X,A4), (R2Q,R3X,A5), (R2Q,R3X,A6), (R2Q, R3X,A7), (R2R,R3S,A1),
(R2R,R3S,A2), (R2R,R3S,A3), (R2R,R3S,A4), (R2R,R3S, A5), (R2R,R3S,A6),
(R2R,R3S,A7), (R2R,R3T,A1), (R2R,R3T,A2), (R2R,R3T, A3), (R2R,R3T,A4),
(R2R,R3T,A5), (R2R,R3T,A6), (R2R,R3T,A7), (R2R,R3U, A1), (R2R,R3U,A2),
(R2R,R3U,A3), (R2R,R3U,A4), (R2R,R3U,A5), (R2R, R3U,A6), (R2R,R3U,A7),
(R2R,R3V,A1), (R2R,R3V,A2), (R2R,R3V,A3), (R2R,R3V, A4), (R2R,R3V,A5),
(R2R,R3V,A6), (R2R,R3V,A7), (R2R,R3W,A1), (R2R, R3W,A2), (R2R,R3W,A3),
(R2R,R3W,A4), (R2R,R3W,A5), (R2R,R3W,A6), (R2R, R3W,A7), (R2R,R3X,A1),
(R2R,R3X,A2), (R2R,R3X,A3), (R2R,R3X,A4), (R2R, R3X,A5), (R2R,R3X,A6),
(R2R,R3X,A7), (R2S,R3S,A1), (R2S,R3S,A2), (R2S,R3S, A3), (R2S,R3S,A4),
(R2S,R3S,A5), (R2S,R3S,A6), (R2S,R3S,A7), (R2S,R3T, A1), (R2S,R3T,A2),
(R2S,R3T,A3), (R2S,R3T,A4), (R2S,R3T,A5), (R2S,R3T, A6), (R2S,R3T,A7),
(R2S,R3U,A1), (R2S,R3U,A2), (R2S,R3U,A3), (R2S,R3U, A4), (R2S,R3U,A5),
(R2S,R3U,A6), (R2S,R3U,A7), (R2S,R3V,A1), (R2S,R3V, A2), (R2S,R3V,A3),
(R2S,R3V,A4), (R2S,R3V,A5), (R2S,R3V,A6), (R2S,R3V, A7), (R2S,R3W,A1),
(R2S,R3W,A2), (R2S,R3W,A3), (R2S,R3W,A4), (R2S, R3W,A5), (R2S,R3W,A6),
(R2S,R3W,A7), (R2S,R3X,A1), (R2S,R3X,A2), (R2S,R3X, A3), (R2S,R3X,A4),
(R2S,R3X,A5), (R2S,R3X,A6), (R2S,R3X,A7), (R2T,R3S, A1), (R2T,R3S,A2),
(R2T,R3S,A3), (R2T,R3S,A4), (R2T,R3S,A5), (R2T,R3S, A6), (R2T,R3S,A7),
(R2T,R3T,A1), (R2T,R3T,A2), (R2T,R3T,A3), (R2T,R3T, A4), (R2T,R3T,A5),
(R2T,R3T,A6), (R2T,R3T,A7), (R2T,R3U,A1), (R2T,R3U, A2), (R2T,R3U,A3),
(R2T,R3U,A4), (R2T,R3U,A5), (R2T,R3U,A6), (R2T,R3U, A7), (R2T,R3V,A1),
(R2T,R3V,A2), (R2T,R3V,A3), (R2T,R3V,A4), (R2T,R3V, A5), (R2T,R3V,A6),
(R2T,R3V,A7), (R2T,R3W,A1), (R2T,R3W,A2), (R2T,R3W, A3), (R2T,R3W,A4),
(R2T,R3W,A5), (R2T,R3W,A6), (R2T,R3W,A7), (R2T,R3X, A1), (R2T,R3X,A2),
(R2T,R3X,A3), (R2T,R3X,A4), (R2T,R3X,A5), (R2T,R3X, A6), (R2T,R3X,A7),
(R2U,R3S,A1), (R2U,R3S,A2), (R2U,R3S,A3), (R2U,R3S, A4), (R2U,R3S,A5),
(R2U,R3S,A6), (R2U,R3S,A7), (R2U,R3T,A1), (R2U,R3T, A2), (R2U,R3T,A3),
(R2U,R3T,A4), (R2U,R3T,A5), (R2U,R3T,A6), (R2U,R3T, A7), (R2U,R3U,A1),
(R2U,R3U,A2), (R2U,R3U,A3), (R2U,R3U,A4), (R2U, R3U,A5), (R2U,R3U,A6),
(R2U,R3U,A7), (R2U,R3V,A1), (R2U,R3V,A2), (R2U,R3V, A3), (R2U,R3V,A4),
(R2U,R3V,A5), (R2U,R3V,A6), (R2U,R3V,A7), (R2U, R3W,A1), (R2U,R3W,A2),
(R2U,R3W,A3), (R2U,R3W,A4), (R2U,R3W,A5), (R2U, R3W,A6),
(R2U,R3W,A7), (R2U,R3X,A1), (R2U,R3X,A2), (R2U, R3X,A3), (R2U,R3X,A4),
(R2U,R3X,A5), (R2U,R3X,A6), and (R2U,R3X,A7).

EXAMPLES

The following Examples describe the invention specifically and are not intended as a limitation with respect to the scope of the invention. The following abbreviations are used as follows:

Me: methyl
Et: ethyl
Bu: butyl
Ac: acetyl
TMS: tetra methyl silane
TMS-Cl: trimethylsilyl chloride
DMSO: dimethyl sulfoxide
r.t.: room temperature

Example 1

Preparation of 5-cyclohexyl-4-(2,2-dimethylpropionoyl)-3-hydroxy-1-(4-isoxazol-3-ylphenyl)-1,5-dihydropyrrol-2-one (I-32)

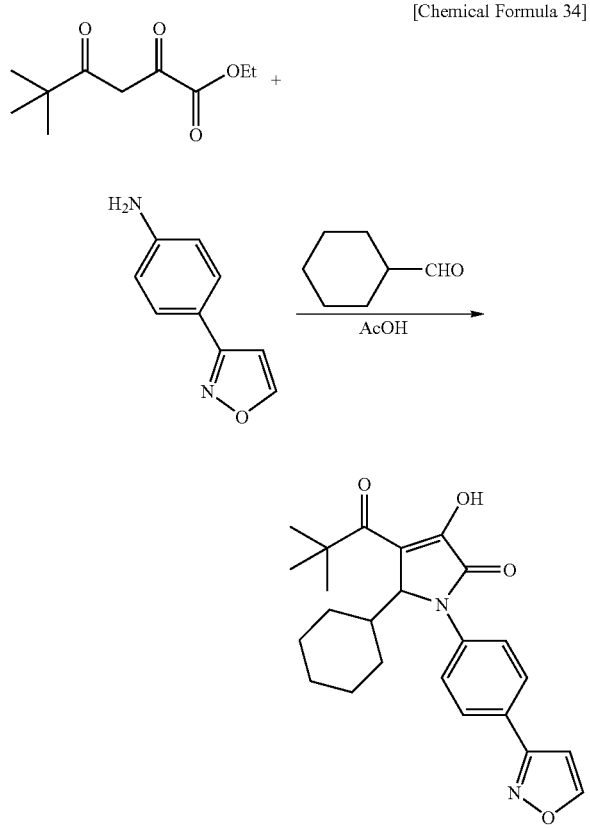

[Chemical Formula 34]

To a mixture of ethyl(trimethylaceto)pyruvate (1.00 g, 5 mmol) and 4-isoxazol-3-yl-aniline (0.80 g, 5 mmol) in acetic acid (4 mL) was added cyclohexane carboaldehyde (0.61 mL, 5 mmol). The mixture was stirred at 95° C. for 5 hr, and cooled to r.t. The precipitate was collected by filtration, washed with ethyl acetate and dried to give 5-cyclohexyl-4-(2,2-dimethylpropionoyl)-3-hydroxy-1-(4-isoxazol-3-ylphenyl)-1,5-dihydropyrrol-2-one (0.60 g, 30%) as pale yellow crystals.

mp: 259-260° C., $^1$H-NMR (δ ppm TMS/DMSO-d6) 0.62-1.78 (11H, m), 1.27 (9H, s), 5.28 (1H, d, J=2.4 Hz), 7.20 (1H, d, J=1.8 Hz), 7.75 (2H, d, J=8.7 Hz), 7.98 (2H, d, J=8.7 Hz), 9.03 (1H, d, J=1.8 Hz), 11.84 (1H, s).

Example 2

Preparation of 5-(3-fluorophenyl)-3-hydroxy-1-(4-isoxazol-3-ylphenyl)-4-(4-methoxybenzoyl)-1,5-dihydropyrrol-2-one (I-26)

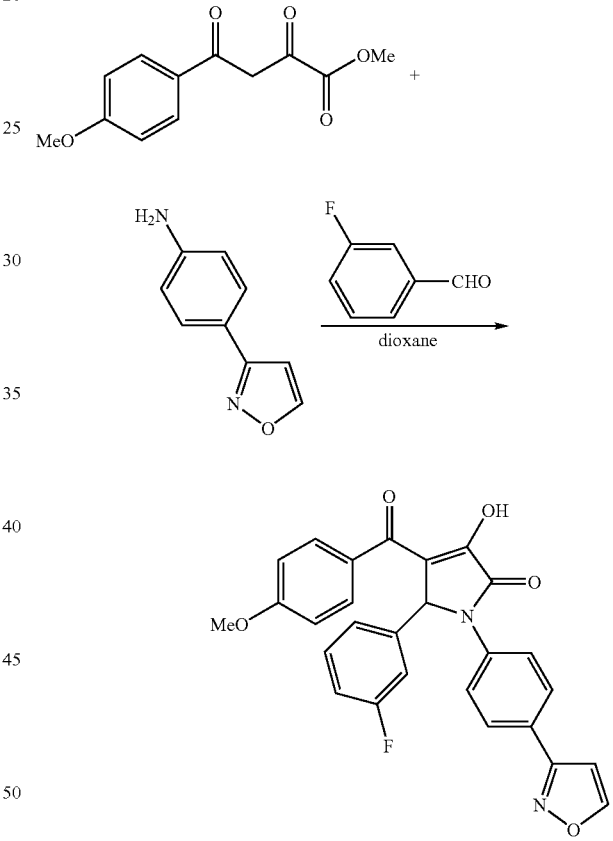

[Chemical Formula 35]

To a mixture of methyl (4-methoxybenzoyl)pyruvate (0.24 g, 1 mmol) and 4-isoxazol-3-ylaniline (0.16 g, 1 mmol) in dioxane (1 mL) was added 3-fluorobenzaldehyde (0.11 mL, 1 mmol). The mixture was stirred at r.t. for two days. Diethyl ether (3 mL) was then added to the mixture, and the precipitate was collected by filtration to give 5-(3-fluorophenyl)-3-hydroxy-1-(4-isoxazol-3-ylphenyl)-4-(4-methoxybenzoyl)-1,5-dihydropyrrol-2-one (0.16 g, 34%) as slightly yellow crystals.

mp: 273-274° C. (decomp.), 1H-NMR (δ ppm TMS/DMSO-d6) 3.83 (3H, s), 6.43 (1H, s), 6.90-7.02 (3H, m), 7.11 (1H, d, J=1.7 Hz), 7.23-7.35 (3H, m), 7.75-7.87 (6H, m), 8.97 (1H, d, J=1.7 Hz), 11.75 (1H, brs).

Example 3

Preparation of 3-tert-butyl-4-cyclohexyl-5-(4-isoxazol-3-ylphenyl)-4,5-dihydro-1H-pyrrolo[3,4-c]pyrazol-6-one (I-96)

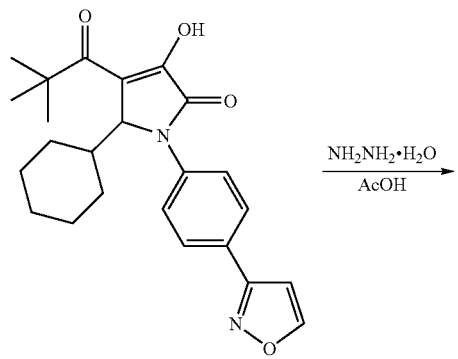

[Chemical Formula 36]

To a mixture of 5-cyclohexyl-4-(2,2-dimethylpropionoyl)-3-hydroxy-1-(4-isoxazol-3-ylphenyl)-1,5-dihydropyrrol-2-one (0.10 g, 0.25 mmol) and acetic acid (1 mL) was added hydrazine monohydrate (0.036 mL, 0.75 mmol). The mixture was stirred at 85° C. for 3 hr. Water (80 mL) was added to the mixture, which was then extracted with ethyl acetate (100 mL). The organic layer was washed with saturated aqueous sodium bicarbonate (80 mL×2), dried over anhydrous magnesium sulfate, and concentrated under reduced pressure. The residue was purified by silica gel column chromatography (ethyl acetate/n-hexane). The crude product was recrystallized from ethyl acetate to give 3-tert-butyl-4-cyclohexyl-5-(4-isoxazol-3-ylphenyl)-4,5-dihydro-1H-pyrrolo[3,4-c]pyrazol-6-one (0.072 g, 71%) as colorless crystals.

mp: 251-252° C., $^1$H-NMR (δ ppm TMS/DMSO-d6) 0.50-2.03 (11H, m), 1.39 (9H, s), 5.60 (1H, s), 7.20 (1H, d, J=1.8 Hz), 7.72 (2H, d, J=8.7 Hz), 7.96 (2H, d, J=8.7 Hz), 9.02 (1H, d, J=1.8 Hz), 13.28 (1H, s).

Example 4

Preparation of 4-(1-ethylpropyl)-5-(4-isoxazol-3-ylphenyl)-3-(6-oxo-1,6-dihydropyridin-3-yl)-4,5-dihydro-1H-pyrrolo[3,4-c]pyrazol-6-one (I-198)

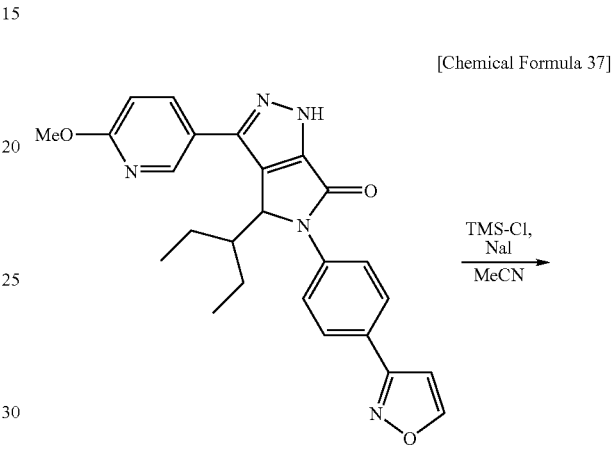

[Chemical Formula 37]

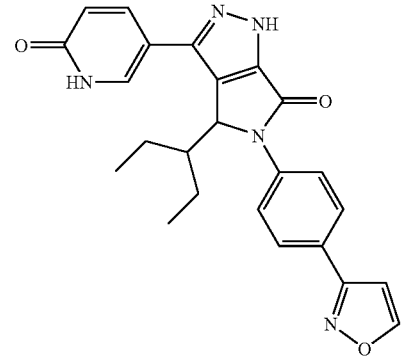

To a mixture of 4-(1-ethylpropyl)-5-(4-isoxazol-3-ylphenyl)-3-(6-methoxypyridin-3-yl)-4,5-dihydro-1H-pyrrolo[3,4-c]pyrazol-6-one (0.067 g, 0.15 mmol) and sodium iodide (0.067 g, 0.45 mmol) in acetonitrile (3 mL) was added chlorotrimethylsilane (0.058 mL, 0.45 mmol). The mixture was heated under reflux with stirring for 1 h. Water (50 mL) and ethyl acetate (50 mL) were added to the mixture, and the precipitate was collected by filtration and dried to give 4-(1-ethylpropyl)-5-(4-isoxazol-3-ylphenyl)-3-(6-oxo-1,6-dihydropyridin-3-yl)-4,5-dihydro-1H-pyrrolo[3,4-c]pyrazol-6-one (0.041 g, 64%) as slightly yellow crystals.

mp: >290° C. (decomp.), $^1$H-NMR (δ ppm TMS/DMSO-d6) 0.50-1.55 (11H, m), 6.00 (1H, d, J=2.5 Hz), 6.49 (1H, d, J=9.4 Hz), 7.18 (1H, d, J=1.8 Hz), 7.70-7.90 (4H, m), 8.01 (2H, d, J=8.4 Hz), 9.02 (1H, d, J=1.8 Hz), 12.04 (1H, brs), 13.78 (1H, brs).

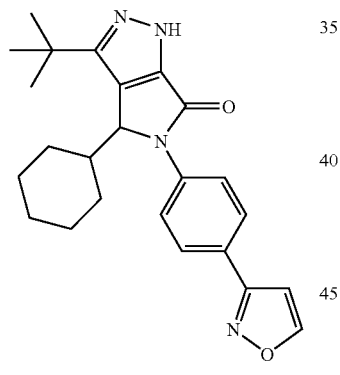

Example 5

Preparation of 3-hydroxy-4-(4-methoxybenzoyl)-1-(4-methoxyiminomethyl-phenyl)-5-phenyl-1,5-dihydropyrrol-2-one (I-199)

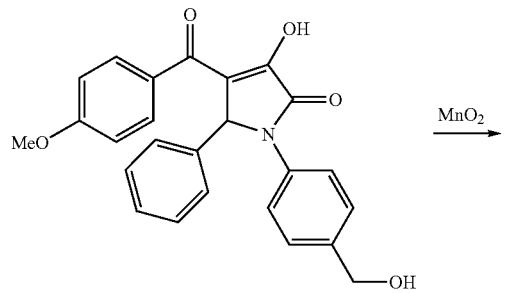

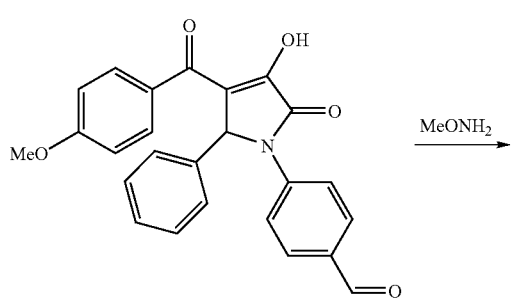

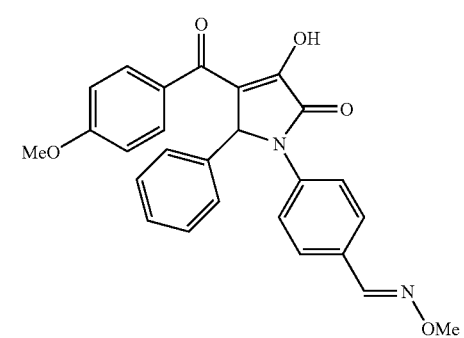

To a mixture of 3-hydroxy-1-(4-hydroxymethylphenyl)-4-(4-methoxy-benzoyl)-5-phenyl-1,5-dihydropyrrol-2-one (0.125 g, 0.3 mmol) and acetone (20 mL) was added manganese oxide (IV) (0.625 g, 7.18 mmol). The mixture was stirred at r.t. for 2.5 hr. Manganese oxide (IV) (0.625 g, 7.18 mmol) was added to the mixture, and the mixture was stirred at r.t. for 4.5 hr. The mixture was filtrated by celite, the filtrate was concentrated under reduced pressure to give a crude product of 1-(4-formylphenyl)-3-hydroxy-4-(4-methoxybenzoyl)-5-phenyl-1,5-dihydropyrrol-2-one. Methanol was added to prepare a 0.1M methanol solution of the crude product.

To the 0.1M methanol solution of 1-(4-formylphenyl)-3-hydroxy-4-(4-methoxybenzoyl)-5-phenyl-1,5-dihydropyrrol-2-one (1 mL, 0.1 mmol) was added O-methylhydroxylammonium chloride (0.025 g, 0.3 mmol) and sodium acetate (0.025 g, 0.3 mmol). The mixture was stirred under reflux for 3 hr. Water (50 mL) was added to the mixture, which was then extracted with ethyl acetate (50 mL). The organic layer was washed with brine (50 mL), dried over anhydrous magnesium sulfate, and concentrated under reduced pressure. To the residue was added ethyl acetate, and the precipitate was collected by filtration and dried to give 3-hydroxy-4-(4-methoxybenzoyl)-1-(4-methoxyiminomethylphenyl)-5-phenyl-1,5-dihydro-pyrrol-2-one (1.3 mg, 3%) as slightly yellow crystals.

mp: 226-229° C., $^1$H-NMR (δ ppm TMS/DMSO-d6) 3.82 (3H, s), 3.85 (3H, s), 6.31 (1H, s), 6.95-7.75 (13H, m), 8.12 (1H, s), 11.63 (1H, brs).

Example 6

Preparation of 1-(1,3-dioxolan-2-yl)-3-hydroxy-4-(4-methoxybenzoyl)-5-phenyl-1,5-dihydropyrrol-2-one (I-200)

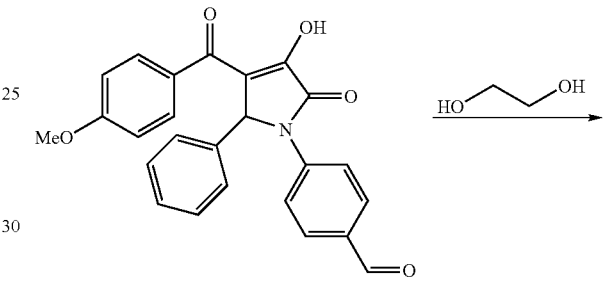

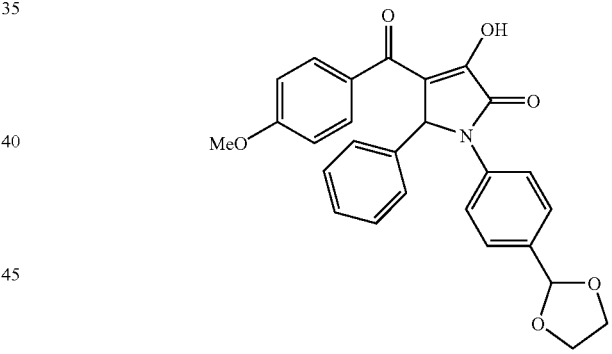

The 0.1M methanol solution of 1-(4-formylphenyl)-3-hydroxy-4-(4-methoxybenzoyl)-5-phenyl-1,5-dihydropyrrol-2-one (1 mL, 0.1 mmol) was concentrated under reduced pressure. Toluene (1 mL), ethylene glycol (0.033 mL, 0.6 mmol) and p-toluenesulfonic acid monohydrate (3.8 mg, 0.02 mmol) was added to the residue. The mixture was heated under azeotropic dehydration for 3 hr. Water (100 mL) was added to the mixture, which was then extracted with ethyl acetate (100 mL). The organic layer was washed with brine (100 mL), dried over anhydrous magnesium sulfate, and concentrated under reduced pressure. To the residue was added ethyl acetate, and the precipitate was collected by filtration and dried to give 1-(1,3-dioxolan-2-yl)-3-hydroxy-4-(4-methoxybenzoyl)-5-phenyl-1,5-dihydro-pyrrol-2-one (3.8 mg, 8%) as pale yellow crystals.

mp: 216-219° C., $^1$H-NMR (δ ppm TMS/DMSO-d6) 3.81 (3H, s), 3.89-4.00 (4H, m), 5.63 (1H, s), 6.26 (1H, s), 6.94-7.75 (13H, m), 11.65 (1H, brs).

181

Example 7

Preparation of 3-hydroxy-1-(4-isoxazol-3-ylphenyl)-4-(4-methoxybenzoyl)-5-(4-piperidine)-1,5-dihydropyrrol-2-one hydrochloride (I-201)

[Chemical Formula 40]

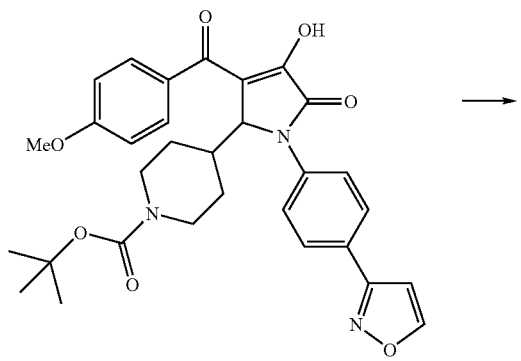

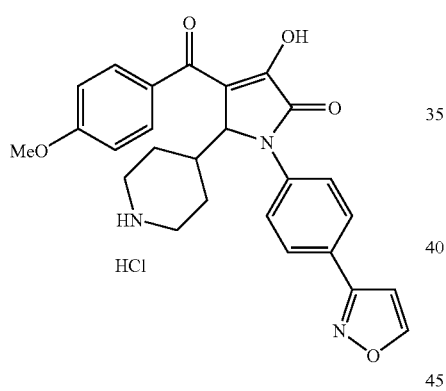

To a mixture of 5-(1-tert-butoxycarbonyl-4-piperidine)-3-hydroxy-1-(4-isoxazol-3-ylphenyl)-4-(4-methoxybenzoyl)-1,5-dihydropyrrol-2-one (0.112 g, 0.2 mmol) and methanol (1 mL) was added hydrochloric acid in dioxane (4 mol/L, 0.2 mL, 0.8 mmol) and the mixture was stirred at r.t. for 2.5 hr. Additional hydrochloric acid in dioxane (4 mol/L, 0.2 mL, 0.8 mmol) was added to the mixture, and the mixture was stirred under reflux for additional 0.5 hr. The mixture was concentrated under reduced pressure to give 3-hydroxy-1-(4-isoxazol-3-ylphenyl)-4-(4-methoxybenzoyl)-5-(4-piperidine)-1,5-dihydropyrrol-2-one hydrochloride (0.098 g, 100%) as slightly brown crystals.

1H-NMR (δ ppm TMS/DMSO-d6) 1.25-2.09 (5H, m), 2.50-2.74 (2H, m), 3.09-3.17 (2H, m), 3.90 (3H, s), 5.58 (1H, s), 7.09 (2H, d, J=8.6 Hz), 7.21 (1H, d, J=1.5 Hz), 7.82-7.89 (4H, m), 8.02 (2H, d, J=8.6 Hz), 8.11 (1H, brs), 8.58 (1H, brs), 9.04 (1H, d, J=1.5 Hz), 11.55 (1H, brs).

182

Example 8

Preparation of 3-(4-methoxyphenyl)-5-(4-oxazol-2-ylphenyl)-4-phenyl-4,5-dihydro-1H-pyrrolo[3,4-c]pyrazol-6-one (I-247)

[Chemical Formula 41]

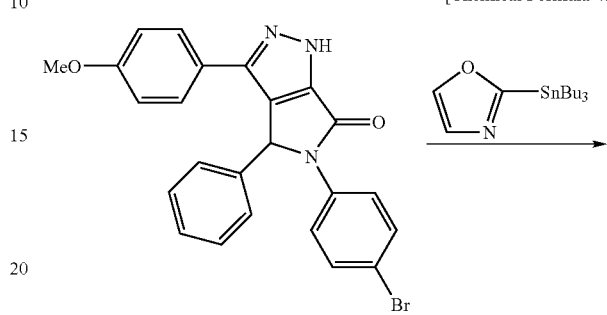

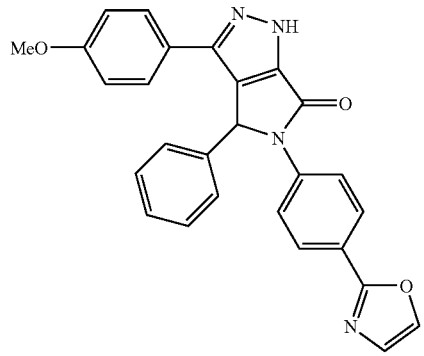

A mixture of 5-(4-bromophenyl)-3-(4-methoxyphenyl)-4-phenyl-4,5-dihydro-1H-pyrrolo[3,4-c]pyrazol-6-one (0.138 g, 0.3 mmol), oxadiazol-2-yl tributyltin (0.134 g, 0.37 mmol), tris(2-furyl)phosphine (0.014 g, 0.06 mmol), tris(dibenzylideneacetone)dipalladium(0) (0.027 g, 0.03 mmol) and dioxane (1.5 mL) was stirred at 130° C. under microwave radiation for 75 min. The reaction mixture was purified by silica gel column chromatography (ethyl acetate/n-hexane). The fraction was concentrated under reduced pressure and the precipitate was collected by filtration to give 3-(4-methoxyphenyl)-5-(4-oxazol-2-ylphenyl)-4-phenyl-4,5-dihydro-1H-pyrrolo[3,4-c]pyrazol-6-one (12 mg, 10%) as colorless crystals.

1H-NMR (δ ppm TMS/DMSO-d6) 3.75 (3H, s), 6.86 (1H, s), 6.91-7.92 (13H, m), 8.17 (1H, s), 14.00 (1H, brs).

Example 9

Preparation of 5-cyclohexyl-3-hydroxy-1-(4-isoxazol-3-ylphenyl)-4-(4-carboxybenzoyl)-1,5-dihydropyrrol-2-one

[Chemical Formula 42]

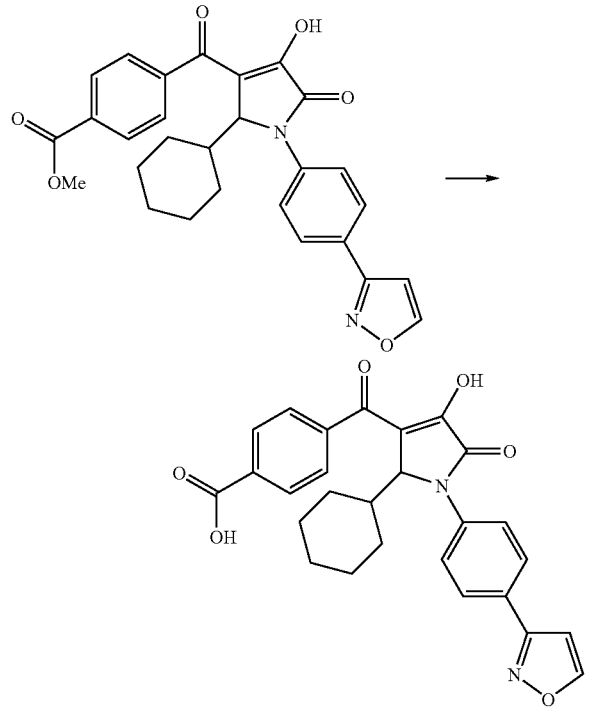

To a mixture of 5-cyclohexyl-3-hydroxy-1-(4-isoxazol-3-ylphenyl)-4-(4-methoxycarbonylbenzoyl)-1,5-dihydropyrrol-2-one (1.98 g, 4.07 mmol), THF (20 mL) and methanol (13 mL) was added aqueous 2N sodium hydroxide (5.09 mL). The mixture was stirred at 80° C. for 2 hr. To the mixture was added 2N hydrochloric acid (5.09 mL) under ice-cooling conditions, and ethyl acetate and water were added. The mixture was stirred at r.t. overnight. The precipitate was collected by filtration to give 5-cyclo hexyl-3-hydroxy-1-(4-isoxazol-3-ylphenyl)-4-(4-carboxybenzoyl)-1,5-dihydropyrrol-2-one (1.70 g, 88%) as yellow crystals.

1H-NMR (δ ppm TMS/DMSO-d6) 0.73-1.80 (11H, m), 5.49 (1H, d, J=2.4 Hz), 7.21 (1H, d, J=1.7 Hz), 7.80-8.11 (8H, m), 9.04 (1H, d, J=1.7 Hz).

Example 10

Preparation of 5-cyclo hexyl-3-hydroxy-1-(4-isoxazol-3-ylphenyl)-4-(4-methylcarbamoylbenzoyl)-1,5-dihydropyrrol-2-one

[Chemical Formula 43]

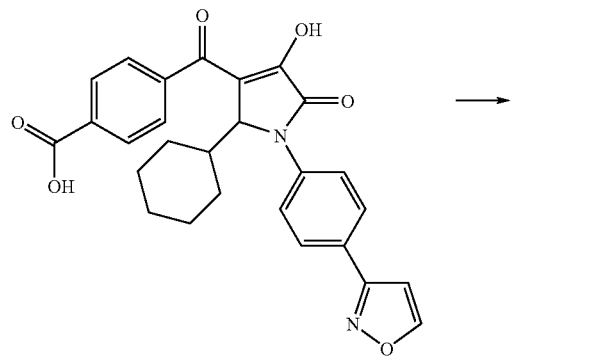

To a mixture of 5-cyclohexyl-3-hydroxy-1-(4-isoxazol-3-ylphenyl)-4-(4-carboxybenzoyl)-1,5-dihydropyrrol-2-one (0.095 g, 0.2 mmol) and DMF (2 mL) was added, methylamine hydrochloride (0.020 g, 0.3 mmol), 1-hydroxybenztriazole (0.041 g, 0.3 mmol), 4-dimethylaminopyridinium (0.005 g, 0.04 mmol), 1-ethyl-3-(3-dimethylaminopropyl)carbodiimide hydrochloride (0.058 g, 0.3 mmol) and triethylamine (0.042 mL, 0.3 mmol). The mixture was stirred at r.t. for 1 hr. Ethyl acetate and water were added, and the precipitate was collected by filtration to give 5-cyclohexyl-3-hydroxy-1-(4-isoxazol-3-ylphenyl)-4-(4-methylcarbamoylbenzoyl)-1,5-dihydropyrrol-2-one (0.062 g, 64%) as pale yellow crystals.

1H-NMR (δ ppm TMS/DMSO-d6) 0.72-1.80 (11H, m), 2.81 (3H, d, J=4.5 Hz), 5.48 (1H, d, J=2.5 Hz), 7.21 (1H, d, J=1.7 Hz), 7.80-8.03 (8H, m), 8.64 (1H, d, J=4.5 Hz), 9.04 (1H, d, J=1.7 Hz), 11.73 (1H, brs).

Example 11

Preparation of 3-t-butyl-5-(4-isoxazol-4-ylphenyl)-4-(2-methoxyphenyl)-4,5-dihydro-1H-pyrrolo[3,4-c]pyrazol-6-one

[Chemical Formula 44]

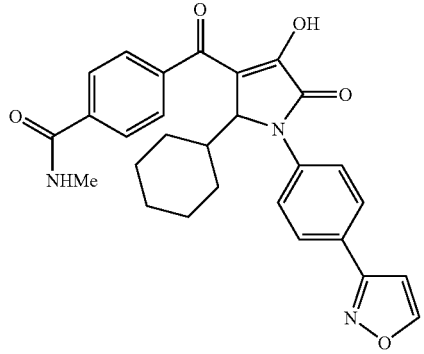

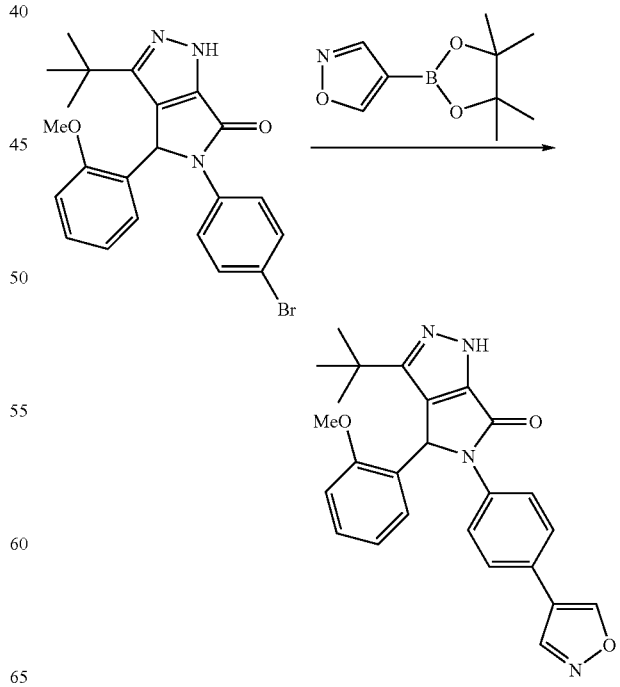

To a mixture of 5-(4-bromophenyl)-3-t-butyl-4-(2-methoxyphenyl)-4,5-dihydro-1H-pyrrolo[3,4-c]pyrazol-6-one (0.10 g, 0.23 mmol), 4-(4,4,5,5-tetramethyl-1,3-2-dioxaborolan-2-yl)isoxazole (0.066 g, 0.34 mmol), tripotassium phosphate (0.145 g, 0.68 mmol), ethylene glycol dimethylether (3 mL) and water (0.6 mL), [1,1'-bis(diphenylphosphino)ferrocene]dichloropalladium(II) dichloromethane complex (0.018 g, 0.023 mmol) was added under a nitrogen atmosphere, and the mixture was stirred under reflux for 4 hr. The mixture was purified by silica gel column chromatography (ethyl acetate/n-hexane) to give 3-t-butyl-5-(4-isoxazol-4-ylphenyl)-4-(2-methoxyphenyl)-4,5-dihydro-1H-pyrrolo[3,4-c]pyrazol-6-one (0.012 g, 12%) as colorless crystals.

1H-NMR (δ ppm TMS/DMSO-d6) 1.05 (9H, s), 3.91 (3H, s), 6.22-7.61 (9H, m), 9.09 (1H, s), 9.36 (1H, s), 13.34 (1H, s).

Example 12

Preparation of 3-t-butyl-5-(4-fur-3-ylphenyl)-4-(2-methoxyphenyl)-4,5-dihydro-1H-pyrrolo[3,4-c]pyrazol-6-one

[Chemical Formula 45]

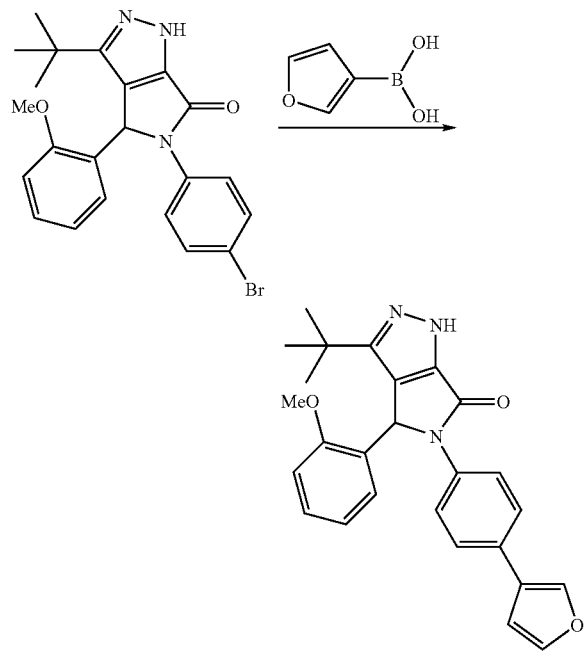

To a mixture of 5-(4-bromophenyl)-3-t-butyl-4-(2-methoxyphenyl)-4,5-dihydro-1H-pyrrolo[3,4-c]pyrazol-6-one (0.10 g, 0.23 mmol), 3-furylboronic acid (0.038 g, 0.34 mmol), tripotassium phosphate (0.096 g, 0.45 mmol) and butanol (1 mL), (2',4',6'-tri-isopropylbiphenyl-2-yl)phosphine (0.009 g, 0.02 mmol) and tris(dibenzylideneacetone)dipalladium(0) (0.004 g, 0.004 mmol) were added under a nitrogen atmosphere, and the mixture was stirred under reflux for 3 hr. The reaction mixture was purified by silica gel column chromatography (ethyl acetate/n-hexane). The fraction was concentrated under reduced pressure and the precipitate was collected by filtration to give 3-t-butyl-5-(4-fur-3-ylphenyl)-4-(2-methoxyphenyl)-4,5-dihydro-1H-pyrrolo[3,4-c]pyrazol-6-one (0.061 g, 63%) as colorless crystals.

1H-NMR (δ ppm TMS/DMSO-d6) 1.05 (9H, s), 3.90 (3H, s), 6.37-7.56 (10H, m), 7.70 (1H, s), 8.11 (1H, s), 13.32 (1H, s).

Example 13

Preparation of 5-cyclohexyl-3-hydroxy-4-(4-hydroxybenzoyl)-1-(4-isoxazol-3-ylphenyl)-1,5-dihydropyrrol-2-one

[Chemical Formula 46]

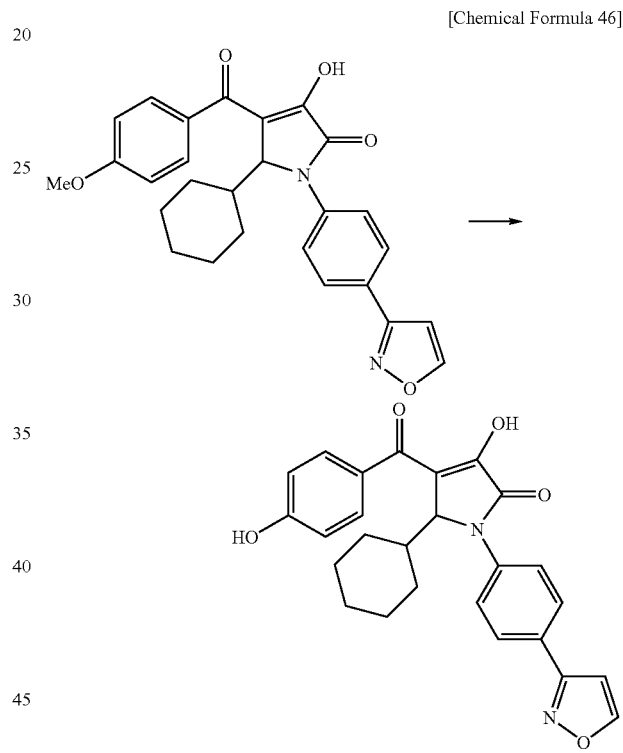

To a mixture of 5-cyclohexyl-3-hydroxy-1-(4-isoxazol-3-ylphenyl)-4-(4-methoxybenzoyl)-1,5-dihydropyrrol-2-one (0.229 g, 0.5 mmol) and dichloromethane (10 mL), 1M boron tribromide in dichloromethane (5.0 mL, 5 mmol) was added under ice-cooling conditions and the mixture was stirred at r.t. for 3 days. Small amount of potassium carbonate was added under ice-cooling conditions to degrade excess boron tribromide. 1N aqueous sodium hydroxide was added and the mixture was washed with ethyl acetate. The aqueous layer was neutralized with 1N hydrochloric acid, the precipitate was collected by filtration and washed with hot ethyl acetate to give 5-cyclohexyl-3-hydroxy-4-(4-hydroxybenzoyl)-1-(4-isoxazol-3-ylphenyl)-1,5-dihydropyrrol-2-one (0.068 g, 31%) as colorless crystals.

1H-NMR (δ ppm TMS/DMSO-d6) 0.73-1.80 (11H, m), 5.41 (1H, d, J=2.5 Hz), 6.88-6.91 (2H, m), 7.20 (1H, d, J=1.7 Hz), 7.78-8.01 (6H, m), 9.03 (1H, d, J=1.7 Hz), 10.42 (1H, brs), 11.14 (1H, brs).

Example 14

Preparation of 5-cyclohexyl-3-hydroxy-4-(4-hydroxy methylbenzoyl)-1-(4-isoxazol-3-ylphenyl)-1,5-dihydropyrrol-2-one

[Chemical Formula 47]

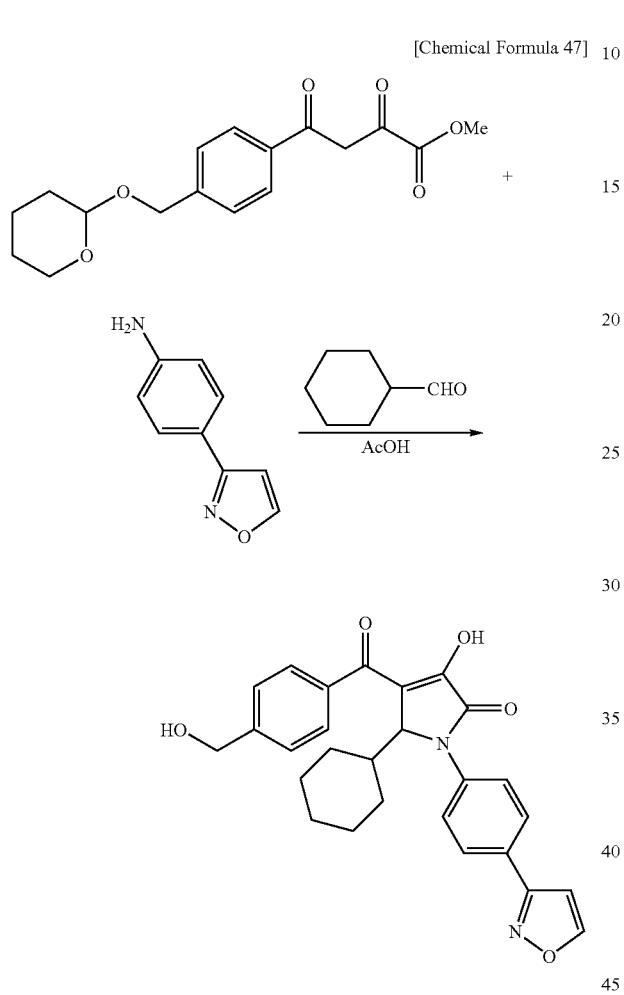

To a mixture of methyl 4-(2-tetrahydro-2H-pyranoxy methyl)benzoyl-pyruvate (0.17 g, 0.53 mmol), 4-isoxazol-3-ylaniline (0.085 g, 0.53 mmol) and acetic acid (1 mL), cyclohexane carboaldehyde (0.064 mL, 0.53 mmol) was added. The mixture was stirred at 95° C. for 0.5 hr, and cooled to r.t. The precipitate was collected by filtration and washed with ethyl acetate to give crude precursor. Methanol (5 mL), THF (5 mL) and pyridinium p-toluenesulfonate (0.027 g, 0.11 mmol) were added to the precursor, and the mixture was stirred at 60° C. for 0.5 hr. Water was added to the mixture, which was then extracted with chloroform. The organic layer was dried over anhydrous magnesium sulfate, and concentrated under reduced pressure. The residue was recrystallized from ethyl acetate to give 5-cyclohexyl-3-hydroxy-4-(4-hydroxy methylbenzoyl)-1-(4-isoxazol-3-yl-phenyl)-1,5-dihydropyrrol-2-one (0.022 g, 9%) as colorless crystals.

1H-NMR (δ ppm TMS/DMSO-d6) 0.62-1.78 (11H, m), 4.61 (2H, d, J=5.6 Hz), 5.38 (1H, t, J=5.6 Hz), 5.47 (1H, d, J=2.0 Hz), 7.21 (1H, d, J=1.7 Hz), 7.49-8.02 (8H, m), 9.03 (1H, d, J=1.7 Hz), 11.40 (1H, brs).

General Procedure 1

Preparation of Isolated Enantiomer

[Chemical Formula 48]

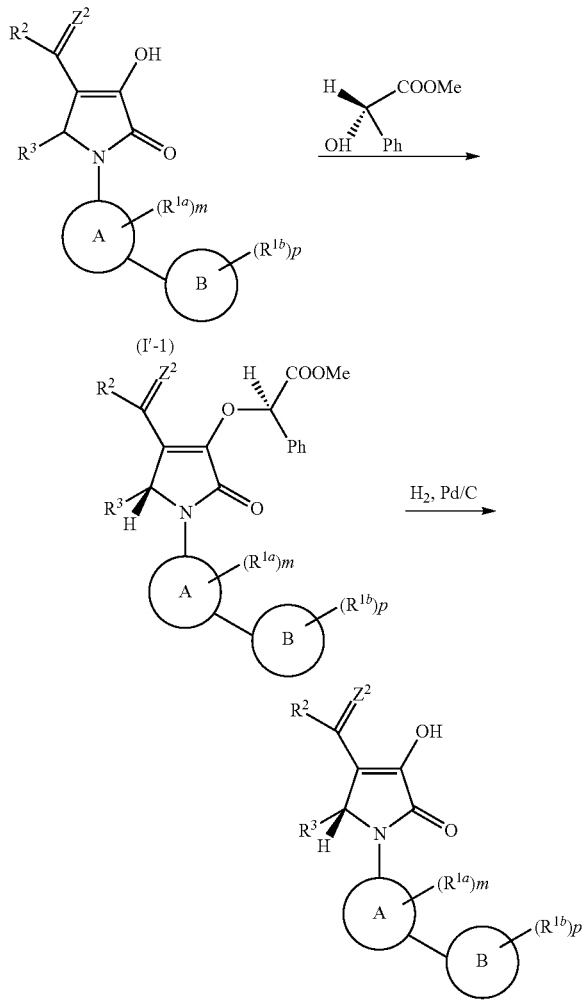

wherein all the variables are as defined above.

Compound (I'-1) and an optical resolving reagent (e.g., (S)-methyl 2-hydroxy-2-phenyl acetate) are reacted in an appropriate solvent with a condensing agent (e.g., isopropyl azodicarboxylate), and the mixture is purified by conventional methods (e.g., column chromatography, recrystallization, etc.) to obtain an isolated diastereomer having desired configuration. The diastereomer obtained is subjected to deprotection (e.g., hydrogenation) to afford desired enantiomer. The optical resolving reagent is used in an amount of 1 to 4 equivalent, preferably 1 to 2.5 equivalent, in respect of compound (I'-1).

Solvent that can be used includes aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, etc.), amides (e.g., dimethylformamide, dimethylacetamide, N-methylpyrrolidone) and mixture thereof, etc.

Reaction temperature may be −10° C. to 150° C., preferably 0° C. to 50° C. Although reaction time depends on the compound used, it may be 10 minutes to 48 hr.

According to General Procedure 1, following compounds were prepared.

Example 15

Preparation of (+)-4-(2,2-dimethylpropionoyl)-3-hydroxy-1-(4-isoxazol-3-ylphenyl)-5-(2-methoxyphenyl)-1,5-dihydropyrrol-2-one

[Chemical Formula 49]

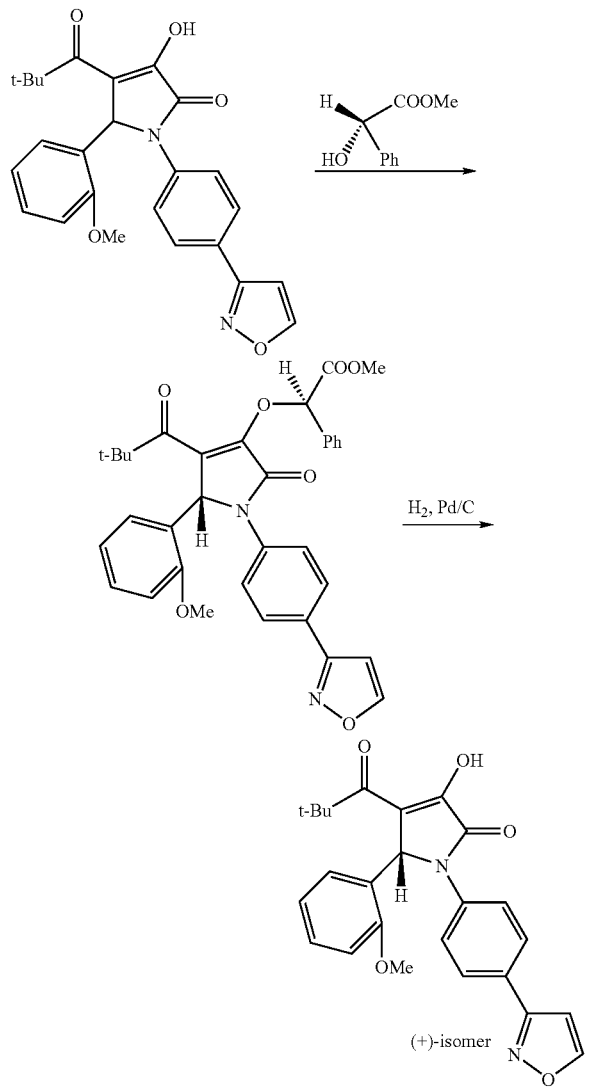

To a mixture of 4-(2,2-dimethylpropionoyl)-3-hydroxy-1-(4-isoxazol-3-ylphenyl)-5-(2-methoxyphenyl)-1,5-dihydropyrrol-2-one (0.43 g, 1 mmol), (S)-methyl 2-hydroxy-2-phenyl acetate (0.23 g, 1.4 mmol), tri-phenylphosphine (0.34 g, 1.3 mmol) and THF (10 mL), isopropyl azodicarboxylate (0.26 mL, 1.3 mmol) was added under ice-cooling and the mixture was stirred at r.t. for 0.5 hr. The reaction mixture was concentrated under reduced pressure. The residue was purified by silica gel column chromatography (ethyl acetate/n-hexane) to obtain diastereomer mixture, which was then recrystallized from ethyl acetate/n-hexane to give diastereomer (0.14 g, 25%) as colorless crystals.

To a solution the diastereomer (0.058 g, 0.1 mmol) in dioxane (3 mL), 10% palladium on carbon (0.026 g) was added. The mixture was hydrogenated at r.t. for 2 hr. The reaction mixture was filtrated by celite and the filtrate was concentrated under reduced pressure. The residue was purified by silica gel column chromatography (ethyl acetate/n-hexane) to give (+)-4-(2,2-dimethylpropionoyl)-3-hydroxy-1-(4-isoxazol-3-ylphenyl)-5-(2-methoxyphenyl)-1,5-dihydropyrrol-2-one (0.043 g, 100%, optical purity: 100% ee) as colorless crystals.

$[\alpha]_D$: +62.5±2.0° (in $CHCl_3$), 1H-NMR (δ ppm TMS/DMSO-d6) 1.10 (9H, s), 3.89 (3H, brs), 6.39 (1H, brs), 6.70-7.82 (9H, m), 8.95 (1H, d, J=1.8 Hz), 12.08 (1H, brs).

General Procedure 2

Preparation of Isoxazole

[Chemical Formula 50]

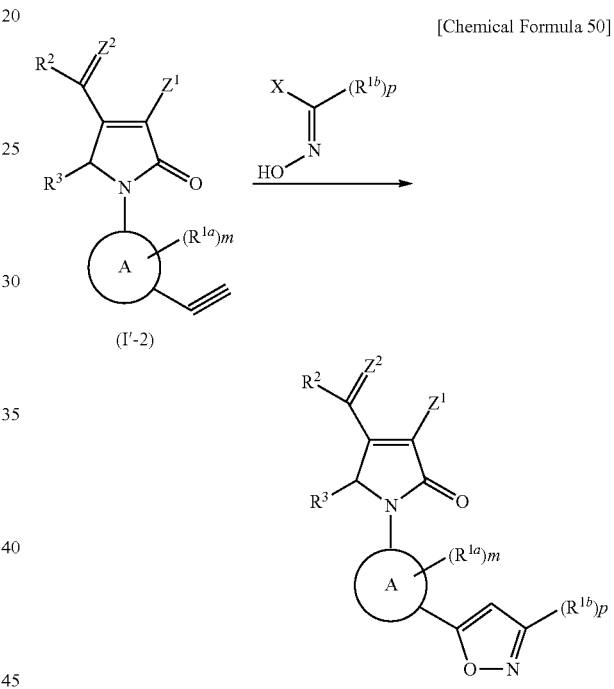

wherein X is halogen; all the other variables are as defined above.

Compound (I'-2), hydroxyimino halide and base are reacted in an appropriate solvent. If necessary, obtained compound may be purified according to conventional methods (e.g., column chromatography, recrystallization, etc.). The hydroxyimino halide is used in an amount of 1 to 5 equivalent, preferably 1 to 2.5 equivalent, in respect of compound (I'-2).

Solvent that can be used includes aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, etc.), amides (e.g., dimethylformamide, dimethylacetamide, N-methylpyrrolidone) and a mixture thereof, etc.

Base that can be used includes, for example, metal hydroxide (e.g., sodium hydroxide, potassium hydroxide, etc.), metal hydride (e.g., sodium hydride, lithium hydride, etc.), metal carbonate (e.g., sodium carbonate, potassium carbonate, calcium carbonate, etc.), etc., and it is used in an amount of 2 equivalent or more, preferably 2 to 10 equivalent, in respect of compound (I'-2).

Reaction temperature may be −40° C. to 150° C., preferably 0° C. to 50° C. Although reaction time depends on the compound used, it may be 10 minutes to 48 hr.

According to General Procedure 2, following compounds were prepared.

Example 16

Preparation of 3-t-butyl-5-[4-(3-ethoxycarbonyl-5-isoxazolyl)phenyl]-4-(2-methoxyphenyl)-4,5-dihydro-1H-pyrrolo[3,4-c]pyrazol-6-one

[Chemical Formula 51]

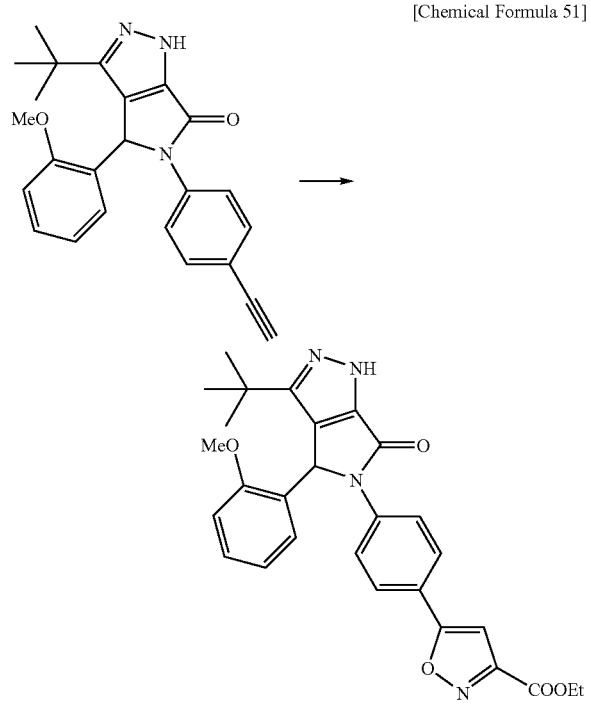

To a mixture of 3-t-butyl-5-(4-ethynylphenyl)-4-(2-methoxyphenyl)-4,5-dihydro-1H-pyrrolo[3,4-c]pyrazol-6-one (1.51 g, 3.9 mmol), ethyl 2-chloro-2-hydroxyiminoacetate (1.19 g, 7.8 mmol) and THF (4 mL), triethylamine (1.09 mL, 7.8 mmol) in THF (3 mL) was added dropwise under ice-cooling conditions, and the mixture was stirred at 0° C. for 4 hr. Ethyl 2-chloro-2-hydroxyiminoacetate (1.19 g, 7.8 mmol) was added, and further triethylamine (0.81 mL, 5.9 mmol) in THF (3 mL) was added dropwise. The mixture was stirred at 0° C. for 2 hr and left stand overnight. The precipitate was removed by filtration, the filtrate was concentrated under reduced pressure. The residue was purified by silica gel column chromatography (ethyl acetate/n-hexane) to give 3-t-butyl-5-[4-(3-ethoxycarbonyl-5-isoxazolyl)phenyl]-4-(2-methoxyphenyl)-4,5-dihydro-1H-pyrrolo[3,4-c]-pyrazol-6-one (1.26 g, 64%) as a colorless solid.

1H-NMR (δ ppm TMS/DMSO-d6) 1.13 (9H, s), 1.43 (3H, t, J=7.1), 3.50 (0.5H, s), 4.01 (2.5H, s), 4.45 (2H, q, J=7.3), 6.01 (0.3H, s), 6.74-6.88 (2.7H, m), 6.91 (1H, d, J=8.6), 7.19 (1H, t, J=7.4), 7.70 (2H, d, J=8.6), 7.81 (2H, d, J=8.6).

Example 17

Preparation of 3-t-butyl-5-[4-(3-carboxy-5-isoxazolyl)phenyl]-4-(2-methoxyphenyl)-4,5-dihydro-1H-pyrrolo[3,4-c]pyrazol-6-one

[Chemical Formula 52]

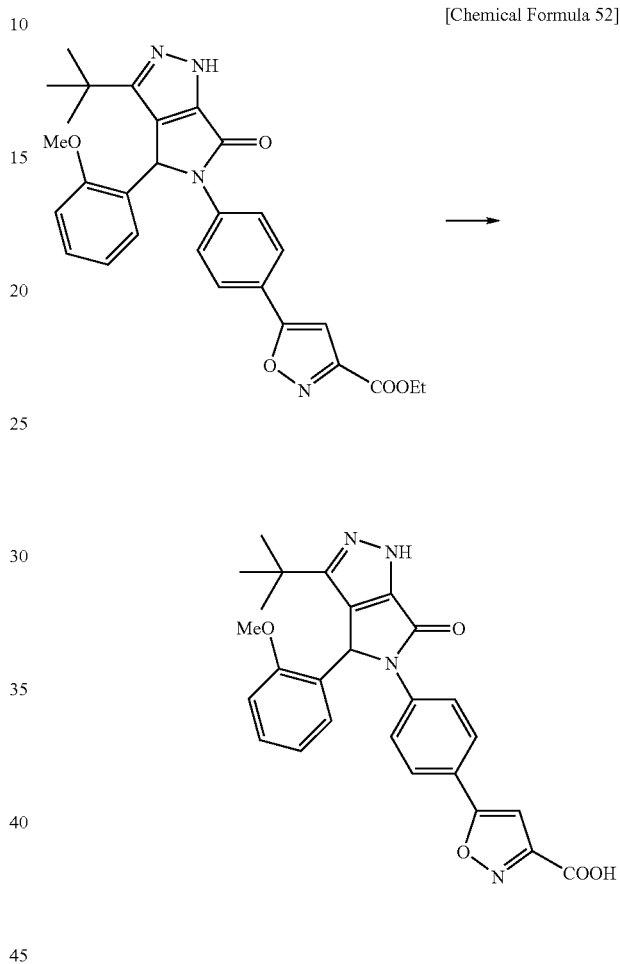

To a mixture of 3-t-butyl-5-[4-(3-ethoxycarbonyl-5-isoxazolyl)phenyl]-4-(2-methoxyphenyl)-4,5-dihydro-1H-pyrrolo[3,4-c]pyrazol-6-one (1.26 g, 2.5 mmol), methanol (4 mL), THF (4 mL) and water (3 mL), 2N aqueous sodium hydroxide (1.5 mL, 3 mmol) was added and the mixture was stirred at 50° C. for 1 hr. Water (40 mL) and 1N hydrochloric acid (2 mL) were added to the mixture, which was then extracted with ethyl acetate. The organic layer was washed with brine, dried over anhydrous sodium sulfate, and concentrated under reduced pressure. The crude product was suspended in ether, and the precipitate was collected to give 3-t-butyl-5-[4-(3-carboxy-5-isoxazolyl)phenyl]-4-(2-methoxyphenyl)-4,5-dihydro-1H-pyrrolo[3,4-c]pyrazol-6-one (0.84 g, 71%) as pale yellow crystals.

1H-NMR (δ ppm TMS/DMSO-d6) 1.05 (9H, s), 3.96 (3H, s), 6.50 (0.3H, s), 6.68-6.94 (2.7H, m), 7.00-7.25 (2H, m), 7.29 (1H, s), 7.77 (2H, d, J=8.6), 7.87 (2H, d, J=8.6), 13.43 (1H, brs), 13.97 (1H, brs).

Example 18

Preparation of 3-t-butyl-5-[4-(3-dimethylcarbamoyl-5-isoxazolyl)phenyl]-4-(2-methoxyphenyl)-4,5-dihydro-1H-pyrrolo[3,4-c]pyrazol-6-one

[Chemical Formula 53]

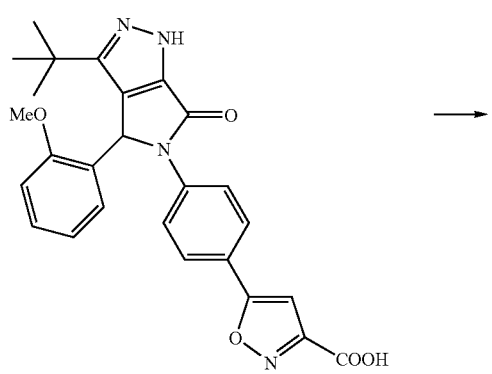

Example 19

Preparation of 3-t-butyl-5-[4-(3-hydroxymethyl-5-isoxazolyl)phenyl]-4-(2-methoxyphenyl)-4,5-dihydro-1H-pyrrolo[3,4-c]pyrazol-6-one

[Chemical Formula 54]

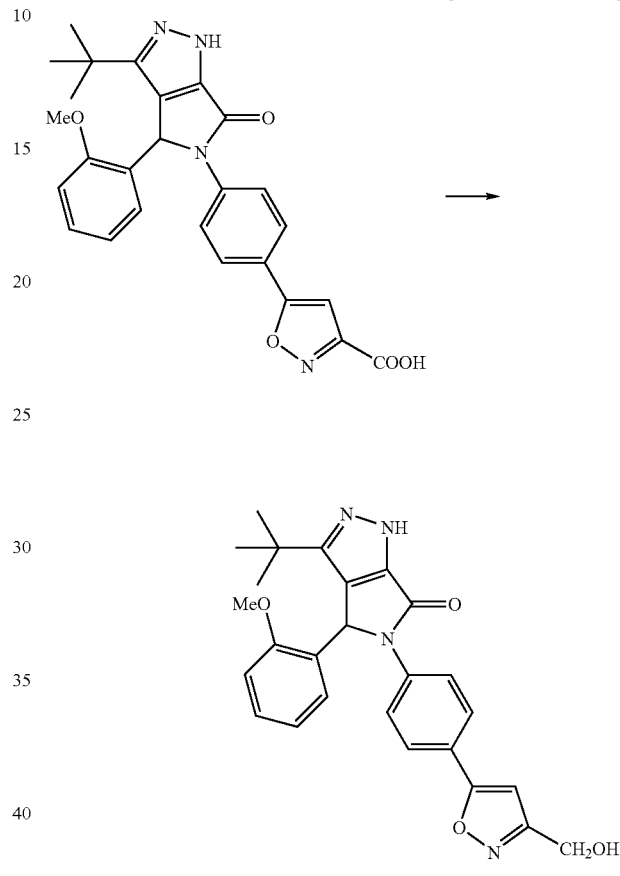

To a mixture of 3-t-butyl-5-[4-(3-carboxy-5-isoxazolyl)phenyl]-4-(2-methoxyphenyl)-4,5-dihydro-1H-pyrrolo[3,4-c]pyrazol-6-one (0.080 g, 0.17 mmol) and DMF (2 mL), dimethylamine hydrochloride (0.021 g, 0.25 mmol), 1-hydroxybenztriazole (0.034 g, 0.25 mmol), 4-dimethylaminopyridinium (0.004 g, 0.03 mmol), 1-ethyl-3-(3-dimethylaminopropyl)carbodiimide hydrochloride (0.048 g, 0.25 mmol) and triethylamine (0.035 mL, 0.25 mmol) was added, and the mixture was stirred at r.t. for 2 hr. Ethyl acetate and water were added to the mixture, and the precipitate was collected by filtration to give 5-cyclohexyl-3-hydroxy-1-(4-isoxazol-3-ylphenyl)-4-(4-methylcarbamoylbenzoyl)-1,5-dihydropyrrol-2-one (0.055 g, 65%) as pale yellow crystals.

1H-NMR (δ ppm TMS/DMSO-d6) 1.05 (9H, s), 3.02 (3H, s), 3.39 (1H, s), 6.50 (0.3H, m), 6.65-6.96 (2.7H, m), 7.06 (1H, d, J=8.1), 7.14 (1H, s), 7.19 (1H, t, J=7.6), 7.76 (2H, d, J=8.6), 7.84 (2H, d, J=8.6), 13.32 (1H, brs).

To a mixture of 3-t-butyl-5-[4-(3-carboxy-5-isoxazolyl)phenyl]-4-(2-methoxyphenyl)-4,5-dihydro-1H-pyrrolo[3,4-c]pyrazol-6-one (0.080 g, 0.17 mmol), triethylamine (0.031 mL, 0.22 mmol) and THF (2 mL), ethyl chlorocarbonate (0.019 mL, 0.20 mmol) was added under ice-cooling conditions and the mixture stirred at r.t. for 2 hr. Sodium borohydride (0.026 g, 0.68 mmol), water (0.3 mL) and methanol (1 mL) were added to the mixture and the mixture was stirred at r.t. for 10 min. Water was added to the mixture, the mixture was extracted with ethyl acetate. The organic layer was washed with 1N hydrochloric acid, saturated sodium bicarbonate and brine, dried over anhydrous sodium sulfate, and concentrated under reduced pressure. The residue was crystallized from dichloromethane, diethyl ether and ethyl acetate, and the precipitate was collected by filtration to give 3-t-butyl-5-[4-(3-hydroxymethyl-5-isoxazolyl)-phenyl]-4-(2-methoxyphenyl)-4,5-dihydro-1H-pyrrolo[3,4-c]pyrazol-6-one (0.068 g, 88%) as colorless crystals.

1H-NMR (δ ppm TMS/DMSO-d6) 1.03 (9H, s), 3.39 (1H, s), 3.94 (2H, s), 4.51 (2H, d, J=26.9), 5.52 (1H, t, J=5.8), 6.47 (0.3H, s), 6.65-6.84 (2.7H, m), 6.88 (1H, s), 7.05 (1H, d, J=8.1), 7.19 (1H, t, J=7.6), 7.73 (2H, d, J=8.6), 7.78 (2H, d, J=8.6), 13.13 (0.3H, brs), 13.39 (0.6H, brs), 13.58 (0.1H, brs).

General Procedure 3

Preparation of Boc-protected Amine

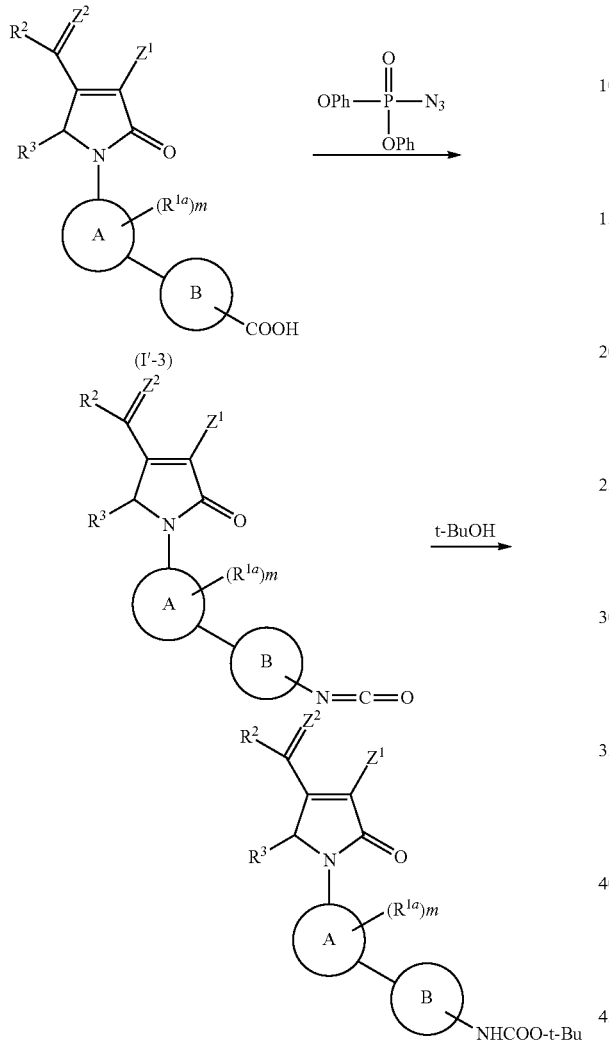

wherein all the variables are as defined above.

Compound (I'-3), base and azidating agent (e.g., diphenyl phosphorylazido) are reacted in an appropriate solvent, and t-butanol and desiccant agent (e.g., sodium sulfate, molecular sieve powder) are added. If necessary, obtained compound may be purified according to conventional methods (e.g., column chromatography, recrystallization, extraction, etc.). The azidating agent is used in an amount of 1 to 4 equivalent, preferably 1 to 2.5 equivalent, in respect of compound (I'-3).

Solvent that can be used includes aromatic hydrocarbons (e.g., toluene, benzene, xylene, etc.), saturated hydrocarbons (e.g., cyclohexane, hexane, etc.), ethers (e.g., tetrahydrofuran, diethyl ether, dioxane, etc.) and a mixture thereof, etc.

Base that can be used includes, for example, metal hydroxide (e.g., sodium hydroxide, potassium hydroxide, etc.), metal hydride (e.g., sodium hydride, lithium hydride, etc.), metal carbonate (e.g., sodium carbonate, potassium carbonate, calcium carbonate, etc.), etc. It may be used in an amount of one equivalent or more, preferably 1 to 5 equivalent, in respect of compound (I'-2).

Reaction temperature may be 0° C. to 150° C., preferably 40° C. to 120° C. Although reaction time depends on the compound used, it may be 10 minutes to 48 hr.

According to General Procedure 3, following compounds were prepared.

Example 20

Preparation of 3-t-butyl-5-[4-(3-t-butoxycarbonylamino-5-isoxazolyl)-phenyl]-4-(2-methoxyphenyl)-4,5-dihydro-1H-pyrrolo[3,4-c]pyrazol-6-one

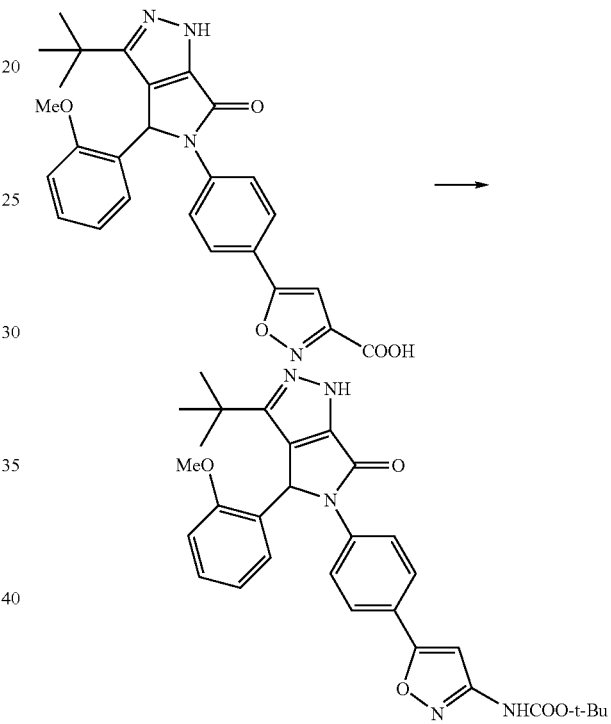

To a mixture of 3-t-butyl-5-[4-(3-carboxy-5-isoxazolyl)phenyl]-4-(2-methoxyphenyl)-4,5-dihydro-1H-pyrrolo[3,4-c]pyrazol-6-one (0.948 g, 2.0 mmol), triethylamine (0.33 mL, 2.4 mmol) and DMF (15 mL), diphenyl phosphorylazido (0.52 mL, 2.4 mmol) was added, and the mixture was stirred at 60° C. for 2 hr. Then, t-butanol (15 mL) and molecular sieve powder 4A (2 g) was added and the mixture was stirred at 90° C. for 3 hr. Insoluble matter was removed by filtration, water was added and the mixture was extracted with ethyl acetate. The organic layer was washed with aqueous ammonium chloride and brine, dried over anhydrous sodium sulfate, and concentrated under reduced pressure. The residue was crystallized from dichloromethane to give 3-t-butyl-5-[4-(3-t-butoxy-carbonylamino-5-isoxazolyl)phenyl]-4-(2-methoxyphenyl)-4,5-dihydro-1H-pyrrolo[3,4-c]pyrazol-6-one (0.566 g, 52%) as colorless crystals.

1H-NMR (δ ppm TMS/DMSO-d6) 1.05 (9H, s), 1.47 (9H, s), 3.95 (3H, s), 6.77-6.80 (3H, m), 7.00-7.11 (2H, m), 7.19 (1H, m), 7.72 (2H, d, J=8.6), 7.77 (2H, d, J=8.6), 10.34 (1H, s), 13.24 (1H, brs).

Example 21

Preparation of 3-t-butyl-5-[4-(3-amino-5-isoxazolyl) phenyl]-4-(2-methoxyphenyl)-4,5-dihydro-1H-pyrrolo[3,4-c]pyrazol-6-one

Example 22

Preparation of 4-(1,2-dioxopropyl)-3-hydroxy-1-(4-isoxazol-3-ylphenyl)-5-(2-methoxyphenyl)-1,5-dihydropyrrol-2-one

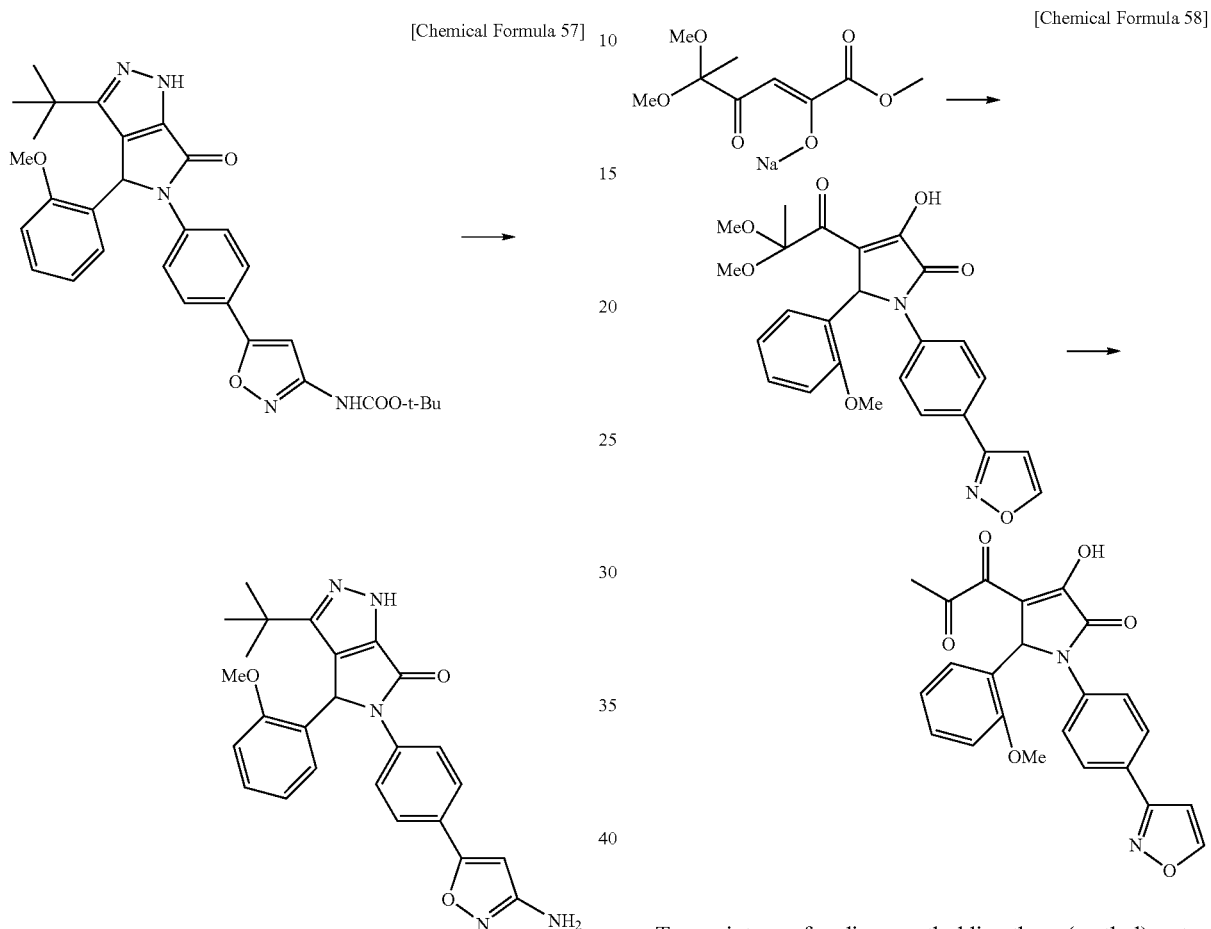

[Chemical Formula 57]

[Chemical Formula 58]

To a mixture of 3-t-butyl-5-[4-(3-t-butoxy carbonylamino-5-isoxazolyl)-phenyl]-4-(2-methoxyphenyl)-4,5-dihydro-1H-pyrrolo[3,4-c]pyrazol-6-one (0.036 g, 0.7 mmol) and methanol (2 mL), conc. hydrochloric acid (0.07 mL) was added, and the mixture was stirred at 60° C. for 2 hr. The precipitate was collected by filtration and recrystallized (methanol/dichloromethane) to give 3-t-butyl-5-[4-(3-amino-5-isoxazolyl)phenyl]-4-(2-methoxyphenyl)-4,5-dihydro-1H-pyrrolo[3,4-c]pyrazol-6-one (0.02 g, 68%) as pale yellow crystals.

1H-NMR (δ ppm TMS/DMSO-d6) 1.05 (9H, s), 3.38 (1H, s), 3.94 (2H, s), 5.60 (2H, s), 6.21 (1H, s), 6.44 (0.3H, s), 6.65-6.94 (2.7H, m), 7.04 (1H, d, J=8.1), 7.19 (1H, t, J=7.6), 7.67 (4H, s), 13.11 (0.2H, brs), 13.37 (0.7H, brs), 13.56 (0.1H, brs).

To a mixture of sodium methyldimethoxy(methyl)acetopyruvate (0.24 g, 1 mmol), 4-isoxazol-3-ylaniline (0.16 g, 1 mmol) and acetic acid (2 mL), 2-methoxybenzaldehyde (0.14 g, 1 mmol) was added and the mixture was stirred overnight at r.t. Then, water was added, and the precipitate was collected by filtration and recrystallized (dichloromethane/ether) to give 4-(2,2-dimethoxypropionoyl)-3-hydroxy-1-(4-isoxazol-3-ylphenyl)-5-(2-methoxyphenyl)-1,5-dihydropyrrol-2-one (0.22 g, 47%) as pale yellow crystals.

4-(2,2-dimethoxypropionoyl)-3-hydroxy-1-(4-isoxazol-3-ylphenyl)-5-(2-methoxyphenyl)-1,5-dihydropyrrol-2-one (0.08 g, 0.17 mmol) was added with acetic acid (0.1 mL) and water (0.9 mL). The mixture was stirred at 95° C. for 15 min. Then, water was added, the mixture was extracted with ethyl acetate. The organic layer was dried over anhydrous sodium sulfate, and concentrated under reduced pressure. The residue was crystallized from dichloromethane and ether to give 4-(1,2-dioxopropyl)-3-hydroxy-1-(4-isoxazol-3-ylphenyl)-5-(2-methoxyphenyl)-1,5-dihydropyrrol-2-one (0.05 g, 70%) as yellow crystals.

1H-NMR (δ ppm TMS/DMSO-d6) 2.24 (3H, s), 3.80 (3H, s), 6.38 (1H, s), 6.82 (1H, t, J=7.3), 6.93 (1H, d, J=7.3), 7.08 (1H, d, J=1.6), 7.13-7.18 (2H, m), 7.70-7.84 (4H, m), 8.96 (1H, d, J=1.6).

The following compounds, which structures and properties are shown bellow, were prepared according to the procedure as described above in the synthetic route, General Procedures and Examples.

| Compound No. | Structure | mp(° C.) or Supplier and Item No. | MS m/z [M+] |
|---|---|---|---|
| I-1 | 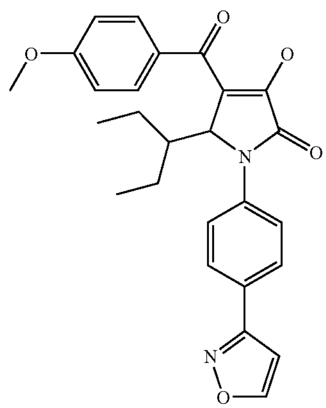 | 241-244 dec | 447 |
| I-2 | 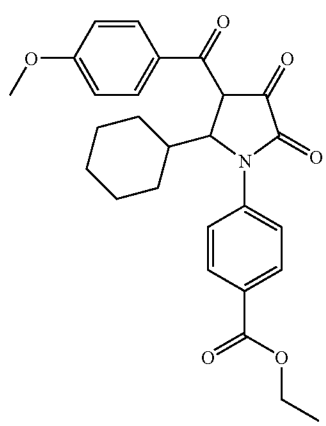 | 252-255 | 464 |
| I-3 | Chiral | | 492 |

| | | | |
|---|---|---|---|
| I-4 | 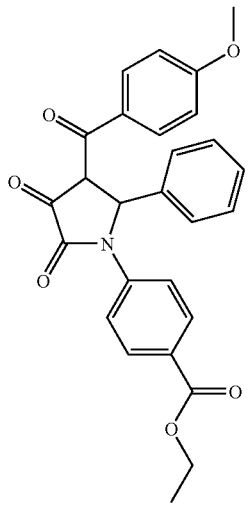 | Pharmeks PHAR123923 | 458 |
| I-5 | 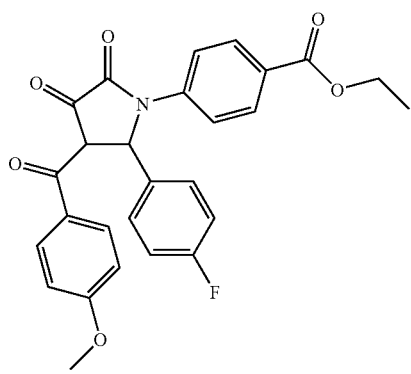 | Pharmeks PHAR136129 | 476 |
| I-6 | 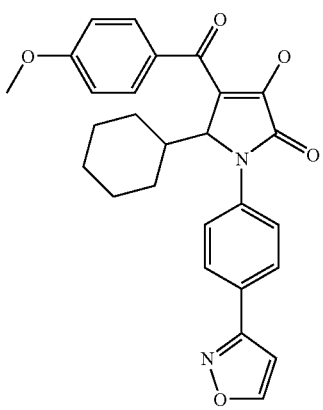 | 271-273 | 459 |
| I-7 | 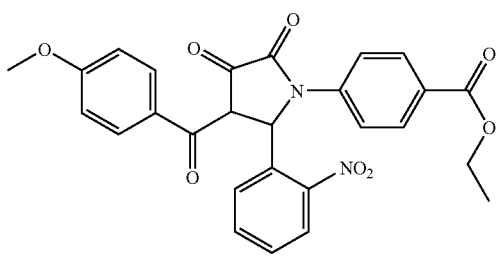 | Pharmeks PHAR135367 | 503 |

| | | | |
|---|---|---|---|
| I-8 | 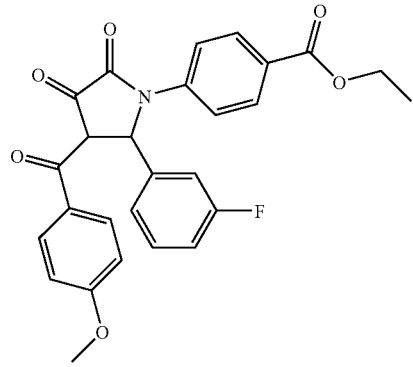 | Pharmeks PHAR137229 | 476 |
| I-9 | 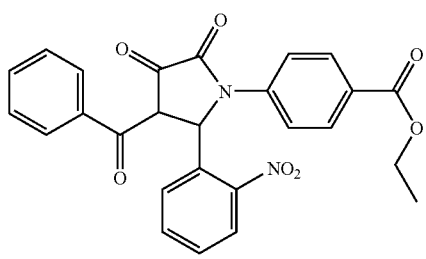 | Pharmeks PHAR140686 | 473 |
| I-10 | 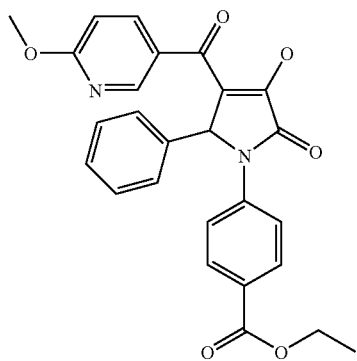 | | 459 |
| I-11 | 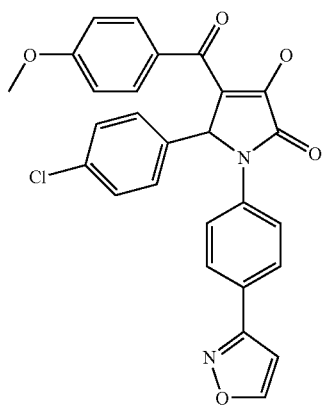 | 268-270(d) | 487 |

| | | | |
|---|---|---|---|
| I-12 | 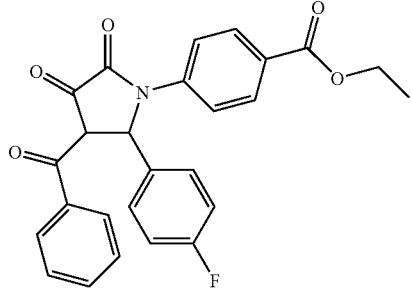 | Pharmeks PHAR139255 | 446 |
| I-13 | 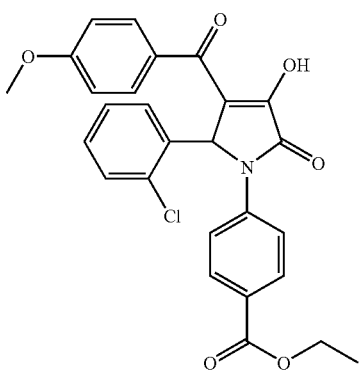 | CSC C11050380 | 492 |
| I-14 | 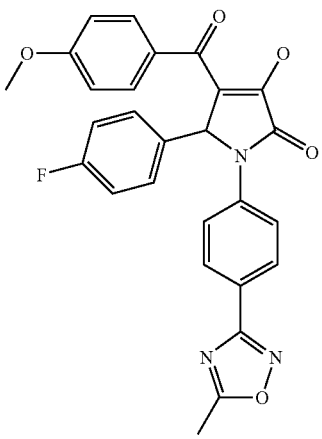 | 236-239 | 486 |
| I-15 | 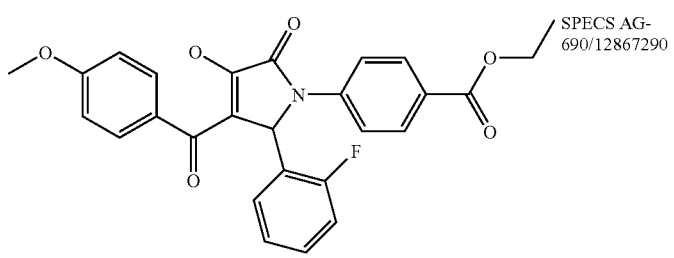 | SPECS AG-690/12867290 | 476 |

| | | | |
|---|---|---|---|
| I-16 | 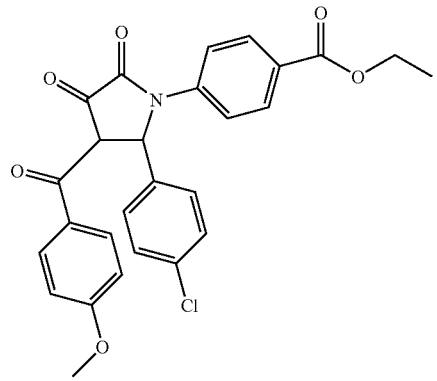 | Pharmeks PHAR146510 | 492 |
| I-17 | 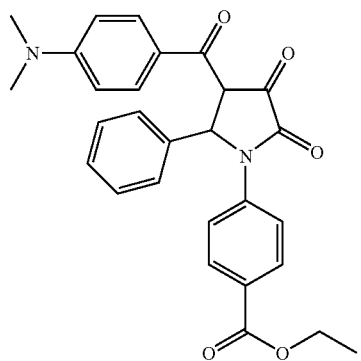 | | 471 |
| I-18 | 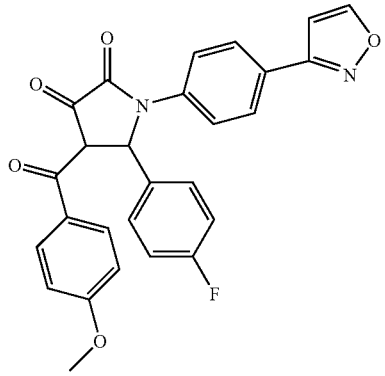 | 269-274(d) | 471 |
| I-19 | 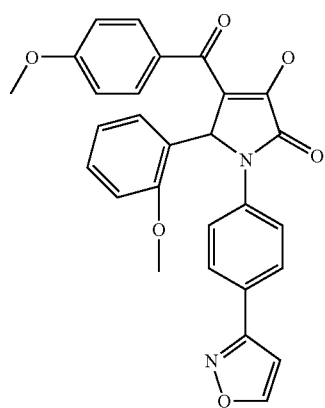 | 221-223 | 483 |

| | | |
|---|---|---|
| I-20 | 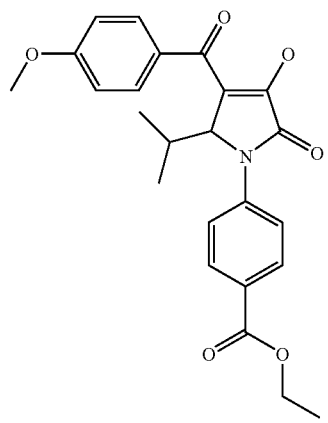 | 424 |
| I-21 | 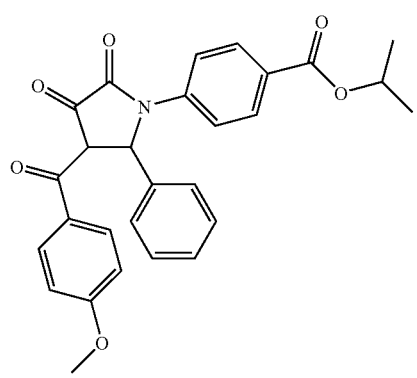 | 472 |
| I-22 | 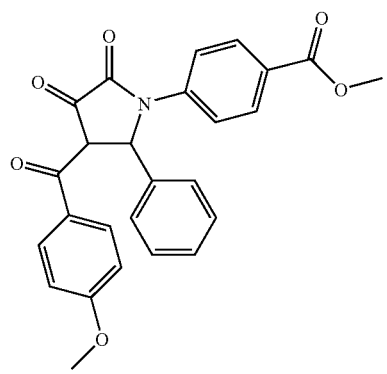 | 444 |
| I-23 | 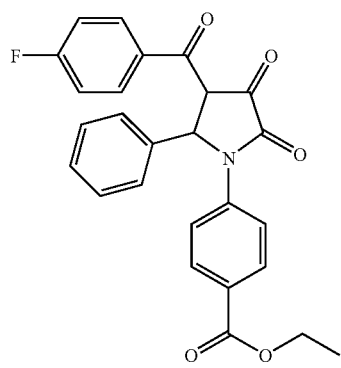 | 446 |

| | | | |
|---|---|---|---|
| I-24 | 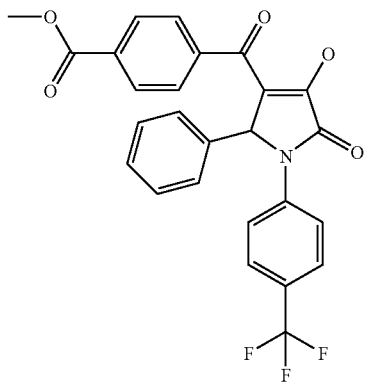 | | 482 |
| I-25 | 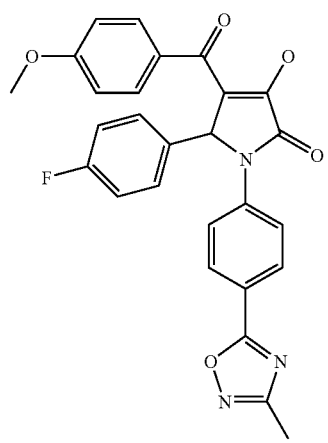 | 236-239 | 486 |
| I-26 | 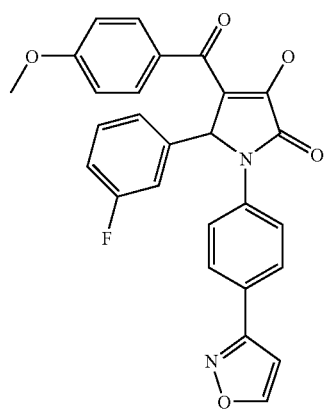 | 273-274(d) | 471 |
| I-27 | 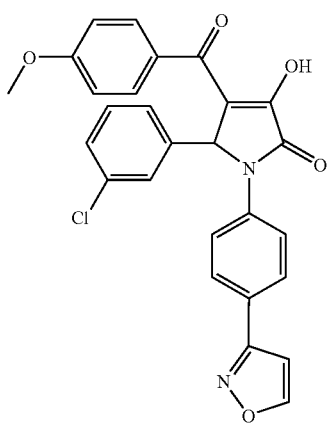 | 238-240 | 487 |

| | | | |
|---|---|---|---|
| I-28 | 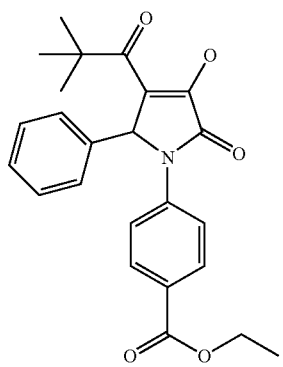 | | 408 |
| I-29 | 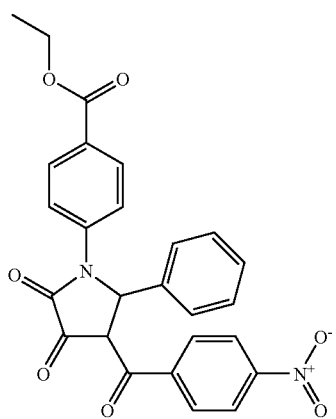 | Pharmeks PHAR057684 | 473 |
| I-30 | 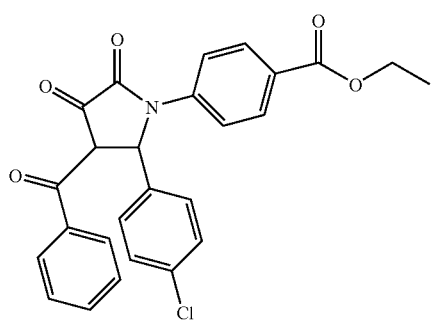 | Pharmeks PHAR155987 | 462 |
| I-31 | 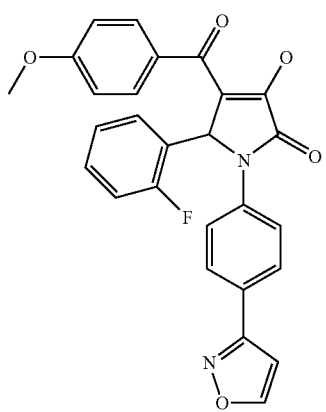 | 270-271(d) | 471 |

| | | | |
|---|---|---|---|
| I-32 | 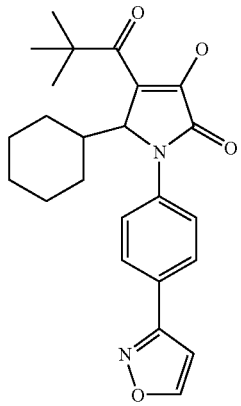 | 259-260 | 409 |
| I-33 | 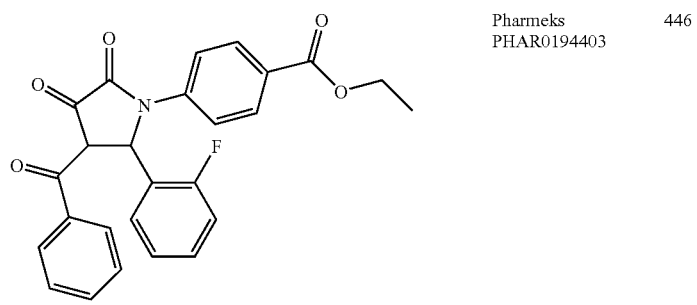 | Pharmeks PHAR0194403 | 446 |
| I-34 | 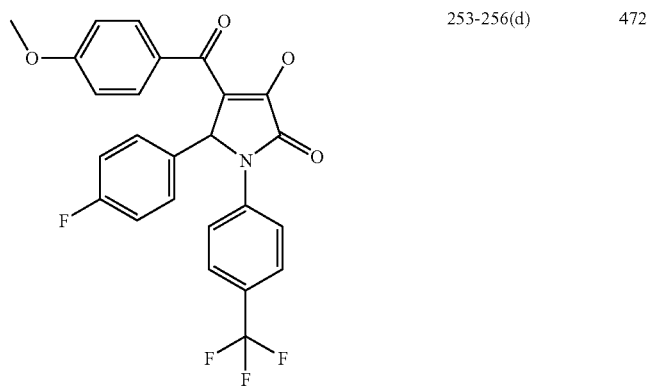 | 253-256(d) | 472 |
| I-35 | 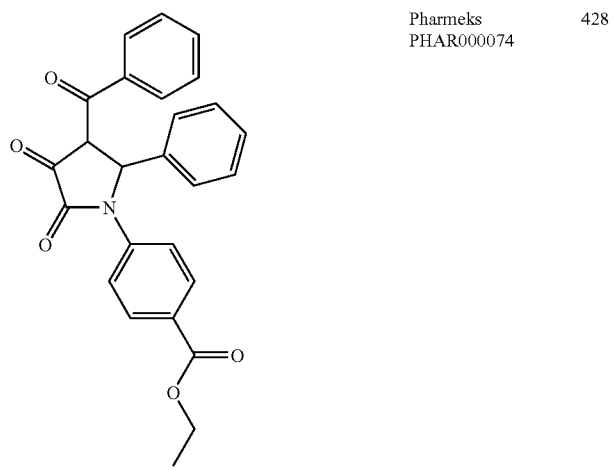 | Pharmeks PHAR000074 | 428 |

| | | | |
|---|---|---|---|
| I-36 | 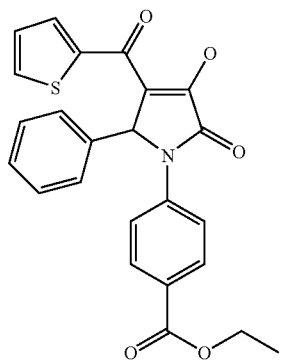 | | 434 |
| I-37 | 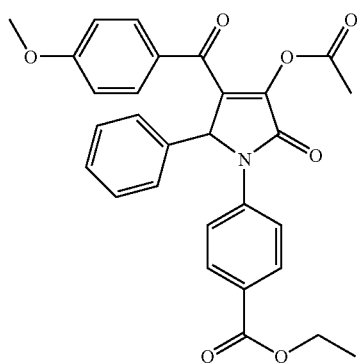 | | 500 |
| I-38 | 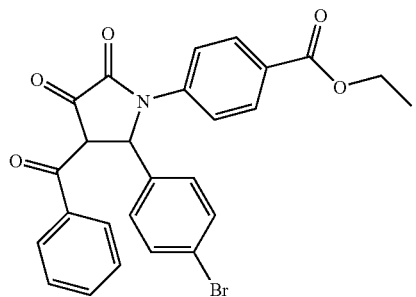 | Pharmeks PHAR040562 | 507 |
| I-39 | 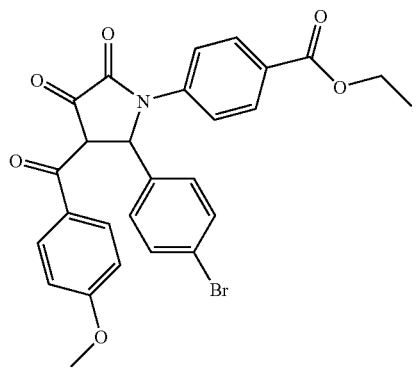 | Pharmeks PHAR135263 | 537 |

-continued
| | | | |
|---|---|---|---|
| I-40 | 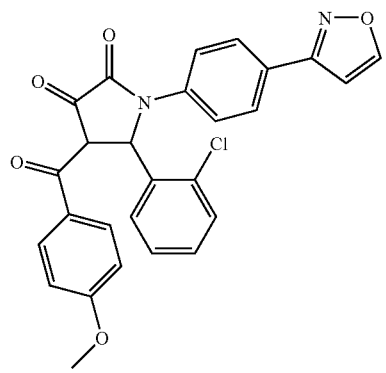 | 254-258(d) | 487 |
| I-41 | 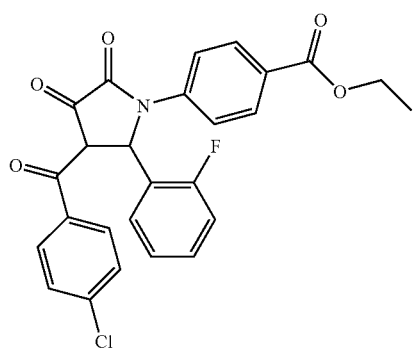 | Pharmeks PHAR131877 | 480 |
| I-42 | 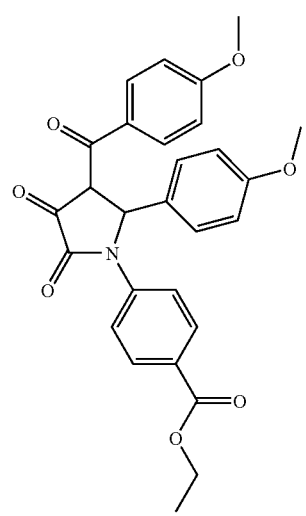 | Pharmeks PHAR127015 | 488 |
| I-43 | 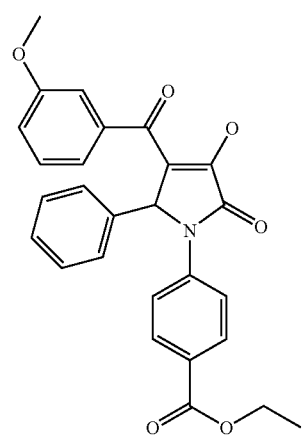 | | 458 |

| | | | |
|---|---|---|---|
| I-44 | 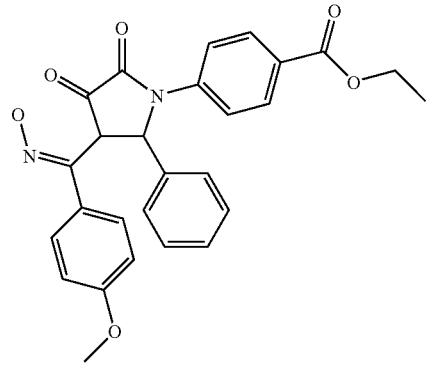 | | 473 |
| I-45 | 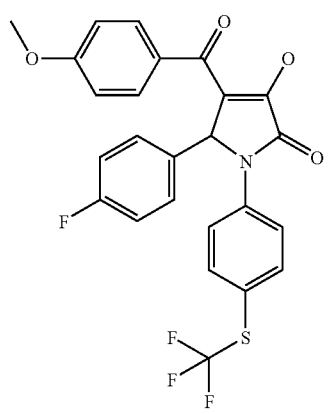 | 225-228(d) | 504 |
| I-46 | 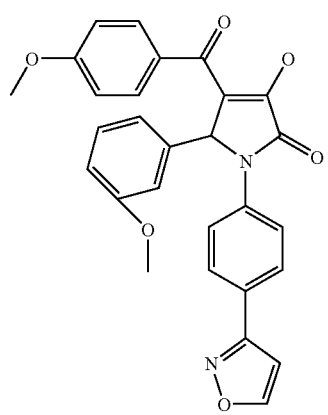 | 238-240 | 483 |
| I-47 | 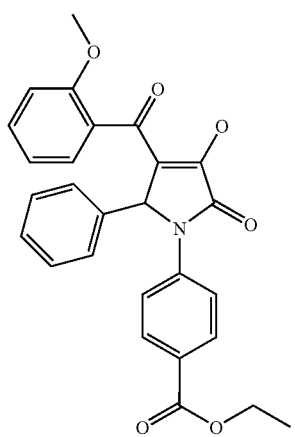 | | 458 |

| | | | |
|---|---|---|---|
| I-48 | 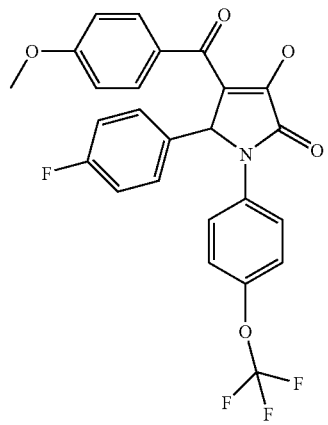 | 241-244 | 488 |
| I-49 | 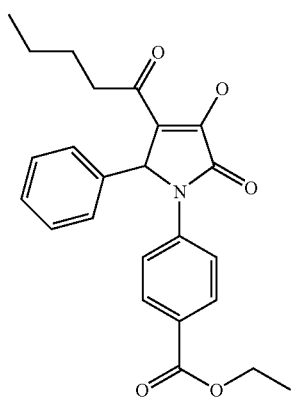 | | 408 |
| I-50 | 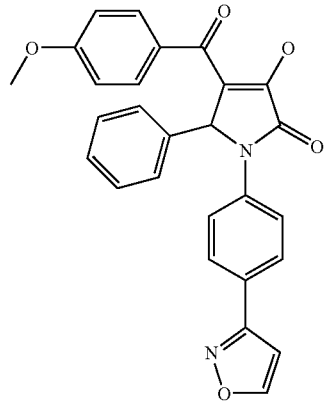 | 271-274 | 453 |
| I-51 | 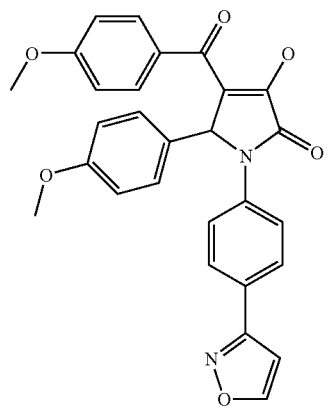 | | 483 |

-continued
| | | | |
|---|---|---|---|
| I-52 | 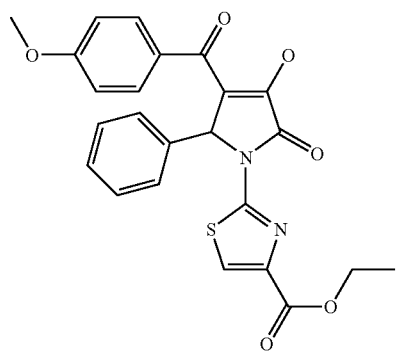 | | 465 |
| I-53 | 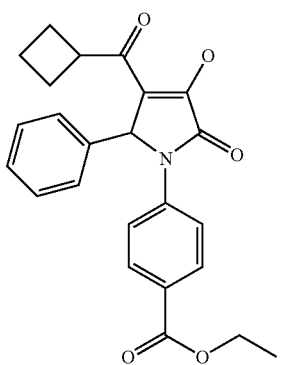 | | 406 |
| I-54 | 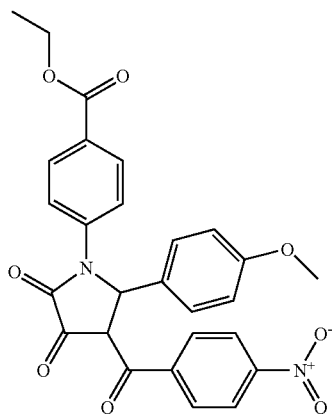 | Pharmeks PHAR027786 | 503 |
| I-55 | 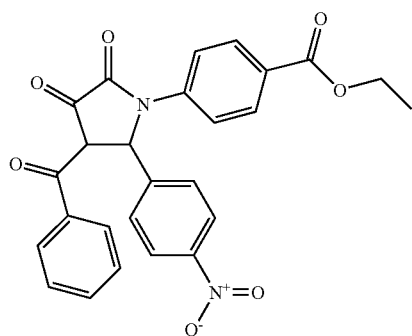 | Pharmeks PHAR124807 | 473 |

| | | | |
|---|---|---|---|
| I-56 | 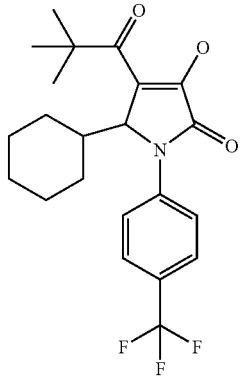 | 238-239 | 410 |
| I-57 | 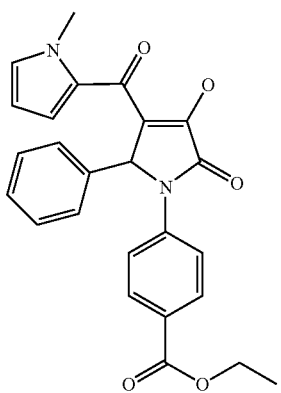 | | 431 |
| I-58 | 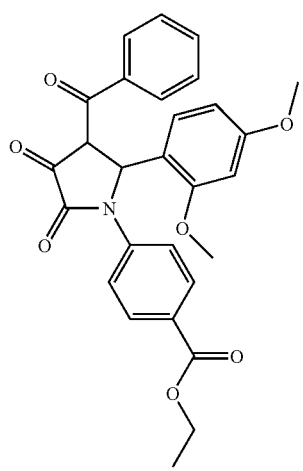 | Pharmeks PHAR122989 | 488 |
| I-59 | 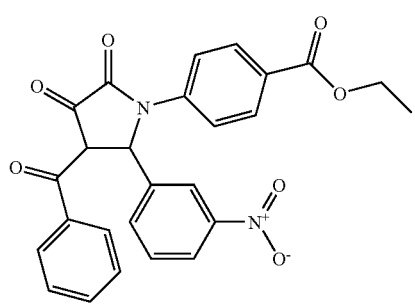 | Pharmeks PHAR138937 | 473 |

| | | | |
|---|---|---|---|
| I-60 | 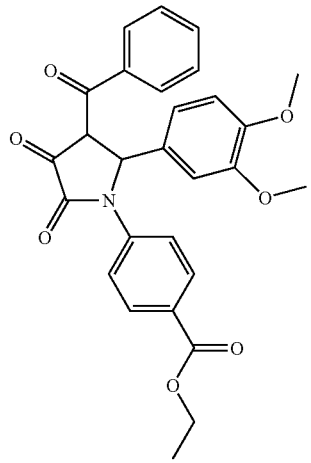 | Pharmeks PHAR142165 | 488 |
| I-61 | 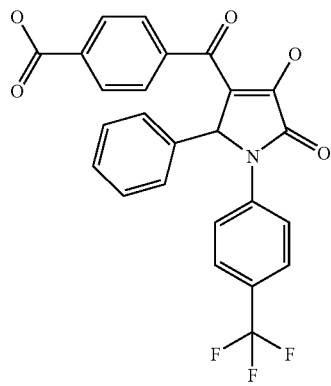 | | 468 |
| I-62 | 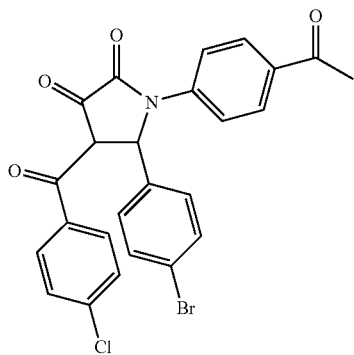 | Pharmeks PHAR105869 | 511 |

| | | | |
|---|---|---|---|
| I-63 | 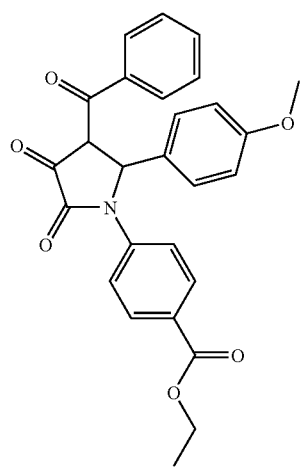 | Pharmeks PHAR026958 | 458 |
| I-64 | 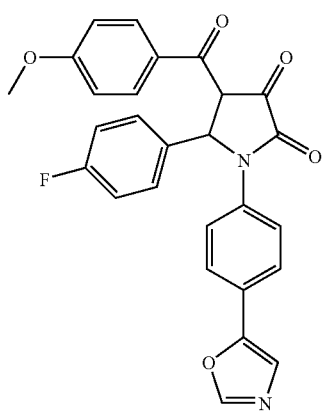 | 245-246 | 471 |
| I-65 | 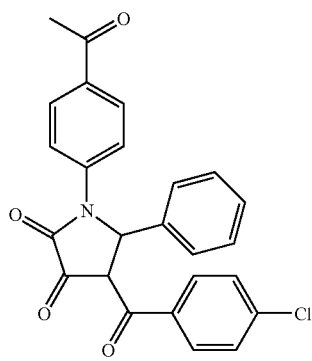 | Pharmeks PHAR128015 | 432 |
| I-66 | 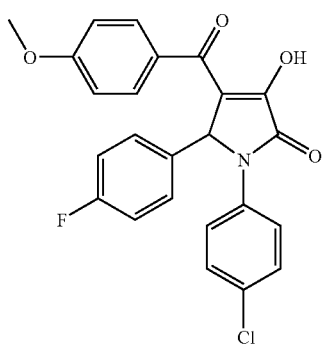 | | 438 |

| | | | |
|---|---|---|---|
| I-67 | 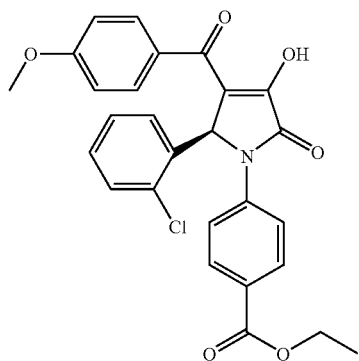 | | 492 |
| I-68 | 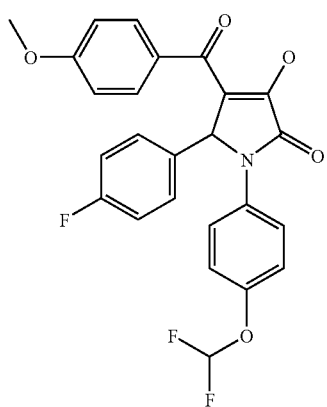 | | 470 |
| I-69 | 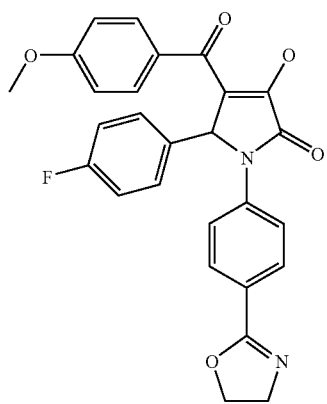 | 189-192 | 473 |
| I-70 | 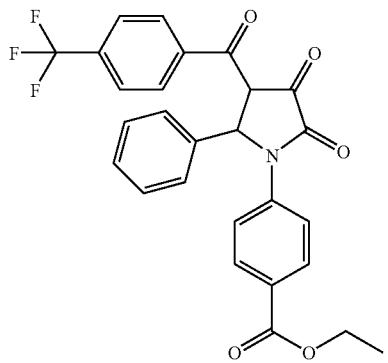 | | 496 |

| | | | |
|---|---|---|---|
| I-71 | 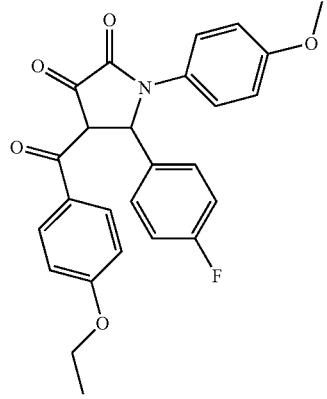 | Pharmeks PHAR121051 | 448 |
| I-72 | 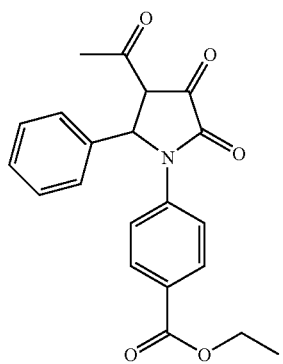 | | 366 |
| I-73 | 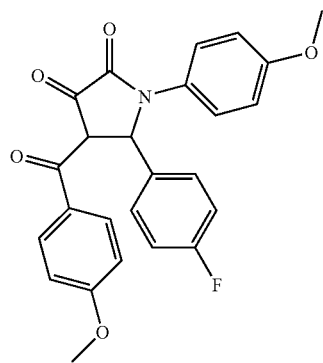 | 245-247 | 434 |
| I-74 | 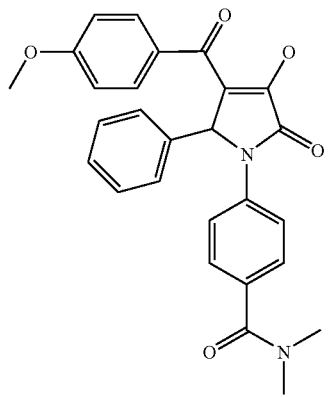 | | 457 |

| | | | |
|---|---|---|---|
| I-75 | 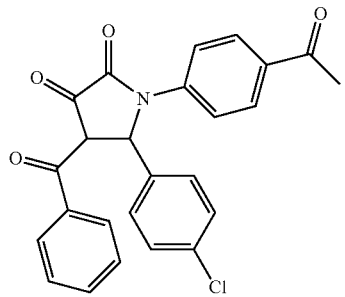 | Pharmeks PHAR041216 | 432 |
| I-76 | 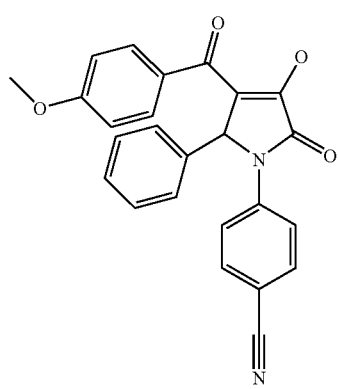 | | 411 |
| I-77 | 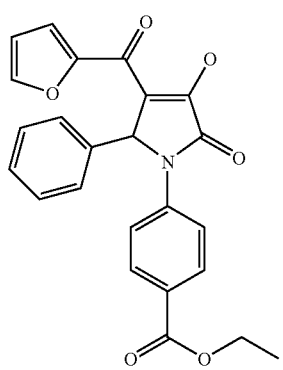 | | 418 |
| I-78 | 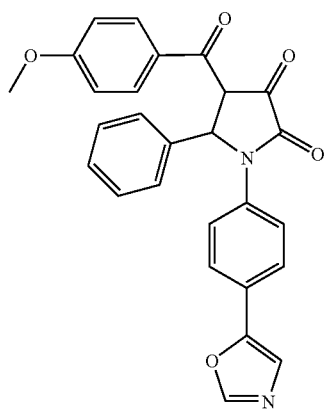 | 253-254 | 453 |

-continued
| | | | |
|---|---|---|---|
| I-79 | 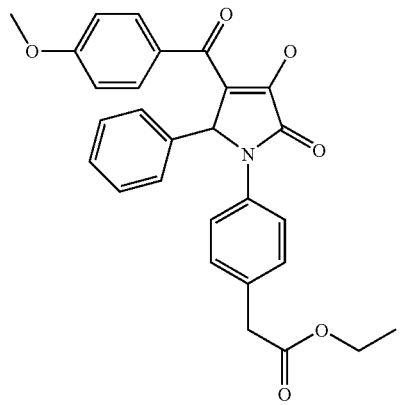 | | 472 |
| I-80 | 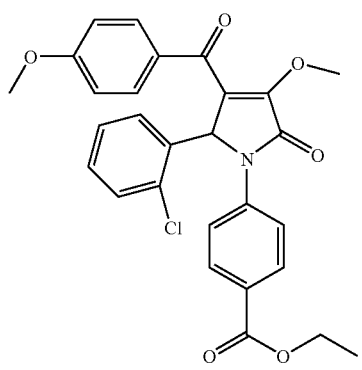 | | 506 |
| I-81 | 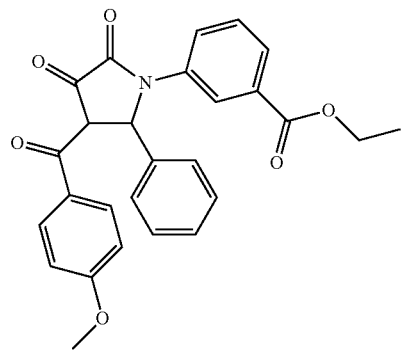 | | 458 |
| I-83 | 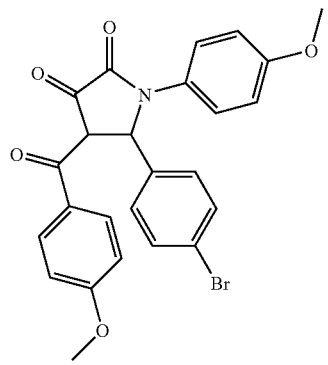 | Pharmeks PHAR032514 | 495 |

-continued
| | | | |
|---|---|---|---|
| I-84 | 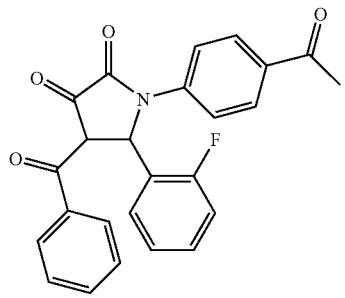 | Pharmeks PHAR137490 | 416 |
| I-85 | 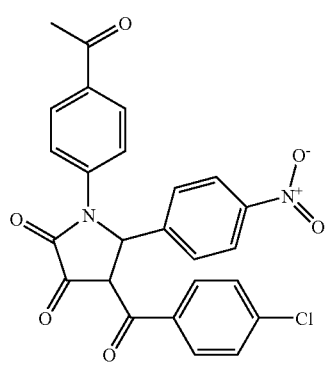 | Pharmeks PHAR140664 | 477 |
| I-86 | 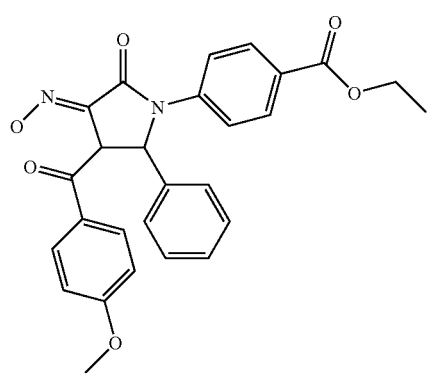 | | 473 |
| I-87 | 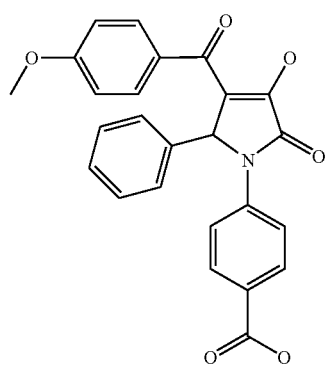 | 268-271 | 430 |

| | | | |
|---|---|---|---|
| I-88 | 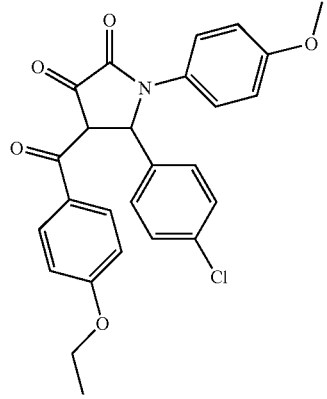 | Pharmeks PHAR124071 | 464 |
| I-89 | 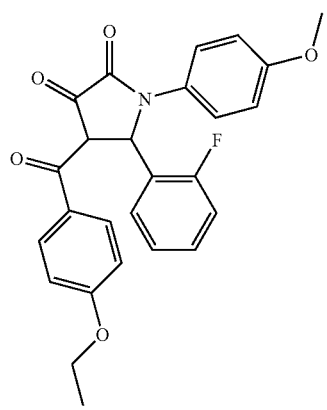 | Pharmeks PHAR127988 | 448 |
| I-90 | 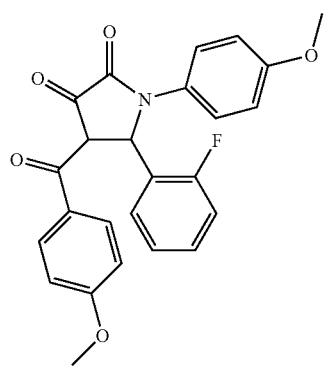 | Pharmeks PHAR138301 | 434 |
| I-91 | 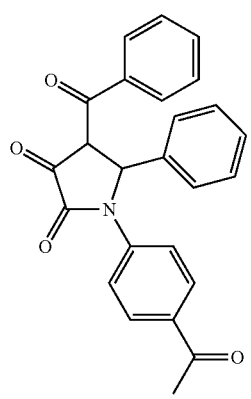 | Interbioscreen STOCK2S-84529 | 398 |

-continued
| | | | |
|---|---|---|---|
| I-92 | 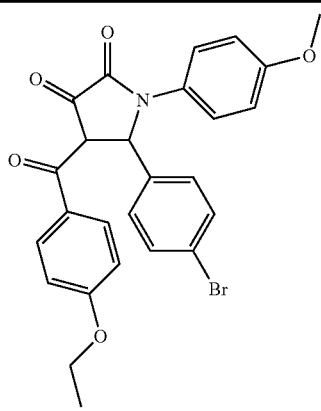 | Pharmeks PHAR068896 | 509 |
| I-93 | 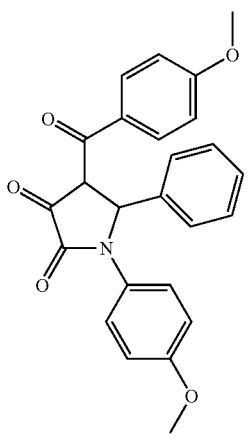 | Pharmeks PHAR012733 | 416 |
| I-94 | 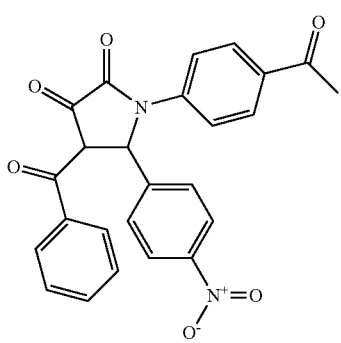 | Pharmeks PHAR106162 | 443 |
| I-95 | 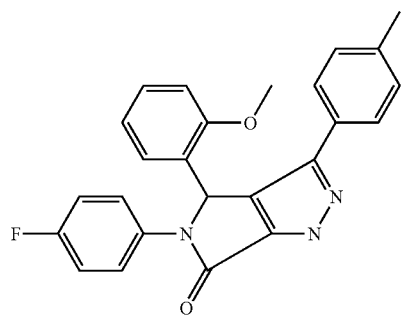 | IFLAB F0851-0720 | 414 |

-continued
| | | | |
|---|---|---|---|
| I-96 | 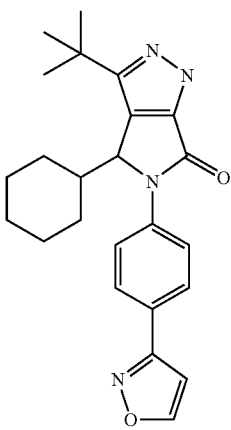 | 251-252 | 405 |
| I-97 | 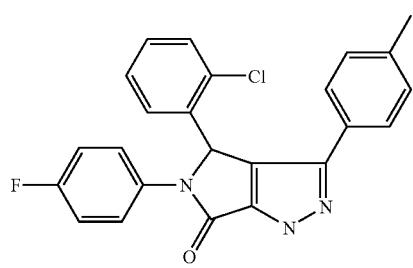 | CSC D34650002 | 418 |
| I-98 | 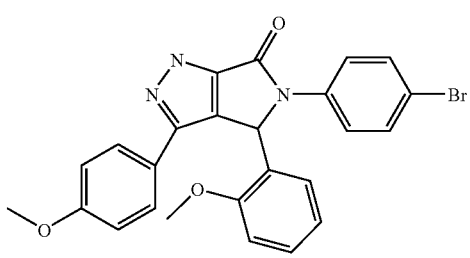 | ChemDiv C390-0063 | 491 |
| I-99 | 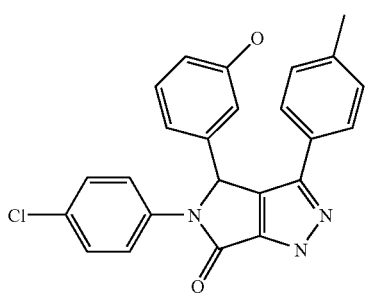 | ChemDiv C390-0059 | 416 |
| I-100 | 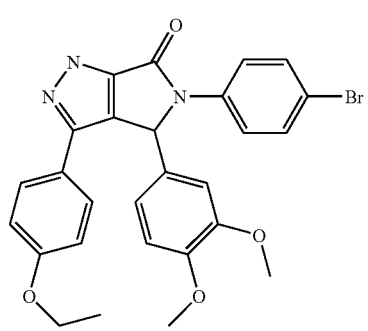 | ChemDiv C390-0113 | 535 |

| | | | |
|---|---|---|---|
| I-101 | 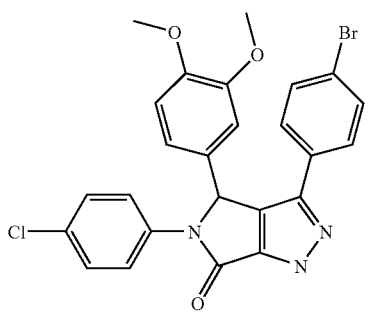 | ChemDiv C390-0021 | 525 |
| I-102 | 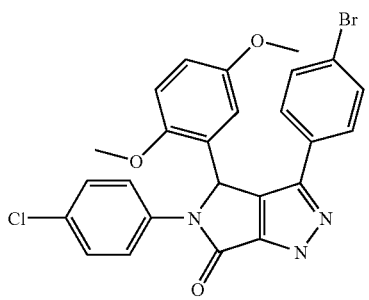 | ChemDiv C390-0023 | 525 |
| I-103 | 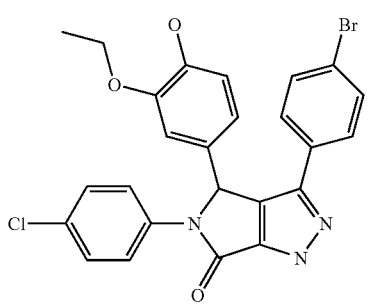 | ChemDiv C390-0025 | 525 |
| I-104 | 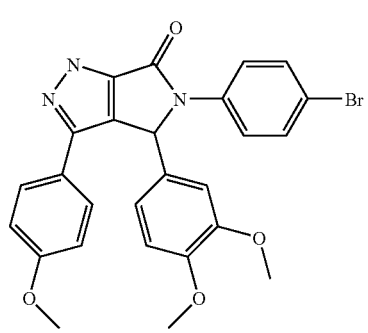 | ChemDiv C390-0081 | 521 |
| I-105 | 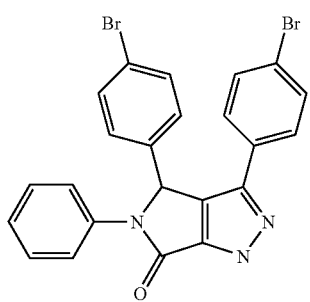 | ASINEX BAS 0898828 | 510 |

| | | | |
|---|---|---|---|
| I-106 | 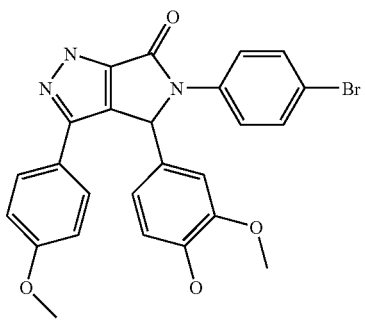 | ChemDiv C390-0083 | 507 |
| I-107 | 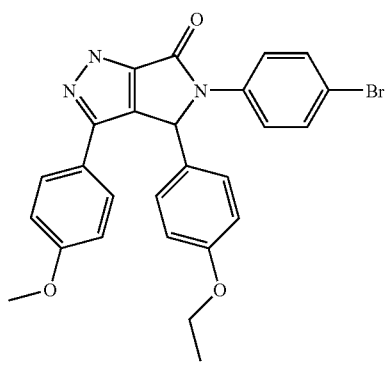 | ChemDiv C390-0085 | 505 |
| I-108 | 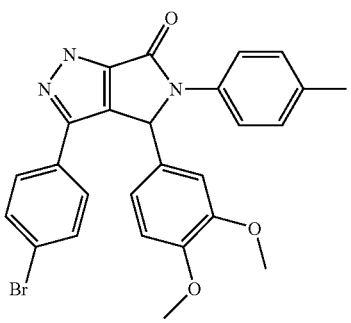 | ChemDiv C390-0305 | 505 |
| I-109 | 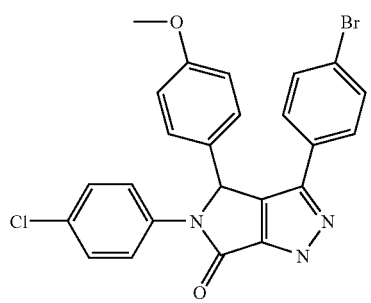 | ChemDiv C390-0003 | 495 |
| I-110 | 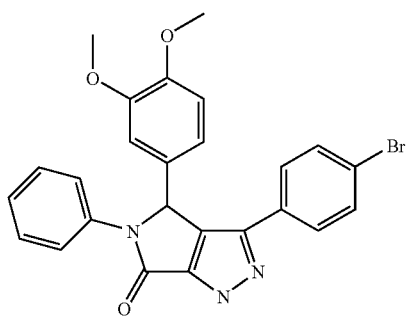 | ChemDiv 5340-2243 | 491 |

| | | | |
|---|---|---|---|
| I-111 | 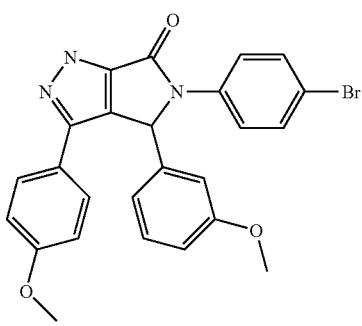 | ChemDiv C390-0066 | 491 |
| I-112 | 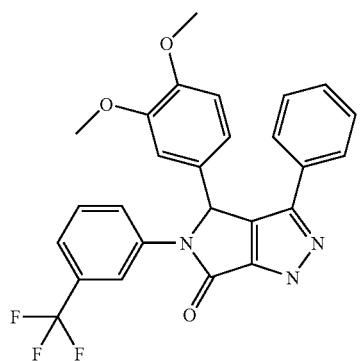 | SPECS AG-690/12413258 | 480 |
| I-113 | 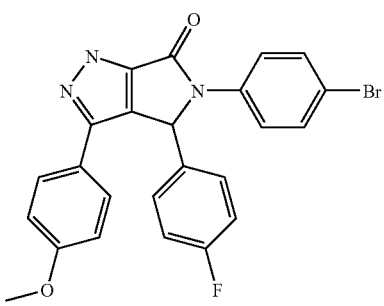 | ChemDiv C390-0070 | 479 |
| I-114 | 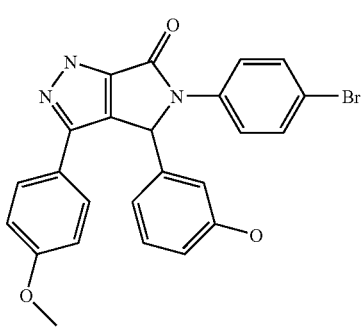 | ChemDiv C390-0091 | 477 |
| I-115 | 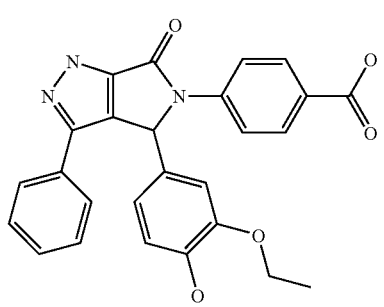 | ChemDiv C390-0180 | 456 |

| | | | |
|---|---|---|---|
| I-116 | 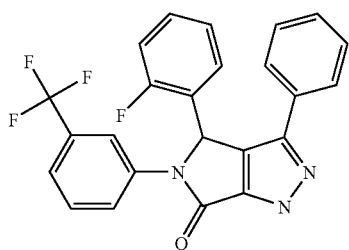 | CSC D50050967 | 438 |
| I-117 | 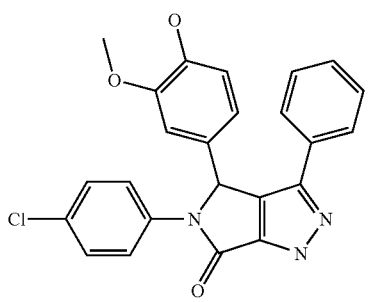 | CSC D50050972 | 432 |
| I-118 | 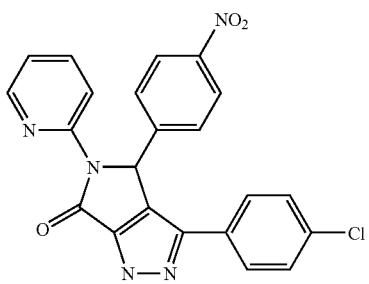 | IFLAB F0907-1024 | 432 |
| I-119 | 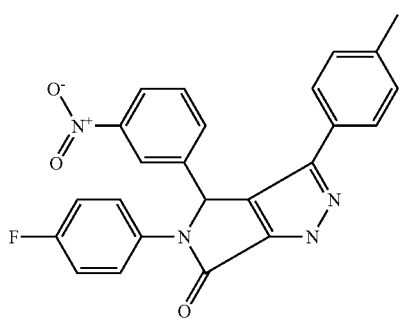 | IFLAB F0908-5466 | 429 |
| I-120 | 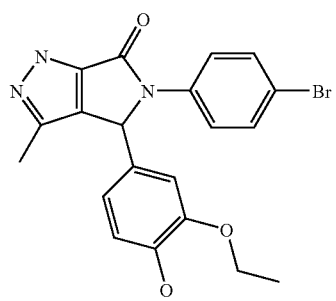 | ChemDiv C390-0148 | 429 |

| | | | |
|---|---|---|---|
| I-121 | 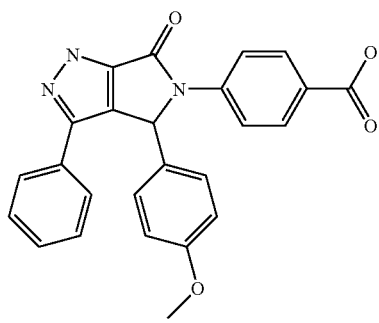 | ChemDiv C390-0158 | 426 |
| I-122 | 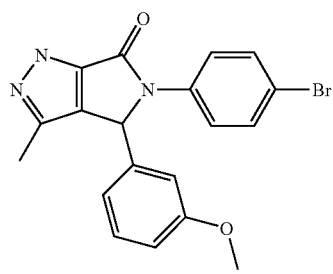 | ChemDiv C390-0130 | 399 |
| I-123 | 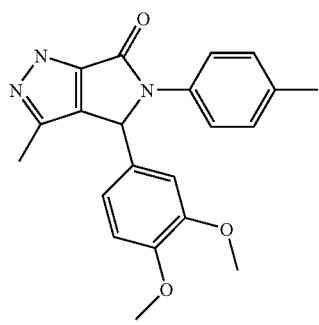 | ChemDiv C390-0241 | 364 |
| I-124 | 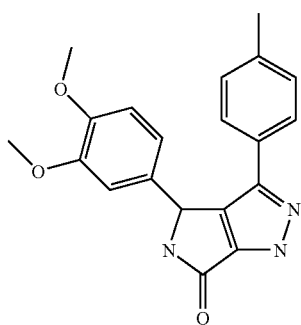 | ChemDiv C390-0577 | 350 |
| I-125 | 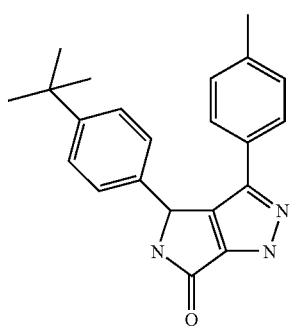 | ChemDiv C390-0573 | 346 |

| | | | |
|---|---|---|---|
| I-126 | 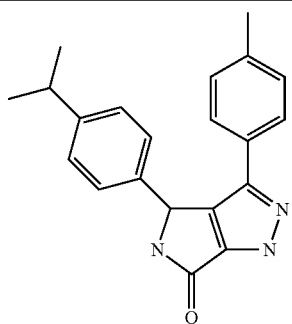 | ChemDiv C390-0587 | 332 |
| I-127 | 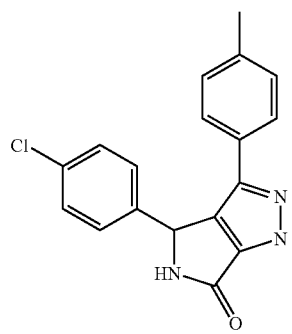 | ChemDiv C390-0571 | 324 |
| I-128 | 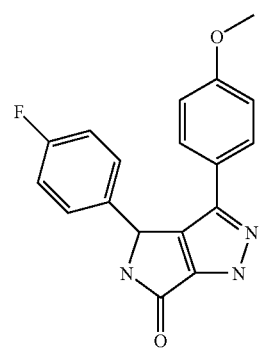 | ChemDiv C390-0605 | 324 |
| I-129 | 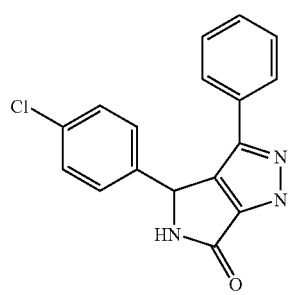 | ChemDiv C390-0540 | 310 |
| I-130 | 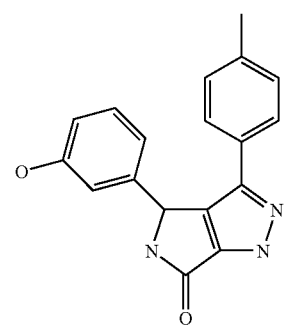 | ChemDiv C390-0594 | 306 |

| | | | |
|---|---|---|---|
| I-131 | 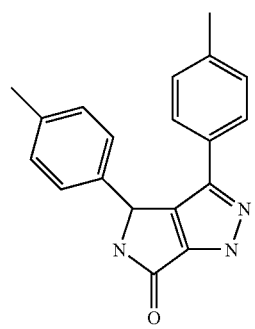 | ChemDiv C390-0569 | 304 |
| I-132 | 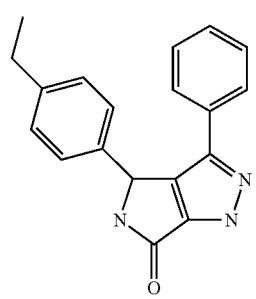 | ChemDiv C390-0545 | 304 |
| I-133 | 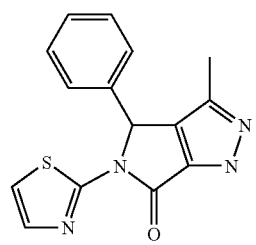 | CSC D500050981 | 297 |
| I-134 | 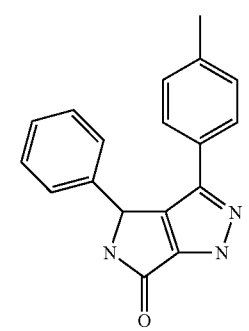 | ChemDiv C390-0565 | 290 |
| I-135 | 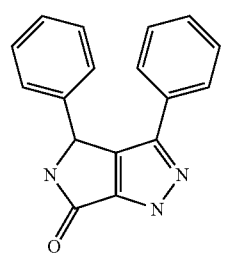 | CSC D50050853 | 276 |

| | | | |
|---|---|---|---|
| I-136 | 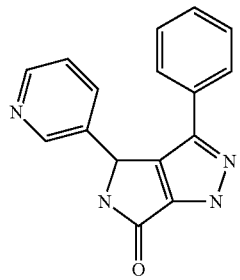 | ChemDiv C390-0562 | 277 |
| I-137 | 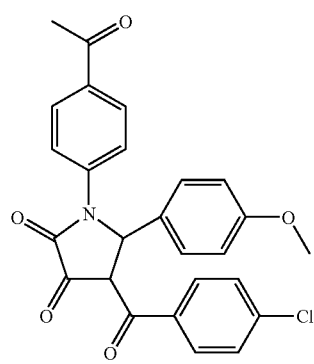 | Interbioscreen STOCK3S-19371 | |
| I-138 | 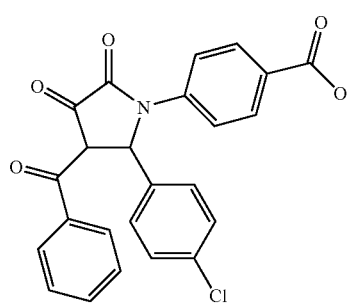 | Interbioscreen STOCK3S-27961 | |
| I-139 | 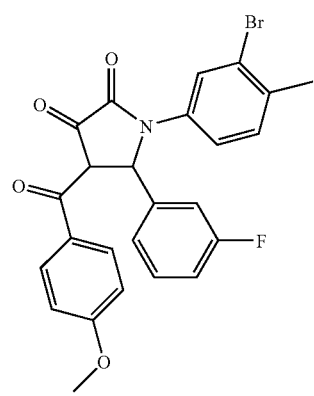 | Chemical Block A2826/0119344 | |

I-140 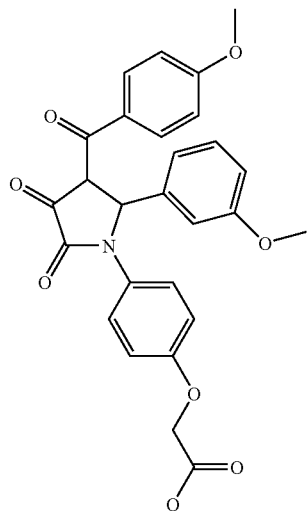 Chemical Block
A2846/0120094
I-141 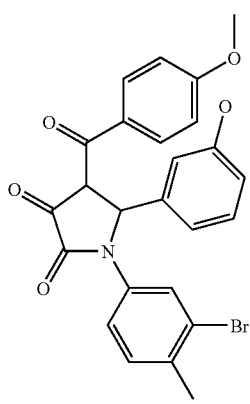 Chemical Block
A2864/0120776
I-142 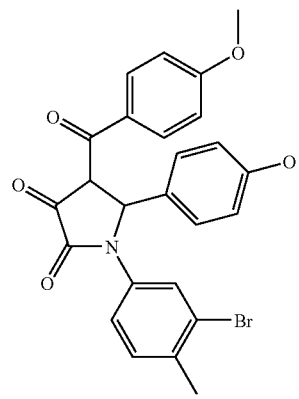 Chemical Block
A2921/0123016

| | | |
|---|---|---|
| I-143 | 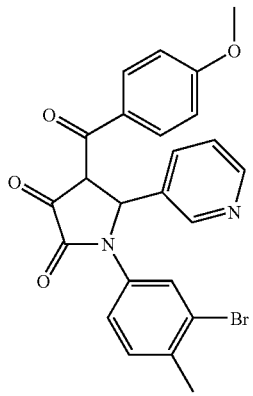 | Chemical Block A2956/0124459 |
| I-144 | 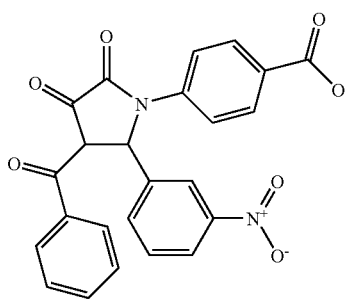 | Pharmeks PHAR020271 |
| I-145 | 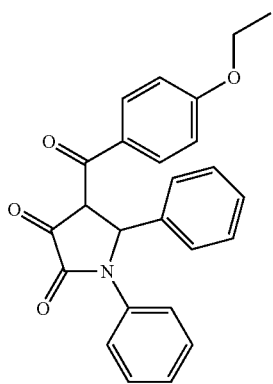 | Pharmeks PHAR033094 |
| I-146 | 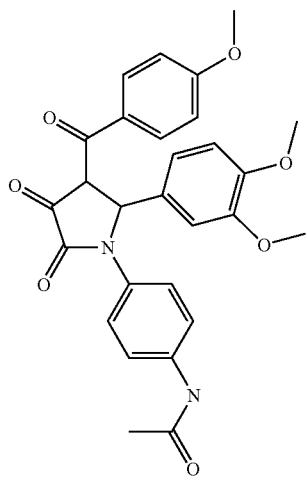 | Pharmeks PHAR036801 |

| | | |
|---|---|---|
| I-147 | 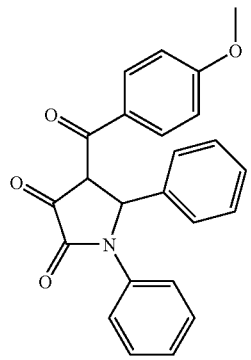 | Pharmeks PHAR050263 |
| I-148 | 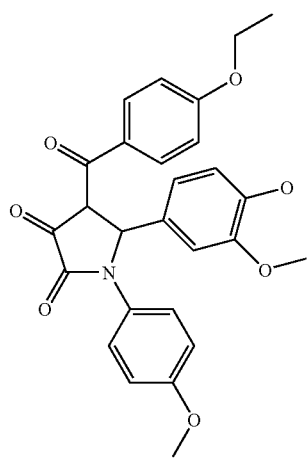 | Pharmeks PHAR062175 |
| I-149 | 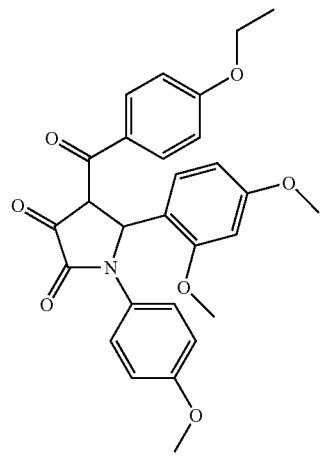 | Pharmeks PHAR067480 |

| | | |
|---|---|---|
| I-150 | 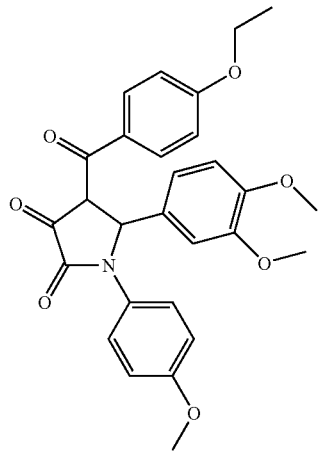 | Pharmeks PHAR070697 |
| I-151 | 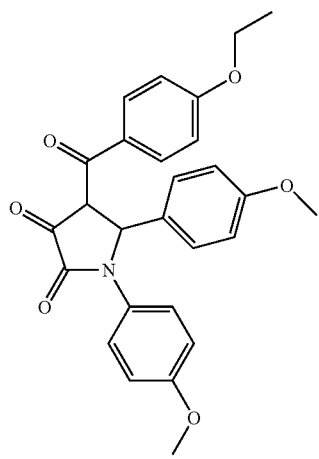 | Pharmeks PHAR071219 |
| I-152 | 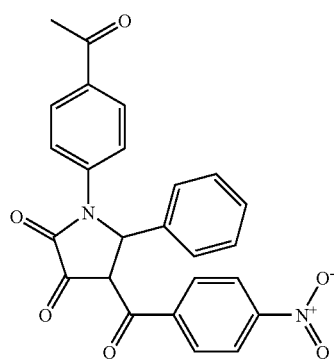 | Pharmeks PHAR079682 |
| I-153 | 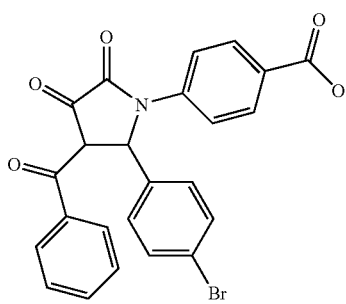 | Pharmeks PHAR087561 |

| | | |
|---|---|---|
| I-154 | 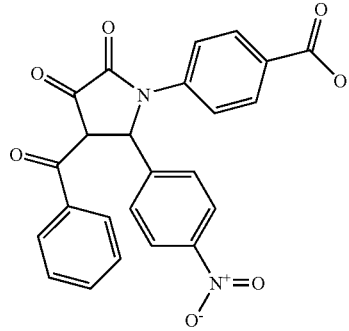 | Pharmeks PHAR094621 |
| I-155 | 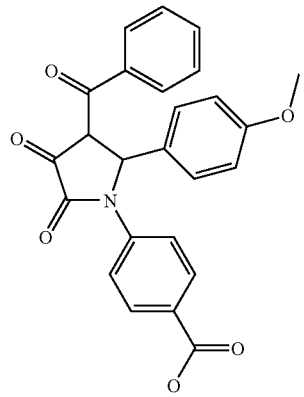 | Pharmeks PHAR104096 |
| I-156 | 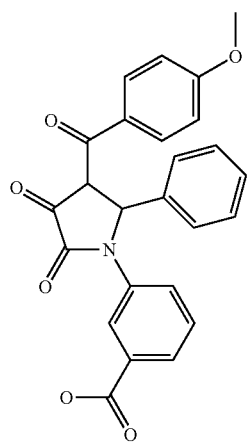 | Pharmeks PHAR107350 |
| I-157 | 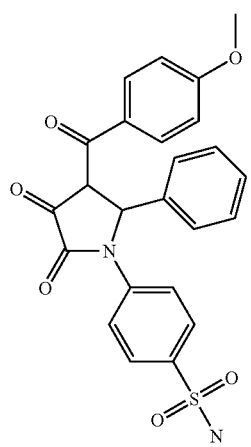 | Pharmeks PHAR111534 |

| | | |
|---|---|---|
| I-158 | 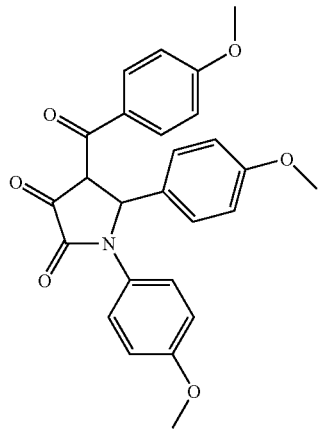 | Pharmeks PHAR115440 |
| I-159 | 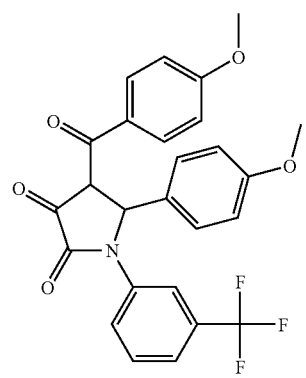 | Pharmeks PHAR117573 |
| I-160 | 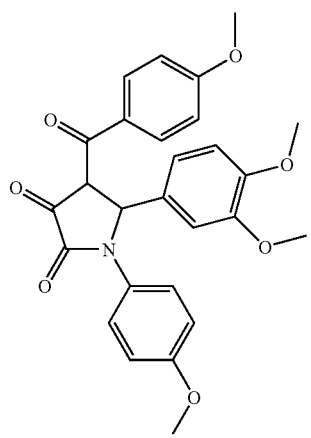 | Pharmeks PHAR118326 |
| I-161 | 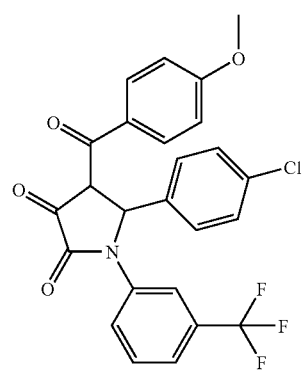 | Pharmeks PHAR119097 |

| | | |
|---|---|---|
| I-162 | 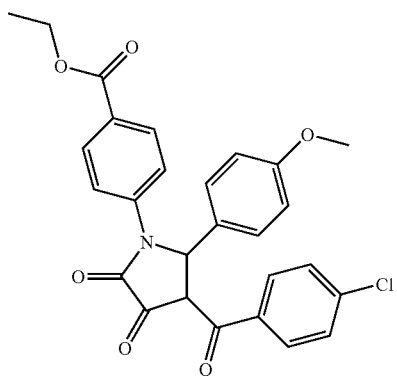 | Pharmeks PHAR120941 |
| I-163 | 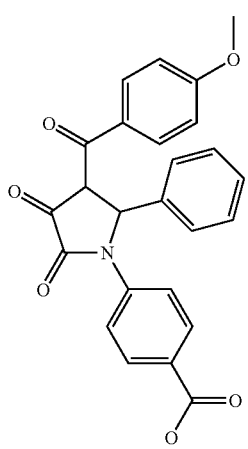 | Pharmeks PHAR127775 |
| I-164 | 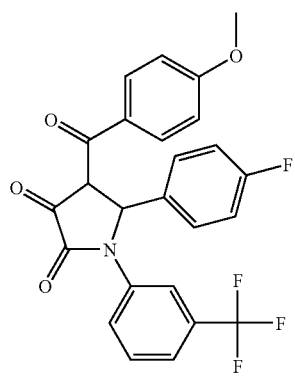 | Pharmeks PHAR128943 |
| I-165 | 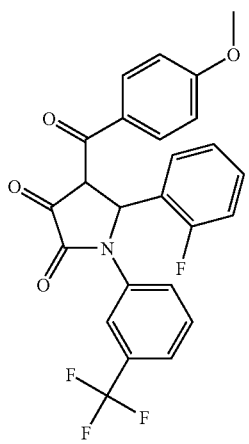 | Pharmeks PHAR130612 |

I-166 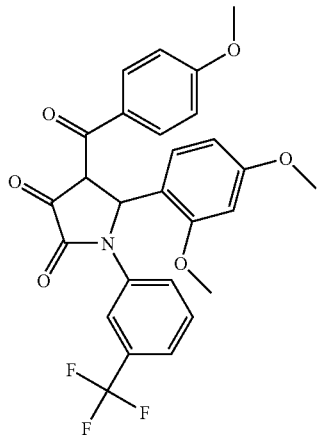 Pharmeks PHAR134114
I-167 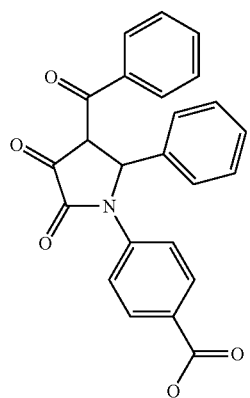 Pharmeks PHAR135268
I-168 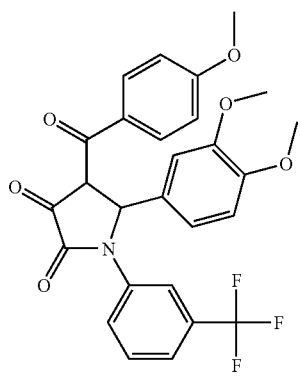 Pharmeks PHAR137109
I-169 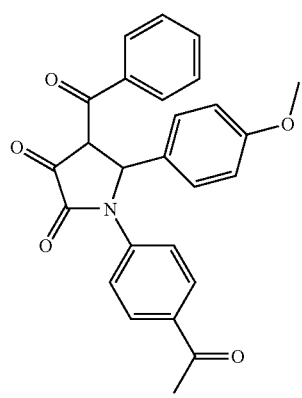 Pharmeks PHAR138274

| | | |
|---|---|---|
| I-170 | 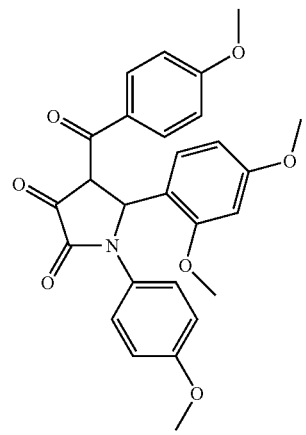 | Pharmeks PHAR138772 |
| I-171 | 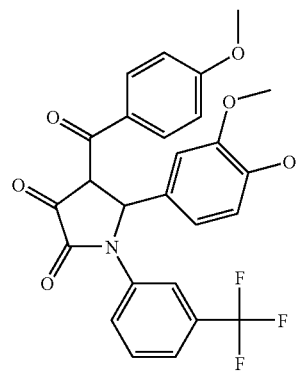 | Pharmeks PHAR140674 |
| I-172 | 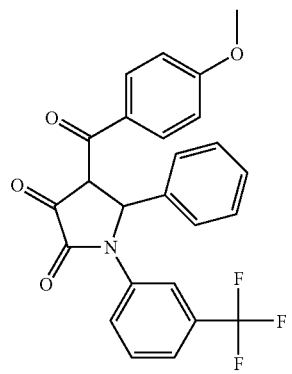 | Pharmeks PHAR144655 |
| I-173 | 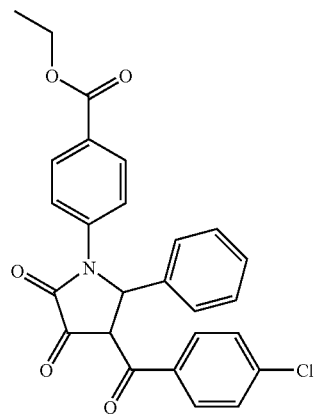 | Pharmeks PHAR157855 |

| | | |
|---|---|---|
| I-174 | 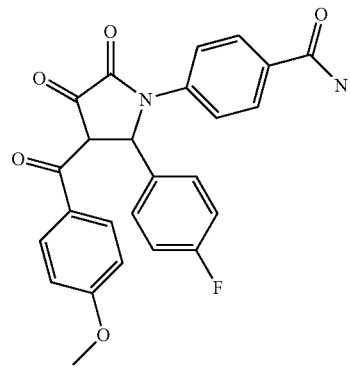 | 447 |
| I-175 | 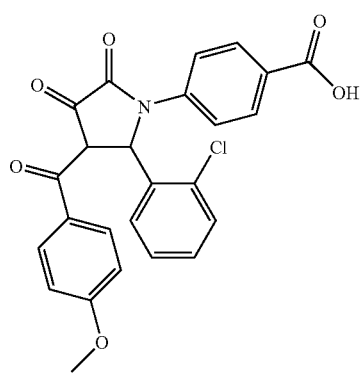 | 464 |
| I-176 | 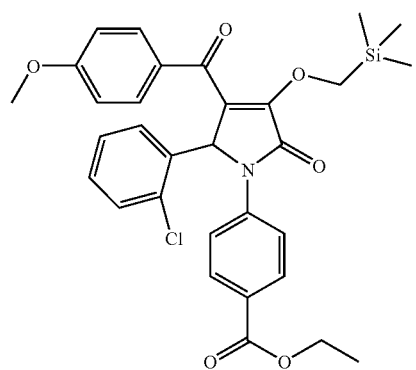 | 578 |
| I-177 | 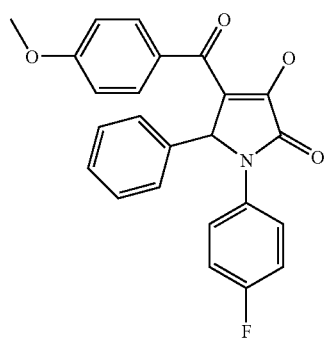 | 404 |

| | | |
|---|---|---|
| I-178 | 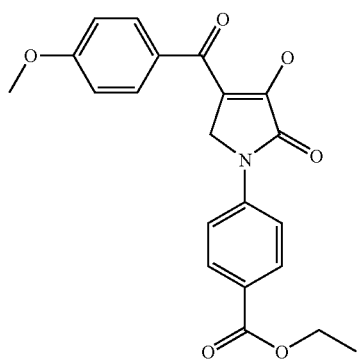 | 382 |
| I-180 | 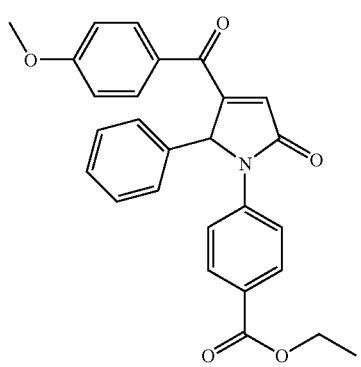 | 442 |
| I-181 | 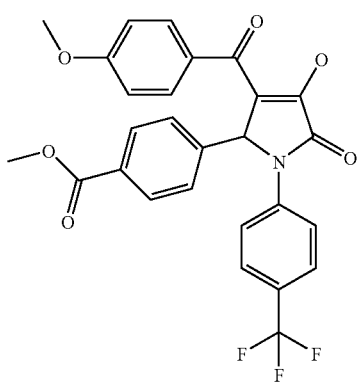 | 512 |
| I-182 | 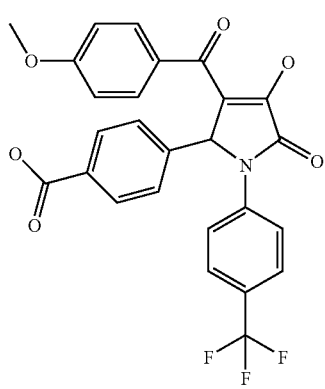 | 498 |

| | | | |
|---|---|---|---|
| I-183 | 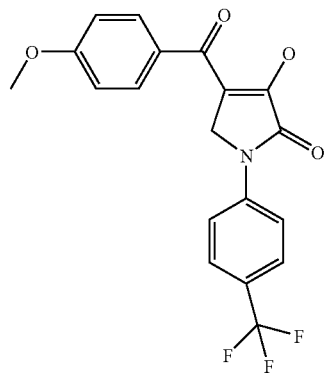 | | 378 |
| I-184 | 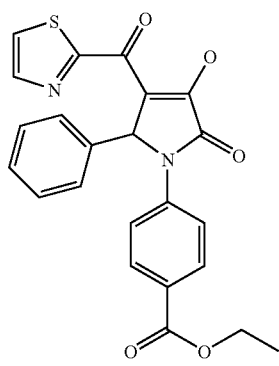 | | 435 |
| I-185 | 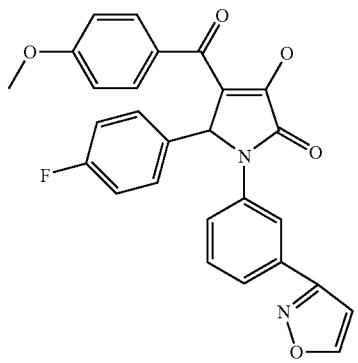 | 193-196 | 471 |
| I-189 | 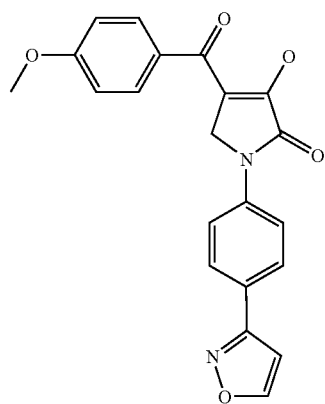 | | 377 |

| | | | |
|---|---|---|---|
| I-191 | 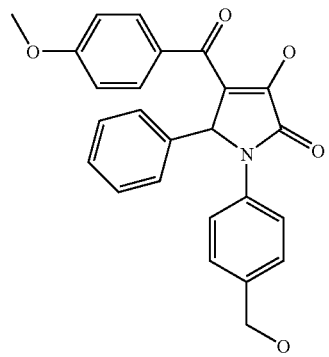 | | 416 |
| I-192 | 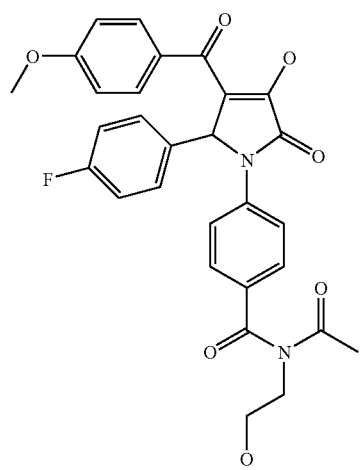 | | 533 |
| I-193 | 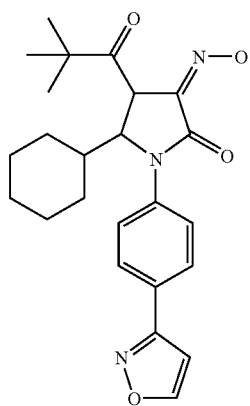 | 255-256 | 424 |
| I-194 | 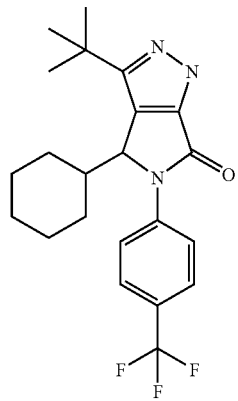 | 245-246 | 406 |

| | | | |
|---|---|---|---|
| I-195 | 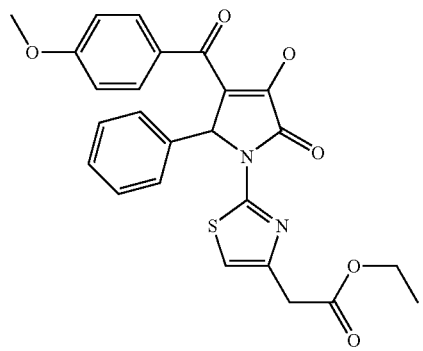 | | 479 |
| I-196 | 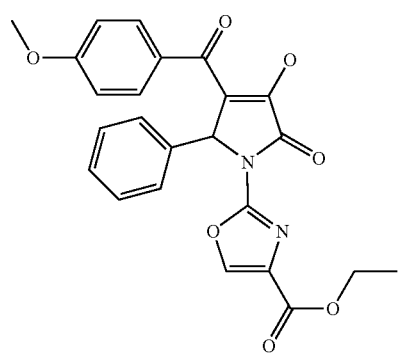 | | 449 |
| I-197 | 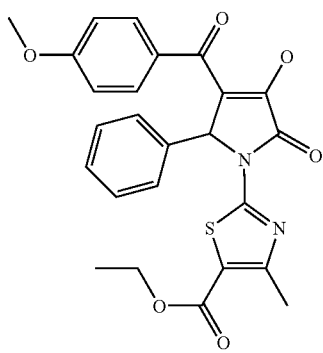 | | 479 |
| I-198 | 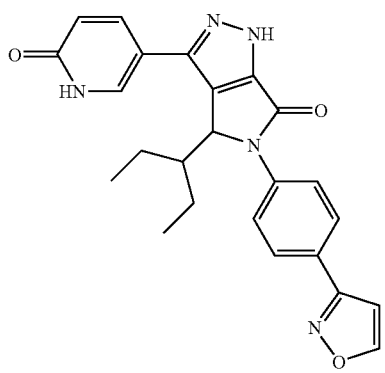 | >290 | 430 |

| | | | |
|---|---|---|---|
| I-199 | 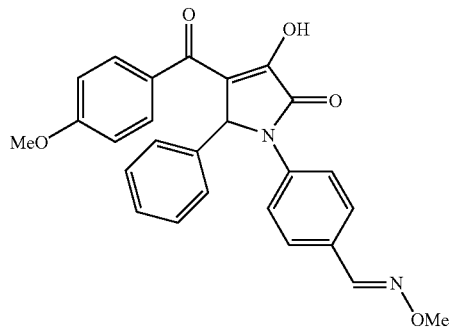 | 226-229 | 443 |
| I-200 | 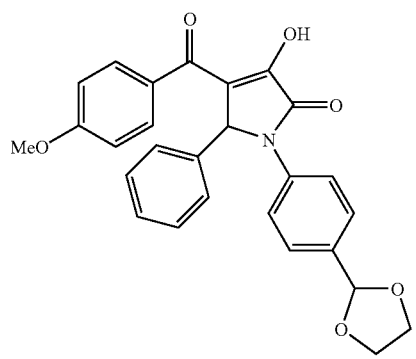 | 216-219 | 458 |
| I-201 | 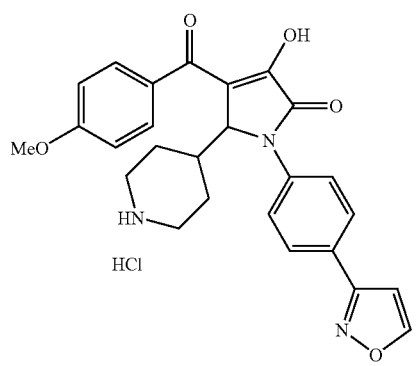 | | 460 |
| I-202 | 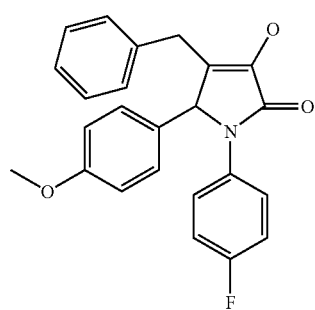 | 177-178 | |

| | | | |
|---|---|---|---|
| I-203 | 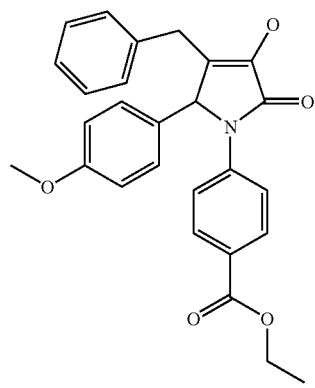 | 160-161 | |
| I-204 | 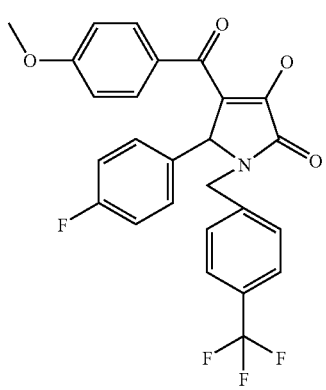 | 234-237 | 486 |
| I-205 | 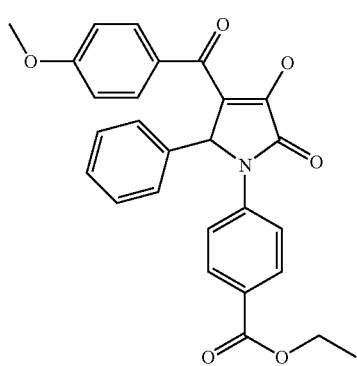 | | |
| I-206 | 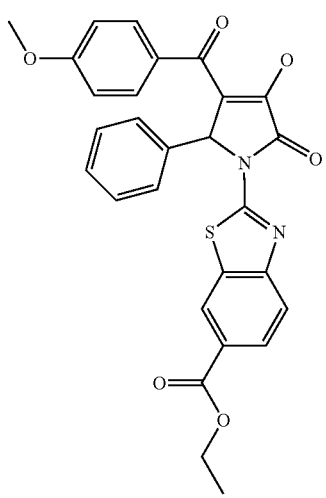 | | 515 |

| | | | |
|---|---|---|---|
| I-207 | 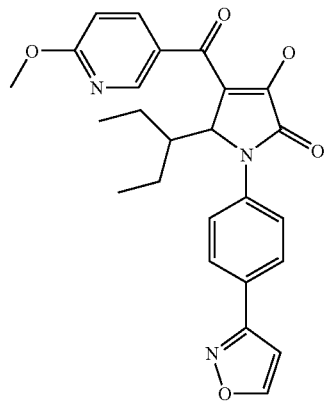 | 246-249 | 448 |
| I-208 | 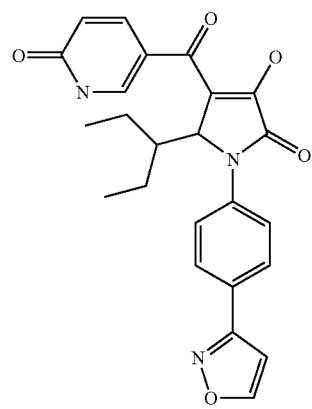 | >290 | 434 |
| I-209 | 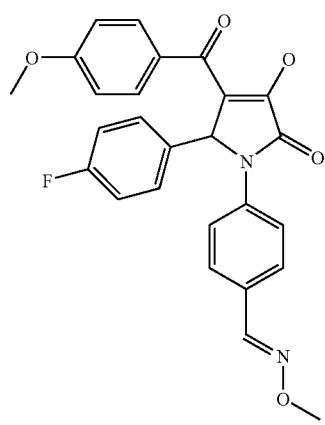 | 232-235 | 461 |
| I-210 | 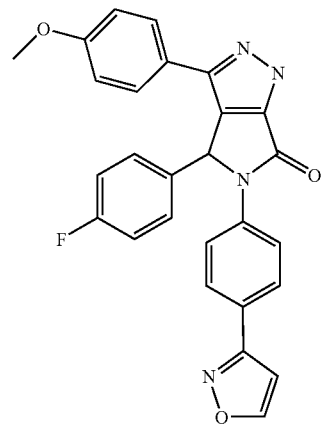 | 164-166 | 467 |

| | | | |
|---|---|---|---|
| I-211 | 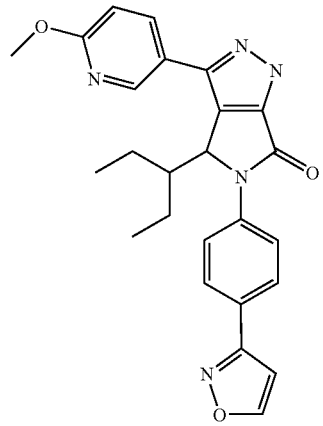 | 226-228 | 444 |
| I-213 | 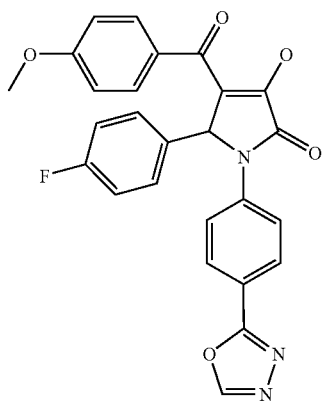 | 244-247 | 471 |
| I-214 | 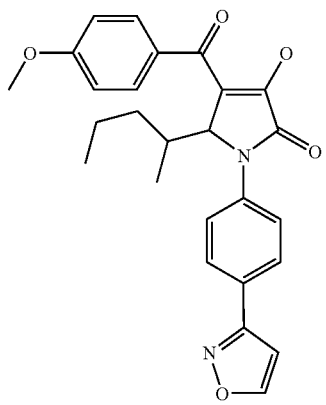 | 227-232 | 447 |
| I-215 | 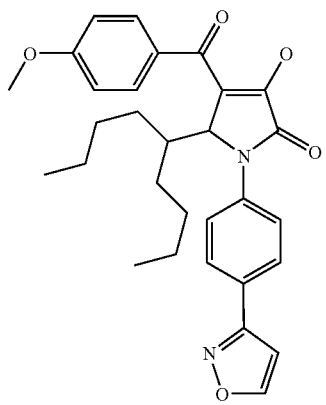 | 207-210 | 503 |

| | | | |
|---|---|---|---|
| I-216 | 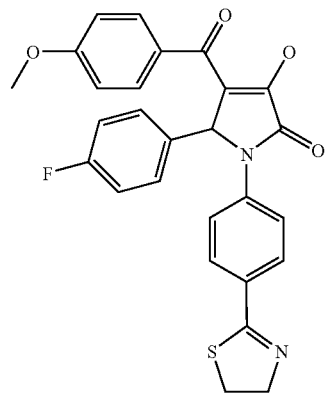 | 229-232 | 489 |
| I-217 | 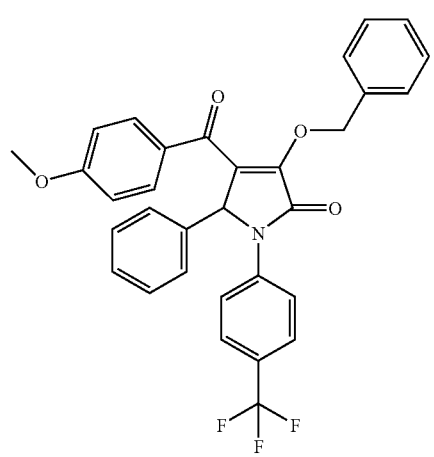 | 173-174 | |
| I-218 | 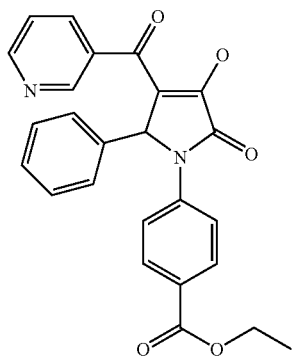 | | |
| I-219 | 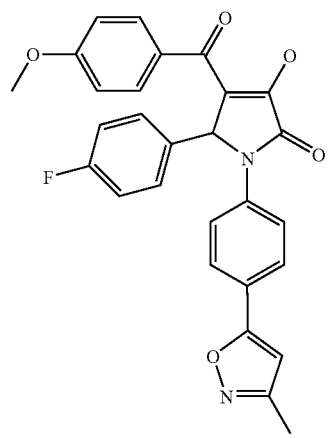 | 249-252 | 485 |

| | | | |
|---|---|---|---|
| I-220 | 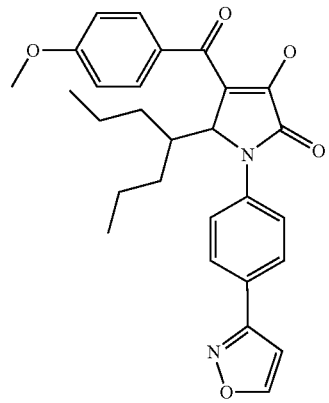 | 229-231 | 475 |
| I-221 | 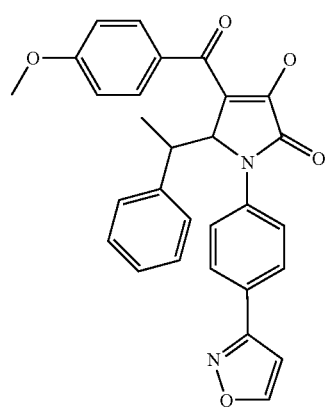 | 241-244 | 481 |
| I-222 | 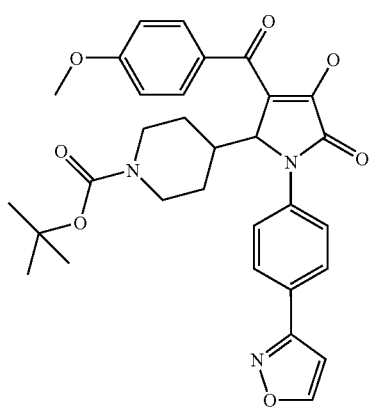 | 247-249 | 560 |
| I-223 | 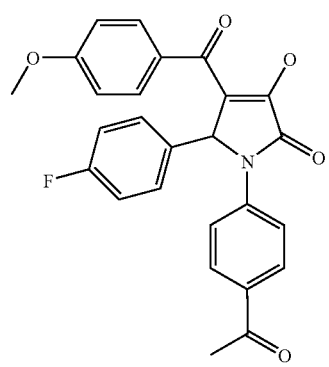 | amorphous | 446 |

| | | | |
|---|---|---|---|
| I-224 | 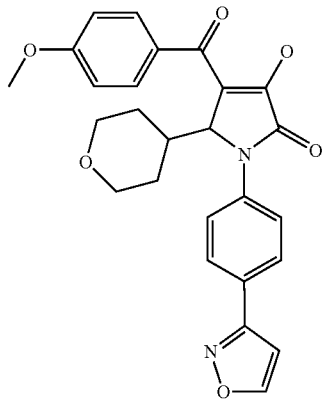 | 268-272 | 461 |
| I-225 | 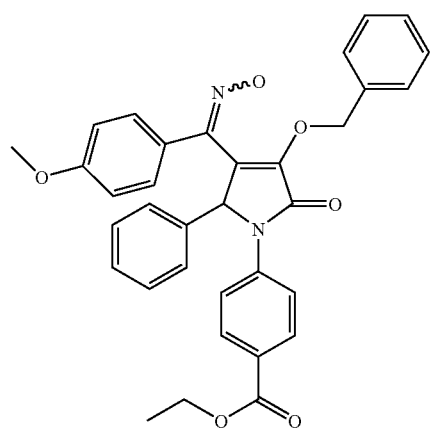 | 196-201 | |
| I-226 | 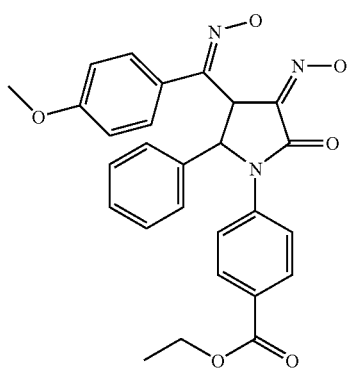 | 219-221 dec | |
| I-227 | 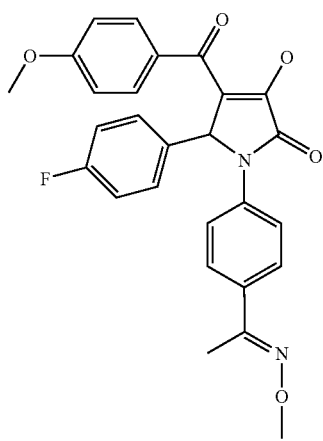 | 221-224 | 475 |

| | | -continued | | |
|---|---|---|---|---|
| I-228 | 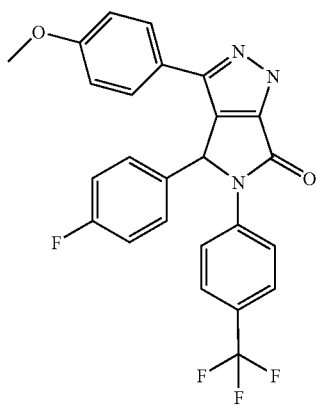 | | 217-218 | 468 |
| I-229 | 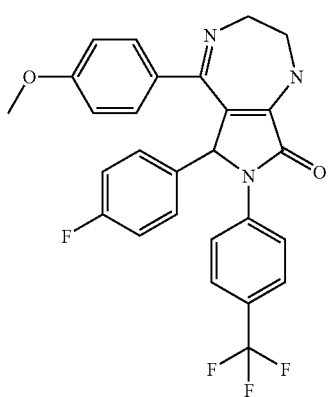 | | 213-215 | |
| I-230 | 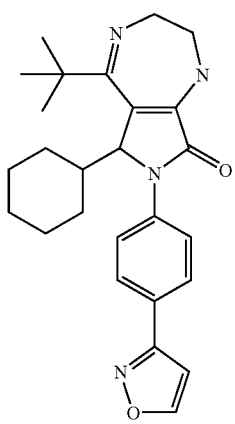 | | 229-230 | 433 |
| I-231 | 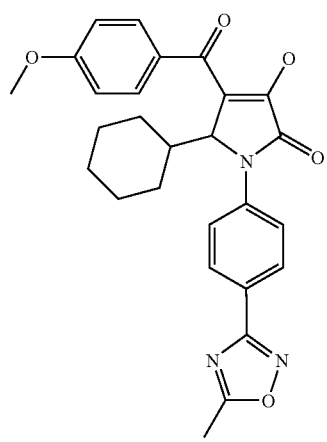 | | 245-248 | 474 |

-continued
| | | | |
|---|---|---|---|
| I-232 | 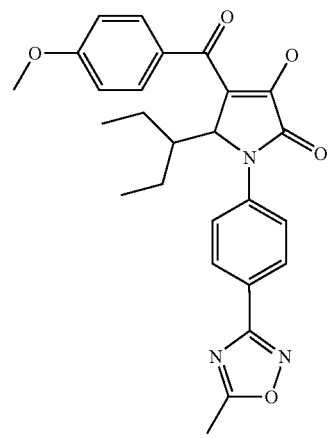 | 223-225 | 462 |
| I-233 | 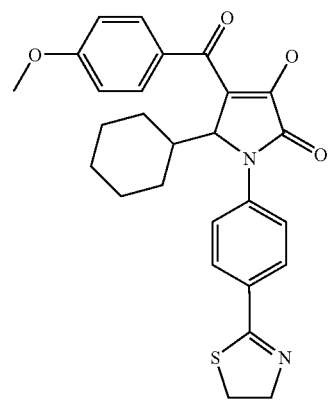 | 247-250 | 477 |
| I-234 | 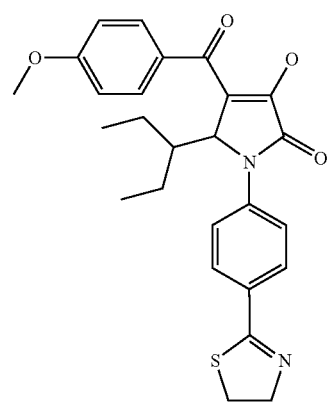 | 230-233 | 465 |

| | | | |
|---|---|---|---|
| I-235 | 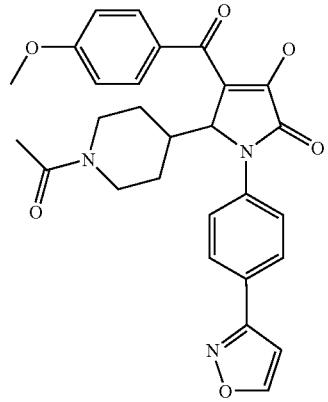 | | 502 |
| I-236 | 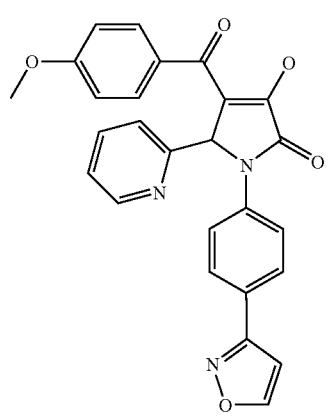 | 232-234 | 454 |
| I-237 | 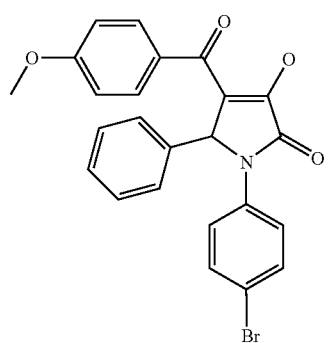 | 233-236 | 465 |
| I-238 | 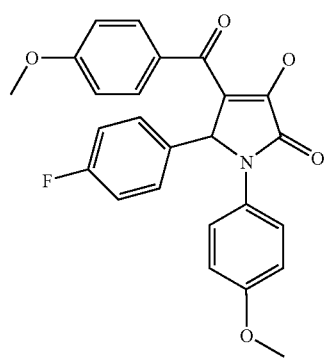 | 245-247 | 434 |

| | | | |
|---|---|---|---|
| I-239 | 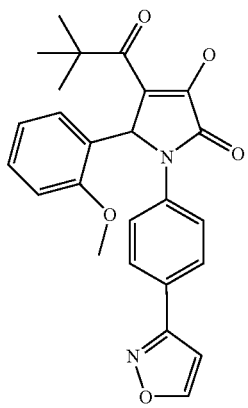 | 227-228 | 433 |
| I-240 | 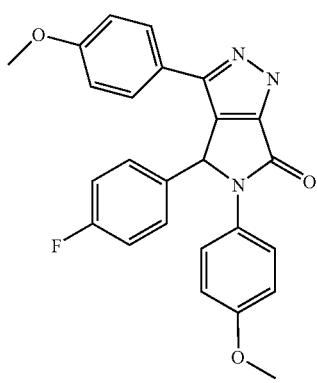 | | 430 |
| I-241 | 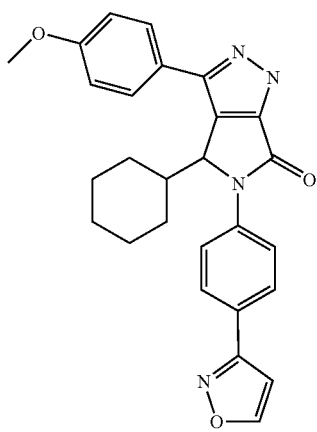 | | 455 |
| I-242 | 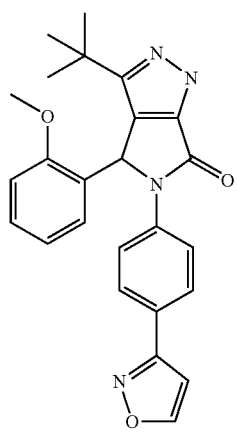 | | 429 |

| | | |
|---|---|---|
| I-243 | 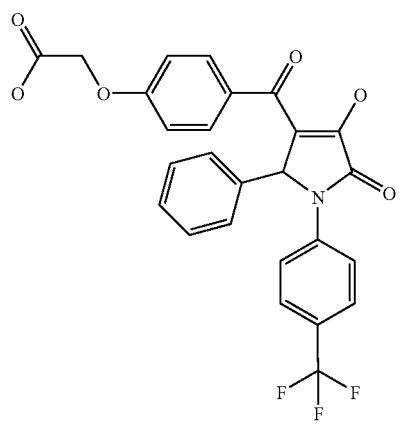 | 498 |
| I-244 | 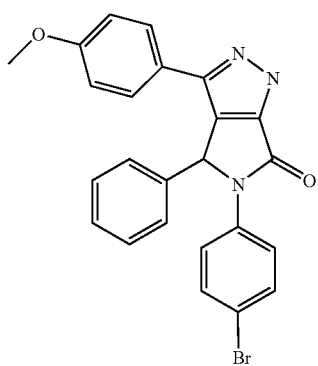 | 461 |
| I-245 | 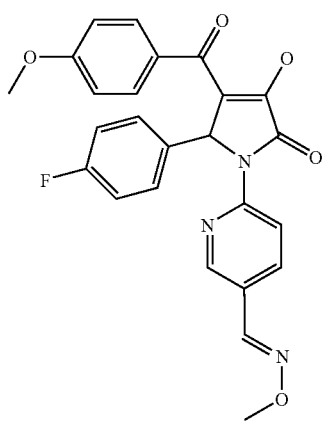 | 462 |
| I-246 | 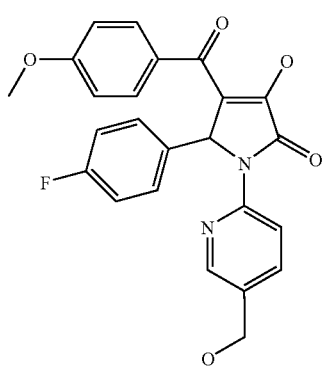 | 435 |

| | | |
|---|---|---|
| I-247 | 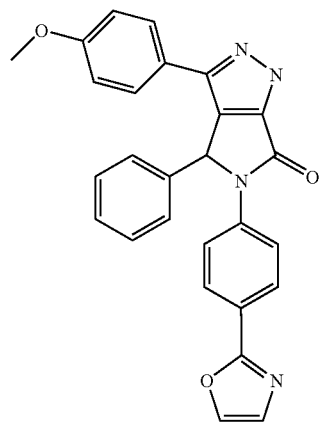 | 449 |
| I-248 | 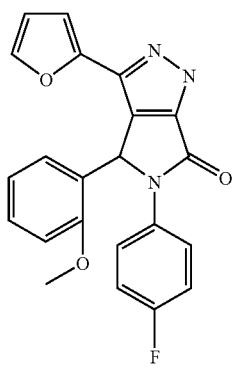 | 390 |
| I-249 | 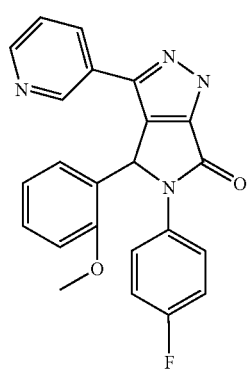 | 401 |
| I-250 | 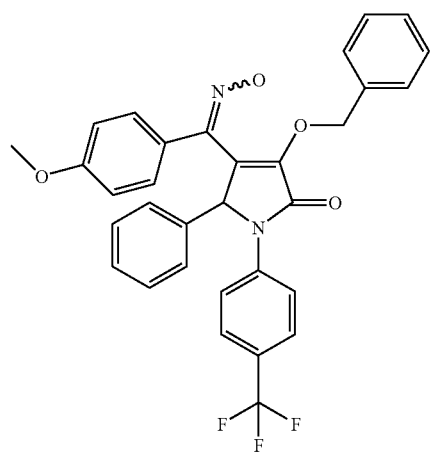 | 197-204 |

| | | |
|---|---|---|
| I-251 | 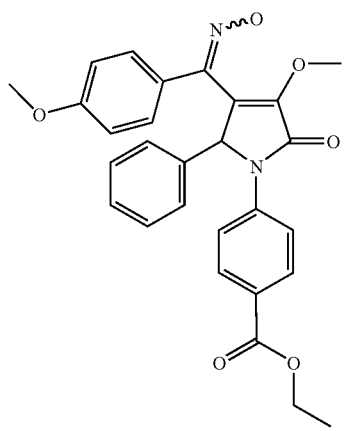 | 468 |
| I-252 | 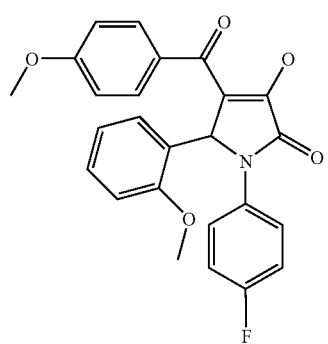 | 434 |
| I-253 | 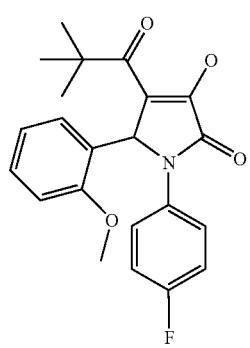 | 384 |
| I-254 | 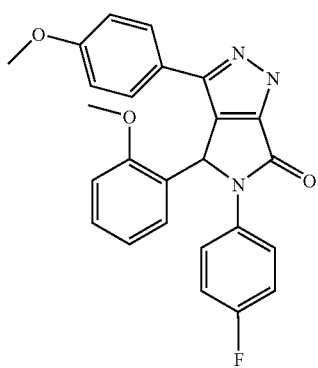 | 430 |

| | | |
|---|---|---|
| I-255 | 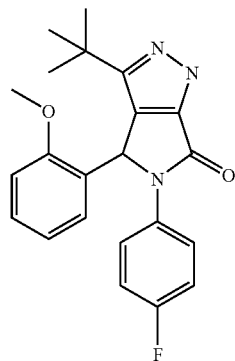 | 380 |
| I-256 | 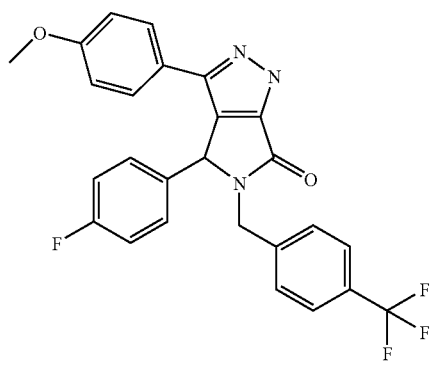 | 482 |
| I-257 | 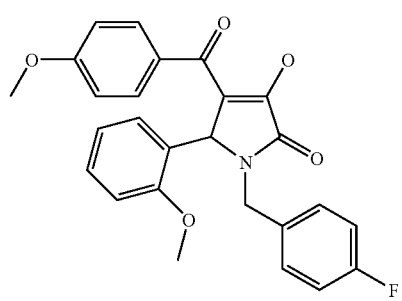 | 448 |
| I-258 | 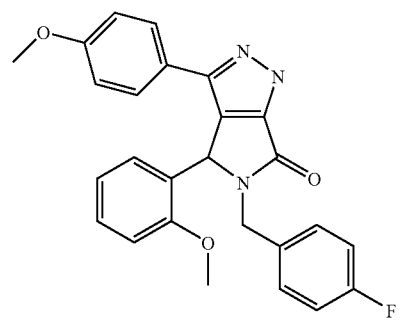 | 444 |

| | | |
|---|---|---|
| I-259 | 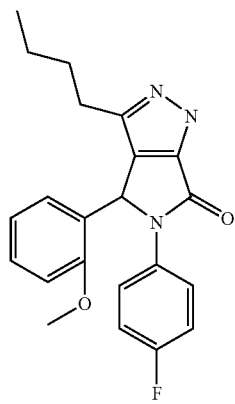 | 380 |
| I-260 | 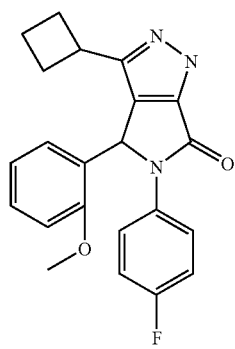 | 378 |
| I-261 | 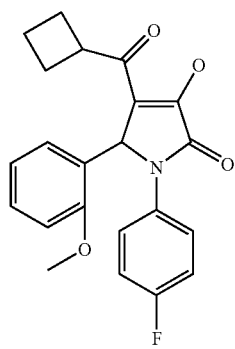 | 382 |
| I-262 | 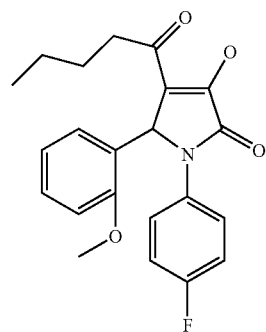 | 384 |

| | | |
|---|---|---|
| I-263 | 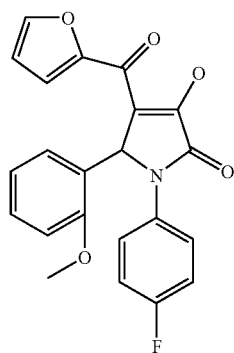 | 394 |
| I-264 | 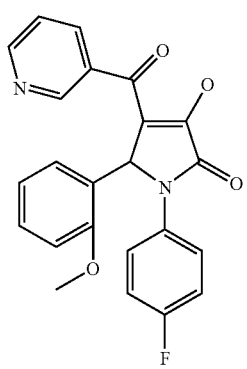 | 405 |
| I-265 | 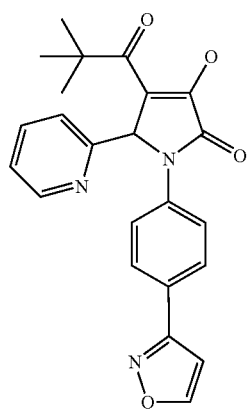 | 404 |
| I-266 | 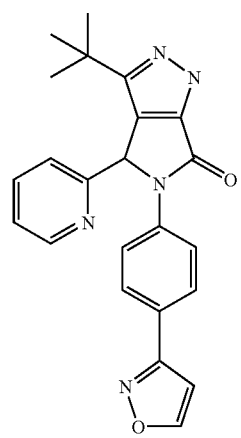 | 400 |

-continued
| | | |
|---|---|---|
| I-267 | 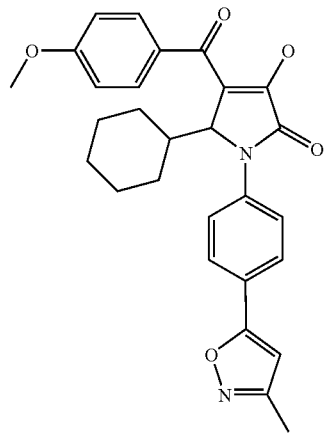 | 473 |
| I-268 | 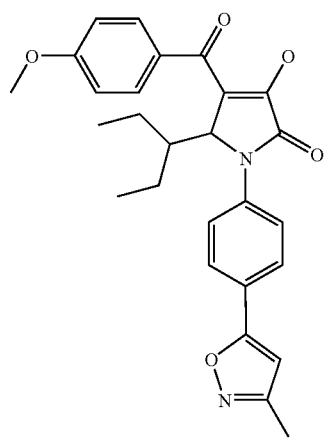 | 461 |
| I-269 | 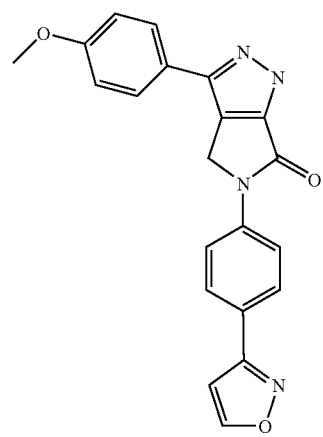 | 373 |
| I-270 | 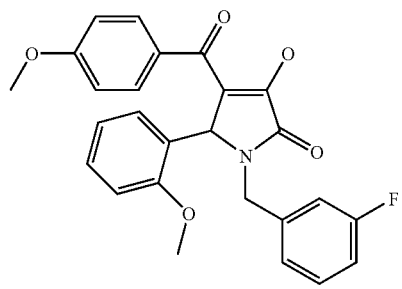 | 448 |

| | | |
|---|---|---|
| I-271 | 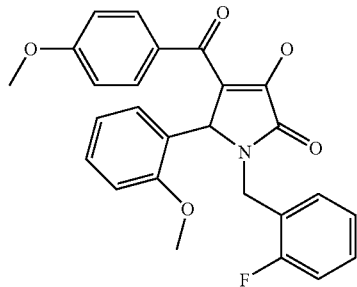 | 448 |
| I-272 | 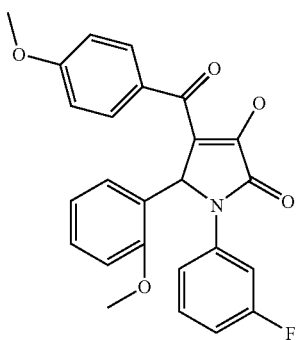 | 434 |
| I-273 | 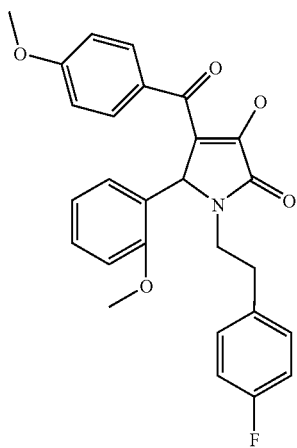 | 462 |
| I-274 | 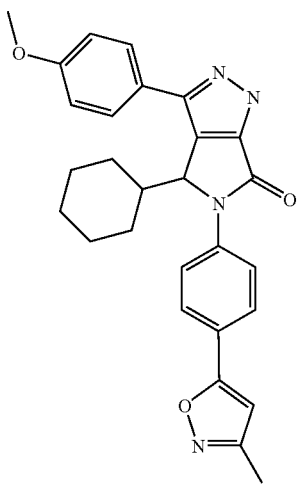 | 468 |

| | | |
|---|---|---|
| I-275 | 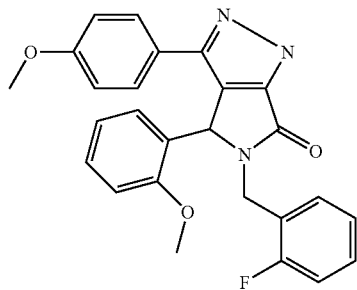 | 444 |
| I-276 | 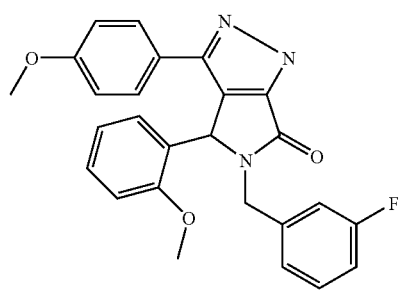 | 444 |
| I-277 | 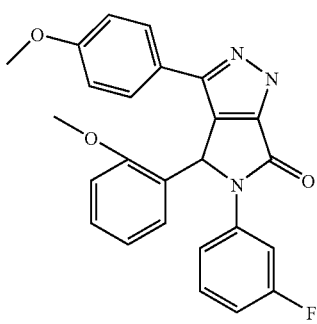 | 430 |
| I-278 | 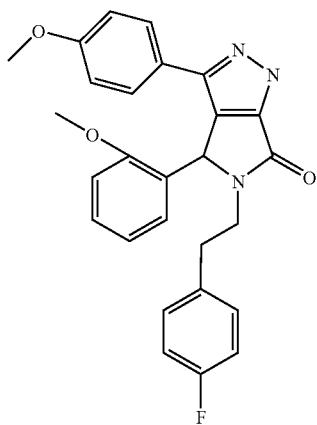 | 458 |

| | | |
|---|---|---|
| I-279 | 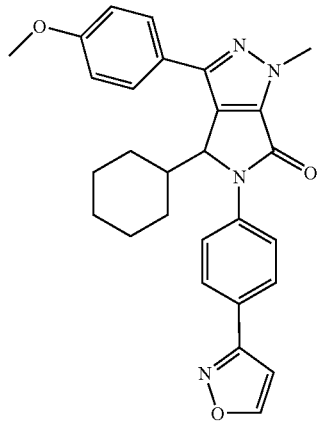 | 469 |
| I-281 | 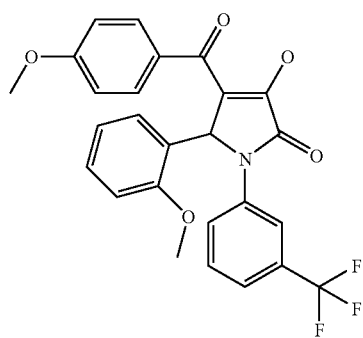 | 484 |
| I-282 | 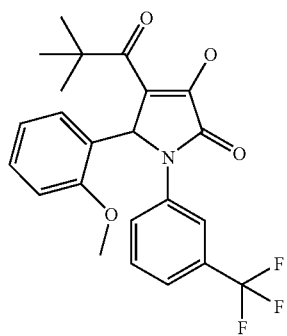 | 434 |
| I-283 | 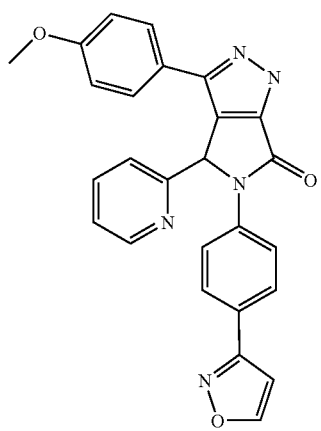 | 450 |

| | | | |
|---|---|---|---|
| I-284 | 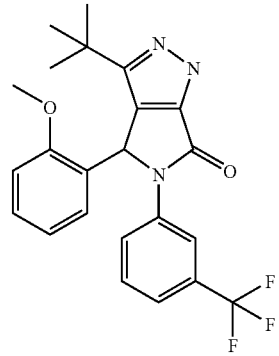 | | 430 |
| I-285 | 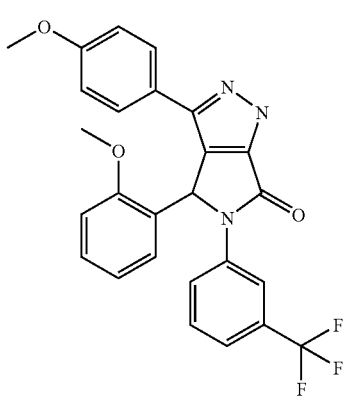 | | 480 |
| Compound No. | Structure | mp(° C.) | MS m/z [M+] |
|---|---|---|---|
| II-1 | 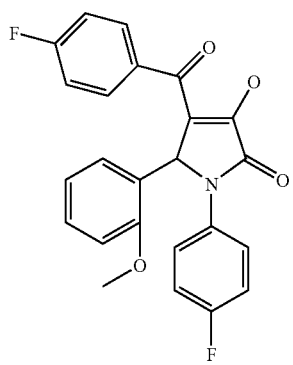 | | 422 |
| II-2 | 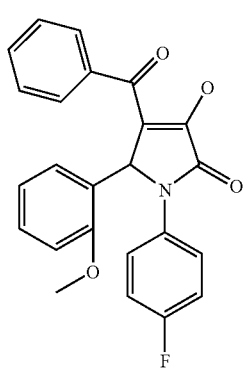 | | 404 |

| | | |
|---|---|---|
| II-3 | 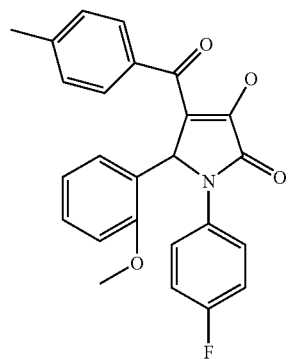 | 418 |
| II-4 | 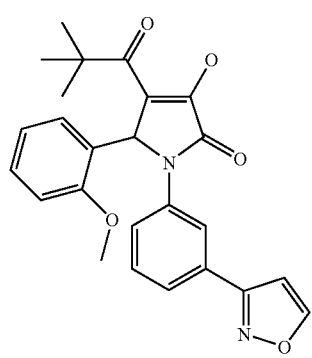 | 433 |
| II-5 | 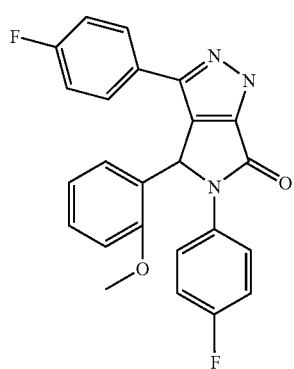 | 418 |
| II-6 | 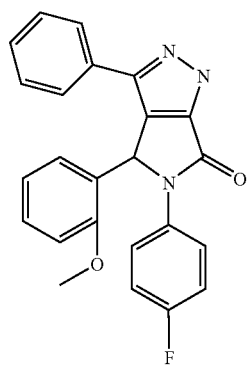 | 400 |

| | | | |
|---|---|---|---|
| II-7 | 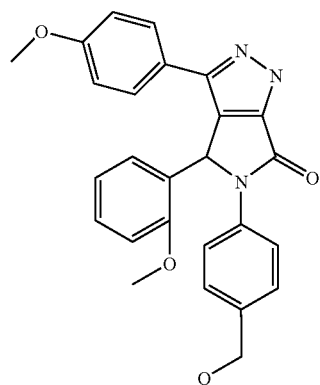 | | 442 |
| II-8 | 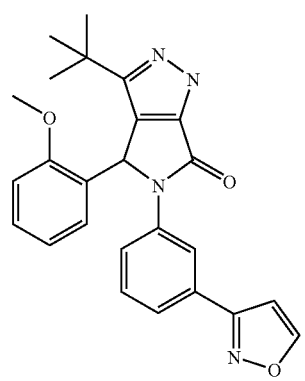 | 202 | 429 |
| II-9 | 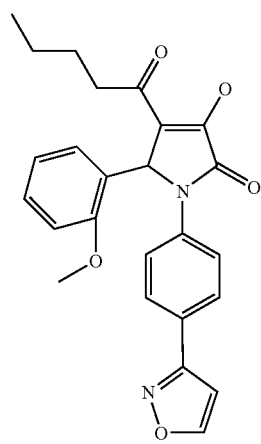 | | 433 |
| II-10 | 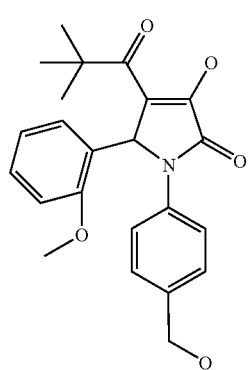 | | 396 |

| | | |
|---|---|---|
| II-11 | 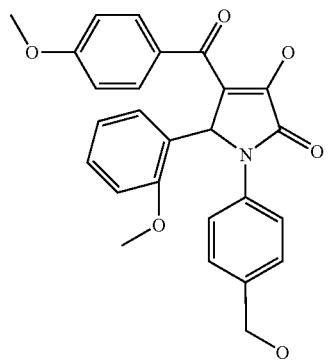 | 446 |
| II-12 | 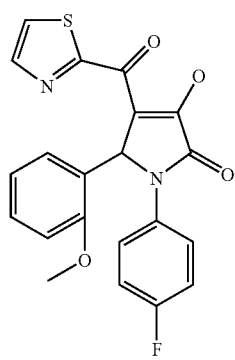 | 411 |
| II-13 | 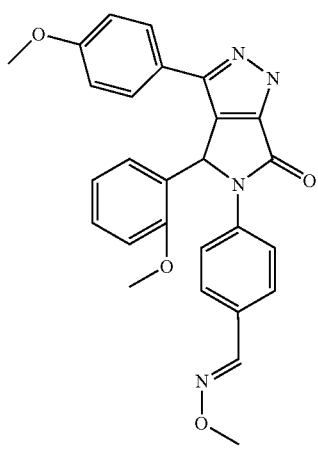 | 469 |
| II-14 | 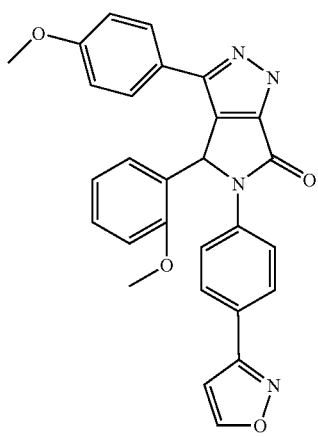 | 479 |

-continued
| | | |
|---|---|---|
| II-15 | 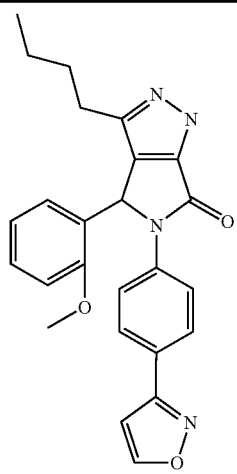 | 429 |
| II-16 | 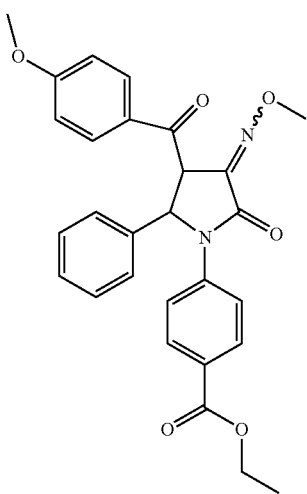 | 487 |
| II-17 | 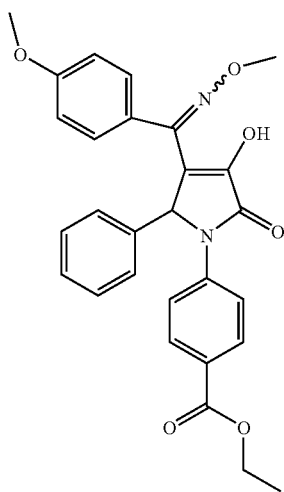 | 487 |

| | | |
|---|---|---|
| II-18 | 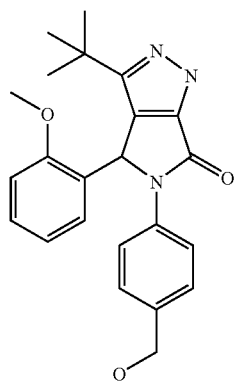 | 392 |
| II-19 | 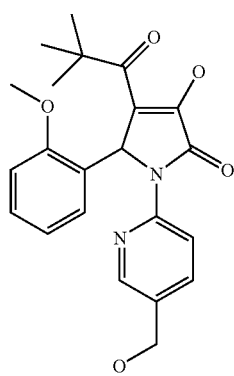 | 397 |
| II-20 | 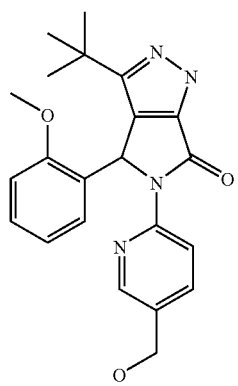 | 393 |
| II-21 | 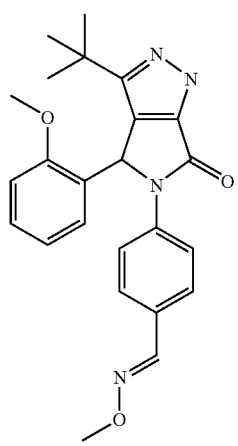 | 419 |

| | | |
|---|---|---|
| II-22 | 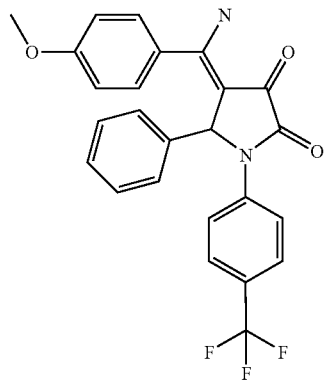 | 453 |
| II-23 | 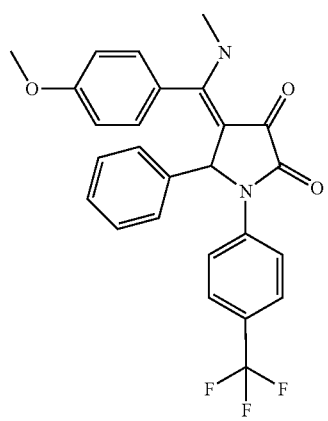 | 467 |
| II-24 | 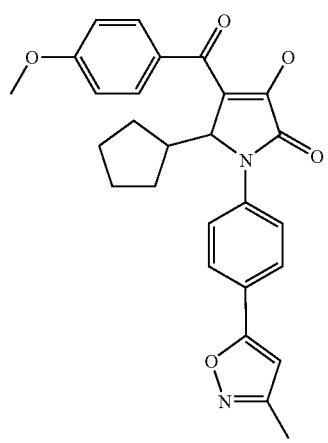 | 459 |

| | | |
|---|---|---|
| II-25 | 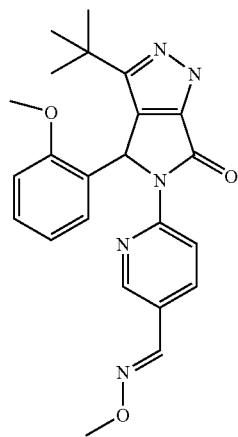 | 420 |
| II-26 | 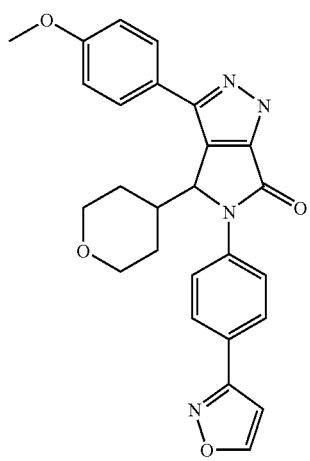 | 457 |
| II-27 | 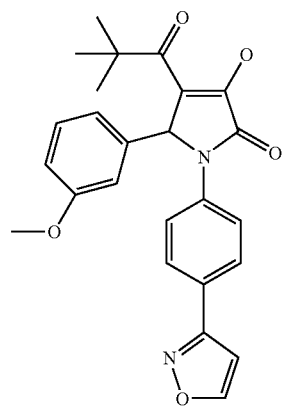 | 433 |

| | | |
|---|---|---|
| II-28 | 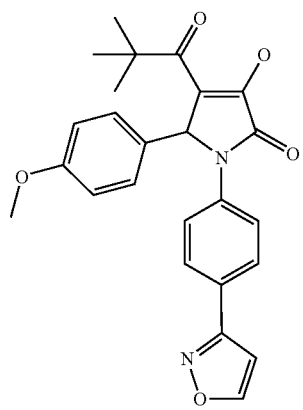 | 433 |
| II-29 | 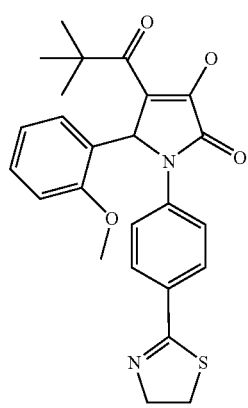 | 451 |
| II-30 | 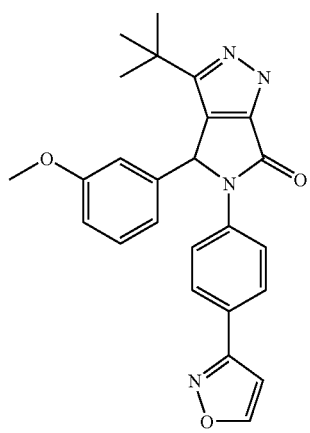 | 429 |
| II-31 | 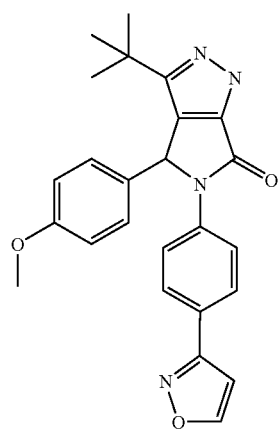 | 429 |

| | | |
|---|---|---|
| II-32 | 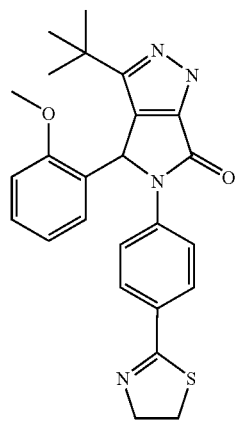 | 447 |
| II-33 | 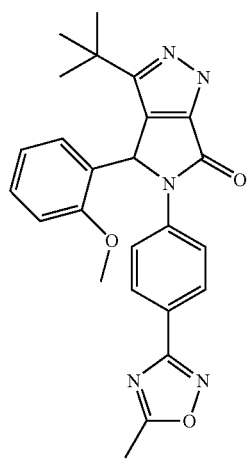 | 444 |
| II-34 | 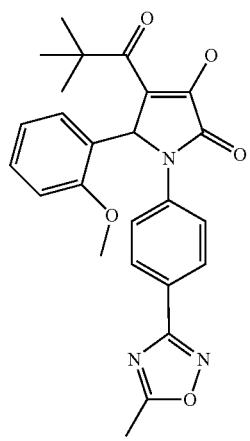 | 448 |

| | | |
|---|---|---|
| II-35 | 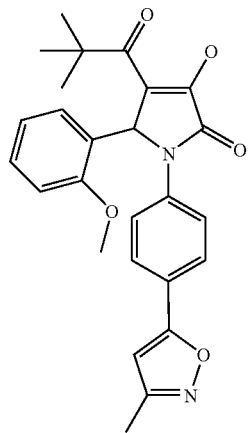 | 447 |
| II-36 | 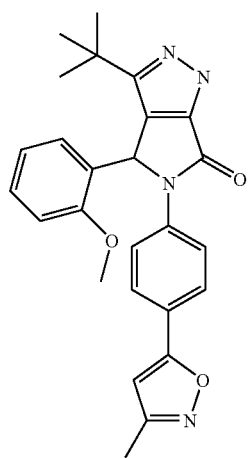 | 443 |
| II-37 | 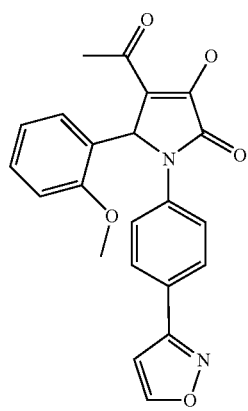 | 391 |

| | | | |
|---|---|---|---|
| II-38 | 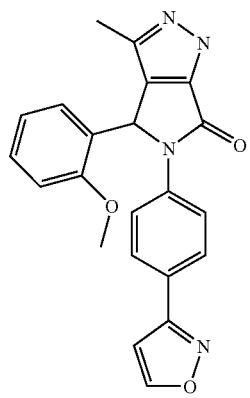 | | 387 |
| II-39 | 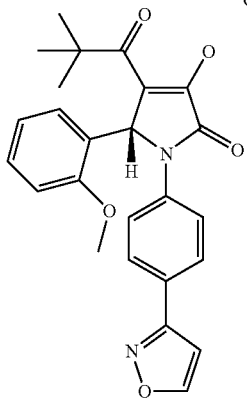 | Chiral | 433 |
| II-40 | 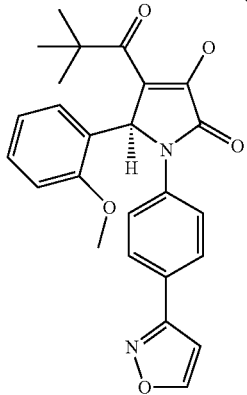 | Chiral | 433 |
| II-41 | 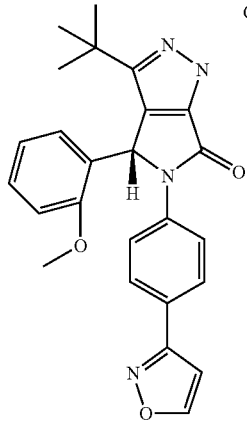 | Chiral | 429 |

| | | | |
|---|---|---|---|
| II-42 | 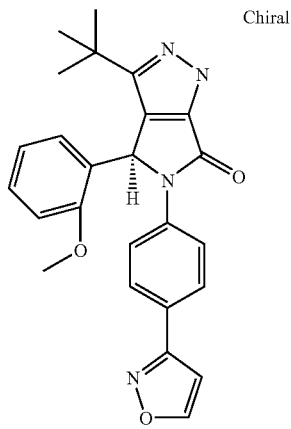 Chiral | 429 |
| II-43 | 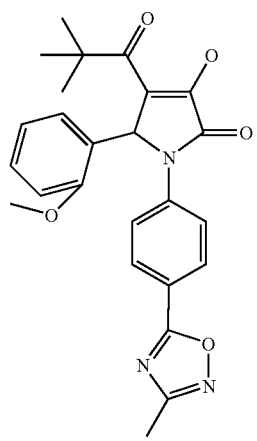 | 448 |
| II-44 | 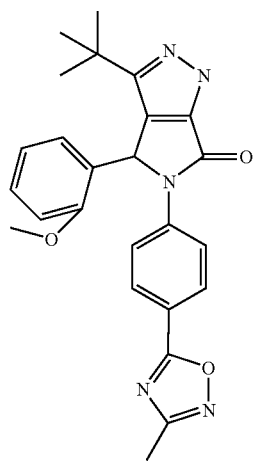 | 444 |

-continued
| | | |
|---|---|---|
| II-45 | 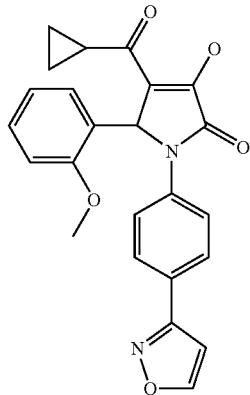 | 417 |
| II-46 | 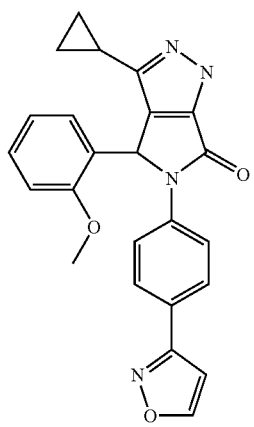 | 413 |
| II-47 | 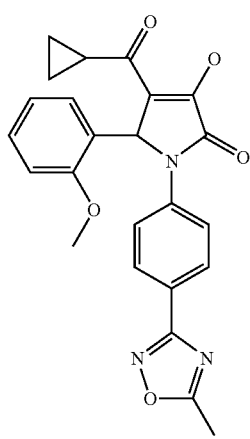 | 432 |

| | | |
|---|---|---|
| II-48 | 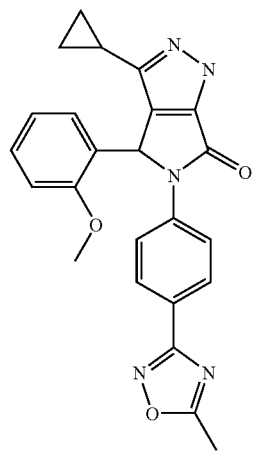 | 428 |
| II-49 | 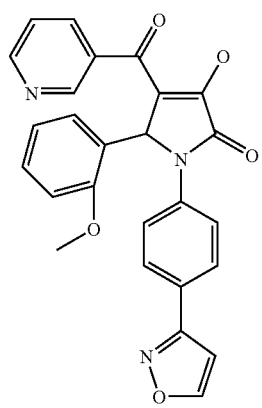 | 454 |
| II-50 | 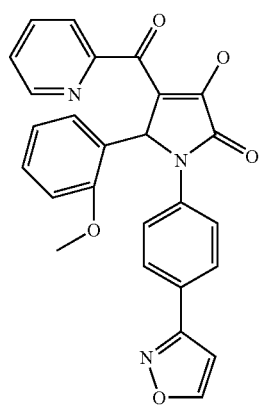 | 454 |

| | | |
|---|---|---|
| II-51 | 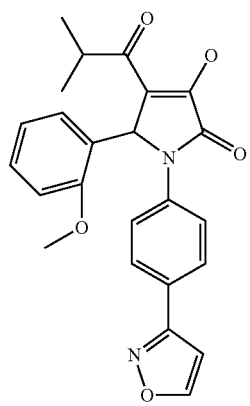 | 419 |
| II-52 | 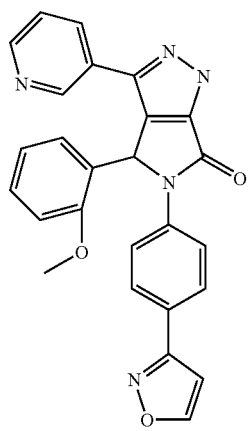 | 450 |
| II-53 | 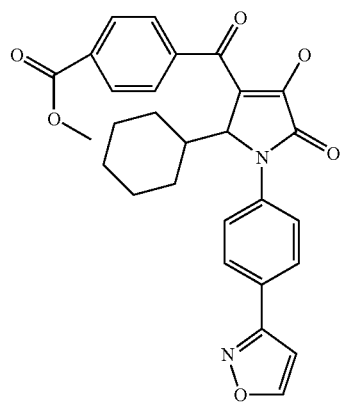 | 487 |
| II-54 | 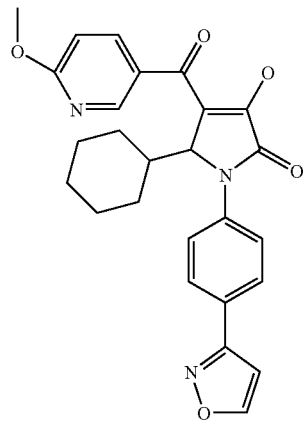 | 460 |

| II-55 | 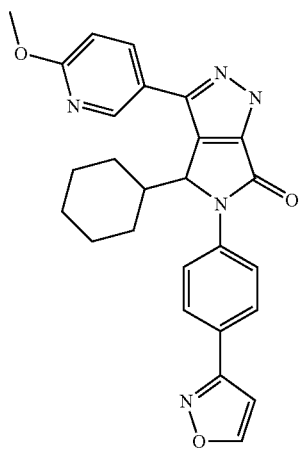 | 456 |
| II-56 | 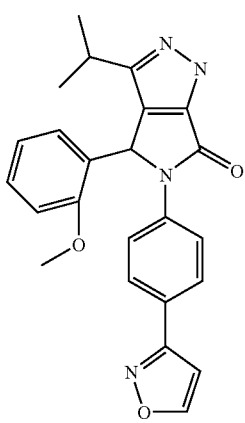 | 415 |
| II-57 | 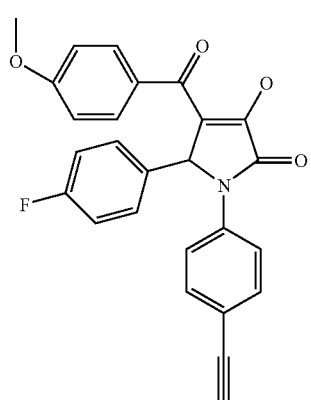 | 428 |

-continued
| | | |
|---|---|---|
| II-58 | 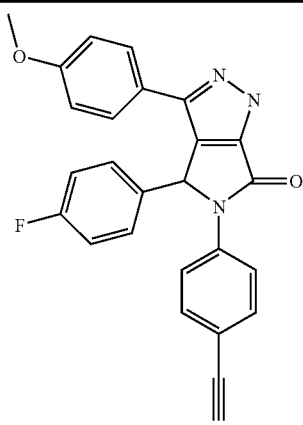 | 424 |
| II-59 | 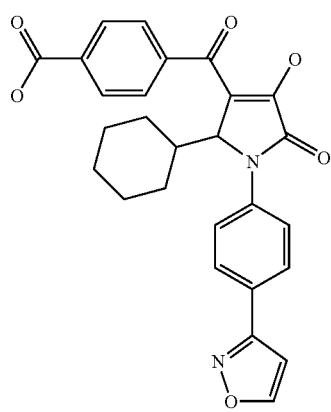 | 473 |
| II-60 | 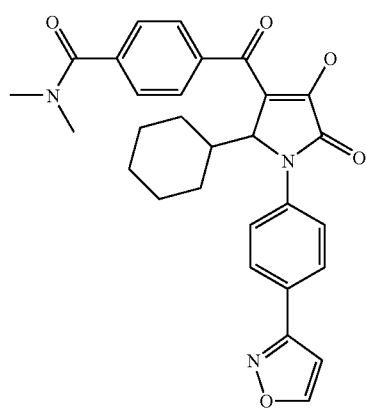 | 500 |
| II-61 | 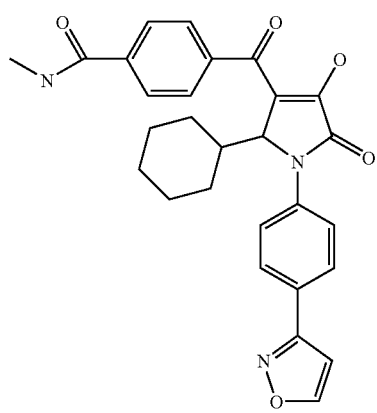 | 486 |

-continued
| | | |
|---|---|---|
| II-62 | 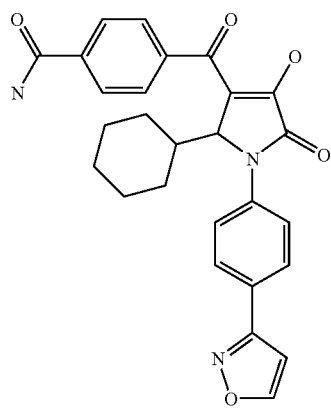 | 472 |
| II-63 | 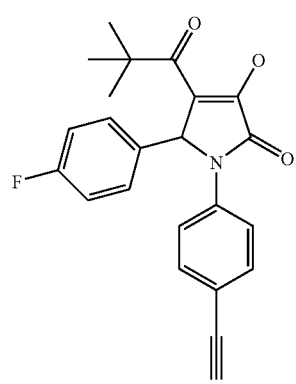 | 378 |
| II-64 | 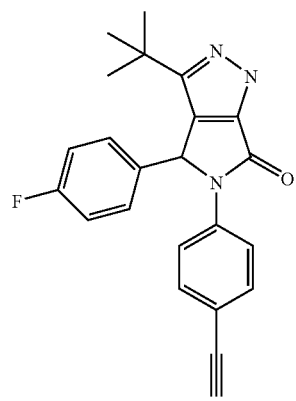 | 374 |
| II-65 | 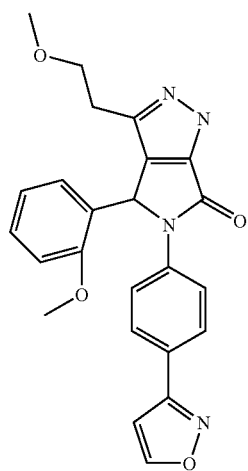 | 431 |

| | | |
|---|---|---|
| II-66 | 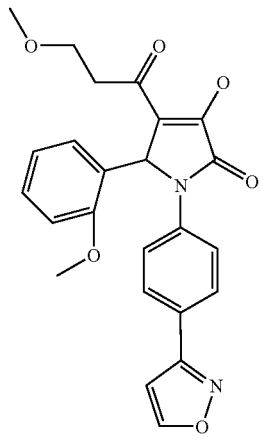 | 435 |
| II-67 | 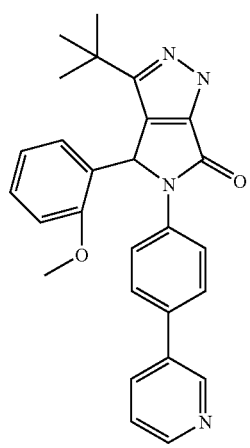 | 439 |
| II-68 | 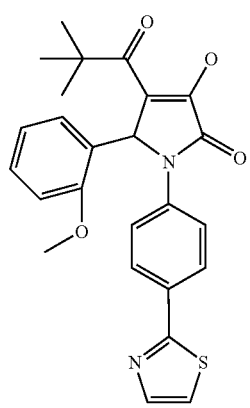 | 449 |

| | | |
|---|---|---|
| II-69 | 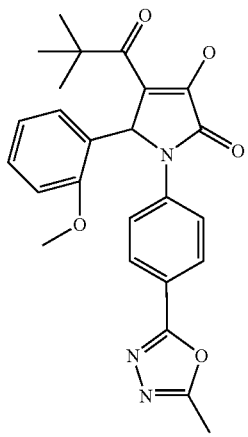 | 448 |
| II-70 | 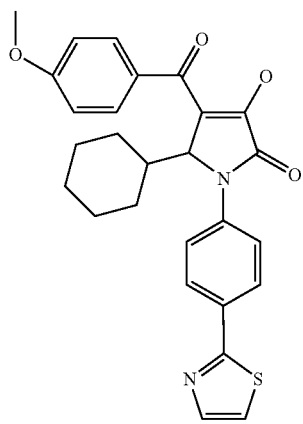 | 475 |
| II-71 | 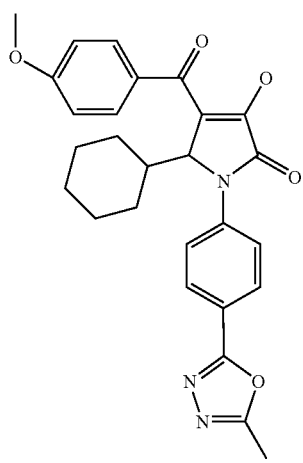 | 474 |

| | | |
|---|---|---|
| II-72 | 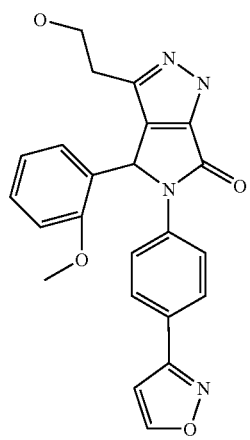 | 417 |
| II-73 | 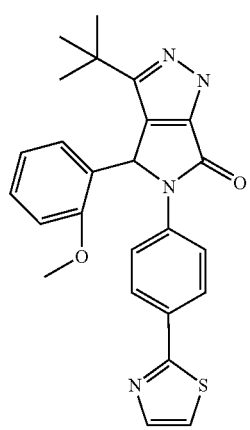 | 445 |
| II-74 | 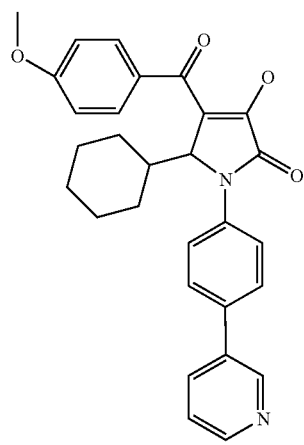 | 469 |

| | | |
|---|---|---|
| II-75 | 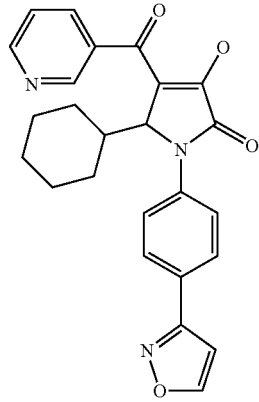 | 430 |
| II-76 | 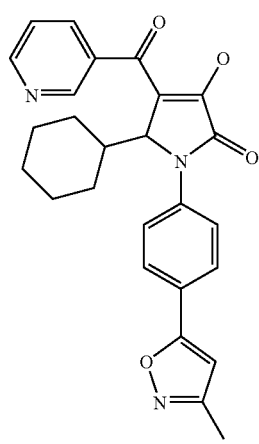 | 444 |
| II-77 | 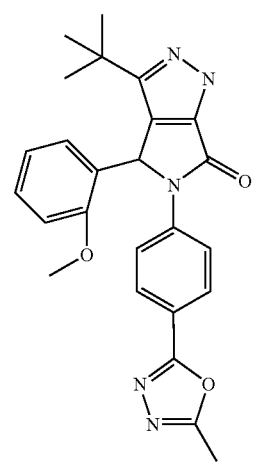 | 444 |

| | | |
|---|---|---|
| II-78 | 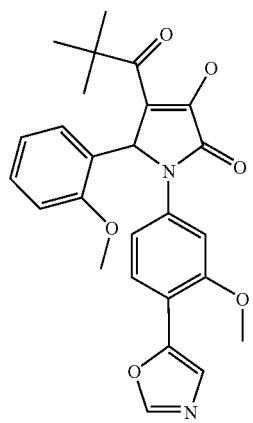 | 463 |
| II-79 | 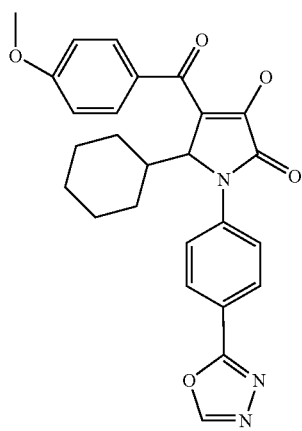 | 460 |
| II-80 | 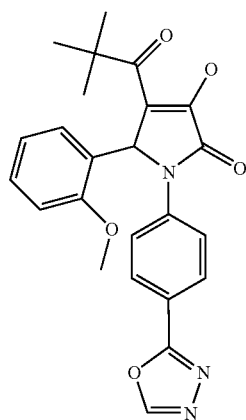 | 434 |

| | | |
|---|---|---|
| II-81 | 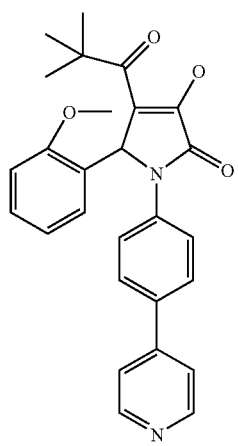 | 443 |
| II-82 | 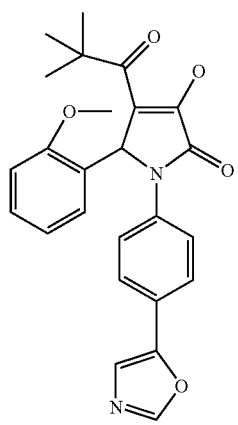 | 433 |
| II-83 | 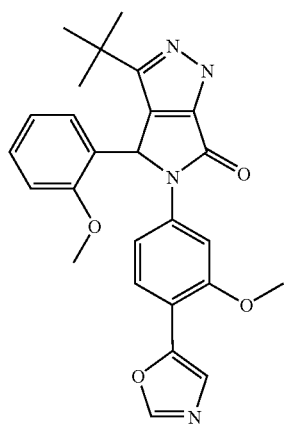 | 459 |

| | | |
|---|---|---|
| II-84 | 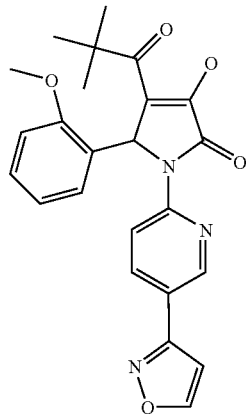 | 434 |
| II-85 | 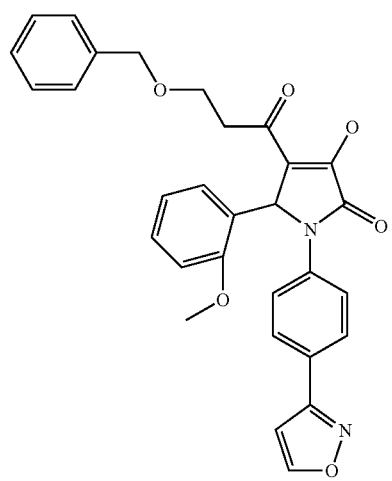 | 511 |
| II-86 | 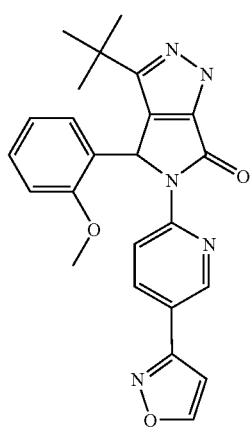 | 430 |

| | | |
|---|---|---|
| II-87 | 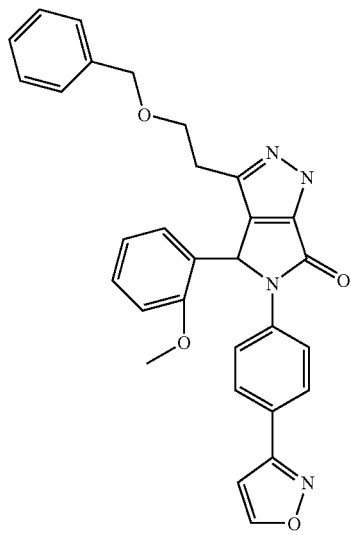 | 507 |
| II-88 | 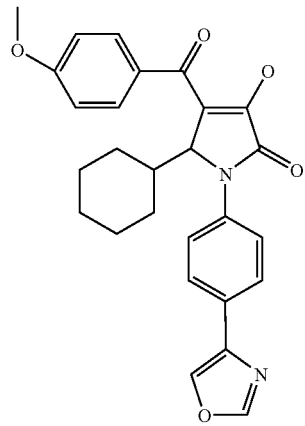 | 459 |
| II-89 | 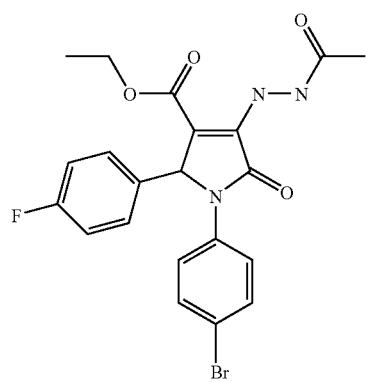 | 477 |

| | | |
|---|---|---|
| II-90 | 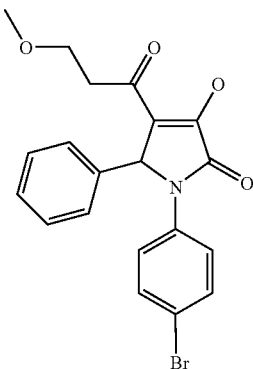 | 417 |
| II-91 | 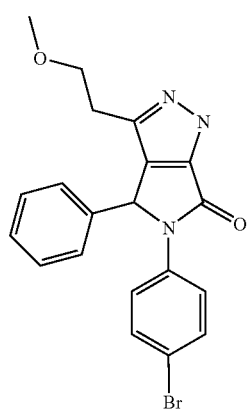 | 413 |
| II-92 | 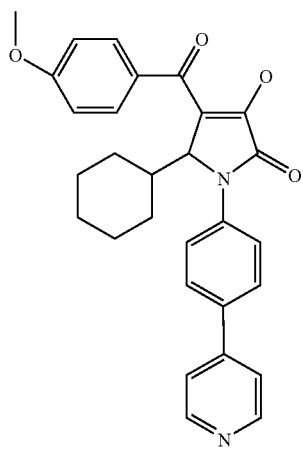 | 469 |

| | | |
|---|---|---|
| II-93 | 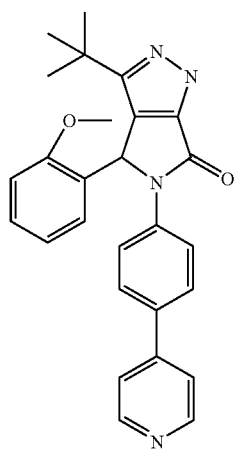 | 439 |
| II-94 | 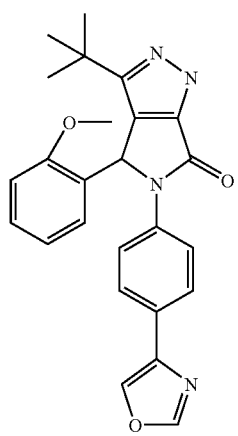 | 429 |
| II-95 | 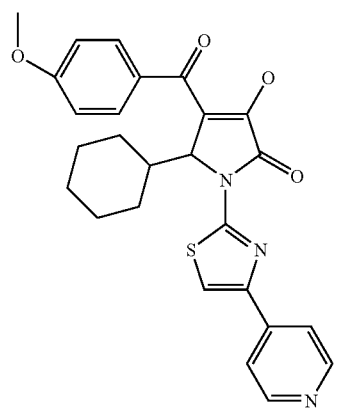 | 476 |

II-96 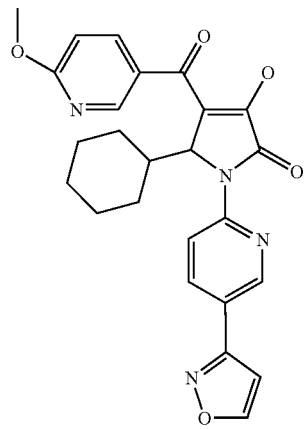 461
II-97 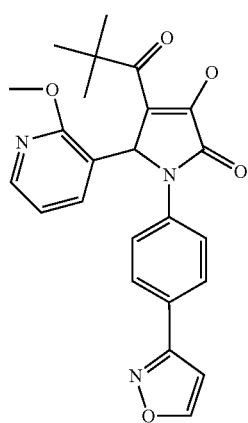 434
II-98 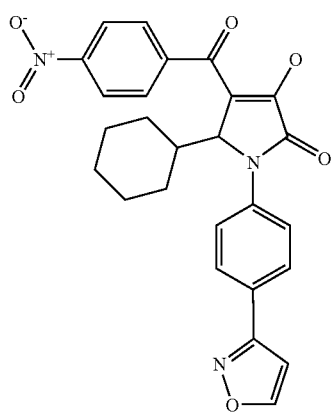 474

| | | |
|---|---|---|
| II-99 | 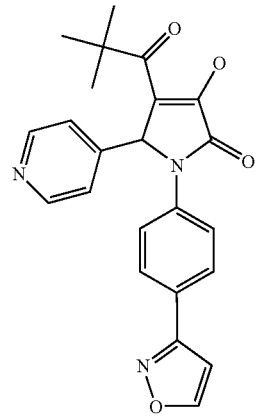 | 404 |
| II-100 | 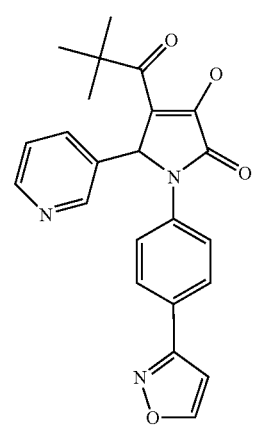 | 404 |
| II-101 | 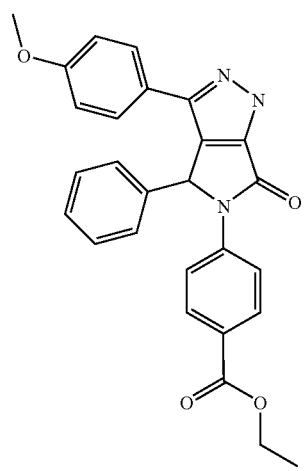 | 454 |

| | | |
|---|---|---|
| II-102 | 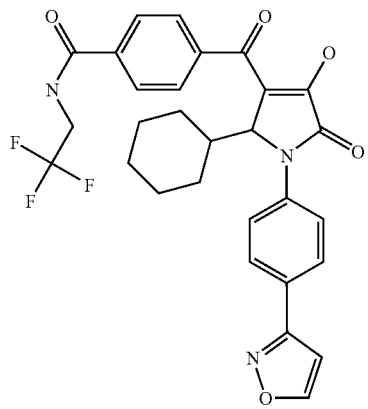 | 554 |
| II-103 | 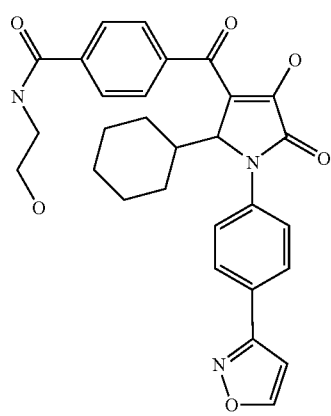 | 516 |
| II-104 | 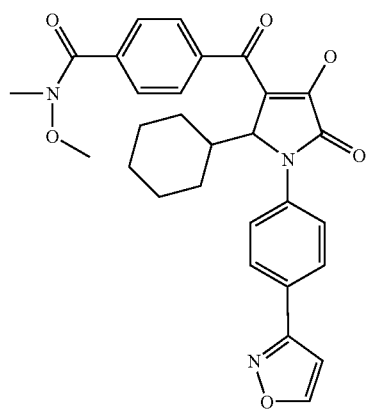 | 516 |

-continued
| | | |
|---|---|---|
| II-105 | 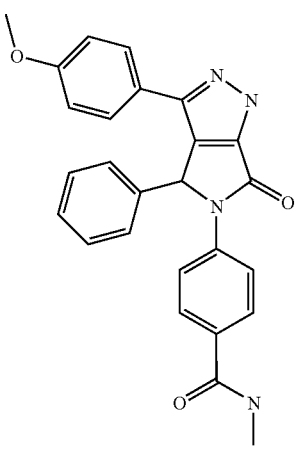 | 439 |
| II-106 | 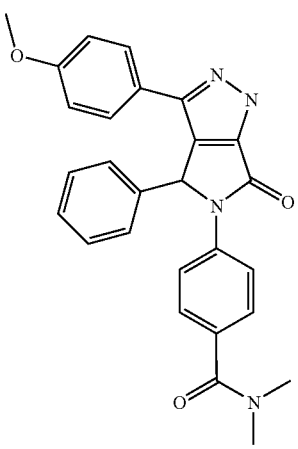 | 453 |
| II-107 | 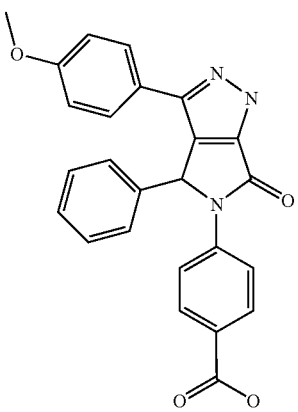 | 426 |

| | | |
|---|---|---|
| II-108 | 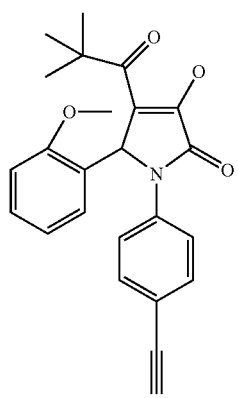 | 390 |
| II-109 | 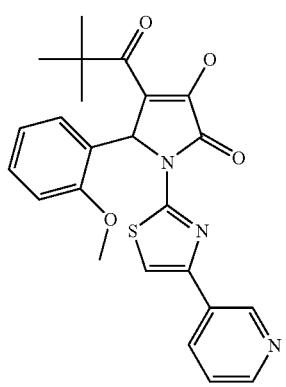 | 450 |
| II-110 | 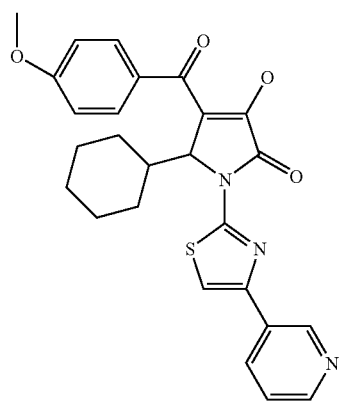 | 476 |
| II-111 | 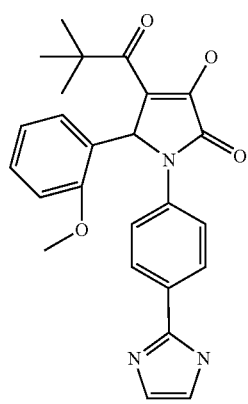 | 432 |

| | | |
|---|---|---|
| II-112 | 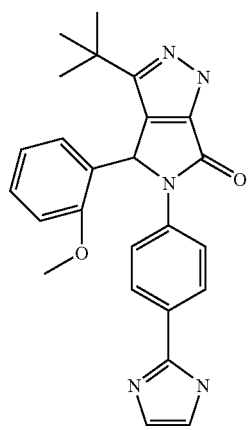 | 428 |
| II-113 | 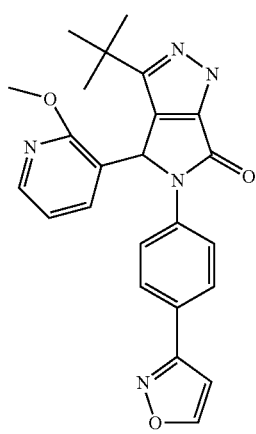 | 430 |
| II-114 | 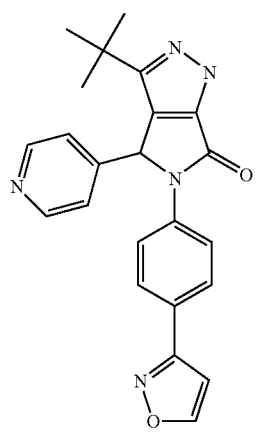 | 400 |

| | | |
|---|---|---|
| II-115 | 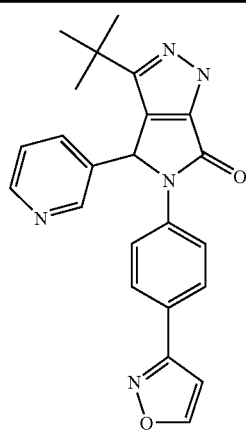 | 400 |
| II-116 | 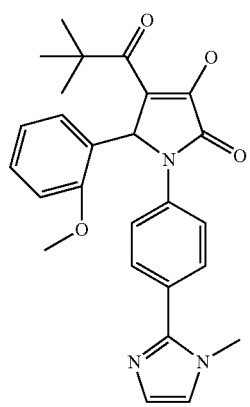 | 446 |
| II-117 | 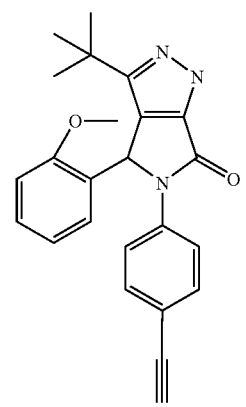 | 386 |
| II-118 | 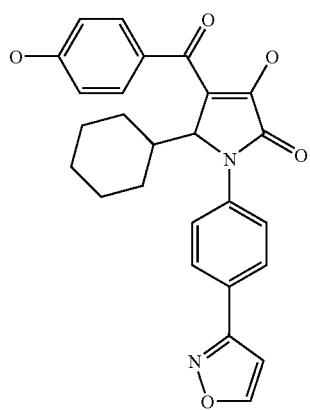 | 445 |

| | | |
|---|---|---|
| II-119 | 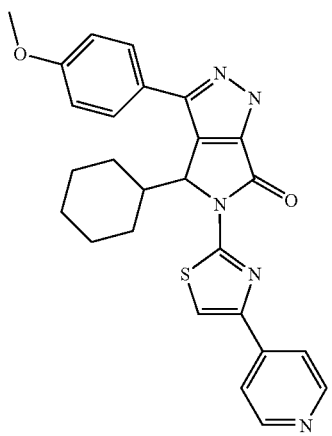 | 472 |
| II-120 | 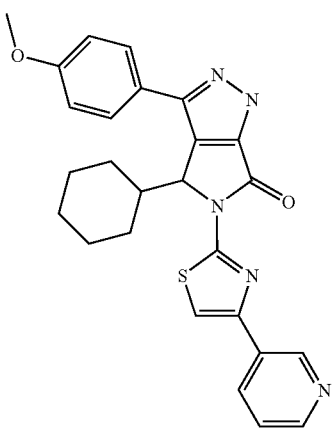 | 472 |
| II-121 | 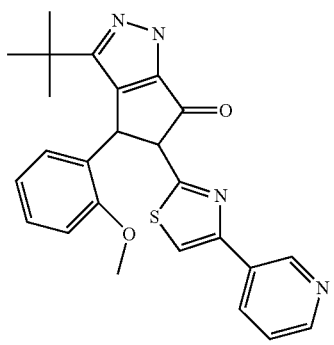 | 446 |
| II-122 | 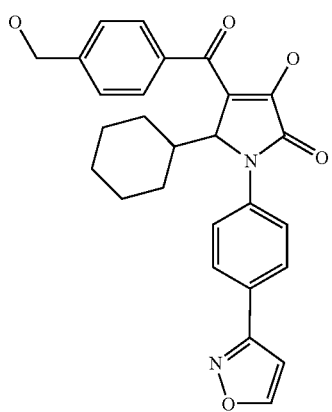 | 459 |

| | | |
|---|---|---|
| II-122 | 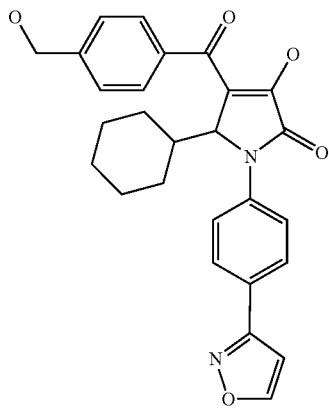 | 459 |
| II-123 | 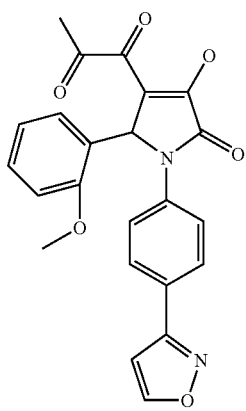 | 419 |
| II-124 | 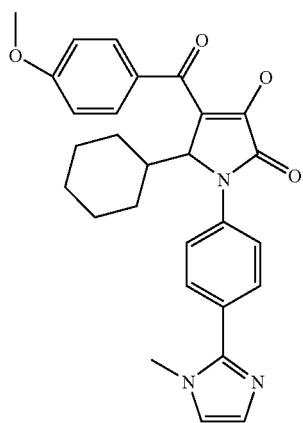 | 472 |

411
412
-continued
| | | |
|---|---|---|
| II-125 | 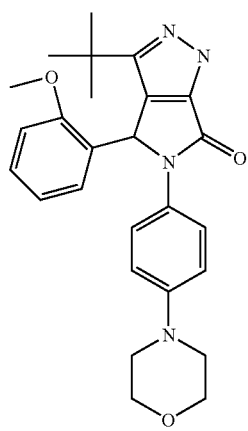 | 447 |
| II-126 | 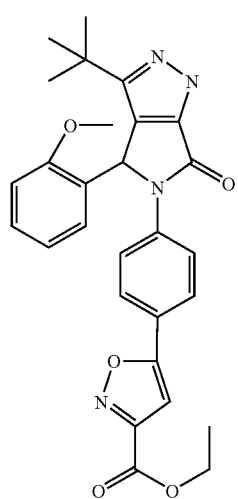 | 501 |
| II-127 | 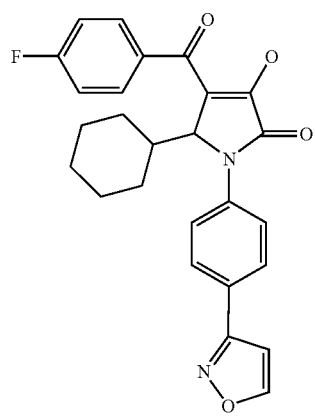 | 447 |

| | | |
|---|---|---|
| II-128 | 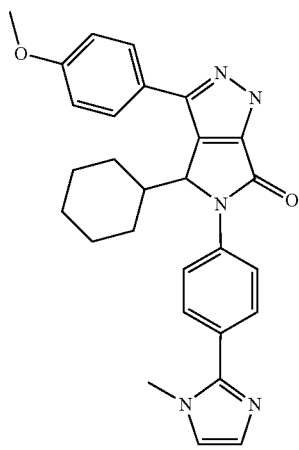 | 468 |
| II-129 | 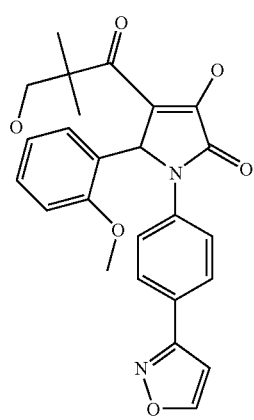 | 449 |
| II-130 | 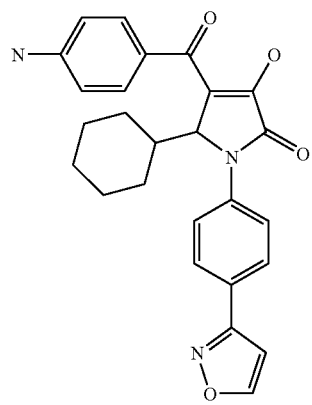 | 444 |

| | | |
|---|---|---|
| II-131 | 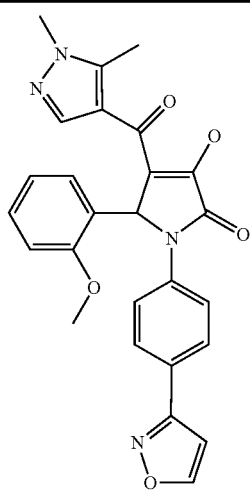 | 471 |
| II-132 | 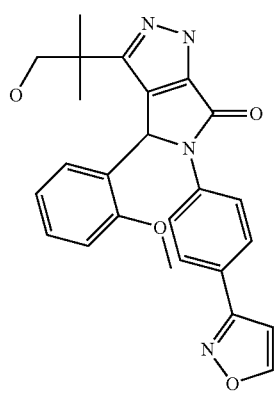 | 445 |
| II-133 | 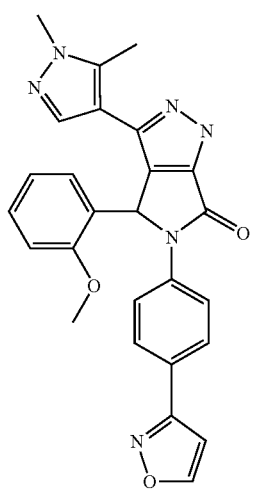 | 467 |

| | | |
|---|---|---|
| II-134 | 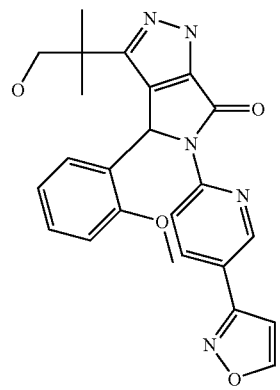 | 446 |
| II-135 | 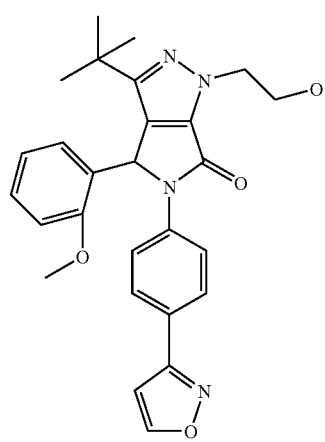 | 473 |
| II-136 | 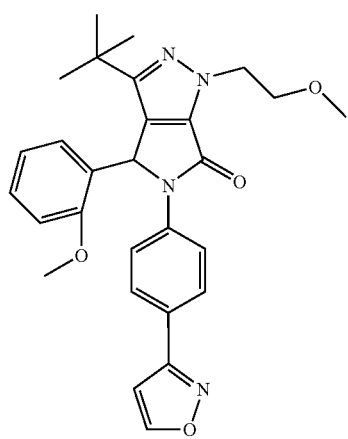 | 487 |

| | | |
|---|---|---|
| II-137 | 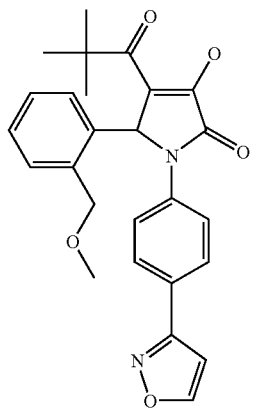 | 447 |
| II-138 | 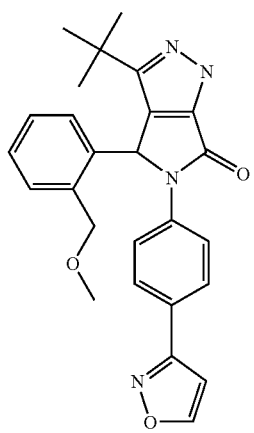 | 443 |
| II-139 | 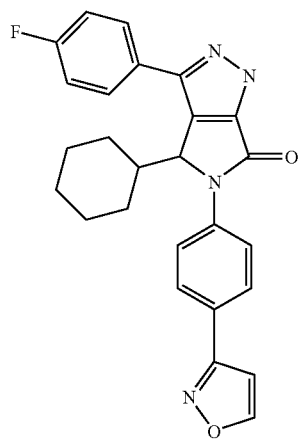 | 443 |

-continued
| | | |
|---|---|---|
| II-140 | 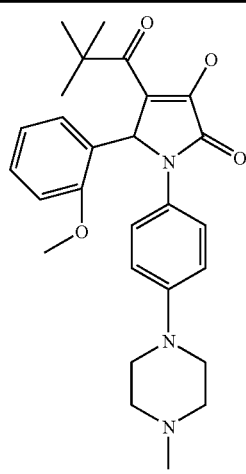 | 464 |
| II-141 | 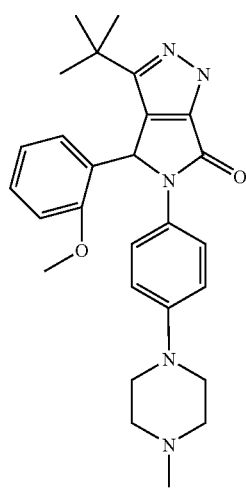 | 460 |
| II-142 | 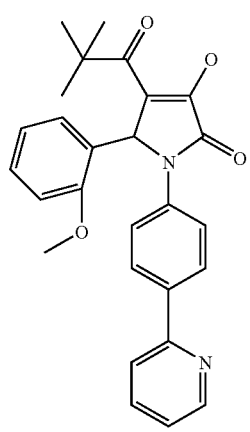 | 443 |

| | | |
|---|---|---|
| II-143 | 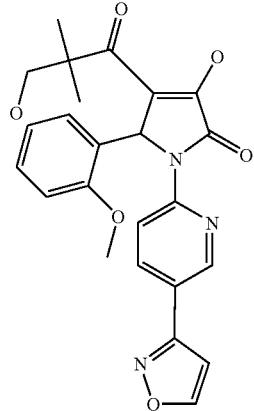 | 450 |
| II-144 | 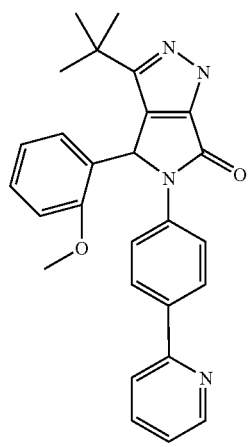 | 439 |
| II-145 | 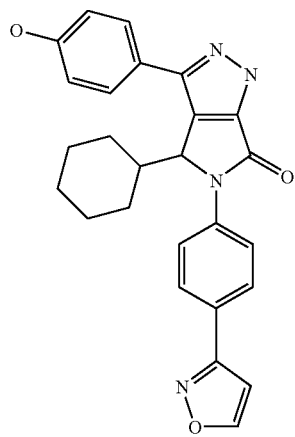 | 441 |

| | | |
|---|---|---|
| II-146 | 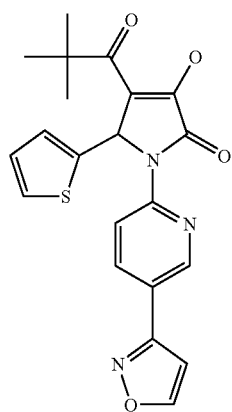 | 410 |
| II-147 | 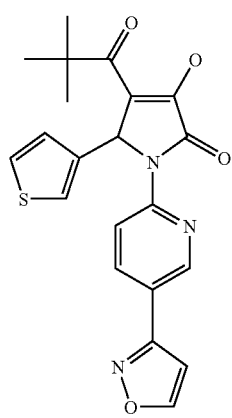 | 410 |
| II-148 | 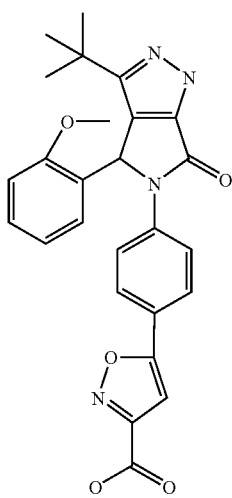 | 473 |

| | | |
|---|---|---|
| II-149 | 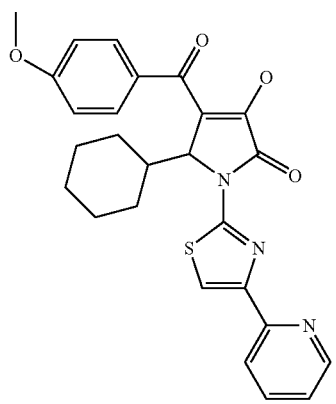 | 476 |
| II-150 | 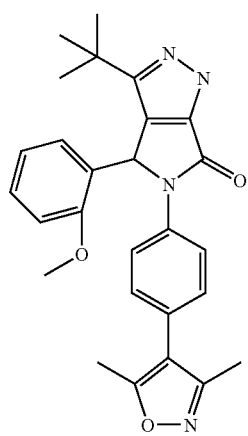 | 457 |
| II-151 | 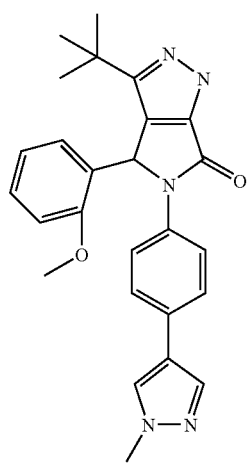 | 442 |

| | | |
|---|---|---|
| II-152 | 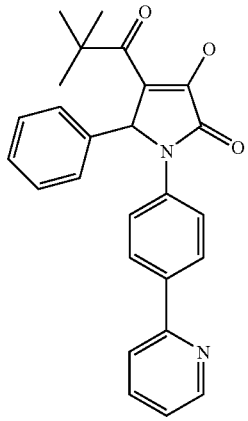 | 413 |
| II-153 | 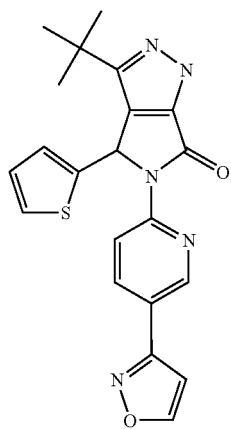 | 406 |
| II-154 | 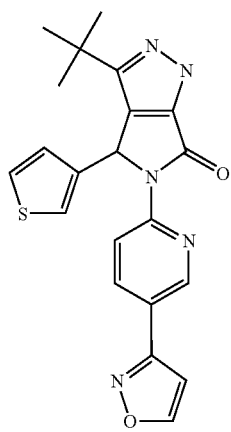 | 406 |

| | | | |
|---|---|---|---|
| II-155 | 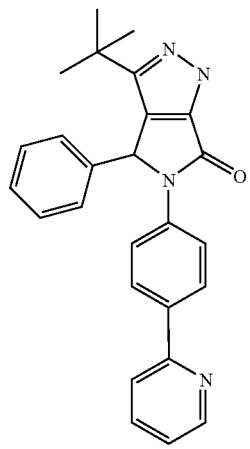 | | 409 |
| II-156 | 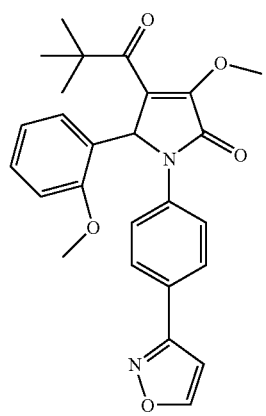 | 136-137 | 447 |
| II-157 | 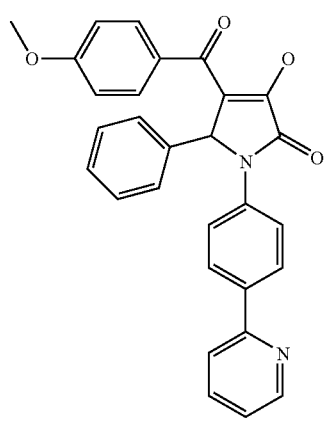 | | 463 |

| | |
|---|---|
| II-158 | 459 |
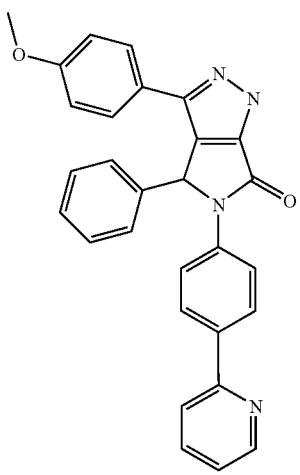
| | |
|---|---|
| II-159 | 442 |
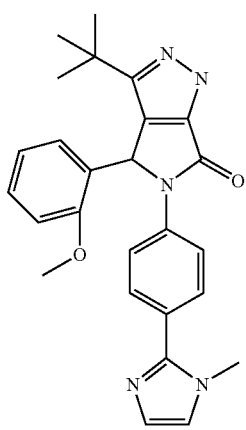
| | |
|---|---|
| II-160 | 472 |
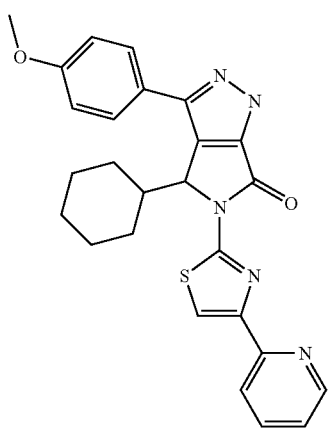

| | | |
|---|---|---|
| II-161 | 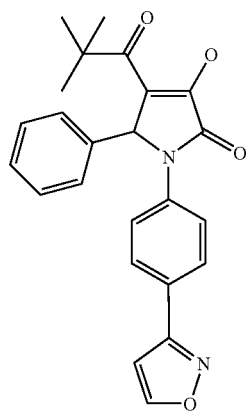 | 403 |
| II-162 | 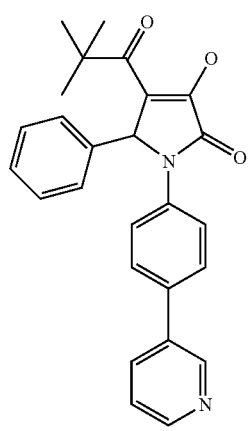 | 413 |
| II-163 | 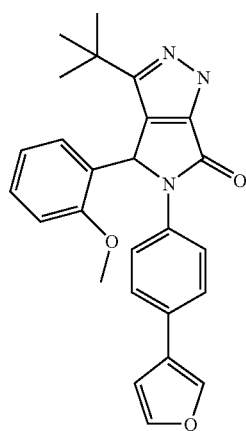 | 428 |

| | | |
|---|---|---|
| II-164 | 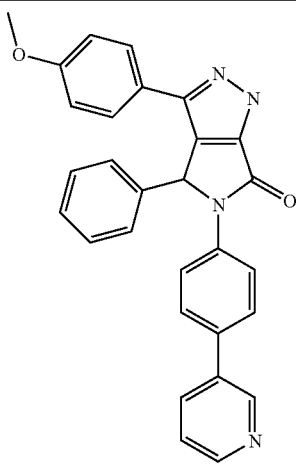 | 459 |
| II-165 | 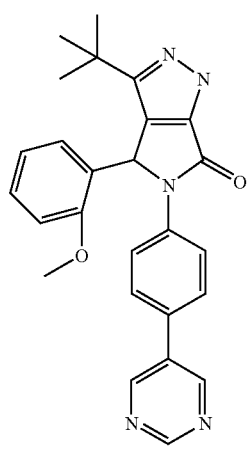 | 440 |
| II-166 | 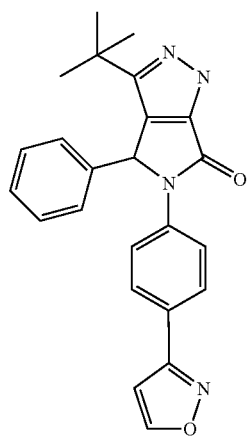 | 399 |

-continued
| | | |
|---|---|---|
| II-167 | 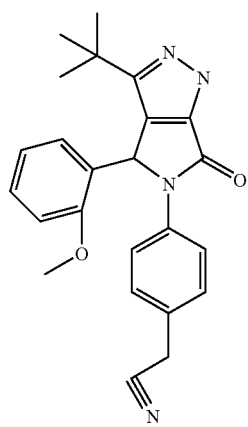 | 401 |
| II-168 | 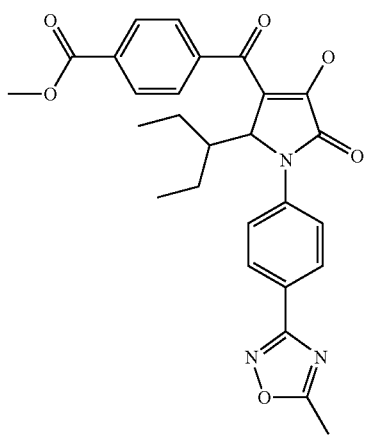 | 490 |
| II-169 | 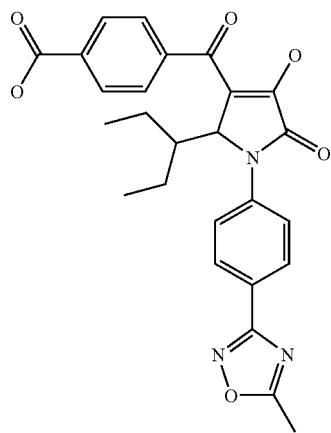 | 476 |

| | | |
|---|---|---|
| II-170 | 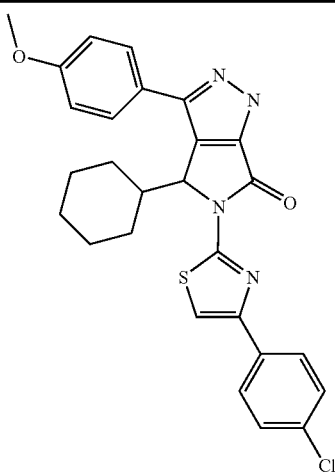 | 506 |
| II-171 | 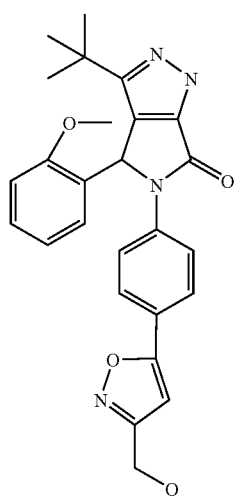 | 459 |
| II-172 | 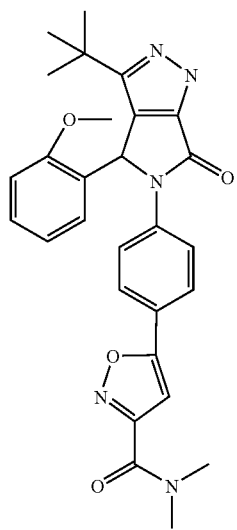 | 500 |

| | | |
|---|---|---|
| II-173 | 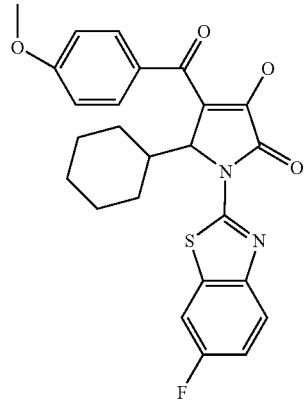 | 467 |
| II-174 | 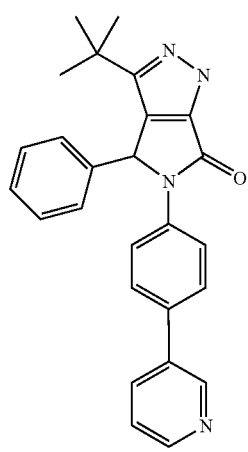 | 409 |
| II-175 | 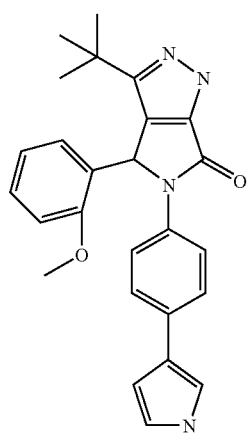 | 427 |

| | | |
|---|---|---|
| II-176 | 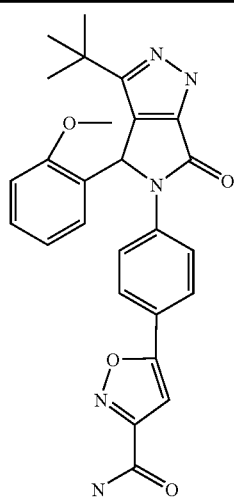 | 472 |
| II-177 | 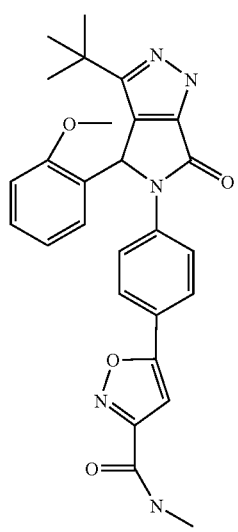 | 486 |
| II-178 | 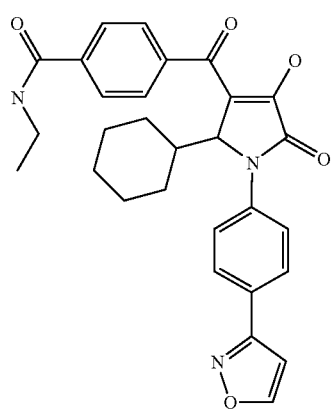 | 500 |

| | | |
|---|---|---|
| II-179 | 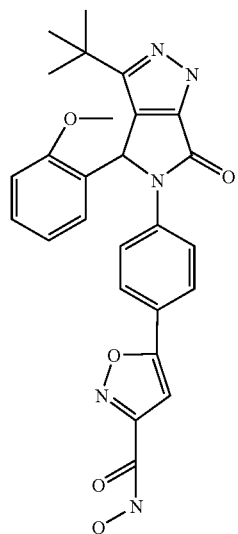 | 488 |
| II-180 | 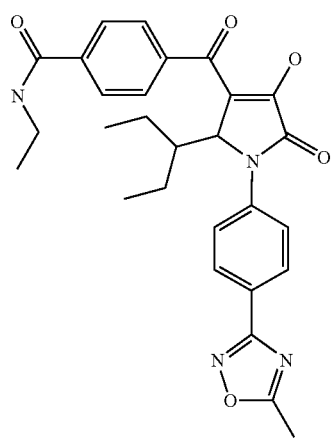 | 503 |
| II-181 | 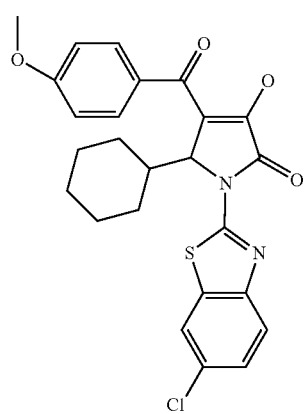 | 483 |

| | | |
|---|---|---|
| II-182 | 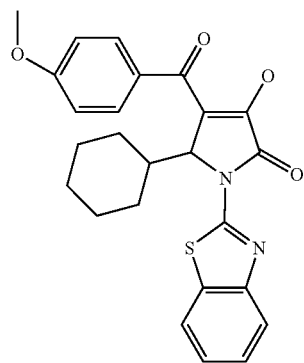 | 449 |
| II-183 | 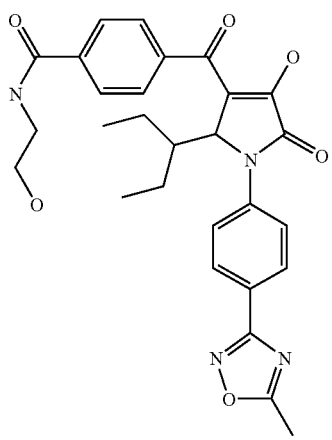 | 519 |
| II-184 | 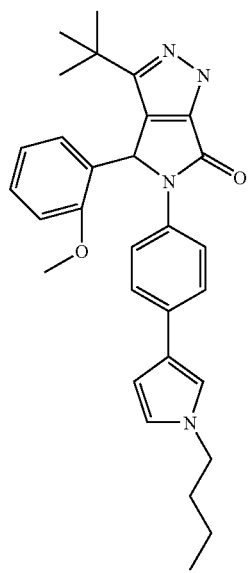 | 483 |

| | | |
|---|---|---|
| II-185 | 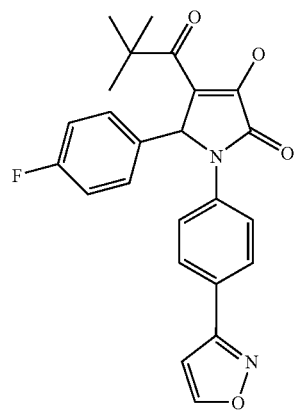 | 421 |
| II-186 | 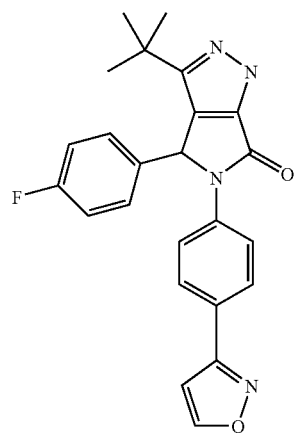 | 417 |
| II-187 | 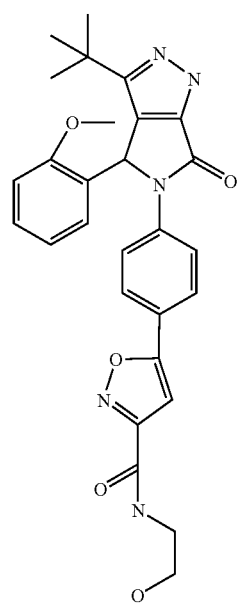 | 516 |

| II-188 | 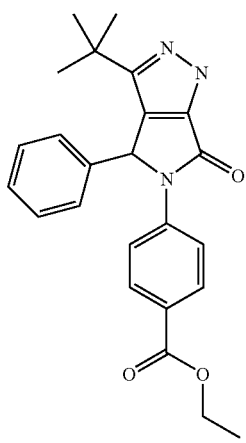 | 404 |
| II-189 | 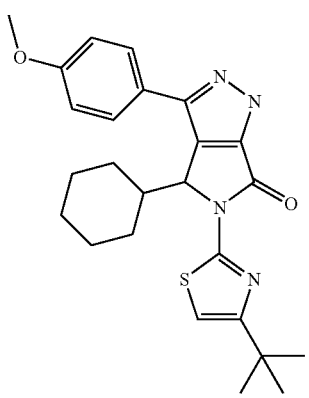 | 451 |
| II-190 | 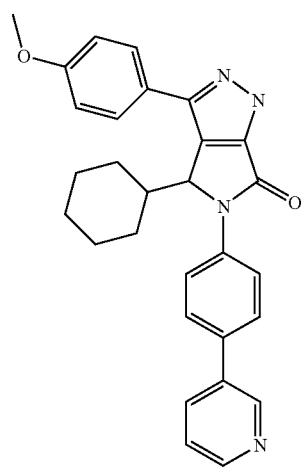 | 465 |

| | | |
|---|---|---|
| II-191 | 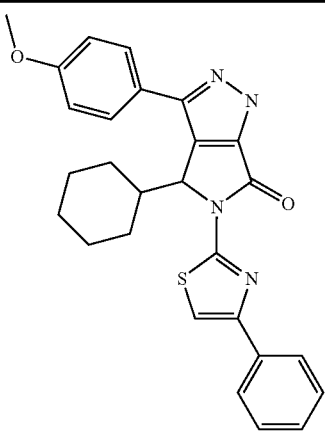 | 471 |
| II-192 | 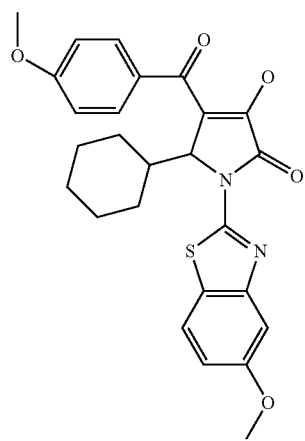 | 479 |
| II-193 | 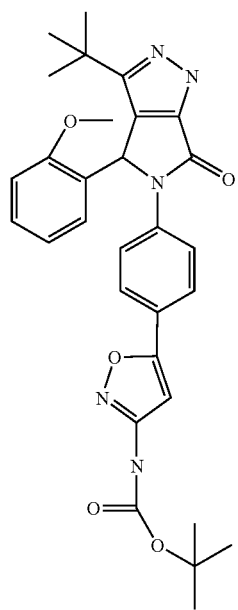 | 544 |

-continued
| | | |
|---|---|---|
| II-194 | 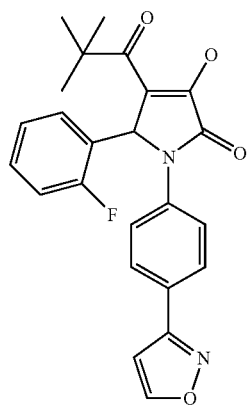 | 421 |
| II-195 | 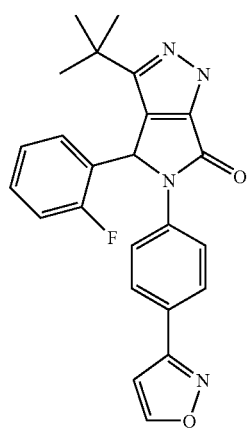 | 417 |
| II-196 | 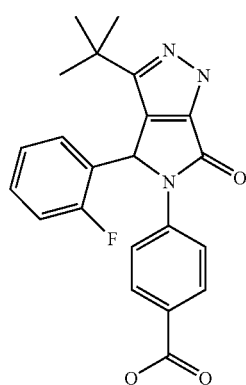 | 394 |
| II-197 | 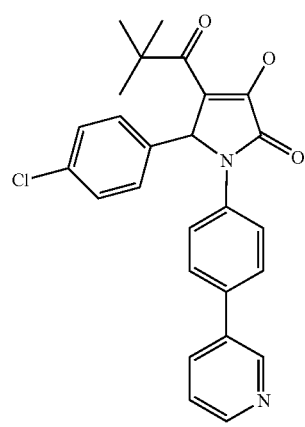 | 447 |

| | | |
|---|---|---|
| II-198 | 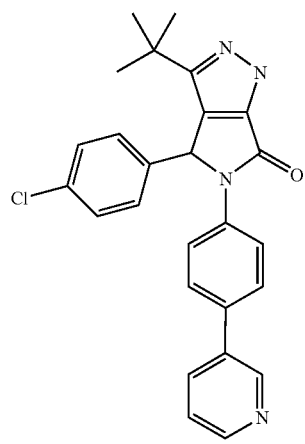 | 443 |
| II-199 | 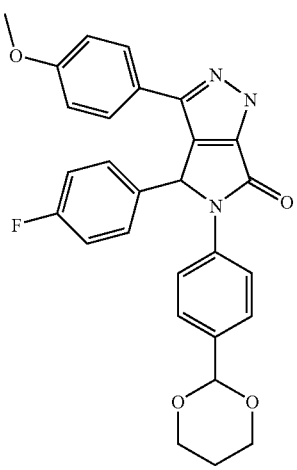 | 486 |
| II-200 | 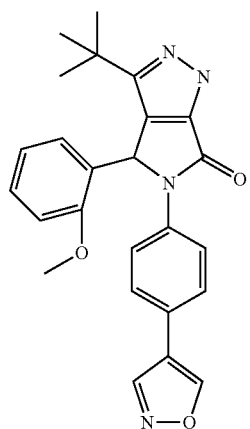 | 429 |

| | | |
|---|---|---|
| II-201 | 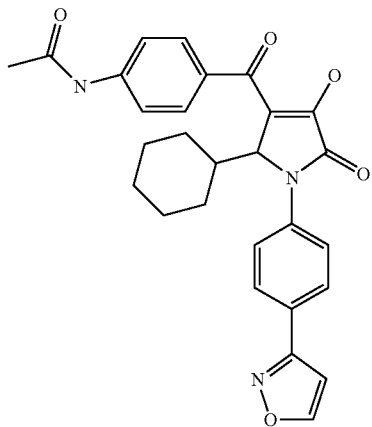 | 486 |
| II-202 | 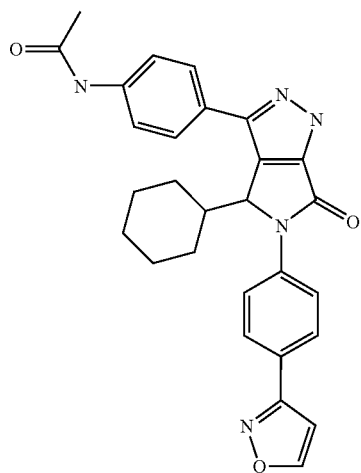 | 482 |
| II-203 | 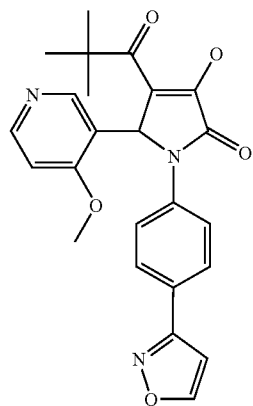 | 434 |

-continued
| | | |
|---|---|---|
| II-204 | 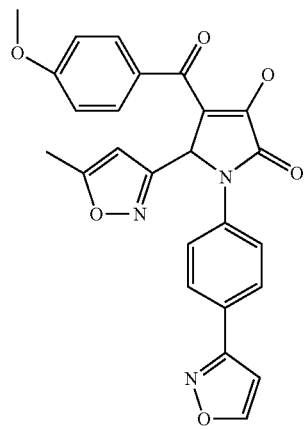 | 458 |
| II-205 | 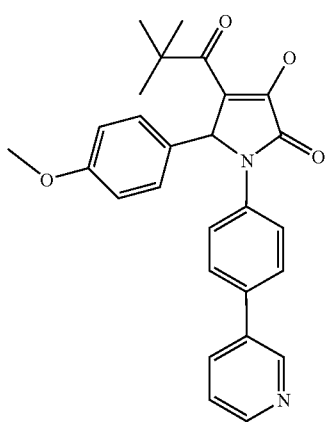 | 443 |
| II-206 | 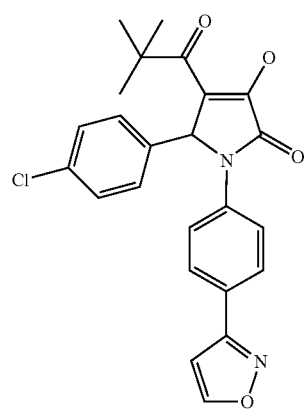 | 437 |

| | | |
|---|---|---|
| II-207 | 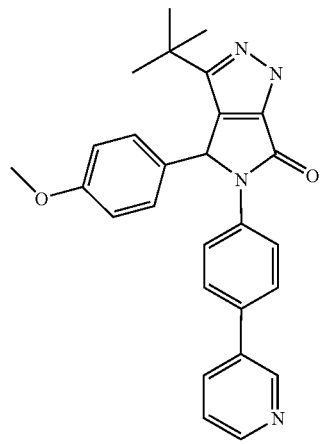 | 439 |
| II-208 | 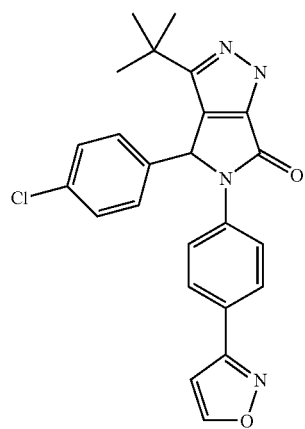 | 433 |
| II-209 | 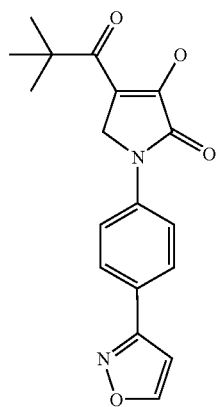 | 327 |

| | | |
|---|---|---|
| II-210 | 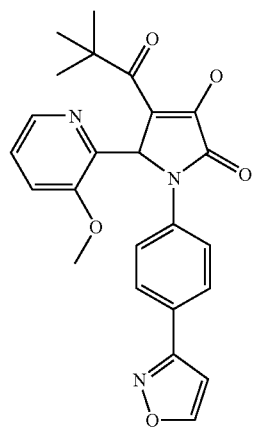 | 434 |
| II-211 | 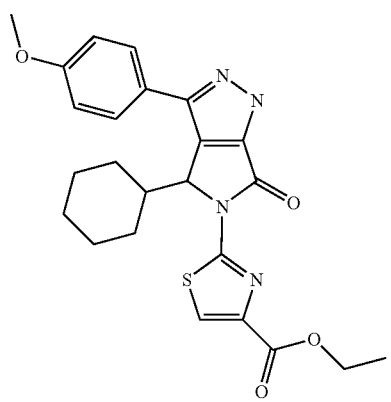 | 467 |
| II-212 | 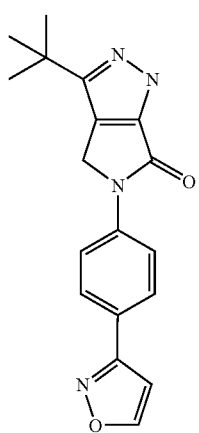 | 323 |

| | | |
|---|---|---|
| II-213 | 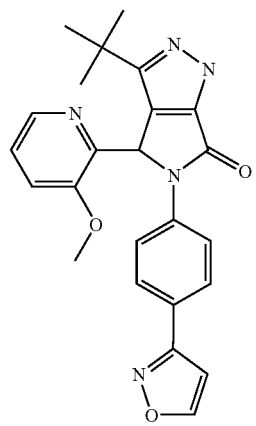 | 430 |
| II-214 | 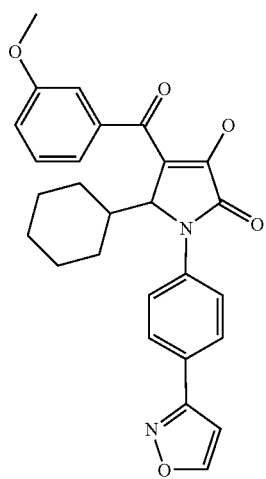 | 459 |
| II-215 | 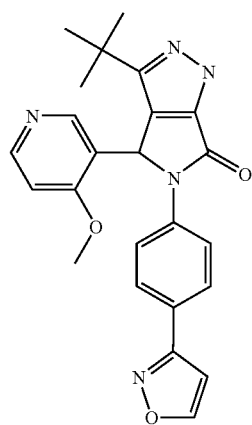 | 430 |

| | | |
|---|---|---|
| II-216 | 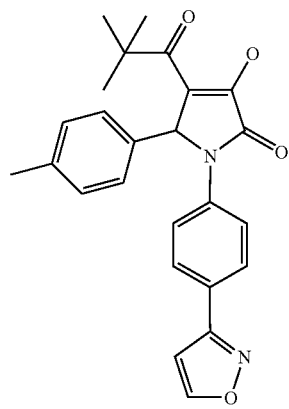 | 417 |
| II-217 | 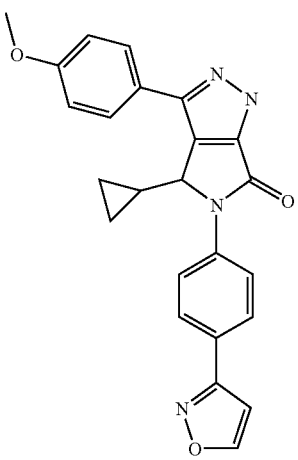 | 413 |
| II-218 | 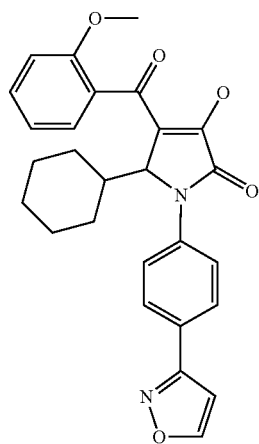 | 459 |

| | | |
|---|---|---|
| II-219 | 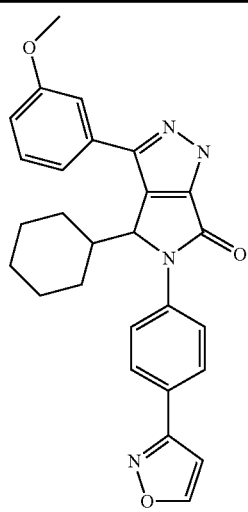 | 455 |
| II-220 | 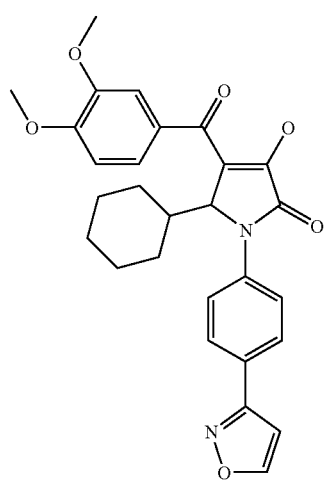 | 489 |
| II-221 | 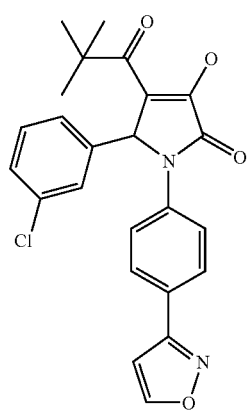 | 437 |

| | | |
|---|---|---|
| II-222 | 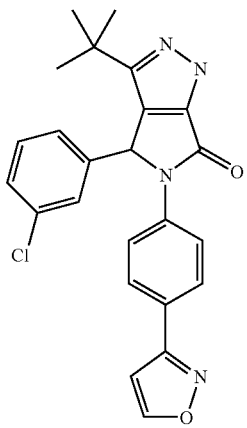 | 433 |
| II-223 | 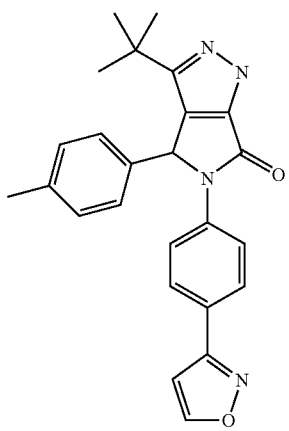 | 413 |
| II-224 | 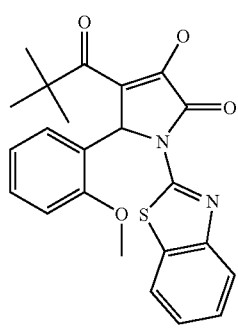 | 423 |
| II-225 | 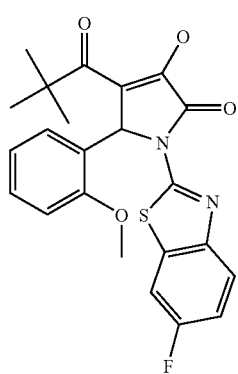 | 441 |

| | | |
|---|---|---|
| II-226 | 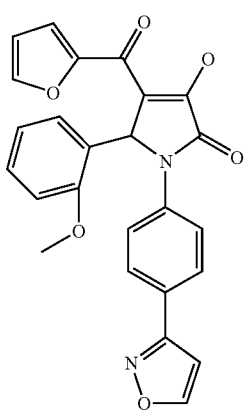 | 443 |
| II-227 | 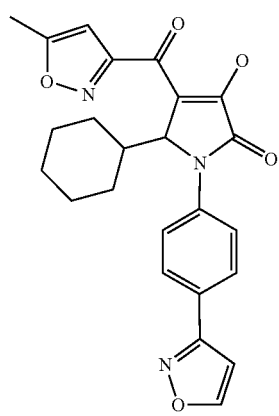 | 434 |
| II-228 | 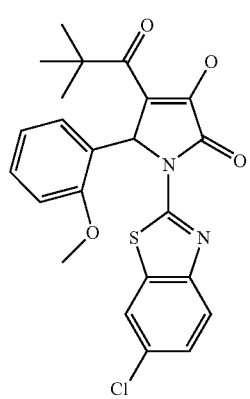 | 457 |
| II-229 | 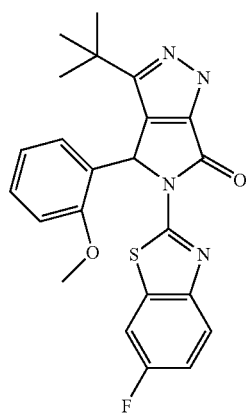 | 437 |

| | | |
|---|---|---|
| II-230 | 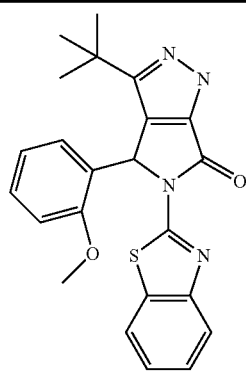 | 419 |
| II-231 | 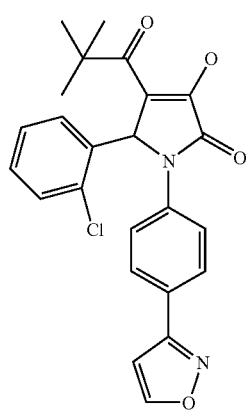 | 437 |
| II-232 | 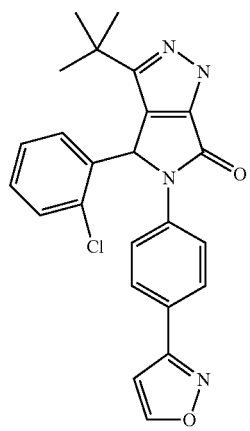 | 433 |
| II-233 | 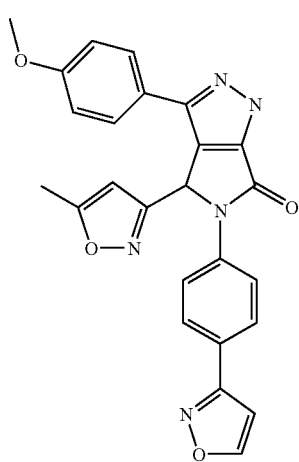 | 454 |

| | | |
|---|---|---|
| II-234 | 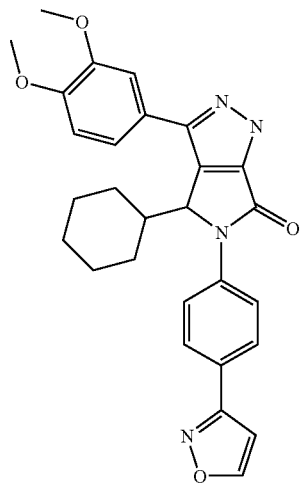 | 485 |
| II-235 | 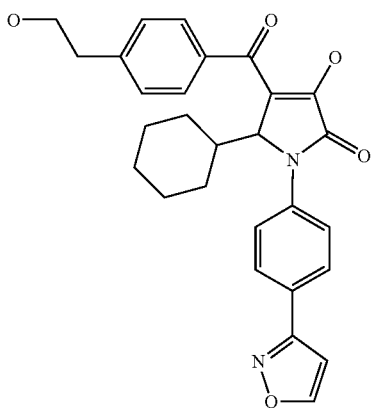 | 473 |
| II-236 | 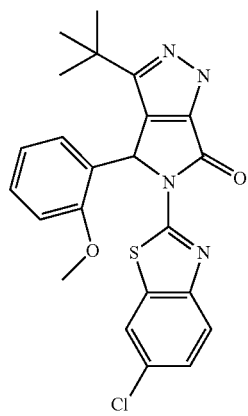 | 453 |

| | | |
|---|---|---|
| II-237 | 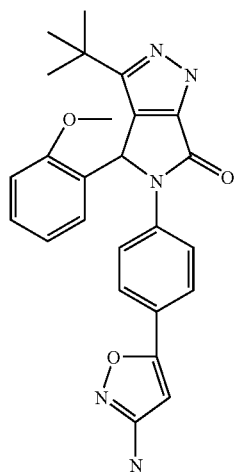 | 444 |
| II-238 | 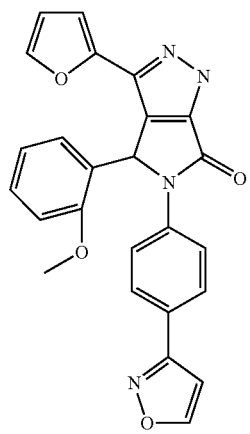 | 439 |
| II-239 | 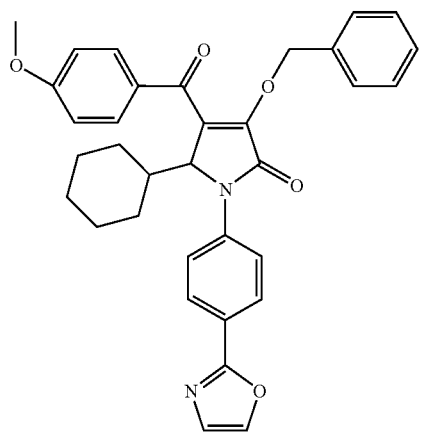 | 549 |

| | | |
|---|---|---|
| II-240 | 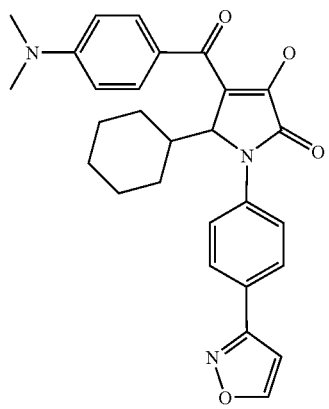 | 472 |
| II-241 | 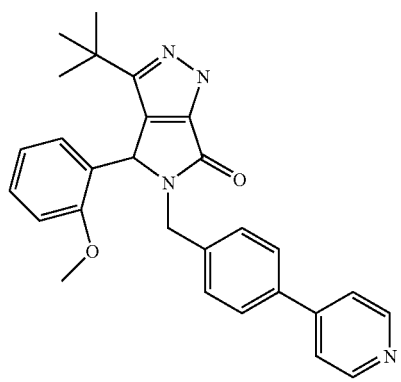 | 453 |
| II-242 | 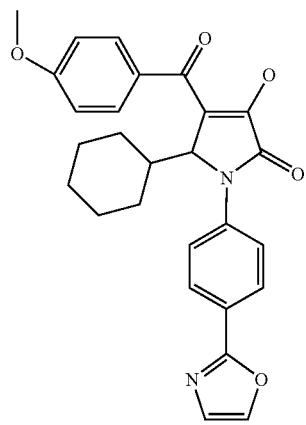 | 459 |

| | | |
|---|---|---|
| II-243 | 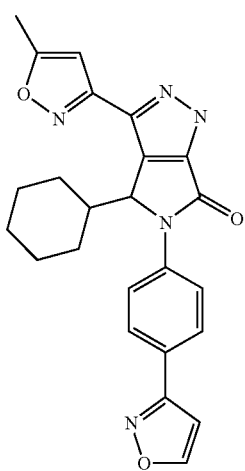 | 430 |
| II-244 | 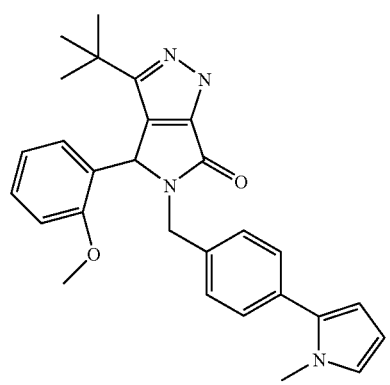 | 455 |
| II-245 | 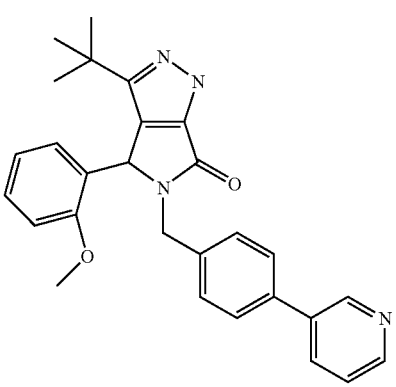 | 453 |

| | | |
|---|---|---|
| II-246 | 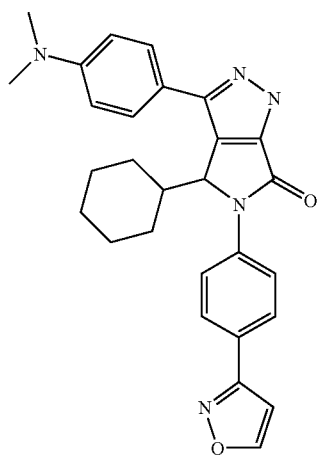 | 468 |
| II-247 | 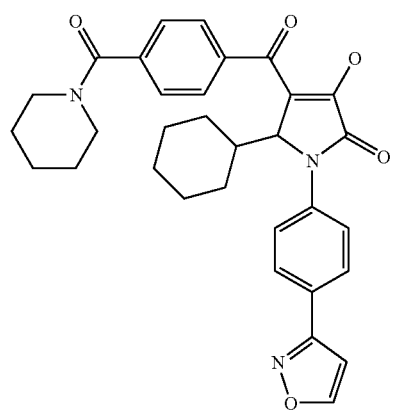 | 540 |
| II-248 | 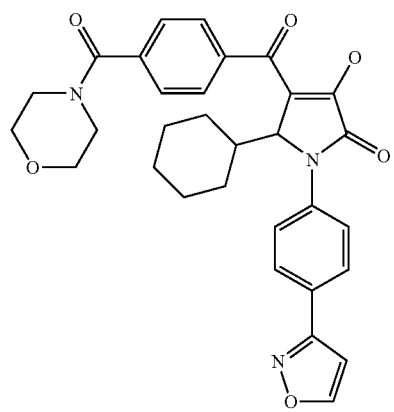 | 542 |

| | | |
|---|---|---|
| II-249 | 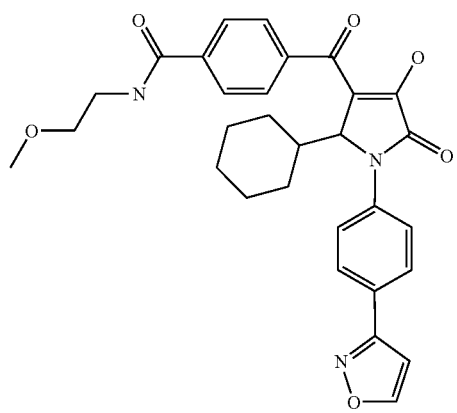 | 530 |
| II-250 | 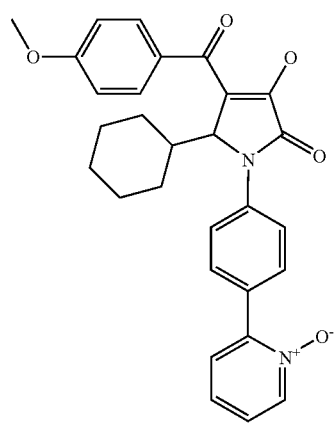 | 485 |
| II-251 | 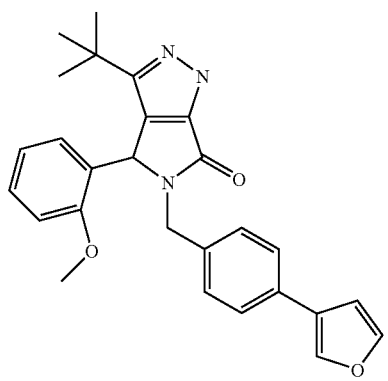 | 442 |
| II-252 | 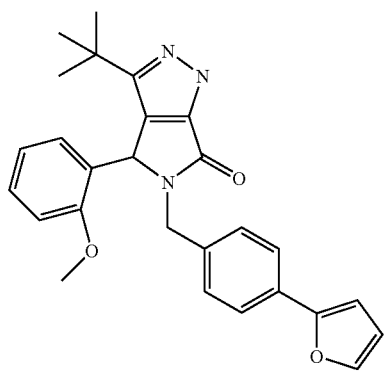 | 442 |

-continued
| | | |
|---|---|---|
| II-253 | 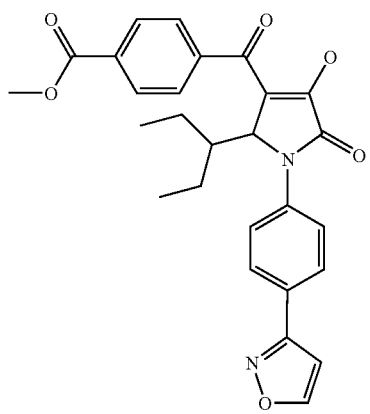 | 475 |
| II-254 | 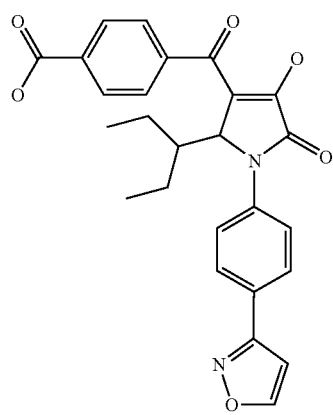 | 461 |
| II-255 | 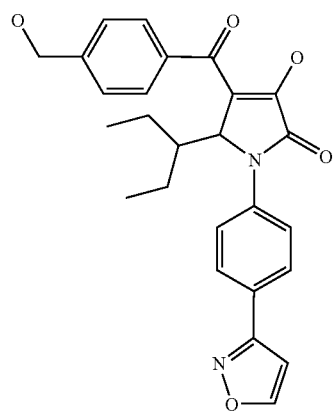 | 447 |
| II-256 | 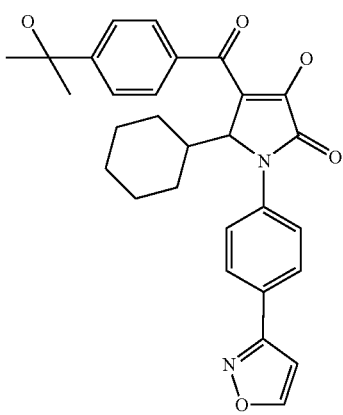 | 487 |

| | | |
|---|---|---|
| II-257 | 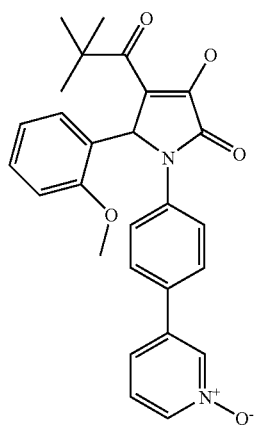 | 459 |
| II-258 | 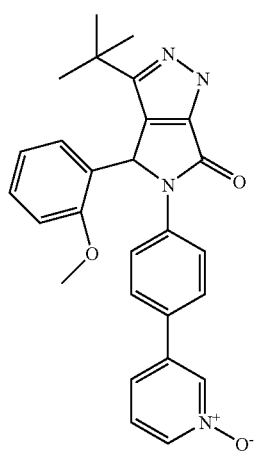 | 455 |
| II-259 | 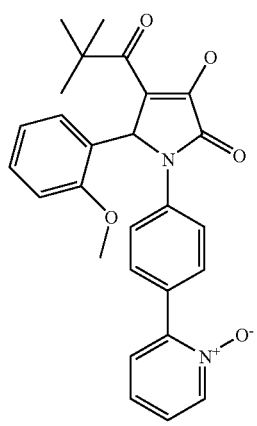 | 459 |

-continued
| | | |
|---|---|---|
| II-260 | 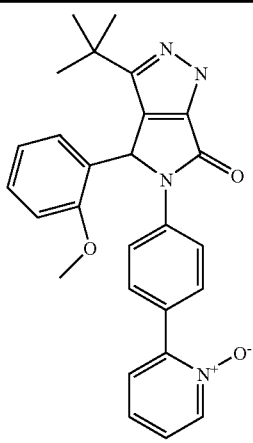 | 455 |
| II-261 | 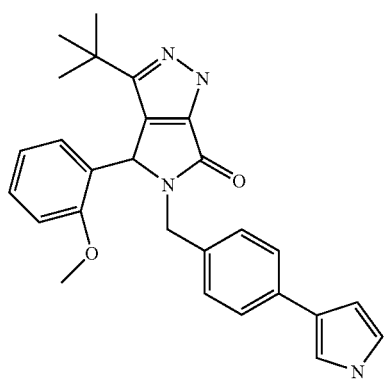 | 441 |
| II-262 | 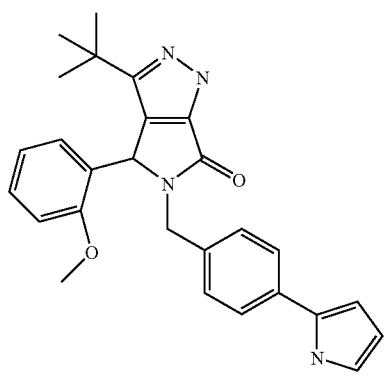 | 441 |
In the above Tables,
[Chemical Formula 59]
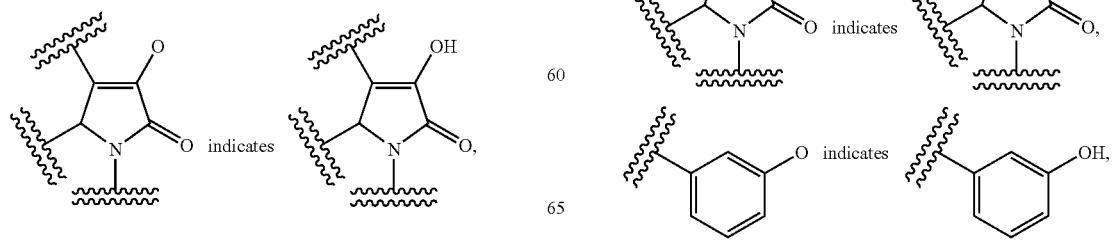

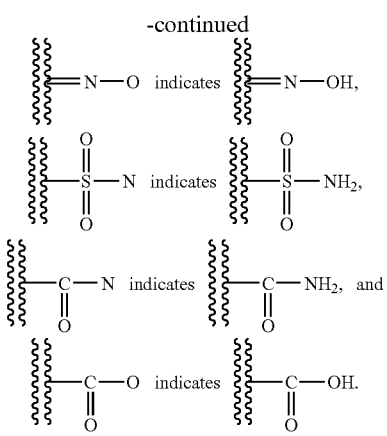

Test Examples

Stably expressing cell line (C6BU-1 cell transfected with human P2X$_3$ receptor gene (GenBank accession number Y07683)) was used. The cells were seeded in a 96-well microtiter plate at a concentration of 8000 cells/well and cultured in the medium (8.3% fetal bovine serum, 8.3% horse serum, 1% antibiotic and antifungal in DMEM) for one day at 37° C. under 5% carbon dioxide atmosphere. The medium was replaced with 4 μM Fluo-3-AM solution (pH7.5) containing 20 mM HEPES, 137 mM NaCl, 2.7 mM KCl, 0.9 mM MgCl$_2$, 5.0 mM CaCl$_2$, 5.6 mM D-glucose, 2.5 mM probenecid, 10% BSA, and 0.08% Pluronic F-127, and incubated at 37° C. under 5% dioxide carbon atmosphere for one hour. The plate was washed with washing buffer (20 mM HEPES, 137 mM NaCl, 2.7 mM KCl, 0.9 mM MgCl$_2$, 5.0 mM CaCl$_2$, 5.6 mM D-glucose, 2.5 mM probenecid, pH7.5), and each well was added with 40 μL of this buffer. The plate was placed in High-Throughput Screening System FDSS 3000 (Hamamatsu Photonics K.K.). Measurement of fluorescence intensity by FDSS 3000 was started, and 40 μL of DMSO solutions containing different concentrations of the test compound as prepared by dilution with dilution buffer (20 mM HEPES, 137 mM NaCl, 2.7 mM KCl, 0.9 mM MgCl$_2$, 5.0 mM CaCl$_2$, 5.6 mM D-glucose, 2.5 mM probenecid, 0.1% Pluronic F-127, pH7.5) were dispensed to each well through the built-in automatic dispenser. Five minutes after, 40 nM ATP solution (50 μL) prepared by dilution with the dilution buffer was dispensed through the built-in automatic dispenser, and the measurement of fluorescence intensity was continued for 3 min. For each well, the specific maximum fluorescence intensity was calculated as the ratio of the maximum fluorescence intensity after addition of the ATP solution to the fluorescence intensity at the starting of the measurement. The 50% inhibitory concentration (IC$_{50}$) was calculated under the assumption that the specific maximum fluorescence intensity without test compound is 0% inhibition and that the specific maximum fluorescence intensity when the dilution buffer was added in place of ATP solution is 100% inhibition, to evaluate the inhibitory activity of the test compound. FDSS software (Hamamatsu Photonics K.K.) was used for calculation of the specific maximum fluorescence intensity. IC$_{50}$ was calculated using Microsoft™ Excel™ (Microsoft Corporation) and XLfit™ (ID Business Solutions Ltd.).

The results of the compounds of the invention are shown in the following tables.

TABLE 189

| Compound No. | P2X$_3$ IC$_{50}$ (μM) |
|---|---|
| I-1 | 0.01 |
| I-2 | 0.01 |
| I-4 | 0.02 |
| I-6 | 0.03 |
| I-20 | 0.14 |
| I-21 | 0.16 |
| I-24 | 0.18 |
| I-25 | 0.18 |
| I-28 | 0.26 |
| I-36 | 0.38 |
| I-44 | 0.56 |
| I-45 | 0.58 |
| I-48 | 0.97 |
| I-49 | 1.02 |
| I-52 | 1.27 |
| I-53 | 1.28 |
| I-57 | 1.53 |
| I-62 | 1.96 |
| I-66 | 3.46 |
| I-69 | 3.78 |
| I-72 | 4.79 |
| I-74 | 5.92 |
| I-76 | 6.48 |
| I-77 | 8.01 |
| I-79 | 8.95 |
| I-88 | 15.43 |
| I-95 | 0.56 |
| I-96 | 0.92 |
| I-118 | 17.80 |
| I-122 | 19.30 |
| I-124 | 22.00 |
| I-251 | 1.40 |
| I-260 | 5.63 |
| I-273 | 2.20 |
| I-278 | 1.40 |

TABLE 190

| Compound No. | P2X$_3$ IC$_{50}$(μM) |
|---|---|
| II-5 | 1.37 |
| II-9 | 0.86 |
| II-13 | 0.57 |
| II-14 | 0.38 |
| II-16 | 1.506 |
| II-17 | 0.305 |
| II-22 | 2.31 |
| II-29 | 0.59 |
| II-30 | 0.69 |
| II-40 | 0.37 |
| II-41 | 0.17 |
| II-45 | 1.07 |
| II-57 | 1.68 |
| II-64 | 1.31 |
| II-72 | 0.66 |
| II-75 | 0.37 |
| II-85 | 2.52 |
| II-87 | 1.32 |
| II-95 | 0.71 |
| II-98 | 0.07 |
| II-106 | 2.08 |
| II-123 | 2.09 |
| II-129 | 0.74 |
| II-130 | 0.13 |
| II-171 | 0.95 |
| II-172 | 2.00 |
| II-181 | 0.33 |
| II-183 | 0.032 |
| II-193 | 2.27 |
| II-201 | 0.01 |
| II-202 | 1.624 |
| II-217 | 1.87 |

As shown, the compounds of the invention showed inhibiting activity on P2X$_3$ receptor. Furthermore, as the compounds of the invention are effective to P2X₃ subtype, the compounds also have inhibiting activity on P2X₂/₃ receptor, which comprises P2X₃ subtype.

INDUSTRIAL APPLICABILITY

The compound of the invention has antagonizing effect on P2X₃ and/or P2X₂/₃ receptor and is useful in the treatment of diseases or conditions associated with a P2X₃ and/or P2X₂/₃ receptor, such as chronic pain, overactive bladder, etc.

What is claimed is:

1. A compound of the formula (I'):

[Chemical Formula 4]

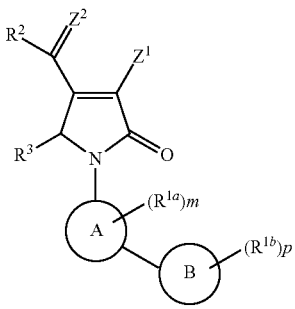

(I')

wherein

[Chemical Formula 5]

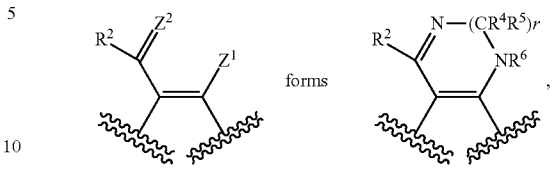

forms in which $R^4$ and $R^5$ are independently hydrogen or lower alkyl, $R^6$ is hydrogen or lower alkyl optionally substituted, r is 0;

A is phenyl, and B is heterocyclyl;

$R^{1a}$ and $R^{1b}$ are independently halogen, hydroxy, lower alkyl optionally substituted, lower alkenyl optionally substituted, lower alkynyl optionally substituted, lower alkoxy optionally substituted, lower alkylthio optionally substituted, acyl optionally substituted, carboxy, lower alkoxycarbonyl optionally substituted, carbamoyl optionally substituted, lower alkylcarbamoyl optionally substituted, amino optionally substituted, sulfamoyl optionally substituted, cyano or nitro;

m and p are independently an integer 0 to 2;

$R^2$ is alkyl optionally substituted; and $R^3$ is hydrogen or lower alkyl optionally substituted; or a pharmaceutically acceptable salt thereof.

2. A pharmaceutical composition comprising a compound according to claim 1 or a pharmaceutically acceptable salt thereof and a pharmaceutically acceptable carrier.

3. A method for the treatment of chronic pain and/or overactive bladder comprising administering an effective amount of a compound according to claim 1 or a pharmaceutically acceptable salt thereof to a patient in need thereof.

\* \* \* \* \*